US008153682B2

(12) United States Patent
Branum et al.

(10) Patent No.: US 8,153,682 B2
(45) Date of Patent: Apr. 10, 2012

(54) SULFONAMIDES AS TRPM8 MODULATORS

(75) Inventors: Shawn T. Branum, Raritan, NJ (US);
Raymond W. Colburn, Spring House, PA (US); Scott L. Dax, Landenberg, PA (US); Christopher M. Flores, Spring House, PA (US); Michele C. Jetter, Norristown, PA (US); Yi Liu, Spring House, PA (US); Donald Ludovici, Spring House, PA (US); Mark J. Macielag, Cranbury, NJ (US); Jay M. Matthews, Spring House, PA (US); James J. McNally, Spring House, PA (US); Laura M. Reaney, Spring House, PA (US); Ronald K. Russell, Raritan, NJ (US); Ning Qin, Spring House, PA (US); Christopher Teleha, Spring House, PA (US); Kenneth M. Wells, Raritan, NJ (US); Scott C. Youells, Spring House, PA (US); Mark A. Youngman, Spring House, PA (US)

(73) Assignee: Janssen Pharmaceutica, NV (BE)

( * ) Notice: Subject to any disclaimer, the term of this patent is extended or adjusted under 35 U.S.C. 154(b) by 0 days.

(21) Appl. No.: 12/175,740

(22) Filed: Jul. 18, 2008

(65) Prior Publication Data

US 2009/0264474 A1 Oct. 22, 2009

Related U.S. Application Data

(60) Provisional application No. 60/950,456, filed on Jul. 18, 2007.

(51) Int. Cl.
| | |
|---|---|
| C07D 419/12 | (2006.01) |
| C07D 417/12 | (2006.01) |
| C07D 413/12 | (2006.01) |
| C07D 409/04 | (2006.01) |
| C07D 409/12 | (2006.01) |
| C07D 333/66 | (2006.01) |
| A61K 31/5377 | (2006.01) |
| A61K 31/496 | (2006.01) |
| A61K 31/4535 | (2006.01) |
| A61K 31/433 | (2006.01) |
| A61K 31/4245 | (2006.01) |
| A61K 31/422 | (2006.01) |
| A61K 31/4196 | (2006.01) |
| A61K 31/4192 | (2006.01) |
| A61K 31/4178 | (2006.01) |
| A61K 31/4025 | (2006.01) |
| A61K 31/381 | (2006.01) |

(52) U.S. Cl. ........ 514/443; 514/414; 514/364; 514/394; 514/382; 514/397; 514/361; 514/442; 514/252.13; 514/233.5; 514/324; 514/228.2; 514/360; 514/384; 514/374; 514/406; 548/454; 548/131; 548/305.1; 548/252; 548/311.4; 548/129; 548/525; 548/122; 548/263.2; 548/235; 548/127; 548/364.4; 548/143; 544/376; 544/146; 544/62; 546/202; 549/57

(58) Field of Classification Search ............. 549/57; 514/443, 414, 364, 394, 382, 397, 361, 422, 514/252.13, 233.5, 324, 228.2, 360, 384, 514/374, 406; 548/454, 131, 305.1, 252, 548/311.4, 129, 525, 122, 253.2, 235, 127, 548/364.4, 143; 544/376, 146, 62; 546/202
See application file for complete search history.

(56) References Cited

FOREIGN PATENT DOCUMENTS

| | | | |
|---|---|---|---|
| EP | 1911753 A | | 4/2007 |
| WO | WO 9928306 A1 | * | 6/1999 |
| WO | WO 2007/013691 A | | 2/2007 |
| WO | WO 2007/017094 A | | 2/2007 |

OTHER PUBLICATIONS

Patani et al. Chem. Rev. 1996, 96, 3147-3176.*
Sheridan, R.P. J. Chem. Inf. Comput. Sci. 2002, 42, 103-108.*
Jordan, V. C. Nature Reviews: Drug Discovery, 2, 2003, pp. 205-213.*
Souillac, et al., Characterization of Delivery Systems, Differential Scanning Calorimetry, pp. 217-218 (in Encyclopedia of Controlled Drug Delivery, 1999, John Wiley & Sons, pp. 212-227.*
Vippagunta et al. Advanced Drug Delivery Reviews, 48 (2001), pp. 3-26.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Beers et al. Bioorganic & Medicinal Chemistry 1997, 5, 779-786.*
Beers, S.A., et al. "N-(5-Substituted) Thiophene-2-Alkylsulfonamides as Potent Inhibitors of 5-Lipoxygenase", Bioorganic & Medicinal Chemistry, Elsevier Science Ltd., GB, vol. 5, No. 4, pp. 779-786 1997.
Cheruku, Srinivasa R., et al. "Carbon Isosteres of the 4-Aminopyridine Substructure of Chloroquine: Effects on p$K$ a, Hematin Binding, Inhibition of Hemozoin Formation, and Parasite Growth", J. Med. Chem. 2003, 46, pp. 3166-3169.
Casy, Alan F., et al. "Opioid Analgesics, Chemistry and receptors", Plenum Press. 1986, pp. 229-249.

* cited by examiner

Primary Examiner — Joseph Kosack
Assistant Examiner — Matthew P Coughlin

(57) ABSTRACT

Disclosed are compounds, compositions and methods for treating various diseases, syndromes, conditions and disorders, including pain. Such compounds are represented by Formula I as follows:

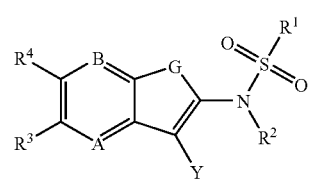

(I)

wherein A, B, G, Y, $R^1$, $R^2$, $R^3$, and $R^4$ are defined herein.

37 Claims, No Drawings

SULFONAMIDES AS TRPM8 MODULATORS

CROSS-REFERENCE TO RELATED APPLICATIONS

This application claims priority to U.S. Provisional Patent Application No. 60/950,456, filed Jul. 18, 2007, which is hereby incorporated by reference in its entirety.

FIELD OF THE INVENTION

The present invention relates to sulfonamides that act as modulators of the TRPM8 receptor. The present invention also relates to processes for the preparation of sulfonamides and to their use in treating various diseases, syndromes, and disorders, including, those that cause inflammatory or neuropathic pain, cold intolerance or cold allodynia, peripheral vascular pain, itch, urinary incontinence, chronic obstructive pulmonary disease (COPD), pulmonary hypertension and anxiety, including other stress-related disorders, and combinations thereof.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRPM8 (McKemy D. D., et al., *Nature* 2002, 416 (6876), 52-58). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRPM8 is known to be stimulated by cool to cold temperatures as well as by chemical agents such as menthol and icilin, which may be responsible for the therapeutic cooling sensation that these agents provoke.

TRPM8 is located on primary nociceptive neurons (A-delta and C-fibers) and is also modulated by inflammation-mediated second messenger signals (Abe, J., et al., *Neurosci Lett* 2006, 397(1-2), 140-144; Premkumar, L. S., et al., *J. Neurosci,* 2005, 25(49), 11322-11329). The localization of TRPM8 on both A-delta and C-fibers may provide a basis for abnormal cold sensitivity in pathologic conditions wherein these neurons are altered, resulting in pain, often of a burning nature (Kobayashi, K., et al., *J Comp Neurol,* 2005, 493(4), 596-606; Roza, C., et al., *Pain,* 2006, 120(1-2), 24-35; and Xing, H., et al., *J Neurophysiol,* 2006, 95(2), 1221-30). Cold intolerance and paradoxical burning sensations induced by chemical or thermal cooling closely parallel symptoms seen in a wide range of clinical disorders and thus provide a strong rationale for the development of TRPM8 modulators as novel antihyperalgesic or antiallodynic agents. TRPM8 is also known to be expressed in the brain, lung, bladder, gastrointestinal tract, blood vessels, prostate and immune cells, thereby providing the possibility for therapeutic modulation in a wide range of maladies.

International patent application WO 2006/040136 A1 from Bayer Healthcare AG purportedly describes substituted 4-benzyloxy-phenylmethylamide derivatives as cold menthol receptor-1 (CMR-1) antagonists for the treatment of urological disorders. International patent application WO 2006/040103 A1 from Bayer Healthcare AG purportedly describes methods and pharmaceutical compositions for treatment and/or prophylaxis of respiratory diseases or disorders. International patent applications WO 2007/017092A1, WO 2007/017093A1 and WO 2007/017094A1, from Bayer Healthcare AG, purportedly describe benzyloxyphenylmethyl carbamate, substituted 2-benzyloxybenzoic acid amide and substituted 4-benzyloxybenzoic acid amide derivatives for the treatment of diseases associated with the cold menthol receptor (CMR), a.k.a. TRPM8.

There is a need in the art for TRPM8 antagonists that can be used to treat a disease, syndrome, or condition in a mammal in which the disease, syndrome, or condition is affected by the modulation of TRPM8 receptors, such as pain, the diseases that lead to such pain, and pulmonary or vascular dysfunction.

SUMMARY OF THE INVENTION

The present invention provides, inter alia, compounds of Formula (I)

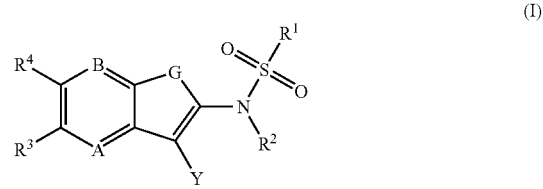

wherein
 A is $CR^5$ or N;
 B is $CR^6$ or N; with the proviso that A and B are $C(R^5)$ and $C(R^6)$, respectively, when G is $S(O)_2$;
 G is S or $S(O_2)$;
 Y is
  (i) H;
  (ii) isopropenyl;
  (iii) $C_{1-6}$ alkylcarbonyl optionally substituted with 1 chloro or 1 to 3 fluoro substituents;
  (iv) $C_{3-6}$ cycloalkylcarbonyl;
  (v) phenylcarbonyl optionally substituted with one to three substituents independently selected from $C_{1-4}$ alkyl, fluoro, or chloro;
  (vi) phenylcarbonyl substituted with trifluoromethyl and optionally one additional substituent selected from trifluoromethyl, chloro, fluoro, or $C_{1-4}$ alkyl;
  (vii) heteroaryl optionally substituted with one to two substituents independently selected from chloro, fluoro, bromo, trifluoromethyl, $C_{1-4}$ alkoxy, hydroxy, $C_{1-4}$ alkyl, $C_{1-3}$ alkoxycarbonyl, $C_{1-3}$ alkylthio, cyano, amino, $C_{1-3}$ alkylamino, or di($C_{1-3}$)alkylamino;
  (viii) benzo-fused heteroaryl optionally substituted with one to two substituents independently selected from chloro, fluoro, bromo, trifluoromethyl, $C_{1-4}$ alkyl, $C_{1-4}$ alkoxy, hydroxy, $C_{1-4}$ alkoxycarbonyl, $C_{1-3}$ alkylthio, cyano, amino, $C_{1-3}$ alkylamino, or di($C_{1-3}$)alkylamino;
  (ix) bromo;
  (x) chloro;
  (xi) fluoro;
  (xii) iodo;
  (xiii) cyano;
  (xiv) formyl;
  (xv) $C_{1-6}$ alkyl optionally substituted with 1 to 3 substituents independently selected from hydroxy, fluoro, or chloro;
  (xvi) $C(OH)(C_{1-3}$ alkyl$)_2$;
  (xvii) $C_{3-6}$ cycloalkyl;
  (xviii) $C_{1-2}$ alkyl substituted with 1 substituent independently selected from $C_{1-4}$ alkoxycarbonyl, cyano, $C_{1-3}$ alkylthio, $C_{1-4}$ alkoxy, or $NR^7R^8$ wherein $R^7$ is hydrogen, $C_{1-4}$ alkyl, $C_{1-3}$ alkylcarbonyl, or $C_{1-3}$ alkylsulfonyl and $R^8$ is hydrogen or $C_{1-4}$ alkyl; or $R^7$ and $R^8$ are taken together with the nitrogen atom to which they are attached to form a 5 or 6 membered ring optionally containing one additional heteroatom selected from nitrogen, oxygen, or sulfur;

(xix) $C_{1-4}$ alkoxycarbonyl;

(xx) $C_{1-3}$ alkoxy;

(xxi) hydroxy;

(xxii) $C_{6-10}$ aryl optionally substituted with one to three substituents independently selected from chloro, fluoro, bromo, $C_{1-4}$ alkoxy, hydroxy, $C_{1-3}$ alkoxycarbonyl, $C_{1-3}$ alkylthio, cyano, amino, $C_{1-2}$ alkylamino, di($C_{1-2}$)alkylamino, or $C_{1-6}$ alkyl optionally substituted with one to three halogen substituents; with the proviso that not more than two of the substituents are selected from the group consisting of $C_{1-3}$ alkoxycarbonyl, $C_{1-3}$ alkylthio, cyano, amino, $C_{1-2}$ alkylamino, di($C_{1-2}$)alkylamino, and $C_{1-6}$ alkyl substituted with one to three halogen substituents;

(xxiii) $NR^9R^{10}$ wherein $R^9$ is hydrogen, $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; and wherein said 5 or 6 membered ring is optionally substituted with a $C_{1-4}$ alkyl substituent; with the proviso that when G is S and $R^{10}$ is hydrogen, $R^9$ is other than hydrogen and $C_{1-4}$ alkyl;

(xxiv) aminocarbonyl;

(xxv) methylaminocarbonyl;

(xxvi) dimethylaminocarbonyl; or (xxvii) arylhydroxy($C_{1-3}$)alkyl;

$R^1$ is (i) $CF_3$;

(ii) $C_{1-6}$ alkyl optionally substituted with 1 substituent selected from $C_{1-3}$ alkylsulfonyl, $C_{1-4}$ alkoxycarbonyl, formyl, hydroxy, carboxy, trifluoromethyl, $C_{1-4}$ alkoxy, $C_{1-3}$ alkylthio, bromo, cyano, $R^{11}$, or $R^{12}$;

(iii) aryl($C_{1-2}$ alkyl) wherein the ring of the aryl group is optionally substituted with 1 to 3 substituents independently selected from $C_{1-4}$ alkyl, fluoro, chloro, trifluoromethyl, hydroxy, $C_{1-4}$ alkoxy, $C_{1-4}$ alkoxycarbonyl, or carboxy; with the proviso that not more than two of the substituents are selected from the group consisting of trifluoromethyl, $C_{1-4}$ alkoxycarbonyl, and carboxy;

(iv) heteroaryl($C_{1-6}$ alkyl) wherein the heteroaryl group is bound through a nitrogen heteroatom and is selected from imidazolyl, triazolyl, or tetrazolyl; and wherein the imidazolyl group is optionally substituted with 1 substituent selected from $C_{1-4}$ alkyl, fluoro, chloro, trifluoromethyl, hydroxy, $C_{1-4}$ alkoxy, $C_{1-4}$ alkoxycarbonyl, carboxy, aminomethyl, methylamino-methyl, or dimethylamino-methyl; and imidazolyl is optionally substituted with one additional substituent selected from $C_{1-4}$ alkyl, fluoro, or chloro;

(v) $C_{3-8}$ cycloalkyl or cyclohexyl substituted at the 4-position with one substituent selected from the group consisting of cyano, $C_{1-4}$ alkoxycarbonyl, carboxy, aminocarbonyl, $C_{1-3}$ alkylaminocarbonyl, di($C_{1-3}$ alkyl)aminocarbonyl, amino-methyl, methylamino-methyl, dimethylamino-methyl, $R^{11}$, and $R^{12}$;

(vi) benzo-fused $C_{5-6}$cycloalkyl attached at the benzo portion of the ring system, and wherein the $C_{5-6}$cycloalkyl portion of benzo-fused $C_{5-6}$cycloalkyl is optionally substituted with amino, ($C_{1-3}$alkyl)amino, or di($C_{1-3}$alkyl)amino;

(vii) phenyl substituted with 3- or 4-imidazolyl, wherein the point of attachment of the imidazolyl is through a nitrogen heteroatom; and wherein the imidazolyl is optionally independently substituted with one to two substituents selected from the group consisting of $C_{1-3}$ alkyl, 2-cyano, chloro, bromo, amino-$C_{1-2}$ alkyl, ($C_{1-2}$ alkyl)amino-$C_{1-2}$ alkyl, and di($C_{1-2}$ alkyl)amino-$C_{1-2}$ alkyl; wherein di($C_{1-3}$ alkyl) is optionally taken together with the nitrogen atom to which it is attached to form a 5 or 6 membered ring optionally containing one additional heteroatom selected from nitrogen, oxygen, or sulfur; and wherein the ring formed by di($C_{1-3}$ alkyl) amino is optionally substituted with $C_{1-3}$alkyl; with the proviso that not more than one of the substituents is amino-$C_{1-2}$ alkyl, ($C_{1-2}$ alkyl)amino-$C_{1-2}$ alkyl, or di($C_{1-2}$ alkyl)amino-$C_{1-2}$ alkyl;

(viii) phenyl optionally substituted with one to three substituents independently selected from $C_{1-4}$ alkyl optionally substituted with one to three chloro or fluoro substituents or one hydroxy substituent, chloro, fluoro, bromo, $C_{1-4}$ alkoxy, trifluoromethoxy, 3- or 4-phenyloxy, 3- or 4-heteroaryloxy wherein the heteroaryl ring is a 6 membered ring containing carbon ring members and 1 or 2 nitrogen heteroatom ring members, $C_{1-3}$ alkylsulfonyl, $C_{1-4}$ alkoxycarbonyl, $C_{1-3}$ alkylthio, hydroxy, carboxy, cyano, nitro, 3- or 4-heteroaryl wherein said heteroaryl is other than imidazolyl, $C_{1-3}$ alkylcarbonyl, aminocarbonyl, $C_{1-3}$ alkylaminocarbonyl, di($C_{1-3}$)alkylaminocarbonyl, $C_{1-3}$ alkylsulfonylaminocarbonyl, di($C_{1-3}$)alkylaminosulfonyl, $P(O)(OC_{1-3}$ alkyl$)_2$, $P(O)(OH)_2$, $SO_3H$, $C(O)NHOH$, $C(=N)NH_2$, $C(=NOH)NH_2$, $C(=N(methylcarbonyloxy))NH_2$, or $SO_2NH_2$; with the proviso that not more than two of the substituents are selected from the group consisting of trifluoromethoxy, 3- or 4-substituted phenyloxy, 3- or 4-heteroaryloxy, $C_{1-3}$ alkylsulfonyl, $C_{1-4}$ alkoxycarbonyl, $C_{1-3}$ alkylthio, carboxy, cyano, 3- or 4-heteroaryl, $C_{1-3}$ alkylcarbonyl, aminocarbonyl, $C_{1-3}$ alkylaminocarbonyl, di($C_{1-3}$)alkylaminocarbonyl, $C_{1-3}$ alkylsulfonylaminocarbonyl, di($C_{1-3}$)alkylaminosulfonyl, and $P(O)(OC_{1-3}$ alkyl$)_2$ and not more than one of the substituents is selected from the group consisting of —$P(O)(OH)_2$, —$SO_3H$, carboxy, $C(O)NHOH$, $C(=N)NH_2$, $C(=NOH)NH_2$, $C(=N(C_{1-3}$alkylcarbonyloxy$))NH_2$, and —$SO_2NH_2$; wherein the phenyloxy is optionally substituted with one to two substituents independently selected from the group consisting of methyl and fluoro; and wherein the heteroaryl substituent is optionally independently substituted with one to two substituents selected from the group consisting of $C_{1-3}$ alkyl, trifluoromethyl, trifluoromethoxy, cyano, amino, methylamino, dimethylamino, chloro, bromo, carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl)amino-$C_{1-2}$ alkyl; with the proviso that not more than one of the substituents is selected from the group consisting of carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl)amino-$C_{1-2}$ alkyl;

(ix) naphthyl optionally substituted with one substituent selected from the group consisting of hydroxy, chloro, fluoro, bromo, $C_{1-4}$ alkoxycarbonyl, and carboxy;

(x) $C_{6-10}$ aryl substituted with phenyl optionally substituted with one to two substituents selected from chloro, fluoro, $C_{1-4}$ alkoxy, $C_{1-4}$ alkoxycarbonyl, carboxy, hydroxy, or $C_{1-3}$ alkyl;

(xi) phenyl substituted with $R^{11}$ or $R^{12}$ at the 3 or 4 position; and optionally one additional substituent selected from fluoro, chloro, or $C_{1-3}$ alkyl;

(xii) pyridin-3-yl substituted at a carbon atom other than that adjacent to the carbon bearing $S(O)_2$ with a substituent selected from N-imidazolyl, oxadiazolyl, thiazolyl, $R^{11}$, or $R^{12}$; wherein pyridin-3-yl is optionally substituted with one additional substituent selected from fluoro, chloro, or $C_{1-3}$ alkyl; and further, wherein the N-imidazolyl group is optionally substituted with one to two substituents, and the oxadiazolyl and thiazolyl groups are optionally substituted one substituent, said substituent(s) independently selected from the group consisting of $C_{1-4}$ alkyl, trifluoromethyl, cyano, amino, methylamino, dimethylamino, chloro, bromo, carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl)amino-$C_{1-2}$ alkyl; with the proviso that not more than one of the substituents is selected from the group consisting of carboxy, $C_{1-2}$ alkoxycarbonyl, $C_{1-2}$ alkoxycarbonylmethyl, carboxymethyl, trifluoromethyl, cyano, amino-$C_{1-2}$ alkyl, ($C_{1-2}$ alkyl)amino-$C_{1-2}$ alkyl, and di($C_{1-2}$ alkyl)amino-$C_{1-2}$ alkyl;

(xiii) imidazolyl substituted with $R^{11}$ or $R^{12}$; and imidazolyl is optionally substituted at a nitrogen heteroatom with $C_{1-4}$ alkyl;

(xiv) a ring selected from phenyl or pyridin-3-yl, wherein said ring is substituted with $NR^{15}R^{16}$; wherein $R^{15}$ is hydrogen, $C_{1-4}$ alkyl, $C_{1-4}$ alkylcarbonyl, trifluoromethylcarbonyl, trifluoromethylsulfonyl, $C_{3-6}$ cycloalkylsulfonyl, or $C_{1-3}$ alkylsulfonyl; and $R^{16}$ is hydrogen or $C_{1-4}$ alkyl; or $R^{15}$ and $R^{16}$ are taken together with the nitrogen atom to which they are attached to form a 5 or 6 membered ring optionally containing one additional heteroatom selected from nitrogen, oxygen, or sulfur optionally substituted with one or two oxo substituents; and wherein the ring formed by $NR^{15}R^{16}$ is optionally substituted with $C_{1-3}$alkyl, $C_{1-2}$ alkoxycarbonyl, or carboxy; and wherein said phenyl is optionally substituted with one to two additional substituents independently selected from the group consisting of $C_{1-4}$ alkyl, $C_{1-4}$ alkoxy, hydroxy, fluoro, chloro, and bromo;

(xv) phenyl substituted with $C(O)NR^{17}R^{18}$ wherein $R^{17}$ is hydrogen, $C_{1-4}$ alkyl, $C_{1-4}$ alkylcarbonyl, pyrrolidin-3-yl, or $C_{1-3}$ alkylsulfonyl; and $R^{18}$ is hydrogen or $C_{1-4}$ alkyl; or $R^{17}$ and $R^{18}$ are taken together with the nitrogen atom to which they are attached to form a 5 or 6 membered ring optionally containing one additional heteroatom selected from nitrogen, oxygen, or sulfur; and wherein said ring is optionally substituted with $C_{1-3}$alkyl;

(xvi) phenyl substituted with 4 or 5 fluoro substituents;

(xvii) phenyl substituted at the 4-position with -Q-C($R^xR^y$)—($CH_2$)$_{0-1}CO_2H$ wherein Q is a bond or O; and wherein $R^x$ and $R^y$ are independently hydrogen or methyl; or $R^x$ and $R^y$ are taken together with the carbon atom to which they are both attached to form a cyclopropyl ring;

(xviii) heteroaryl optionally substituted with one to three substituents independently selected from $C_{1-4}$ alkyl, chloro, fluoro, bromo, trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, di($C_{1-3}$)alkylamino, morpholin-4-yl, or heteroaryl; wherein the heteroaryl group is optionally independently substituted with one to two substituents selected from the group consisting of $C_{1-3}$ alkyl, trifluoromethyl, fluoro, and chloro; with the proviso that not more than two of the substituents are selected from the group consisting of trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, and di($C_{1-3}$)alkylamino;

(xix) benzo-fused heteroaryl optionally substituted at a carbon atom with one to three substituents independently selected from $C_{1-4}$ alkyl, chloro, fluoro, bromo, difluoromethyl, trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, or di($C_{1-3}$)alkylamino; with the proviso that not more than two of the substituents are selected from the group consisting of trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, and di($C_{1-3}$)alkylamino; and benzo-fused heteroaryl is optionally substituted at a nitrogen atom with $C_{1-3}$ alkyl;

(xx) benzo-fused heterocycle optionally substituted with one to two substituents independently selected from trifluoromethyl, $C_{1-3}$ alkylcarbonyl, $C_{1-4}$ alkyl, $C_{1-4}$ alkoxy, trifluoromethylcarbonyl, fluoro, chloro, bromo, hydroxy, oxo, carboxy, or $C_{1-4}$ alkoxycarbonyl; such that when the benzo-fused heterocycle is substituted on the heterocyclic ring, the substituents on the heterocyclic ring are selected from oxo, hydroxy, $C_{1-4}$ alkyl, or trifluoromethylcarbonyl; with the proviso that not more than one substituent is trifluoromethylcarbonyl; and with the proviso that when the benzo-fused heterocycle is substituted with trifluoromethylcarbonyl, at least one of the ring members of the heterocycle is a nitrogen heteroatom and the point of attachment to the trifluoromethylcarbonyl substituent is through the nitrogen heteroatom;

(xxi) amino;

(xxii) $C_{1-6}$ alkylamino; or (xxiii) di($C_{1-6}$ alkyl)amino;

$R^2$ is (i) $C_{3-6}$ cycloalkyl;

(ii) $C_{1-2}$ alkyl substituted with adamantyl or norbornanyl;

(iii) $C_{1-6}$ alkyl substituted with two $C_{6-10}$ aryl groups wherein one of said aryl groups is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl; and the other of said aryl groups is optionally substituted with 1 substituent selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl;
(iv) $C_{1-6}$ alkyl substituted with one $C_{6-10}$ aryl group and optionally one additional substituent selected from hydroxy or oxo, wherein said $C_{6-10}$ aryl group is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$) alkylamino, and $C_{1-3}$ alkylcarbonyl;
(v) $C_{1-6}$ alkyl substituted with phenyl, wherein phenyl is substituted with 4 or 5 fluoro substituents; or phenyl is substituted with methoxy and 3 to 4 fluoro substituents;
(vi) $C_{1-6}$ alkyl substituted with one heteroaryl group and optionally one additional substituent selected from oxo or hydroxy wherein said heteroaryl group is optionally substituted with one to three fluoro substituents or 1 substituent selected from chloro, bromo, trifluoromethyl, $C_{1-4}$ alkoxy, hydroxy, $C_{1-4}$ alkoxycarbonyl, $C_{1-3}$ alkylthio, cyano, or $C_{1-4}$ alkyl;
(vii) $C_{1-6}$ alkyl substituted with one benzo-fused heteroaryl group and optionally one additional substituent selected from oxo or hydroxy, wherein said benzo-fused heteroaryl group is optionally substituted with 1 substituent selected from chloro, fluoro, bromo, trifluoromethyl, $C_{1-4}$ alkoxy, hydroxy, $C_{1-4}$ alkoxycarbonyl, $C_{1-3}$ alkylthio, cyano, or $C_{1-4}$ alkyl;
(viii) $C_{1-6}$ alkyl substituted with one heterocycle group wherein said heterocycle group is optionally substituted with one to three substituents independently selected from $C_{1-4}$ alkyl, $C_{1-4}$ alkoxycarbonyl, oxo, or hydroxy; with the proviso that not more than two of the substituents are selected from the group consisting of oxo and hydroxy;
(ix) $C_{1-6}$ alkyl substituted with benzo[1,3]dioxol-5-yl, 2,2-difluoro-benzo[1,3]dioxol-5-yl, or 2,3-dihydro-benzo[1,4]dioxin-6-yl; or
(x) $C_{2-6}$ alkyl optionally substituted with 1 to 2 substituents independently selected from cyano, trifluoromethyl, $C_{1-6}$ alkylcarbonyl, $C_{1-6}$ alkylthio, $C_{1-6}$ alkylsulfonyl, amino, $C_{1-3}$ alkylamino, di($C_{1-3}$)alkylamino, $C_{2-6}$ alkenyl, $C_{2-6}$ alkynyl, fluoro, $C_{1-6}$ alkoxy, $C_{1-6}$ alkoxycarbonyl, $C_{1-4}$ alkoxycarbonylamino, hydroxy, P(O)(OC$_{1-3}$)$_2$, $C_{3-6}$ cycloalkyloxy, $C_{3-6}$ cycloalkyl, or $C_{5-8}$ cycloalkyl optionally substituted with one to three substituents independently selected from the group consisting of halogen, hydroxy, oxo and $C_{1-4}$ alkyl optionally substituted with one to three substituents independently selected from halogen or hydroxy; with the proviso that not more than one of the substituents on the $C_{1-4}$ alkyl of the $C_{1-4}$ alkyl substituted $C_{5-8}$ cycloalkyl is hydroxy, and not more than two of the substituents on the $C_{5-8}$ cycloalkyl are oxo;

$R^3$ is
(i) hydrogen,
(ii) $C_{1-6}$ alkyl,
(iii) trifluoromethyl,
(iv) $C_{1-4}$ alkoxy,
(v) bromo,
(vi) chloro,
(vii) fluoro, or
(viii) hydroxy;

$R^4$ is
(i) hydrogen,
(ii) fluoro,
(iii) chloro, or
(iv) methyl;

$R^5$ is hydrogen;

$R^6$ is
(i) hydrogen,
(ii) fluoro,
(iii) chloro,
(iv) methoxy, or
(v) methyl;

$R^{11}$ is selected from

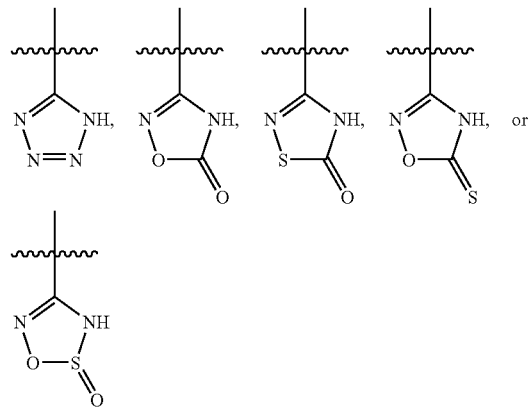

$R^{12}$ is selected from

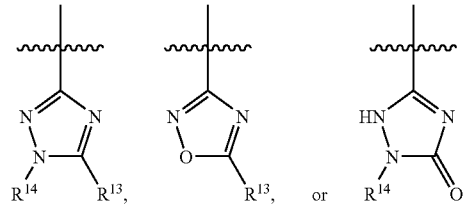

wherein $R^{13}$ is H, —$C_{1-4}$ alkyl, —CH$_2$CO$_2$CH$_3$, —CH$_2$NH(C$_{1-3}$alkyl), —CH$_2$N(C$_{1-3}$alkyl)$_2$, or —CH$_2$CO$_2$H; and $R^{14}$ is —$C_{6-10}$ aryl, —$C_{1-6}$ alkyl, —$C_{1-3}$ alkyl-OH, or —$C_{1-3}$ alkylCO$_2$H;

with the proviso that when $R^1$ is $C_{6-10}$ aryl, wherein $C_{6-10}$ aryl is phenyl, substituted with carboxy at the 2 position, Y is not hydrogen;

with the proviso that when $R^2$ is $C_{1-6}$ alkyl substituted with at least one P(O)(OCH$_3$)$_2$ substituent, $R^1$ is optionally substituted $C_{6-10}$ aryl;

with the proviso that when $R^2$ is $C_{1-6}$ alkyl substituted with at least one $C_{1-6}$ alkoxycarbonyl substituent, $R^1$ is optionally substituted $C_{6-10}$ aryl;

with the proviso that when Y is unsubstituted phenyl, and $R^1$ is ethyl, $R^2$ is not 4-fluoro-3-trifluoromethyphenylmethyl;

with the proviso that when $R^2$ is $C_{1-6}$ alkyl substituted with an unsubstituted heterocycle comprising at least one nitrogen heteroatom, the point of attachment to the pendant group is through a nitrogen heteroatom;

with the proviso that when $R^2$ is substituted or unsubstituted $C_{1-6}$ alkyl, $R^1$ is other than phenyl substituted at the 3-position with $R^{11}$ or $R^{12}$;

with the proviso that Formula (I) is other than a compound wherein G is S, Y is H, $R^1$ is 4-cyanophenyl, $R^2$ is 4,4,4-trifluorobutyl, $R^3$, $R^4$, $R^5$, and $R^6$ are hydrogen, A is $CR^5$, and B is $CR^6$;

a compound wherein G is S, Y is bromo, $R^1$ is 4-carboxyphenyl, $R^2$ is octahydro-quinolizin-1-ylmethyl, $R^3$, $R^4$, $R^5$, and $R^6$ are hydrogen, A is $CR^5$, and B is $CR^6$;

a compound wherein G is S, Y is 1-hydroxyethyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is methyl, $R^1$ is 4-piperazin-1-ylcarbonylphenyl, $R^2$ is 2-(cyclopropyl)ethyl, $R^3$, $R^4$, $R^5$, and $R^6$ are hydrogen, A is $CR^5$, and B is $CR^6$;

a compound wherein G is S, Y is methylcarbonylamino, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is S, Y is H, $R^1$ is 3-aminocarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is bromo, $R^1$ is 4-(1-hydroxy-1-methyl-ethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is methylaminocarbonyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is $S(O_2)$, Y is methyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound wherein G is S, Y is H, $R^1$ is 4-(5-thioxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound wherein G is S, Y is 4-methyl-piperazin-1-ylcarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is bromo, $R^1$ is 4-(1-hydroxyethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is dimethylaminomethyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is S, Y is H, $R^1$ is 3-cyanophenyl, $R^2$ is 5,5,5-trifluoropentyl, $R^3$, $R^4$, $R^5$, and $R^6$ are hydrogen, A is $CR^5$, and B is $CR^6$;

a compound wherein G is S, Y is methylcarbonyl, $R^1$ is 4-carboxyphenyl, $R^2$ is 3-fluoropropyl, $R^3$, $R^4$, $R^5$, and $R^6$ are hydrogen, A is $CR^5$, and B is $CR^6$;

a compound wherein G is S, Y is H, $R^1$ is 4-carboxyphenyl, $R^2$ is 2-fluoroethyl, $R^3$, $R^4$, $R^5$, and $R^6$ are hydrogen, A is $CR^5$, and B is $CR^6$;

a compound wherein G is S, Y is H, $R^1$ is 4-carboxyphenyl, $R^2$ is 3-fluoropropyl, $R^3$, $R^4$, $R^5$, and $R^6$ are hydrogen, A is $CR^5$, and B is $CR^6$; and a compound wherein G is S, Y is methyl, $R^1$ is 4-carboxyphenyl, $R^2$ is 2-fluoroethyl, $R^3$, $R^4$, $R^5$, and $R^6$ are hydrogen, A is $CR^5$, and B is $CR^6$;

a compound wherein G is $S(O_2)$, Y is methyl, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound wherein G is S, Y is H, $R^1$ is 3-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

and enantiomers, diastereomers, solvates, and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent and a compound of Formula (I) or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a TRPM8-modulated disorder in a subject, including a mammal and/or human in which the disease, syndrome, or condition is affected by the modulation of TRPM8 receptors, such as pain, the diseases that lead to such pain, and pulmonary or vascular dysfunction using a compound of Formula (I). In particular, the methods of the present invention are directed to treating or ameliorating a TRPM8 receptor-modulated disorder including inflammatory pain, cold-intolerance or cold allodynia, peripheral vascular pain, itch, urinary incontinence, chronic obstructive pulmonary disease, pulmonary hypertension and anxiety, including other stress-related disorders, using a compound of Formula (I).

The present invention also provides, inter alia, methods for producing the instant compounds and pharmaceutical compositions and medicaments thereof. A process included in the scope of this invention includes the following process for the preparation of Compound 306

Compound 306

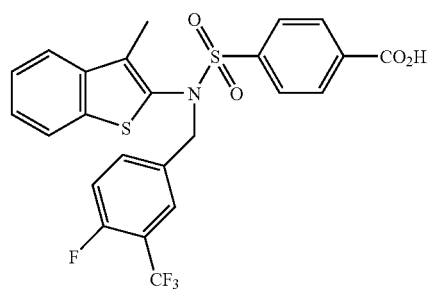

Comprising, consisting of and/or consisting essentially of

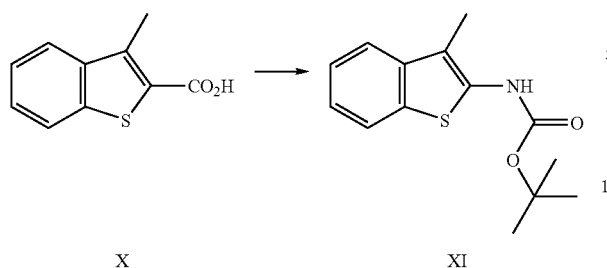

X    XI reacting a compound of formula X with t-butyl alcohol and a tertiary amine; in an organic solvent; followed by the addition of a mixture of diphenylphosphorylazide in an organic solvent; at temperature of about 110° C.; to yield a compound of formula XI;

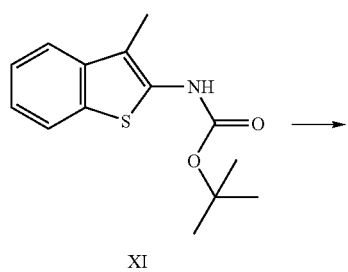

XI reacting a compound of formula XI with a mineral acid or organic acid; neat or in an organic solvent; at temperature of from about 21° C. to about 22° C.; to yield a compound of formula XII;

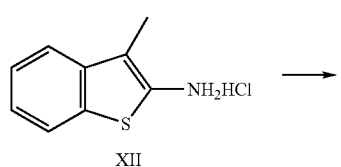

XII

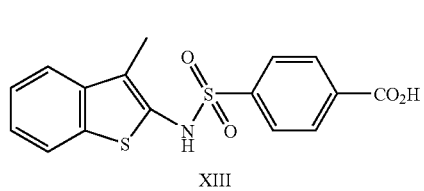

XIII reacting a compound of formula XII with 4-(chlorosulfonyl)benzoic acid; in an organic solvent; at a temperature of about 21° C. to about 22° C.; to afford a compound of Formula XIII;

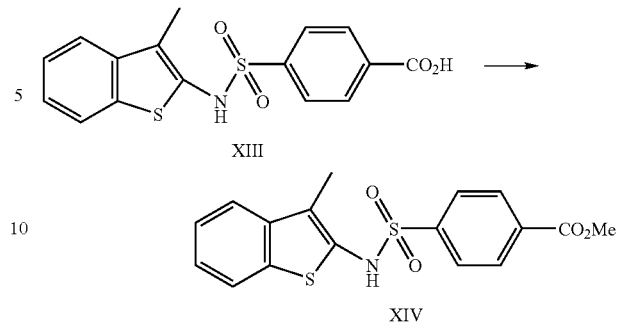

XIII

XIV reacting a compound of Formula XIII in the presence of methanol; followed by the addition of sulfuric acid; at a temperature of from about 64° C. to about 65° C.; to afford a compound of the Formula XIV;

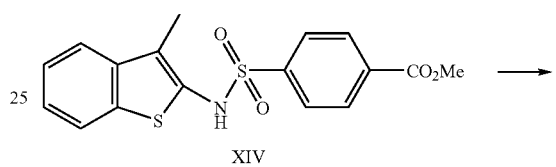

XIV

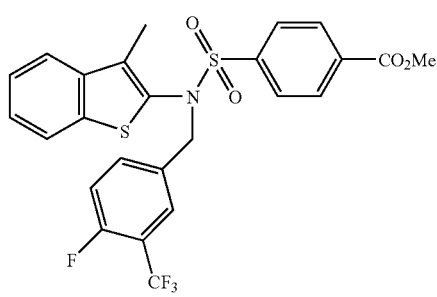

Compound 141 reacting a compound of Formula XIV in an organic solvent; in the presence of an inorganic base; followed by the addition of 4-fluoro-3-(trifluoromethyl)benzyl bromide; at a temperature of from about 21° C. to about 22° C.; to afford Compound 141;

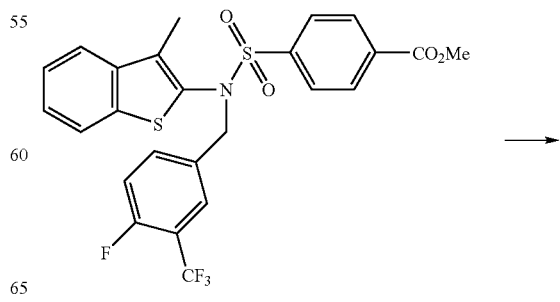

Compound 141

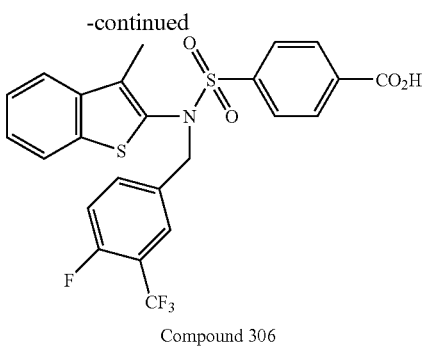

Compound 306 treating Compound 141 with a metal hydroxide; neat or in an organic solvent; at a temperature of about 64° C. to about 66° C.; to afford Compound 306.

DETAILED DESCRIPTION OF ILLUSTRATIVE EMBODIMENTS

The present invention provides, inter alia, compounds of Formula (I)

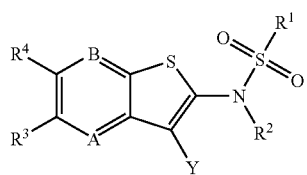

wherein

A is $CR^5$ or N;
B is $CR^6$ or N;
Y is
(i) H;
(ii) $C_{1-6}$ alkylcarbonyl optionally substituted with 1 chloro substituent or 1 to 3 fluoro substituents;
(iii) $C_{3-6}$ cycloalkylcarbonyl;
(iv) phenylcarbonyl optionally substituted with one to three substituents independently selected from $C_{1-4}$ alkyl, fluoro, or chloro;
(v) phenylcarbonyl substituted with trifluoromethyl and optionally one additional substituent selected from trifluoromethyl, chloro, fluoro, or $C_{1-4}$ alkyl;
(vi) heteroaryl optionally substituted with one to two substituents independently selected from chloro, fluoro, bromo, trifluoromethyl, $C_{1-4}$ alkoxy, hydroxy, $C_{1-4}$ alkyl, $C_{1-3}$ alkoxycarbonyl, $C_{1-3}$ alkylthio, cyano, amino, $C_{1-3}$ alkylamino, or di($C_{1-3}$)alkylamino;
(vii) benzo-fused heteroaryl optionally substituted with one to two substituents independently selected from chloro, fluoro, bromo, trifluoromethyl, $C_{1-4}$ alkyl, $C_{1-4}$ alkoxy, hydroxy, $C_{1-4}$ alkoxycarbonyl, $C_{1-3}$ alkylthio, cyano, amino, $C_{1-3}$ alkylamino, or di($C_{1-3}$)alkylamino;
(viii) bromo;
(ix) chloro;
(x) fluoro;
(xi) iodo;
(xii) cyano;
(xiii) formyl;
(xiv) $C_{1-6}$ alkyl optionally substituted with 1 to 3 substituents independently selected from hydroxy, fluoro, or chloro;
(xv) $C(OH)(C_{1-3}$ alkyl$)_2$;
(xvi) $C_{3-6}$ cycloalkyl;
(xvii) $C_{1-6}$ alkyl substituted with 1 substituent independently selected from $C_{1-4}$ alkoxycarbonyl, cyano, $C_{1-3}$ alkylthio, $C_{1-4}$ alkoxy, or $NR^7R^8$ wherein $R^7$ is hydrogen, $C_{1-4}$ alkyl, $C_{1-3}$ alkylcarbonyl, or $C_{1-3}$ alkylsulfonyl and $R^8$ is hydrogen or $C_{1-4}$ alkyl; or $R^7$ and $R^8$ are taken together with the nitrogen atom to which they are attached to form a 5 or 6 membered ring optionally containing one additional heteroatom selected from nitrogen, oxygen, or sulfur;
(xviii) $C_{1-4}$ alkoxycarbonyl;
(xix) $C_{1-3}$ alkoxy;
(xx) hydroxy;
(xxi) $C_{6-10}$ aryl optionally with one to three substituents independently selected from chloro, fluoro, bromo, $C_{1-4}$ alkoxy, hydroxy, $C_{1-3}$ alkoxycarbonyl, $C_{1-3}$ alkylthio, cyano, amino, $C_{1-2}$ alkylamino, di($C_{1-2}$)alkylamino, or $C_{1-6}$ alkyl optionally substituted with one to three halogen substituents; with the proviso that not more than two of the substituents are selected from the group consisting of $C_{1-3}$ alkoxycarbonyl, $C_{1-3}$ alkylthio, cyano, amino, $C_{1-2}$ alkylamino, di($C_{1-2}$)alkylamino, and $C_{1-6}$ alkyl substituted with one to three halogen substituents;
(xxii) $NR^9R^{10}$ wherein $R^9$ is hydrogen, $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; or
(xxiii) arylhydroxy($C_{1-3}$)alkyl;
$R^1$ is
(i) $C_{1-6}$ alkyl optionally substituted with 1 substituent selected from $C_{1-3}$ alkylsulfonyl, $C_{1-4}$ alkoxycarbonyl, hydroxy, carboxy, trifluoromethyl, $C_{1-4}$ alkoxy, $C_{1-3}$ alkylthio, or cyano;
(ii) aryl($C_{1-2}$ alkyl) wherein the ring of the aryl group is optionally substituted with 1 to 3 substituents independently selected from $C_{1-4}$ alkyl, fluoro, chloro, trifluoromethyl, hydroxy, $C_{1-4}$ alkoxy, $C_{1-4}$ alkoxycarbonyl, or carboxy; with the proviso that not more than two of the substituents are selected from the group consisting of trifluoromethyl, $C_{1-4}$ alkoxycarbonyl, and carboxy;
(iii) heteroaryl($C_{1-2}$ alkyl) wherein the ring of the heteroaryl group is optionally substituted with 1 to 2 substituents independently selected from $C_{1-4}$ alkyl, fluoro, chloro, trifluoromethyl, hydroxy, $C_{1-4}$ alkoxy, $C_{1-4}$ alkoxycarbonyl, or carboxy;
(iv) $C_{3-8}$ cycloalkyl;
(v) $C_{6-10}$ aryl optionally substituted with one to three substituents independently selected from $C_{1-4}$ alkyl optionally substituted with one to three chloro or fluoro substituents, chloro, fluoro, bromo, $C_{1-4}$ alkoxy, phenyloxy, heteroaryloxy wherein the heteroaryl ring is a 6 membered ring containing carbon ring members and 1 or 2 nitrogen heteroatom ring members, $C_{1-3}$ alkylsulfonyl, $C_{1-4}$ alkoxycarbonyl, $C_{1-3}$ alkylthio, hydroxy, carboxy, cyano, heteroaryl, $C_{1-3}$ alkylcarbonyl, aminocarbonyl, $C_{1-3}$ alkylaminocarbonyl, di($C_{1-3}$)alkylaminocarbonyl, $P(O)(OC_{1-3}$ alkyl$)_2$, $P(O)(OH)_2$, $SO_3H$, $C(O)NHOH$, or $SO_2NH_2$; with the proviso that not more than two of the substituents are selected from the group consisting of phenyloxy, heteroaryloxy, $C_{1-3}$ alkylsulfonyl, $C_{1-4}$ alkoxycarbonyl, $C_{1-3}$ alkylthio, carboxy, cyano, heteroaryl, $C_{1-3}$ alkylcarbonyl, aminocarbonyl, $C_{1-3}$ alkylaminocarbonyl, di($C_{1-3}$)alkylaminocarbonyl, and $P(O)(OC_{1-3}$ alkyl$)_2$ and not more than one of the substituents is selected from the group consisting of —P(O)(OH)$_2$, —SO$_3$H, carboxy, C(O)NHOH, and —SO$_2$NH$_2$;
(vi) C$_{6-10}$ aryl substituted with phenyl optionally substituted with one to two substituents selected from chloro, fluoro, C$_{1-4}$ alkoxy, C$_{1-4}$ alkoxycarbonyl, carboxy, hydroxy, or C$_{1-3}$ alkyl;
(vii) phenyl substituted with R$^{11}$ or R$^{12}$ at the 3 or 4 position; and optionally one additional substituent selected from fluoro, chloro, or C$_{1-3}$ alkyl;
(viii) phenyl substituted with 4 or 5 fluoro substituents;
(ix) heteroaryl optionally substituted with one to three substituents independently selected from C$_{1-4}$ alkyl, chloro, fluoro, bromo, trifluoromethyl, C$_{1-4}$ alkoxy, oxo, hydroxy, C$_{1-4}$ alkoxycarbonyl, C$_{1-3}$ alkylthio, cyano, carboxy, amino, C$_{1-3}$ alkylamino, or di(C$_{1-3}$)alkylamino; with the proviso that not more than two of the substituents are selected from the group consisting of trifluoromethyl, C$_{1-4}$ alkoxy, oxo, hydroxy, C$_{1-4}$ alkoxycarbonyl, C$_{1-3}$ alkylthio, cyano, carboxy, amino, C$_{1-3}$ alkylamino, and di(C$_{1-3}$)alkylamino;
(x) benzo-fused heteroaryl optionally substituted with one to three substituents independently selected from C$_{1-4}$ alkyl, chloro, fluoro, bromo, trifluoromethyl, C$_{1-4}$ alkoxy, oxo, hydroxy, C$_{1-4}$ alkoxycarbonyl, C$_{1-3}$ alkylthio, cyano, carboxy, amino, C$_{1-3}$ alkylamino, or di(C$_{1-3}$)alkylamino; with the proviso that not more than two of the substituents are selected from the group consisting of trifluoromethyl, C$_{1-4}$ alkoxy, oxo, hydroxy, C$_{1-4}$ alkoxycarbonyl, C$_{1-3}$ alkylthio, cyano, carboxy, amino, C$_{1-3}$ alkylamino, and di(C$_{1-3}$)alkylamino;
(xi) benzo-fused heterocycle optionally substituted with one to two substituents independently selected from trifluoromethyl, C$_{1-3}$ alkylcarbonyl, C$_{1-4}$ alkyl, C$_{1-4}$ alkoxy, trifluoromethylcarbonyl, fluoro, chloro, bromo, hydroxy, oxo, carboxy, or C$_{1-4}$ alkoxycarbonyl; such that when the benzo-fused heterocycle is substituted on the heterocyclic ring, the substituents on the heterocyclic ring are selected from oxo, hydroxy, C$_{1-4}$ alkyl, or trifluoromethylcarbonyl; with the proviso that not more than one substituent is trifluoromethylcarbonyl; and with the proviso that when the benzo-fused heterocycle is substituted with trifluoromethylcarbonyl, at least one of the ring members of the heterocycle is a nitrogen heteroatom and the point of attachment to the trifluoromethylcarbonyl substituent is through the nitrogen heteroatom;
(xii) amino;
(xiii) C$_{1-6}$ alkylamino; or
(xiv) di(C$_{1-6}$ alkyl)amino;
R$^2$ is
(i) C$_{3-6}$ cycloalkyl;
(ii) C$_{1-2}$ alkyl substituted with adamantyl;
(iii) C$_{1-6}$ alkyl substituted with two C$_{6-10}$ aryl groups wherein one of said aryl groups is optionally substituted with 1 to 3 substituents independently selected from chloro, fluoro, bromo, C$_{1-4}$ alkyl, C$_{1-4}$ alkoxy optionally substituted with 1 to 3 fluoro substituents, hydroxy, C$_{1-4}$ alkoxycarbonyl, C$_{1-3}$ alkylthio, cyano, trifluoromethyl, aminocarbonyl, C$_{1-3}$ alkylaminocarbonyl, di(C$_{1-3}$)alkylaminocarbonyl, C$_{1-3}$ alkylsulfonyl optionally substituted with 1 to 3 fluoro substituents, nitro, amino, C$_{1-3}$ alkylamino, di(C$_{1-3}$)alkylamino, or C$_{1-3}$ alkylcarbonyl; with the proviso that not more than two of the substituents are selected from the group consisting of C$_{1-4}$ alkoxy substituted with 1 to 3 fluoro substituents, C$_{1-4}$ alkoxycarbonyl, C$_{1-3}$ alkylthio, cyano, trifluoromethyl, aminocarbonyl, C$_{1-3}$ alkylaminocarbonyl, di(C$_{1-3}$)alkylaminocarbonyl, C$_{1-3}$ alkylsulfonyl optionally substituted with 1 to 3 fluoro substituents, nitro, amino, C$_{1-3}$ alkylamino, di(C$_{1-3}$)alkylamino, and C$_{1-3}$ alkylcarbonyl; and the other of said aryl groups is optionally substituted with 1 substituent selected from chloro, fluoro, bromo, C$_{1-4}$ alkyl, C$_{1-4}$ alkoxy optionally substituted with 1 to 3 fluoro substituents, hydroxy, C$_{1-4}$ alkoxycarbonyl, C$_{1-3}$ alkylthio, cyano, trifluoromethyl, aminocarbonyl, C$_{1-3}$ alkylaminocarbonyl, di(C$_{1-3}$)alkylaminocarbonyl, C$_{1-3}$ alkylsulfonyl optionally substituted with 1 to 3 fluoro substituents, nitro, amino, C$_{1-3}$ alkylamino, di(C$_{1-3}$)alkylamino, or C$_{1-3}$ alkylcarbonyl;
(iv) C$_{1-6}$ alkyl substituted with one C$_{6-10}$ aryl group and optionally one additional substituent selected from hydroxy or oxo, wherein said C$_{6-10}$ aryl group is optionally substituted with 1 to 3 substituents independently selected from chloro, fluoro, bromo, C$_{1-4}$ alkyl, C$_{1-4}$ alkoxy optionally substituted with 1 to 3 fluoro substituents, hydroxy, C$_{1-4}$ alkoxycarbonyl, C$_{1-3}$ alkylthio, cyano, trifluoromethyl, aminocarbonyl, C$_{1-3}$ alkylaminocarbonyl, di(C$_{1-3}$)alkylaminocarbonyl, C$_{1-3}$ alkylsulfonyl optionally substituted with 1 to 3 fluoro substituents, nitro, amino, C$_{1-3}$ alkylamino, di(C$_{1-3}$)alkylamino, or C$_{1-3}$ alkylcarbonyl; with the proviso that not more than two of the substituents are selected from the group consisting of C$_{1-4}$ alkoxy substituted with 1 to 3 fluoro substituents, C$_{1-4}$ alkoxycarbonyl, C$_{1-3}$ alkylthio, cyano, trifluoromethyl, aminocarbonyl, C$_{1-3}$ alkylaminocarbonyl, di(C$_{1-3}$)alkylaminocarbonyl, C$_{1-3}$ alkylsulfonyl optionally substituted with 1 to 3 fluoro substituents, nitro, amino, C$_{1-3}$ alkylamino, di(C$_{1-3}$)alkylamino, and C$_{1-3}$ alkylcarbonyl;
(v) C$_{1-6}$ alkyl substituted with one heteroaryl group and optionally one additional substituent selected from oxo or hydroxy wherein said heteroaryl group is optionally substituted with 1 substituent selected from chloro, fluoro, bromo, trifluoromethyl, C$_{1-4}$ alkoxy, hydroxy, C$_{1-4}$ alkoxycarbonyl, C$_{1-3}$ alkylthio, cyano, or C$_{1-4}$ alkyl;
(vi) C$_{1-6}$ alkyl substituted with one benzo-fused heteroaryl group and optionally one additional substituent selected from oxo or hydroxy, wherein said benzo-fused heteroaryl group is optionally substituted with 1 substituent selected from chloro, fluoro, bromo, trifluoromethyl, C$_{1-4}$ alkoxy, hydroxy, C$_{1-4}$ alkoxycarbonyl, C$_{1-3}$ alkylthio, cyano, or C$_{1-4}$ alkyl;
(vii) C$_{1-6}$ alkyl substituted with one heterocycle group wherein said heterocycle group is optionally substituted with one to three substituents independently selected from C$_{1-4}$ alkyl, C$_{1-4}$ alkoxycarbonyl, oxo, or hydroxy; with the proviso that not more than two of the substituents are selected from the group consisting of oxo and hydroxy; or
(viii) C$_{1-6}$ alkyl optionally substituted with 1 to 2 substituents independently selected from cyano, trifluoromethyl, C$_{1-6}$ alkylcarbonyl, C$_{1-6}$ alkylthio, C$_{1-6}$ alkylsulfonyl, amino, C$_{1-3}$ alkylamino, di(C$_{1-3}$)alkylamino, C$_{2-6}$ alkenyl, C$_{2-6}$ alkynyl, fluoro, C$_{1-6}$ alkoxy, C$_{1-6}$ alkoxycarbonyl, C$_{1-4}$ alkoxycarbonylamino, hydroxy, P(O)(OC$_{1-3}$)$_2$, C$_{3-4}$ cycloalkyl, or C$_{5-8}$ cycloalkyl optionally substituted with one to three substituents independently selected from the group consisting of halogen, hydroxy, oxo and C$_{1-4}$ alkyl optionally substituted with one to three substituents independently selected from halogen or hydroxy; with the proviso that not more than one of the substituents on the C$_{1-4}$ alkyl of the C$_{1-4}$ alkyl substituted $C_{5-8}$ cycloalkyl is hydroxy, and not more than two of the substituents on the $C_{5-8}$ cycloalkyl are oxo;

$R^3$ is
(i) hydrogen,
(ii) $C_{1-6}$ alkyl,
(iii) trifluoromethyl,
(ix) $C_{1-4}$ alkoxy,
(x) bromo,
(xi) chloro,
(xii) fluoro, or
(xiii) hydroxy;

$R^4$ is
(i) hydrogen,
(ii) fluoro,
(iii) chloro, or
(iv) methyl;

$R^5$ is hydrogen;

$R^6$ is
(i) hydrogen,
(ii) fluoro,
(iii) chloro,
(iv) methoxy, or
(v) methyl;

$R^{11}$ is selected from

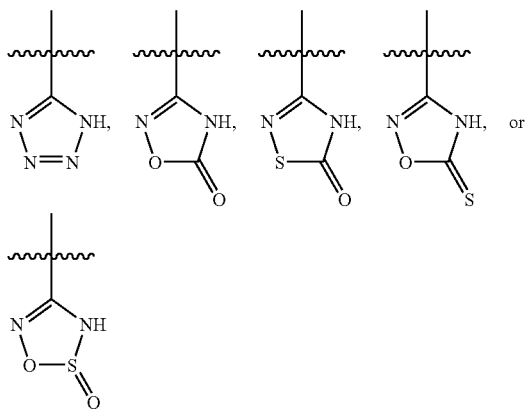

$R^{12}$ is selected from

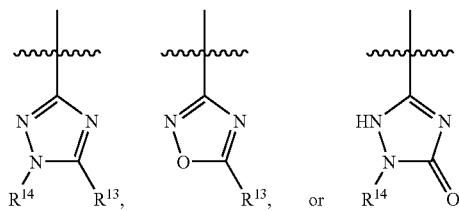

wherein $R^{13}$ is H, —$C_{1-4}$ alkyl, —$CH_2CO_2CH_3$, or —$CH_2CO_2H$; and $R^{14}$ is —$C_{6-10}$ aryl, —$C_{1-6}$ alkyl, —$C_{1-3}$ alkyl-OH, or —$C_{1-3}$alkylCO$_2$H;

with the proviso that when $R^1$ is $C_{6-10}$ aryl, wherein $C_{6-10}$ aryl is phenyl, substituted with carboxy at the 2 position, Y is not hydrogen;

with the proviso that when $R^2$ is $C_{1-6}$ alkyl substituted with at least one P(O)(OCH$_3$)$_2$ substituent, $R^1$ is optionally substituted $C_{6-10}$ aryl;

with the proviso that when $R^2$ is $C_{1-6}$ alkyl substituted with at least one $C_{1-6}$ alkoxycarbonyl substituent, $R^1$ is optionally substituted $C_{6-10}$ aryl;

with the proviso that when Y is unsubstituted phenyl, and $R^1$ is ethyl, $R^2$ is not 4-fluoro-3-trifluoromethyphenylmethyl;

with the proviso that when $R^2$ is $C_{1-6}$ alkyl substituted with an unsubstituted heterocycle comprising at least one nitrogen heteroatom, the point of attachment to the pendant group is through a nitrogen heteroatom;

and enantiomers, diastereomers, racemates, and pharmaceutically acceptable salts thereof.

As used herein, with reference to substituents, the term "independently" means that when more than substituent is possible, the substituents may be the same or different from each other.

As used herein, unless otherwise noted, the term "alkyl" whether used alone or as part of a substituent group, refers to straight and branched carbon chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)$_2$amino- the $C_{1-6}$alkyl groups of the dialkylamino may be the same or different.

As used herein, unless otherwise noted, the term "alkoxy" refers to an —O-alkyl group, wherein the term "alkyl" is as defined above.

As used herein, unless otherwise noted, the terms "alkenyl" and "alkynyl" refer to straight and branched carbon chains having 2 or more carbon atoms, wherein an alkenyl chain contains at least one double bond and an alkynyl chain contains at least one triple bond.

As used herein, unless otherwise noted, the term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

As used herein, unless otherwise noted, the term "heterocycle" refers to a nonaromatic monocyclic or bicyclic ring system having 3 to 10 ring members and which contains carbon atoms and from 1 to 4 heteroatoms independently selected from the group consisting of N, O, and S. Included within the term heterocycle is a nonaromatic cyclic ring of 5 to 7 members in which 1 to 2 members are nitrogen, or a nonaromatic cyclic ring of 5 to 7 members in which zero, one or two members are nitrogen and up to two members are oxygen or sulfur and at least one member must be either nitrogen, oxygen or sulfur; wherein, optionally, the ring contains zero to one unsaturated bonds, and, optionally, when the ring is of 6 or 7 members, it contains up to two unsaturated bonds. The carbon atom ring members that form a heterocycle ring may be fully saturated or partially saturated. The term "heterocycle" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

As used herein, unless otherwise noted, the term "benzofused heterocycle" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. The benzo-fused heterocycle ring is attached to its pendant group at a carbon atom of the benzene ring.

As used herein, unless otherwise noted, the term "aryl" refers to an unsaturated, aromatic monocyclic or bicyclic ring of 6 to 10 carbon members. Examples of aryl rings include phenyl and naphthalenyl.

As used herein, unless otherwise noted, the term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to three additional nitrogens. In the case of 6 membered rings, the heteroaryl ring preferably contains from one to three nitrogen atoms. For the case wherein the 6 membered ring has three nitrogens, at most two nitrogen atoms are adjacent. When a heteroaryl is bicyclic, at least one heteroatom is present in each ring. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl and pyrazinyl. Unless otherwise noted, the heteroaryl is attached to its pendant group at any heteroatom or carbon atom that results in a stable structure.

As used herein, unless otherwise noted, the term "benzo fused heteroaryl" refers to a 5 to 6 membered monocyclic heteroaryl ring fused to a benzene ring. The heteroaryl ring contains carbon atoms and from 1 to 4 heteroatoms independently selected from the group consisting of N, O, and S. Examples of heteroaryl groups with the optionally fused benzene rings include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolinyl, isoquinolinyl and quinazolinyl. Unless otherwise noted, the benzo-fused heteroaryl is attached to its pendant group at any heteroatom or carbon atom that results in a stable structure.

The term "halogen" or "halo" refers to fluorine, chlorine, bromine and iodine.

The term "formyl" refers to the group —C(=O)H.

As used herein, unless otherwise noted, the term "alkylsulfonyl," refers to the group —S(O)$_2$—R' where R' is an alkyl group as previously defined.

As used herein, unless otherwise noted, the term "alkylsulfanyl," refers to the group —SR' where R' is an alkyl group as previously defined.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

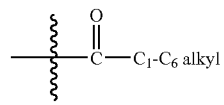

As used herein, the term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of formula (I) can be selected by one of ordinary skill in the art to provide compounds that are chemically stable and that can be readily synthesized by techniques known in the art as well as those methods set forth herein.

The term "subject" as used herein, refers to an animal, preferably a mammal, most preferably a human, who has been the object of treatment, observation or experiment.

The term "therapeutically effective amount" as used herein, refers to an amount of an active compound or pharmaceutical agent that elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

As used herein, the term "composition" is intended to encompass a product comprising the specified ingredients in therapeutically effective amounts, as well as any product that results, directly or indirectly, from combinations of the specified ingredients in the specified amounts.

For the purposes of the present invention, the term "antagonist" is used to refer to a compound capable of producing, depending on the circumstance, a functional antagonism of an ion channel, including but not limited to competitive antagonists, non-competitive antagonists, desensitizing agonists, and partial agonists.

For the purposes of the present invention, the term "inflammatory hypersensitivity" is used to refer to a condition that is characterized by one or more hallmarks of inflammation, including edema, erythema, hyperthermia and pain, and/or by an exaggerated physiologic or pathophysiologic response to one or more than one type of stimulation, including thermal, mechanical and/or chemical stimulation.

For purposes of the present invention, the term "TRPM8-modulated" is used to refer to the condition of being affected by the modulation of the TRPM8 receptor, including but not limited to, the state of being mediated by the TRPM8 receptor.

Compounds of the present invention include those wherein:
a) A is $CR^5$;
b) A is N; with the proviso that A is not N when G is $S(O_2)$;
c) B is $CR^6$;
d) B is N; with the proviso that B is not N when G is $S(O_2)$;
e) A is $CR^5$ and B is $CR^6$;
f) A is $CR^5$ and B is CH;
g) A is N and B is $CR^6$; with the proviso that A is not N when G is $S(O_2)$;
h) A is N and B is CH; with the proviso that A is not N when G is $S(O_2)$;
i) B is N and A is $CR^5$; with the proviso that B is not N when G is $S(O_2)$;
j) G is S;
k) G is $S(O_2)$; and A and B are $C(R^5)$ and $C(R^6)$, respectively;
l) Y is H;
m) Y is isopropenyl;
n) Y is $C_{1-6}$ alkylcarbonyl optionally substituted with 1 chloro substituent or 1 to 3 fluoro substituents;
o) Y is $C_{3-6}$ cycloalkylcarbonyl;
p) Y is phenylcarbonyl optionally substituted with one to three substituents independently selected from $C_{1-4}$ alkyl, fluoro, or chloro;
q) Y is phenylcarbonyl substituted with trifluoromethyl and optionally one additional substituent selected from trifluoromethyl, chloro, fluoro, or $C_{1-4}$ alkyl;
r) Y is heteroaryl optionally substituted with one to two substituents independently selected from chloro, fluoro, bromo, trifluoromethyl, $C_{1-4}$ alkoxy, hydroxy, $C_{1-4}$ alkyl, $C_{1-3}$ alkoxycarbonyl, $C_{1-3}$ alkylthio, cyano, amino, $C_{1-3}$ alkylamino, or di($C_{1-3}$)alkylamino;
s) Y is benzo-fused heteroaryl optionally substituted with one to two substituents independently selected from chloro, fluoro, bromo, trifluoromethyl, $C_{1-4}$ alkyl, $C_{1-4}$ alkoxy, hydroxy, $C_{1-4}$ alkoxycarbonyl, $C_{1-3}$ alkylthio, cyano, amino, $C_{1-3}$ alkylamino, or di($C_{1-3}$)alkylamino;
t) Y is bromo;
u) Y is chloro;
v) Y is fluoro;
w) Y is iodo;
x) Y is cyano;
y) Y is formyl;
z) Y is $C_{1-6}$ alkyl optionally substituted with 1 to 3 substituents independently selected from hydroxy, fluoro, or chloro;
aa) Y is $C(OH)(C_{1-3}$ alkyl$)_2$;
bb) Y is $C_{3-6}$ cycloalkyl;
cc) Y is $C_{1-2}$ alkyl substituted with 1 substituent independently selected from $C_{1-4}$ alkoxycarbonyl, cyano, $C_{1-3}$ alkylthio, $C_{1-4}$ alkoxy, or $NR^7R^8$ wherein $R^7$ is hydrogen, $C_{1-4}$ alkyl, $C_{1-3}$ alkylcarbonyl, or $C_{1-3}$ alkylsulfonyl and $R^8$ is hydrogen or $C_{1-4}$ alkyl; or $R^7$ and $R^8$ are taken together with the nitrogen atom to which they are attached to form a 5 or 6 membered ring optionally containing one additional heteroatom selected from nitrogen, oxygen, or sulfur;
dd) Y is $C_{1-4}$ alkoxycarbonyl;
ee) Y is $C_{1-3}$ alkoxy;
ff) Y is hydroxy;
gg) Y is $C_{6-10}$ aryl optionally with one to three substituents independently selected from chloro, fluoro, bromo, $C_{1-4}$ alkoxy, hydroxy, $C_{1-3}$ alkoxycarbonyl, $C_{1-3}$ alkylthio, cyano, amino, $C_{1-2}$ alkylamino, di($C_{1-2}$)alkylamino, or $C_{1-6}$ alkyl optionally substituted with one to three halogen substituents; with the proviso that not more than two of the substituents are selected from the group consisting of $C_{1-3}$ alkoxycarbonyl, $C_{1-3}$ alkylthio, cyano, amino, $C_{1-2}$ alkylamino, di($C_{1-2}$)alkylamino, and $C_{1-6}$ alkyl substituted with one to three halogen substituents;
hh) Y is $NR^9R^{10}$ wherein $R^9$ is hydrogen, $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; and wherein said 5 or 6 membered ring is optionally substituted with a $C_{1-4}$ alkyl substituent; with the proviso that when G is S and $R^{10}$ is hydrogen, $R^9$ is other than hydrogen and $C_{1-4}$ alkyl;
ii) Y is aminocarbonyl;
ii) Y is methylaminocarbonyl;
kk) Y is dimethylaminocarbonyl;
ll) Y is arylhydroxy($C_{1-3}$)alkyl;
mm) Y is hydrogen; isopropenyl; pyrimidinyl; thienyl; bromo; chloro; fluoro; iodo; cyano; formyl; aminocarbonyl; methylaminocarbonyl; dimethylaminocarbonyl; $C_{1-6}$ alkylcarbonyl; $C_{3-6}$ cycloalkyl; $C_{1-3}$ alkoxy; $C_{1-2}$ alkyl optionally substituted with 1 to 3 groups independently selected from hydroxy, $C_{1-4}$ alkoxy, fluoro, chloro, or $NR^7R^8$ wherein $R^7$ is hydrogen, $C_{1-4}$ alkyl, $C_{1-3}$ carbonyl, or $C_{1-3}$ alkylsulfonyl and $R^8$ is hydrogen or $C_{1-4}$ alkyl or $R^7$ and $R^8$ are taken together with the nitrogen atom to which they are attached to form a 5 or 6 membered ring optionally containing one additional heteroatom selected from nitrogen, oxygen, or sulfur; $NR^9R^{10}$ wherein $R^9$ is $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; and wherein said 5 or 6 membered ring is optionally substituted with a $C_{1-4}$ alkyl substituent; with the proviso that when G is S and $R^{10}$ is hydrogen, $R^9$ is other than hydrogen and $C_{1-4}$ alkyl; or $C_{6-10}$ aryl optionally substituted with 1 to three groups independently selected from chloro, fluoro, or bromo; or Y is methylamino or dimethylamino when G is $S(O)_2$;
nn) Y is hydrogen, isopropenyl, formyl, methyl, isopropyl, trifluoromethyl, methoxy, chloro, acetyl, hydroxymethyl, 1-hydroxyethyl, 1-methoxyethyl, 1-hydroxy-1-methyl-ethyl, methylamino-methyl, dimethylaminomethyl, n-propylamino-methyl, pyrrolidin-1-ylmethyl, 4-methyl-piperazin-1-yl, piperazin-1-yl; cyclopropyl, cyclobutyl, cyclopentyl, aminocarbonyl, methylaminocarbonyl, dimethylaminocarbonyl, methylcarbonyl, methanesulfonylamino, bromo, cyano, pyrimidin-5-yl, thien-3-yl, 2-fluorophenyl, or 4-fluorophenyl; or Y is methylamino or dimethylamino when G is $S(O)_2$;

oo) Y is hydrogen, methyl, isopropyl, isopropenyl, trifluoromethyl, methoxy, chloro, acetyl, hydroxymethyl, 1-hydroxyethyl, 1-methoxyethyl, 1-hydroxy-1-methylethyl, methylamino-methyl, dimethylamino-methyl, cyclopropyl, cyclobutyl, cyclopentyl, aminocarbonyl, methylaminocarbonyl, dimethylaminocarbonyl, methylcarbonyl, or bromo; or Y is dimethylamino when G is $SO_2$;

pp) $R^1$ is $C_{6-10}$ aryl, wherein when $C_{6-10}$ aryl is phenyl, substituted with carboxy at the 2 position, Y is chloro;

qq) $R^1$ is $CF_3$;

rr) $R^1$ is $C_{1-6}$ alkyl optionally substituted with 1 substituent selected from $C_{1-3}$ alkylsulfonyl, $C_{1-4}$ alkoxycarbonyl, formyl, hydroxy, carboxy, trifluoromethyl, $C_{1-4}$ alkoxy, $C_{1-3}$ alkylthio, bromo, cyano, $R^{11}$, or $R^{12}$;

ss) $R^1$ is aryl($C_{1-2}$ alkyl) wherein the ring of the aryl group is optionally substituted with 1 to 3 substituents independently selected from $C_{1-4}$ alkyl, fluoro, chloro, trifluoromethyl, hydroxy, $C_{1-4}$ alkoxy, $C_{1-4}$ alkoxycarbonyl, or carboxy; with the proviso that not more than two of the substituents are selected from the group consisting of trifluoromethyl, $C_{1-4}$ alkoxycarbonyl, and carboxy;

tt) $R^1$ is heteroaryl($C_{1-6}$ alkyl) wherein the heteroaryl group is bound through a nitrogen heteroatom and is selected from imidazolyl, triazolyl, or tetrazolyl; wherein the imidazolyl group is optionally substituted with 1 substituent selected from $C_{1-4}$ alkyl, trifluoromethyl, hydroxy, $C_{1-4}$ alkoxy, $C_{1-4}$ alkoxycarbonyl, carboxy, aminomethyl, methylamino-methyl, or dimethylamino-methyl; and imidazolyl is optionally substituted with one additional substitutent selected from fluoro and chloro;

uu) $R^1$ is unsubstituted $C_{3-8}$ cycloalkyl or cyclohexyl substituted at the 4-position with one substituent selected from the group consisting of cyano, $C_{1-4}$ alkoxycarbonyl, carboxy, aminocarbonyl, $C_{1-3}$ alkylaminocarbonyl, di($C_{1-3}$ alkyl)aminocarbonyl, aminomethyl, methylamino-methyl, dimethylamino-methyl, $R^{11}$, and $R^{12}$;

vv) $R^1$ is benzo-fused $C_{5-6}$cycloalkyl attached at the benzo portion of the ring system, and wherein the $C_{5-6}$cycloalkyl portion of benzo-fused $C_{5-6}$cycloalkyl is optionally substituted with amino, methylamino, or dimethylamino;

ww) phenyl substituted with 3- or 4-imidazolyl, wherein the point of attachment of the imidazolyl is through a nitrogen heteroatom; and wherein the imidazolyl is optionally independently substituted with one to two substituents selected from the group consisting of $C_{1-3}$ alkyl, 2-cyano, chloro, bromo, amino-$C_{1-2}$ alkyl, ($C_{1-2}$ alkyl)amino-$C_{1-2}$ alkyl, and di($C_{1-2}$ alkyl)amino-$C_{1-2}$ alkyl; wherein di($C_{1-3}$ alkyl) is optionally taken together with the nitrogen atom to which it is attached to form a 5 or 6 membered ring optionally containing one additional heteroatom selected from nitrogen, oxygen, or sulfur; and wherein the ring formed by di($C_{1-3}$ alkyl) amino is optionally substituted with $C_{1-3}$alkyl; with the proviso that not more than one of the substituents is amino-$C_{1-2}$ alkyl, ($C_{1-2}$ alkyl)amino-$C_{1-2}$ alkyl, or di($C_{1-2}$ alkyl)amino-$C_{1-2}$ alkyl;

xx) $R^1$ is $C_{6-10}$ aryl optionally substituted with one to three substituents independently selected from $C_{1-4}$ alkyl optionally substituted with one to three chloro or fluoro substituents, chloro, fluoro, bromo, $C_{1-4}$ alkoxy, phenyloxy, heteroaryloxy wherein the heteroaryl ring is a 6 membered ring containing carbon ring members and 1 or 2 nitrogen heteroatom ring members, $C_{1-3}$ alkylsulfonyl, $C_{1-4}$ alkoxycarbonyl, $C_{1-3}$ alkylthio, hydroxy, carboxy, cyano, heteroaryl, $C_{1-3}$ alkylcarbonyl, aminocarbonyl, $C_{1-3}$ alkylaminocarbonyl, di($C_{1-3}$) alkylaminocarbonyl, $P(O)(OC_{1-3}$ alkyl$)_2$, $P(O)(OH)_2$, $SO_3H$, $C(O)NHOH$, or $SO_2NH_2$; with the proviso that not more than two of the substituents are selected from the group consisting of phenyloxy, heteroaryloxy, $C_{1-3}$ alkylsulfonyl, $C_{1-4}$ alkoxycarbonyl, $C_{1-3}$ alkylthio, hydroxy, carboxy, cyano, heteroaryl, $C_{1-3}$ alkylcarbonyl, aminocarbonyl, $C_{1-3}$ alkylaminocarbonyl, di($C_{1-3}$)alkylaminocarbonyl, and $P(O)(OC_{1-3}$ alkyl$)_2$ and not more than one of the substituents is selected from the group consisting of —$P(O)(OH)_2$, —$SO_3H$, —$C(O)NHOH$, and —$SO_2NH_2$;

yy) $R^1$ is phenyl optionally substituted with one to three substituents independently selected from $C_{1-4}$ alkyl optionally substituted with one to three chloro or fluoro substituents or one hydroxy substituent, chloro, fluoro, bromo, $C_{1-4}$ alkoxy, trifluoromethoxy, 3- or 4-phenyloxy, 3- or 4-heteroaryloxy wherein the heteroaryl ring is a 6 membered ring containing carbon ring members and 1 or 2 nitrogen heteroatom ring members, $C_{1-3}$ alkylsulfonyl, $C_{1-4}$ alkoxycarbonyl, $C_{1-3}$ alkylthio, hydroxy, carboxy, cyano, nitro, 3- or 4-heteroaryl, $C_{1-3}$ alkylcarbonyl, aminocarbonyl, $C_{1-3}$ alkylaminocarbonyl, di($C_{1-3}$) alkylaminocarbonyl, $C_{1-3}$ alkylsulfonylaminocarbonyl, di($C_{1-3}$)alkylaminosulfonyl, $P(O)(OC_{1-3}$ alkyl$)_2$, $P(O)(OH)_2$, $SO_3H$, $C(O)NHOH$, $C(=N)NH_2$, $C(=NOH)NH_2$, $C(=N(methylcarbonyloxy))NH_2$, or $SO_2NH_2$; with the proviso that not more than two of the substituents are selected from the group consisting of trifluoromethoxy, 3- or 4-phenyloxy, 3- or 4-heteroaryloxy, $C_{1-3}$ alkylsulfonyl, $C_{1-4}$ alkoxycarbonyl, $C_{1-3}$ alkylthio, carboxy, cyano, 3- or 4-heteroaryl wherein the heteroaryl is other than imidazolyl, $C_{1-3}$ alkylcarbonyl, aminocarbonyl, $C_{1-3}$ alkylaminocarbonyl, di($C_{1-3}$)alkylaminocarbonyl, $C_{1-3}$ alkylsulfonylaminocarbonyl, and $P(O)(OC_{1-3}$ alkyl$)_2$ and not more than one of the substituents is selected from the group consisting of —$P(O)(OH)_2$, —$SO_3H$, carboxy, $C(O)NHOH$, $C(=N)NH_2$, $C(=NOH)NH_2$, $C(=N(C_{1-3}alkylcarbonyloxy))NH_2$, and —$SO_2NH_2$; wherein the phenyloxy is optionally substituted with one to two substituents independently selected from the group consisting of methyl and fluoro; and wherein the heteroaryl substituent is optionally independently substituted with one to two substituents selected from the group consisting of $C_{1-4}$ alkyl, trifluoromethyl, trifluoromethoxy, cyano, amino, methylamino, dimethylamino, chloro, bromo, carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl) amino-$C_{1-2}$ alkyl, and di($C_{1-2}$ alkyl)amino-$C_{1-2}$ alkyl; with the proviso that not more than one of the substituents is selected from the group consisting of carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl) amino-$C_{1-2}$ alkyl, and di($C_{1-2}$ alkyl)amino-$C_{1-2}$ alkyl;

zz) $R^1$ is naphthyl optionally substituted with one substituent selected from the group consisting of hydroxy, chloro, fluoro, bromo, $C_{1-4}$ alkoxycarbonyl, and carboxy;

aaa) $R^1$ is $C_{6-10}$ aryl substituted with phenyl optionally substituted with one to two substituents selected from chloro, fluoro, $C_{1-4}$ alkoxy, $C_{1-4}$ alkoxycarbonyl, carboxy, hydroxy, amino, di($C_{1-3}$)alkylamino, $C_{1-3}$ alkylamino, or $C_{1-3}$ alkyl;

bbb) $R^1$ is a ring selected from indanyl or tetralinyl wherein said ring is attached via an unsaturated carbon atom and the saturated portion of the ring is substituted with amino, ($C_{1-3}$ alkyl)amino, or di($C_{1-3}$ alkyl)amino;

ccc) $R^1$ is phenyl substituted with $R^{11}$ or $R^{12}$ at the 3 or 4 position; and phenyl is optionally substituted with one additional substituent selected from fluoro, chloro, or $C_{1-3}$ alkyl;

ddd) $R^1$ is pyridin-3-yl substituted at a carbon atom other than that adjacent to the carbon bearing $S(O)_2$ with a substituent selected from N-imidazolyl, oxadiazolyl, thiazolyl, $R^{11}$, or $R^{12}$; wherein pyridin-3-yl is optionally substituted with one additional substituent selected from fluoro, chloro, or $C_{1-3}$ alkyl; and further, wherein the N-imidazolyl group is optionally substituted with one to two substituents, and the oxadiazolyl and thiazolyl groups are optionally substituted one substituent, said substituent(s) independently selected from the group consisting of $C_{1-4}$ alkyl, trifluoromethyl, cyano, amino, methylamino, dimethylamino, chloro, bromo, carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl)amino-$C_{1-2}$ alkyl; with the proviso that not more than one of the substituents is selected from the group consisting of carboxy, $C_{1-2}$ alkoxycarbonyl, $C_{1-2}$ alkoxycarbonylmethyl, carboxymethyl, trifluoromethyl, cyano, amino-$C_{1-2}$ alkyl, ($C_{1-2}$ alkyl)amino-$C_{1-2}$ alkyl, and di($C_{1-2}$ alkyl)amino-$C_{1-2}$ alkyl;

eee) $R^1$ is imidazolyl substituted with $R^{11}$ or $R^{12}$; and imidazolyl is optionally substituted at a nitrogen atom with $C_{1-4}$ alkyl;

fff) $R^1$ is a ring selected from phenyl or pyridin-3-yl, wherein said ring is substituted with $NR^{15}R^{16}$; wherein $R^{15}$ is hydrogen, $C_{1-4}$ alkyl, $C_{1-4}$ alkylcarbonyl, trifluoromethylcarbonyl, trifluoromethylsulfonyl, $C_{3-6}$ cycloalkylsulfonyl, or $C_{1-3}$ alkylsulfonyl; and $R^{16}$ is hydrogen or $C_{1-4}$ alkyl; or $R^{15}$ and $R^{16}$ are taken together with the nitrogen atom to which they are attached to form a 5 or 6 membered ring optionally containing one additional heteroatom selected from nitrogen, oxygen, or sulfur optionally substituted with one or two oxo substituents; and wherein the ring formed by $NR^{15}R^{16}$ is optionally substituted with $C_{1-3}$ alkyl, $C_{1-2}$ alkoxycarbonyl, or carboxy; and wherein said phenyl is optionally substituted with one to two additional substituents independently selected from the group consisting of $C_{1-4}$ alkyl, $C_{1-4}$ alkoxy, hydroxy, fluoro, chloro, and bromo;

ggg) $R^1$ is phenyl substituted with $C(O)NR^{17}R^{18}$ wherein $R^{17}$ is hydrogen, $C_{1-4}$ alkyl, $C_{1-4}$ alkylcarbonyl, pyrrolidin-3-yl, or $C_{1-3}$ alkylsulfonyl; and $R^{18}$ is hydrogen or $C_{1-4}$ alkyl; or $R^{17}$ and $R^{18}$ are taken together with the nitrogen atom to which they are attached to form a 5 or 6 membered ring optionally containing one additional heteroatom selected from nitrogen, oxygen, or sulfur; and wherein said ring is optionally substituted with $C_{1-3}$ alkyl;

hhh) $R^1$ is phenyl substituted with 4 or 5 fluoro substituents;

iii) $R^1$ is phenyl substituted at the 4-position with -Q-C($R^xR^y$)—$(CH_2)_{0-1}CO_2H$ wherein Q is a bond or O; and wherein $R^x$ and $R^y$ are independently hydrogen or methyl; or $R^x$ and $R^y$ are taken together with the carbon atom to which they are both attached to form a cyclopropyl ring;

jjj) $R^1$ is heteroaryl optionally substituted with one to three substituents independently selected from $C_{1-4}$ alkyl, chloro, fluoro, bromo, trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, or di($C_{1-3}$)alkylamino; with the proviso that not more than two of the substituents are selected from the group consisting of trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, and di($C_{1-3}$)alkylamino;

kkk) $R^1$ is benzo-fused heteroaryl optionally substituted with one to three substituents independently selected from $C_{1-4}$ alkyl, chloro, fluoro, bromo, trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, or di($C_{1-3}$)alkylamino; with the proviso that not more than two of the substituents are selected from the group consisting of trifluoromethyl, $C_{1-4}$ alkoxy, oxo, hydroxy, $C_{1-4}$ alkoxycarbonyl, $C_{1-3}$ alkylthio, cyano, carboxy, amino, $C_{1-3}$ alkylamino, and di($C_{1-3}$)alkylamino;

lll) $R^1$ is benzo-fused heterocycle optionally substituted with one to two substituents independently selected from trifluoromethyl, $C_{1-3}$ alkylcarbonyl, $C_{1-4}$ alkyl, $C_{1-4}$ alkoxy, trifluoromethylcarbonyl, fluoro, chloro, bromo, hydroxy, oxo, carboxy, or $C_{1-4}$ alkoxycarbonyl; such that when the benzo-fused heterocycle is substituted on the heterocyclic ring, the substituents on the heterocyclic ring are selected from oxo, hydroxy, $C_{1-4}$ alkyl, or trifluoromethylcarbonyl; with the proviso that not more than one substituent is trifluoromethylcarbonyl; and with the proviso that when the benzo-fused heterocycle is substituted with trifluoromethylcarbonyl, at least one of the ring members of the heterocycle is a nitrogen heteroatom and the point of attachment to the trifluoromethylcarbonyl substituent is through the nitrogen heteroatom;

mmm) $R^1$ is amino;

nnn) $R^1$ is $C_{1-6}$ alkylamino;

ooo) $R^1$ is di($C_{1-6}$ alkyl)amino;

ppp) $R^1$ is $C_{1-6}$ alkyl optionally substituted with 1 substituent selected from the group consisting of $C_{1-3}$ alkylsulfonyl, $C_{1-3}$ alkoxycarbonyl, hydroxy, carboxy, formyl, trifluoromethyl, bromo, and a 5 to 6 membered heteroaryl optionally substituted with $C_{1-4}$ alkyl, aminomethyl, methylamino-methyl, or dimethylamino-methyl;

qqq) $R^1$ is methyl, ethyl, propyl, butyl, phenylmethyl, carboxymethyl, methoxycarbonylmethyl, 2-(methoxycarbonyl)ethyl, 2,2,2-trifluoroethyl, 2-bromoethyl, 2-hydroxyethyl, 2-formylethyl, 2-carboxyethyl, 3-bromopropyl, 3-hydroxypropyl, 3-(methoxycarbonyl)propyl, 3-(imidazol-1-yl)propyl, 4-(imidazol-1-yl)butyl, 3-hydroxy-3-methyl-butyl, 4-bromobutyl, 4-hydroxybutyl, 4-(4-methyl-piperazin-1-yl)butyl, 4-hydroxy-4-methylpentyl, or methanesulfonylmethyl;

rrr) $R^1$ is phenyl optionally substituted with one to three substituents independently selected from hydroxy, fluoro, chloro, bromo, cyano, nitro, 3- or 4-heteroaryl, 3- or 4-phenyloxy, 3- or 4-heteroaryloxy, $C_{1-3}$ alkylsulfonylaminocarbonyl, di($C_{1-3}$)alkylaminosulfonyl, $C(=NOH)NH_2$, $C(O)NHOH$, $C(C=N(methylcarbonyloxy))NH_2$, aminocarbonyl, $C_{1-4}$ alkyl substituted with one to three chloro or fluoro substitituents or one hydroxy substituent, $C_{1-3}$ alkylcarbonyl, $C_{1-3}$ alkoxycarbonyl, $C_{1-3}$ alkoxy, or carboxy; wherein the phenyloxy is optionally substituted with one to two substituents independently selected from the group consisting of methyl and fluoro;

sss) $R^1$ is phenyl optionally substituted with one to three substituents independently selected from $C_{1-4}$ alkyl optionally substituted with one hydroxy substituent, hydroxy, fluoro, bromo, cyano, nitro, thiadazolyl, pyrazol-1-yl, 2-methyl-pyrimidin-4-yl, oxazol-5-yl, 1H-tetrazol-5-yl, 2H-tetrazol-5-yl, 1H-tetrazol-5-yl, 3- or 4-phenyloxy, 3- or 4-pyridinyloxy, methanesulfonylaminocarbonyl, di(methyl)aminosulfonyl, C(=NOH)NH$_2$, C(O)NHOH, C(C=N(methylcarbonyloxy))NH$_2$, trifluoromethyl, methoxycarbonyl, aminocarbonyl, methoxy, or carboxy; wherein the phenyloxy is optionally substituted with a fluoro substituent;

ttt) $R^1$ is phenyl substituted with $R^{11}$ or $R^{12}$ at the 3 or 4 position; and optionally one additional substituent selected from fluoro, chloro, or $C_{1-3}$ alkyl;

uuu) $R^1$ is phenyl, 3-cyanophenyl, 4-cyanophenyl, 2,5-dibromophenyl, 4-bromophenyl, 4-nitrophenyl, 3-hydroxyphenyl, 4-hydroxyphenyl, 4-(1-hydroxy-1-methyl-ethyl)phenyl, phenyl, 4-hydroxy-3-fluorophenyl, 4-[1,2,3]thiadiazol-4-ylphenyl, 4-(5-oxo-4,5-dihydro-[1,2,4]thiadiazol-3-yl)phenyl, 4-(5-oxo-4,5-dihydro-[1,2,4]oxadiazol-3-yl)phenyl, 4-(2-oxo-2,3-dihydro-2λ4-[1,2,3,5]oxathiadiazol-4-yl)phenyl, 4-(5-oxo-4,5-dihydro-1H-[1,2,4]triazol-3-yl)phenyl, 4-(1-methyl-5-oxo-4,5-dihydro-1H-[1,2,4]triazol-3-yl)-phenyl, 3-(5-methyl-[1,3,4]oxadiazol-2-yl)phenyl, 3-phenoxyphenyl, 3-fluoro-4-(phenylmethoxy)phenyl, 3-fluoro-4-(4-fluorophenylmethoxy)phenyl, 4-pyridin-3-yloxyphenyl, 4-pyridin-4-yloxyphenyl, 3-fluorophenyl, 2-fluorophenyl, 4-perfluoromethylphenyl, 4-methoxycarbonylphenyl, 4-methylcarbonylphenyl, 3-methoxycarbonylphenyl, 2-methoxycarbonylphenyl, 3-dimethylaminosulfonylphenyl, 4-(methanesulfonylaminocarbonyl)phenyl, 4-fluorophenyl, 3,4-difluorophenyl, 4-methoxyphenyl, 4-aminocarbonyl, 4-carboxyphenyl, 3-carboxyphenyl, 2-carboxyphenyl, 4-(2-dimethylaminomethyl-imidazol-1-yl)phenyl, 4-(N-hydroxy-acetamidinyl)phenyl, 4-hydroxyaminocarbonylphenyl, 4-(N-(methylcarbonyloxy)acetamidinyl)phenyl, 4-(pyrazol-1-yl)phenyl, 3-(2-methyl-pyrimidin-4-yl)phenyl, 4-(oxazol-5-yl)phenyl, 3-(1H-tetrazol-5-yl)phenyl, 3-(2H-tetrazol-5-yl)phenyl, 4-(1H-tetrazol-5-yl)phenyl, or 3-methoxyphenyl;

vvv) $R^1$ is 2-aminoindan-5-yl;

www) $R^1$ is pyridin-3-yl substituted with 5-oxo-4,5-dihydro-[1,2,4]oxadiazol-3-yl or 1H-tetrazol-5-yl;

xxx) $R^1$ is a ring selected from phenyl or pyridin-3-yl wherein said ring is substituted with NR$^{15}$R$^{16}$; wherein R$^{15}$ is hydrogen, $C_{1-4}$ alkyl, methylcarbonyl, trifluoromethylcarbonyl, cyclopropylsulfonyl, or $C_{1-3}$ alkylsulfonyl; and R$^{16}$ is hydrogen or $C_{1-4}$ alkyl; or R$^{15}$ and R$^{16}$ are taken together with the nitrogen atom to which they are attached to form morpholin-4-yl, piperazin-1-yl, piperadin-1-yl, thiomorpholin-4-yl, or pyrrolidin-1-yl; and wherein the ring formed by NR$^{15}$R$^{16}$ is optionally substituted with $C_{1-3}$alkyl; and wherein said phenyl is optionally substituted with one to two additional substituents independently selected from the group consisting of methoxy, hydroxy, chloro, and bromo;

yyy) $R^1$ is phenyl substituted with C(O)NR$^{17}$R$^{18}$ wherein R$^{17}$ is hydrogen, $C_{1-4}$ alkyl, pyrrolidin-3-yl, or $C_{1-3}$ alkylsulfonyl; and R$^{18}$ is hydrogen; or R$^{17}$ and R$^{18}$ are taken together with the nitrogen atom to which they are attached to form 4-methyl-piperazin-1-yl;

zzz) $R^1$ is pyridinyl, quinolinyl, quinoxalinyl, imidazo[2,1-b]thiazol-5-yl, thienyl, imidazolyl, benzothiophenyl, benzothiazolyl, benzooxazolyl, isoxazolyl, isoquinolinyl, benzooxazinyl, thiadiazolyl, furanyl, thiazolyl, pyrazolyl, imidazolyl, benzoxadiazolyl, benzothiadiazolyl, benzimidazolyl, pyrimidinyl, or furanyl, any of which can be optionally substituted with one to three substituents independently selected from $C_{1-3}$ alkyl, $C_{1-3}$ alkoxy, hydroxy, oxo, chloro, bromo, trifluoromethyl, $C_{1-3}$ alkoxycarbonyl, $C_{1-3}$ alkylthio, di($C_{1-3}$)alkylamino, or heteroaryl selected from the group consisting of 1H-tetrazol-5-yl, isoxazolyl, and pyrazolyl; wherein the heteroaryl other than tetrazol-5-yl is optionally independently substituted with one to two substituents selected from the group consisting of $C_{1-3}$ alkyl, chloro, and trifluoromethyl; with the proviso that not more than two of the substituents are selected from the group consisting of hydroxy, heteroaryl, and oxo;

aaaa) $R^1$ is pyridinyl, quinolinyl, quinoxalinyl, imidazo[2,1-b]thiazol-5-yl, thienyl, imidazolyl, benzothiophenyl, benzothiazolyl, benzimidazolyl, furanyl, isoquinolinyl, thiazolyl, pyrazolyl, imidazolyl, or pyrimidinyl, any of which can be optionally substituted with one to three substituents independently selected from $C_{1-3}$ alkyl, methoxy, hydroxy, oxo, chloro, bromo, trifluoromethyl, methoxycarbonyl, carboxy, methylthio, dimethylamino, or heteroaryl selected from the group consisting of 1H-tetrazol-5-yl, isoxazolyl, and pyrazolyl; wherein the heteroaryl other than tetrazol-5-yl is optionally independently substituted with one to two substituents selected from the group consisting of $C_{1-3}$ alkyl, chloro, and trifluoromethyl; with the proviso that not more than two of the substituents are selected from the group consisting of hydroxy, heteroaryl, and oxo;

bbbb) $R^1$ is tetrahydroisoquinolinyl, dihydrobenzooxazinyl, tetrahydropyrimidinyl, or dihydrobenzooxazolyl, any of which can be optionally substituted with one to two substituents independently selected from $C_{1-4}$ alkyl, trifluoromethylcarbonyl, or oxo; with the proviso that not more than one substituent is trifluoromethylcarbonyl and the point of attachment to the trifluoromethylcarbonyl substituent is through a nitrogen heteroatom;

cccc) $R^1$ is 1-methyl-1H-imidazol-4-yl, pyridin-3-yl, 6-(1H-tetrazol-5-yl)pyridin-3-yl, 2-chloropyridin-3-yl, 6-chloropyridin-3-yl, 6-dimethylaminopyridin-3-yl, 2-dimethylaminopyridin-3-yl, 6-methoxypyridin-3-yl, 2-methoxypyridin-3-yl, 5-bromo-6-chloropyridin-3-yl, 5,6-dichloropyridin-3-yl, 6-methylthiopyridin-3-yl, 2-methylthiopyridin-3-yl, quinoxalin-5-yl, thien-2-yl, thien-3-yl, 4-carboxythien-2-yl, 5-carboxy-3-methyl-thien-2-yl, 5-(5-trifluoromethyl-isoxazol-3-yl)-thien-2-yl, 5-(2-methyl-5-trifluoromethyl-2H-pyrazol-3-yl)-thien-2-yl, 6-chloro-imidazo[2,1-b]thiazol-5-yl, benzo[b]thiophen-2-yl, quinolin-8-yl, 8-methoxyquinolin-5-yl, isoquinolin-5-yl, benzothiazol-6-yl, benzimidazol-2-yl, 1-methylbenzimidazol-2-yl, 5-chloro-1-methyl-benzimidazol-2-yl, 2-oxo-2,3-dihydro-benzooxazol-6-yl, 4-methyl-3,4-dihydro-2H-benzo[1,4]oxazin-7-yl, 2,4-dihydroxy-6-methylpyrimidin-5-yl, 2-(2,2,2-trifluoro-acetyl)-1,2,3,4-tetrahydro-isoquinolin-8-yl, 2-(2,2,2-trifluoro-acetyl)-1,2,3,4-tetrahydro-isoquinolin-7-yl, 2-methyl-1,2,3,4-tetrahydro-isoquinolin-7-yl, 1,3,5- trimethyl-1H-pyrazol-4-yl, 1-methyl-3-trifluoromethyl-1H-pyrazol-4-yl, 5-methoxycarbonylfuran-2-yl, 5-carboxyfuran-2-yl, 2,4-dimethyl-thiazol-5-yl, 1,2,3,4-tetrahydro-isoquinolin-8-yl, or 2-chloropyridin-5-yl;

dddd) $R^1$ is 1-methyl-1H-imidazol-4-yl, pyridin-3-yl, 6-(1H-tetrazol-5-yl)pyridin-3-yl, 2-chloropyridin-3-yl, 2-chloropyridin-5-yl, 6-chloropyridin-3-yl, 6-dimethylaminopyridin-3-yl, 2-dimethylaminopyridin-3-yl, 6-methoxypyridin-3-yl, 2-methoxypyridin-3-yl, 5-bromo-6-chloropyridin-3-yl, 5,6-dichloropyridin-3-yl, 6-methylthiopyridin-3-yl, quinoxalin-5-yl, thien-2-yl, thien-3-yl, 4-carboxythien-2-yl, 5-carboxy-3-methyl-thien-2-yl, 6-chloro-imidazo[2,1-b]thiazol-5-yl, benzo[b]thiophen-2-yl, quinolin-8-yl, 8-methoxyquinolin-5-yl, isoquinolin-5-yl, 2-methyl-1,2,3,4-tetrahydro-isoquinolin-7-yl, benzothiazol-6-yl, benzimidazol-2-yl, 2-oxo-2,3-dihydro-benzooxazol-6-yl, 4-methyl-3,4-dihydro-2H-benzo[1,4]oxazin-7-yl, 2,4-dihydroxy-6-methylpyrimidin-5-yl, 1,3,5-trimethyl-1H-pyrazol-4-yl, 1-methyl-3-trifluoromethyl-1H-pyrazol-4-yl, 5-methoxycarbonylfuran-2-yl, 2,4-dimethyl-thiazol-5-yl, 1,2,3,4-tetrahydro-isoquinolin-8-yl, or 2-(2,2,2-trifluoro-acetyl)-1,2,3,4-tetrahydro-isoquinolin-8-yl;

eeee) $R^1$ is thienyl optionally independently substituted with one to two substituents selected from the group consisting of methyl or carboxy; imidazolyl optionally substituted with 1 methyl substituent; pyridinyl optionally substituted with 1H-tetrazol-5-yl, dimethylamino, chloro, methoxy, or methylthio, and optionally substituted with one additional bromo or chloro substituent; furanyl optionally substituted with 1 methoxycarbonyl substituent; quinolinyl optionally substituted with 1 methoxy substituent; isoquinolinyl; benzothiophenyl; imidazo[2,1-b]thiazol-5-yl optionally substituted with 1 chloro substituent; benzothiazolyl; benzimidazol-2-yl; dihydrobenzooxazolyl optionally substituted with one oxo substituent; dihydrobenzooxazinyl optionally substituted with one substituent selected from methyl or oxo; pyrimidinyl optionally substituted with from one to three substituents independently selected from oxo or hydroxy; tetrahydroisoquinolinyl optionally substituted on a nitrogen heteroatom with a trifluoromethylcarbonyl substituent; or pyrazolyl optionally substituted with from one to three substituents selected from methyl or trifluoromethyl with the proviso that not more than 1 substituent is trifluoromethyl;

ffff) $R^1$ is amino, methylamino, or dimethylamino;

gggg) $R^2$ is $C_{1-2}$ alkyl substituted with adamantyl;

hhhh) $R^2$ is $C_{1-6}$ alkyl substituted with two $C_{6-10}$ aryl groups wherein one of said aryl groups is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl; and the other of said aryl groups is optionally substituted with 1 substituent selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl;

iiii) $R^2$ is $C_{1-6}$ alkyl substituted with one $C_{6-10}$ aryl group and optionally one additional substituent selected from hydroxy or oxo, wherein said $C_{6-10}$ aryl group is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$) alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$) alkylamino, and $C_{1-3}$ alkylcarbonyl;

jjjj) $R^2$ is $C_{1-6}$ alkyl substituted with phenyl, wherein phenyl is substituted with 4 or 5 fluoro substituents; or phenyl is substituted with methoxy and 3 to 4 fluoro substituents;

kkkk) $R^2$ is $C_{1-6}$ alkyl substituted with one heteroaryl group and optionally one additional substituent selected from oxo or hydroxy wherein said heteroaryl group is optionally substituted with one to three fluoro substituents or 1 substituent selected from chloro, bromo, trifluoromethyl, $C_{1-4}$ alkoxy, hydroxy, $C_{1-4}$ alkoxycarbonyl, $C_{1-3}$ alkylthio, cyano, or $C_{1-4}$ alkyl;

llll) $R^2$ is $C_{1-6}$ alkyl substituted with one benzo-fused heteroaryl group and optionally one additional substituent selected from oxo or hydroxy, wherein said benzo-fused heteroaryl group is optionally substituted with 1 substituent selected from chloro, fluoro, bromo, trifluoromethyl, $C_{1-4}$ alkoxy, hydroxy, $C_{1-4}$ alkoxycarbonyl, $C_{1-3}$ alkylthio, cyano, or $C_{1-4}$ alkyl;

mmmm) $R^2$ is $C_{1-6}$ alkyl substituted with one heterocycle group wherein said heterocycle group is optionally substituted with one to three substituents independently selected from $C_{1-4}$ alkyl, $C_{1-4}$ alkoxycarbonyl, oxo, or hydroxy; with the proviso that not more than two of the substituents are selected from the group consisting of oxo and hydroxy;

nnnn) $R^2$ is $C_{1-6}$ alkyl substituted with benzo[1,3]dioxol-5-yl, 2,2-difluoro-benzo[1,3]dioxol-5-yl, or 2,3-dihydro-benzo[1,4]dioxin-6-yl;

oooo) $R^2$ is $C_{2-6}$ alkyl optionally substituted with 1 to 2 substituents independently selected from cyano, trifluoromethyl, $C_{1-6}$ alkylcarbonyl, $C_{1-6}$ alkylthio, $C_{1-6}$ alkylsulfonyl, amino, $C_{1-3}$ alkylamino, di($C_{1-3}$)alkylamino, $C_2$-6 alkenyl, $C_{2-6}$ alkynyl, fluoro, $C_{1-6}$ alkoxy, $C_{1-6}$ alkoxycarbonyl, $C_{1-4}$ alkoxycarbonylamino, hydroxy, $P(O)(OC_{1-3})_2$, $C_{3-6}$ cycloalkyloxy, $C_{3-4}$ cycloalkyl, or $C_{5-8}$ cycloalkyl optionally substituted with one to three substituents independently selected from the group consisting of halogen, hydroxy, oxo and $C_{1-4}$ alkyl optionally substituted with one to three substituents independently selected from halogen or hydroxy; with the proviso that not more than one of the substituents on the $C_{1-4}$ alkyl of the $C_{1-4}$ alkyl substituted $C_{5-8}$ cycloalkyl is hydroxy, and not more than two of the substituents on the $C_{5-8}$ cycloalkyl are oxo;

pppp) $R^2$ is $C_{1-6}$ alkyl substituted with one substituent selected from cyclopropyl, cyclobutyl, cyclopentyl, or cyclohexyl;

qqqq) $R^2$ is cyclopropylmethyl, cyclobutylmethyl, cyclopentylmethyl, 2-(cyclopropyl)ethyl, or cyclohexylmethyl;

rrrr) $R^2$ is $C_{1-6}$ alkyl substituted with one substituent selected from pyrrolidinyl, imidazolidinyl, morpholinyl, tetrahydropyranyl, or piperidinyl; any of which is optionally substituted with from one to three substituents independently selected from $C_{1-4}$ alkyl, $C_{1-4}$ alkoxycarbonyl, or oxo; with the proviso that not more than two of the substituents are oxo;

ssss) $R^2$ is 2-(2-oxo-pyrrolidin-1-yl)-ethyl, (N-tert-butoxycarbonylpyrrolidinyl)methyl, (2,5-dioxo-pyrrolidin-1-yl)-ethyl, morpholin-4-yl-ethyl, tetrahydropyran-4-yl-methyl, 2-(piperidin-1-yl)ethyl, 2-(morpholin-4-yl) ethyl, (N-tert-butoxycarbonylpyrrolidinyl)methyl, 5-oxo-pyrrolidin-2-ylmethyl, 2-(morpholin-4-yl)ethyl, (N-tert-butoxycarbonylpyrrolidinyl)methyl, 2-(2-oxo-imidazolidin-1-yl)ethyl, 2-(piperidin-1-yl)ethyl, 5-oxo-pyrrolidin-2-ylmethyl, pyrrolidin-2-ylmethyl, or piperidin-4-ylmethyl;

tttt) $R^2$ is $C_{1-6}$ alkyl substituted with phenyl optionally substituted with one to three substituents independently selected from $C_{1-4}$ alkyl, trifluoromethyl, $C_{1-4}$ alkoxy optionally substituted with 1 to 3 fluoro substituents, $C_{1-3}$ alkylthio, trifluoromethylthio, $C_{1-3}$ alkoxycarbonyl, aminocarbonyl, $C_{1-3}$ alkylaminocarbonyl, di($C_{1-3}$) alkylaminocarbonyl, $C_{1-4}$ alkylsulfonyl optionally substituted with 1 to 3 fluoro substituents, chloro, fluoro, bromo, hydroxy, or nitro with the proviso that not more than two of the substituents are selected from the group consisting of trifluoromethyl, $C_{1-4}$ alkoxy substituted with 1 to 3 fluoro substituents, $C_{1-3}$ alkylthio, trifluoromethylthio, $C_{1-3}$ alkoxycarbonyl, aminocarbonyl, $C_{1-3}$ alkylaminocarbonyl, di($C_{1-3}$) alkylaminocarbonyl; $C_{1-4}$ alkylsulfonyl optionally substituted with 1 to 3 fluoro substituents, and nitro;

uuuu) $R^2$ is $C_{1-6}$ alkyl substituted with phenyl optionally substituted with one to two substituents independently selected from methoxy, fluoro, nitro, trifluoromethoxy, trifluoromethyl, methylthio, trifluoromethylthio, methoxycarbonyl, methylsulfonyl, trifluoromethylsulfonyl, methyl, chloro, bromo, or hydroxy;

vvvv) $R^2$ is 3-methoxyphenylmethyl, 4-methoxyphenylmethyl, 2-fluorophenylmethyl, 3-fluorophenylmethyl, 4-fluorophenylmethyl, 3,4,5-trifluorophenylmethyl, 3,4-difluorophenylmethyl, 2-nitrophenylmethyl, 2-trifluoromethoxyphenylmethyl, 3-trifluoromethoxyphenylmethyl, 4-trifluoromethoxyphenylmethyl, 4-difluoromethoxyphenylmethyl, 4-chloro-2-fluoro-5-methoxyphenylmethyl, phenylmethyl, 4-fluoro-3-trifluoromethylphenylmethyl, 4-fluoro-2-trifluoromethylphenylmethyl, 2-methylphenylmethyl, 3-methylphenylmethyl, 2,5-dichlorophenylmethyl, 3-chloro-4-fluorophenylmethyl, 4-chloro-3-fluorophenylmethyl, 2-(phenyl)ethyl, 4-chlorophenylmethyl, 2-methoxyphenylmethyl, 5-bromo-2-methoxyphenylmethyl, 3-methoxyphenylmethyl, 4-fluoro-3-methoxyphenylmethyl, 2-bromo-5-methoxyphenylmethyl, 4-methoxy-3-bromophenylmethyl, 3-nitrophenylmethyl, 3-methoxycarbonylphenylmethyl, 4-methoxycarbonylphenylmethyl, 4-trifluoromethylthiophenylmethyl, 4-trifluoromethylsulfonylphenylmethyl, or 3-hydroxyphenylmethyl;

wwww) $R^2$ is $C_{1-6}$ alkyl substituted with one substituent selected from pyridinyl, benzo[1,3]dioxol-5-ylmethyl, 2,2-difluoro-benzo[1,3]dioxol-5-ylmethyl, or quinolinyl; wherein said pyridinyl is optionally substituted with one to three fluoro substitutents or 1 substituent selected from chloro, bromo, trifluoromethyl, $C_{1-4}$ alkoxy, hydroxy, $C_{1-4}$ alkoxycarbonyl, $C_{1-3}$ alkylthio, cyano, or $C_{1-4}$ alkyl;

xxxx) $R^2$ is quinolin-8-ylmethyl, benzo[1,3]dioxol-5-ylmethyl, 2,2-difluoro-benzo[1,3]dioxol-5-ylmethyl, pyridin-2-ylmethyl, pyridin-3-ylmethyl, pyridin-4-ylmethyl, 2,3,6-trifluoro-pyridin-4-ylmethyl, or 2-fluoro-pyridin-4-ylmethyl;

yyyy) $R^2$ is $C_{1-2}$ alkyl substituted with adamantyl; or $R^2$ is $C_{1-6}$ alkyl optionally substituted with 1 to 2 substituents independently selected from $C_{1-6}$ alkoxy; $C_{1-4}$ alkoxycarbonylamino; di($C_{1-3}$)alkylamino; $C_{1-6}$ alkylsulfonyl; $C_{1-6}$ alkylthio; fluoro; $C_{2-6}$ alkenyl; $C_{1-6}$ alkoxycarbonyl; hydroxy; trifluoromethyl; $C_{2-6}$ alkynyl; $C_{1-6}$ alkylcarbonyl; $P(O)(OC_{1-3})_2$; $C_{3-6}$ cycloalkyloxy; or amino;

zzzz) $R^2$ is ethyl, 2-(tertbutoxy)ethyl, propyl, butyl, isobutyl, pentyl, hexyl, allyl, 2-(tert-butoxycarbonylamino) ethyl, 2-(dimethylamino)ethyl, 2-(methanesulfonyl) ethyl, 2-(methoxycarbonyl)-2(R)-methylethyl, 2-(methoxycarbonyl)-2(S)-methylethyl, 2-(methylsulfanyl)ethyl, methoxycarbonylmethyl, 2-methoxyethyl, 3-methoxy-3-methyl-butyl, 3,3,3,-trifluoropropyl, 4,4,4-trifluorobutyl, 5,5,5-trifluoropentyl, pent-3-ynyl, 2-fluoroethyl, 3-fluoropropyl, 2,2-difluoroethyl, 2-cyclohexyloxy-ethyl, 2-t-butoxyethyl, 3-t-butoxypropyl, 5-(ethoxycarbonyl)pentyl, 2(R),3-dihydroxypropyl, 2(S)-methoxycarbonyl-2-methylethyl, 2(R)-methoxycarbonyl-2-methylethyl, or 3-(methylcarbonyl)propyl;

a5) $R^3$ is hydrogen;

b5) $R^3$ is $C_{1-6}$ alkyl;

c5) $R^3$ is trifluoromethyl;

d5) $R^3$ is $C_{1-4}$ alkoxy;

e5) $R^3$ is bromo;

f5) $R^3$ is chloro;

g5) $R^3$ is fluoro;

h5) $R^3$ is hydroxy;

i5) $R^4$ is hydrogen;

j5) $R^4$ is fluoro;

k5) $R^4$ is chloro;

l5) $R^4$ is methyl;

m5) $R^5$ is hydrogen;

n5) $R^6$ is hydrogen, o5) $R^6$ is fluoro, p5) $R^6$ is chloro, q5) $R^6$ is methoxy, r5) $R^6$ is methyl;

s5) $R^{11}$ is selected from

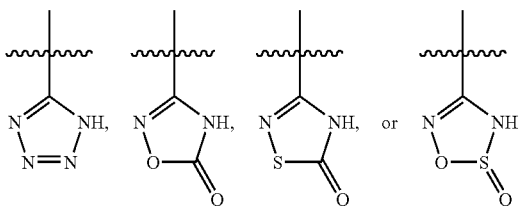

t5) $R^{12}$ is selected from

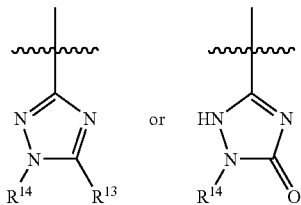

wherein $R^{13}$ is H, —$C_{1-4}$ alkyl, —$CH_2NH(C_{1-3}$alkyl), —$CH_2NH(C_{1-3}$alkyl$)_2$, or —$CH_2CO_2H$; and $R^{14}$ is —$C_{1-2}$ alkyl, —$C_{1-3}$ alkyl-OH, or —$C_{1-3}$alkyl$CO_2H$;

and any combination of embodiments a) through t5) above, provided that it is understood that combinations in which different embodiments of the same substituent would be combined are excluded; and with the proviso that when $R^1$ is $C_{6-10}$ aryl, wherein $C_{6-10}$ aryl is phenyl, substituted with carboxy at the 2 position, Y is not hydrogen; when $R^2$ is $C_{1-6}$ alkyl substituted with at least one $P(O)(OCH_3)_2$ substituent, $R^1$ is optionally substituted $C_{6-10}$ aryl; when $R^2$ is $C_{1-6}$ alkyl substituted with at least one $C_{1-6}$ alkoxycarbonyl substituent, $R^1$ is optionally substituted $C_{6-10}$ aryl; when Y is unsubstituted phenyl, and $R^1$ is ethyl, $R^2$ is not 4-fluoro-3-trifluoromethylphenylmethyl; when $R^2$ is $C_{1-6}$ alkyl substituted with an unsubstituted heterocycle comprising at least one nitrogen heteroatom, the point of attachment to the pendant group is through a nitrogen heteroatom; when $R^2$ is substituted or unsubstituted $C_{1-6}$ alkyl, $R^1$ is other than phenyl substituted at the 3-position with $R^{11}$ or $R^{12}$;

with the proviso that Formula (I) is other than a compound selected from the group consisting of a compound wherein G is S, Y is H, $R^1$ is 4-cyanophenyl, $R^2$ is 4,4,4-trifluorobutyl, $R^3$, $R^4$, $R^5$, and $R^6$ are hydrogen, A is $CR^5$, and B is $CR^6$;

a compound wherein G is S, Y is bromo, $R^1$ is 4-carboxyphenyl, $R^2$ is octahydro-quinolizin-1-ylmethyl, $R^3$, $R^4$, $R^5$, and $R^6$ are hydrogen, A is $CR^5$, and B is $CR^6$;

a compound wherein G is S, Y is 1-hydroxyethyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is methyl, $R^1$ is 4-piperazin-1-ylcarbonylphenyl, $R^2$ is 2-(cyclopropyl)ethyl, $R^3$, $R^4$, $R^5$, and $R^6$ are hydrogen, A is $CR^5$, and B is $CR^6$;

a compound wherein G is S, Y is methylcarbonylamino, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is S, Y is H, $R^1$ is 3-aminocarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is bromo, $R^1$ is 4-(1-hydroxy-1-methyl-ethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is methylaminocarbonyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is $S(O_2)$, Y is methyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound wherein G is S, Y is H, $R^1$ is 4-(5-thioxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound wherein G is S, Y is 4-methyl-piperazin-1-ylcarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is bromo, $R^1$ is 4-(1-hydroxyethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound wherein G is S, Y is dimethylaminomethyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound wherein G is S, Y is H, $R^1$ is 3-cyanophenyl, $R^2$ is 5,5,5-trifluoropentyl, $R^3$, $R^4$, $R^5$, and $R^6$ are hydrogen, A is $CR^5$, and B is $CR^6$;

a compound wherein G is S, Y is methylcarbonyl, $R^1$ is 4-carboxyphenyl, $R^2$ is 3-fluoropropyl, $R^3$, $R^4$, $R^5$, and $R^6$ are hydrogen, A is $CR^5$, and B is $CR^6$;

a compound wherein G is S, Y is H, $R^1$ is 4-carboxyphenyl, $R^2$ is 2-fluoroethyl, $R^3$, $R^4$, $R^5$, and $R^6$ are hydrogen, A is $CR^5$, and B is $CR^6$;

a compound wherein G is S, Y is H, $R^1$ is 4-carboxyphenyl, $R^2$ is 3-fluoropropyl, $R^3$, $R^4$, $R^5$, and $R^6$ are hydrogen, A is $CR^5$, and B is $CR^6$; and a compound wherein G is S, Y is methyl, $R^1$ is 4-carboxyphenyl, $R^2$ is 2-fluoroethyl, $R^3$, $R^4$, $R^5$, and $R^6$ are hydrogen, A is $CR^5$, and B is $CR^6$;

a compound wherein G is $S(O_2)$, Y is methyl, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound wherein G is S, Y is H, $R^1$ is 3-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

and enantiomers, diastereomers, solvates, and pharmaceutically acceptable salts thereof.

Compounds of Formula (I) include compounds of Formula (II)

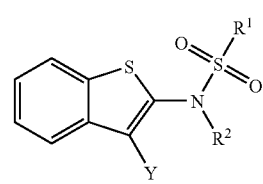

(II)

wherein Y, $R^1$ and $R^2$ are as defined herein; and enantiomers, diastereomers, racemates, solvates, and pharmaceutically acceptable salts thereof.

Compounds of Formula (I) include compounds of Formula (III)

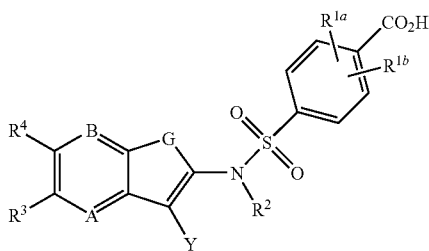

(III)

wherein A, B, G, Y, and $R^2$ are as defined herein;
$R^{1a}$ and $R^{1b}$ are selected from the group consisting of
a) 2-methyl and H;
b) 2-fluoro and hydrogen;
c) 3-fluoro and hydrogen;
d) 3-methyl and hydrogen;
e) 3-fluoro and 5-fluoro;
f) 2-fluoro and 5-fluoro;
g) 2-chloro and hydrogen;
h) 3-chloro and hydrogen;
i) 2-chloro and 6-chloro;
j) 2-trifluoromethyl and hydrogen;
k) 3-trifluoromethyl and hydrogen;
l) 3-trifluoromethoxy and hydrogen; and
m) 3-cyano and hydrogen;
and enantiomers, diastereomers, solvates, and pharmaceutically acceptable salts thereof.

A further embodiment of the present invention is directed to a compound of Formula (I) selected from:

a compound of formula (I) wherein G is S, Y is 1-hydroxy-1-methylethyl, c is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is adamant-1-ylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is adamant-1-ylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is cyclohexylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methyl-3,4-dihydro-2H-benzo[1,4]oxazine-7-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-hydroxyphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is thien-2-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is acetyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is thien-2-yl, $R^2$ is 4-trifluoromethyl-3-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-[1,2,3]thiadiazol-4-yl-phenyl, $R^2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is hydroxymethyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is formyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is pyridin-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-methylphenylmethyl, $R_3$, $R_4$, $R_5$, and $R_6$ are hydrogen, A is $CR_5$, and B is $CR_6$;

a compound of formula (I) wherein G is S, Y is Br, $R^1$ is phenyl, $R^2$ is 4-methoxy-3-bromophenylmethyl, $R^3$, $R^4$, $R^5$, and $R^6$ are hydrogen, A is $CR^5$, and B is $CR^6$;

a compound of formula (I) wherein G is S, Y is Br, $R^1$ is thien-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is pyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is thien-2-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(piperidin-1-yl)ethyl, $R^3$, $R^4$, $R^5$, and $R^6$ are hydrogen, A is $CR^5$, and B is $CR^6$;

a compound of formula (I) wherein G is S, Y is Br, $R^1$ is 3-fluorophenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-oxo-2,3-dihydro-benzooxazol-6-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-methoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is thien-3-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-hydroxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is quinolin-8-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is acetyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is thien-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Cl, $R^1$ thien-3-yl, $R^{12}$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is thien-2-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is methyl, $R^1$ is pyridin-3-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is acetyl, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is Br, $R^1$ is 3-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is methyl, $R^1$ is 3-phenoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is dimethylamino, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is 2-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxyphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is pyridin-3-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 2-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-fluorophenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is formyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is n-hexyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-phenylpropyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-phenylethyl, $R^3$, $R^4$, $R^5$, and $R^6$ are hydrogen, A is $CR^5$, and B is $CR^6$;

a compound of formula (I) wherein G is S, Y is methyl, $R^1$ is 2-fluorophenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Br, $R^1$ is dimethylamino, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 4-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is cyano, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-nitrophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 4-chlorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(methoxycarbonyl)-2(R)-methylethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-fluorophenylmethyl, $R^3$, $R^4$, $R^5$, and $R^6$ are hydrogen, A is $CR^5$, and B is $CR^6$;

a compound of formula (I) wherein G is S, Y is formyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is pyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is quinolin-6-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is formyl, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2(S)-methoxycarbonyl-2-methylethyl, $R^3$, $R^4$, $R^5$, and $R^6$ are hydrogen, A is $CR^5$, and B is $CR^6$;

a compound of formula (I) wherein G is S, Y is Br, $R^1$ is pyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is n-butyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 5-(ethoxycarbonyl)pentyl, $R^3$, $R^4$, $R^5$, and $R^6$ are hydrogen, A is $CR^5$, and B is $CR^6$;

a compound of formula (I) wherein G is S, Y is pyrimidin-5-yl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is formyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-chlorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is methyl, $R^2$ is 4-fluoro-3-trifluoromethylphenylmethyl, $R^3$, $R^4$, $R^5$, and $R^6$ are hydrogen, A is $CR^5$ and B is $CR^6$;

a compound of formula (I) wherein G is S, Y is hydroxymethyl, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3,4-difluorophenylmethyl, $R^3$ and $R^4$ are hydrogen, $R^6$ is hydrogen, A is N, and B is $CR^6$;

a compound of formula (I) wherein G is S, Y is Cl, $R^1$ is phenyl, $R^2$ is 3,4-difluorophenylmethyl, $R^3$ and $R^4$ are hydrogen, $R^6$ is hydrogen, A is N, and B is $CR^6$;

a compound of formula (I) wherein G is S, Y is Br, $R^1$ is phenyl, $R^2$ is pyridin-2-ylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2(R)-methoxycarbonyl-2-methylethyl $R^3$, $R^4$, $R^5$, and $R^6$ are hydrogen, A is $CR^5$, and B is $CR^6$;

a compound of formula (I) wherein G is S, Y is Br, $R^1$ is 3-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(methylsulfanyl)ethyl, $R^3$, $R^4$, $R^5$, and $R^6$ are hydrogen, A is $CR^5$, and B is $CR^6$;

a compound of formula (I) wherein G is S, Y is acetyl, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(tert-butoxy)ethyl $R^3$, $R^4$, $R^5$, and $R^6$ are hydrogen, A is $CR^5$, and B is $CR^6$;

a compound of formula (I) wherein G is S, Y is methyl, $R^1$ is quinolin-8-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 1-methyl-1H-imidazol-4-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is dimethylamino, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is formyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-1H-imidazol-4-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is benzothiazol-6-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-methoxyethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2,4-dimethyl-thiazol-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(methoxycarbonyl)-2(S)-methylethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-methoxyethyl, $R^3$, $R^4$, $R^5$, and $R^6$ are hydrogen, A is $CR^5$, and B is $CR^6$;

a compound of formula (I) wherein G is S, Y is Br, $R^1$ is n-propyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is pyridin-3-yl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxy-3-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ ethyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-nitrophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxyphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is isoquinolin-5-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 3-hydroxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-methoxyphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is (N-tert-butoxycarbonylpiperidin-4-yl)methyl, $R^3$, $R^4$, $R^5$, and $R^6$ are hydrogen, A is $CR^5$, and B is $CR^6$;

a compound of formula (I) wherein G is S, Y is methyl, $R^1$ is 1,3,5-trimethyl-1H-pyrazol-4-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is acetyl, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-chloropyridin-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is pyridin-3-ylmethyl, $R^3$, $R^4$, $R^5$, and $R^6$ are hydrogen, A is $CR^5$, and B is $CR^6$;

a compound of formula (I) wherein G is S, Y is Br, $R^1$ is dimethylamino, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is thien-3-yl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is quinolin-6-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-phenylethyl, $R^3$, $R^4$, $R^5$, and $R^6$ are hydrogen, A is $CR^5$, and B is $CR^6$;

a compound of formula (I) wherein G is S, Y is methyl, $R^1$ is 2-chloropyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is thien-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(phenyl)ethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is H, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is ethyl, $R^3$, $R^4$, $R^5$, and $R^6$ are hydrogen, A is $CR^5$, and B is $CR^6$;

a compound of formula (I) wherein G is S, Y is methyl, $R^1$ is 2,4-dihydroxy-6-methyl-pyrimidin-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 3-fluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 4-hydroxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 3-(methylcarbonyl)propyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is n-butyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is cyclohexylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3-hydroxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(piperidin-1-yl)ethyl, $R^3$, $R^4$, $R^5$, and $R^6$ are hydrogen, A is $CR^5$, and B is $CR^6$;

a compound of formula (I) wherein G is S, Y is formyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is methoxycarbonylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 4-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is isoquinolin-5-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is quinolin-8-yl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is formyl, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is isoquinolin-5-yl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-1H-imidazol-4-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3-fluorophenylmethyl, $R^3$, $R^4$, $R^5$, and $R^6$ are hydrogen, A is $CR^5$, and B is $CR^6$;

a compound of formula (I) wherein G is S, Y is acetyl, $R^1$ is ethyl, $R^2$ is n-butyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is allyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-methylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-methoxyphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 2-methoxyethyl, $R^3$, $R^4$, $R^5$, and $R^6$ are hydrogen, A is $CR^5$, and B is $CR^6$;

a compound of formula (I) wherein G is S, Y is Br, $R^1$ is n-butyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is quinolin-6-yl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is n-butyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is methoxycarbonylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2,2-difluoroethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is pent-3-ynyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is Br, $R^1$ is dimethylamino, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R_2$ is 2,2-difluoroethyl, $R^3$, $R^4$, $R^5$, and $R^6$ are hydrogen, A is $CR^5$, and B is $CR^6$;

a compound of formula (I) wherein G is S, Y is Cl, $R^1$ is 3-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is pyridin-4-ylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is pyridin-2-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 3-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 3-fluorophenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is cyclohexylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(methylsulfanyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is (N-tert-butoxycarbonylpyrrolidin-2-yl)methyl, $R^3$, $R^4$, $R^5$, and $R^6$ are hydrogen, A is $CR^5$, and B is $CR^6$;

a compound of formula (I) wherein G is S, Y is H, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(tert-butoxycarbonylamino)ethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 3-oxo-3,4-dihydro-2H-benzo[1,4]oxazin-6-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 5-bromo-2-methoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is pyridin-3-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-methylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is methanesulfonylmethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is ethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is 2-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is quinolin-8-ylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-bromo-5-methoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-nitrophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-fluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is Br, $R^1$ is 4-carboxyphenyl, $R^2$ is 2,2-difluoroethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3-methylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is cyclohexylmethyl, $R^3$, $R^4$, $R^5$, and $R^6$ are hydrogen, A is $CR^5$, and B is $CR^6$;

a compound of formula (I) wherein G is S, Y is H, $R^1$ is n-propyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3-nitrophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3,4-difluorophenylmethyl, $R^3$, $R^4$, and $R^5$, are hydrogen, A is $CR^5$, and B is N;

a compound of formula (I) wherein G is S, Y is H, $R^1$ is phenyl, $R^2$ is 3-methoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-phenylethyl, $R^3$, $R^4$, $R^5$, and $R^6$ are hydrogen, A is $CR^5$, and B is $CR^6$;

a compound of formula (I) wherein G is S, Y is methyl, $R^1$ is benzo[b]thiophen-2-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-chlorophenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 4-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is (N-tert-butoxycarbonylpyrrolidin-2-yl)methyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(methanesulfonyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2,2-difluoroethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(dimethylamino)ethyl, $R^3$, $R^4$, $R^5$, and $R^6$ are hydrogen, A is $CR^5$, and B is $CR^6$;

a compound of formula (I) wherein G is S, Y is H, $R^1$ is n-butyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is allyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-trifluoromethoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is 1-methyl-1H-imidazol-4-yl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is N-methylpyrrolidin-2(S)-ylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-methoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is pyridin-2-ylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(dimethylphospho)ethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is cyclohexyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-(methylsulfanyl)ethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is pyridin-3-ylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 4-methoxyphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(dimethylamino)ethyl, $R^3$, $R^4$, $R^5$, and $R^6$ are hydrogen, A is $CR^5$, and B is $CR^6$;

a compound of formula (I) wherein G is S, Y is H, $R^1$ is methyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is ethyl, $R^2$ is 2,2-difluoroethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is (N-tert-butoxycarbonylpyrrolidin-2-yl)methyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-1H-imidazol-4-yl, $R^2$ is quinolin-8-yl methyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(methanesulfonyl)ethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-(2-oxo-pyrrolidin-1-yl)ethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 2-aminoethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is pent-3-ynyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-(methylsulfanyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 1,2,3,4-tetrahydro-isoquinolin-8-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is dimethylamino, $R^2$ is 2,2-difluoroethyl, $R^3$, $R^4$, $R^5$, and $R^6$ are hydrogen, A is $CR^5$, and B is $CR^6$;

a compound of formula (I) wherein G is S, Y is Br, $R^1$ is amino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(2,5-dioxo-pyrrolidin-1-yl)ethyl, $R^3$, $R^4$, $R^5$, and $R^6$ are hydrogen, A is $CR^5$, and B is $CR^6$;

a compound of formula (I) wherein G is S, Y is acetyl, $R^1$ is ethyl, $R^2$ is 2-(tert-butoxy)ethyl, $R^3$, $R^4$, $R^5$, and $R^6$ are hydrogen, A is $CR^5$, and B is $CR^6$;

a compound of formula (I) wherein G is S, Y is Cl, $R^1$ is amino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 3-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is thien-3-yl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 2-fluorophenyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-oxo-pyrrolidin-5(R)-ylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-oxo-pyrrolidin-5(S)-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(2,2,2-trifluoro-acetyl)-1,2,3,4-tetrahydro-isoquinolin-8-yl, $R^2$ is 4-fluoro-3-trifluoromethylphenylmethyl, $R^3$, $R^4$, $R^5$, and $R^6$ are hydrogen, A is $CR^5$, and B is $CR^6$;

compound of formula (I) wherein G is S, Y is acetyl, $R^1$ is ethyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is H, $R^1$ is amino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Cl, $R^1$ is 2-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-methoxyethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is Br, $R^1$ is 2-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is pyridin-3-yl, $R^2$ is 3,4-difluorophenylmethyl, $R^3$ is hydrogen, $R^4$ is methoxy, $R^5$ and $R^6$ are hydrogen, A is $CR^5$, and B is $CR^6$;

a compound of formula (I) wherein G is S, Y is H, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-oxo-pyrrolidin-5(S)-ylmethyl, $R^3$, $R^4$, $R^5$, and $R^6$ are hydrogen, A is $CR^5$, and B is $CR^6$;

a compound of formula (I) wherein G is S, Y is acetyl, $R^1$ is ethyl, $R^2$ is 2-(morpholin-4-yl)ethyl, $R^3$, $R^4$, $R^5$, and $R^6$ are hydrogen, A is $CR^5$, and B is $CR^6$;

a compound of formula (I) wherein G is S, Y is 4-fluorophenyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(2-oxo-pyrrolidin-1-yl)ethyl, $R^3$, $R^4$, $R^5$, and $R^6$ are hydrogen, A is $CR^5$, and B is $CR^6$;

a compound of formula (I) wherein G is S, Y is Br, $R^1$ is 4-trifluoromethylphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is pyridin-4-ylmethyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 3,4-difluorophenylmethyl, $R^3$ is hydrogen, $R^4$ is Cl, $R^5$ is hydrogen, $R^6$ is methoxy, A is $CR^5$, and B is $CR^6$;

a compound of formula (I) wherein G is S, Y is H, $R^1$ is phenyl, $R^2$ is 3,4-difluorophenylmethyl, $R^3$, $R^4$, and $R^5$ are hydrogen, $R^6$ is methoxy, A is $CR^5$, and B is $CR^6$;

a compound of formula (I) wherein G is S, Y is methyl, $R^1$ is benzo[b]thiophen-2-yl, $R^2$ is quinolin-8-yl methyl, $R^3$, $R^4$, $R^5$, and $R^6$ are hydrogen, A is $CR^5$, and B is $CR^6$;

a compound of formula (I) wherein G is S, Y is H, $R^1$ is 4-trifluoromethylphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2(R),3-dihydroxypropyl, $R^3$, $R^4$, $R^5$, and $R^6$ are hydrogen, A is $CR^5$, and B is $CR^6$;

a compound of formula (I) wherein G is S, Y is Cl, $R^1$ is phenyl, $R^2$ is 3,4-difluorophenylmethyl, $R^3$, $R^4$, and $R^5$ are hydrogen, $R^6$ is methoxy, A is $CR^5$, and B is $CR^6$;

a compound of formula (I) wherein G is S, Y is methyl, $R^1$ is phenylmethyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is Br, $R^1$ is phenyl, $R^2$ is 2-(2-oxo-imidazolidin-1-yl)-ethyl, $R^3$, $R^4$, $R^5$, and $R^6$ are hydrogen, A is $CR^5$, and B is $CR^6$; or a compound of formula (I) wherein G is S, Y is Cl, $R^1$ is phenyl, $R^2$ is 2-(2-oxo-imidazolidin-1-yl)ethyl, $R^3$, $R^4$, $R^5$, and $R^6$ are hydrogen, A is $CR^5$, and B is $CR^6$;

a compound of formula (I) wherein G is S, Y is bromo, $R^1$ is amino, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is bromo, $R^1$ is amino, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-methylcarbonylphenyl, $R^2$ is 4-fluoro-3-trifluoromethylphenylmethyl, $R^4$, $R^5$, and $R^6$ are hydrogen, A is $CR^5$, and B is $CR^6$;

a compound of formula (I) wherein G is S, Y is chloro, $R^1$ is methylamino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 2-chloropyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 6-chloro-pyridin-3-yl, $R^2$ is 4-fluoro-3-trifluoromethylphenylmethyl $R^3$, $R^4$, $R^5$, and $R^6$ are hydrogen, A is $CR^5$, and B is $CR^6$;

a compound of formula (I) wherein G is S, Y is bromo, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, R$^1$ is dimethylamino, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is 1-hydroxy-1-methyl-ethyl, R$^1$ is phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is dimethylamino, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methylcarbonyl, R$^1$ is 4-carboxyphenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is 2-chloropyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is 6-chloro-pyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 2-chloropyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is pyridin-3-yl, R$^2$ is 3-fluoro-4-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is pyridin-3-yl, R$^2$ is 4-trifluoromethoxyphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is pyridin-3-yl, R$^2$ is 3-chloro-6-fluorophenylmethyl, R$^3$, R$^4$, R$^5$, and R$^6$ are hydrogen, A is CR$^5$, and B is CR$^6$;

a compound of formula (I) wherein G is S, Y is trifluoromethyl, R$^1$ is phenyl, R$^2$ is 4-trifluoromethoxyphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-(2-methyl-5-trifluoromethyl-2H-pyrazol-3-yl)-thien-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-methoxycarbonyl-furan-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 1-methyl-3-trifluoromethyl-1H-pyrazol-4-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-(5-trifluoromethyl-isoxazol-3-yl)-thien-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-bromo-6-chloropyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5,6-dichloropyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(pyrazol-1-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 3-(5-methyl-[1,3,4]oxadiazol-2-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(oxazol-5-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is 1-hydroxy-ethyl, R$^1$ is 4-carboxyphenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 3-chloro-4-methylcarbonylamino-phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 6-chloro-imidazo[2,1-b]thiazol-5-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 6-chloro-pyridin-3-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methylcarbonyl, R$^1$ is 4-methoxycarbonylphenyl, R$^2$ is n-butyl, R$^3$, R$^4$, R$^5$, and R$^6$ are hydrogen, A is CR$^5$, and B is CR$^6$;

a compound of formula (I) wherein G is S, Y is H, R$^1$ is pyridin-3-yl, R$^2$ is n-butyl, R$^3$, R$^4$, R$^5$, and R$^6$ are hydrogen, A is CR$^5$, and B is CR$^6$;

a compound of formula (I) wherein G is S, Y is 1-hydroxy-1-methyl-ethyl, R$^1$ is 4-(1-hydroxy-1-methyl-ethyl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is methylcarbonyl, R$^1$ is 4-carboxyphenyl, R$^2$ is n-butyl, R$^3$, R$^4$, R$^5$, and R$^6$ are hydrogen, A is CR$^5$, and B is CR$^6$;

a compound of formula (I) wherein G is S, Y is 1-hydroxy-1-methyl-ethyl, R$^1$ is 4-carboxyphenyl, R$^2$ is n-butyl, R$^3$, R$^4$, R$^5$, and R$^6$ are hydrogen, A is CR$^5$, and B is CR$^6$;

a compound of formula (I) wherein G is S, Y is 1-hydroxy-1-methyl-ethyl, R$^1$ is 4-methylcarbonylphenyl, R$^2$ is n-butyl, R$^3$, R$^4$, R$^5$, and R$^6$ are hydrogen, A is CR$^5$, and B is CR$^6$;

a compound of formula (I) wherein G is S, Y is bromo, R$^1$ is pyridin-3-yl, R$^2$ is n-butyl, R$^3$, R$^4$, R$^5$, and R$^6$ are hydrogen, A is CR$^5$, and B is CR$^6$;

a compound of formula (I) wherein G is S, Y is dimethylamino-methyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methylamino-methyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is n-propylamino-methyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is pyrrolidin-1-ylmethyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, $R^1$ is methanesulfonyl-methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methylcarbonylphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(2-methyl-pyrimidin-4-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(2-methyl-pyrimidin-4-yl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 8-methoxyquinolin-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 8-methoxyquinolin-5-yl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2-methoxypyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-dimethylaminopyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-methoxypyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-dimethylaminopyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is methanesulfonyl-methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 2-t-butoxyethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 3,4-difluoro-phenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is 3-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1-hydroxy-1-methyl-ethyl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-pyridin-4-yloxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-pyridin-3-yloxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1-hydroxy-1-methyl-ethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-methoxycarbonylphenyl, $R^2$ is 4-fluoro-3-trifluoromethylphenylmethyl, $R^4$ is fluoro, $R^3$, $R^5$, and $R^6$ are hydrogen, A is $CR^5$, and B is $CR^6$;

a compound of formula (I) wherein G is S, Y is methyl, $R^1$ is 3-carboxyphenyl, $R^2$ is 4-fluoro-3-trifluoromethylphenylmethyl, leis fluoro, $R^3$, $R^5$, and $R^6$ are hydrogen, A is $CR^5$, and B is $CR^6$;

a compound of formula (I) wherein G is S, Y is methyl, $R^1$ is 2-methylthio-pyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-methylthiopyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is pyridin-3-yl, $R^2$ is 3-methoxycarbonylphenylmethyl, $R^3$, $R^4$, $R^5$, and $R^6$ are hydrogen, A is $CR^5$, and B is $CR^6$;

a compound of formula (I) wherein G is S, Y is H, $R^1$ is pyridin-3-yl, $R^2$ is 4-methoxycarbonylphenylmethyl, $R^3$, $R^4$, $R^5$, and $R^6$ are hydrogen, A is $CR^5$, and B is $CR^6$;

a compound of formula (I) wherein G is S, Y is pyrrolidin-1-ylmethyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is methyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is pyridin-3-yl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2-oxo-2,3-dihydro-benzooxazol-6-yl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is propyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is pentyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is hexyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 3-t-butoxypropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 2-t-butoxyethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is propyl, $R^3$, $R^4$, $R^5$, and $R^6$ are hydrogen, A is $CR^5$, and B is $CR^6$;

a compound of formula (I) wherein G is S, Y is bromo, $R^1$ is pyridin-3-yl, $R^2$ is 3-methoxycarbonylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is pyridin-3-yl, $R^2$ is 4-methoxycarbonylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is pyridin-3-yl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is chloro, $R^1$ is pyridin-3-yl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4,4,4-trifluoro-butyl, $R^3$, $R^4$, $R^5$, and $R^6$ are hydrogen, A is $CR^5$, and B is $CR^6$;

a compound of formula (I) wherein G is S, Y is H, $R^1$ is 4-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 4,4,4-trifluorobutyl, $R^4$ is fluoro, $R^3$, $R^5$, and $R^6$ are hydrogen, A is $CR^5$, and B is $CR^6$;

a compound of formula (I) wherein G is S, Y is H, $R^1$ is 4-aminocarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-aminocarbonylphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 3-t-butoxypropyl, $R^3$, $R^4$, $R^5$, and $R^6$ are hydrogen, A is $CR^5$, and B is $CR^6$;

a compound of formula (I) wherein G is S, Y is methylamino-methyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is dimethylamino-methyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is formyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is dimethylamino-methyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is H, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methoxy, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methoxy, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4,4,4-trifluorobutyl, $R^4$ is fluoro, $R^3$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-fluoro-3-trifluoromethylphenylmethyl, $R^4$ is fluoro, $R^3$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is $S(O_2)$, Y is H, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is bromo, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is H, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is bromo, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is methoxy, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is bromo, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is $S(O_2)$, Y is methoxy, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is cyclobutylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is cyclopentylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is bicyclo[2.2.1]hept-2-ylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is tetrahydropyran-4-ylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-dimethylamino-ethyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-dimethylaminophenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-pyrrolidin-1-ylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-morpholin-4-yl-phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(1-methyl-piperazin-4-yl)phenyl, $R^2$ is n-butyl, $R^4$, $R^5$, and $R^6$ are hydrogen, A is $CR^5$, and B is $CR^6$;

a compound of formula (I) wherein G is S, Y is methyl, $R^1$ is 2-dimethylaminopyridin-3-yl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is n-butyl, $R^4$ is fluoro, $R^3$, $R^5$, and $R^6$ are hydrogen, A is $CR^5$, and B is $CR^6$;

a compound of formula (I) wherein G is S, Y is H, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is isobutyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-cyclohexyloxy-ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 3-methoxy-3-methyl-butyl, $R^4$, $R^5$, and $R^6$ are hydrogen, A is $CR^5$, and B is $CR^6$;

a compound of formula (I) wherein G is S, Y is methyl, $R^1$ is 3-(2H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is dimethylaminocarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylaminocarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is aminocarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is methylcarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 3-dimethylaminosulfonylphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 3-dimethylaminosulfonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is 1-hydroxy-1-methyl-ethyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is 1-hydroxy-ethyl, $R^1$ is phenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is aminocarbonyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methylaminocarbonyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is dimethylaminocarbonyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is aminocarbonyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is dimethylaminocarbonyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(2-oxo-2,3-dihydro-2λ4-[1,2,3,5]oxathiadiazol-4-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(N-hydroxy-acetamidinyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(N-(methylcarbonyloxy)acetamidinyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(N-hydroxy-acetamidinyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-bromophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is chloro, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is chloro, $R^1$ is 4-carboxyphenyl, $R^2$ is cyclopropylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-thioxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(N-hydroxy-acetamidinyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(2-oxo-2,3-dihydro-2λ4-[1,2,3,5]oxathiadiazol-4-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is chloro, $R^1$ is 4-(2-oxo-2,3-dihydro-2λ4-[1,2,3,5]oxathiadiazol-4-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-fluorophenylmethyl, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3-chloro-4-fluorophenylmethyl, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-difluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-methanesulfonylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is pentafluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-trifluoromethylsulfonylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is pyridin-2-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3-fluoro-4-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-nitrophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-aminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methylcarbonylamino, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is cyclopentyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is cyclopentyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is n-butyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methoxycarbonylphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methanesulfonylamino, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonylamino, R$^1$ is phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 2-carboxyethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is H, R$^1$ is 4-(5-oxo-4,5-dihydro-[1,2,4]oxadiazol-3-yl)phenyl, R$^2$ is 4,4,4-trifluorobutyl, R$^3$, R$^4$, R$^5$, and R$^6$ are hydrogen, A is CR$^5$, and B is CR$^6$;

a compound of formula (I) wherein G is S, Y is bromo, R$^1$ is 4-(5-oxo-4,5-dihydro-[1,2,4]oxadiazol-3-yl)phenyl, R$^2$ is 4,4,4-trifluorobutyl, R$^3$, R$^4$, R$^5$, and R$^6$ are hydrogen, A is CR$^5$, and B is CR$^6$;

a compound of formula (I) wherein G is S, Y is chloro, R$^1$ is 4-(5-oxo-4,5-dihydro-[1,2,4]oxadiazol-3-yl)-phenyl, R$^2$ is 4,4,4-trifluoro-butyl, R$^3$, R$^4$, R$^5$, and R$^6$ are hydrogen, A is CR$^5$, and B is CR$^6$;

a compound of formula (I) wherein G is S, Y is 1-hydroxy-1-methyl-ethyl, R$^1$ is 4-methoxycarbonylphenyl, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3,4,5-trifluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2-fluoro-5-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2,5-dichlorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-chloro-3-fluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-fluoro-2-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is benzo[1,3]dioxol-5-ylmethyl R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2,2-difluoro-benzo[1,3]dioxol-5-ylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3,4-dimethoxyphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethylthiophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxythien-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-carboxy-3-methylthien-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 5-carboxyfuran-2-yl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 4-methoxycarbonylphenyl, R$^2$ is 4,4,4-trifluorobutyl, R$^3$, R$^4$, R$^5$, and R$^6$ are hydrogen, A is CR$^5$, and B is CR$^6$;

a compound of formula (I) wherein G is S, Y is chloro, R$^1$ is 4-methoxycarbonylphenyl, R$^2$ is 5,5,5-trifluoropentyl, R$^3$, R$^4$, R$^5$, and R$^6$ are hydrogen, A is CR$^5$, and B is CR$^6$;

a compound of formula (I) wherein G is S, Y is H, R$^1$ is methylamino, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is methylamino, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is 1S*-hydroxy-ethyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is 1R*-hydroxy-ethyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S(O$_2$), Y is dimethylamino, R$^1$ is 4-carboxyphenyl, R$^2$ is n-butyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 4,4,4-trifluorobutyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 5,5,5-trifluoropentyl R$^3$, R$^4$, R$^5$, and R$^6$ are hydrogen, A is CR$^5$, and B is CR$^6$;

a compound of formula (I) wherein G is S, Y is methyl, R$^1$ is 4-(1H-tetrazol-5-yl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is 4-(2-oxo-2,3-dihydro-2λ4-[1,2,3,5]oxathiadiazol-4-yl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is 4-(5-oxo-4,5-dihydro-[1,2,4]oxadiazol-3-yl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is 4-(1H-tetrazol-5-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(2-oxo-2,3-dihydro-2λ4-[1,2,3,5]oxathiadiazol-4-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropyl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is methylamino, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is methylamino, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-(hydroxyaminocarbonyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-fluoro-3-trifluoromethylphenylmethyl, $R^4$ is trifluoromethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is n-butyl, $R^4$ is trifluoromethyl, $R^3$, $R^5$, and $R^6$ are hydrogen, A is $CR_5$, and B is $CR_6$;

a compound of formula (I) wherein G is S, Y is bromo, $R^1$ is 4-(morpholin-4-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-dimethylaminophenyl, $R^2$ is n-butyl, $R^3$, $R^4$, $R^5$, and $R^6$ are hydrogen, A is $CR^5$, and B is $CR^6$;

a compound of formula (I) wherein G is S, Y is chloro, $R^1$ is 4-dimethylaminophenyl, $R^2$ is n-butyl, $R^3$, $R^4$, $R^5$, and $R^6$ are hydrogen, A is $CR^5$, and B is $CR^6$;

a compound of formula (I) wherein G is S, Y is chloro, $R^1$ is 4-morpholin-4-yl-phenyl, $R^2$ is n-butyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-methoxycarbonylphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-methoxycarbonylphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1H-tetrazol-5-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 3-cyanophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 3-cyanophenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is H, $R^1$ is 3-cyanophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 3-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is bromo, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 3-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(1H-tetrazol-5-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(2-oxo-2,3-dihydro-2λ4-[1,2,3,5]oxathiadiazol-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(2-oxo-2,3-dihydro-2λ4-[1,2,3,5]oxathiadiazol-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-aminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-amino-3-chloro-phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-amino-3-bromophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(2-oxo-2,3-dihydro-2λ4-[1,2,3,5]oxathiadiazol-4-yl)phenyl, $R^2$ is 3,3,3-trifluoropropyl, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(2-oxo-2,3-dihydro-2λ4-[1,2,3,5]oxathiadiazol-4-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]oxadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(2-oxo-2,3-dihydro-2λ4-[1,2,3,5]oxathiadiazol-4-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(2-oxo-2,3-dihydro-2λ4-[1,2,3,5]oxathiadiazol-4-yl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(2-oxo-2,3-dihydro-2λ4-[1,2,3,5]oxathiadiazol-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(methanesulfonylaminocarbonyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(2-oxo-2,3-dihydro-2λ4-[1,2,3,5]oxathiadiazol-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(2-oxo-2,3-dihydro-2λ4-[1,2,3,5]oxathiadiazol-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is $S(O_2)$, Y is methyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(1H-tetrazol-5-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]thiadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is dimethylamino, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is methylamino, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is 4-methyl-piperazin-1-yl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is amino, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is piperazin-1-yl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is $S(O_2)$, Y is methylamino, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is $S(O_2)$, Y is 4-methyl-piperazin-1-yl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-amino-3-bromophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-methanesulfonylaminophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-aminophenyl, $R^2$ is 4-fluoro-3-trifluoromethylphenylmethyl $R^3$, $R^4$, $R^5$, and $R^6$ are hydrogen, A is $CR^5$, and B is $CR^6$;

a compound of formula (I) wherein G is S, Y is H, $R^1$ is 4-bromophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-bromophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 3-bromo-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is trifluoromethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is trifluoromethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is trifluoromethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is trifluoromethyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-aminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-amino-3-chloro-phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-methanesulfonylaminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 5,5,5-trifluoropentyl, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 3,5-dichloro-4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is chloro, $R^1$ is 3,5-dichloro-4-(methanesulfonylamino)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 3-bromo-4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]thiadiazol-3-yl)-phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]thiadiazol-3-yl)-phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-dimethylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-methylaminophenyl, $R^2$ is 2-(cyclopropyl)ethyl, $R^4$, $R^5$, and $R^6$ are hydrogen, A is $CR^5$, and B is $CR^6$;

a compound of formula (I) wherein G is S, Y is chloro, $R^1$ is 3-chloro-4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 3-bromo-4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-trifluoromethylcarbonylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-trifluoromethylcarbonylaminophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxypropyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(2,2,2-trifluoro-acetyl)-1,2,3,4-tetrahydro-isoquinolin-7-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(2-dimethylaminomethyl-imidazol-1-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is methylamino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 3-methanesulfonylaminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is chloro, $R^1$ is 3-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 3-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(cyclopropylsulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(cyclopropylsulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 1H-benzimidazol-2-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is quinoxalin-5-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-benzimidazol-2-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is quinoxalin-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-formylethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxy-3-methyl-butyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S Y is methyl, $R^1$ is 1H-benzimidazol-2-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 5-chloro-1-methyl-benzimidazol-2-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 1H-benzimidazol-2-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 1H-benzimidazol-2-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 3-chloro-4-fluorophenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 3-chloro-4-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-diethylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(thiomorpholin-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(morpholin-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(piperazin-1-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-methanesulfonylamino-2-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-methanesulfonylamino-2-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-benzimidazol-2-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 1-methyl-benzimidazol-2-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-amino-indan-5-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(thiomorpholin-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(morpholin-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(piperidin-1-yl)phenyl, $R^2$ is 2-(cyclopropyl)ethyl $R^3$, $R^4$, $R^5$, and $R^6$ are hydrogen, A is $CR^5$, and B is $CR^6$;

a compound of formula (I) wherein G is S, Y is methyl, $R^1$ is 4-(piperidin-1-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-(methoxycarbonyl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-(methoxycarbonyl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(methoxycarbonyl)propyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-hydroxybutyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-hydroxy-4-methylpentyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methoxycarbonylmethyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxy-3-methyl-butyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxypropyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-carboxypropyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 5-chloro-2-methoxy-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-methyl-1,2,3,4-tetrahydro-isoquinolin-7-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropenyl, $R^1$ is ethyl, $R^2$ is 4-chloro-2-fluoro-5-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-bromopropyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is cyclopropyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-bromobutyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-cyanophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-cyanophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-3-fluorophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-3-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 2-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(4-methyl-piperazin-1-ylcarbonyl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(imidazol-1-yl)propyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(imidazol-1-yl)butyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 2-hydroxy-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(pyrrolidin-3S-ylaminocarbonyl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(pyrrolidin-3R-ylaminocarbonyl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1H-tetrazol-5-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-dimethylamino-pyridin-3-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 6-dimethylamino-pyridin-3-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 6-morpholin-4-yl-pyridin-3-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 6-dimethylamino-pyridin-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-morpholin-4-yl-pyridin-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methoxycarbonylmethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is carboxymethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-hydroxyethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-methoxycarbonylethyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxy-3-methyl-butyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-bromoethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-morpholin-4-yl-pyridin-3-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(morpholin-4-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]oxadiazol-3-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 2,4,5-trifluoro-3-methoxyphenylmethyl, $R^3$, $R^4$, $R^5$, and $R^6$ are hydrogen, A is $CR^5$, and B is $CR^6$;

a compound of formula (I) wherein G is S, Y is isopropenyl, $R^1$ is ethyl, $R^2$ is 2,4,5-trifluoro-3-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-(1H-tetrazol-5-yl)pyridin-3-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 6-(1H-tetrazol-5-yl)pyridin-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-(1H-tetrazol-5-yl)pyridin-3-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 6-(5-oxo-4,5-dihydro-[1,2,4]oxadiazol-3-yl)pyridin-3-yl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 6-(5-oxo-4,5-dihydro-[1,2,4]oxadiazol-3-yl)-pyridin-3-yl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 6-(5-oxo-4,5-dihydro-[1,2,4]oxadiazol-3-yl)pyridin-3-yl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-1H-[1,2,4]triazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1-methyl-5-oxo-4,5-dihydro-1H-[1,2,4]triazol-3-yl)-phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is phenyl, $R^2$ is 4-fluoro-3-trifluoromethylphenylmethyl, $R^3$, $R^4$, and $R^5$ are hydrogen, A is $CR^5$, and B is N;

a compound of formula (I) wherein G is S, Y is chloro, $R^1$ is 3-carboxyphenyl, $R^2$ is 4-fluoro-3-trifluoromethylphenylmethyl, $R^3$, $R^4$, and $R^5$ are hydrogen, A is $CR^5$, and B is N;

a compound of formula (I) wherein G is S, Y is chloro, $R^1$ is 4-carboxyphenyl, $R^2$ is 3,3,3-trifluoropropyl, $R^3$, $R^4$, and $R^5$ are hydrogen, A is $CR^5$, and B is N;

a compound of formula (I) wherein G is S, Y is chloro, $R^1$ is 3-methoxycarbonylphenyl, $R^2$ is 4-fluoro-3-trifluoromethylphenylmethyl, $R^3$, $R^4$, and $R^5$ are hydrogen, A is $CR^5$, and B is N;

a compound of formula (I) wherein G is S, Y is H, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-fluoroethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is 1-methoxyethyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 3,4-difluorophenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3,4-difluorophenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is H, $R^1$ is ethyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2-fluoro-pyridin-4-ylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 3,4-difluorophenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methoxymethyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is phenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is 2,5-dibromophenyl, $R^2$ is 3,4-difluorophenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is ethyl, $R^2$ is 2-fluoro-pyridin-4-ylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 2-fluoro-pyridin-4-ylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is ethyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 4-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is 1-methoxyethyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is ethyl, $R^2$ is 2,3,5-trifluoro-pyridin-4-ylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3,4-difluorophenyl, $R^2$ is 2-fluoroethyl, $R^3$, $R^4$, $R^5$, and $R^6$ are hydrogen, A is $CR^5$, and B is $CR^6$;

a compound of formula (I) wherein G is S, Y is H, $R^1$ is 4-methoxycarbonylphenyl, $R^2$ is 3-fluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-methoxycarbonylphenyl, $R^2$ is 2-fluoroethyl, $R^3$, $R^4$, $R^5$, and $R^6$ are hydrogen, A is $CR^5$, and B is $CR^6$;

a compound of formula (I) wherein G is S, Y is H, $R^1$ is phenyl, $R^2$ is 2-fluoroethyl, $R^3$, $R^4$, $R^5$, and $R^6$ are hydrogen, A is $CR^5$, and B is $CR^6$;

a compound of formula (I) wherein G is S, Y is methyl, $R^1$ is 3-fluoro-4-(4-fluorophenylmethoxy)phenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-fluoro-4-(phenylmethoxy)phenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is H, R¹ is ethyl, R² is 2-fluoro-pyridin-4-ylmethyl, R³, R⁴, R⁵, and R⁶ are hydrogen, A is CR⁵, and B is CR⁶;

a compound of formula (I) wherein G is S, Y is methylcarbonyl, R¹ is ethyl, R² is 2-fluoro-pyridin-4-ylmethyl, R³, R⁴, R⁵, and R⁶ are hydrogen, A is CR⁵, and B is CR⁶;

a compound of formula (I) wherein G is S, Y is bromo, R¹ is n-butylamino, R² is n-butyl, R³, R⁴, R⁵, and R⁶ are hydrogen, A is CR⁵, and B is CR⁶;

a compound of formula (I) wherein G is S, Y is H, R¹ is n-butylamino, R² is n-butyl, R³, R⁴, R⁵, and R⁶ are hydrogen, A is CR⁵, and B is CR⁶;

or a pharmaceutically acceptable salt form thereof.

A further embodiment of the present invention is directed to compounds of formula (I) wherein the compounds have a formula selected from the group consisting of a) Cpd 306

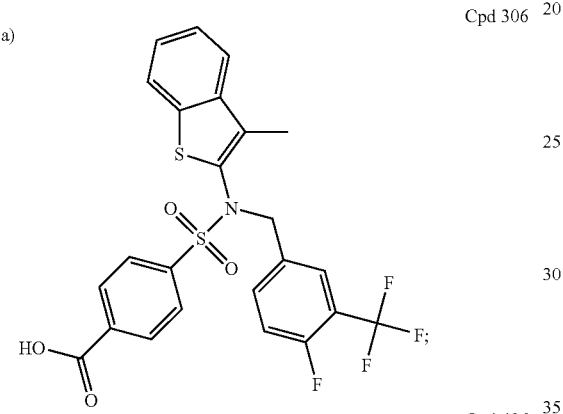

b) Cpd 496

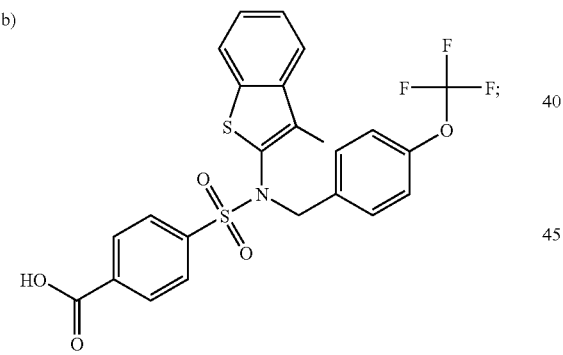

c) Cpd 777

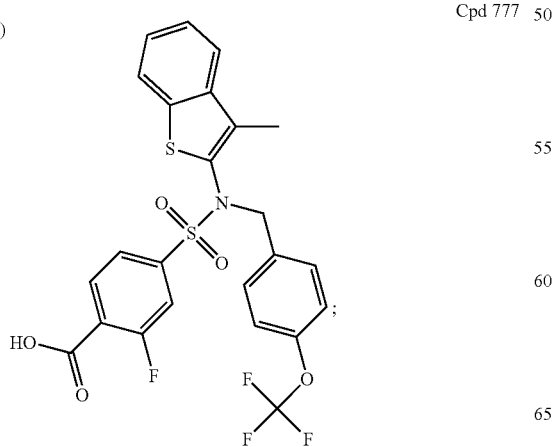

d) Cpd 788

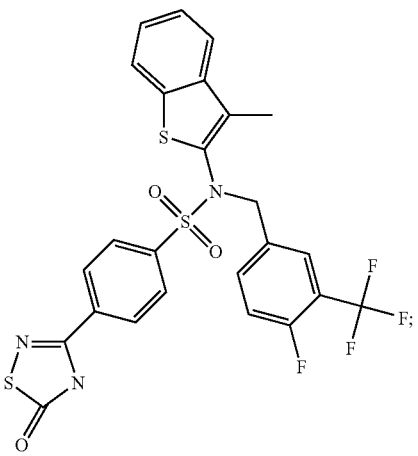

e) Cpd 810 f) Cpd 813

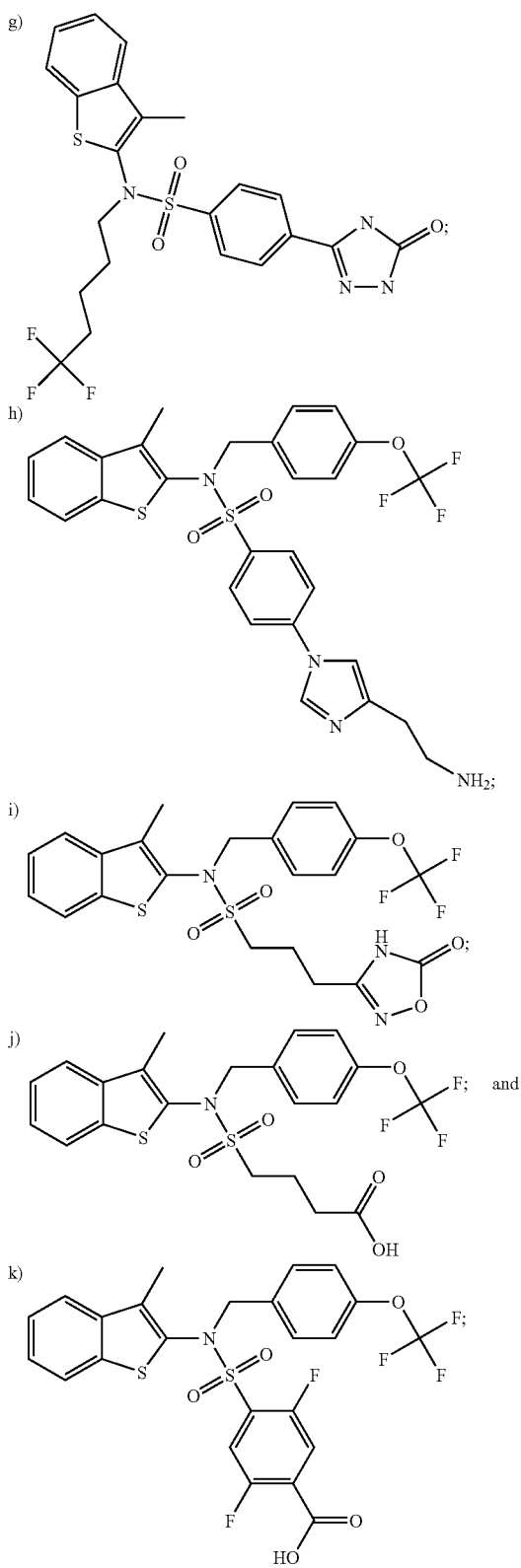

Cpd 815 or a pharmaceutically acceptable salt form thereof.

For use in medicine, salts of compounds of formula (I) refer to non-toxic "pharmaceutically acceptable salts." Other salts may, however, be useful in the preparation of compounds of formula (I) or of their pharmaceutically acceptable salts thereof. Suitable pharmaceutically acceptable salts of compounds of formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, (x-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholin, piperazine, potassium hydroxide, 1-(2-hydroxyethyl)-pyrrolidine, secondary amine, sodium hydroxide, triethanolamine, tromethamine and zinc hydroxide.

Embodiments of the present invention include prodrugs of compounds of formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula I.

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+) - \text{enantiomer} = \frac{(mass(+) - \text{enantiomer})}{(mass(+) - \text{enantiomer}) + (mass(-) - \text{enantiomer})} \times 100$$

Another embodiment of the present invention is a composition, including a pharmaceutical composition, comprising, consisting of, and consisting essentially of the (−)-enantiomer of a compound of formula (I) wherein said composition is substantially free from the (+)-isomer of said compound. In the present context, substantially free means less than about 25%, preferably less than about 10%, more preferably less than about 5%, even more preferably less than about 2% and even more preferably less than about 1% of the (+)-isomer calculated as $$\%(-) - \text{enantiomer} = \frac{(mass(-) - \text{enantiomer})}{(mass(+) - \text{enantiomer}) + (mass(-) - \text{enantiomer})} \times 100$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of formula (I) and at least one pharmaceutically acceptable carrier, pharmaceutically acceptable excipient, and/or pharmaceutically acceptable diluent By way of example, in the pharmaceutical compositions of embodiments of the present invention, the compounds of formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include exilirs, solutions, syrups, and suspensions; each optionally containing flavoring agents and coloring agents.

Alternatively, compounds of formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of formula (I) or a pharmaceutical composition thereof includes a dose range from about 0.1 mg to about 3000 mg, in particular from about 1 mg to about 1000 mg or, more particularly, from about 10 mg to about 500 mg of active ingredient in a regimen of about 1 to 4 times per day for an average (70 kg) human; although, it is apparent to one skilled in the art that the therapeutically effective amount for active compounds of the invention will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of the inventive compound as the active ingredient.

Advantageously, a compound of formula (I) may be administered in a single daily dose, or the total daily dosage may be administered in divided doses of two, three and four times daily.

Optimal dosages of a compound of formula (I) to be administered may be readily determined and will vary with the particular compound used, the mode of administration, the strength of the preparation, and the advancement of the disease, syndrome, condition, or disorder. In addition, factors associated with the particular subject being treated, including subject age, weight, diet and time of administration, will result in the need to adjust the dose to achieve an appropriate therapeutic level. The above dosages are thus exemplary of the average case. There can be, of course, individual instances wherein higher or lower dosage ranges are merited, and such are within the scope of this invention.

Compounds of formula (I) may be administered in any of the foregoing compositions and dosage regimens or by means of those compositions and dosage regimens established in the art whenever use of a compound of formula (I) is required for a subject in need thereof.

As antagonists of the TRPM8 ion channel, the compounds of formula (I) are useful in methods for treating and preventing a disease, a syndrome, a condition, or a disorder in a subject, including an animal, a mammal and a human in which the disease, the syndrome, the condition, or the disorder is affected by the modulation of TRPM8 receptors. Such methods comprise, consist of, and consist essentially of administering to a subject, including an animal, a mammal, and a human in need of such treatment or prevention a therapeutically effective amount of a compound, salt, or solvate of formula (I). In particular, the compounds of formula (I) are useful for preventing or treating pain, or diseases, syndromes, conditions, or disorders causing such pain, or pulmonary or vascular dysfunction. More particularly, the compounds of formula (I) are useful for preventing or treating inflammatory pain, inflammatory hypersensitivity conditions, neuropathic pain, anxiety, depression, and cardiovascular disease aggravated by cold, including peripheral vascular disease, vascular hypertension, pulmonary hypertension, Raynaud's disease, and coronary artery disease, by administering to a subject in need thereof a therapeutically effective amount of a compound of formula (I).

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis.

One type of inflammatory pain is inflammatory hyperalgesia, which can be further distinguished as inflammatory somatic hyperalgesia or inflammatory visceral hyperalgesia. Inflammatory somatic hyperalgesia can be characterized by the presence of an inflammatory hyperalgesic state in which a hypersensitivity to thermal, mechanical and/or chemical stimuli exists. Inflammatory visceral hyperalgesia can also be characterized by the presence of an inflammatory hyperalgesic state, in which an enhanced visceral irritability exists.

Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease or ulcerative colitis.

One embodiment of the present invention is directed to a method for treating inflammatory somatic hyperalgesia in which a hypersensitivity to thermal, mechanical and/or chemical stimuli exists, comprising the step of administering to a mammal in need of such treatment a therapeutically effective amount of a compound, salt or solvate of formula (I).

A further embodiment of the present invention is directed to a method for treating inflammatory visceral hyperalgesia in which a enhanced visceral irritability exists, comprising, consisting of, and/or consisting essentially of the step of administering to a subject in need of such treatment a therapeutically effective amount of a compound, salt or solvate of formula (I).

A further embodiment of the present invention is directed to a method for treating neuropathic cold allodynia in which a hypersensitivity to a cooling stimuli exists, comprising, consisting of, and/or consisting essentially of the step of administering to a subject in need of such treatment a therapeutically effective amount of a compound, salt or solvate of formula (I).

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS J/JJ) and radiculopathy.

Examples of anxiety include social anxiety, post traumatic stress disorder, phobias, social phobia, special phobias, panic disorder, obsessive compulsive disorder, acute stress, disorder, separation anxiety disorder, and generalized anxiety disorder.

Examples of depression include major depression, bipolar disorder, seasonal affective disorder, post natal depression, manic depression, and bipolar depression.

General Synthetic Methods

Representative compounds of the present invention can be synthesized in accordance with the general synthetic methods described below and illustrated in the schemes that follow. Since the schemes are an illustration, the invention should not be construed as being limited by the specific chemical reactions and specific conditions described in the schemes and examples. The various starting materials used in the schemes are commercially available or may be prepared by methods well within the skill of persons versed in the art. The variables are as defined herein and within the skill of persons versed in the art.

Abbreviations used in the instant specification, particularly the schemes and examples, are as follows:

| | |
|---|---|
| AcCl | acetyl chloride |
| AcOH | glacial acetic acid |
| Bn or Bzl | benzyl |
| DBU | 1,8-diazabicyclo[5.4.0]undec-7-ene |
| DCC | dicyclohexylcarbodiimide |
| DCE | 1,2-dichloroethane |
| DCM | dichloromethane |
| DEAD | diethyl azodicarboxylate |
| DIEA | diisopropyl-ethyl amine |
| DMAP | 4-(dimethylamino)pyridine |
| DMF | N,N-dimethylformamide |
| DMSO | dimethylsulfoxide |
| DPPA | diphenylphosphoryl azide |
| EDC | 1-ethyl-3-(3-dimethylaminopropyl) carbodiimide hydrochloride |
| ESI | electron-spray ionization |
| EtOAc | ethyl acetate |
| EtOH | ethanol |
| h | hour |
| HATU | 2-(1H-7-azabenzotriazol-1-yl)-1,1,3,3-tetramethyl uranium hexafluorophosphate methanaminium |
| HBTU | O-benzotriazole-N,N,N',N'-tetramethyl uronium hexafluorophosphate |
| HEK | human embryonic kidney |
| HPLC | high performance liquid chromatography |
| LHMDS | lithium bis(trimethylsilyl)amide |
| mCPBA | meta-chloroperbenzoic acid |
| Me | methyl |
| MeOH | methanol |
| MHz | megahertz |
| min | minutes |
| MS | mass spectroscopy |
| NaHMDS | sodium bis(trimethylsilyl)amide |
| NBS | N-bromosuccinimide |
| NCS | N-chlorosuccinimide |
| NMR | nuclear magnetic resonance |
| NT | not tested |
| PCC | pyridinium chlorochromate |
| Ph | phenyl |
| Pd/C | palladium on activated carbon |
| $Pd_2(dba)$ | [tris(dibenzylideneacetone)dipalladium (0)] |
| $Ph_3P$ | triphenylphosphine |
| PPA | polyphosphoric acid |
| rt | room temperature |
| TCDI | 1,1'-thiocarbonyldiimidazole |
| $TEA/Et_3N$ | triethylamine |
| TFA | trifluoroacetic acid |
| THF | tetrahydrofuran |
| TMS | tetramethylsilane |
| TMSCN | trimethylsilyl cyanide |

Scheme A illustrates a route for the synthesis of compounds of formula (I)-A wherein A and B are $C(R^5)$ and $C(R^6)$, respectively; G is S; Y is hydrogen, alkyl, chloro, trifluoromethyl, $C_{1-3}$ alkoxy, $C_{3-6}$ cycloalkyl, aryl, heteroaryl, or benzo-fused heteroaryl; and $R^1$, $R^2$, $R^3$, $R^4$, $R^5$, and $R^6$ are as defined herein.

Scheme A

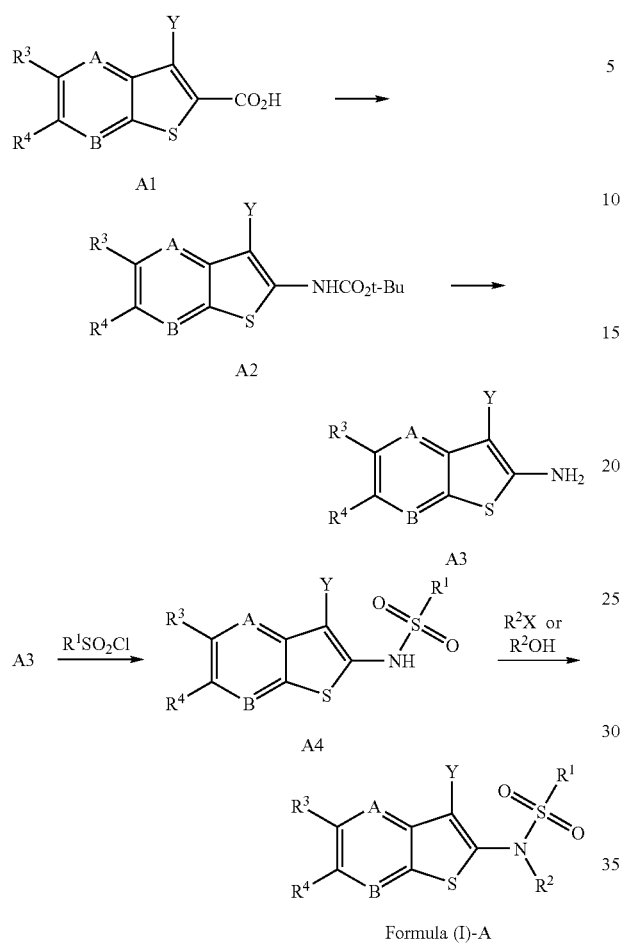

Formula (I)-A

A compound of the formula A1 is either commercially available or may be prepared by known methods described in the scientific literature. A compound of the formula A1 may be converted to a compound of the formula A2 using diphenylphosphoryl azide, tert-butanol and an organic base. A compound of the formula A2 may be converted to the corresponding amine, a compound of the formula A3, by the action of HCl or another mineral acid, or by the action of an organic acid, such as trifluoroacetic acid. A compound of the formula A3 may be treated with an appropriately substituted sulfonyl chloride in the presence of a base, and optionally in the presence of an aprotic organic solvent, to afford a compound of the formula A4. A compound of the formula A4 may be treated with a base such as sodium hydride, lithium bis(trimethylsilyl)amide, n-butyllithium or potassium tert-butoxide followed by alkylation with a compound of the formula, $R^2X$, where X is a leaving group such as bromo, chloro, iodo, tosylate, mesylate, and the like, to afford a compound of the formula (I)-A. Alternatively, a compound of the formula A4 may be treated with a triarylphosphine such as triphenylphosphine, tri-o-tolylphosphine, tri-2-furylphosphine and the like; a $C_{1-6}$ dialkyl azodicarboxylate such as diethyl-, diisopropyl-, or di-t-butyl-azodicarboxylate, and the like; and an appropriately substituted alcohol, $R^2OH$, to afford a compound of the formula (I)-A.

Scheme B illustrates a route for the synthesis of compounds of formula (I)-B wherein A and B are $C(R^5)$ and $C(R^6)$, respectively; G is S; Y is hydrogen, alkyl, or chloro; and $R^1$, $R^2$, $R^3$, $R^4$, $R^5$, and $R^6$ are as defined herein.

Scheme B

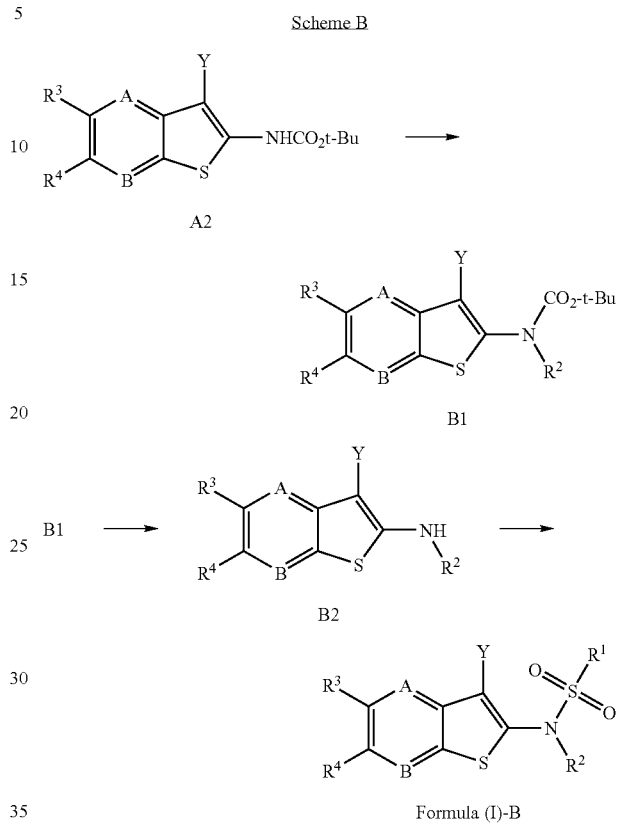

Formula (I)-B

A compound of the formula A2 may be treated with a base such as sodium hydride, lithium bis(trimethylsilyl)amide, n-butyllithium or potassium tert-butoxide followed by alkylation with a compound of the formula, $R^2X$, where X is a leaving group such as bromo, chloro, iodo, tosylate or mesylate, to afford a compound of the formula B1. A compound of the formula B1 may be converted to the corresponding amine, a compound of the formula B2, by the action of HCl or another mineral acid, or by the action of an organic acid, such as trifluoroacetic acid. A compound of the formula B2 may be treated with an appropriately substituted sulfonyl chloride or trifluoromethylsulfonic anhydride in the presence of a base to afford a compound of the formula (I)-B.

Scheme C illustrates a route for the synthesis of compounds of formula (I)-C wherein $Y_C$ is chloro, bromo, or iodo; A and B are $C(R^5)$ and $C(R^6)$, respectively; G is S; and $R^1$, $R^2$, $R^3$, $R^4$, $R^5$, and $R^6$ are as defined herein.

Scheme C

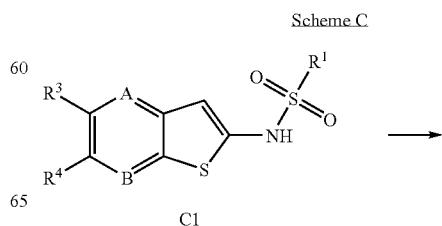

C1

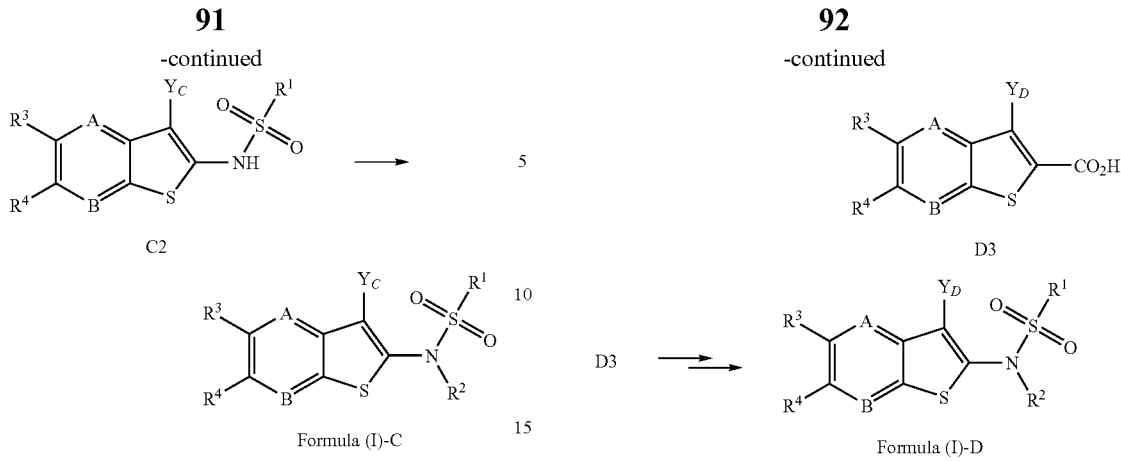

A compound of the formula C1, prepared using chemistry described in scheme A may be converted to a compound of the formula C2, wherein $Y_C$ is chloro, bromo or iodo, by the action of appropriate reagents. For example, treatment of a compound of the formula C1 with N-chlorosuccinimide, chlorine, or sulfuryl chloride affords a compound of the formula C2 wherein $Y_C$ is chloro; similarly, treatment of a compound of the formula C1 with N-bromosuccinimide or bromine affords a compound of the formula C2 wherein $Y_C$ is bromo; and treatment with N-iodosuccinimide or iodine affords a compound of the formula C2 wherein $Y_C$ is iodo. A compound of the formula C2 may be treated with a base such as sodium hydride, lithium bis(trimethylsilyl)amide, n-butyllithium or potassium tert-butoxide followed by alkylation with a compound of the formula, $R^2X$, where X is a leaving group, such as bromo, chloro, iodo, tosylate, mesylate, and the like, to afford a compound of the formula (I)-C. Alternatively, a compound of formula C2 may be treated with a triarylphosphine such as triphenylphosphine, tri-o-tolylphosphine, tri-2-furylphosphine and the like; a $C_{1-6}$ dialkyl azodicarboxylate such as diethyl-, diisopropyl-, and di-t-butyl-azodicarboxylate, and the like; and an appropriately substituted alcohol, $R^2OH$, to afford a compound of the formula (I)-C.

Scheme D illustrates a route for the synthesis of compounds of formula (I)-D wherein G is S; $Y_D$ is hydrogen or alkyl; and A, B, $R^1$, $R^2$, $R^3$ and $R^4$ are as defined herein.

Scheme D

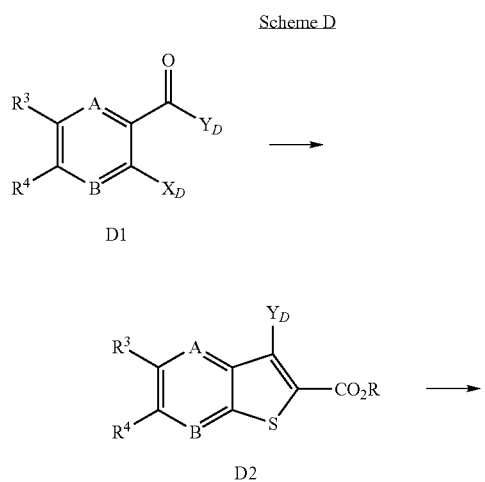

A compound of the formula D1 is either commercially available or may be prepared by known methods described in the scientific literature. A compound of the formula D1, wherein $X_D$ is chloro or fluoro and $Y_D$ is hydrogen or alkyl, may be reacted with an R-substituted thioglycolate (wherein R is $C_{1-6}$alkyl) in the presence of base to afford a compound of the formula D2, which may be saponified to afford a compound of the formula D3 using conventional chemistry known to one skilled in the art. Using synthetic methods outlined in scheme A, a compound of the formula D3 may be converted to compounds of the formula (I)-D.

Scheme E illustrates a route for the synthesis of compounds of the formula (I)-E wherein $Y_E$ is chloro or bromo; A is nitrogen, B is $C(R^6)$; G is S; and $R^1$, $R^2$, $R^3$, $R^4$ and $R^6$ are as defined herein.

Scheme E

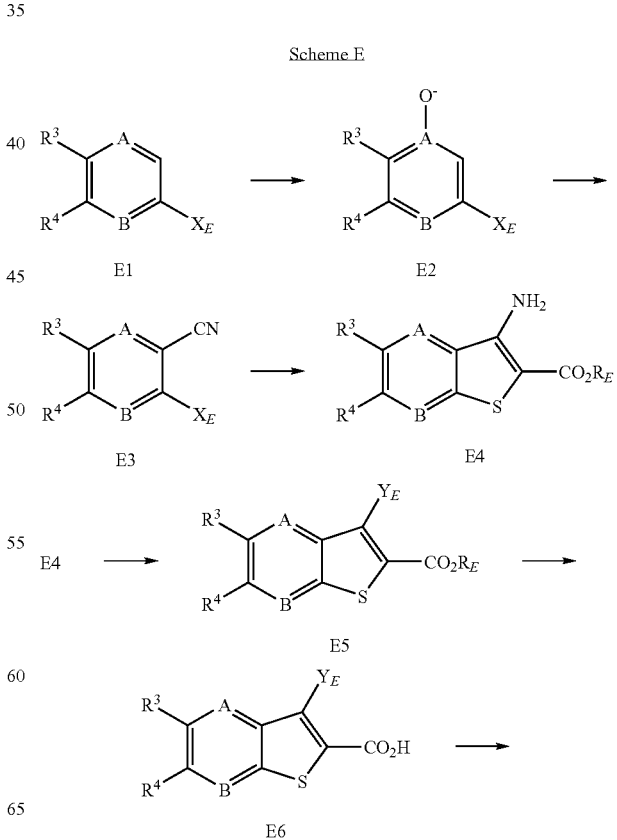

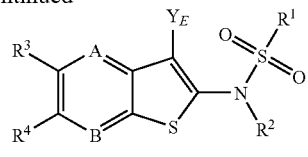

Formula (I)-E

A compound of the formula E1, wherein $X_E$ is a suitable leaving group such as bromo, chloro, iodo, tosylate, mesylate, or the like, is either commercially available or may be prepared by known methods described in the scientific literature. A compound of the formula E1 may be treated with a suitable oxidizing agent, such as peroxide, peracetic acid or meta-chloroperbenzoic acid, using methods known to one skilled in the art, to afford a compound of the formula E2. A compound of the formula E2 may be converted to a compound of the formula E3 using trimethylsilyl cyanide in the presence of a base. A compound of the formula E3 may be reacted with an ($R_E$)-substituted thioglycolate, wherein $R_E$ is $C_{1-6}$ alkyl, in the presence of a base to afford a compound of the formula E4. A compound of the formula E4 may be treated with sodium nitrite or potassium nitrite in the presence of copper (I) chloride and hydrogen chloride to afford a compound of the formula E5 wherein $Y_E$ is chloro; or, in the presence of copper (I) bromide and hydrogen bromide to afford a compound of the formula E5 wherein $Y_E$ is bromo. A compound of the formula E5 may be saponified to the corresponding carboxylic acid of a compound of the formula E6 using conventional chemistry known to one skilled in the art. Using the chemistry outlined in scheme A, a compound of the formula E6 may be converted to a compound of the formula (I)-E.

Scheme F illustrates a route for the synthesis of compounds of the formula (I)-F wherein A is nitrogen, B is C($R^6$); G is S; Y is hydrogen; and $R^1$, $R^2$, $R^3$, $R^4$ and $R^6$ are as defined herein.

Scheme F

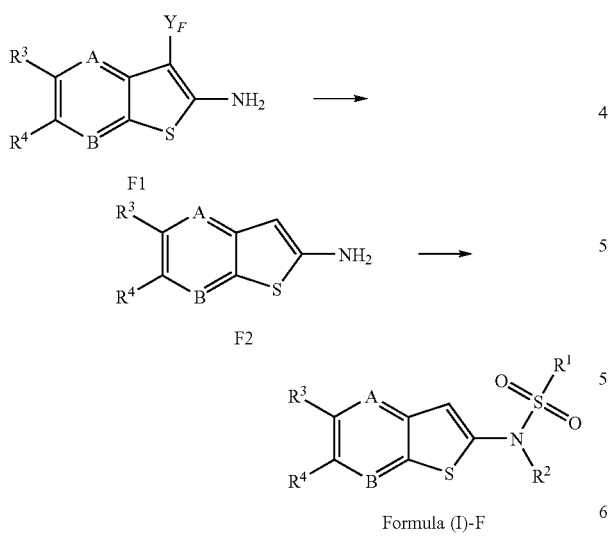

Formula (I)-F

A compound of the formula F1 (wherein $Y_F$ is chloro or bromo) may be prepared from a compound of the formula E6 using the synthetic methods described herein for the conversion of a compound of the formula A1 to a compound of the formula A3. A compound of the formula F1 may be converted to a compound of the formula F2 by the action of a palladium catalyst, in the presence of hydrogen gas or a source of hydrogen such as 1,3-cyclohexadiene or ammonium formate. Using the chemistry outlined in scheme A, a compound of the formula F2 may be converted to a compound of the formula (I)-F.

Scheme G illustrates a route for the synthesis of compounds of the formula (I)-G wherein $Y_G$ is bromo, chloro or iodo; G is S; and A, B, $R^1$, $R^2$, $R^3$ and $R^4$ are as defined herein.

Scheme G

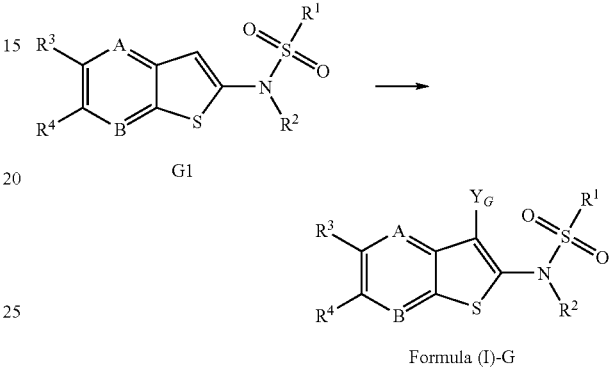

Formula (I)-G

A compound of the formula G1 may be converted to a compound of the formula (I)-G by the action of reagents such as N-chlorosuccinimide, chlorine, or sulfuryl chloride to afford a compound of the formula (I)-G, wherein $Y_G$ is chloro. Likewise, a compound of the formula (I)-G, wherein $Y_G$ is bromo, may be afforded by the action of N-bromosuccinimide or bromine; and a compound of the formula (I)-G, wherein $Y_G$ is iodo, may be afforded by the action of N-iodosuccinimide or iodine.

Scheme H illustrates a route for the synthesis of compounds of the formula (I)-H wherein G is S; Y is cyano and A, B, $R^1$, $R^2$, $R^3$ and $R^4$ are as defined herein.

Scheme H

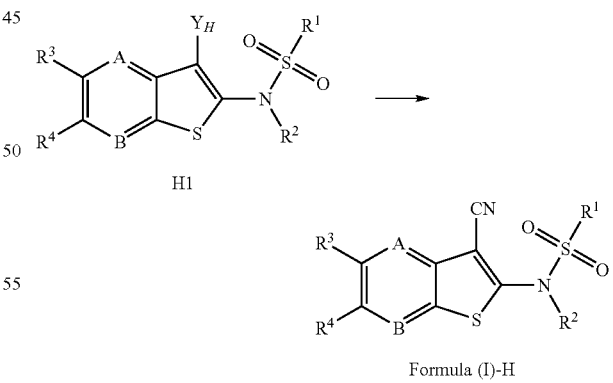

Formula (I)-H

A compound of the formula H1, wherein $Y_H$ is bromo or iodo, may be reacted with copper(I) cyanide to afford a compound of the formula (I)-H.

Scheme I illustrates a route for the synthesis of compounds of the formula (I)-I wherein G is S; Y, is a substituted aryl, heteroaryl, or benzo-fused heteroaryl as defined herein; and A, B, $R^1$, $R^2$, $R^3$ and $R^4$ are as defined in formula (I).

Scheme I

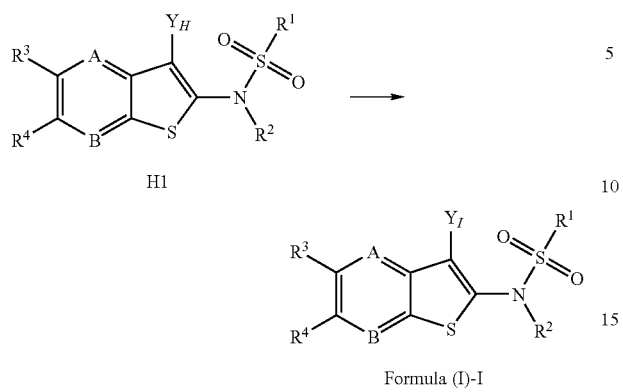

Formula (I)-I

A compound of the formula H1, wherein $Y_H$ is bromo or iodo, may be treated with an appropriately substituted aryl-, heteroaryl-, or benzo-fused heteroaryl-boronic acid or ester; in the presence of a palladium catalyst; and a base such as cesium carbonate, sodium bicarbonate, potassium fluoride, and the like; to afford a compound of the formula (I)-I.

Scheme J illustrates a route for the synthesis of compounds of formula (I)-J wherein A and B are $C(R^5)$ and $C(R^6)$, respectively; G is S; $R_J$ is $C_{1-6}$ alkyl, $C_{3-6}$ cycloalkyl, or aryl; $R^1$ and $R^2$ are other than a nitrogen-containing heteroaryl, and wherein $R^3$, $R^4$, $R^5$, and $R^6$ are as defined herein. One skilled in the art will recognize that conventional protection and deprotection steps may be required for certain chemical groups of $R_1$ and $R_2$ that are sensitive to the reaction conditions described in Scheme J.

Scheme J

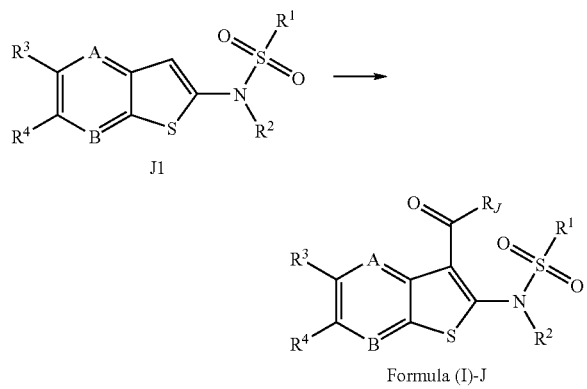

Formula (I)-J

A compound of the formula J1, prepared using chemistry described in scheme C, may be converted to a compound of the formula (I)-J by the action of an $R_J$-substituted acid chloride and a Lewis acid, such as tin(IV) chloride or aluminum (III) chloride or other reagents and methods known to one skilled in the art.

Scheme K illustrates an alternate route to compounds of the formula (I)-J, wherein A and B are $C(R^5)$ and $C(R^6)$, respectively; G is S; $R_J$ is $C_{1-6}$ alkyl, $C_{3-6}$ cycloalkyl, or aryl; $R^1$ and $R^2$ are other than a nitrogen-containing heteroaryl; and wherein $R^3$, $R^4$, $R^5$, and $R^6$ are as defined herein.

Scheme K

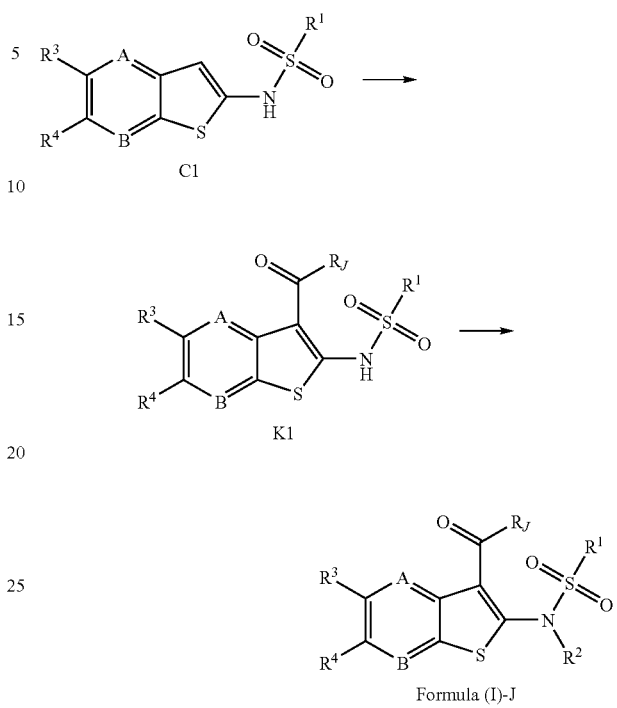

Formula (I)-J

A compound of the formula C1 may be treated with an $R_J$-substituted acid chloride and a Lewis acid such as tin(IV) chloride or aluminum(III) chloride, to afford a product of the formula K1. A compound of the formula K1 may be treated with a base, such as sodium hydride, lithium bis(trimethylsilyl)amide, n-butyllithium or potassium tert-butoxide, followed by alkylation with a compound of the formula $R^2X$, defined herein, to afford a compound of the formula (I)-J. Alternatively, a compound of formula K1 may be treated with a triarylphosphine such as triphenylphosphine, tri-o-tolylphosphine, tri-2-furylphosphine and the like; a $C_{1-6}$ dialkyl azodicarboxylate such as diethyl-, diisopropyl-, or di-t-butyl-azodicarboxylate, and the like; and an appropriately substituted alcohol, $R^2OH$, to afford a compound of the formula (I)-J.

Scheme L illustrates a route for the synthesis of compounds of the formula (I)-L wherein A and B are $C(R^5)$ and $C(R^6)$, respectively; G is S; $R^1$ and $R^2$ are other than a nitrogen-containing heteroaryl; and $R^3$, $R^4$, $R^5$, and $R^6$ are as defined herein. One skilled in the art will recognize that conventional protection and deprotection steps may be required for certain chemical groups of $R_1$ and $R_2$ that are sensitive to the reaction conditions described in Scheme L.

Scheme L

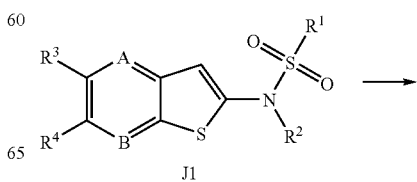

-continued

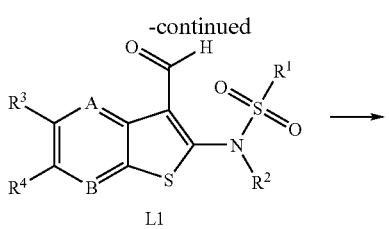
L1

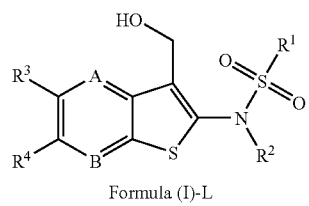
Formula (I)-L

A compound of the formula J1 may be treated with dichloromethyl methyl ether and a Lewis acid such as titanium(IV) chloride, to afford a compound of the formula L1. A compound of the formula L1 may be converted to a compound of the formula (I)-L using a reducing agent such as borane, sodium borohydride, lithium borohydride, and the like, to effect reduction of an aldehyde to an alcohol.

Scheme M illustrates a route for the synthesis of compounds of the formula (I)-M wherein $R_M$ is $C_{1-5}$alkyl or $C_{6-10}$aryl; A and B are $C(R^5)$ and $C(R^6)$, respectively; G is S; $R^1$ and $R^2$ are other than a nitrogen-containing heteroaryl; and $R^3$, $R^4$, $R^5$, and $R^6$ are as defined herein. One skilled in the art will recognize that conventional protection and deprotection steps may be required for certain chemical groups of $R^1$ and $R^2$ that are sensitive to the reaction conditions described in Scheme M.

Scheme M

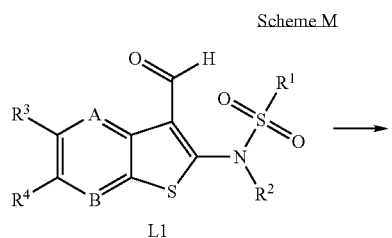
L1

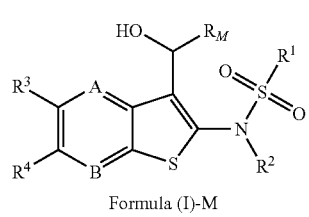
Formula (I)-M

A compound of the formula L1 may be treated with a metal-alkyl compound, such as $C_{1-5}$alkylmagnesium bromide, $C_{1-5}$alkylzinc chloride or $C_{1-5}$alkyllithium, to afford a compound of the formula (I)-M wherein $R_M$ is $C_{1-5}$alkyl. Similarly, a compound of the formula L1 may be treated with an metal-aryl compound, such as $C_{6-10}$arylmagnesium bromide, $C_{6-10}$arylzinc chloride or $C_{6-10}$aryllithium, to afford a compound of the formula (I)-M wherein $R_M$ is $C_{6-10}$aryl.

Scheme N illustrates an alternate route to the compounds of the formula (I)-M wherein $R_M$ is $C_{1-5}$alkyl. In formula (I)-N, A and B are $C(R^5)$ and $C(R^6)$, respectively; G is S; $R^1$ and $R^2$ are other than a nitrogen-containing heteroaryl; and $R^3$, $R^4$, $R^5$, and $R^6$ are as defined herein. One skilled in the art will recognize that conventional protection and deprotection steps may be required for certain chemical groups of $R_1$ and $R_2$ that are sensitive to the reaction conditions described in Scheme N.

Scheme N

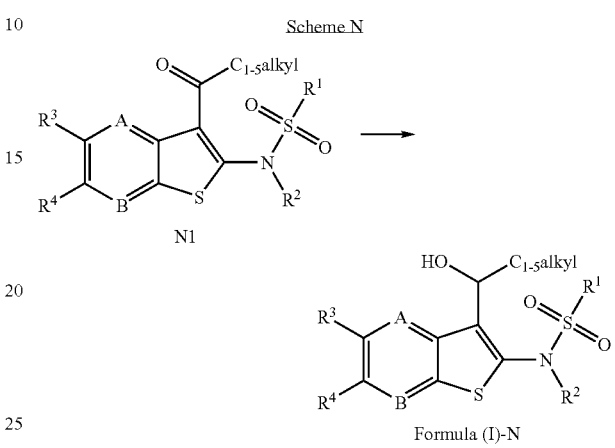

A compound of the formula N1 may be converted to a compound of the formula (I)-N using reagents such as borane, sodium borohydride, lithium borohydride, and the like, to effect reduction of a ketone to an alcohol.

Scheme O illustrates a route for the synthesis of compounds of the formula (I)-O wherein A and B are $C(R^5)$ and $C(R^6)$, respectively; G is S; $R^1$ and $R^2$ are other than a nitrogen-containing heteroaryl; and $R^3$, $R^4$, $R^5$, and $R^6$ are as defined herein. One skilled in the art will recognize that added conventional protection and deprotection steps may be required for certain chemical groups of $R^1$ and $R^2$ that are sensitive to the reaction conditions described in Scheme O.

Scheme O

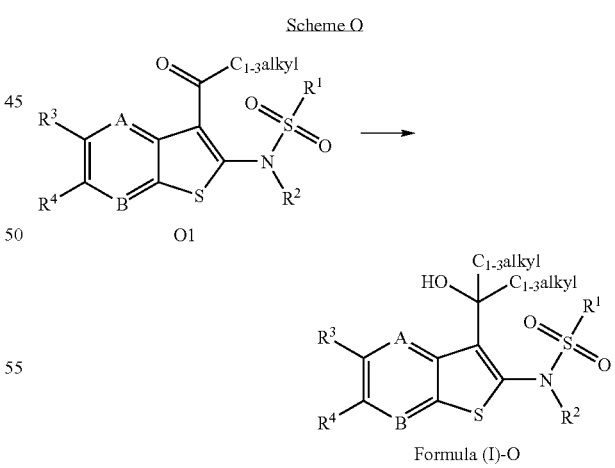

A compound of the formula O1 may be treated with a metal-$C_{1-3}$alkyl compound, such as $C_{1-3}$alkylmagnesium bromide, $C_{1-3}$alkylzinc chloride or $C_{1-3}$alkyllithium, to afford a compound of the formula (I)-O.

Scheme P illustrates a route for the synthesis of compounds of formula (I)-P wherein G is S; and Y, A, B, $R^2$, $R^3$ and $R^4$ are as defined herein.

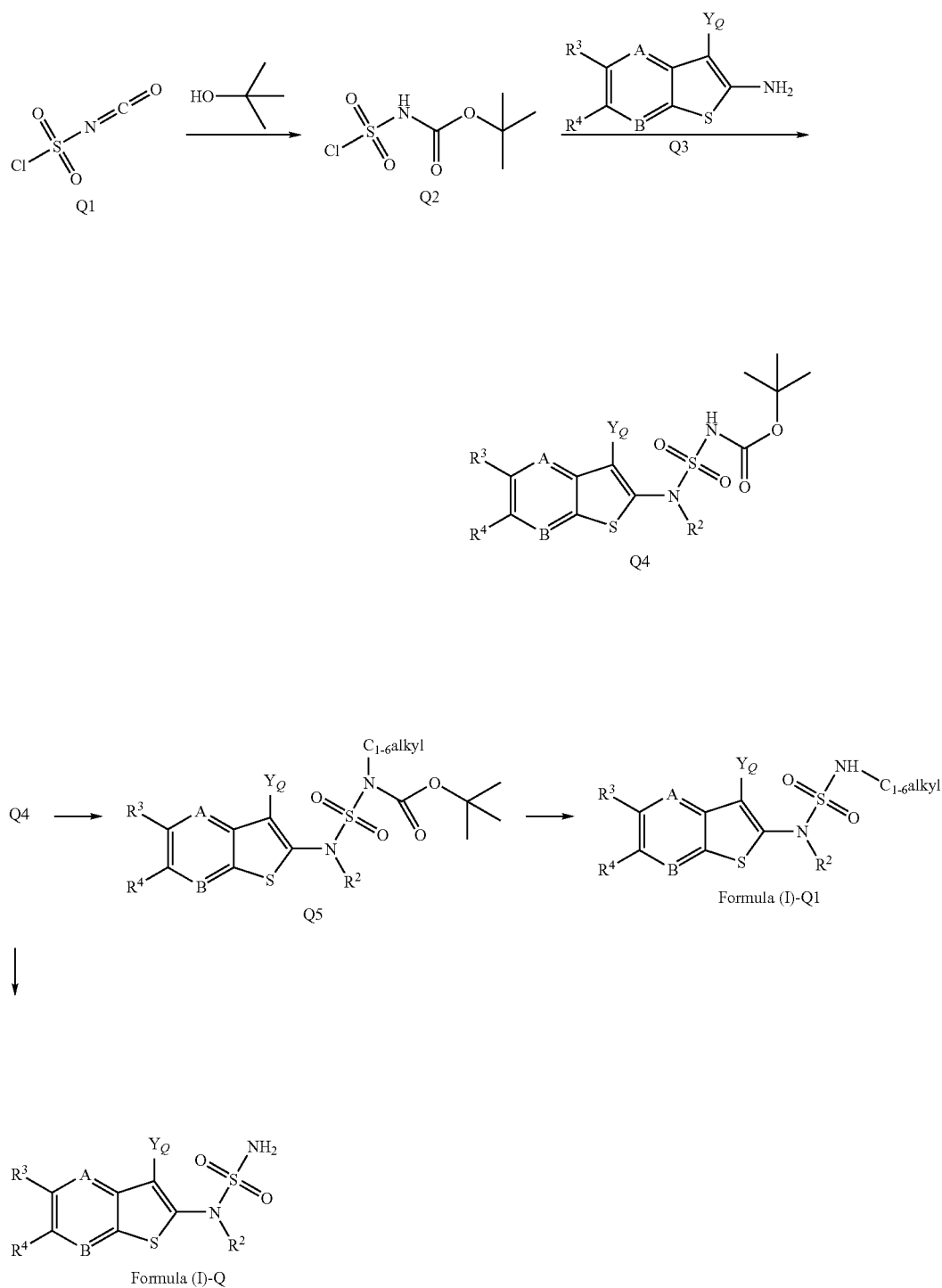

Chlorosulfonyl isocyanate, compound Q1, may be treated with tert-butanol to afford compound Q2, which may be reacted with a compound of the formula Q3 to afford a compound of the formula Q4. A compound of the formula Q4 may be converted to the corresponding amine, a compound of the formula (I)-Q, by the action of HCl or another mineral acid, or by the action of an organic acid, such as trifluoroacetic acid. Alkylation of a compound of the formula Q4 using a conventional alkylating agent such as $C_{1-6}$alkyl halide or $C_{1-6}$alkyl tosylate, in the presence of a base such as sodium hydride, affords a compound of the formula Q5 which, upon amino deprotection, affords a compound of the formula (I)-Q1.

Scheme R illustrates a route for the synthesis of compounds of the formula (I)-R and formula (I)-R1 wherein $Y_R$ is chloro, bromo or iodo; G is S; $R^1$ is amino or $C_{1-6}$ alkylamino, respectively; and A, B, $R^2$, $R^3$ and $R^4$ are as defined herein.

Scheme P

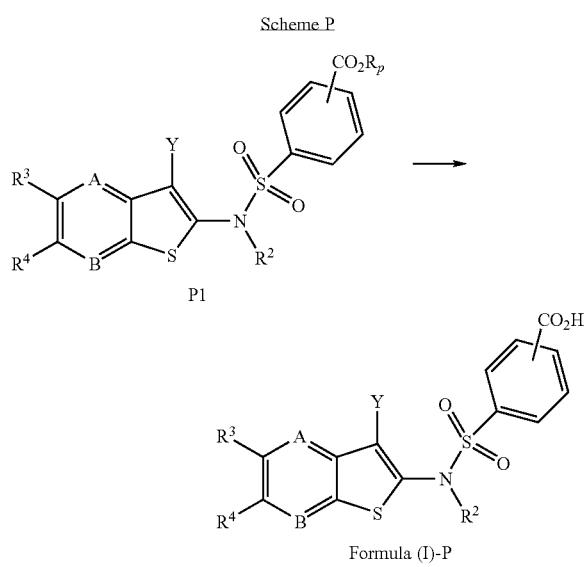

A compound of the formula P1 (wherein $R_p$ is $C_{1-4}$ alkyl) may be prepared using chemistry described in scheme A. A compound of the formula P1 may be converted to a compound of the formula (I)-P by the action of agents such as hydroxide, hydrochloric acid, trimethylsilyl iodide, or other reagents and conditions known to one skilled in the art, to effect the conversion of esters to carboxylic acids.

Scheme Q illustrates a route for the synthesis of compounds of the formula (I)-Q and formula (I)-Q1 wherein $Y_Q$ is hydrogen, $C_{1-6}$ alkyl, or chloro; G is S; and A, B, $R^2$, $R^3$ and $R^4$ are as defined herein.

A compound of the formula $R^1$ may be converted to a compound of the formula $R^2$, wherein $Y_R$ is chloro, bromo or iodo, using chemistry described in scheme C for the conversion of a compound of the formula C1 to a compound of the formula C2. A compound of the formula $R^2$ may be converted to a compound of the formula (I)-R, using chemistry described in scheme Q for the conversion of a compound of the formula Q4 to a compound of the formula (I)-Q. A compound of the formula $R^2$ may be alkylated using conventional alkylating agents and condition such as a $C_{1-6}$alkyl halide in the presence of TEA or pyridine to afford a compound of the formula $R^3$. Subsequent removal of the amino protecting group as described herein affords a compound of the formula (I)-R1.

Scheme S illustrates a route for the synthesis of compounds of formula (I)-S wherein $Y_{S2}$ is $C_{1-3}$dialkylamino, or a 5 or 6 membered heterocycle with 1 to 2 nitrogens, wherein the point of attachment is via a nitrogen atom; G is S; and A, B, $R^1$, $R^2$, $R^3$ and $R^4$ are as defined herein.

Scheme S

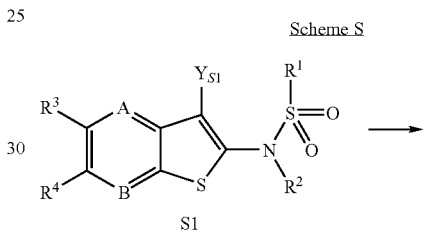

Scheme R

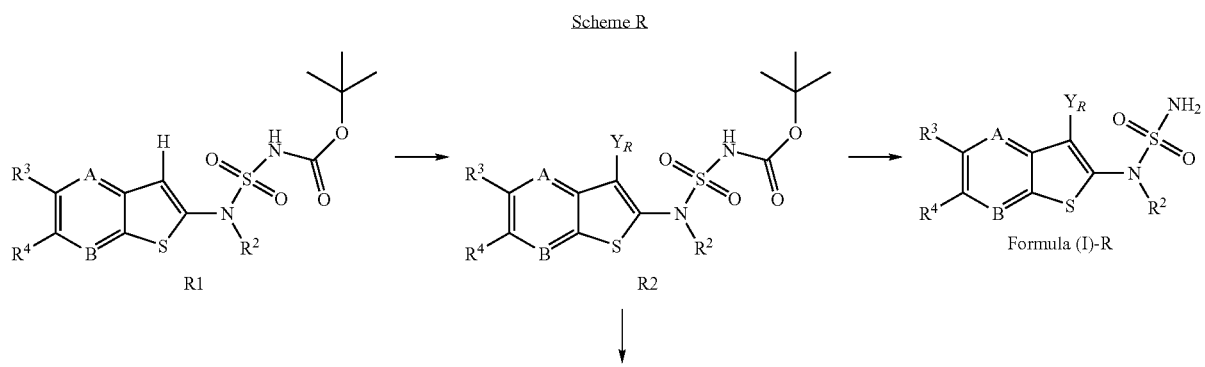

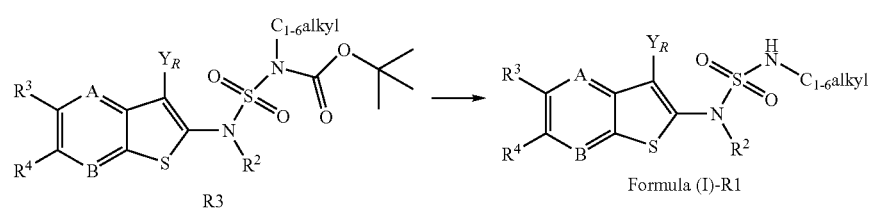

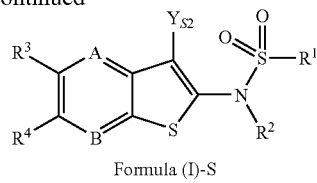

Formula (I)-S

A compound of the formula S1 wherein $Y_{S1}$ is bromo or iodo, may be converted to a compound of the formula (I)-S by the action of an appropriately substituted amine, in the presence of a palladium catalyst and a base.

Scheme T illustrates a route for the synthesis of compounds of formula (I)-T, wherein W is O or S; G is S; and A, B, Y, $R^2$, $R^3$ and $R^4$ are as defined herein.

Scheme T

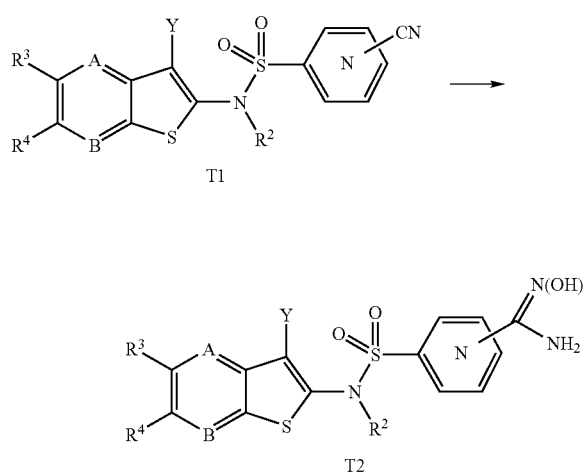

Formula (I)-T

= phenyl or pyridin-3-yl

A compound of the formula T1 may be treated with hydroxylamine hydrochloride, in the presence of a tertiary base such as triethylamine, to afford a compound of the formula T2. A compound of the formula T2 may be converted to a compound of the formula (I)-T by the reaction of either 1,1'-thiocarbonyldiimidazole (W=S) or 1,1'-carbonyldiimidazole (W=O).

Scheme U illustrates a route for the synthesis of compounds of formula (I)-U wherein G is S; and A, B, Y, $R^2$, $R^3$, and $R^4$ are as defined herein.

Scheme U

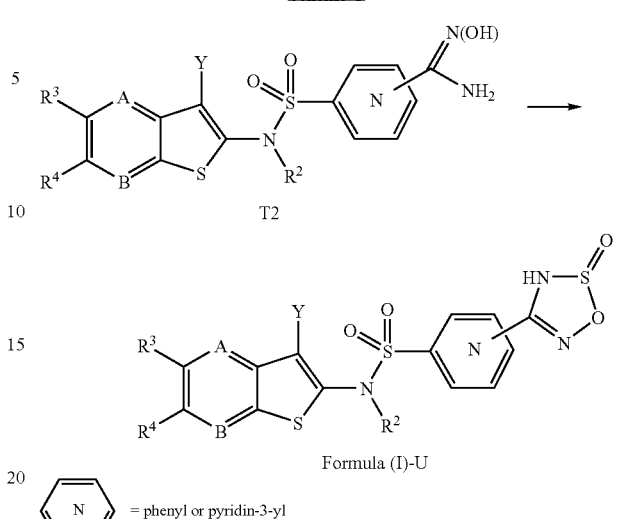

Formula (I)-U

= phenyl or pyridin-3-yl

A compound of the formula T2 may be treated with thionyl chloride, in the presence of a non-nucleophilic base, such as pyridine, to afford a compound of the formula (I)-U.

Scheme V illustrates a route for the synthesis of compounds of the formula (I)-V wherein G is S; and A, B, Y, $R^2$, $R^3$, and $R^4$ are as defined herein.

Scheme V

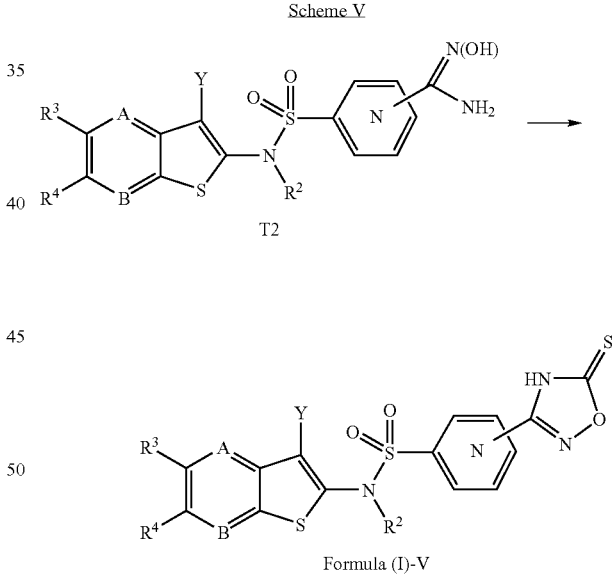

Formula (I)-V

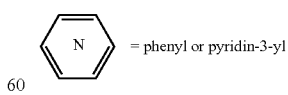
= phenyl or pyridin-3-yl

A compound of the formula T2 may be treated with a base, such as sodium hydride, in the presence of carbon disulfide, to afford a compound of the formula (I)-V.

Scheme W illustrates a route for the synthesis of compounds of formula (I)-W wherein G is S; and A, B, Y, $R^2$, $R^3$, $R^4$, $R^{13}$, and $R^{14}$ are as defined herein.

Scheme W

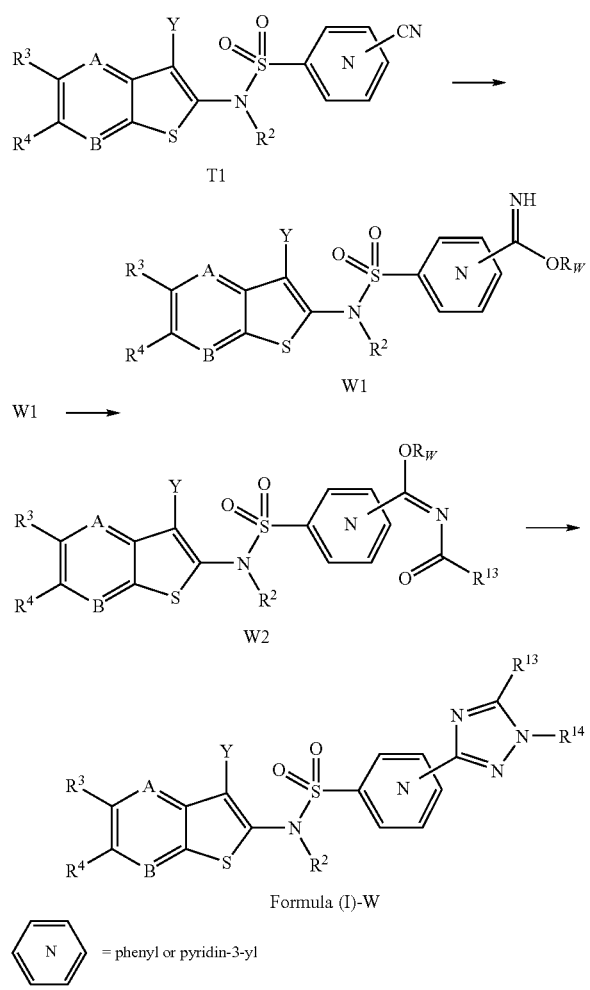

A compound of the formula T1, may be converted to a compound of the formula W1 wherein $R_W$ is methyl or ethyl, by treatment of a compound of the formula T1 with an alcohol, such as methanol or ethanol, in the presence of hydrochloric acid. A compound of the formula W1 may be treated with a base, such as triethylamine, in the presence of a $R^{13}$-substituted acid chloride, to afford a compound of the formula W2. Treatment of a compound of the formula W2 with a $R^{14}$-substituted hydrazine, may afford a compound of the formula (I)-W.

Scheme X illustrates a route for the synthesis of compounds of the formula (I)-X wherein G is S; and A, B, Y, $R^2$, $R^3$, $R^4$, and $R^{13}$ are as defined herein.

Scheme X

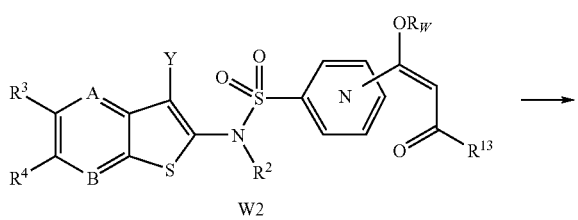

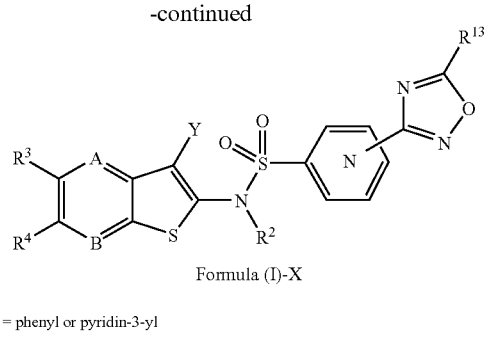

A compound of the formula W2 may be treated with a base, such as sodium methoxide, and in the presence of hydroxylamine hydrochloride, to afford a compound of the formula (I)-X.

Scheme Y illustrates a route for the synthesis of compounds of the formula (I)-Y wherein G is S; and A, B, Y, $R^2$, $R^3$, $R^4$, and $R^{14}$ are as defined herein.

Scheme Y

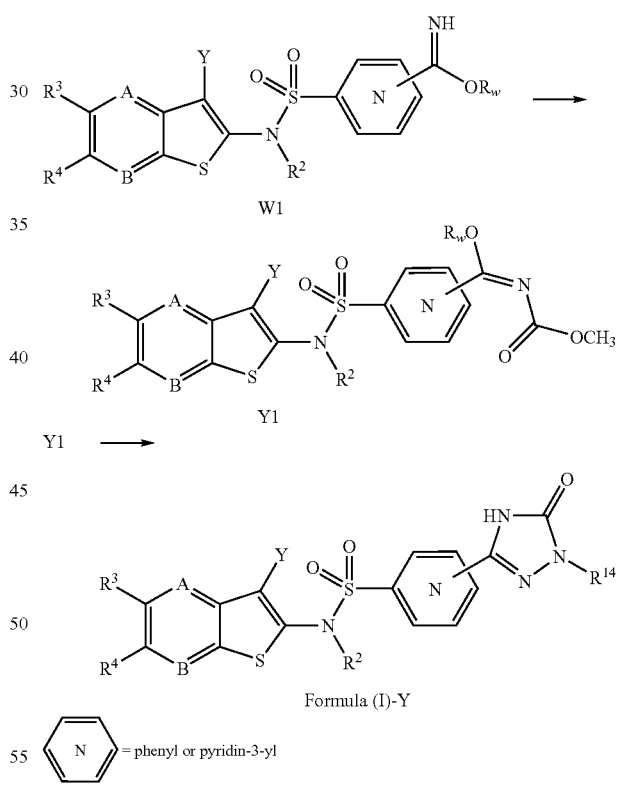

A compound of the formula W1 may be treated with 2,4,6-trimethylpyridine, in the presence of methyl chloroformate, to afford a compound of the formula Y1. Treatment of a compound of the formula Y1 with a $R^{14}$-substituted hydrazine, may afford a compound of the formula (I)-Y.

Scheme Z illustrates a route for the synthesis of compounds of the formula (I)-Z wherein $R^3$ is a substituent as defined herein other than bromo; G is S; and A, B, $R^1$, $R^2$, and $R^4$ are as defined herein.

Scheme Z

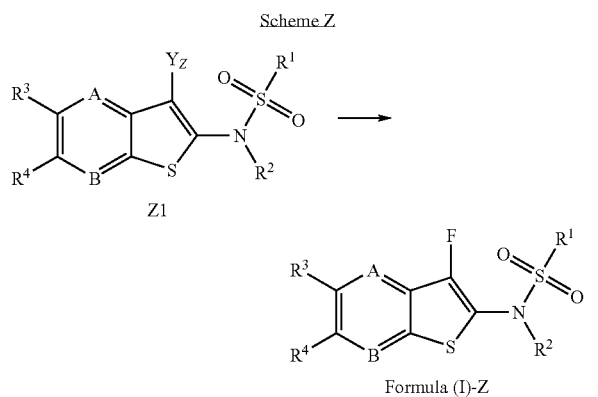

Formula (I)-Z

A compound of the formula Z1 may be prepared according to the chemistry described in scheme A. A compound of the formula Z1, wherein $Y_Z$ is bromo or iodo, may be reacted with an $C_{1-4}$ alkyllithium, followed by treatment with an electrophilic fluorinating reagent such as $FClO_3$ or N-fluorobenzenesulfonamide, to afford a compound of the formula (I)-Z.

Scheme AA illustrates a route for the synthesis of compounds of the formula (I)-AA wherein G is S; and A, B, Y, $R^2$, $R^3$, and $R^4$ are as defined herein.

Scheme AA

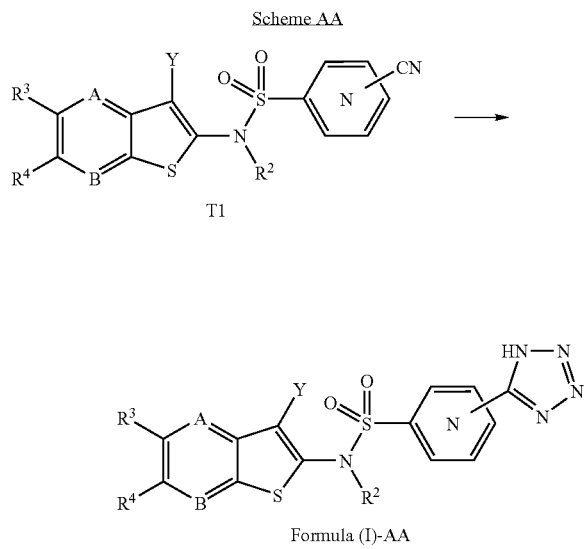

Formula (I)-AA

 = phenyl or pyridin-3-yl

A compound of the formula T1 may be treated with sodium azide, in the presence of a ammonium chloride or triethylamine hydrochloride, to afford a compound of the formula (I)-AA.

Scheme BB illustrates a route for the synthesis of compounds of the formula (I)-BB wherein A and B are $C(R^5)$ and $C(R^6)$, respectively; G is S; Y is $C_{1-2}$ alkyl substituted with $NR^7R^8$; and $R^1$, $R^2$, $R^3$ and $R^4$ are as defined herein.

Scheme BB

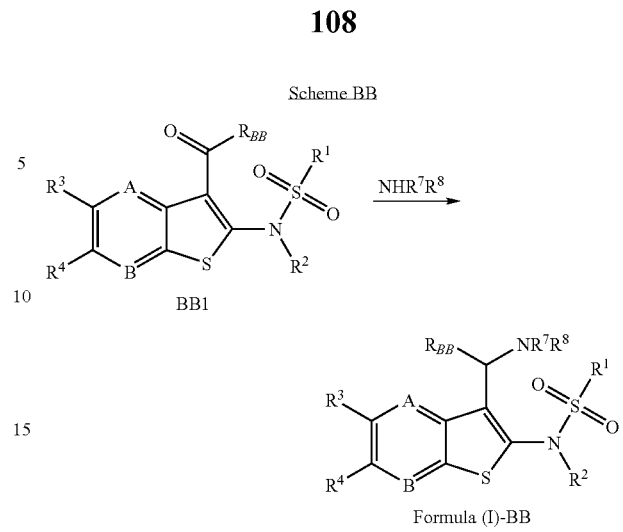

Formula (I)-BB $R_{BB}$ is H or Me

A compound of the formula BB1 ($R_{BB}$ is hydrogen or methyl) may be reacted with an amine of the formula $NHR^7R^8$ (wherein $R^7$ is other than $C_{1-3}$ alkylcarbonyl and $C_{1-3}$ alkylsulfonyl and $R^8$ is $C_{1-4}$ alkyl) in the presence of a hydride source such as sodium borohydride, sodium triacetoxyborohydride, and the like, in an organic solvent to afford a compound of the formula (I)-BB. A compound of the formula (I)-BB wherein $R^7$ is hydrogen may be treated in the presence of a base, optionally in the presence of an organic solvent, with an appropriately substituted acylating agent such as a $C_{1-3}$alkyl acid chloride, or with an appropriately substituted sulfonylating agent, to afford a corresponding compound of the present invention wherein $R^7$ is $C_{1-3}$ alkylcarbonyl or $C_{1-3}$ alkylsulfonyl, respectively.

Scheme CC illustrates a route for the synthesis of intermediates of the formula CC6 wherein A and B are $C(R^5)$ and $C(R^6)$, respectively; G is S; $Y_{CC}$ is $C_{1-6}$alkyl; and $R^1$, $R^2$, $R^3$ and $R^4$ are as defined herein.

Scheme CC

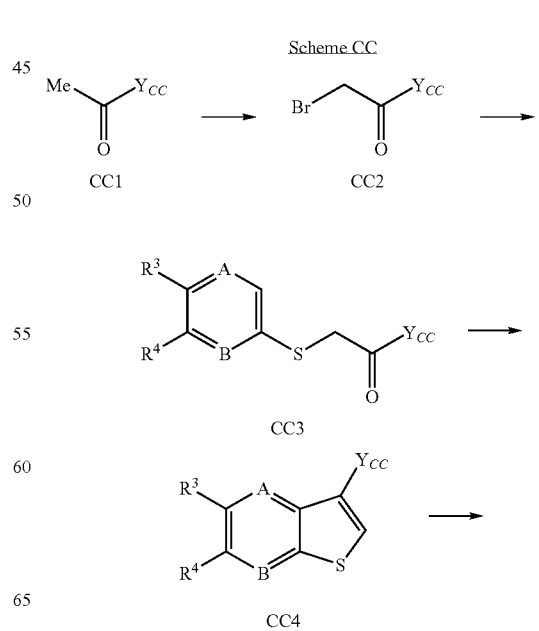

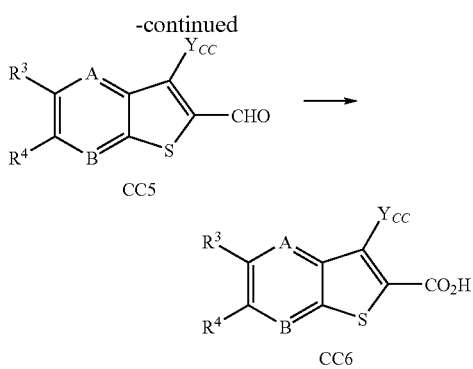

A compound of the formula CC1 is either commercially available or may be prepared by known methods such as those described in the scientific literature. A compound of the formula CC1 may be converted to a methyl bromide of the formula CC2 by the action of bromine in methanol. The bromide of a compound of the formula CC2 may undergo a nucleophilic displacement with an appropriately substituted thiol, in the presence of a base, to afford a compound of the formula CC3, which may subsequently be cyclized in the presence of PPA, optionally in an organic solvent such as chlorobenzene, to afford a compound of the formula CC4. Deprotonation with an organometallic base such as n-butyllithium followed by the addition of DMF affords an aldehyde of the formula CC5. The aldehyde group may be oxidized in the presence of a strong oxidizing agent such as potassium permanganate to afford a carboxylic acid of the formula CC6, which may be converted to a compound of the general formula (I) by the synthetic methods outlined in scheme A.

Scheme DD illustrates a route for the synthesis of compounds of the formula (I)-DD wherein A and B are $C(R^5)$ and $C(R^6)$, respectively; G is $S(O_2)$; $R^1$ is other than an $C_{1-3}$ alkylthio-substituted substituent; and Y, $R^2$, $R^3$ and $R^4$ are as defined herein.

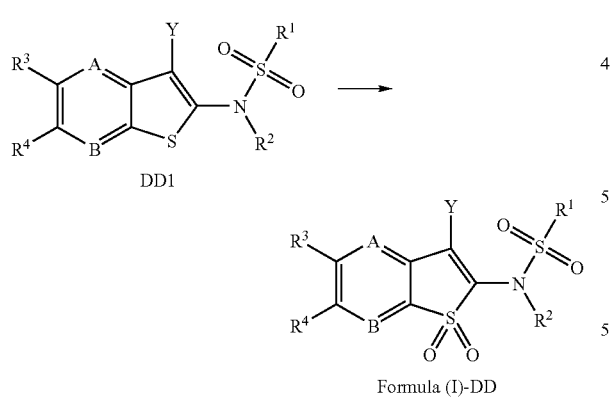

A compound of the formula DD1 may be prepared by the synthetic methods described herein. A compound of the formula DD1 may be treated with and oxidizing agent such as mCPBA, oxone, peracetic acid, and the like, in an organic solvent such as chloroform to afford a compound of the formula (I)-DD.

Scheme EE illustrates a route for the synthesis of compounds of the formula (I)-EE wherein A and B are $C(R^5)$ and $C(R^6)$, respectively; G is $S(O_2)$; Y is $C_{1-3}$ alkoxy; and $R^1$, $R^2$, $R^3$ and $R^4$ are as defined herein.

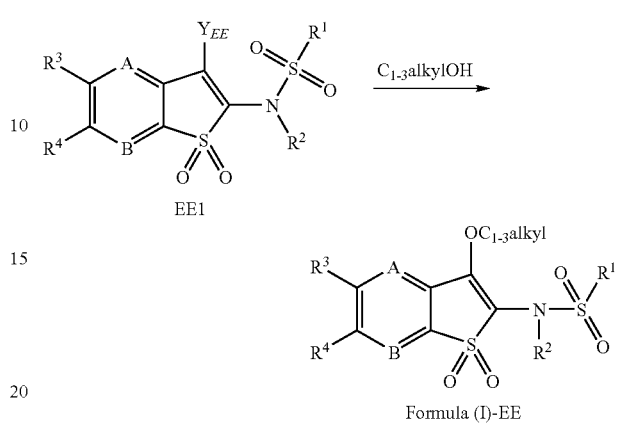

A compound of the formula EE1 wherein $Y_{EE}$ is chloro, bromo, or iodo, may be treated with a strong non-nucleophilic base such as sodium hydride, a lower alkoxide, sodium hydroxide or potassium hydroxide, DBU, and the like; in the presence of a $C_{1-3}$ alcoholic solvent; to afford the corresponding compound of the formula (I)-EE wherein Y is a $C_{1-3}$ alkoxy group.

Scheme FF illustrates a route for the synthesis of compounds of the formula (I)-FF wherein A and B are $C(R^5)$ and $C(R^6)$, respectively; G is $S(O_2)$; Y is $NR^9R^{10}$; $R^1$ is other than $C_{1-6}$ alkyl substituted with bromo; and $R^2$, $R^3$ and $R^4$ are as defined herein.

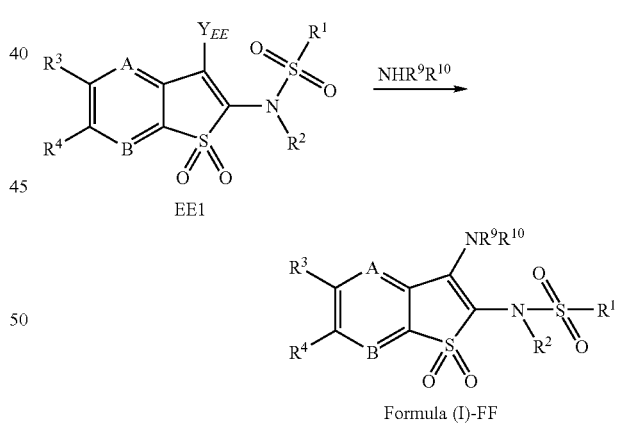

A compound of the formula EE1 may be treated with an appropriately substituted amine of the formula $NHR^9R^{10}$ (wherein $R^9$ is other than $C_{1-3}$ alkylcarbonyl and $C_{1-3}$ alkylsulfonyl and $R^{10}$ is $C_{1-4}$ alkyl) in an aprotic organic solvent to afford a compound of the formula (I)-FF. A compound of the formula (I)-FF wherein $R^9$ is hydrogen may be treated in the presence of a base, optionally in the presence of an organic solvent, with an appropriately substituted acylating agent such as a $C_{1-3}$ alkyl acid chloride, or with an appropriately substituted sulfonylating agent, to afford a corresponding compound of the present invention wherein $R^9$ is $C_{1-3}$ alkylcarbonyl or $C_{1-3}$ alkylsulfonyl, respectively.

Scheme GG illustrates a route for the synthesis of compounds of the formula (I)-GG wherein A and B are C(R⁵) and C(R⁶), respectively; G is S; R¹ and R² are other than a nitrogen containing heteroaryl; $R_G$ and $R_{G1}$ are independently hydrogen or methyl such that Y is aminocarbonyl, methylaminocarbonyl, or dimethylaminocarbonyl; and R³ and R⁴ are as defined herein.

Scheme GG

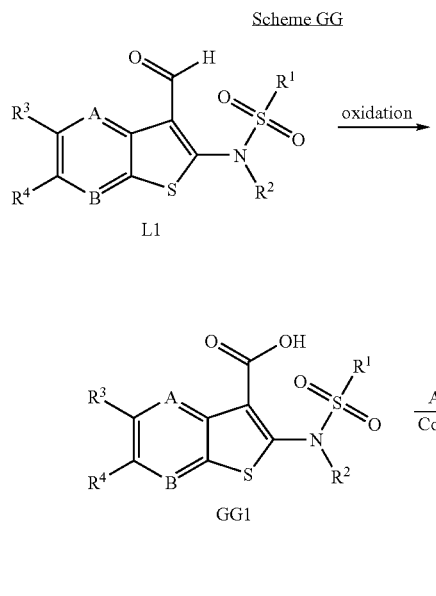

A compound of the formula L1 wherein Y is formyl may be converted to a carboxylic acid of the formula GG1 by the action of an oxidizing agent such as potassium permanganate. Treatment of a compound of the formula GG1 with an amine of the formula $NHR_GR_{G1}$ in the presence of a coupling agent such as HBTU, DCC, HATU, and the like; and a tertiary amine such as diisopropylethylamine; in an aprotic solvent, affords an amide of the formula (I)-GG.

Scheme HH illustrates a route for the synthesis of compounds of the formula (I)-HH wherein A and B are C(R⁵) and C(R⁶), respectively; G is S; Y is NR⁹R¹⁰, R⁹ is $C_{1-3}$ alkylcarbonyl or $C_{1-3}$ alkylsulfonyl, and R¹⁰ is hydrogen.

Scheme HH

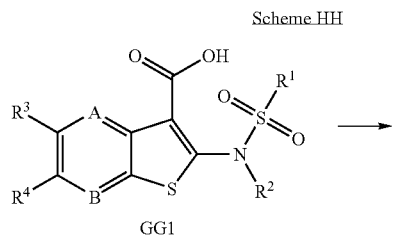

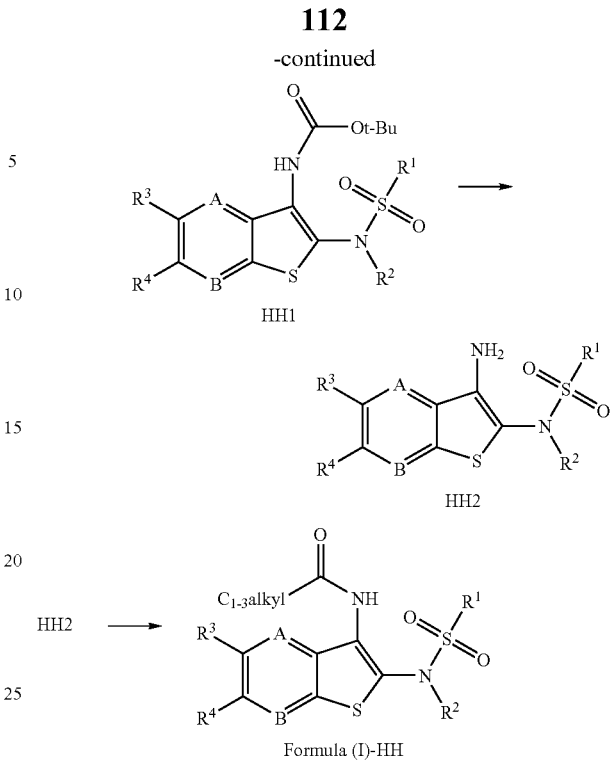

A compound of the formula GG1 may be treated with DPPA and tBuOH in the presence of a tertiary amine such as DIEA to afford a t-butyl carbamate of the formula HH1. Upon treatment with a mineral acid such as HCl in dioxane, the corresponding amine of the formula HH2 may be prepared. The amino group of a compound of the formula HH2 may be acylated with a $C_{1-3}$alkyl-substituted acid chloride or anhydride to afford a compound of the formula (I)-HH. Further treatment with a conventional $C_{1-3}$ alkylating agent may provide compounds of the present invention wherein R¹⁰ is $C_{1-3}$alkyl. Likewise, a compound of the formula HH2 may be treated with an appropriately substituted sulfonylating agent to afford a corresponding compound of the present invention wherein R⁹ is $C_{1-3}$ alkylsulfonyl, respectively.

Scheme II illustrates a route for the synthesis of compounds of the formula (I)-II wherein A and B are C(R⁵) and C(R⁶), respectively; G is S; R¹ is CF₃; and Y, R², R³ and R⁴ are as defined herein.

Scheme II

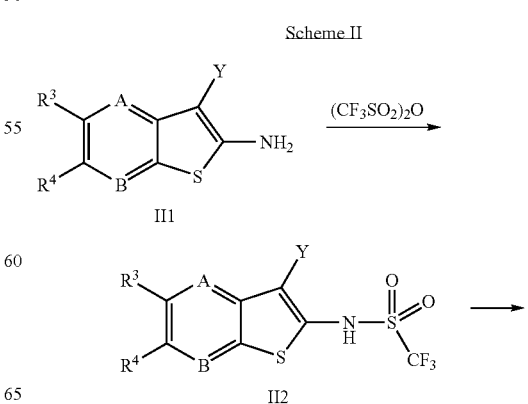

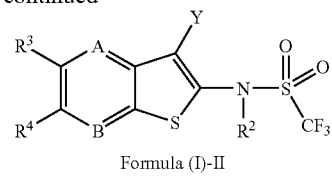

Formula (I)-II

A compound of the formula II1 may be converted to a compound of the formula II2 by the action of trifluoromethanesulfonic anhydride and a tertiary amine followed by treatment with hydroxide. A compound of the formula II2 may be treated with a base such as sodium hydride, lithium bis(trimethylsilyl)amide, n-butyllithium or potassium tert-butoxide followed by alkylation with a compound of the formula, $R^2X$, where X is a leaving group such as bromo, chloro, iodo, tosylate, mesylate, and the like, to afford a compound of the formula (I)-II. Alternatively, a compound of the formula II2 may be treated with a triarylphosphine such as triphenylphosphine, tri-o-tolylphosphine, tri-2-furylphosphine and the like; a $C_{1-6}$ dialkyl azodicarboxylate such as diethyl-, diisopropyl-, or di-t-butyl-azodicarboxylate, and the like; and an appropriately substituted alcohol, $R^2OH$, to afford a compound of the formula (I)-II.

Scheme JJ illustrates a route for the synthesis of compounds of the formula (I)-JJ wherein $R^1$ is $C_{1-6}$ alkyl substituted with hydroxy; formula (I)-JJ1 wherein $R^1$ is $C_{1-6}$ alkyl substituted with bromo; and formula (I)-JJ2 wherein $R^1$ is unsubstituted $C_{3-8}$ cycloalkyl; A and B are $C(R^5)$ and $C(R^6)$, respectively; and G, Y, $R^2$, $R^3$ and $R^4$ are as defined herein.

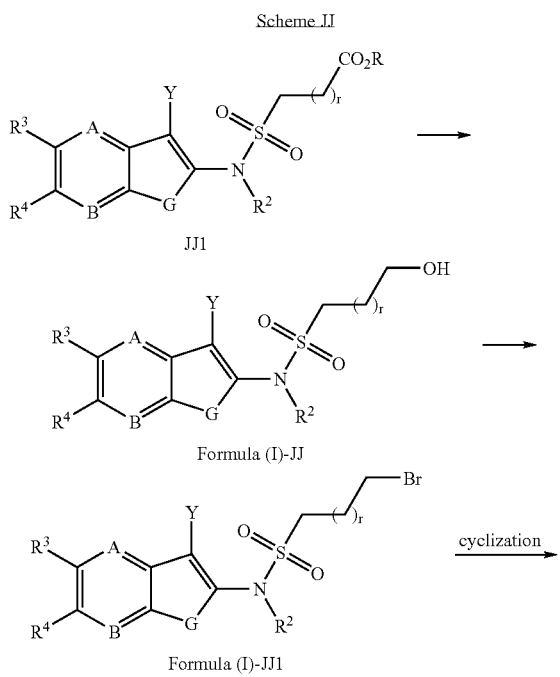

Scheme JJ r = 1-6

A compound of the formula JJ1 (wherein R is $C_{1-4}$ alkyl) may be prepared according to the synthetic methods outlined in scheme A using an appropriately substituted alkylating agent of the formula $R^2X$ or $R^2OH$. A compound of the formula JJ1 may be converted to its corresponding alcohol of the formula (I)-JJ by the action of a reducing agent such as lithium aluminum hydride, lithium borohydride, and the like. The alcohol of the formula (I)-JJ may be treated with a brominating agent such as thionyl bromide; phosphorus tribromide; carbon tetrabromide in the presence of a triarylphosphine such as triphenylphosphine, tri-o-tolylphosphine, tri-2-furylphosphine; and the like, to afford a bromide of the formula (I)-JJ wherein $R^1$ is $C_{1-6}$ alkyl substituted with bromo. Treatment with a base such as sodium imidazolide, DBU, potassium tert-butoxide, and LDA, affords a cyclized product of the formula (I)-JJ2 wherein $R^1$ is unsubstituted $C_{3-8}$ cycloalkyl.

Scheme KK illustrates a route for the synthesis of compounds of the formula (I)-JJ wherein $R^1$ is $C_{1-6}$ alkyl substituted with a heteroaryl as defined herein, wherein the point of attachment is a nitrogen atom; A and B are $C(R^5)$ and $C(R^6)$, respectively; and G, Y, $R^2$, $R^3$ and $R^4$ are as defined herein.

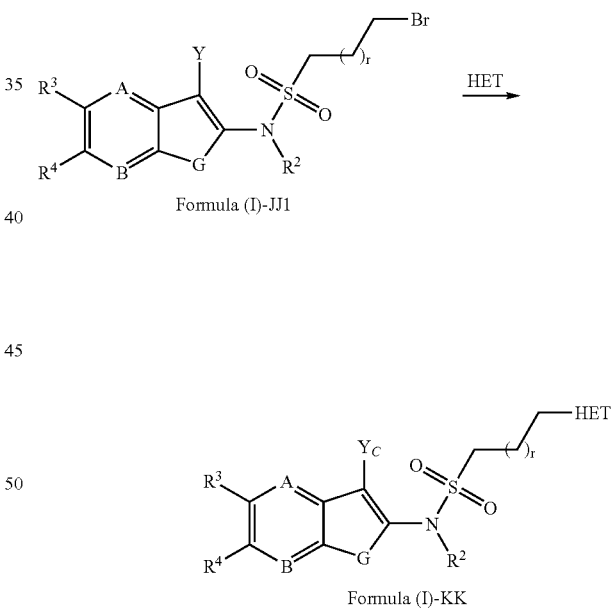

Scheme KK

A bromide of the formula (I)-JJ1 may be displaced by a 5 to 6 membered NH-containing heteroaryl (HET) in an organic solvent to afford a compound of the formula (I)-KK.

Scheme LL illustrates a route for the synthesis of compounds of the formula (I)-LL wherein $R^1$ is phenyl substituted with C(O)NHOH; and G, A, B, Y, $R^2$, $R^3$ and $R^4$ are as defined herein. One skilled in the art will recognize that added protection and deprotection steps may be required for certain chemical groups of Y that are sensitive to the reaction conditions described in Scheme LL.

Scheme LL

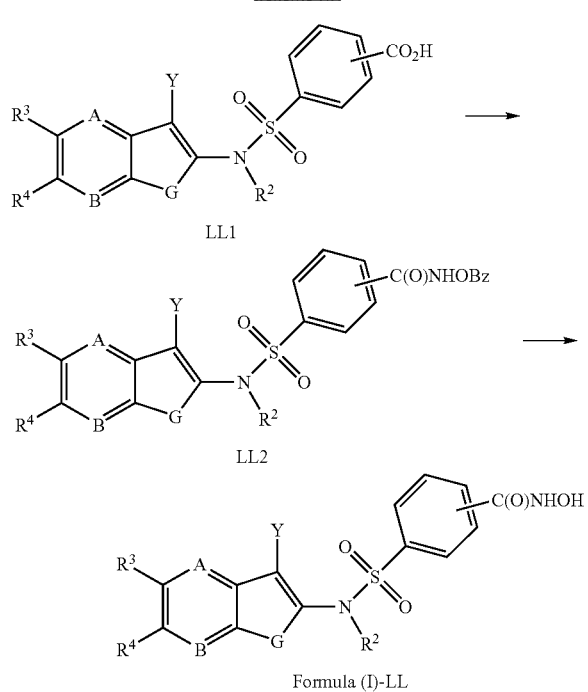

A compound of the formula LL1 may be treated with O-benzyl-hydroxylamine in the presence of a coupling agent such as EDC, HATU, HBTU, and the like to afford a compound of the formula LL2. Removal of the benzyl group by the action of boron tribromide or TFA in an organic solvent such as DCM; or with a palladium catalyst in the presence of a hydrogen source such as hydrogen gas; affords a compound of the formula (I)-LL.

Scheme MM illustrates a route for the synthesis of compounds of the formula (I)-MM wherein $R^1$ is heteroaryl; and formula (I)-MM1 wherein $R^1$ is a benzo-fused heteroaryl substituted at a nitrogen atom within the ring with $C_{1-3}$ alkyl; G is S; and Y, A, B, $R^2$, $R^3$ and $R^4$ are as defined herein.

Scheme MM

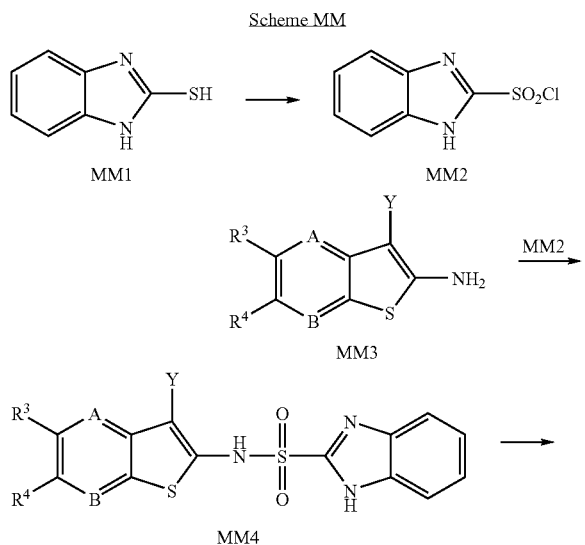

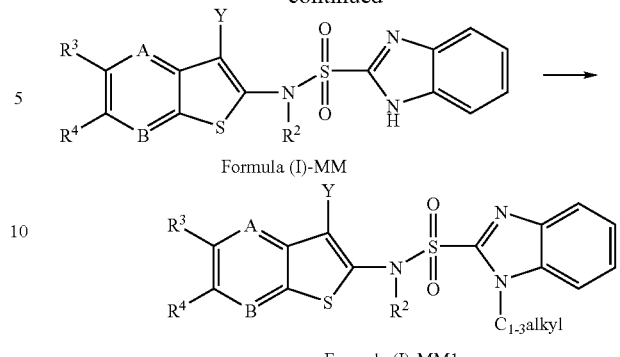

A compound of the formula MM1 is either commercially available or may be prepared by known methods such as those described in the scientific literature. A compound of the formula MM1 may be converted to a useful intermediate of the formula MM2 by the action of aqueous acetic acid and chlorine gas. A compound of the formula MM3 may be sulfonylated with a sulfonyl chloride of the formula MM2 to afford a compound of the formula MM4. The $R^2$ group of the present invention may be installed as previously described herein to afford a compound of the formula (I)-MM. Treatment of a compound of the formula (I)-MM with a base such as DBU in the presence of an alkylating agent such as a $C_{1-3}$ alkyl halide or dimethylsulfate in DMF affords a methylated compound of the formula (I)-MM1 of the present invention.

Scheme NN illustrates a route for the synthesis of compounds of the formula (I)-NN wherein G is S; $Y_{NN}$ is bromo, chloro, iodo; and A, B, $R^2$, $R^3$, and $R^4$ are as defined herein.

Scheme NN

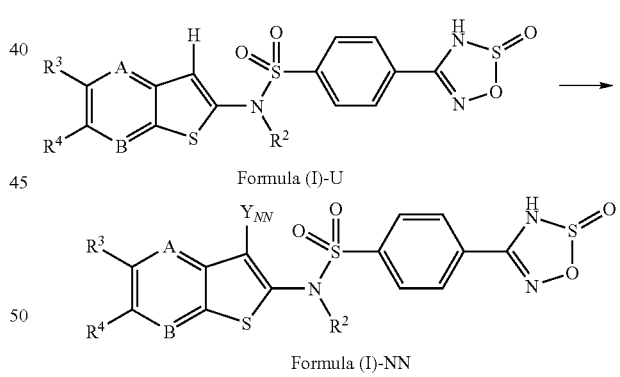

A compound of the formula (I)-U may be treated with N-chlorosuccinimide or chlorine to afford a compound of the formula (I)-NN, wherein $Y_{NN}$ is chloro. Likewise, a compound of the formula (I)-NN wherein $Y_{NN}$ is bromo may be afforded by the action of N-bromosuccinimide or bromine; and a compound of the formula (I)-NN wherein $Y_{NN}$ is iodo may be afforded by the action of N-iodosuccinimide or iodine.

Scheme OO illustrates a route for the synthesis of compounds of the formula (I)-OO wherein G is S; $R^1$ is a ring selected from phenyl or pyridin-3-yl, wherein said ring is substituted with $NR^{15}R^{16}$ wherein $NR^{15}R^{16}$ is other than $NH_2$; and A, B, Y, $R^2$, $R^3$, and $R^4$ are as defined herein.

Scheme OO

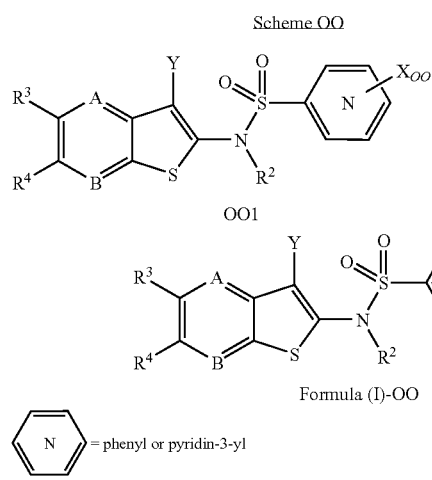

A compound of the formula OO1 (wherein $X_{oo}$ is a reactive leaving group such as fluoro, chloro, or bromo) may be prepared according to the synthetic methods described herein. A compound of the formula OO1 may be treated with a cyclic or acyclic amine of the formula $HNR^{15}R^{16}$ under basic conditions, in the presence of a palladium catalyst such as $Pd_2(dba)$ and an appropriate ligand such as 4,5-bis(diphenylphosphino)-9,9-dimethylxanthene, to afford a compound of the formula (I)-OO.

Scheme PP illustrates a route for the synthesis of compounds of the formula (I)-PP wherein G is S; $R^1$ is phenyl substituted with $C(O)NR^{17}R^{18}$ wherein $R^{17}$ is $C_{1-3}$ alkylsulfonyl and $R^{18}$ is hydrogen; and A, B, Y, $R^2$, $R^3$, and $R^4$ are as defined herein.

One skilled in the art will recognize that added protection and deprotection steps may be required for certain chemical groups of Y that are sensitive to the reaction conditions described in Scheme PP.

Scheme PP

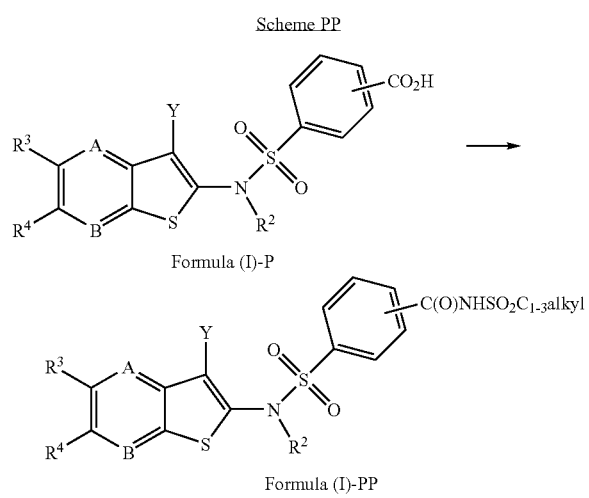

A compound of the formula (I)-P may be treated with the coupling agent CDI, followed by the addition of a $C_{1-3}$alkylsulfonamide in the presence of DBU and dimethylaminopyridine to afford a compound of the formula (I)-PP.

Scheme QQ illustrates a route for the synthesis of compounds of the formula (I)-QQ wherein G is S; $R^1$ is a ring selected from indanyl or tetralinyl, wherein said ring is attached via an unsaturated carbon atom and the unsaturated portion of the ring is substituted with an amino, alkylamino, or dialkylamino group; and A, B, Y, $R^2$, $R^3$, and $R^4$ are as defined herein.

Scheme QQ

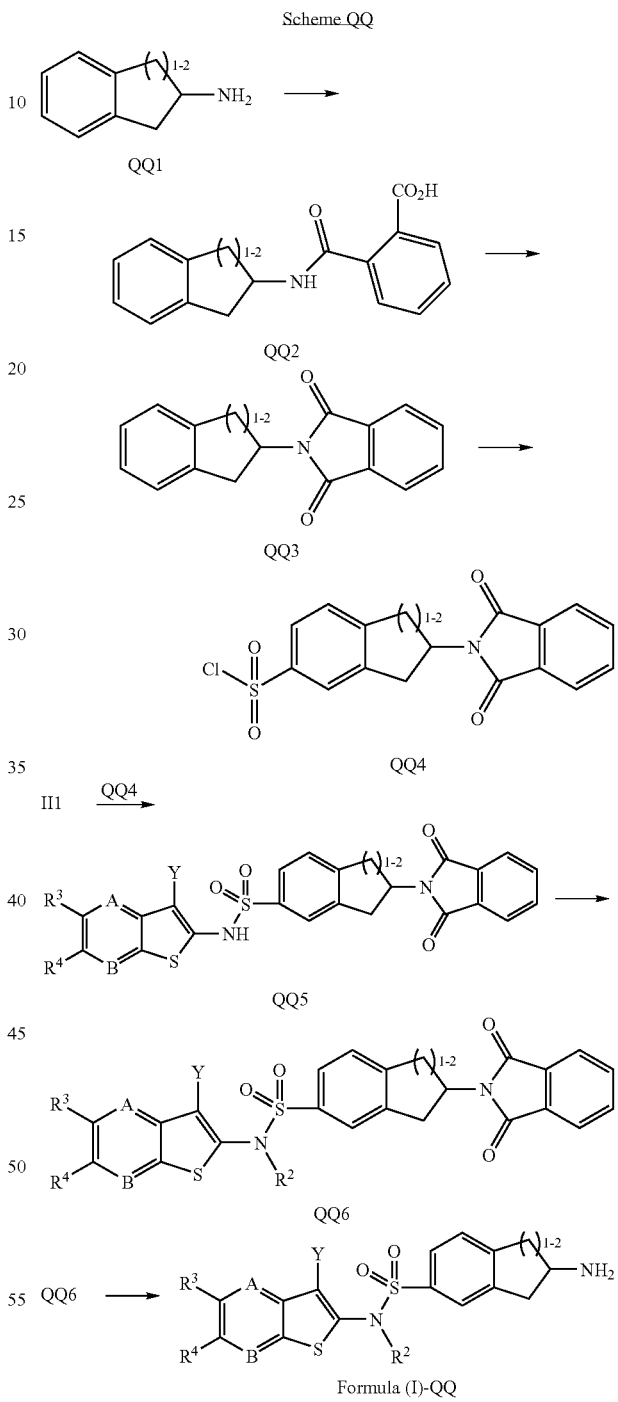

A compound of the formula QQ1 is either commercially available or may be prepared by known methods such as those described in the scientific literature. A compound of the formula QQ1 may be treated with phthalic anhydride to afford a compound of the formula QQ2, which may be converted to a compound of the formula QQ3 by the action of DMF and DMAP. A compound of the formula QQ3 may be treated with chlorosulfonic acid to afford a compound of the formula QQ4. A compound of the formula II1 may be sulfonylated with a compound of the formula QQ4 in the presence of an aprotic organic base, such as pyridine, to afford a compound of the formula QQ5. A compound of the formula QQ5 may be alkylated as described herein to install the $R^2$ group and form a compound of the formula QQ6. Treatment of the phthalimido group of a compound of the formula QQ6 with hydrazine in methanol affords a compound of the formula (I)-QQ.

Scheme RR illustrates a route for the synthesis of compounds of the formula (I)-RR wherein G is S; $R^1$ is phenyl substituted with $C(O)NR^{17}R^{18}$; and A, B, Y, $R^2$, $R^3$, and $R^4$ are as defined herein.

One skilled in the art will recognize that added protection and deprotection steps may be required for certain chemical groups of Y that are sensitive to the reaction conditions described in Scheme RR.

Scheme RR

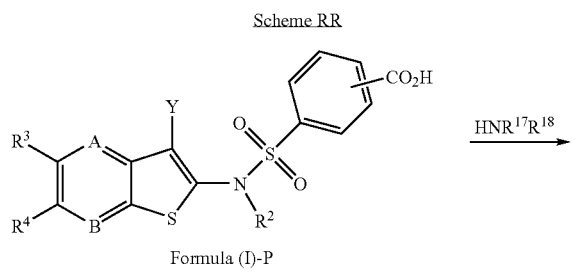

Formula (I)-P

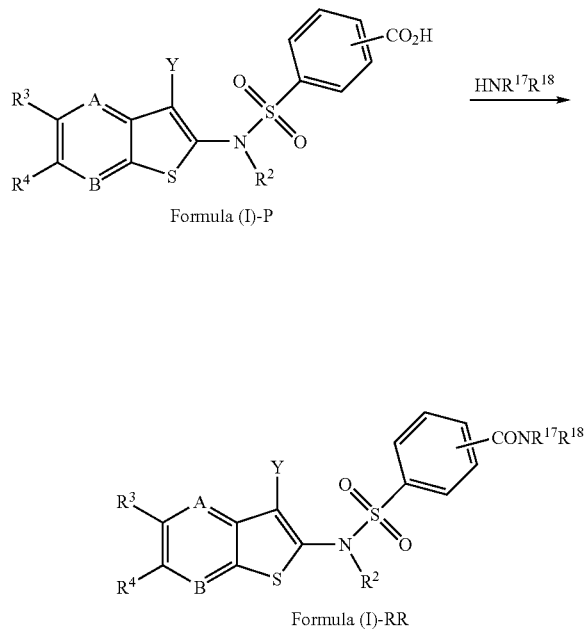

Formula (I)-RR

A compound of the formula (I)-P may be coupled with an amine of the formula $HNR^{17}R^{18}$, wherein $R^{17}$ and $R^{18}$ are as defined herein, in the presence of a coupling agent such as HATU, DCC, and the like, and a tertiary amine such as DIEA, to afford a compound of the formula (I)-RR.

Scheme SS illustrates a route for the synthesis of compounds of the formula (I)-SS wherein G is S; Y is isopropenyl; and A, B, $R^1$, $R^2$, $R^3$, and $R^4$ are as defined herein.

Scheme SS

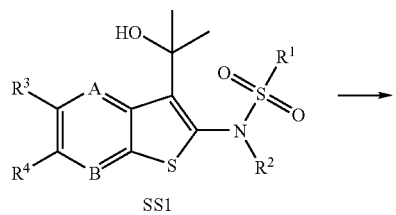

SS1

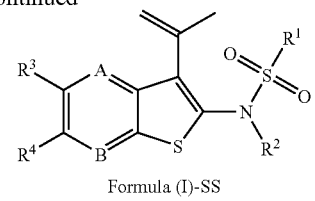

Formula (I)-SS

A compound of the formula SS1 may be treated with an solution of a mineral acid such as HCl, or an organic acid such as trifluoroacetic acid, to afford a dehydrated compound of the formula (I)-SS.

Scheme TT illustrates a route for the synthesis of compounds of the formula (I)-TT wherein Y is other than bromo or iodo; $R^1$ is phenyl substituted with carboxy; $R^2$ is other than an aromatic bromide; and A, B, G, $R^3$, and $R^4$ are as defined herein.

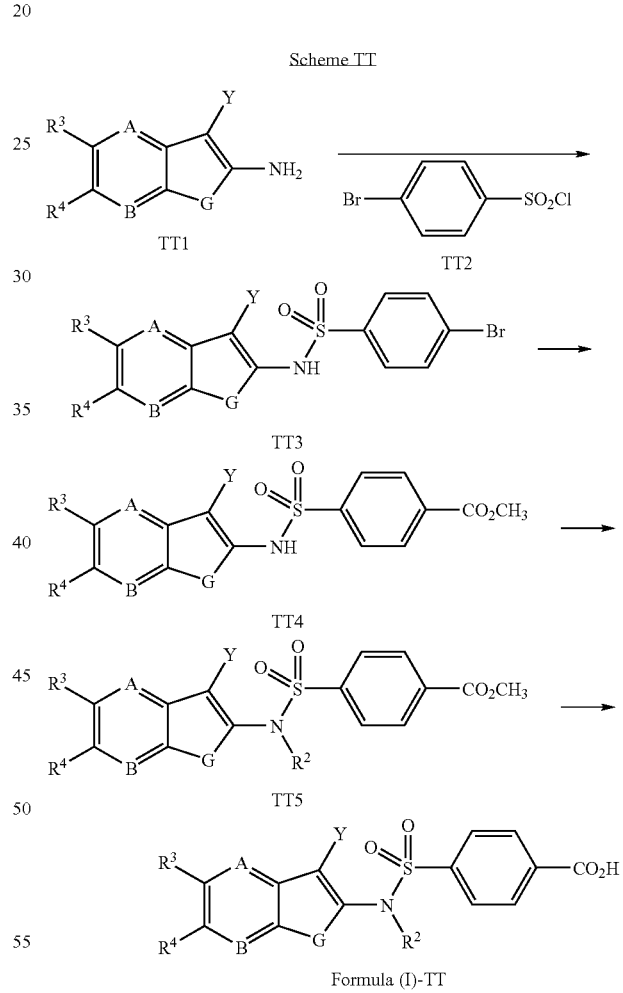

Formula (I)-TT

A compound of the formula TT1 may be prepared using the synthetic methods outlined herein. A compound of the formula TT1 may be sulfonylated with a bromo-substituted phenylsulfonyl chloride of the formula TT2 in the presence of a base such as pyridine or DIEA to afford a compound of the formula TT3. A compound of the formula TT3 may be converted to its corresponding ester of the formula TT4 by the action of carbon monoxide in the presence of a palladium catalyst and an alcoholic solvent, such as methanol. A compound of the formula TT4 may be alkylated with an appropriate $R^2$-substituted alkylating agent as described herein to afford a compound of the formula TT5 which, upon saponification with hydroxide, affords a carboxylic acid of the formula (I)-TT.

Scheme UU illustrates a route for the synthesis of compounds of the formula (I)-UU wherein $R^1$ is phenyl substituted at the 3- or 4-position with imidazolyl substituted with an aminomethyl, methylamino-methyl, or dimethylaminomethyl substitutent; $R_U$ and $R_{U1}$ are independently hydrogen or methyl; and A, B, G, Y, $R^2$, $R^3$, and $R^4$ are as defined herein.

Scheme MV illustrates a route for the synthesis of compounds of the formula (I)-VV wherein $R^1$ is phenyl substituted with $NR^{15}R^{16}$ wherein $R^{15}$ is hydrogen or $C_{1-3}$alkylsulfonyl; and $R^{16}$ is as defined; and A, B, G, $R^2$, $R^3$, and $R^4$ are as defined herein.

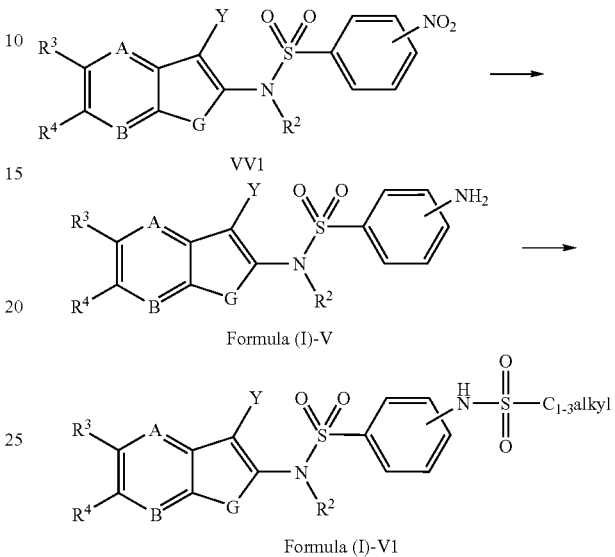

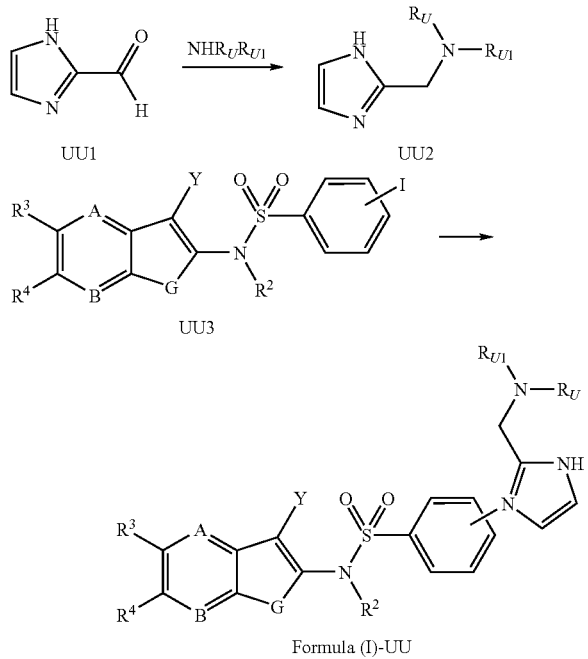

A compound of the formula VV1 is either commercially available or may be prepared by known methods such as those described in the scientific literature. The reduction of the nitro group of a compound of the formula VV1 may be achieved by a number of conventional methods, such as in the presence of a palladium catalyst under a hydrogen gas atmosphere in an alcoholic solvent such as methanol; or, by the action of iron metal in the presence of a suitable acidic reagent or solvent such as hydrochloric acid or acetic acid; or by using zinc and ammonium chloride in methanol and water; to afford the corresponding aniline of the formula (I)-V. A compound of the formula (I)-V may be sulfonylated using an appropriately substituted sulfonyl chloride in the presence of a base such as pyridine, DIEA, and the like to afford a compound of the formula (I)-VI. Compounds of the formulae (I)-V and (I)-VI may be alkylated using conventional $C_{1-3}$alkylating agents to afford compounds of the invention wherein $R^{16}$ is an alkyl group.

A compound of the formula UU1 is either commercially available or may be prepared by known methods such as those described in the scientific literature. A compound of the formula UU1 may be treated with an amine of the formula $NHR_U R_{U1}$ in the presence of a hydride source such as sodium borohydride, sodiumtriacetoxyborohydride, and the like, in an alcoholic solvent such as methanol to afford a compound of the formula UU2. A 3- or 4-iodo substituted compound of the formula UU3 may be prepared by the synthetic methods outlined herein. A compound of the formula UU3 may be coupled with a compound of the formula UU2 in the presence of a catalyst such as copper iodide in an organic solvent such as DMSO and a base such as $K_2CO_3$ to afford a compound of the formula (I)-UU.

Scheme WW illustrates a route for the synthesis of compounds of the formula (I)-WW wherein A and B are $C(R^5)$ and $C(R^6)$, respectively; G is S; $R^x$ and $R^y$ are both hydrogen or taken together with the carbon atom to which they are both attached to form a cyclopropyl ring; Q is a bond; m is 0 or 1; and Y, $R^2$, $R^3$ and $R^4$ are as defined herein.

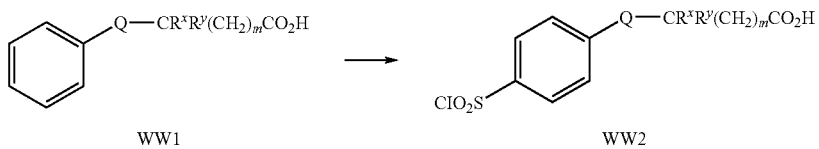

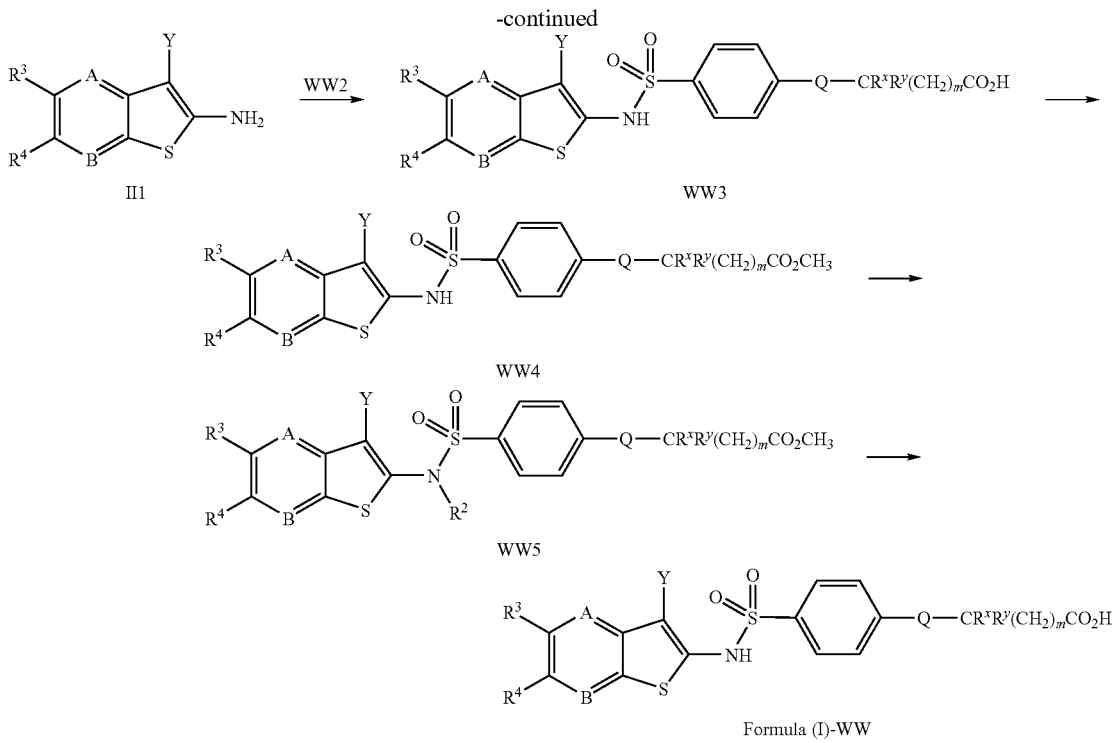

Formula (I)-WW

A compound of the formula WW1 is either commercially available or may be prepared by known methods such as those described in the scientific literature. A compound of the formula WW1 may be converted to a compound of the formula WW2 using chlorosulfonic acid, with or without organic solvent. A compound of the formula II1 may be sulfonylated with a sulfonyl chloride of the formula WW2 to afford a compound of the formula WW3. A compound of formula WW3 may be converted to a methyl ester by treatment with a reagent such as diazomethane, concentrated sulfueric acid in methanol, and the like, to afford a compound of the formula WW4. The $R^2$ group of the present invention may be installed as previously described herein to afford a compound of the formula WW5. A compound of the formula WW5 may be converted to the corresponding carboxylic acid, a compound of the formula (I)-WW, by the action of agents such as hydroxide, hydrochloric acid, trimethylsilyl iodide, or other reagents and conditions known to one skilled in the art, to effect the conversion of esters to carboxylic acids.

Scheme XX illustrates a route for the synthesis of compounds of the formula (I)-XX wherein A and B are $C(R^5)$ and $C(R^6)$, respectively; G is S; $R^xR^y$ are each methyl; Q is a bond; m is 0 or 1; and Y, $R^2$, $R^3$ and $R^4$ are as defined herein.

Scheme XX

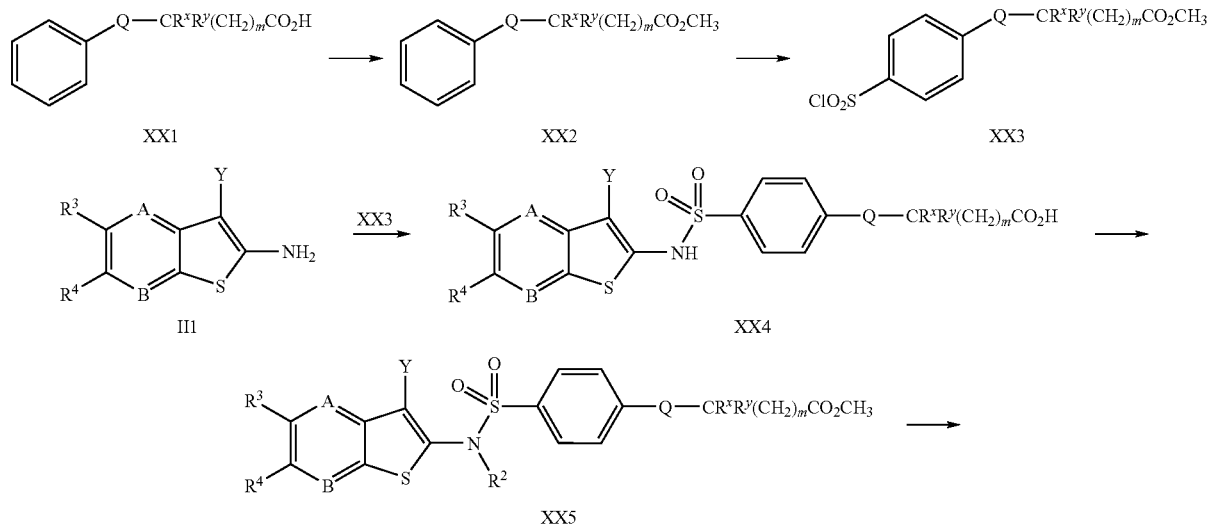

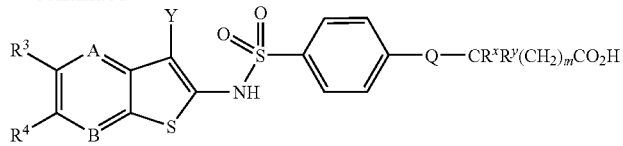

Formula (I)-XX

A compound of the formula XXI is either commercially available or may be prepared by known methods such as those described in the scientific literature. A compound of the formula XXI may be converted to a compound of the formula XX2 by treatment with a reagent such as diazomethane, concentrated sulfuric acid in methanol, and the like, to afford a compound of the formula XX2. A compound of the formula XX2 may be converted to a compound of the formula XX3 using chlorosulfonic acid, with or without organic solvent. A compound of the formula II1 may be sulfonylated with a sulfonyl chloride of the formula XX3 to afford a compound of the formula XX4. The $R^2$ group of the present invention may be installed as previously described herein to afford a compound of the formula XX5. A compound of the formula XX5 may be converted to the corresponding carboxylic acid, a compound of the formula (I)-XX, by the action of agents such as hydroxide, hydrochloric acid, trimethylsilyl iodide, or other reagents and conditions known to one skilled in the art, to effect the conversion of esters to carboxylic acids.

Scheme YY illustrates a route for the synthesis of compounds of the formula (I)-YY wherein A and B are $C(R^5)$ and $C(R^6)$, respectively; G is S; $R^x$ and $R^y$ are independently selected from hydrogen or methyl; or $R^x$ and $R^y$ are taken together with the carbon atom to which they are both attached to form a cyclopropyl ring; Q is oxygen; m is 0 or 1; and Y $R^2$, $R^3$ and $R^4$ are as defined herein.

A compound of the formula YY1 of the present invention may be prepared as previously described herein. A compound of the formula YY1 may be converted to a compound of the formula YY2 by treatment with boron tribromide in dichloromethane. A compound of the formula YY2 may be alkylated with an alkylating agent such as methyl bromoacetate, methyl 2-bromoisobutyrate, and the like, in the presence of a base, such as cesium carbonate or potassium carbonate, in a solvent such as DMF, THF, or DMSO to afford a compound of the formula YY3. A compound of the formula YY3 may be converted to the corresponding carboxylic acid, a compound of the formula (I)-YY, by the action of reagents such as hydroxide, hydrochloric acid, trimethylsilyl iodide, or other reagents and conditions known to one skilled in the art, to effect the conversion of esters to carboxylic acids.

Scheme ZZ illustrates a route for the synthesis of compounds of the formula (I)-ZZ wherein A and B are $C(R^5)$ and $C(R^6)$, respectively; G is S; and Y, $R^2$, $R^3$ and $R^4$ are as defined herein.

Scheme YY

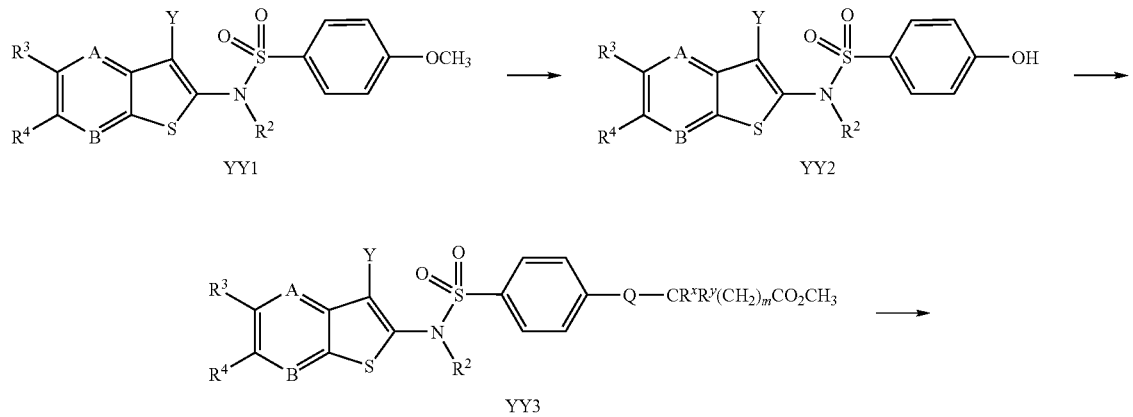

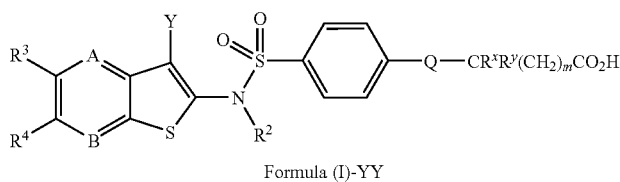

Formula (I)-YY

Scheme ZZ

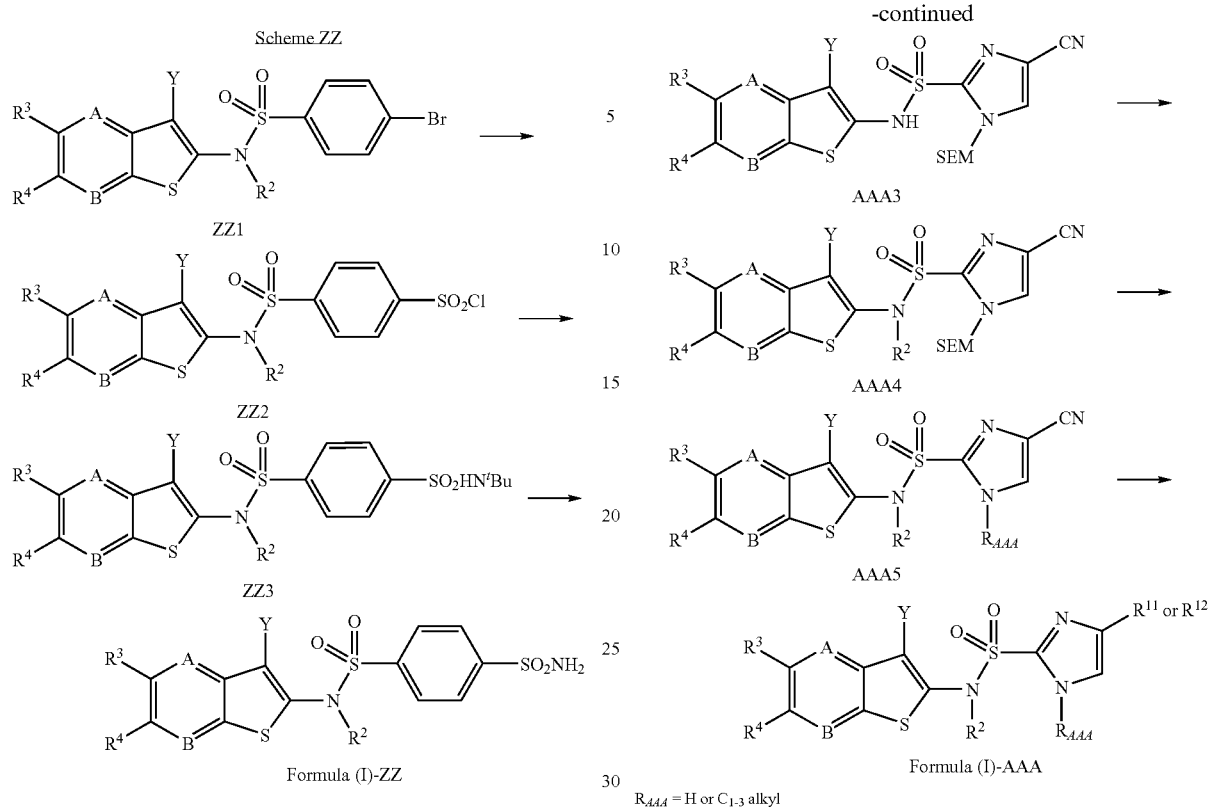

A compound of the formula ZZ1 of the present invention may be prepared as previously described herein. A compound of the formula ZZ1 may be treated with a base, such as n-butyllithium, and sulfur dioxide, followed by treatment with n-chlorosuccinimide, in a solvent such as THF, to afford a compound of formula ZZ2. A compound of formula ZZ2 may be converted to a protected sulfonamide of the formula ZZ3 by treatment with tert-butyl amine. Amino deprotection of a compound of the formula ZZ3 using conventional chemistry known to one skilled in the art provides a compound of formula (I)-ZZ.

Scheme AAA illustrates a route for the synthesis of compounds of the formula (I)-AAA wherein A and B are $C(R^5)$ and $C(R^6)$, respectively; G is S; $R^1$ is imidazolyl substituted with $R^{11}$ or $R^{12}$; and Y, $R^2$, $R^3$ and $R^4$ are as defined herein.

Scheme AAA

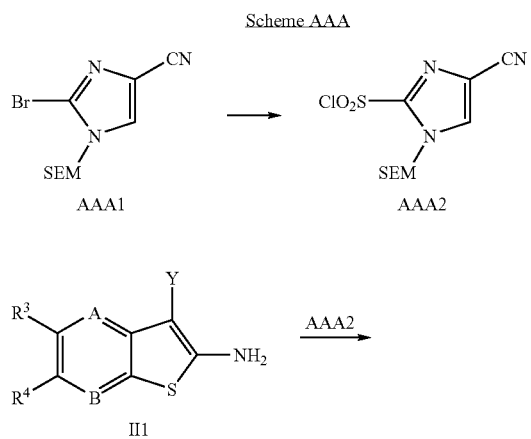

A compound of the formula AAA1 may be prepared by known methods such as those described in the scientific literature (WO2007/124369). A compound of the formula AAA1 may be treated with an alkylmagnesium halide such as ethylmagnesium chloride and a sulfonating agent such as sulfur dioxide, followed by treatment with a chlorinating agent such as N-chlorosuccinimide, in a solvent such as THF, to afford a compound of the formula AAA2. A compound of the formula II1 may be sulfonylated with a sulfonyl chloride of the formula AAA2 to afford a compound of the formula AAA3. The $R^2$ group of the present invention may be installed as previously described herein to afford a compound of the formula AAA4. Amino deprotection of a compound of the formula AAA4 using conventional chemistry known to one skilled in the art provides a compound of the formula AAA5, wherein $R_{AAA}$ is hydrogen. A compound of the formula AAA5 may be converted to a compound of the formula (I)-AAA using chemistry previously described herein. Alternatively, a compound of AAA5 wherein $R_{AAA}$ is hydrogen may be alkylated to form a compound of the formula AAA5 wherein $R_{AAA}$ is $C_{1-3}$ alkyl, via treatment with a base such as DBU or potassium carbonate; and an electrophile such as iodo($C_{1-3}$)alkane or dimethyl sulfate; in a solvent such as DMF. A compound of the formula AAA5 wherein $R_{AAA}$ is $C_{1-3}$ alkyl may be converted to a compound of the formula (I)-AAA using chemistry previously described herein.

Scheme BBB illustrates a route for the synthesis of compounds of the formula (I)-BBB wherein A and B are $C(R^5)$ and $C(R^6)$, respectively; G is S; $R^1$ is cyclohexyl substituted at the 4-position with one substituent selected from $C_{1-4}$ alkoxycarbonyl or carboxy; and Y, $R^2$, $R^3$ and $R^4$ are as defined herein.

Scheme BBB

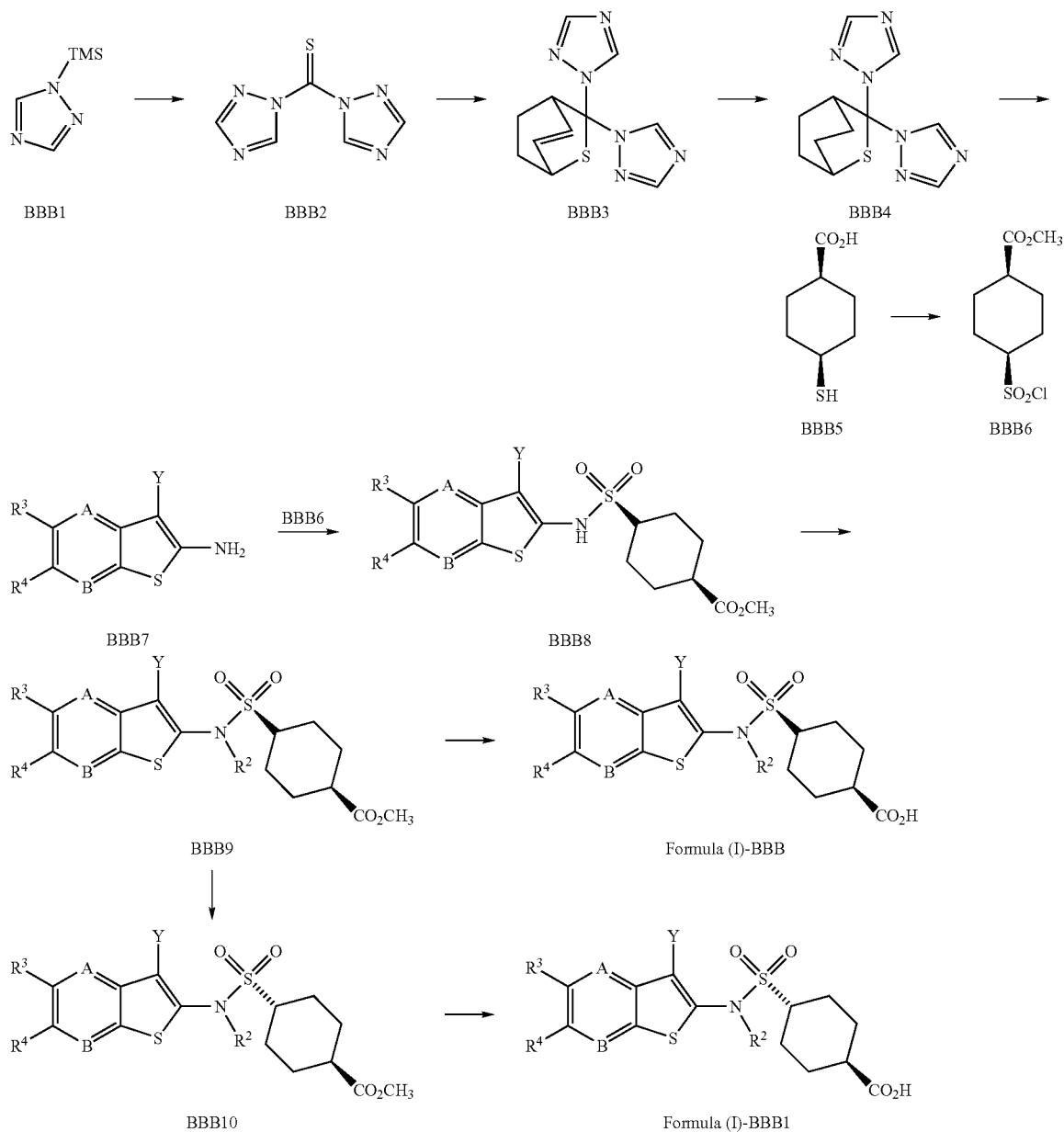

A compound of the formula BBB6 may be prepared by known methods such as those described in the scientific literature (Can. J. Chem., 64(16), 1986, 2184). A compound of the formula BBB1, may be treated with thiophosgene in an aprotic non-polar solvent, such as carbon tetrachloride (J. Org. Chem. 43 (2), 1978, 337-339), to afford a compound of the formula BBB2. A compound of the formula BBB2 may be treated with cyclohexa-1,3-diene in a solvent, such as benzene (J. Org. Chem. 45, 1980, 3713-3716), to afford a compound of the formula BBB3. Reduction of the alkenyl group of formula BBB3 may be achieved using a catalyst, such as palladium, and a hydrogen source in a solvent such as ethyl acetate, to afford a compound of the formula BBB4. A compound of the formula BBB4 may be treated with an acid catalyst, such as sulfuric acid, in methanol to afford a compound of the formula BBB5. A compound of the formula BBB5 may be treated with chorine gas in appropriate solvents such as acetic acid-water or dichloromethane-water to afford a compound of the formula BBB6. A compound of the formula BBB7 may be sulfonylated with a sulfonyl chloride of the formula BBB6 to afford a compound of the formula BBB8. A compound of formula BBB8 can be converted to a compound of formula (I)-BBB using chemistry previously described herein. A compound of the formula BBB9 may be treated with hydroxide to effectively epimerize a stereocenter of the cyclohexyl ring, affording a mixture of stereoisomers of the formula BBB10. Saponification of the esters using chemistry described herein affords the compounds of the formula (I)-BBB1. Pure stereoisomers of the formula BBB10 or (I)-BBB1 may be isolated using convention chromatographic techniques.

Scheme CCC illustrates a route for the synthesis of compounds of the formula (I)-CCC wherein A and B are C($R^5$) and C($R^6$), respectively; G is S; $R^1$ is cyclohexyl substituted at the 4-position with one substitutent selected from cyano, aminocarbonyl, $R^{11}$, or $R^{12}$; and Y, $R^2$, $R^3$ and $R^4$ are as defined herein.

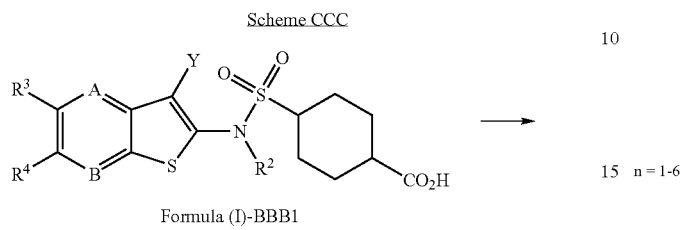

A compound of the formula (I)-BBB1 may be converted to a compound of the formula (I)-CCC by the action of a reagent such as HBTU, CDI or HATU, followed by the addition of gaseous ammonia. A compound of the formula (I)-CCC may be converted to a compound of the formula (I)-CCC1 by the action of reagents such as trifluoroacetic anhydride in pyridine; in a solvent such as dichloromethane. The cyano group of a compound of the formula (I)-CCC1 may be converted to $R^{11}$ and $R^{12}$ groups of the present invention using synthetic methods described in the previous schemes to afford a compound of the formula (I)-CCC2.

Scheme DDD illustrates a route for the synthesis of compounds of the formula (I)-DDD wherein A and B are C($R^5$) and C($R^6$), respectively; G is S; $R^1$ is $R^{11}$ or $R^{12}$; and Y $R^2$, $R^3$ and $R^4$ are as defined herein.

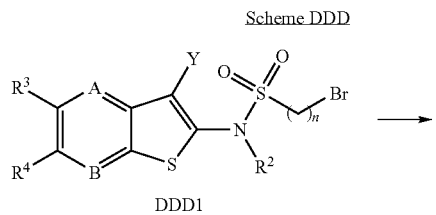

n = 1-6

A compound of the formula DDD1 may be prepared using chemistry previously described herein. A compound of the formula DDD1 may be converted to a compound of the formula DDD2 using sodium cyanide and a polar aprotic solvent such as DMF or DMSO. The cyano group of a compound of the formula DDD2 may be converted to $R^{11}$ and $R^{12}$ groups of the present invention using synthetic methods described in the previous schemes to afford a compound of the formula (I)-DDD.

Scheme EEE illustrates a route for the synthesis of compounds of formula (I)-EEE wherein A and B are C($R^5$) and C($R^6$), respectively; G is S; $Y_{EEE}$ is hydrogen, alkyl, $C_{3-8}$ cycloalkyl, or trifluoromethyl; and $R^1$, $R^2$, $R^3$ and $R^4$ are as defined herein.

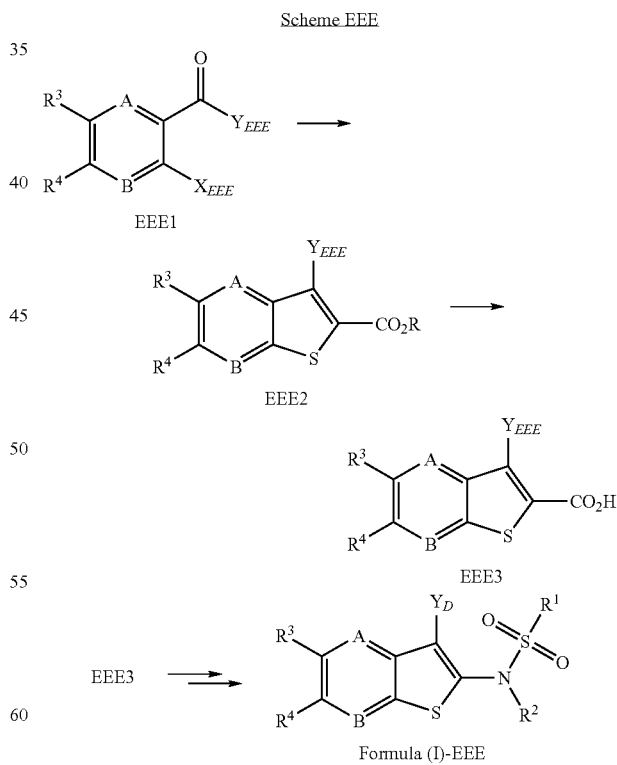

A compound of the formula EEE1 is either commercially available or may be prepared by known methods such as those described in the scientific literature. A compound of the formula EEE1 wherein $X_{EEE}$ is chloro or fluoro may be reacted with an R-substituted thioglycolate (wherein R is $C_{1-6}$alkyl) in the presence of base to afford a compound of the formula EEE2, which may be saponified to afford a compound of the formula EEE3 using conventional chemistry known to one skilled in the art. Using synthetic methods outlined in scheme A, a compound of the formula EEE3 may be converted to compounds of the formula (I)-EEE.

Scheme FFF illustrates a route for the synthesis of compounds of the formula (I)-FFF wherein $Y_{FFF}$ is other than bromo or iodo; G is S; and $R^1$ is $C_{6-10}$aryl substituted with an optionally substituted phenyl; or $R^1$ is phenyl substituted with a heteroaryl; $R^2$ is a substituent that does not include bromo or iodo; $R^3$ is other than bromo; and $R^4$ and $R^6$ are as defined herein.

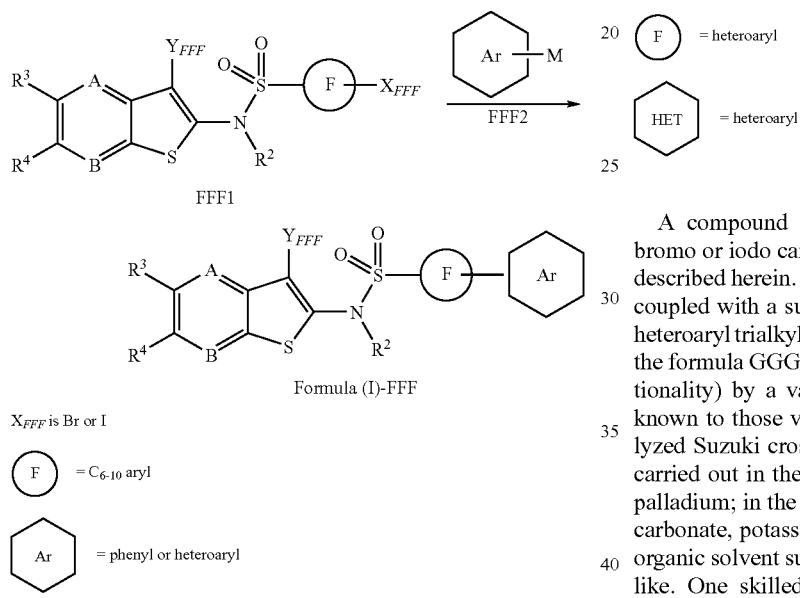

A compound of the formula FFF1 wherein $X_{FFF}$ is bromo or iodo can then prepared according to the chemistry described herein. A compound of the formula FFF1 may be coupled with a suitably substituted aryl boronic acid, aryl trialkylsilane, aryl tin reagent, and the like of the formula FFF2 (wherein M is the reactive coupling functionality) by a variety of coupling reactions that are well known to those versed in the art, such as a palladium-catalyzed Suzuki cross-coupling reaction. The reaction may be carried out in the presence or absence of added ligands for palladium; in the presence of a suitable base such as cesium carbonate, potassium carbonate, or sodium carbonate; in an organic solvent such as ethanol, THF, DMF, toluene, and the like. One skilled in the art will recognize that in some instances it may be favorable to reverse the coupling partners such that ring F bears the reactive coupling functionality M, and the Ar ring of the formula FFF2 bears halide $X_{FFF}$.

Scheme GGG illustrates a route for the synthesis of compounds of the formula (I)-GGG wherein $Y_{GGG}$ is other than bromo or iodo; G is S; and $R^1$ is heteroaryl substituted with an optionally substituted phenyl or heteroaryl; $R^2$ is a substituent that does not include bromo or iodo; $R^3$ is other than bromo; and $R^4$ and $R^6$ are as defined herein.

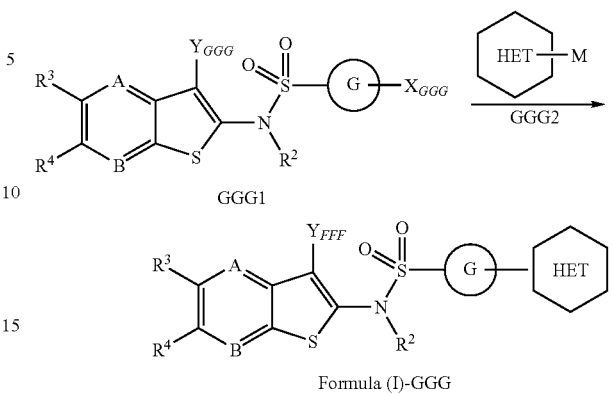

A compound of the formula GGG1 wherein $X_{GGG}$ is bromo or iodo can then prepared according to the chemistry described herein. A compound of the formula GGG1 may be coupled with a suitably substituted heteroaryl boronic acid, heteroaryl trialkylsilane, heteroaryl tin reagent, and the like of the formula GGG2 (wherein M is the reactive coupling functionality) by a variety of coupling reactions that are well known to those versed in the art, such as a palladium-catalyzed Suzuki cross-coupling reaction. The reaction may be carried out in the presence or absence of added ligands for palladium; in the presence of a suitable base such as cesium carbonate, potassium carbonate, or sodium carbonate; in an organic solvent such as ethanol, THF, DMF, toluene, and the like. One skilled in the art will recognize that in some instances it may be favorable to reverse the coupling partners such that ring G bears the reactive coupling functionality M, and the HET ring of the formula GGG2 bears halide $X_{GGG}$.

Scheme HHH illustrates a route for the synthesis of compounds of the formula (I)-HHH wherein $R^1$ is phenyl substituted at the 3- or 4-position with imidazolyl substituted with an 2-aminoethyl, 2-($C_{1-2}$ alkylamino)ethyl, or 2-(di($C_{1-2}$ alkyl)amino)ethyl substitutent; $R_H$ and $R_{H1}$ are independently hydrogen or $C_{1-2}$ alkyl; or $R_H$ and $R_{H1}$ are taken together with the nitrogen atom to which it is attached to form a 5 or 6 membered ring optionally containing one additional heteroatom selected from nitrogen, oxygen, or sulfur; and wherein the ring formed by di($C_{1-2}$ alkyl)amino is optionally substituted with $C_{1-3}$alkyl; and A, B, G, Y, $R^2$, $R^3$, and $R^4$ are as defined herein.

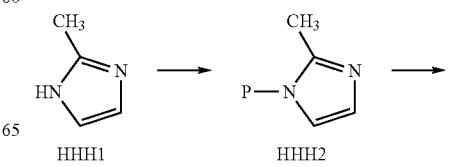

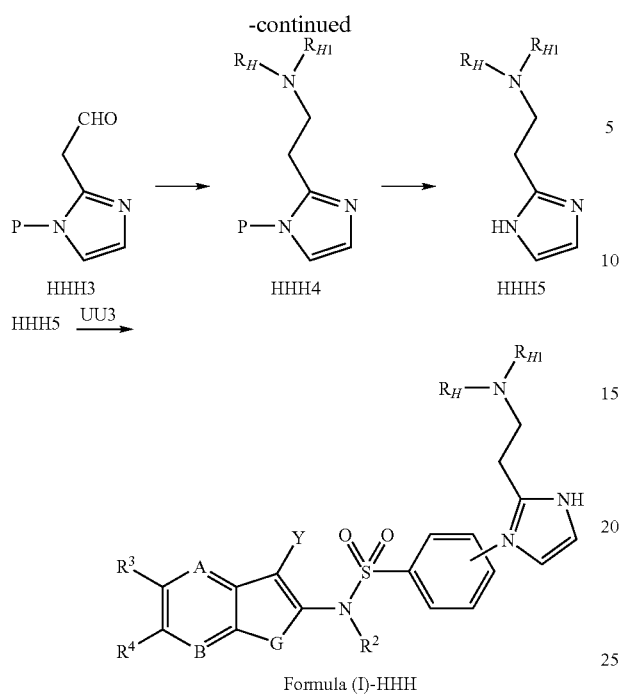

Formula (I)-HHH

A compound of the formula HHH1 is either commercially available or may be prepared by known methods such as those described in the scientific literature. The nitrogen heteroatom of a compound of the formula HHH1 may be protected with an appropriate protecting group (P) such as a trityl group, to afford a compound of the formula HHH2. A compound of the formula HHH2 may be treated with a strong base such as n-butyllithium followed by the addition of ethylchloroformate in an organic aprotic solvent afford an aldehyde of the formula HHH3 (Synlett 1999, No 12, 1875-1878). A compound of the formula HHH3 may undergo a reductive alkylation with an amine of the formula $NHR_H R_{H1}$ in the presence of a hydride source such as sodium borohydride, sodiumtriacetoxyborohydride, and the like, in an alcoholic solvent such as methanol to afford a compound of the formula HHH4. Conventional removal of the nitrogen protecting group affords a compound of the formula HHH5. A compound of the formula UU3 may be coupled with a compound of the formula HHH5 in an organic solvent such as DMSO and a base such as $K_2CO_3$ to afford a compound of the formula (I)-HHH.

Compounds of Formula (I) that are chiral may be separated into their enantiomers by chromatography on a chiral stationary phase. Alternatively, basic or acidic compounds and intermediates to compounds of the present invention may be converted to diastereomeric salts by mixture with a chiral acid or base, respectively, and resolved into their enantiomers by fractional crystallization.

It is generally preferred that the respective product of each process step be separated from other components of the reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and heptanes are typical hydrocarbon solvents and dichloromethane and dichloroethane are representative halogenated hydrocarbon solvents. In those cases where the product is isolated as the acid addition salt the free base may be obtained by techniques known to those skilled in the art. In those cases in which the product is isolated as an acid addition salt, the salt may contain one or more equivalents of the acid. Enantiomers of the compounds of the present invention may be separated using chiral HPLC.

SPECIFIC EXAMPLES

Reagents were purchased from commercial sources. Microanalyses were performed at Quantitative Technologies, Inc., Whitehouse, N.J. and are expressed in percentage by weight of each element per total molecular weight. Nuclear magnetic resonance (NMR) spectra for hydrogen atoms were measured in the indicated solvent with (TMS) as the internal standard on a Bruker Avance (300, 400, or 500 MHz) spectrometer. The values are expressed in parts per million downfield from TMS. The mass spectra (MS) were determined on a Micromass Platform LC spectrometer or an Agilent 1100 series LC/MSD spectrometer using an electrospray technique. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted. Where reactions were carried out in a microwave reactor, a Personal Chemistry Smith Synthesizer™ was used.

Example 1

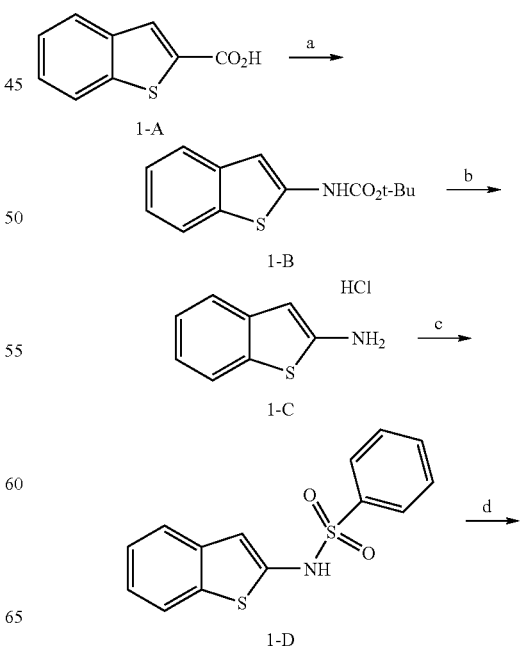

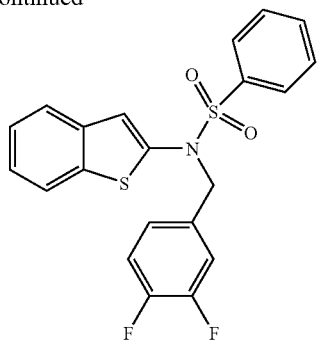

Compound 1 a) DPPA, DIEA, t-BuOH; b) HCl, dioxane; c) benzenesulfonyl chloride, pyridine; d) NaH, 3,4-difluorobenzy bromide, DMF.

Benzo[b]thiophen-2-yl-carbamic acid tert-butyl ester (1-B). A solution of compound 1-A (14.4 g, 80.6 mmol), N,N-diisopropylethylamine (15.5 mL, 88.6 mmol) and diphenylphosphoryl azide (20.8 mL, 96.7 mmol) in t-butanol (150 mL) was heated at reflux for 8 h. The solvent was evaporated in vacuo, and the residue purified by flash column chromatography on silica gel, eluting with dichloromethane, to afford compound 1-B as a colorless solid (18.9 g, 94%). $^1$H-NMR (DMSO-d$_6$): δ 1.50 (s, 9H), 6.78 (s, 1H), 7.16 (d of d, 1H), 7.27 (d of d, 1H), 7.58 (d, 1H), 7.77 (d, 1H), 10.70 (br s, 1H); MS: m/z 250.2 (MH$^+$).

Benzo[b]thiophen-2-ylamine hydrochloride (1-C). Compound 1-B (1.45 g, 5.81 mmol) was added to a solution of HCl in dioxane (4 N, 20 mL), and the mixture was stirred at rt until all the starting material was consumed. The mixture was diluted with diethyl ether, the product collected by filtration, and washed with diethyl ether, to afford compound 1-C as an off-white solid (0.89 g, 83%). $^1$H-NMR (DMSO-d$_6$): δ 6.43 (s, 1H), 6.8-7.2 (br s, 3H) superimposed on 7.05 (m, 1H) and 7.20 (m, 1H), 7.45 (d, 1H), 7.66 (d, 1H); MS: m/z 150.1 (MH$^+$).

N-Benzo[b]thiophen-2-yl-benzenesulfonamide (1-D). Benzenesulfonyl chloride (0.661 mL, 5.15 mmol) was added to a solution of compound 1-C (0.87 g, 4.69 mmol) in pyridine (10 mL) at 0° C. The ice bath was removed and the solution was stirred at ambient temperature for 2 h. The solvent was evaporated in vacuo, and the residue was partitioned between 2 N HCl and dichloromethane. The organic layer was dried over magnesium sulfate and the solvent evaporated in vacuo. The residue was pre-absorbed on silica gel and purified by flash column chromatography, eluting with a gradient of ethyl acetate (10-50%) in heptane, to afford compound 1-D as a colorless solid (1.19 g, 88%). $^1$H-NMR (CDCl$_3$): δ 6.96 (s, 1H), 7.25-7.34 (m, 2H), 7.44-7.49 (m, 2H), 7.55-7.66 (m, 3H), 7.84-7.88 (m, 2H); MS: m/z 290.1 (MH$^+$).

Compound 1

N-Benzo[b]thiophen-2-yl-N-(3,4-difluoro-benzyl)-benzenesulfonamide. Sodium hydride (60% in oil, 100 mg, 2.48 mmol) was added to a solution of compound 1-D (655 mg, 2.26 mmol) in DMF (8 mL) at 0° C. and the resultant mixture was stirred at 0° C. for 15 min. 3,4-Difluorobenzylbromide (0.318 mL, 2.48 mmol) was added to the reaction mixture, and the resultant solution was stirred at ambient temperature overnight. Water was added to the solution, and the product was extracted into ethyl acetate. The organic layer was washed with water (3×), brine, dried over sodium sulfate, filtered, and the solvent evaporated in vacuo. The residue was purified on silica gel by flash column chromatography eluting with a gradient of ethyl acetate (0-40%) in heptane, to afford compound 1 as a colorless solid (570 mg, 61%). $^1$H-NMR (DMSO-d$_6$): δ 4.74 (s, 2H), 7.00-7.10 (s superimposed on m, 3H), 7.15-7.21 (m, 1H), 7.26-7.36 (m, 2H), 7.49-7.54 (m, 2H), 7.62-7.67 (m, 3H), 7.73-7.78 (m, 2H); MS: m/z 416.1 (MH$^+$).

Following the procedure described above for Example 1 and substituting the appropriate reagents, starting materials and purification methods known to those skilled in the art, the following compounds of the present invention were prepared:

Compound 2

N-(3,4-Difluoro-benzyl)-N-(3-methyl-benzo[b]thiophen-2-yl)-1-methyl-1H-imidazole-4-sulfonamide. $^1$H-NMR (DMSO-d$_6$): δ 2.02 (s, 3H), 3.72 (s, 3H), 4.82 (s, 2H), 7.10-7.17 (m, 1H), 7.32-7.41 (m, 4H), 7.63-7.68 (m, 1H), 7.79-7.84 (m, 1H), 7.88 (s, 1H), 8.00 (s, 1H); MS: m/z 434.26 (MH$^+$).

Compound 3

N-Benzo[b]thiophen-2-yl-N-(3-fluoro-benzyl)-benzenesulfonamide. $^1$H-NMR (CDCl$_3$): δ 4.76 (s, 2H), 6.94-6.98 (m, 3H), 7.27-7.32 (m, 4H), 7.48-7.53 (d of d, 2H), 7.60-7.64 (m, 3H), 7.66-7.78 (m, 2H); MS: m/z 398.1 (MH$^+$).

Compound 4

N-(3-Chloro-benzo[b]thiophen-2-yl)-N-(4-fluoro-benzyl)-benzenesulfonamide. $^1$H-NMR (DMSO-d$_6$): δ 4.81 (s, 2H), 7.10 (t, 2H), 7.28-7.32 (m, 2H), 7.46-7.52 (m, 2H), 7.67-7.72 (m, 3H), 7.82 (t, 1H), 7.90-7.97 (m, 3H); MS: m/z 432.1 (MH$^+$).

Compound 5

N-(3-Chloro-benzo[b]thiophen-2-yl)-N-quinolin-8-ylmethyl-benzenesulfonamide. $^1$H-NMR (DMSO-d$_6$): δ 5.56 (s, 2H), 7.43 (m, 3H), 7.57 (t, 1H), 7.63-7.74 (m, 3H), 7.78-7.96 (m, 6H), 8.31 (d of d, 1H), 8.75 (d of d, 1H); MS: m/z 465.1 (MH$^+$).

Compound 6

N-(3-Chloro-benzo[b]thiophen-2-yl)-N-(4-trifluoromethoxy-benzyl)-benzenesulfonamide. $^1$H-NMR (DMSO-d$_6$): δ 4.86 (s, 2H), 7.29 (d, 2H), 7.40-7.51 (m, 4H), 7.67-7.72 (m, 3H), 7.80 (t, 1H), 7.90-7.97 (m, 3H); MS: m/z 498.1 (MH$^+$).

Compound 7

N-(3-Chloro-benzo[b]thiophen-2-yl)-N-(4-fluoro-3-trifluoromethyl-benzyl)-benzenesulfonamide. $^1$H-NMR (DMSO-d$_6$): δ 4.93 (s, 2H), 7.41-7.54 (m, 3H), 7.65-7.73 (m, 5H), 7.83 (t, 1H), 7.92-8.00 (m, 3H); MS: m/z 500.1 (MH$^+$).

Compound 8

N-(3-Chloro-benzo[b]thiophen-2-yl)-N-(4-trifluoromethyl-benzyl)-benzenesulfonamide. $^1$H-NMR (DMSO-d$_6$): δ 4.94 (s, 2H), 7.46-7.60 (m, 4H), 7.66-7.72 (m, 5H), 7.83 (t, 1H), 7.91-7.99 (m, 3H); MS: m/z 482.1 (MH$^+$).

Compound 9

N-(Benzo[b]thiophen-2-yl)-N-(3,4-difluoro-benzyl)-pyridine-2-sulfonamide. $^1$H-NMR (DMSO-d$_6$): δ 5.10 (s, 2H), 7.17 (s, 1H), 7.25-7.32 (m, 3H), 7.37-7.46 (m, 2H), 7.69-7.73 (m, 1H), 7.76-7.82 (m, 2H), 7.95 (d, 1H), 8.09-8.14 (m, 1H), 8.89 (d, 1H); MS: m/z 417.1 (MH$^+$).

Compound 10

N-(3-Methyl-benzo[b]thiophen-2-yl)-N-(quinolin-8-ylmethyl)-1-methyl-1H-imidazole-4-sulfonamide. $^1$H-NMR (DMSO-d$_6$): δ 2.10 (s, 3H), 3.78 (s, 3H), 5.63 (s, 2H), 7.27-7.35 (m, 2H), 7.48-7.62 (m, 3H), 7.70-7.78 (m, 1H), 7.83-7.97 (m, 3H), 8.04 (s, 1H), 8.35 (d, 1H), 8.87 (d, 1H); MS: m/z 449.1 (MH$^+$).

Compound 11

N-(3-Methyl-benzo[b]thiophen-2-yl)-N-(4-trifluoromethoxy-benzyl)-1-methyl-1H-imidazole-4-sulfonamide. $^1$H-NMR (DMSO-d$_6$): δ 1.96 (s, 3H), 3.73 (s, 3H), 4.85 (s, 2H), 7.28 (d, 2H), 7.32-7.48 (m, 4H), 7.61-7.65 (m, 1H), 7.79-7.83 (m, 1H) 7.86 (s, 1H), 7.99 (s, 1H); MS: m/z 482.1 (MH$^+$).

Compound 12

N-(3,4-Difluoro-benzyl)-N-(3-methyl-benzo[b]thiophen-2-yl)-pyridine-3-sulfonamide. $^1$H-NMR (DMSO-d$_6$): δ 1.98 (s, 3H), 4.81 (br s, 2H), 7.13-7.17 (m, 1H), 7.33-7.42 (m, 4H), 7.68-7.76 (m, 2H), 7.82-7.88 (m, 1H), 8.27-8.31 (m, 1H), 8.97 (d of d, 1H), 9.02 (d, 1H); MS: m/z 431.1 (MH$^+$).

Compound 13

N-(3-Methyl-benzo[b]thiophen-2-yl)-N-(4-trifluoromethoxy-benzyl)-pyridine-3-sulfonamide. $^1$H-NMR (DMSO-d$_6$): δ 1.92 (s, 3H), 4.83 (br s, 2H), 7.30 (d, 2H), 7.36-7.46 (m, 4H), 7.67-7.76 (m, 2H), 7.83-7.87 (m, 1H), 8.28 (d, 1H), 8.97 (d, 1H), 9.01 (d, 1H); MS: m/z 479.1 (MH$^+$).

Compound 14

N-(3-Methyl-benzo[b]thiophen-2-yl)-N-(quinolin-8-ylmethyl)-pyridine-3-sulfonamide. $^1$H-NMR (DMSO-d$_6$): δ 1.83 (s, 3H), 5.51 (s, 2H), 7.29-7.38 (m, 2H), 7.47-7.53 (m, 2H), 7.55-7.60 (m, 1H), 7.70-7.80 (m, 3H), 7.90 (d, 1H), 8.34 (d, 2H), 8.80 (d, 1H), 8.97 (d, 1H), 9.02 (d, 1H); MS: m/z 446.1 (MH$^+$).

Compound 15

N-(3,4-Difluoro-benzyl)-N-(3-methyl-benzo[b]thiophen-2-yl)-thiophene-3-sulfonamide. $^1$H-NMR (DMSO-d$_6$): δ 1.99 (s, 3H), 4.76 (br s, 2H), 7.10-7.16 (m, 1H), 7.28-7.45 (m, 4H), 7.49-7.51 (m, 1H), 7.63-7.70 (m, 1H), 7.81-7.85 (m, 1H), 7.89-7.92 (m, 1H), 8.37-8.38 (m, 1H); MS: m/z 451.0 (MH$^+$).

Compound 16

N-(3-Methyl-benzo[b]thiophen-2-yl)-N-(4-trifluoromethoxy-benzyl)-thiophene-3-sulfonamide. $^1$H-NMR (DMSO-d$_6$): δ 1.94 (s, 3H), 4.78 (br s, 2H), 7.12 (d, 1H), 7.21-7.41 (m, 4H), 7.49-7.51 (m, 1H), 7.64-7.68 (m, 1H), 7.82-7.85 (m, 1H), 7.89-7.92 (m, 1H), 8.37-8.38 (m, 1H); MS: m/z 484.0 (MH$^+$).

Compound 17

N-(3-Methyl-benzo[b]thiophen-2-yl)-N-(quinolin-8-ylmethyl)-thiophene-3-sulfonamide. $^1$H-NMR (DMSO-d$_6$): δ 1.94 (s, 3H), 5.50 (s, 2H), 7.30-7.33 (m, 2H), 7.49-7.60 (m, 3H), 7.69-7.77 (m, 1H), 7.82-7.91 (m, 4H), 8.32-8.39 (m, 2H), 8.83-8.85 (m, 1H); MS: m/z 451.0 (MH$^+$).

Compound 18

N-(3,4-Difluoro-benzyl)-N-(3-methyl-benzo[b]thiophen-2-yl)-benzo[b]thiophene-2-sulfonamide. $^1$H-NMR (DMSO-d$_6$): δ 2.03 (s, 3H), 4.86 (br s, 2H), 7.14-7.20 (m, 1H), 7.30-7.47 (m, 3H), 7.54-7.75 (m, 3H), 7.82-7.87 (m, 1H), 8.10 (d, 1H), 8.20 (d, 1H), 8.26 (s, 1H); MS: m/z 486.1 (MH$^+$).

Compound 19

N-(3-Methyl-benzo[b]thiophen-2-yl)-N-(quinolin-8-ylmethyl)-benzo[b]thiophene-2-sulfonamide. $^1$H-NMR (DMSO-d$_6$): δ 1.97 (s, 3H), 5.60 (s, 2H), 7.30-7.35 (m, 2H), 7.47-7.65 (m, 6H), 7.73-7.78 (m, 1H), 7.83 (d, 1H), 7.89 (d, 1H), 8.12 (d, 1H), 8.21 (d, 1H), 8.27 (s, 1H), 8.32 (d of d, 1H), 8.76-8.79 (m, 1H); MS: m/z 501.1 (MH$^+$).

Compound 20

N-(3,4-Difluoro-benzyl)-N-(3-methyl-benzo[b]thiophen-2-yl)-quinoline-8-sulfonamide. $^1$H-NMR (DMSO-d$_6$): δ 1.74 (s, 3H), 5.29 (br s, 2H), 5.55 (br s, 1H), 7.16-7.22 (m, 1H), 7.27-7.44 (m, 4H), 7.56-7.61 (m, 1H), 7.64-7.70 (m, 2H), 7.82-7.87 (m, 1H), 8.23 (d of d, 1H), 8.36-8.40 (m, 1H), 8.65-8.67 (m, 1H), 9.28-9.30 (m, 1H); MS: m/z 481.2 (MH$^+$).

Compound 21

N-(3-Methyl-benzo[b]thiophen-2-yl)-N-(4-trifluoromethoxy-benzyl)-quinoline-8-sulfonamide. $^1$H-NMR (DMSO-d$_6$): δ 1.70 (s, 3H), 5.32 (br s, 2H), 5.77 (br s, 1H), 7.26-7.35 (m, 4H), 7.44 (d, 2H), 7.54-7.59 (m, 1H), 7.62-7.69 (m, 2H), 7.83-7.87 (m, 1H), 8.22 (d of d, 1H), 8.38 (d of d, 1H), 8.66 (d of d, 1H), 9.28-9.33 (m, 1H); MS: m/z 529.2 (MH$^+$).

Compound 22

N-(3-Methyl-benzo[b]thiophen-2-yl)-N-(quinolin-8-ylmethyl)-quinoline-8-sulfonamide. $^1$H-NMR (DMSO-d$_6$): δ 1.64 (s, 3H), 6.06 (s, 2H), 7.21-7.25 (m, 2H), 7.43-7.48 (m, 2H), 7.58-7.69 (m, 3H), 7.83-7.87 (m, 1H), 7.91-7.98 (m, 2H), 8.24-8.39 (m, 3H), 8.65-8.72 (m, 2H), 9.29-9.30 (m, 1H); MS: m/z 496.2 (MH$^+$).

Compound 23

N-(3-Chloro-benzo[b]thiophen-2-yl)-N-(3-fluoro-benzyl)-benzenesulfonamide. $^1$H-NMR (DMSO-d$_6$): δ 4.85 (s, 2H), 7.04-7.15 (m, 2H), 7.27-7.37 (m, 1H), 7.46-7.52 (m, 2H), 7.66-7.97 (m, 8H); MS: m/z 432.1 (MH$^+$).

Compound 24

N-(3-Chloro-benzo[b]thiophen-2-yl)-N-(3,4-difluoro-benzyl)-benzenesulfonamide. $^1$H-NMR (DMSO-d$_6$): δ 4.83

(s, 2H), 7.10-7.18 (m, 1H), 7.27-7.38 (m, 2H), 7.47-7.54 (m, 2H), 7.66-7.75 (m, 3H), 7.80-7.85 (m, 1H), 7.89-7.99 (m, 3H); MS: m/z 450.1 (MH$^+$).

Compound 25

N-(3,4-Difluoro-benzyl)-N-(3-methyl-benzo[b]thiophen-2-yl)-3-methoxy-benzenesulfonamide. $^1$H-NMR (DMSO-d$_6$): δ 1.97 (s, 3H), 3.82 (s, 3H), 4.75 (br s, 2H), 7.08-7.15 (m, 1H), 7.26-7.45 (m, 7H), 7.60 (t, 1H), 7.66-7.70 (m, 1H), 7.82-7.88 (m, 1H); MS: m/z 460.1 (MH$^+$).

Compound 26

N-(3,4-Difluoro-benzyl)-N-(3-methyl-benzo[b]thiophen-2-yl)-4-methoxy-benzenesulfonamide. $^1$H-NMR (DMSO-d$_6$): δ 1.98 (s, 3H), 3.88 (s, 3H), 4.70 (br s, 2H), 7.08-7.21 (m, 3H), 7.26-7.41 (m, 4H), 7.65-7.70 (m, 1H), 7.77-7.85 (m, 3H); MS: m/z 460.2 (MH$^+$).

Compound 27

N-(3,4-Difluoro-benzyl)-N-(3-methyl-benzo[b]thiophen-2-yl)-isoquinoline-5-sulfonamide. $^1$H-NMR (DMSO-d$_6$): δ 1.74 (s, 3H), 4.89 (br s, 2H), 7.06-7.13 (m, 1H), 7.24-7.42 (m, 4H), 7.58-7.64 (m, 1H), 7.75-7.80 (m, 1H), 7.88 (t, 1H), 8.33 (d, 1H), 8.45 (d, 1H), 8.56-8.61 (m, 2H), 9.59 (s, 1H); MS: m/z 481.2 (MH$^+$).

Compound 28

N-(3-Methyl-benzo[b]thiophen-2-yl)-N-(4-trifluoromethoxy-benzyl)-isoquinoline-5-sulfonamide. $^1$H-NMR (DMSO-d$_6$): δ 1.76 (s, 3H), 6.03 (s, 2H), 7.25-7.72 (m), 8.25 (t, 1H), 8.76-8.92 (m, 4H), 10.47 (s, 1H); MS: m/z 529.1 (MH$^+$).

Compound 29

N-(3-Methyl-benzo[b]thiophen-2-yl)-N-(quinolin-8-ylmethyl)-isoquinoline-5-sulfonamide. $^1$H-NMR (DMSO-d$_6$): δ 1.47 (s, 3H), 5.54 (s, 2H), 7.27-7.52 (m, 5H), 7.60 (d, 1H), 7.72-7.76 (m, 1H), 7.87 (d, 1H), 8.01 (t, 1H), 8.30-8.35 (m, 1H), 8.61-8.68 (m, 3H), 8.71-8.76 (m, 2H), 9.87 (s, 1H); MS: m/z 496.2 (MH$^+$).

Compound 30

N-(3,4-Difluoro-benzyl)-N-(3-methyl-benzo[b]thiophen-2-yl)-quinoline-6-sulfonamide. $^1$H-NMR (DMSO-d$_6$): δ 1.97 (s, 3H), 4.85 (br s, 2H), 7.12-7.20 (m, 1H), 7.29-7.42 (m, 4H), 7.64-7.71 (m, 1H), 7.76-7.85 (m, 2H), 8.21 (d of d, 1H), 8.35 (d, 1H), 8.74-8.80 (m, 2H), 9.19-9.21 (m, 1H); MS: m/z 481.2 (MH$^+$).

Compound 31

N-(3-Methyl-benzo[b]thiophen-2-yl)-N-(4-trifluoromethoxy-benzyl)-quinoline-6-sulfonamide. $^1$H-NMR (DMSO-d$_6$): δ 1.92 (s, 3H), 4.87 (s, 2H), 7.27-7.46 (m, 6H), 7.64-7.69 (m, 1H), 7.77-7.87 (m, 2H), 8.22 (d of d, 1H), 8.37 (d, 1H), 8.75-8.83 (m, 2H), 9.22 (d of d, 1H); MS: m/z 529.2 (MH$^+$).

Compound 32

N-(3-Methyl-benzo[b]thiophen-2-yl)-N-(quinolin-8-ylmethyl)-quinoline-6-sulfonamide. $^1$H-NMR (DMSO-d$_6$): δ 1.84 (s, 3H), 5.57 (s, 2H), 7.27-7.34 (m, 2H), 7.45-7.59 (m, 3H), 7.70-7.90 (m, 4H), 8.21 (d of d, 1H), 8.29 (d, 2H), 8.68-8.73 (m, 2H), 8.76 (d of d, 1H), 9.15 (d of d, 1H); MS: m/z 496.2 (MH$^+$).

Compound 33

N-(Benzo[b]thiophen-2-yl)-N-(3,4-difluoro-benzyl)-pyridine-3-sulfonamide. $^1$H-NMR (DMSO-d$_6$): δ 4.94 (s, 2H), 7.17-7.25 (m, 2H), 7.30-7.44 (m, 4H), 7.68-7.77 (m, 2H), 7.80-7.87 (m, 1H), 8.21-8.26 (m, 1H), 8.94 (d of d, 1H), 8.98 (d, 1H); MS: m/z 417.0 (MH$^+$).

Compound 34

N-Benzo[b]thiophen-2-yl-N-(3,4-difluoro-benzyl)-methanesulfonamide. $^1$H-NMR (DMSO-d$_6$): δ 3.28 (s, 3H), 4.19 (s, 2H), 7.18-7.24 (m, 1H), 7.31-7.45 (m, 5H), 7.73-7.78 (m, 1H), 7.82-7.89 (m, 1H); MS: m/z 354.1 (MH$^+$).

Compound 35

N-(Benzo[b]thiophen-2-yl)-N-(3,4-difluoro-benzyl)-ethanesulfonamide. $^1$H-NMR (DMSO-d$_6$): δ 1.32 (t, 3H), 3.44 (q, 2H), 4.97 (s, 2H), 7.17-7.24 (m, 1H), 7.30-7.46 (m, 5H), 7.71-7.78 (m, 1H), 7.82-7.87 (m, 1H); MS: m/z 368.1 (MH$^+$).

Compound 36

N-(Benzo[b]thiophen-2-yl)-N-(3,4-difluoro-benzyl)-propane-1-sulfonamide. $^1$H-NMR (DMSO-d$_6$): δ 1.01 (t, 3H), 1.72-1.87 (m, 2H), 3.37-3.44 (m, 2H), 4.95 (s, 2H), 7.16-7.23 (m, 1H), 7.30-7.46 (m, 5H), 7.70-7.76 (m, 1H), 7.81-7.88 (m, 1H); MS: m/z 382.2 (MH$^+$).

Compound 37

N-(Benzo[b]thiophen-2-yl)-N-(3,4-difluoro-benzyl)-butane-1-sulfonamide. $^1$H-NMR (DMSO-d$_6$): δ 0.892 (t, 3H), 1.35-1.48 (m, 2H), 1.67-1.79 (m, 2H), 3.40-3.45 (m, 2H), 4.96 (s, 2H), 7.16-7.23 (m, 1H), 7.30-7.45 (m, 5H), 7.71-7.77 (m, 1H), 7.82-7.88 (m, 1H); MS: m/z 396.1 (MH$^+$).

Compound 38

N-(3-Fluoro-4-trifluoromethyl-benzyl)-N-(3-methyl-benzo[b]thiophen-2-yl)-thiophene-2-sulfonamide. $^1$H-NMR (DMSO-d$_6$): δ 2.01 (s, 3H), 4.87 (br s, 2H), 7.32-7.50 (m, 4H), 7.63-7.73 (m, 3H), 7.83-7.88 (m, 2H), 8.17 (d of d, 1H); MS: m/z 486.1 (MH$^+$).

Compound 39

N-(4-Fluoro-3-trifluoromethyl-benzyl)-N-(3-methyl-benzo[b]thiophen-2-yl)-pyridine-3-sulfonamide. $^1$H-NMR (DMSO-d$_6$): δ 1.97 (s, 3H), 4.92 (br s, 2H), 7.37-7.53 (m, 3H), 7.63-7.79 (m, 4H), 7.84-7.88 (m, 1H), 8.27-8.32 (m, 1H), 8.97-9.04 (m, 2H); MS: m/z 481.2 (MH$^+$).

Compound 40

N-(4-Fluoro-3-trifluoromethyl-benzyl)-N-(3-methyl-benzo[b]thiophen-2-yl)-ethanesulfonamide. $^1$H-NMR (DMSO-d$_6$): δ 1.35 (t, 3H), 2.04 (s, 3H), 3.46 (q, 2H), 4.89 (s, 2H), 7.37-7.49 (m, 3H), 7.62-7.71 (m, 3H), 7.85-7.92 (m, 1H); MS: m/z 432.1 (MH$^+$).

Compound 41

N-(3,4-Difluoro-benzyl)-N-(3-methyl-benzo[b]thiophen-2-yl)-ethanesulfonamide. $^1$H-NMR (DMSO-d$_6$): δ 1.35 (t, 3H), 2.06 (s, 3H), 3.44 (q, 2H), 4.79 (s, 2H), 7.10-7.17 (m, 1H), 7.29-7.44 (m, 4H), 7.67-7.72 (m, 1H), 7.87-7.90 (m, 1H); MS: m/z 382.2 (MH$^+$).

Compound 42

N-(3-Methyl-benzo[b]thiophen-2-yl)-N-(4-trifluoromethoxy-benzyl)-ethanesulfonamide. $^1$H-NMR (DMSO-d$_6$): δ 1.35 (t, 3H), 1.99 (s, 3H), 3.44 (q, 2H), 4.82 (s, 2H), 7.30 (d, 2H), 7.36-7.43 (m, 4H), 7.65-7.70 (m, 1H), 7.86-7.90 (m, 1H); MS: m/z 430.2 (MH$^+$).

Compound 43

N-(Benzo[b]thiophen-2-yl)-N-(4-fluoro-3-trifluoromethyl-benzyl)-ethanesulfonamide. $^1$H-NMR (DMSO-d$_6$): δ 1.33 (t, 3H), 3.46 (q, 2H), 5.07 (s, 2H), 7.30-7.40 (m, 3H), 7.50 (t, 1H), 7.70-7.77 (m, 3H) and 7.83-7.88 (m, 1H); MS: m/z 418.0 (MH$^+$).

Compound 44

N-(3,4-Difluoro-benzyl)-N-(3-methyl-benzo[b]thiophen-2-yl)-N',N'-dimethylsulfamide. $^1$H-NMR (DMSO-d$_6$): δ 2.09 (s, 3H), 2.87 (s, 6H), 4.72 (s, 2H), 7.07-7.14 (m, 1H), 7.27-7.42 (m, 4H), 7.66-7.72 (m, 1H), 7.84-7.91 (m, 1H); MS: m/z 397.0 (MH$^+$).

Compound 45

N-(Benzo[b]thiophen-2-yl)-N-(4-fluoro-3-trifluoromethyl-benzyl)-methanesulfonamide. $^1$H-NMR (DMSO-d$_6$): δ 3.30 (s, 3H), 5.01 (s, 2H), 7.31-7.38 (m, 2H), 7.40 (s, 1H), 7.49 (t, 1H), 7.70-7.78 (m, 3H), 7.83-7.89 (m, 1H); MS: m/z 404.1 (MH$^+$).

Compound 46

N-(Benzo[b]thiophen-2-yl)-N-(4-chloro-benzyl)-benzenesulfonamide. $^1$H-NMR (CDCl$_3$): δ 4.76 (s, 2H), 7.00 (s, 1H), 7.21-7.32 (m, 6H), 7.48-7.53 (m, 2H), 7.61-7.66 (m, 3H), 7.76-7.80 (m, 2H); MS: m/z 414.0 (MH$^+$).

Compound 47

N-(Benzo[b]thiophen-2-yl)-N-(2-methoxy-benzyl)-benzenesulfonamide. $^1$H-NMR (CDCl$_3$): δ 3.71 (s, 3H), 4.90 (s, 2H), 6.76-6.78 (d, 1H), 6.86-6.90 (t, 1H), 7.01 (s, 1H), 7.17-7.22 (m, 1H), 7.22-7.32 (m, 3H), 7.42-7.51 (m, 3H), 7.58-7.64 (m, 2H), 7.77-7.82 (d, 2H); MS: m/z 410.1 (MH$^+$).

Compound 48

N-(Benzo[b]thiophen-2-yl)-N-(3-methoxy-benzyl)-benzenesulfonamide. $^1$H-NMR (CDCl$_3$): δ 3.74 (s, 3H), 4.78 (s, 2H), 6.75-6.78 (m, 1H), 6.88-6.91 (m, 2H), 7.01 (s, 1H), 7.15-7.19 (m, 1H), 7.25-7.31 (m, 2H), 7.48-7.52 (m, 2H), 7.59-7.64 (m, 3H), 7.76-7.78 (d, 2H); MS: m/z 410.1 (MH$^+$).

Compound 49

N-(Benzo[b]thiophen-2-yl)-N-(4-methoxy-benzyl)-benzenesulfonamide. $^1$H-NMR (CDCl$_3$): δ 3.74 (s, 3H), 4.74 (s, 2H), 6.76-6.81 (d, 2H), 6.97 (s, 1H), 7.21-7.31 (m, 4H), 7.47-7.51 (m, 2H), 7.59-7.65 (m, 3H), 7.76-7.80 (d, 2H); MS: m/z 410.1 (MH$^+$), 432.0 (MNa$^+$).

Compound 50

N-(Benzo[b]thiophen-2-yl)-N-(2-fluoro-benzyl)-benzenesulfonamide. $^1$H-NMR (CDCl$_3$): δ 4.92 (s, 2H), 6.92-6.97 (m, 1H), 7.01 (s, 1H), 7.06-7.11 (m, 1H), 7.19-7.31 (m, 3H), 7.48-7.53 (m, 3H), 7.60-7.65 (m, 3H), 7.77-7.81 (d, 2H); MS: m/z 398.1 (MH$^+$).

Compound 51

N-(Benzo[b]thiophen-2-yl)-N-(3-nitro-benzyl)-benzenesulfonamide. $^1$H-NMR (CDCl$_3$): δ 4.89 (s, 2H), 7.05 (s, 1H), 7.26-7.31 (m, 2H), 7.46-7.54 (m, 3H), 7.62-7.68 (m, 3H), 7.74-7.79 (m, 3H), 8.05-8.19 (m, 2H); MS: m/z 425.1 (MH$^+$).

Compound 52

N-(Benzo[b]thiophen-2-yl)-N-(pyridin-2-ylmethyl)-benzenesulfonamide. $^1$H-NMR (CDCl$_3$): δ 5.17 (s, 2H), 7.07 (s, 1H), 7.26-7.32 (m, 3H), 7.38-7.43 (m, 1H), 7.48-7.55 (m, 2H), 7.60-7.67 (m, 2H), 7.77-7.79 (m, 2H), 7.87-7.89 (m, 1H), 7.94-7.98 (m, 1H), 8.59-8.61 (m, 1H); MS: m/z 381.0 (MH$^+$).

Compound 53

N-(Benzo[b]thiophen-2-yl)-N-(pyridin-3-ylmethyl)-benzenesulfonamide. $^1$H-NMR (CDCl$_3$): δ 4.97 (s, 2H), 7.07 (s, 1H), 7.32-7.34 (m, 2H), 7.52-7.57 (m, 3H), 7.63-7.71 (m, 3H), 7.76-7.83 (m, 3H), 8.48-8.49 (m, 1H), 8.75-8.76 (m, 1H), 8.83 (s, 1H); MS: m/z 381.0 (MH$^+$).

Compound 54

N-(Benzo[b]thiophen-2-yl)-N-(pyridin-4-ylmethyl)-benzenesulfonamide $^1$H-NMR (CDCl$_3$): δ 5.02 (s, 2H), 7.13 (s, 1H), 7.33-7.37 (m, 2H), 7.53-7.57 (m, 2H), 7.63-7.71 (m, 3H), 7.76-7.78 (m, 2H), 7.84-7.88 (m, 2H), 8.81-8.84 (m, 2H); MS: m/z 381.0 (MH$^+$).

Compound 55

N-(Benzo[b]thiophen-2-yl)-N-(2-nitro-benzyl)-benzenesulfonamide. $^1$H-NMR (CDCl$_3$): δ 5.29 (s, 2H), 7.11 (s, 1H), 7.27-7.31 (m, 2H), 7.40-7.44 (m, 1H), 7.50-7.54 (m, 2H), 7.61-7.69 (m, 4H), 7.78-7.80 (m, 2H), 7.97-8.03 (m, 2H); MS: m/z 425.1 (MH$^+$).

Compound 56

N-(Benzo[b]thiophen-2-yl)-N-(2-trifluoromethoxy-benzyl)-benzenesulfonamide. $^1$H-NMR (CDCl$_3$): δ 4.93 (s, 2H), 7.01 (s, 1H), 7.15-7.18 (m, 1H), 7.23-7.30 (m, 4H), 7.49-7.53 (m, 2H), 7.59-7.66 (m, 4H), 7.78-7.79 (m, 2H); MS: m/z 464.1 (MH$^+$).

Compound 57

N-(Benzo[b]thiophen-2-yl)-N-(3-trifluoromethoxy-benzyl)-benzenesulfonamide. $^1$H-NMR (CDCl$_3$): δ 4.81 (s, 2H), 7.01 (s, 1H), 7.07-7.09 (m, 1H), 7.19 (s, 1H), 7.25-7.31 (m, 4H), 7.48-7.53 (m, 2H), 7.61-7.66 (m, 3H), 7.76-7.78 (m, 2H); MS: m/z 464.1 (MH$^+$).

Compound 58

N-(Benzo[b]thiophen-2-yl)-N-(4-trifluoromethoxy-benzyl)-benzenesulfonamide. $^1$H-NMR (CDCl$_3$): δ 4.80 (s, 2H), 7.01 (s, 1H), 7.10-7.12 (d, 2H), 7.28-32 (m, 2H), 7.35-7.37 (m, 2H), 7.48-7.52 (m, 2H), 7.61-7.65 (m, 3H), 7.75-7.77 (m, 2H); MS: m/z 464.0 (MH$^+$).

Compound 59

N-(Benzo[b]thiophen-2-yl)-N-(benzyl)-benzenesulfonamide. $^1$H-NMR (CDCl$_3$): δ 4.80 (s, 2H), 6.99 (s, 1H), 7.22-7.28 (m, 5H), 7.31-7.33 (m, 2H), 7.48-7.51 (m, 2H), 7.59-7.64 (m, 3H), 7.77-7.79 (m, 2H); MS: m/z 380.1 (MH$^+$).

Compound 60

N-(Benzo[b]thiophen-2-yl)-N-(4-fluoro-3-methoxy-benzyl)-benzenesulfonamide. $^1$H-NMR (CDCl$_3$): δ 3.82 (s, 3H), 4.75 (s, 2H), 6.72-6.78 (m, 1H), 6.89-6.94 (m, 1H), 6.98-6.99 (m, 2H), 7.28-7.31 (m, 2H), 7.48-7.53 (m, 2H), 7.61-7.64 (m, 3H), 7.76-7.78 (m, 2H); MS: m/z 428.1 (MH$^+$).

Compound 61

N-(Benzo[b]thiophen-2-yl)-N-(4-fluoro-3-trifluoromethyl-benzyl)-benzenesulfonamide. $^1$H-NMR (CDCl$_3$): δ 4.80 (s, 2H), 7.03 (s, 1H), 7.08-7.14 (m, 1H), 7.28-7.34 (m, 2H), 7.49-7.55 (m, 5H), 7.63-7.68 (m, 3H), 7.75-7.77 (m, 2H); MS: m/z 466.0 (MH$^+$).

Compound 62

N-(Benzo[b]thiophen-2-yl)-N-(2-methyl-benzyl)-benzenesulfonamide. $^1$H-NMR (CDCl$_3$): δ 2.39 (s, 3H), 4.81 (s, 2H), 6.97 (s, 1H), 7.01-7.05 (m, 1H), 7.09-7.12 (m, 2H), 7.20-7.29 (m, 3H), 7.49-7.53 (m, 2H), 7.58-7.66 (m, 3H), 7.77-7.81 (d, 2H); MS: m/z 394.0 (MH$^+$).

Compound 63

N-(Benzo[b]thiophen-2-yl)-N-(3-methyl-benzyl)-benzenesulfonamide. $^1$H-NMR (CDCl$_3$): δ 2.25 (s, 3H), 4.76 (s, 2H), 7.00 (s, 1H), 7.02-7.04 (m, 1H), 7.09-7.16 (m, 3H), 7.47-7.53 (m, 2H), 7.59-7.64 (m, 3H), 7.76-7.78 (m, 2H); MS: m/z 394.0 (MH$^+$).

Compound 64

N-(4-Fluoro-3-trifluoromethyl-benzyl)-N-(3-methyl-benzo[b]thiophen-2-yl)-3-fluoro-4-methoxybenzenesulfonamide. $^1$H-NMR (DMSO-d$_6$): δ 1.98 (s, 3H), 3.97 (s, 3H), 4.87 (s, 2H), 7.35-7.48 (m, 4H), 7.62-7.71 (m, 4H), 7.76-7.88 (m, 2H); MS: m/z 528.0 (MH$^+$), 550.0 (MNa$^+$).

Compound 65

N-(4-Fluoro-3-trifluoromethyl-benzyl)-N-(3-methyl-benzo[b]thiophen-2-yl)-benzothiazole-6-sulfonamide. $^1$H-NMR (DMSO-d$_6$): δ 1.96 (s, 3H), 4.90 (s, 2H), 7.33-7.52 (m, 3H), 7.63-7.70 (m, 3H), 7.78-7.83 (m, 1H), 7.97-8.01 (m, 1H), 8.31-8.42 (d, 1H), 8.91 (s, 1H), 9.77 (s, 1H); MS: m/z 537.0 (MH$^+$).

Compound 66

N-(4-Fluoro-3-trifluoromethyl-benzyl)-N-(3-methyl-benzo[b]thiophen-2-yl)-2-oxo-2,3-dihydro-benzooxazole-6-sulfonamide. $^1$H-NMR (DMSO-d$_6$): δ 1.98 (s, 3H), 4.84 (s, 2H), 7.28-7.48 (m, 4H), 7.60-7.70 (m, 4H), 7.81-7.86 (m, 2H), 12.35 (s, 1H); MS: m/z 537.0 (MH$^+$).

Compound 67

N-(4-Fluoro-3-trifluoromethyl-benzyl)-N-(3-methyl-benzo[b]thiophen-2-yl))-3-oxo-3,4-dihydro-2H-benzo[1,4]oxazine-6-sulfonamide. $^1$H-NMR (DMSO-d$_6$): δ 1.97 (s, 3H), 4.79 (m, 4H), 7.20-7.23 (d, 1H), 7.29-7.51 (m, 4H), 7.61-7.72 (m, 3H), 7.81-7.90 (m, 1H), 10.91 (s, 1H); MS: m/z 551.1 (MH$^+$).

Compound 68

N-(4-Fluoro-3-trifluoromethyl-benzyl)-N-(3-methyl-benzo[b]thiophen-2-yl)-4-methyl-3,4-dihydro-2H-benzo[1,4]oxazine-7-sulfonamide. $^1$H-NMR (DMSO-d$_6$): δ 1.99 (s, 3H), 2.82 (s, 3H), 4.33-4.36 (m, 2H), 4.78 (s, 2H), 6.97-6.91 (d, 1H), 6.98-7.00 (m, 1H), 7.04-7.09 (m, 2H), 7.32-7.46 (m, 3H), 7.59-7.69 (m, 3H), 7.83-7.87 (m, 1H); MS: m/z 551.1 (MH$^+$).

Compound 69

N-(4-Fluoro-3-trifluoromethyl-benzyl)-N-(3-methyl-benzo[b]thiophen-2-yl)-4-[1,2,3]thiadiazol-4-yl-benzenesulfonamide. $^1$H-NMR (DMSO-d$_6$): δ 1.98 (s, 3H), 4.92 (s, 2H), 7.34-7.51 (m, 3H), 7.65-7.71 (m, 3H), 7.82-7.85 (m, 1H), 8.04-8.06 (d, 2H), 8.44-8.47 (d, 2H), 9.92 (s, 1H); MS: m/z 564.0 (MH$^+$), 586.0 (MNa$^+$).

Compound 70

N-(4-Fluoro-3-trifluoromethyl-benzyl)-N-(3-methyl-benzo[b]thiophen-2-yl)-3-phenoxy-benzenesulfonamide. $^1$H-NMR (DMSO-d$_6$): δ 1.87 (s, 3H), 5.06 (s, 2H), 7.05-7.08 (d, 1H), 7.21-7.39 (m, 6H), 7.43-7.54 (m, 3H), 7.62-7.86 (m, 6H); MS: m/z 572.1 (MH$^+$).

Compound 71

N-(3-Methyl-benzo[b]thiophen-2-yl)-N-(4-fluoro-3-trifluoromethylbenzyl)-2-carbomethoxypropanesulfonamide. $^1$H-NMR (DMSO-d$_6$): δ 2.01 (s, 3H), 2.82-2.89 (t, 2H), 3.65 (s, 3H), 3.71-3.75 (t, 2H), 4.89 (s, 2H), 7.39-7.48 (m, 3H), 7.59-7.71 (m, 3H), 7.84-7.92 (m, 1H); MS: m/z 490.0 (MH$^+$), 512.0 (MNa$^+$).

Compound 72

N-(3-Methyl-benzo[b]thiophen-2-yl)-N-(4-fluoro-3-trifluoromethylbenzyl)-(2,4-dihydroxy-6-methyl-pyrimidine-5-yl)sulfonamide $^1$H-NMR (DMSO-d$_6$): δ 1.94 (s, 3H), 2.08 (s, 3H), 4.98 (s, 3H), 7.34-7.50 (m, 3H), 7.60-7.69 (m, 3H), 7.84-7.92 (m, 1H), 11.66 (s, 1H), 11.85 (s, 1H); MS: m/z 528.0 (MH$^+$).

Compound 73

N-(4-Fluoro-3-trifluoromethyl-benzyl)-N-(3-methyl-benzo[b]thiophen-2-yl)-2-(2,2,2-trifluoro-acetyl)-1,2,3,4-tetrahydro-isoquinoline-8-sulfonamide. $^1$H-NMR (DMSO-d$_6$): δ 1.94-1.98 (m, 3H), 3.02-3.09 (m, 2H), 3.80-3.90 (m, 2H), 4.76-4.90 (m, 4H), 7.34-7.53 (m, 4H), 7.60-7.69 (m, 5H), 7.82-7.85 (m, 1H), 7.96 (s, 1H); MS: m/z 631.0 (MH$^+$).

Compound 74

N-(4-Fluoro-3-trifluoromethyl-benzyl)-N-(3-methyl-benzo[b]thiophen-2-yl)-1,3,5-trimethyl-1H-pyrazole-4-sulfonamide. $^1$H-NMR (DMSO-d$_6$): δ 2.04 (s, 6H), 2.18 (s, 3H), 3.72 (s, 3H), 4.76 (s, 2H), 7.34-7.46 (m, 3H), 7.60-7.69 (m, 3H), 7.82-7.89 (m, 1H); MS: m/z 512.0 (MH$^+$).

Compound 75

N-(4-Fluoro-3-trifluoromethyl-benzyl)-N-(3-methyl-benzo[b]thiophen-2-yl)-2,4-dimethyl-thiazole-5-sulfonamide. $^1$H-NMR (DMSO-d$_6$): δ 2.04 (s, 3H), 2.29 (s, 3H), 2.71 (s, 3H), 4.83 (s, 2H), 7.35-7.51 (m, 3H), 7.63-7.75 (m, 3H), 7.88-7.92 (m, 1H); MS: m/z 515.0 (MH$^+$).

Compound 76

N-(4-Fluoro-3-trifluoromethyl-benzyl)-N-(3-methyl-benzo[b]thiophen-2-yl)-6-chloro-pyridine-3-sulfonamide. $^1$H-NMR (DMSO-d$_6$): δ 2.01 (s, 3H), 4.83 (s, 2H), 7.35-7.51 (m, 3H), 7.63-7.75 (m, 3H), 7.88-7.92 (m, 2H), 8.31-8.34 (m, 1H), 8.90 (d, 1H); MS: m/z 515.0 (MH$^+$).

Compound 77

N-(4-Fluoro-3-trifluoromethyl-benzyl)-N-(3-methyl-benzo[b]thiophen-2-yl)-2-chloro-pyridine-3-sulfonamide. $^1$H-NMR (DMSO-d$_6$): δ 1.02 (s, 3H), 5.15 (s, 2H), 7.35-7.40 (m, 2H), 7.45-7.75 (m, 5H), 7.82-7.85 (m, 1H), 8.26-8.32 (m, 1H), 8.72-8.77 (m, 1H); MS: m/z 515.0 (MH$^+$).

Compound 78

N-(Benzo[b]thiophen-2-yl)-N-(4-fluoro-3-trifluoromethyl-benzyl)-thiophene-3-sulfonamide. $^1$H-NMR (DMSO-d$_6$): δ 4.98 (s, 2H), 7.19 (s, 1H), 7.31-7.34 (m, 2H), 7.42-7.43 (m, 1H), 7.46-7.51 (m, 1H), 7.68-7.75 (m, 3H), 7.82-7.90 (m, 2H), 8.38-8.39 (m, 1H); MS: m/z 472.0 (MH$^+$).

Compound 462

N-(Benzo[b]thiophen-2-yl)-N-(4-fluoro-3-trifluoromethyl-benzyl)-3-N',N'-dimethylsulfamoyl-benzenesulfonamide. MS: m/z 573.2 (MH$^+$).

Compound 825

N-(Benzyl)-N-(3-methyl-benzo[b]thiophen-2-yl)-3,4-difluoro-benzenesulfonamide $^1$H-NMR (CDCl$_3$): δ 2.02 (s, 3H), 4.78 (br s, 2H), 7.28 (s, 5H), 7.41 (m, 3H), 7.62 (m, 2H), 7.72 (m, 2H); MS: m/z 452.0 (MNa$^+$).

Compound 826

N-(4-Fluoro-benzyl)-N-(3-methyl-benzo[b]thiophen-2-yl)-3,4-difluoro-benzenesulfonamide. $^1$H NMR (CDCl$_3$) δ 2.02 (s, 3H), 4.72 (br s, 2H), 6.95 (m, 2H), 7.22 (m, 2H), 7.42 (m, 3H), 7.61 (m, 2H), 7.72 (m, 2H); MS: m/z 447.9 (MH$^+$), 470.0 (MNa$^+$).

Compound 828

N-(Benzo[b]thiophen-2-yl)-N-(4-fluoro-3-methoxy-benzyl)-ethanesulfonamide. MS: m/z 380.0 (MH$^+$), 402 (MNa$^+$).

Compound 829

N-(2-Fluoro-pyridin-4-ylmethyl)-N-(3-methyl-benzo[b]thiophen-2-yl)-ethanesulfonamide. $^1$H-NMR (CDCl$_3$): δ 1.42 (t, 3H), 2.12 (s, 3H), 3.23 (q, 2H), 4.79 (s, 2H), 6.81 (s, 1H), 7.13 (m, 1H), 7.33 (m, 2H), 7.52 (m, 1H), 7.67 (m, 1H), 8.12 (m, 1H); MS: m/z 365.0 (MH$^+$).

Compound 845

3-Fluoro-N-(4-fluoro-benzyl)-4-(4-fluoro-benzyloxy)-N-(3-methyl-benzo[b]thiophen-2-yl)-benzenesulfonamide. MS: m/z 554.0 (MH$^+$), 576.0 (MNa$^+$).

Compound 846

N-(Benzyl)-4-benzyloxy-3-fluoro-N-(3-methyl-benzo[b]thiophen-2-yl)-benzenesulfonamide. MS: m/z 540.0 (MNa$^+$).

Example 2

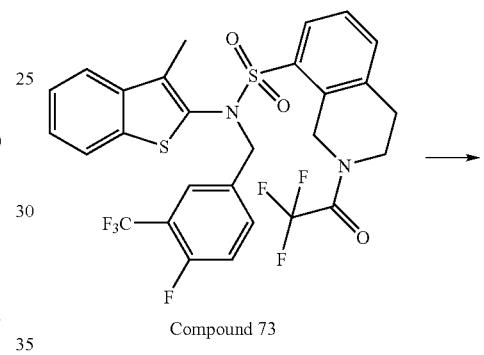

Compound 73

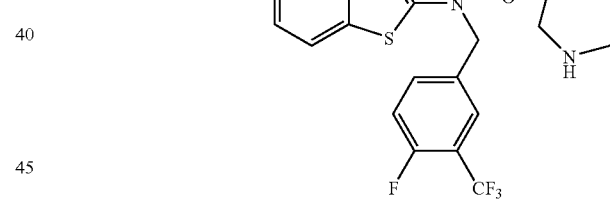

a) K$_2$CO$_3$, MeOH, H$_2$O.

Compound 79

Compound 79

N-(4-Fluoro-3-trifluoromethyl-benzyl)-N-(3-methyl-benzo[b]thiophen-2-yl)-1,2,3,4-tetrahydro-isoquinoline-8-sulfonamide. To a solution of potassium carbonate (0.066 g; 0.48 mmol) in methanol and water (2 mL/2 mL) was added compound 73 (0.06 g; 0.095 mmol) and the reaction was stirred for 18 h at room temperature. The reaction was partitioned between ethyl acetate and water, the layers separated, organics washed with brine, dried over sodium sulfate, flute filtered and the solvent evaporated under reduced pressure. The crude residue was purified by reverse-phase semi-prep HPLC (Gemini, C$_{18}$ column; 100×30 mm I.D.; 5µ) eluting with a 40% to 60% MeCN—H$_2$O gradient to afford compound 79 as a yellow oil (0.035 g, 57%). $^1$H-NMR (DMSO-d$_6$): δ 1.95 (s, 3H), 3.15 (m, 2H), 3.46 (m, 2H), 4.38 (m, 2H), 4.83 (m, 2H), 7.37-7.88 (m, 10H), 9.11 (s, 1H); MS: m/z 535.0 (MH$^+$).

Example 3

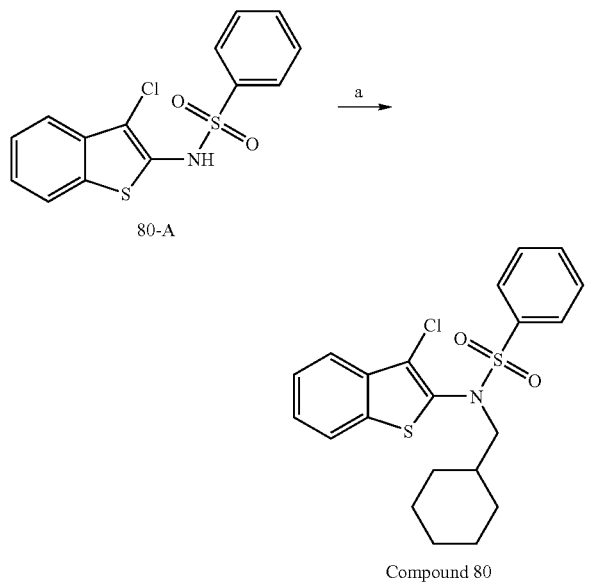

a) Ph$_3$P, DEAD, cyclohexylmethanol, THF.

Compound 80

N-(3-Chloro-benzo[b]thiophen-2-yl)-N-(cyclohexylmethyl)-benzenesulfonamide. To triphenylphosphine (0.157 g, 0.60 mmol) dissolved in dry tetrahydrofuran (5 mL) was added a solution of DEAD (0.260 g of 40% solution by weight in toluene, 0.60 mmol). The reaction mixture was stirred at room temperature for 2 minutes, to which was added compound 80-A (0.130 g, 0.40 mmol). Cyclohexyl methanol (0.048 mL, 0.48 mmol) was added and the reaction mixture was stirred at room temperature for 16 h. The reaction mixture was evaporated in vacuo, the residue dissolved in 10 mL of dichloromethane, washed with 10 mL of brine, dried over Na$_2$SO$_4$, filtered and the solvent was evaporated in vacuo. The product was purified by flash column chromatography on silica gel eluting with an ethyl acetate-heptane (10-20%) gradient afford compound 80 as a light yellow solid, (0.121 g, 72%). $^1$H-NMR (CDCl$_3$): δ 0.88-1.0 (m, 2H), 1.14-1.27 (m, 3H), 1.30-1.37 (m, 1H), 1.38-1.44 (m, 2H), 1.45-1.48 (m, 1H), 1.62-1.87 (m, 2H), 3.47 (d, 2H), 7.41-7.52 (m, 4H), 7.59-7.64 (m, 1H), 7.70-7.73 (m, 1H), 7.74-7.82 (m, 3H); MS: m/z 420.1 (MH$^+$).

Following the procedure described above for Example 3 and substituting the appropriate reagents, starting materials and purification methods known to those skilled in the art, the following compounds of the present invention were prepared:

Compound 81

N-(2-tert-Butoxy-ethyl)-N-(3-chloro-benzo[b]thiophen-2-yl)-benzenesulfonamide. $^1$H-NMR (CDCl$_3$): δ 1.10 (s, 9H), 3.56 (t, 2H), 3.83 (t, 2H), 7.42-7.52 (m, 4H), 7.56-7.68 (m, 1H), 7.70-7.78 (m, 2H), 7.85-7.87 (d, 2H); MS: m/z 446.1 (MNa$^+$).

Compound 82

N-(3-Chloro-benzo[b]thiophen-2-yl)-N-[2-(2-oxo-pyrrolidin-1-yl)-ethyl]-benzenesulfonamide. $^1$H-NMR (CDCl$_3$): δ 2.06-2.16 (m, 2H), 2.48-2.53 (m, 2H), 3.49-3.73 (m, 2H), 3.87-3.91 (m, 2H), 7.44-7.81 (m, 9H); MS: m/z 435.1 (MH$^+$).

Compound 83

N-(Butyl)-N-(3-chloro-benzo[b]thiophen-2-yl)-benzenesulfonamide. 1H-NMR (CDCl$_3$): δ 0.85-0.90 (m, 3H), 1.34-1.55 (m, 4H), 3.62-3.67 (t, 2H), 7.43-7.53 (m, 4H), 7.60-7.68 (m, 1H), 7.69-7.73 (m, 1H), 7.74-7.85 (m, 3H); MS: m/z 380.1 (MH$^+$).

Compound 84

N-(Allyl)-N-(3-chloro-benzo[b]thiophen-2-yl)-benzenesulfonamide. $^1$H-NMR (CDCl$_3$): δ 4.28-4.31 (m, 2H), 5.08-5.18 (m, 2H), 5.80-5.91 (m, 1H), 7.40-7.50 (m, 2H), 7.52-7.63 (m, 2H), 7.64-7.87 (m, 5H); MS: m/z 364.0 (MH$^+$).

Compound 85

N-(3-Chloro-benzo[b]thiophen-2-yl)-N-(phenethyl)-benzenesulfonamide. $^1$H-NMR (CDCl$_3$): δ 2.89-2.94 (m, 2H), 3.85-3.90 (m, 2H), 7.13-7.28 (m, 6H), 7.43-7.51 (m, 4H), 7.58-7.82 (m, 4H); MS: m/z 364.0 (MH$^+$).

Compound 86

N-(3-Chloro-benzo[b]thiophen-2-yl)-N-[2-(carbo-tert-butoxyamino)ethyl]-benzenesulfonamide. $^1$H-NMR (CDCl$_3$): δ 1.38 (s, 9H), 3.28-3.32 (t, 2H), 3.75-3.79 (t, 2H), 5.03 (s, 1H, NH), 7.43-7.55 (m, 4H), 7.62-7.85 (m, 5H); MS: m/z 489.1 (MNa$^+$).

Compound 87

N-(3-Chloro-benzo[b]thiophen-2-yl)-N-(2-dimethylamino-ethyl)-benzenesulfonamide. $^1$H-NMR (CDCl$_3$): δ 2.98 (s, 6H), 3.38-3.42 (t, 2H), 4.06-4.11 (t, 2H), 7.48-7.57 (m, 4H), 7.67-7.82 (m, 5H); MS: m/z 395.1 (MH$^+$).

Compound 88

N-(3-Chloro-benzo[b]thiophen-2-yl)-N-(2-methanesulfonyl-ethyl)-benzenesulfonamide. $^1$H-NMR (CDCl$_3$): δ 3.03 (s, 3H), 3.40-3.45 (t, 2H), 4.11-4.16 (m, 2H), 7.47-7.57 (m, 4H), 7.66-7.85 (m, 5H); MS: m/z 430.0 (MH$^+$).

Compound 89

N-(3-Chloro-benzo[b]thiophen-2-yl)-N-{1-(carbo-tert-butoxy)pyrrolidin-2-yl]-methyl}-benzenesulfonamide. $^1$H-NMR (CDCl$_3$): δ 1.29 (s, 9H), 1.94-2.01 (m, 3H), 2.35 (bs, 1H), 3.35-3.36 (m, 2H), 3.61-3.82 (m, 3H), 7.39-7.54 (m, 4H), 7.59-7.71 (m, 2H), 7.75-7.81 (m, 3H); MS: m/z 407.1 (MH$^+$-BOC).

Compound 90

N-(3-Chloro-benzo[b]thiophen-2-yl)-N-{1-(carbo-tert-butoxy)piperidin-4-yl]-methyl}-benzenesulfonamide.

¹H-NMR (CDCl₃): δ 1.58-1.65 (m, 5H), 1.73 (s, 9H), 3.52-3.54 (bd, 2H), 4.06-4.10 (bd, 2H), 7.44-7.53 (m, 4H), 7.61-7.66 (m, 1H), 7.70-7.77 (m, 1H), 7.78-7.81 (m, 3H); MS: m/z 543.2 (MNa⁺).

Compound 91

N-(3-Chloro-benzo[b]thiophen-2-yl)-N-[2-(2-oxo-imidazolidin-1-yl)-ethyl]-benzenesulfonamide. ¹H-NMR (CDCl₃): δ 3.37-3.44 (m, 4H), 3.61-3.66 (m, 2H), 3.85-3.89 (m, 2H), 7.43-7.53 (m, 4H), 7.61-7.66 (m, 1H), 7.70-7.83 (m, 4H); MS: m/z 436.4 (MH⁺).

Compound 92

N-(3-Chloro-benzo[b]thiophen-2-yl)-N-(2-morpholin-4-yl-ethyl)-benzenesulfonamide. ¹H-NMR (CDCl₃): δ 2.39-2.42 (m, 4H), 2.53-2.57 (m, 2H), 3.57-3.60 (m, 4H), 3.79-3.83 (m, 2H), 7.43-7.53 (m, 3H), 7.71-7.84 (m, 3H), 7.85-7.86 (m, 2H); MS: m/z 437.1 (MH⁺).

Compound 93

N-(3-Methyl-benzo[b]thiophen-2-yl)-N-[2(R)-methyl-2-carbomethoxy-ethyl]-benzenesulfonamide. ¹H-NMR (CDCl₃): δ 1.27 (s, 3H), 2.34 (s, 3H), 2.61-2.68 (m, 1H), 3.42-4.17 (m, 5H), 7.33-7.40 (m, 2H), 7.42-7.62 (m, 2H), 7.64-7.78 (m, 5H); MS: m/z 404.1 (MH⁺).

Compound 94

N-(3-Methyl-benzo[b]thiophen-2-yl)-N-[2(S)-methyl-2-carbomethoxy-ethyl]-benzenesulfonamide. ¹H-NMR (CDCl₃): δ 1.26 (s, 3H), 2.33 (s, 3H), 2.61-2.68 (m, 1H), 3.49 (s, 3H), 3.58 (s, 2H), 7.33-7.42 (m, 2H), 7.42-7.61 (m, 2H), 7.62-7.78 (m, 5H); MS: m/z 404.1 (MH⁺).

Compound 95

N-(3-Methyl-benzo[b]thiophen-2-yl)-N-(2-morpholin-4-yl-ethyl)-benzenesulfonamide. ¹H-NMR (CDCl₃): δ 2.36 (s, 3H), 2.41-2.51 (m, 6H), 3.57-3.74 (m, 6H), 7.33-7.40 (m, 2H), 7.48-7.61 (m, 2H), 7.62-7.66 (m, 3H), 7.69-7.81 (m, 2H); MS: m/z 417.3 (MH⁺).

Compound 96

N-(3-Methyl-benzo[b]thiophen-2-yl)-N-(2-piperidin-1-yl-ethyl)-benzenesulfonamide. ¹H-NMR (CDCl₃): δ 1.26-1.53 (m, 2H), 2.35 (m, 7H), 2.44-2.49 (t, 2H), 3.52-3.66 (m, 2H), 7.33-7.40 (m, 2H), 7.47-7.52 (m, 2H), 7.59-7.71 (m, 3H), 7.71-7.82 (m, 2H); MS: m/z 415.2 (MH⁺).

Compound 97

N-(Cyclopropylmethyl)-N-(3-methyl-benzo[b]thiophen-2-yl)-benzenesulfonamide. ¹H-NMR (CDCl₃): δ 0.18-0.20 (m, 2H), 0.43-0.46 (m, 2H), 0.92-1.00 (m, 1H), 2.39 (s, 3H), 7.35-7.39 (m, 2H), 7.48-7.53 (m, 2H), 7.59-7.71 (m, 3H), 7.72-7.81 (m, 2H); MS: m/z 358.2 (MH⁺).

Compound 98

N-(3-Methyl-benzo[b]thiophen-2-yl)-N-(2-methylsulfanyl-ethyl)-benzenesulfonamide. ¹H-NMR (CDCl₃): δ 2.09 (s, 3H), 2.35 (s, 3H), 2.62-2.67 (m, 2H), 3.74 (bs, 2H), 7.35-7.41 (m, 2H), 7.48-7.55 (m, 2H), 7.60-7.72 (m, 3H), 7.78-7.82 (m, 2H); MS: m/z 378.1 (MH⁺).

Compound 99

N-(2-Methoxy-ethyl)-N-(3-methyl-benzo[b]thiophen-2-yl)-benzenesulfonamide. ¹H-NMR (CDCl₃): δ 2.32 (s, 3H), 3.29 (s, 3H), 3.45-3.50 (m, 2H), 3.72 (bs, 2H), 7.35-7.41 (m, 2H), 7.46-7.54 (m, 2H), 7.59-7.73 (m, 3H), 7.79-7.83 (m, 2H); MS: m/z 362.1 (MH⁺).

Compound 100

N-(2-tert-Butoxy-ethyl)-N-(3-methyl-benzo[b]thiophen-2-yl)-benzenesulfonamide. ¹H-NMR (CDCl₃): δ 1.10 (s, 9H), 2.30 (s, 3H), 3.46-3.50 (t, 2H), 3.71 (bs, 2H), 7.35-7.39 (m, 2H), 7.47-7.52 (m, 2H), 7.59-7.70 (m, 3H), 7.80-7.83 (m, 2H); MS: m/z 404.2 (MH⁺).

Compound 101

N-(3-Methyl-benzo[b]thiophen-2-yl)-N-(carbomethoxy-methyl)-benzenesulfonamide. ¹H-NMR (CDCl₃): δ 1.10 (s, 9H), 2.33 (s, 3H), 3.70 (s, 3H), 4.42 (s, 2H), 7.35-7.40 (m, 2H), 7.47-7.53 (m, 2H), 7.60-7.70 (m, 3H), 7.79-7.84 (m, 2H); MS: m/z 376.2 (MH⁺).

Compound 102

N-(2,2-Difluoro-ethyl)-N-(3-methyl-benzo[b]thiophen-2-yl)-benzenesulfonamide. ¹H-NMR (CDCl₃): δ 2.30 (s, 3H), 3.88 (bs, 2H), 5.83-6.12 (m, 1H), 7.37-7.41 (m, 2H), 7.51-7.56 (m, 2H), 7.65-7.72 (m, 3H), 7.78-7.81 (m, 2H); MS: m/z 368.1 (MH⁺).

Compound 103

N-(3-Methyl-benzo[b]thiophen-2-yl)-N-{[1-(carbo-tert-butoxy)pyrrolidin-2-yl]-methyl}-benzenesulfonamide. ¹H-NMR (CDCl₃): δ 1.17-1.36 (m, 11H), 1.82-1.97 (m, 2H), 2.32-2.52 (m, 2H), 3.21-3.46 (m, 2H), 3.59-3.74 (m, 1H), 7.31-7.41 (m, 2H), 7.46-7.51 (m, 2H), 7.58-7.79 (m, 5H); MS: m/z 487.2 (MH⁺).

Compound 104

N-(3-Methyl-benzo[b]thiophen-2-yl)-N-(phenethyl)-benzenesulfonamide. ¹H-NMR (CDCl₃): δ 2.31 (s, 3H), 2.82-2.89 (t, 2H), 3.66-3.93 (bs, 2H), 7.10-7.17 (m, 2H), 7.22-7.30 (m, 3H), 7.37-7.42 (m, 2H), 7.46-7.53 (m, 2H), 7.57-7.65 (m, 1H), 7.69-7.78 (m, 4H); MS: m/z 408.1 (MH⁺).

Compound 105

N-(2-Methoxy-ethyl)-N-(3-methyl-benzo[b]thiophen-2-yl)-ethanesulfonamide. ¹H-NMR (CDCl₃): δ 1.43-1.47 (t, 3H), 2.42 (s, 3H), 3.23-3.31 (q, 2H), 3.84-3.88 (t, 2H), 7.38-7.41 (m, 2H), 7.69-7.75 (m, 2H); MS: m/z 314.1 (MH⁺).

Compound 106

N-(3-Methyl-benzo[b]thiophen-2-yl)-N-(3,3,3-trifluoro-propyl)-ethanesulfonamide. ¹H-NMR (CDCl₃): δ 1.43-1.48 (t, 3H), 2.42 (s, 3H), 2.45-2.52 (m, 2H), 3.18-3.25 (q, 2H), 3.91-3.97 (m, 2H), 7.41-7.44 (m, 2H), 7.70-7.78 (m, 2H); MS: m/z 352.2 (MH⁺).

Compound 107

N-(3-Methyl-benzo[b]thiophen-2-yl)-N-(pent-3-ynyl)-ethanesulfonamide. $^1$H-NMR (CDCl$_3$): δ 1.43-1.48 (t, 3H), 1.73-1.74 (t, 3H), 2.43 (s, 3H), 3.19-3.27 (q, 2H), 3.78-3.83 (t, 2H), 7.37-7.41 (m, 2H), 7.69-7.75 (m, 2H); MS: m/z 322.2 (MH$^+$).

Compound 108

N-(3-Methyl-benzo[b]thiophen-2-yl)-N-(2-methylsulfanyl-ethyl)-ethanesulfonamide. $^1$H-NMR (CDCl$_3$): δ 1.43-1.48 (t, 3H), 2.11 (s, 3H), 2.44 (s, 3H), 2.66-2.71 (t, 2H), 3.20-3.27 (m, 2H), 3.85-3.90 (t, 2H), 7.38-7.42 (m, 2H), 7.70-7.76 (m, 2H); MS: m/z 330.1 (MH$^+$).

Compound 109

N-(3-Methyl-benzo[b]thiophen-2-yl)-N-(5-oxo-(S)-pyrrolidin-2-ylmethyl)-ethanesulfonamide. $^1$H-NMR (CDCl$_3$): δ 1.42-1.47 (t, 3H), 2.31-2.37 (m, 4H), 2.44 (s, 3H), 3.17-3.24 (q, 2H), 3.76-3.85 (m, 3H), 5.73 (bs, 1H), 7.41-7.44 (m, 2H), 7.70-7.76 (m, 2H); MS: m/z 353.1 (MH$^+$).

Compound 110

N-(2-tert-Butoxy-ethyl)-N-(3-methyl-benzo[b]thiophen-2-yl)-ethanesulfonamide. $^1$H-NMR (CDCl$_3$): δ 1.18 (s, 9H), 1.43-1.54 (q, 3H), 2.42 (s, 3H), 3.28-3.35 (q, 2H), 3.48-3.52 (t, 2H), 3.80-3.84 (t, 2H), 5.73 (bs, 1H), 7.37-7.40 (m, 2H), 7.68-7.75 (m, 2H); MS: m/z 356.3 (MH$^+$).

Compound 111

N-(2,2-Difluoro-ethyl)-N-(3-methyl-benzo[b]thiophen-2-yl)-ethanesulfonamide. $^1$H-NMR (CDCl$_3$): δ 1.44-1.49 (t, 3H), 2.43 (s, 3H), 3.22-3.35 (q, 2H), 3.95-4.06 (t, 2H), 5.78-6.18 (tt, 1H), 7.40-7.43 (m, 2H), 7.71-7.76 (m, 2H); MS: m/z 320.1 (MH$^+$).

Compound 112

N-(Cyclopropylmethyl)-N-(3-methyl-benzo[b]thiophen-2-yl)-ethanesulfonamide. $^1$H-NMR (CDCl$_3$): δ 0.00-0.35 (m, 2H), 0.24-0.30 (m, 2H), 0.78-0.88 (m, 1H), 1.19-1.24 (t, 3H), 2.24 (s, 3H), 2.95-3.02 (q, 2H), 3.32-3.34 (td 2H), 7.15-7.19 (m, 2H), 7.48-7.54 (m, 2H); MS: m/z 310.2 (MH$^+$).

Compound 113

N-(3-Methyl-benzo[b]thiophen-2-yl)-N-(2-morpholin-4-yl-ethyl)-ethanesulfonamide. $^1$H-NMR (CDCl$_3$): δ 1.43-1.47 (t, 3H), 2.44 (s, 3H), 2.46-2.54 (m, 4H), 3.24-3.33 (q, 2H), 3.65-3.69 (m, 4H), 3.78-3.84 (m, 2H), 7.37-7.43 (m, 2H), 7.69-7.76 (m, 2H); MS: m/z 369.1 (MH$^+$).

Compound 114

N-(3-Methyl-benzo[b]thiophen-2-yl)-N-{[1-(carbo-tert-butoxy)pyrrolidin-2-yl]-methyl}-ethanesulfonamide. $^1$H-NMR (CDCl$_3$): δ 1.20-1.47 (m, 12H), 2.06-2.25 (m, 4H), 2.43 (s, 3H), 3.11-3.41 (m, 4H), 3.60-3.95 (m, 3H), 7.31-7.47 (m, 2H), 7.64-7.78 (m, 2H); MS: m/z 439.2 (MH$^+$).

Compound 115

N-(Benzo[b]thiophen-2-yl)-N-(phenethyl)-benzenesulfonamide. $^1$H-NMR (DMSO-d$_6$): δ 2.83 (t, 2H), 3.89 (t, 2H), 7.19-7.25 (m, 4H), 7.26-7.33 (m, 2H), 7.34-7.41 (m, 2H), 7.58 (t, 2H), 7.66-7.74 (m, 3H), 7.77-7.81 (m, 1H), 7.85-7.90 (m, 1H); MS: m/z 394.2 (MH$^+$).

Compound 116

N-(Allyl)-N-(benzo[b]thiophen-2-yl)-benzenesulfonamide. $^1$H NMR-(DMSO-d$_6$): δ 4.32 (d, 2H), 5.15 (dd, 1H), 5.26 (dd, 1H), 5.75-5.86 (m, 1H), 7.16 (s, 1H), 7.31-7.38 (m, 2H), 7.62 (t, 2H), 7.71-7.79 (m, 4H), 7.82-7.87 (m, 1H); MS: m/z 330.1 (MH$^+$).

Compound 117

N-(Benzo[b]thiophen-2-yl)-N-(butyl)-benzenesulfonamide. $^1$H-NMR (DMSO-d$_6$): δ 0.85 (t, 3H), 1.34 (m, 2H), 1.48 (m, 2H), 3.64 (t, 2H), 7.21 (s, 1H), 7.32-7.39 (m, 2H), 7.61 (t, 2H), 7.70-7.75 (m, 3H), 7.76-7.80 (m, 1H), 7.83-7.88 (m, 1H); MS: m/z 346.1 (MH$^+$).

Compound 118

N-(Benzo[b]thiophen-2-yl)-N-(cyclohexylmethyl)-benzenesulfonamide. $^1$H-NMR (DMSO-d$_6$): δ 0.90-1.02 (m, 2H), 1.03-1.17 (m, 3H), 1.38-1.49 (m, 1H), 1.54-1.60 (m, 1H), 1.61-1.68 (m, 2H), 1.69-1.77 (m, 2H), 3.47 (d, 2H), 7.22 (s, 1H), 7.32-7.39 (m, 2H), 7.60 (t, 2H), 7.68-7.74 (m, 3H), 7.75-7.80 (m, 1H), 7.83-7.87 (m, 1H); MS: m/z 386.2 (MH$^+$).

Compound 119

N-(Benzo[b]thiophen-2-yl)-N-(cyclohexyl)-benzenesulfonamide. $^1$H-NMR (DMSO-d$_6$): δ 0.79-0.93 (m, 1H), 1.17-1.41 (m, 4H), 1.49 (br d, 1H), 1.64-1.77 (m, 4H), 4.06-4.16 (m, 1H), 7.15 (s, 1H), 7.36-7.43 (m, 2H), 7.64 (t, 2H), 7.69-7.76 (m, 1H), 7.81-7.91 (m, 4H); MS: m/z 372.1 (MH$^+$).

Compound 120

N-(Benzo[b]thiophen-2-yl)-N-(2-methylsulfanyl-ethyl)-benzenesulfonamide. $^1$H-NMR (DMSO-d$_6$): δ 2.08 (s, 3H), 2.65 (t, 2H), 3.85 (t, 2H), 7.23 (s, 1H), 7.33-7.39 (m, 2H), 7.62 (t, 2H), 7.71-7.81 (m, 4H), 7.84-7.89 (m, 1H); MS: m/z 364.2 (MH$^+$).

Compound 121

N-(3-Acetyl-benzo[b]thiophen-2-yl)-N-(butyl)-ethanesulfonamide. $^1$H-NMR (DMSO-d$_6$): δ 0.88 (t, 3H), 1.24 (t, 3H), 1.36 (m, 2H), 1.65 (m, 2H), 2.59 (s, 3H), 3.34 (q, 2H), 3.79 (t, 2H), 7.44-7.50 (m, 2H), 7.97-8.02 (m, 1H), 8.06-8.11 (m, 1H); MS: m/z 340.1 (MH$^+$).

Compound 122

N-(3-Acetyl-benzo[b]thiophen-2-yl)-N-(cyclopropylmethyl)-ethanesulfonamide. $^1$H-NMR (DMSO-d$_6$): δ 0.25-0.31 (m, 2H), 0.50-0.56 (m, 2H), 1.05-1.17 (m, 1H), 1.25 (t, 3H), 2.67 (s, 3H), 3.34 (q, 2H), 3.71 (d, 2H), 7.45-7.51 (m, 2H), 7.97-8.03 (m, 1H), 8.09-8.15 (m, 1H); MS: m/z 338.1 (MH$^+$).

Compound 123

N-(3-Acetyl-benzo[b]thiophen-2-yl)-N-(2-tert-butoxyethyl)-ethanesulfonamide. $^1$H-NMR (DMSO-d$_6$): δ 1.09 (s, 9H), 1.27 (t, 3H), 2.65 (s, 3H), 3.40 (q, 2H), 3.56 (t, 2H), 3.93 (t, 2H), 7.44-7.50 (m, 2H), 7.97-8.03 (m, 1H), 8.13-8.18 (m, 1H); MS: m/z 384.1 (MH$^+$).

Compound 124

N-(3-Acetyl-benzo[b]thiophen-2-yl)-N-(2-morpholin-4-yl-ethyl)-ethanesulfonamide. MS: m/z 397.2 (MH$^+$).

Compound 340

N-(Benzo[b]thiophen-2-yl)-N-(butyl)-pyridin-3-yl-sulfonamide. MS: m/z 347.2 (MH$^+$).

Compound 362

N-(Benzo[b]thiophen-2-yl)-N-(4-fluoro-3-trifluoromethyl-benzyl)-C-methanesulfonyl-methanesulfonamide. MS: m/z 482.1 (MH$^+$).

Compound 363

N-(Butyl)-N-(3-methyl-benzo[b]thiophen-2-yl)-methanesulfonamide. MS: m/z 298.0 (MH$^+$).

Compound 364

N-(3-Methyl-benzo[b]thiophen-2-yl)-N-(3,3,3-trifluoro-propyl)-methanesulfonamide. MS: m/z 338.0 (MH$^+$).

Compound 365

N-(Cyclopropylmethyl)-N-(3-methyl-benzo[b]thiophen-2-yl)-methanesulfonamide. MS: m/z 296.0 (MH$^+$).

Compound 366

N-(2-tert-Butoxy-ethyl)-N-(3-methyl-benzo[b]thiophen-2-yl)-methanesulfonamide. MS: m/z 364.0 (MNa$^+$).

Compound 382

N-(Benzo[b]thiophen-2-yl)-N-(butyl)-methanesulfonamide. MS: m/z 284.0 (MH$^+$).

Compound 422

N-(Butyl)-N-(3-methoxy-benzo[b]thiophen-2-yl)-4-carbomethoxybenzenesulfonamide. Compound 422 was prepared as a solid from Example 1, steps A and B, substituting benzo[b]thiophene-2-carboxylic acid with 3-methoxy-benzo[b]thiophene-2-carboxylic acid and from Example 32, steps E and F. $^1$H-NMR (CDCl$_3$): δ 0.88 (t, 3H), 1.29-1.41 (m, 2H), 1.51-1.61 (m, 2H), 3.54 (t, 2H), 3.98 (s, 3H), 4.09 (s, 3H), 7.33-7.39 (m, 2H), 7.55-7.60 (m, 1H), 7.75-7.78 (m, 1H), 7.92 (d, 2H), 8.17 (d, 2H); MS: m/z 434.1 (MH$^+$).

Compound 461

N-(Benzo[b]thiophen-2-yl)-N-(3,3,3-trifluoro-propyl)-3-dimethylsulfamoyl-benzenesulfonamide. MS: m/z 493.0 (MH$^+$).

Compound 476

N-(Benzo[b]thiophen-2-yl)-4-(bromo)-N-(3,3,3-trifluoro-propyl)-benzenesulfonamide. MS: m/z 464, 466 (MH$^+$).

Compound 498

N-(Benzo[b]thiophen-2-yl)-4-nitro-N-(3,3,3-trifluoro-propyl)-benzenesulfonamide. $^1$H-NMR (CDCl$_3$): δ 2.43-2.62 (m, 2H), 3.87-3.96 (m, 2H), 7.23 (s, 1H), 7.35-7.46 (m, 2H), 7.67-7.80 (m, 2H), 7.91 (d, 2H), 8.34 (d, 2H).

Compound 564

N-(2-Cyclopropyl-ethyl)-N-(3-isopropyl-benzo[b]thiophen-2-yl)-4-carbomethoxy-benzenesulfonamide. MS: m/z 458.1 (MH$^+$).

Compound 565

N-(3-Isopropyl-benzo[b]thiophen-2-yl)-N-(5,5,5-trifluoro-pentyl)-4-carbomethoxy-benzenesulfonamide. MS: m/z 514.0 (MH$^+$).

Compound 628

N-(2-Cyclopropyl-ethyl)-N-(3-methyl-benzo[b]thiophen-2-yl)-4-carbomethoxy-benzenesulfonamide. $^1$H-NMR (CDCl$_3$): δ −0.04-0.02 (m, 2H), 0.31-0.51 (m, 2H), 0.55-0.77 (m, 1H), 1.33-1.52 (m, 2H), 2.37 (s, 3H), 3.37-3.82 (m, 2H), 3.94 (s, 3H), 7.30-7.46 (m, 2H), 7.53-7.76 (m, 3H), 7.93 (d, 1H), 8.30 (d, 1H), 8.48 (s, 1H); MS: m/z 430.0 (MH$^+$).

Compound 629

N-(3-Methyl-benzo[b]thiophen-2-yl)-N-(3,3,3-trifluoro-propyl)-4-carbomethoxy-benzenesulfonamide. $^1$H-NMR (CDCl$_3$): δ 2.36 (s, 3H), 2.35-2.55 (m, 2H), 3.67-3.92 (m, 2H), 3.95 (s, 3H), 7.35-7.48 (m, 2H), 7.57-7.76 (m, 3H), 7.90-7.95 (m, 1H), 8.31-8.35 (m, 1H), 8.45-8.47 (m, 1H); MS: m/z 458.0 (MH$^+$).

Compound 630

N-(3-Methyl-benzo[b]thiophen-2-yl)-N-(4,4,4-trifluoro-butyl)-4-carbomethoxy-benzenesulfonamide. MS: m/z 472.0 (MH$^+$).

Compound 631

N-(3-Methyl-benzo[b]thiophen-2-yl)-N-(5,5,5-trifluoro-pentyl)-4-carbomethoxy-benzenesulfonamide. $^1$H-NMR (CDCl$_3$): δ 1.40-1.57 (m, 2H), 1.58-1.76 (m, 2H), 2.13-2.34 (m, 2H), 2.29 (s, 3H), 2.49-2.52 (m, 2H), 3.42-3.82 (m, 2H), 7.68-7.89 (m, 5H), 8.21-8.34 (m, 2H), 8.44-8.45 (m, 1H); MS: m/z 486.0 (MH$^+$).

Compound 817

N-(Benzo[b]thiophen-2-yl)-N-(3-fluoro-propyl)-benzenesulfonamide. $^1$H-NMR (CDCl$_3$): δ 2.02 (m, 2H), 3.78 (t, 2H), 4.55 (dt, 2H), 7.12 (s, 1H), 7.32 (m, 2H), 7.48 (m, 2H), 7.59 (m, 1H), 7.69 (m, 4H); MS: m/z 350.0 (MH$^+$).

Compound 818

N-(2-Fluoro-ethyl)-N-(3-methyl-benzo[b]thiophen-2-yl)-benzenesulfonamide. $^1$H-NMR (CDCl$_3$): δ 2.25 (s, 3H), 3.81 (br s, 2H), 4.38 (t, 1H), 4.48 (t, 1H), 7.31 (m, 2H), 7.46 (m, 2H), 7.61 (m, 3H), 7.75 (m, 2H); MS: m/z 350.0 (MH$^+$).

Compound 819

N-(3-Fluoro-propyl)-N-(3-methyl-benzo[b]thiophen-2-yl)-benzenesulfonamide. $^1$H-NMR (CDCl$_3$): δ 0.88 (m, 2H)2.29 (s, 3H), 1.81-1.98 (m, 2H), 4.45 (dt, 2H), 7.31 (m, 2H), 7.45 (t, 2H), 7.62 (m, 3H), 7.70 (m, 2H); MS: m/z 364.0 (MH$^+$), 386 (MNa$^+$). ,

Compound 823

N-(3-Fluoro-propyl)-N-(3-methyl-benzo[b]thiophen-2-yl)-4-carbomethoxy-benzenesulfonamide. $^1$H-NMR (CDCl$_3$): δ 1.85 (m, 2H), 2.38 (s, 3H), 3.78 (br s, 2H), 3.98 (s, 3H), 4.52 (dt, 2H), 7.39 (m, 2H), 7.69 (m, 2H), 7.84 (d, 2H), 8.17 (d, 2H); MS: m/z 422.0 (MH$^+$), 444 (MNa$^+$).

Compound 831

N-(3-Fluoro-propyl)-N-(3-methyl-benzo[b]thiophen-2-yl)-3,4-difluoro-benzenesulfonamide. MS: m/z 400.0 (MH$^+$), 422 (MNa$^+$).

Compound 840

N-(3-Methyl-benzo[b]thiophen-2-yl)-N-(2,3,5-trifluoro-pyridin-4-ylmethyl)-ethanesulfonamide. $^1$H-NMR (CDCl$_3$): δ 1.45 (t, 3H), 2.23 (s, 3H), 3.32 (q, 2H), 5.08 (s, 2H), 7.41 (m, 2H), 7.65 (m, 1H), 7.72 (m, 1H), 7.81 (s, 1H); MS: m/z 401.0 (MH$^+$), 423 (MNa$^+$).

Compound 841

N-(2-Fluoro-ethyl)-N-(3-methyl-benzo[b]thiophen-2-yl)-3,4-difluoro-benzenesulfonamide. $^1$H-NMR (CDCl$_3$): δ 2.38 (s, 3H), 3.98 (br s, 2H), 4.53 (dt, 2H), 7.34 (m, 1H), 7.53 (m, 2H), 7.62 (m, 1H), 7.72 (m, 3H); MS: m/z 386.0 (MH$^+$), 408 (MNa$^+$).

Compound 842

N-(Benzo[b]thiophen-2-yl)-N-(3-fluoro-propyl)-4-carbomethoxy-benzenesulfonamide. MS: m/z 408.0 (MH$^+$).

Compound 843

N-(Benzo[b]thiophen-2-yl)-N-(2-fluoro-ethyl)-4-carbomethoxy-benzenesulfonamide. MS: m/z 394.0 (MH$^+$), 416 (MNa$^+$).

Compound 844

N-(Benzo[b]thiophen-2-yl)-N-(2-fluoro-ethyl)-benzenesulfonamide. MS m/z 336.0 (MH$^+$).

Compound 847

N-(Benzo[b]thiophen-2-yl)-N-(2-fluoro-pyridin-4-ylmethyl)-ethane-sulfonamide. MS: m/z 351.0 (MH$^+$).

Compound 848

N-(3-Acetyl-benzo[b]thiophen-2-yl)-N-(2-fluoro-pyridin-4-ylmethyl)-ethansulfonamide. MS: m/z 393.0 (MH$^+$), 415 (MNa$^+$).

Example 4

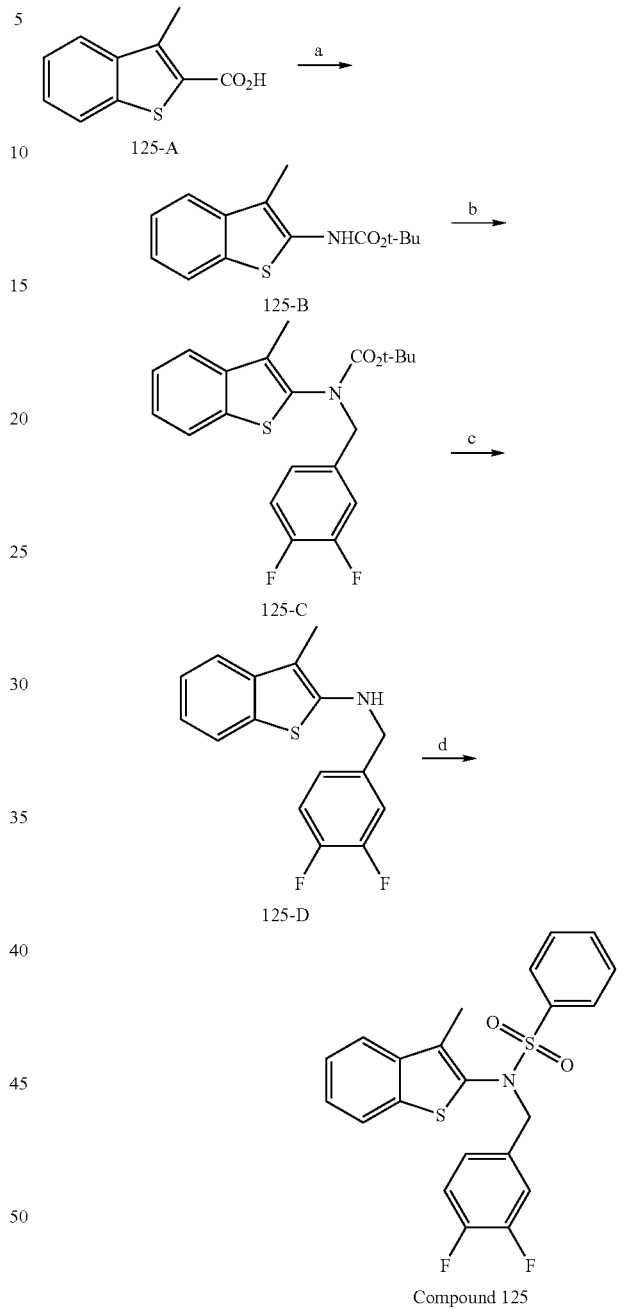

a) DPPA, DIEA, t-BuOH; b) NaH, 3,4-difluorobenzyl bromide, DMF; c) TFA, DCM; d) benzenesulfonyl chloride, DMAP, pyridine.

(3-Methyl-benzo[b]thiophen-2-yl)-carbamic acid tert-butyl ester (125-B) A solution of compound 125-A (3.15 g, 16.4 mmol), N,N-diisopropylethylamine (3.15 mL, 18.0 mmol) and diphenyl phosphoryl azide (4.23 mL, 19.7 mmol) in t-butanol (40 mL) was heated at reflux for 8 h. The solvent was evaporated in vacuo, and the residue partitioned between dichloromethane and 1N aqueous sodium hydroxide. The organic layer was applied to a silica gel column, and the product isolated by flash column chromatography eluting with an ethyl acetate-heptane gradient, to afford compound 125-B as a colorless solid (2.3 g, 53%). $^1$H-NMR (CDCl$_3$): δ

1.48 (s, 9H), 2.26 (s, 3H), 6.74 (br s, 1H), 7.21-7.26 (m, 1H), 7.31-7.36 (m, 1H), 7.54 (d, 1H), 7.71 (d, 1H); MS: m/z 264.1 (MH⁺).

(3,4-Difluoro-benzyl)-(3-methyl-benzo[b]thiophen-2-yl)-carbamic acid tert-butyl ester (125-C) Sodium hydride (60%, 0.37 g, 9.19 mmol) was added to a solution of compound 125-B (2.2 g, 8.35 mmol) in DMF (30 mL), at 0° C. and the resultant mixture was stirred for 15 minutes. 3,4-Difluorobenzylbromide (1.18 mL, 9.2 mmol) was added, and the solution was stirred at ambient temperature for 2 h. The reaction mixture was diluted with water, extracted with ethyl acetate, the organic extract washed with water (3×), brine, dried over sodium sulfate, filtered, and the solvent evaporated in vacuo. The crude residue was purified by flash column chromatography, eluting with an ethyl acetate-heptane gradient, to afford compound 125-C as an oil (2.73 g, 84%). ¹H-NMR (CDCl₃): δ 1.40 (s, 9H), 1.97 (s, 3H), 4.72 (s, 2H), 6.93-7.19 (m, 3H), 7.28-7.39 (m, 2H), 7.61 (d, 1H), 7.70 (d, 1H).

(3,4-Difluoro-benzyl)-(3-methyl-benzo[b]thiophen-2-yl)-amine (125-D). A solution of compound 125-C (2.7 g, 6.9 mmol) in dichloromethane (40 mL) and trifluoroacetic acid (40 mL) was stirred at rt for 4 h. The solvent was evaporated in vacuo, and the residue partitioned between dichloromethane and saturated aqueous sodium bicarbonate. The organic layer was dried over sodium sulfate, and the solvent evaporated in vacuo to afford compound 125-D as a colorless solid (1.86 g, 93%). ¹H-NMR (CDCl₃): δ 2.16 (s, 3H), 4.37 (s, 2H), 7.09-7.32 (m, 5H), 7.40 (d, 1H), 7.60 (d, 1H); MS: m/z 290.1 (MH⁺).

Compound 125

N-(3,4-Difluoro-benzyl)-N-(3-methyl-benzo[b]thiophen-2-yl)-benzenesulfonamide. Benzenesulfonyl chloride (0.121 mL, 0.94 mmol) was added to a solution of compound 125-D (237 mg, 0.473 mmol) and N,N-dimethylaminopyridine (catalytic amount) in pyridine (4 mL), at 0° C. The resultant solution was stirred for 30 min, allowed to warm to room temperature and stirred at ambient temperature overnight. The solvent was evaporated in vacuo, the residue partitioned between 2N HCl and dichloromethane, the layers separated, and the organic layer dried over magnesium sulfate, filtered, and the solvent evaporated in vacuo. The residue was purified by HPLC (C₁₈) eluting with an acetonitrile (0.1% TFA)-water (0.1% TFA) (40-90%) gradient to afford compound 125 as a solid (0.11 g, 54%). ¹H-NMR (CDCl₃): δ 2.04 (s, 3H), 4.64 (br s, 2H), 6.93-7.04 (m, 2H), 7.12-7.17 (m, 1H), 7.31-7.38 (m, 2H), 7.52-7.70 (m, 5H), 7.81-7.84 (m, 2H); MS: m/z 430.1 (MH⁺).

Following the procedure described above for Example 4 and substituting the appropriate reagents, starting materials and purification methods known to those skilled in the art, the following compounds of the present invention were prepared:

Compound 126

N-(3,4-Difluoro-benzyl)-N-(3-methyl-benzo[b]thiophen-2-yl)-phenyl-methanesulfonamide. ¹H-NMR (CDCl₃): δ 2.07 (s, 3H), 4.38 (d of d, 2H), 4.64 (d of d, 2H), 7.15-7.44 (m, 12H), 7.65 (d, 1H); MS: m/z 444.0 (MH⁺).

Compound 127

N-(3,4-Difluoro-benzyl)-N-(3-methyl-benzo[b]thiophen-2-yl)-3-fluoro-benzenesulfonamide. ¹H-NMR (CDCl₃) δ: 2.05 (s, 3H), 4.63 (br s, 2H), 6.94-7.07 (m, 2H), 7.10-7.18 (m, 1H), 7.33-7.40 (m, 3H), 7.50-7.69 (m, 5H); MS: m/z 448.0 (MH⁺).

Compound 128

N-(3,4-Difluoro-benzyl)-N-(3-methyl-benzo[b]thiophen-2-yl)-2-fluoro-benzenesulfonamide. ¹H-NMR (DMSO-d₆): δ 2.50 (s, 3H), 4.88 (br s, 2H), 7.10-7.95 (m, 11H); MS: m/z 448.0 (MH⁺).

Compound 129

N-(3,4-Difluoro-benzyl)-N-(3-methyl-benzo[b]thiophen-2-yl)-thiene-2-ylsulfonamide. ¹H-NMR (DMSO-d₆): δ 2.02 (s, 3H), 4.76 (br s, 2H), 7.14-7.16 (m, 1H), 7.29-7.43 (m, 5H), 7.70 (d of d, 1H), 7.83-7.86 (m, 2H), 8.16 (d of d, 1H); MS: m/z 436.0 (MH⁺).

Compound 130

N-(Benzo[b]thiophen-2-yl)-N-(3,4-difluoro-benzyl)-1-methyl-1H-imidazole-4-sulfonamide. ¹H-NMR (DMSO-d₆): δ 3.71 (s, 3H), 4.98 (s, 2H), 7.17 (s, 1H), 7.23-7.45 (m, 5H), 7.69-7.73 (m, 1H), 7.78-7.81 (m, 1H), 7.92 (s, 1H), 7.95 (s, 1H); MS: m/z 420.1 (MH⁺).

Compound 131

N-(Benzo[b]thiophen-2-yl)-N-(3,4-difluoro-benzyl)-3-fluoro-benzenesulfonamide. ¹H-NMR (DMSO-d₆): δ 4.93 (s, 2H), 7.17-7.24 (m, 2H), 7.30-7.86 (m, 10H); MS: m/z 434.1 (MH⁺).

Compound 132

N-(Benzo[b]thiophen-2-yl)-N-(3,4-difluoro-benzyl)-4-trifluoromethyl-benzenesulfonamide. ¹H-NMR (DMSO-d₆): δ 4.93 (s, 2H), 7.17-7.25 (m, 2H), 7.30-7.44 (m, 4H), 7.71-7.75 (m, 1H), 7.82-7.89 (m, 1H), 8.05-8.07 (m, 4H); MS: m/z 484.2 (MH⁺).

Compound 133

N-(Benzo[b]thiophen-2-yl)-N-(3,4-difluoro-benzyl)-C-methanesulfonyl-methanesulfonamide. ¹H-NMR (DMSO-d₆): δ 3.26 (m, 3H), 4.97 (s, 2H), 5.62 (s, 2H), 7.17-7.23 (m, 1H), 7.33-7.47 (m, 5H), 7.76-7.82 (m, 1H), 7.85-7.90 (m, 1H); MS: m/z 432.0 (MH⁺).

Compound 134

N-(Benzo[b]thiophen-2-yl)-N-(4-fluoro-3-trifluoromethyl-benzyl)-4-methoxy-benzenesulfonamide. ¹H-NMR (DMSO-d₆): δ 3.77 (s, 3H), 4.99 (s, 2H), 7.17 (s, 1H), 7.29-7.38 (m, 5H), 7.45-7.53 (m, 1H), 7.55-7.60 (t, 1H), 7.70-7.76 (m, 3H), 7.82-7.87 (m, 1H); MS: m/z 496.0 (MH⁺).

Compound 135

N-(Benzo[b]thiophen-2-yl)-N-(4-fluoro-3-trifluoromethyl-benzyl)-4-carbomethoxy-benzenesulfonamide. ¹H-NMR (DMSO-d₆): δ 3.91 (s, 3H), 5.01 (s, 2H), 7.19 (s, 1H), 7.30-7.36 (m, 2H), 7.45-7.51 (t, 1H), 7.69-7.73 (m, 3H), 7.82-7.85 (m, 1H), 7.97-7.99 (d, 2H), 8.17-8.20 (d, 2H); MS: m/z 524.1 (MH⁺).

Compound 136

N-(Benzo[b]thiophen-2-yl)-N-(4-fluoro-3-trifluoromethyl-benzyl)-3-carbomethoxy-benzenesulfonamide.
$^1$H-NMR (DMSO-$d_6$): δ 3.87 (s, 3H), 5.02 (s, 2H), 7.21 (s, 1H), 7.32-7.34 (m, 2H), 7.45-7.50 (t, 1H), 7.71-7.73 (m, 3H), 7.81-7.85 (m, 2H), 8.08-8.11 (m, 1H), 8.25-8.26 (m, 1H), 8.30-8.33 (s, 1H); MS: m/z 524.1 (MH$^+$).

Compound 137

N-(3-Methyl-benzo[b]thiophen-2-yl)-N-(4-fluoro-3-trifluoromethyl-benzyl)-3-carbomethoxy-benzenesulfonamide
$^1$H-NMR (DMSO-$d_6$): δ 1.96 (s, 3H), 3.89 (s, 3H), 4.88 (s, 2H), 7.38-7.47 (m, 3H), 7.62-7.68 (m, 2H), 7.69-7.72 (m, 1H), 7.84-7.88 (m, 2H), 8.15-8.18 (m, 1H), 8.27-8.28 (m, 1H), 8.33-8.35 (m, 1H); MS: m/z 538.0 (MH$^+$).

Compound 138

N-(3-Methyl-benzo[b]thiophen-2-yl)-N-(4-fluoro-3-trifluoromethyl-benzyl)-4-carbomethoxy-benzenesulfonamide.
$^1$H-NMR (DMSO-$d_6$): δ 1.94 (s, 3H), 3.93 (s, 3H), 4.89 (s, 2H), 7.36-7.48 (m, 3H), 7.63-7.71 (m, 3H), 7.81-7.86 (m, 1H), 8.02-8.04 (m, 2H), 8.19-8.22 (m, 1H); MS: m/z 538.0 (MH$^+$).

Compound 139

N-(Benzo[b]thiophen-2-yl)-N-(4-fluoro-3-trifluoromethyl-benzyl)-2-carbomethoxy-benzenesulfonamide.
$^1$H-NMR (DMSO-$d_6$): δ 3.77 (s, 3H), 5.08 (s, 2H), 7.24 (s, 1H), 7.31-7.34 (m, 2H), 7.47-7.52 (m, 1H), 7.66-7.85 (m, 8H); MS: m/z 524.1 (MH$^+$).

Example 5

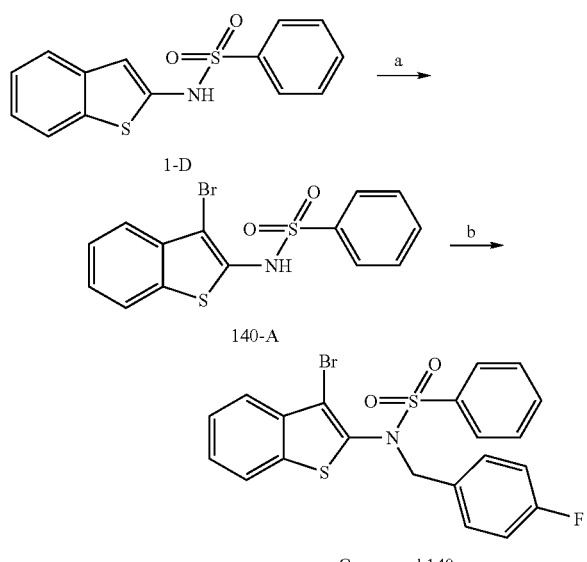

a) Br$_2$, DCM; b) LHMDS, 4-fluorobenzyl bromide, THF.

N-(3-Bromo-benzo[b]thiophen-2-yl)-benzenesulfonamide (140-A). Bromine (36 μL, 0.69 mmol) was added to a solution of compound 1-D (0.20 g, 0.69 mmol) in dichloromethane (10 mL) at 0° C., and stirred for 15 minutes. The resultant solution was washed with water then aqueous NaHSO$_3$, and dried over magnesium sulfate to afford compound 140-A as a blue solid (0.295 g). $^1$H-NMR (CDCl$_3$): δ 6.98 (s, 1H, exchanges with D$_2$O), 7.25-7.44 (m, 4H), 7.49-7.54 (m, 2H), 7.64 (d of d, 1H), 7.78-7.83 (m, 2H); MS: m/z 368 (MH$^+$).

Compound 140

N-(3-Bromo-benzo[b]thiophen-2-yl)-N-(4-fluoro-benzyl)-benzenesulfonamide. Lithium bis(trimethylsilyl)amide (1.0 M in hexanes, 0.67 mL, 0.67 mmol) was added dropwise to a solution of compound 140-A (0.225 g, 0.61 mmol) in THF (3 mL) at −78° C. The solution was stirred at −78° C. for 15 minutes, to which was added a solution of 4-fluorobenzyl bromide (83 μL, 0.67 mmol) in THF (0.5 mL). The reaction mixture was allowed to warm to rt and stirred at ambient temperature for 6 days. The solution was washed with aqueous ammonium chloride, and the solvent was evaporated in vacuo. The crude residue was purified by reverse phase HPLC (C$_{18}$), eluting with an acetonitrile-water (0.1%) (10-90%) gradient to afford compound 140 as a colorless solid (0.130 g, 45%). $^1$H-NMR (CDCl$_3$): δ 4.81 (s, 2H), 6.87-6.97 (m, 2H), 7.20-7.25 (m, 3H), 7.36-7.43 (m, 2H), 7.51-7.56 (m, 2H), 7.63-7.71 (m, 2H), 7.86-7.89 (m, 2H); MS: m/z 476.1 (MH$^+$).

Example 6

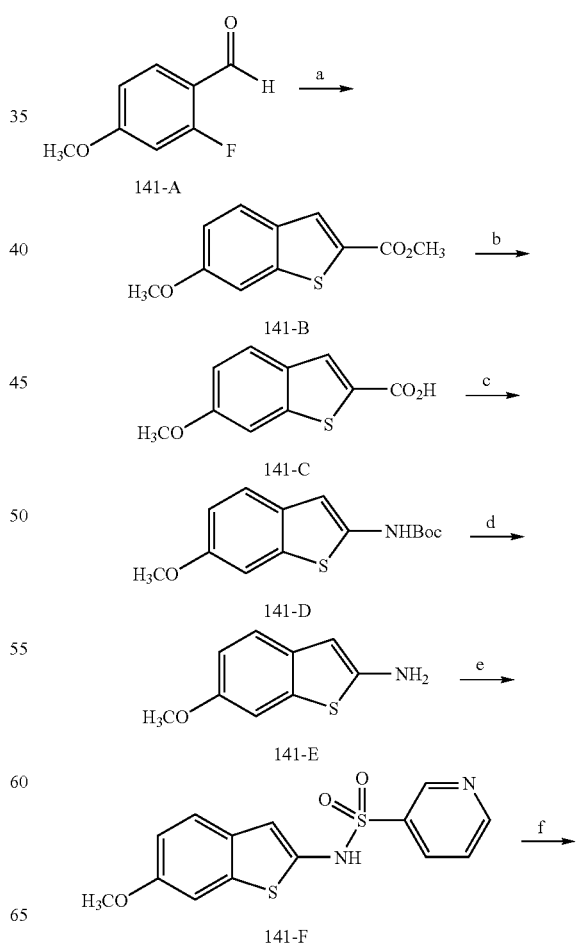

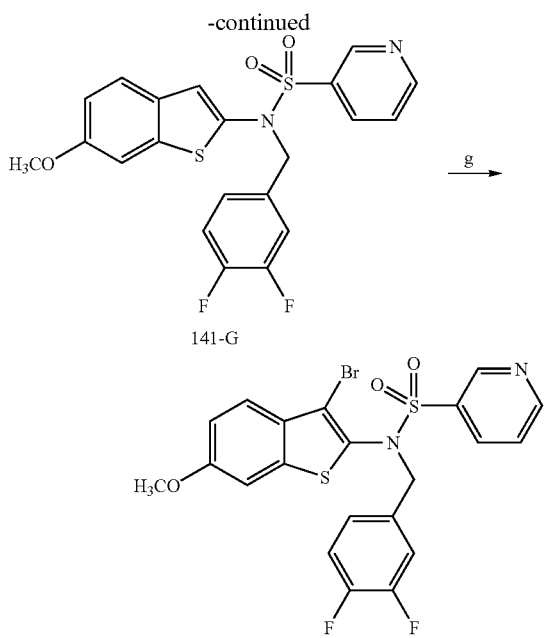

141-G

Compound 141 a) HSCH₂CO₂Me, TEA, DMF; b) NaOH, H₂O, MeOH; c) DPPA, DIEA, t-BuOH; d) HCl, EtOAc; e) 3-pyridinesulfonyl chloride, pyridine; f) KO-t-Bu, 3,4-difluorobenzyl bromide, THF; g) NBS, DCE, AcOH.

6-Methoxy-benzo[b]thiophene-2-carboxylic acid methyl ester (141-B). To a solution of compound 141-A (21.4 g; 139 mmol) in anhydrous DMF (165 mL) was added triethylamine (25.2 mL; 181 mmol) followed methyl thioglycolate (5.3 mL; 278 mmol) and the reaction was heated at 100° C. for 72 h. The reaction was cooled, partitioned between EtOAc and H₂O, the layers separated, the aqueous phase extracted with EtOAc, the organic extracts combined, washed with 3N NaOH, H₂O, brine, dried over Na₂SO₄, filtered, and the solvent evaporated under reduced pressure. The crude residue was triturated with CH₂Cl₂-heptanes, filtered, and the solid washed with heptanes and dried overnight to afford compound 141-B. The filtrate was evaporated and purified by flash column chromatography (SiO₂) eluting with a heptane-EtOAc gradient to afford a second crop of compound 141-B. The combined yield of the two crops afforded a white solid (6.55 g, 21%). ¹H-NMR (DMSO-d₆): δ 3.85 (s, 3H), 3.86 (s, 3H), 7.07-7.10 (m, 1H), 7.63 (s, 1H), 7.89-7.91 (d, 1H), 8.11 (s, 1H); MS: m/z 223.0 (MH⁺).

6-Methoxy-benzo[b]thiophene-2-carboxylic acid (141-C). To a solution of compound 141-B (6.55 g; 29.4 mmol) in methanol (100 mL) was added 1N NaOH (44.2 mL; 44.2 mmol) and the reaction was heated at 65° C. for 18 h. The reaction was cooled, the solvent evaporated under reduced pressure, the residue dissolved in H₂O, cooled to 0° C., acidified with 2N HCl, and the solid filtered, washed with H₂O, and dried in vacuo to afford compound 141-C as a white solid (6.01 g, 98%). ¹H-NMR (DMSO-d₆): δ 3.84 (s, 3H), 7.05-7.08 (m, 1H), 7.60-7.61 (d, 1H), 7.87-7.89 (d, 1H), 8.01 (s, 1H), 13.24 (s, 1H); MS: m/z 208.9 (MH⁺).

6-Methoxy-benzo[b]thiophen-2-yl)-carbamic acid tert-butyl ester (141-D). To a solution of compound 141-C (6.01 g; 28.8 mmol) in tert-butanol (80 mL) was added DPPA (9.30 mL; 43.2 mmol) followed by DIEA (5.51 mL; 31.6 mmol) and the reaction was refluxed for 18 h. The reaction was cooled, the solvent evaporated under reduced pressure, and the crude residue purified by flash column chromatography (SiO₂) eluting with a heptane-EtOAc gradient to afford compound 141-D as a beige solid (5.47 g, 68%). ¹H-NMR (DMSO-d₆): δ 1.49 (s, 9H), 3.77 (s, 3H), 6.68 (s, 1H), 6.89-6.90 (m, 1H), 7.37-7.38 (m, 1H), 7.47-7.52 (m, 1H), 10.52 (s, 1H); MS: m/z 280.0 (MH⁺).

6-(Methoxy-benzo[b]thiophen-2-yl)-amine (141-E). To a solution of compound 141-D (4.94 g; 17.7 mmol) in EtOAc (20 mL), cooled to 0° C., was bubbled HCl₍g₎ until the solution was saturated and the reaction was stirred at ambient temperature for 18 h. The solvent was evaporated under reduced pressure and the resulting residue was triturated with ether, filtered, washed with ether, and dried in vacuo to afford compound 141-E as a beige solid (3.29 g, 86%). MS: m/z 180.0 (MH⁺).

N-(6-Methoxy-benzo[b]thiophen-2-yl)-pyridin-3-yl-sulfonamide (141-F). To a solution of compound 141-E (1.0 g; 4.63 mmol) in pyridine (15 mL), cooled to 0° C., was added 3-pyridyl sulfonyl chloride (1.49 g; 6.95 mmol) and the reaction was allowed to stir at ambient temperature for 2 h. The reaction was diluted with EtOAc, washed with 2N HCl, water, brine, dried over Na₂SO₄, filtered, the solvent evaporated under reduced pressure. The crude residue was purified by trituration of the solid with CH₂Cl₂. The solid was filtered, washed with CH₂Cl₂, and dried in vacuo to afford compound 141-F as a beige solid (1.01 g, 68%). ¹H-NMR (DMSO-d₆): δ 3.76 (s, 3H), 6.86 (s, 1H), 6.91-6.93 (m, 1H), 7.39-7.40 (d, 1H), 7.57-7.59 (d, 1H), 7.62-7.65 (m, 1H), 8.13-8.16 (m, 1H), 8.81-8.82 (m, 1H), 8.90-8.91 (d, 1H), 11.15 (s, 1H); MS: m/z 321.0 (MH⁺).

N-(3,4-Difluoro-benzyl)-N-(6-methoxy-benzo[b]thiophen-2-yl)-pyridin-3-yl-sulfonamide (141-G). To a solution of compound 141-F (0.488 g; 1.52 mmol) in THF (15 mL) was added 1M potassium tert-butoxide (2.28 mL; 2.28 mmol) and the reaction mixture was stirred at ambient temperature for 30 min. 3,4-Difluorobenzyl bromide (0.409 g; 1.97 mmol), dissolved in THF (1.0 mL), was added dropwise, and the reaction was stirred at ambient temperature for 18 h. The reaction was diluted with EtOAc, washed with 2N HCl, water, brine, dried over Na₂SO₄, filtered, the solvent evaporated under reduced pressure. The crude residue was purified by flash column chromatography (SiO₂) eluting with a heptane-EtOAc gradient to afford an oily semi-solid, which was further purified by reverse-phase semi-prep HPLC (Gemini, C-18 column; 100×30 mm I.D.; 5μ) eluting with a 55% to 75% MeCN—H₂O gradient to afford compound 141-G as a white solid (0.447 g, 66%). ¹H-NMR (DMSO-d₆): δ 3.76 (s, 3H), 4.89 (s, 2H), 6.93-6.96 (m, 1H), 7.11 (s, 1H), 7.19-7.20 (m, 1H), 7.34-7.43 (m, 3H), 7.60-7.62 (d, 1H), 7.70-7.73 (m, 1H), 8.21-8.24 (m, 1H), 8.93-8.96 (m, 2H); MS: m/z 447.0 (MH⁺).

Compound 141

N-(3-Bromo-6-methoxy-benzo[b]thiophen-2-yl)-N-(3,4-difluoro-benzyl)-pyridin-3-yl-sulfonamide. To a solution of compound 141-G (0.044 g; 0.097 mmol) in DCE (0.5 mL) and acetic acid (0.5 mL) was added N-bromosuccinimide (0.021 g; 0.117 mmol) and the reaction was stirred at ambient temperature for 6 h. The reaction was diluted with EtOAc, washed with 10% NaHCO₃, water, brine, dried over Na₂SO₄, filtered, the solvent evaporated under reduced pressure. The crude residue was purified by reverse-phase semi-prep HPLC (Gemini, C₁₈ column; 100×30 mm I.D.; 5μ) eluting with a 65% to 85% MeCN—H₂O gradient to afford compound 141 as a beige solid (0.014 g, 28%). ¹H-NMR (DMSO-d₆): δ 3.80 (s, 3H), 4.86 (s, 2H), 7.08-7.16 (m, 2H), 7.32-7.40 (m, 2H), 7.54-7.57 (m, 2H), 7.72-7.75 (m, 1H), 8.29-8.32 (m, 1H), 8.91-8.97 (d, 1H), 9.00-9.05 (m, 1H); MS: m/z 525 (MH$^+$).

Following the procedure described above for Example 6 and substituting the appropriate reagents, starting materials and purification methods known to those skilled in the art, the following compounds of the present invention were prepared:

Compound 142

N-(3,4-Difluoro-benzyl)-N-(7-methoxy-benzo[b]thiophen-2-yl)-benzenesulfonamide. $^1$H-NMR (DMSO-d$_6$): δ 3.88 (s, 3H), 4.88 (s, 2H), 6.87-6.91 (m, 1H), 7.14-7.41 (m, 6H), 7.63-7.79 (m, 2H), 7.80-7.91 (m, 3H); MS: m/z 446.1 (MH$^+$).

Compound 375

N-(6-Fluoro-3-methyl-benzo[b]thiophen-2-yl)-N-(4-fluoro-3-trifluoromethyl-benzyl)-3-carbomethoxy-benzenesulfonamide. MS: m/z 555.9 (MH$^+$).

Compound 412

N-(6-Fluoro-3-methyl-benzo[b]thiophen-2-yl)-N-(4,4,4-trifluoro-butyl)-4-carbomethoxybenzenesulfonamide. MS: m/z 489.9 (MH$^+$).

Example 7

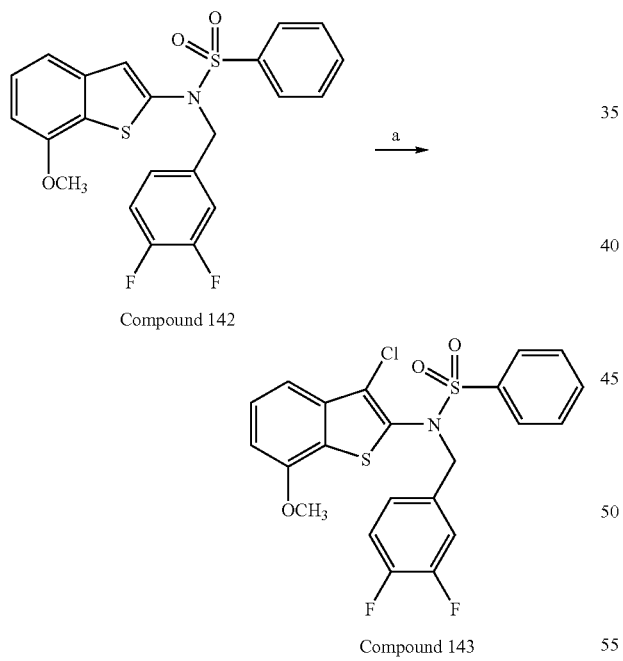

a) NCS, DCE, AcOH.

Compound 143

N-(3-Chloro-7-methoxy-benzo[b]thiophen-2-yl)-N-(3,4-difluoro-benzyl)-benzenesulfonamide. To a solution of compound 142 (0.061 g; 0.137 mmol) in DCE (0.5 mL) and acetic acid (0.5 mL) was added N-chlorosuccinimide (0.027 g; 0.206 mmol) and the reaction was stirred at ambient temperature for 2 h. The reaction was diluted with EtOAc, washed with 10% NaHCO$_3$, water, brine, dried over Na$_2$SO$_4$, filtered, the solvent evaporated under reduced pressure. The crude residue was purified by reverse-phase semi-prep HPLC (Gemini, C$_{18}$ column; 100×30 mm I.D.; 5µ) eluting with a 60% to 80% MeCN—H$_2$O gradient to afford compound 143 as a beige solid (0.011 g, 17%). $^1$H-NMR (CD$_3$OD): δ 3.94 (s, 3H), 4.80 (s, 2H), 6.96-7.23 (m, 5H), 7.27-7.41 (m, 1H), 7.60-7.65 (m, 2H), 7.72-7.76 (m, 1H), 7.87-7.90 (m, 2H); MS: m/z 480.0 (MH$^+$).

Compound 144

N-(3,6-Dichloro-7-methoxy-benzo[b]thiophen-2-yl)-N-(3,4-difluoro-benzyl)-benzenesulfonamide. $^1$H-NMR (CD$_3$OD): δ 3.94 (s, 3H), 4.83 (s, 2H), 6.90-6.92 (m, 1H), 7.03-7.18 (m, 2H), 7.21-7.23 (m, 1H), 7.34-7.36 (m, 1H), 7.61-7.65 (m, 2H), 7.73-7.77 (m, 1H), 7.82-7.90 (m, 2H); MS: m/z 513.9 (MH$^+$).

Example 8

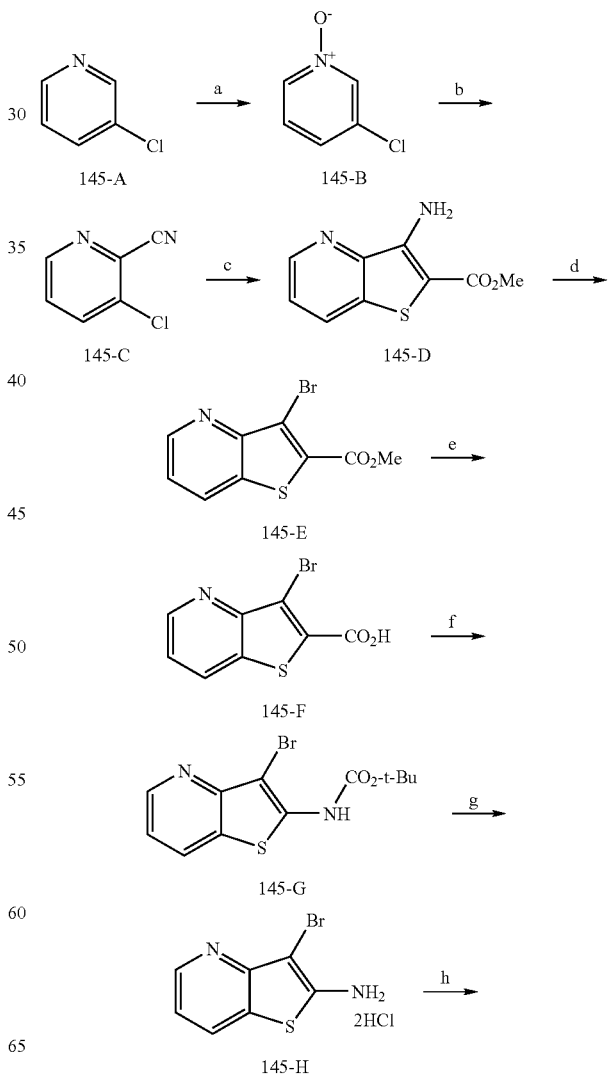

-continued

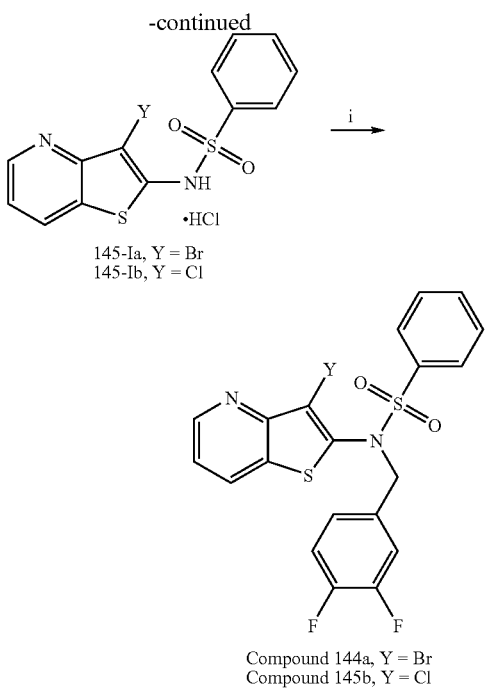

145-Ia, Y = Br
145-Ib, Y = Cl

Compound 144a, Y = Br
Compound 145b, Y = Cl a) H₂O₂ (30%), acetic acid;
b) TMSCN, acetonitrile, TEA;
c) methyl thioglycote, K₂CO₃, acetonitrile;
d) CuBr, NaNO₂, HBr, H₂O;
e) LiOH, H₂O, THF;
f) DPPA, DIEA, t-BuOH;
g) HCl, dioxane;
h) PhSO₂Cl, pyridine;
i) 1.0M NaHMDS, THF, 3,4-difluorobenzyl bromide, DMF.

3-Chloro-pyridine 1-oxide (145-B). To a solution of 3-chloropyridine, (22.71 g, 200 mmol) in acetic acid (80 mL) was added hydrogen peroxide solution (30% aqueous, 40 mL), and the mixture was heated at 80° C. for 15 h. Additional hydrogen peroxide solution (30% aqueous, 5 mL) was added to the reaction mixture and the heating continued an additional 5 h. After cooling, the reaction mixture was quenched into a solution of NaHSO₃ in water (400 mL), using starch-iodine paper to confirm the destruction of excess hydrogen peroxide. The mixture was evaporated in vacuo and partitioned between water (100 mL) and dichloromethane (250 mL). The organics were washed with saturated NaHCO₃ solution (2×100 mL), and brine (100 mL). The combined aqueous layers were extracted with dichloromethane (8×100 mL), the organic extracts were combined, dried over Na₂SO₄, filtered, and evaporated in vacuo. The organic residue was partitioned between dichloromethane/water, treated with solid NaHCO₃, and filtered. The aqueous washes from the first extraction were treated with NaHCO₃, extracted with dichloromethane (3×100 mL), and the combined organics dried with Na₂SO₄, filtered, and evaporated in vacuo to afford compound 145-B as an orange oil (22.37 g, 86%). $^1$H-NMR (DMSO-d₆): δ 7.40-7.53 (m, 2H), 8.22 (d, 1H), 8.52 (s, 1H); MS: m/z 130.1 (MH⁺).

3-Chloro-pyridine-2-carbonitrile (145-C). To a solution of compound 145-B, (22.37 g, 172.7 mmol) in acetonitrile (175 mL) was added triethylamine (48 mL, 346 mmol) and TMS-CN (56 mL, 420 mmol). The solution was heated at reflux for 20 h then evaporated in vacuo. The residue was partitioned between EtOAc (250 mL), 10% aqueous Na₂CO₃ (50 mL), and filtered over celite. The organic portion of the filtrate was washed with 10% aqueous Na₂CO₃ (2×50 mL), brine (50 mL), and the organics dried over Na₂SO₄, filtered, and evaporated in vacuo to afford a dark crystalline residue, which was dissolved in warm diethyl ether (200 mL), filtered, and evaporated in vacuo to afford compound 145-C as a tan-orange powder (23.41 g, 98%). $^1$H-NMR (DMSO-d₆): δ 7.78-7.84 (m, 1H), 8.30 (d, 1H), 8.73 (d, 1H); MS: m/z 139.1 (MH⁺).

3-Amino-thieno[3,2-b]pyridine-2-carboxylic acid methyl ester (145-D). To a solution of compound 145-C (23.41 g, 169.0 mmol) in acetonitrile (170 mL) was added methyl thioglycolate (16.2 mL, 178 mmol) and K₂CO₃ (46.72 g, 338 mmol). The mixture was heated under reflux for 3 h then filtered hot and the filter cake rinsed with acetonitrile. The filter cake was suspended in refluxing acetonitrile, filtered hot, and rinsed with additional acetonitrile. The combined filtrates were evaporated in vacuo, the residue triturated with warm water (250 mL), filtered, and rinsed with water. The solid was dissolved in warm methanol (500 mL), treated with charcoal, filtered, and evaporated in vacuo. The residue was triturated with ethanol (25 mL), filtered, washed with ethanol (25 mL), and dried in vacuo to afford compound 145-D as a brown powder (21.65 g, 62%). $^1$H-NMR (DMSO-d₆): δ 3.83 (s, 3H), 6.91 (s, 2H), 7.52-7.59 (m, 1H), 8.40 (dd, 1H), 8.69 (dd, 1H); MS: m/z 209.1 (MH⁺).

3-Bromo-thieno[3,2-b]pyridine-2-carboxylic acid methyl ester (145-E). To a solution of CuBr (15.09 g, 105.2 mmol) in 48% aqueous HBr (250 mL), cooled in an ice bath, was added compound 145-D (20.82 g, 100 mmol). To the reaction mixture was added a solution of NaNO₂ (8.29 g, 120 mmol) in water (200 mL) drop-wise over 1 h. After 30 min, solid NaNO₂ (0.83 g, 12.0 mmol) was added, and after another 30 min an additional portion of solid NaNO₂ (0.83 g, 12.0 mmol) was added. After 10 min the reaction mixture was carefully poured into a mixture of ice (1 L) and NaHCO₃ (200 g). The mixture was extracted with dichloromethane (5×200 mL), and the combined organic extracts dried over MgSO₄, filtered, and evaporated in vacuo to afford compound 145-E as a brown powder (25.16 g). $^1$H-NMR (DMSO-d₆): δ 3.94 (s, 3H), 7.65 (m, 1H), 8.65 (dd, 1H), 8.88 (dd, 1H); MS: m/z 272.0 (MH⁺).

3-Bromo-thieno[3,2-b]pyridine-2-carboxylic acid (145-F). To a solution of compound 145-E (4.94 g, 18.2 mmol) in 5:1 THF/H₂O (200 mL) was added LiOH.H₂O (0.797 g, 19.0 mmol). The reaction was stirred for 3 days then concentrated in vacuo, to which was added water (100 mL) and 1N HCl (19.0 mL), and the resultant precipitate was isolated by filtration. The solid was rinsed with water and dried under vacuum to afford compound 145-F as a tan-yellow solid (4.51 g, 96%). $^1$H-NMR (DMSO-d₆): δ 7.62 (dd, 1H), 8.62 (dd, 1H), 8.86 (dd, 1H), 14.18 (br s, 1H); MS: m/z 257.9 (MH⁺).

3-Bromo-thieno[3,2-b]pyridin-2-yl)-carbamic acid tert-butyl ester (145-G). A solution of compound 145-F (2.0 g, 7.75 mmol), N,N-diisopropylethylamine (1.49 mL, 8.52 mmol) and diphenyl phosphoryl azide (2.07 mL, 9.30 mmol) in t-butanol (20 mL) was heated at reflux for 16 h. The solvent was evaporated in vacuo, the residue dissolved in dichloromethane, washed with 1N NaOH, brine, dried with Na₂SO₄, and evaporated to afford a crude residue which was purified by flash column chromatography (SiO₂), eluting with dichloromethane to afford compound 145-G as a yellow solid (1.51 g, 56%). $^1$H-NMR (CDCl₃): δ 1.6 (s, 9H), 7.2 (d of d, 1H), 7.5 (br s, 1H), 8.0 (d, 1H), 8.7 (d, 1H); MS: m/z 251 (MH⁺).

3-Bromo-thieno[3,2-b]pyridin-2-ylamine hydrochloride (145-H). Compound 145-G (0.75 g, 2.28 mmol) was added to a solution of HCl in dioxane (4 N, 7.5 mL) and the reaction mixture was stirred at rt for 2 h. The solvent was evaporated under reduced pressure to afford compound 145-H as a yellow solid (0.74 g). ¹H-NMR (DMSO-d₆): δ 7.3 (d, 1H), 8.3 (d, 1H), 8.5 (br s, 2H) superimposed on 8.55 (d, 1H).

N-(3-Bromo-thieno[3,2-b]pyridin-2-yl)-benzenesulfonamide hydrochloride (145-I). To a solution of compound 145-H (0.46 g, 1.52 mmol) in pyridine (4.6 mL), cooled to 0° C., was added benzenesulfonyl chloride (0.206 mL, 1.60 mmol), and the reaction was heated to 50° C. for 72 h. Additional benzenesulfonyl chloride (0.412 mL, 3.20 mmol) was added and the reaction mixture was heated at 50° C. for an additional 16 h. The solvent was evaporated in vacuo, the residue dissolved in dichloromethane and washed with aqueous sodium bicarbonate. The aqueous layer was acidified with 1N HCl, extracted with dichloromethane, and the organic layer was evaporated in vacuo to afford a yellow solid (0.22 g, 36%) as a 1/3.5 mixture of the 3-bromo—and 3-chloro-substituted compounds, 145-Ia and 145-Ib, respectively. ¹H-NMR (DMSO-d₆): δ 7.1-7.2 (m, 1H), 7.4-7.6 (m, 3H), 7.8 (m, 2H), 8.1-8.2 (m, 1H), 8.25-8.35 (m, 1H); MS: m/z 465 and 509 (MH⁺).

Compound 145

N-(3-Bromo-thieno[3,2-b]pyridin-2-yl)-N-(3,4-difluoro-benzyl)-benzenesulfonamide and N-(3-chloro-thieno[3,2-b]pyridin-2-yl)-N-(3,4-difluoro-benzyl)-benzenesulfonamide. To a mixture of compounds 145-Ia and 145-Ib (90 mg, 0.222 mmol) in DMF (1 mL), at rt, was added 11.0M sodium bis(trimethylsilyl)amide in THF (0.44 mL, 0.444 mmol). The solution was stirred 30 min at rt to which was added 3,4-difluorobenzyl bromide (0.029 mL, 0.222 mmol). The resultant solution was stirred at ambient temperature for 16 h, to which was added additional DMF (1 mL) followed by 3,4-difluorobenzyl bromide (0.029 mL, 0.222 mmol), and the reaction mixture stirred at rt for 3 days. The solvent was evaporated and the residue purified by reverse-phase HPLC eluting with an acetonitrile-water gradient. Further purification by flash column chromatography (SiO₂), eluting with dichloromethane, afforded compound 145 as a clear, hard gum (19.7 mg, 18%). ¹H-NMR (DMSO-d₆): δ 4.74 (s, 2H), 7.00-7.10 (s superimposed on m, 3H), 7.15-7.21 (m, 1H), 7.26-7.36 (m, 2H), 7.49-7.54 (m, 2H), 7.62-7.67 (m, 3H), 7.73-7.78 (m, 2H); MS: m/z 416.1 (MH⁺).

Example 9

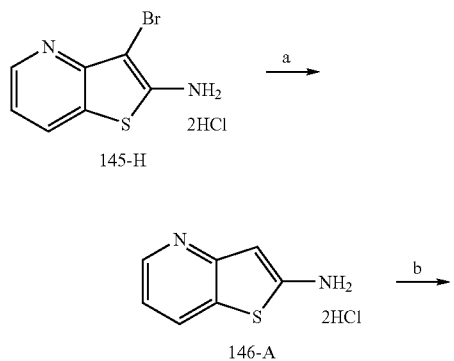

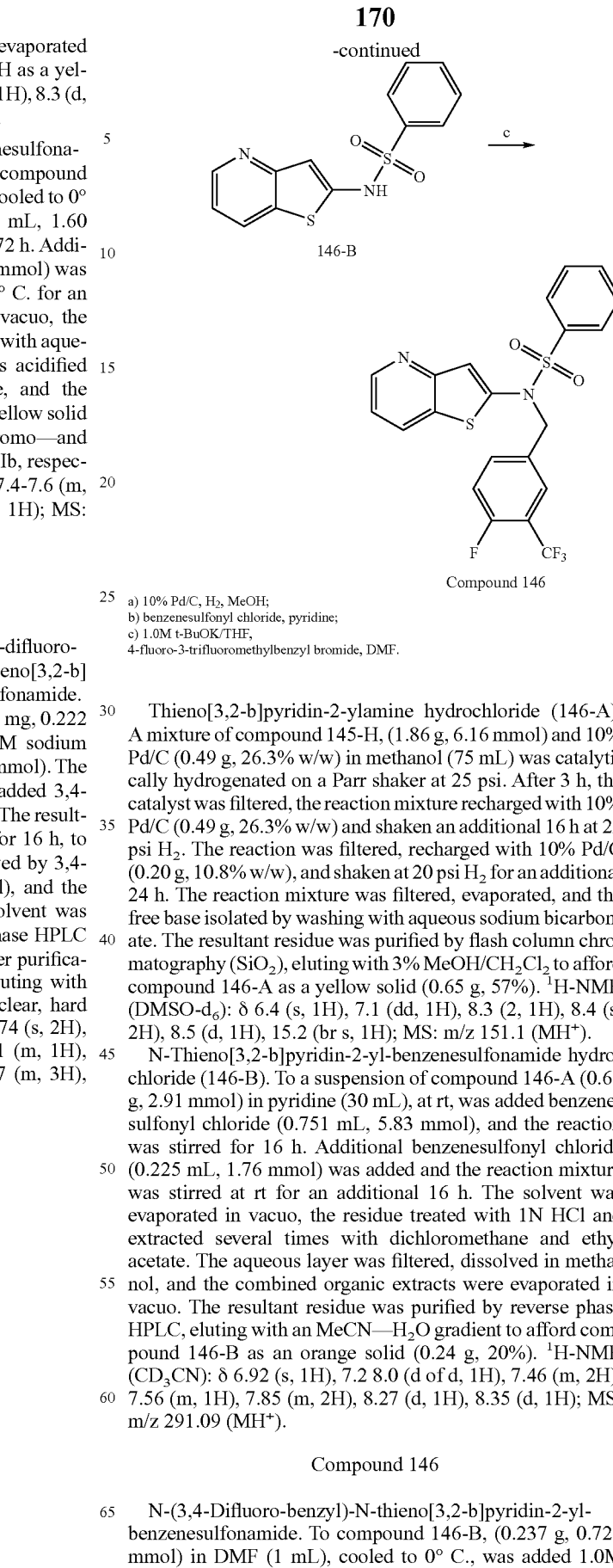

Compound 146 a) 10% Pd/C, H₂, MeOH;
b) benzenesulfonyl chloride, pyridine;
c) 1.0M t-BuOK/THF, 4-fluoro-3-trifluoromethylbenzyl bromide, DMF.

Thieno[3,2-b]pyridin-2-ylamine hydrochloride (146-A). A mixture of compound 145-H, (1.86 g, 6.16 mmol) and 10% Pd/C (0.49 g, 26.3% w/w) in methanol (75 mL) was catalytically hydrogenated on a Parr shaker at 25 psi. After 3 h, the catalyst was filtered, the reaction mixture recharged with 10% Pd/C (0.49 g, 26.3% w/w) and shaken an additional 16 h at 22 psi H₂. The reaction was filtered, recharged with 10% Pd/C (0.20 g, 10.8% w/w), and shaken at 20 psi H₂ for an additional 24 h. The reaction mixture was filtered, evaporated, and the free base isolated by washing with aqueous sodium bicarbonate. The resultant residue was purified by flash column chromatography (SiO₂), eluting with 3% MeOH/CH₂Cl₂ to afford compound 146-A as a yellow solid (0.65 g, 57%). ¹H-NMR (DMSO-d₆): δ 6.4 (s, 1H), 7.1 (dd, 1H), 8.3 (2, 1H), 8.4 (s, 2H), 8.5 (d, 1H), 15.2 (br s, 1H); MS: m/z 151.1 (MH⁺).

N-Thieno[3,2-b]pyridin-2-yl-benzenesulfonamide hydrochloride (146-B). To a suspension of compound 146-A (0.65 g, 2.91 mmol) in pyridine (30 mL), at rt, was added benzenesulfonyl chloride (0.751 mL, 5.83 mmol), and the reaction was stirred for 16 h. Additional benzenesulfonyl chloride (0.225 mL, 1.76 mmol) was added and the reaction mixture was stirred at rt for an additional 16 h. The solvent was evaporated in vacuo, the residue treated with 1N HCl and extracted several times with dichloromethane and ethyl acetate. The aqueous layer was filtered, dissolved in methanol, and the combined organic extracts were evaporated in vacuo. The resultant residue was purified by reverse phase HPLC, eluting with an MeCN—H₂O gradient to afford compound 146-B as an orange solid (0.24 g, 20%). ¹H-NMR (CD₃CN): δ 6.92 (s, 1H), 7.2 8.0 (d of d, 1H), 7.46 (m, 2H), 7.56 (m, 1H), 7.85 (m, 2H), 8.27 (d, 1H), 8.35 (d, 1H); MS: m/z 291.09 (MH⁺).

Compound 146

N-(3,4-Difluoro-benzyl)-N-thieno[3,2-b]pyridin-2-yl-benzenesulfonamide. To compound 146-B, (0.237 g, 0.725 mmol) in DMF (1 mL), cooled to 0° C., was added 1.0M potassium t-butoxide in THF (1.71 mL, 1.71 mmol), dropwise over 5 min. The solution was stirred for 30 min at 0° C., to which was added 4-fluoro-3-trifluoromethylbenzyl bromide (0.132 mL, 0.898 mmol). The resultant solution was stirred 5 min at 0° C. and allowed to warm to rt and stirred overnight. Saturated sodium bicarbonate solution was added, and the mixture evaporated in vacuo. The residue was partitioned between water and diethyl ether, the organic phase separated, and the aqueous phase extracted with diethyl ether. The combined organic phases were evaporated in vacuo and the crude residue purified by reverse-phase HPLC to afford compound 146 as a dark solid (28 mg, 8%). $^1$H-NMR (CDCl$_3$): δ 5.00 (s, 2H), 7.16 (t, 1H), 7.44 (d of d, 1H), 7.56 (m, 3H), 7.69 (m, 3H), 7.85 (m, 1H), 8.33 (d, 2H), 8.57 (d, 1H); MS: m/z 467.09 (MH$^+$).

Example 10

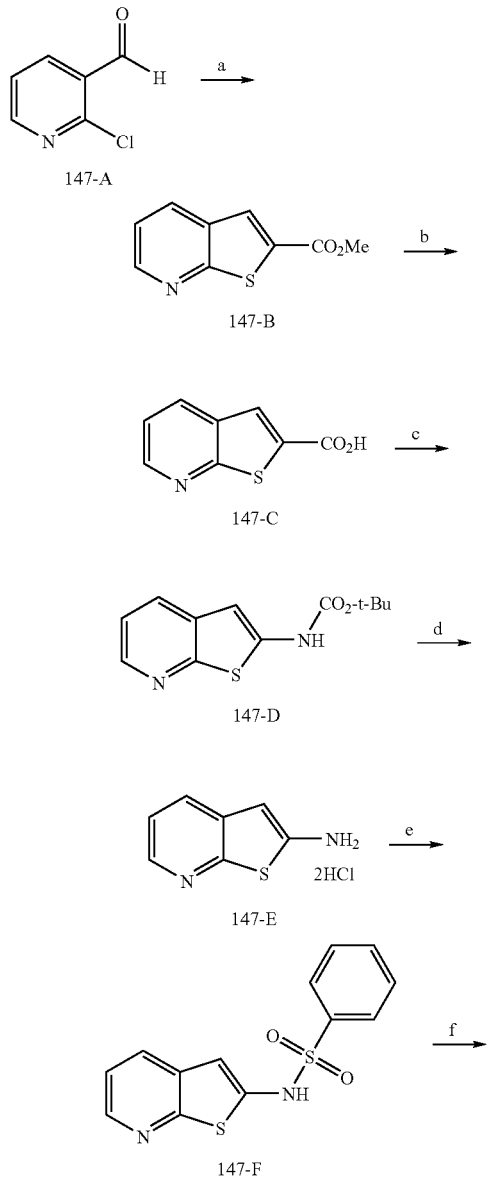

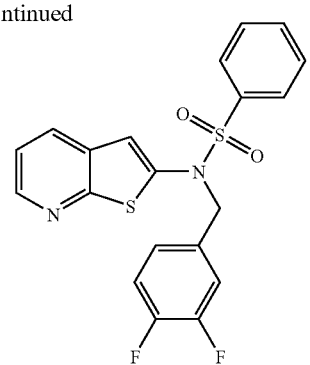

Compound 147 a) Ethyl thioglycolate, TEA, CH$_3$CN; b) NaOH, MeOH; c) DPPA, DIEA, t-BuOH; d) HCl, dioxane; e) benzenesulfonyl chloride, pyridine; f) 1.0M LiHMDS/THF, 3,4-difluorobenzyl bromide, DMF.

Thieno[2,3-b]pyridine-2-carboxylic acid methyl ester (147-B). To 2-chloro-3-pyridine carboxaldehyde, compound 147-A, (5.07 g, 35.8 mmol), dissolved in MeCN (30 mL) was added triethylamine (6.5 mL, 46.5 mmol) followed by methyl thioglycolate (3.49 mL, 38.3 mmol) and the reaction was refluxed for 18 h. The reaction mixture was cooled and the solvent evaporated under reduced pressure. The crude residue was partitioned between H$_2$O and EtOAc, the layers separated and the aqueous phase extracted with EtOAc. The organic layers were combined, washed with H$_2$O, brine, dried over Na$_2$SO$_4$, filtered, and the solvent evaporated under reduced pressure. The crude residue was purified by flash column chromatography (SiO$_2$) eluting with a heptane-EtOAc gradient to afford compound 147-B as a white solid (2.01 g, 29%). $^1$H-NMR (DMSO-d$_6$): δ 3.91 (s, 3H), 7.54-7.57 (m, 1H), 8.23 (s, 1H), 8.43-8.46 (m, 1H), 8.72-8.74 (m, 1H); MS: m/z 194.1 (MH$^+$).

Thieno[2,3-b]pyridine-2-carboxylic acid (147-C). To a solution of compound 147-B (0.508 g, 2.63 mmol) in a mixture of MeOH (15 mL) and H$_2$O (3 mL) was added 3N NaOH (1.9 mL, 5.66 mmol) and the reaction mixture was stirred at ambient temperature for 5 h. The solvent was evaporated under reduced pressure, the residue dissolved in H$_2$O, and acidified with 1N HCl. The precipitate was filtered, washed with H$_2$O, and dried under vacuum to afford compound 147-C as a white solid (0.366 g, 78%). MS: m/z 180.0 (MH$^+$).

Thieno[2,3-b]pyridin-2-yl-carbamic acid tert-butyl ester (147-D) A solution of compound 147-C (0.36 g, 2.00 mmol), N,N-diisopropylethylamine (0.385 mL, 2.21 mmol) and diphenyl phosphoryl azide (0.536 mL, 2.41 mmol) in t-butanol (3.6 mL) was heated at reflux for 16 h. The solvent was evaporated in vacuo, the residue dissolved in dichloromethane, washed with 1 N NaOH, brine, dried with Na$_2$SO$_4$, filtered, and evaporated to afford a residue. Flash column chromatography (SiO$_2$) eluting with dichloromethane afforded compound 147-D as a white solid (0.25 g, 50%). $^1$H-NMR (CDCl$_3$): δ 1.55 (s, 9H), 6.60 (s, 1H), 7.20 (dd, 1H), 7.80 (d, 1H), 8.40 (d, 1H); MS: m/z 251.2 (MH$^+$).

Thieno[2,3-b]pyridin-2-ylamine dihydrochloride (147-E). Compound 147-D (3.76 g, 15.0 mmol) was added to a solution of HCl in dioxane (4 N, 40 mL). The mixture was stirred at rt for 3 days and the solid filtered to afford compound 147-E as a yellow solid (3.24 g, 97%). $^1$H-NMR (DMSO-d$_6$): δ 6.12 (s, 1H), 7.50 (dd, 1H), 8.02 (d, 1H), 8.28 (d, 1H), 9.60 (br s, 3H).

N-Thieno[2,3-b]pyridin-2-yl-benzenesulfonamide (147-F). Compound 147-E (0.22 g, 1.00 mmol) in pyridine (5.0 mL) was stirred at rt for 30 min, to which was added benzenesulfonyl chloride (0.135 mL, 1.05 mmol) and the reaction mixture was stirred at rt for 4 h. Another portion of benzenesulfonyl chloride (0.030 mL, 0.235 mmol) was added and the reaction mixture stirred at rt for 72 h. Water and saturated sodium bicarbonate solution were added and the mixture was extracted with dichloromethane, dried over sodium sulfate and evaporated in vacuo to afford a residue. Flash column chromatography (SiO$_2$) eluting with dichloromethane afforded compound 147-F as a yellow solid (0.24 g, 83%).

Compound 147

N-(3,4-Difluoro-benzyl)-N-thieno[2,3-b]pyridin-2-yl-benzenesulfonamide. To compound 147-F (0.24 g, 0.827 mmol) in DMF (2.5 mL) at rt was added 1.0 M lithium bis(trimethylsilyl)amide in THF (0.87 mL, 0.87 mmol), dropwise, and the solution was stirred 5 min. 3,4-Difluorobenzyl bromide (0.114 mL, 0.868 mmol) was added to the reaction mixture and the resultant solution was stirred at ambient temperature overnight. Additional amounts of 1.0 M lithium bis(trimethylsilyl)amide in THF (0.44 mL, 0.44 mmol) and 3,4-difluorobenzyl bromide (0.052 mL, 0.406 mmol) were added and stirred for 18 h. Saturated sodium bicarbonate solution was added, the mixture evaporated in vacuo, and the residue partitioned between water and diethyl ether and evaporated in vacuo to afford a residue Purification by reverse-phase HPLC eluting with an acetonitrile-water (0.1% TFA) gradient afforded a brownish gum that was dissolved in acetonitrile, and converted to its hydrochloride salt by the addition of ethereal hydrogen chloride. The solid was filtered, washed with diethyl ether, and dried under vacuum to afford compound 147 as a tan solid (32.3 mg, 9%). $^1$H-NMR (DMSO-d$_6$): δ 4.95 (s, 2H), 7.20 (s, 1H), 7.25 (m, 1H), 7.40 (m, 3H), 7.70 (t, 2H), 7.80 (t, 1H), 7.90 (d, 2H), 8.20 (d, 2H), 8.30 (d, 2H), 12.4 (br s, 1H); MS: m/z 417.16 (MH$^+$).

Example 11

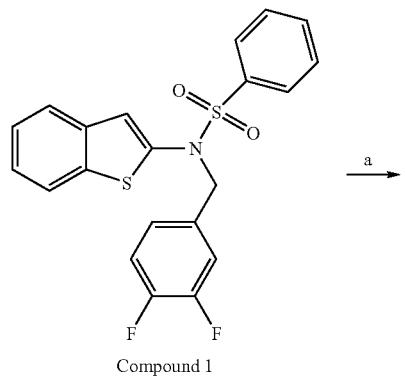

Compound 1

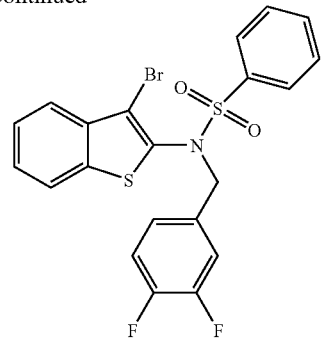

Compound 148 a) NBS, DCE, AcOH.

Compound 148

N-(3-Bromo-benzo[b]thiophen-2-yl)-N-(3,4-difluoro-benzyl)-benzenesulfonamide. To a solution of compound 1 (440 mg, 1.06 mmol) in 1,2-dichloroethane (3 mL) and acetic acid (3 mL), at 0° C., was added N-bromosuccinimide (207 mg, 1.16 mmol), and the reaction mixture was stirred at rt for 1 h. The solvent was evaporated in vacuo, and the residue partitioned between dichloromethane and a saturated solution of aqueous sodium bicarbonate. The organic layer was separated, the product pre-absorbed onto silica gel, and purified by flash column chromatography eluting with an ethyl acetate-heptane gradient (5-50%) to afford compound 148 as a colorless solid (190 mg, 36%). $^1$H-NMR (DMSO-d$_6$): δ 4.82 (s, 2H), 7.11-7.14 (m, 1H), 7.28-7.39 (m, 2H), 7.46-7.58 (m, 2H), 7.67-7.72 (m, 3H), 7.80-7.85 (m, 1H), 7.91-7.97 (m, 3H); MS: m/z 494.1 (MH$^+$).

Following the procedure described above for example 11 and substituting the appropriate reagents, starting materials and purification methods known to those skilled in the art, the following compounds of the present invention were prepared:

Compound 149

N-(3-Bromo-benzo[b]thiophen-2-yl)-N-(3,4-difluoro-benzyl)-pyridin-3-yl-sulfonamide. $^1$H-NMR (DMSO-d$_6$): δ 4.89 (s, 2H), 7.12-7.19 (m, 1H), 7.32-7.42 (m, 2H), 7.48-7.55 (m, 2H), 7.66-7.77 (m, 2H), 7.94-8.00 (m, 1H), 8.30-8.35 (m, 1H), 8.98 (dd, 1H), 9.06 (d, 1H); MS: m/z 495 (MH$^+$).

Compound 150

N-(3-Bromo-benzo[b]thiophen-2-yl)-N-(3,4-difluoro-benzyl)-1-methyl-1H-imidazole-4-sulfonamide. $^1$H-NMR (DMSO-d$_6$): δ 3.75 (s, 3H), 4.87 (s, 2H), 7.11-7.19 (m, 1H), 7.28-7.52 (m, 4H), 7.66-7.72 (m, 1H), 7.90-7.96 (m, 2H), 8.01 (s, 1H); MS: m/z 498 (MH$^+$).

Compound 151

N-(3-Bromo-benzo[b]thiophen-2-yl)-N-(3,4-difluoro-benzyl)-methanesulfonamide. $^1$H-NMR (DMSO-d$_6$): δ 3.39 (s, 3H), 4.87 (s, 2H), 7.15-7.21 (m, 1H), 7.32-7.54 (m, 4H), 7.70-7.76 (m, 1H), 7.95-8.01 (m, 1H); MS: m/z 432.0 (MH$^+$).

Compound 152

N-(3-Bromo-benzo[b]thiophen-2-yl)-N-(3,4-difluoro-benzyl)-ethanesulfonamide. $^1$H-NMR (DMSO-d$_6$): δ 1.39 (t, 3H), 3.51 (q, 2H), 4.88 (s, 2H), 7.12-7.18 (m, 1H), 7.32-7.42 (m, 2H), 7.49-7.54 (m, 2H), 7.71-7.76 (m, 1H), 7.94-7.99 (m, 1H); MS: m/z 446 (MH$^+$).

Compound 153

N-(3-Bromo-benzo[b]thiophen-2-yl)-N-(3,4-difluoro-benzyl)-propane-1-sulfonamide. $^1$H-NMR (DMSO-d$_6$): δ 1.04 (t, 3H), 1.79-1.93 (m, 2H), 3.45-3.51 (m, 2H), 4.87 (s, 2H), 7.12-7.18 (m, 1H), 7.31-7.43 (m, 2H), 7.48-7.55 (m, 2H), 7.70-7.76 (m, 1H), 7.94-7.99 (m, 1H); MS: m/z 460 (MH$^+$).

Compound 154

N-(3-Bromo-benzo[b]thiophen-2-yl)-N-(3,4-difluoro-benzyl)-butane-1-sulfonamide. $^1$H-NMR (DMSO-d$_6$): δ 0.92 (t, 3H), 1.38-1.53 (m, 2H), 1.74-1.86 (m, 2H), 3.45-3.53 (m, 2H), 4.88 (s, 2H), 7.12-7.18 (m, 1H), 7.32-7.43 (m, 2H), 7.48-7.54 (m, 2H), 7.70-7.76 (m, 1H), 7.94-8.00 (m, 1H); MS: m/z 474.1 (MH$^+$).

Compound 155

N-(3-Bromo-benzo[b]thiophen-2-yl)-N-(3,4-difluoro-benzyl)-3-fluoro-benzenesulfonamide. $^1$H-NMR (DMSO-d$_6$): δ 4.87 (br s, 2H), 7.10-7.17 (m, 1H), 7.30-7.41 (m, 2H), 7.47-7.54 (m, 2H), 7.67-7.83 (m, 5H), 7.94-8.01 (m, 1H); MS: m/z 512 (MH$^+$).

Compound 156

N-(3-Bromo-benzo[b]thiophen-2-yl)-N-(3,4-difluoro-benzyl)-4-trifluoromethyl-benzenesulfonamide. $^1$H-NMR (DMSO-d$_6$): δ 4.88 (s, 2H), 7.12-7.18 (m, 1H), 7.30-7.41 (m, 2H), 7.48-7.54 (m, 2H), 7.67-7.73 (m, 1H), 7.96-8.01 (m, 1H), 8.08 (d, 2H), 8.15 (d, 2H); MS: m/z 562 (MH$^+$).

Compound 157

N-(3-Bromo-benzo[b]thiophen-2-yl)-N-(4-fluoro-3-trifluoromethyl-benzyl)-methanesulfonamide. $^1$H-NMR (DMSO-d$_6$): δ 3.40 (s, 3H), 4.96 (s, 2H), 7.43-7.55 (m, 3H), 7.68-7.80 (m, 3H), 7.97-8.02 (m, 1H); MS: m/z 482.1 (MH$^+$).

Compound 158

N-(3-Chloro-benzo[b]thiophen-2-yl)-N-(4-chloro-benzyl)-benzenesulfonamide. $^1$H-NMR (CDCl$_3$): δ 4.79 (s, 2H), 7.21 (s, 4H), 7.38-7.41 (m, 2H) 7.51-7.56 (m, 2H), 7.61-7.72 (m, 3H), 7.85-7.87 (m, 2H); MS: m/z 447.9 (MH$^+$).

Compound 159

N-(3-Bromo-benzo[b]thiophen-2-yl)-N-(4-chloro-benzyl)-benzenesulfonamide. $^1$H-NMR (CDCl$_3$): δ 4.81 (s, 2H), 7.21 (s, 4H), 7.38-7.41 (m, 2H) 7.51-7.56 (m, 2H), 7.63-7.71 (m, 3H), 7.85-7.87 (m, 2H); MS: m/z 492.0 (MH$^+$).

Compound 160

N-(3-Bromo-benzo[b]thiophen-2-yl)-N-(2-methoxy-benzyl)-benzenesulfonamide. $^1$H-NMR (CDCl$_3$): δ 3.55 (s, 3H), 4.93 (s, 2H), 6.68-6.70 (d, 1H), 6.79-6.83 (t, 1H), 7.16-7.20 (m, 1H), 7.30-7.32 (m, 1H), 7.35-7.38 (m, 2H), 7.48-7.52 (m, 2H), 7.59-7.63 (m, 2H), 7.68-7.71 (m, 1H), 7.86-7.89 (m, 2H); MS: m/z 487.9 (MH$^+$).

Compound 161

N-(3-Bromo-benzo[b]thiophen-2-yl)-N-(5-bromo-2-methoxy-benzyl)-benzenesulfonamide. $^1$H-NMR (CDCl$_3$): δ 3.52 (s, 3H), 4.88 (s, 2H), 6.55-6.59 (d, 1H), 7.26-7.29 (m, 1H), 7.38-7.40 (m, 2H), 7.49-7.53 (m, 3H), 7.61-7.66 (m, 2H), 7.70-7.73 (m, 1H), 7.86-7.88 (m, 2H); MS: m/z 567.9 (MH$^+$).

Compound 162

N-(3-Bromo-benzo[b]thiophen-2-yl)-N-(3-methoxy-benzyl)-benzenesulfonamide. $^1$H-NMR (CDCl$_3$): δ 3.72 (s, 3H), 4.82 (s, 2H), 6.74-6.87 (m, 3H), 7.09-7.14 (t, 1H), 7.36-7.40 (m, 2H), 7.51-7.56 (m, 2H), 7.62-7.71 (m, 3H), 7.86-7.89 (m, 2H); MS: m/z 488.0 (MH$^+$).

Compound 163

N-(3-Bromo-benzo[b]thiophen-2-yl)-N-(2-bromo-5-methoxy-benzyl)-benzenesulfonamide. $^1$H-NMR (CDCl$_3$): δ 3.75 (s, 3H), 5.02 (s, 2H), 6.63-6.68 (m, 1H), 7.21-7.22 (m, 1H), 7.26-7.29 (m, 1H), 7.38-7.41 (m, 2H), 7.51-7.55 (m, 2H), 7.63-7.72 (m, 3H), 7.87-7.90 (m, 2H); MS: m/z 567.9, (MH$^+$), 589.8 (MNa$^+$).

Compound 164

N-(3-Bromo-benzo[b]thiophen-2-yl)-N-(4-methoxy-benzyl)-benzenesulfonamide. $^1$H-NMR (CDCl$_3$): δ 3.73 (s, 3H), 4.79 (s, 2H), 6.70-6.74 (m, 2H), 7.15-7.18 (m, 2H), 7.34-7.39 (m, 2H), 7.51-7.55 (m, 2H), 7.61-7.72 (m, 3H), 7.86-7.88 (m, 2H); MS: m/z 488.0 (MH$^+$), 510.0 (MNa$^+$).

Compound 165

N-(3-Bromo-benzo[b]thiophen-2-yl)-N-(3-bromo-4-methoxy-benzyl)-benzenesulfonamide. $^1$H-NMR (CDCl$_3$): δ 3.82 (s, 3H), 4.75 (s, 2H), 6.71-6.73 (d, 1H), 7.15-7.18 (m, 1H), 7.38-7.46 (m, 3H), 7.52-7.57 (m, 2H), 7.64-7.72 (m, 3H), 7.86-7.78 (m, 2H); MS: m/z 567.9 (MH$^+$), 589.8 (MNa$^+$).

Compound 166

N-(3-Bromo-benzo[b]thiophen-2-yl)-N-(2-fluoro-benzyl)-benzenesulfonamide. $^1$H-NMR (CDCl$_3$): δ 4.93 (s, 2H), 6.88-6.93 (t, 1H), 7.02-7.07 (t, 1H), 7.18-7.22 (m, 1H), 7.36-7.47 (m, 3H), 7.49-7.55 (m, 2H), 7.62-7.73 (m, 3H), 7.87-7.90 (d, 2H); MS: m/z 475.9 (MH$^+$).

Compound 167

N-(3-Bromo-benzo[b]thiophen-2-yl)-N-(3-nitro-benzyl)-benzenesulfonamide. $^1$H-NMR (CDCl$_3$): δ 4.94 (s, 2H), 7.39-7.49 (m, 3H), 7.51-7.58 (m, 2H), 7.64-7.76 (m, 4H), 7.88-7.89 (d, 2H), 8.10-8.12 (m, 2H); MS: m/z 524.8 (MH$^+$).

Compound 168

N-(3-Bromo-benzo[b]thiophen-2-yl)-N-(pyridin-2-ylmethyl)-benzenesulfonamide. $^1$H-NMR (CDCl$_3$): δ 5.08 (s, 2H), 7.27-7.31 (m, 1H), 7.37-7.41 (m, 2H), 7.51-7.55 (m, 2H), 7.64-7.74 (m, 3H), 7.80-7.88 (m, 4H), 8.47-8.49 (d, 1H); MS: m/z 459.0 (MH$^+$).

Compound 169

N-(3-Bromo-benzo[b]thiophen-2-yl)-N-(pyridin-3-ylmethyl)-benzenesulfonamide. $^1$H-NMR (CDCl$_3$): δ 4.86 (s, 2H), 7.27-7.30 (m, 1H), 7.38-7.42 (m, 2H), 7.51-7.57 (m, 2H), 7.62-7.71 (m, 3H), 7.83-7.91 (m, 3H), 8.41-8.42 (m, 1H), 8.51-8.42 (m, 1H); MS: m/z 459.0 (MH$^+$).

Compound 170

N-(3-Bromo-benzo[b]thiophen-2-yl)-N-(pyridin-4-ylmethyl)-benzenesulfonamide. $^1$H-NMR (CDCl$_3$): δ 5.07 (s, 2H), 7.44-7.47 (m, 2H), 7.53-7.59 (m, 2H), 7.68-7.73 (m, 3H), 7.83-7.91 (m, 4H), 8.81-8.83 (m, 2H); MS: m/z 459.0, 461.0 (MH$^+$).

Compound 171

N-(3-Bromo-benzo[b]thiophen-2-yl)-N-(2-nitro-benzyl)-benzenesulfonamide. $^1$H-NMR (CDCl$_3$): δ 5.33 (s, 2H), 7.38-7.46 (m, 3H), 7.52-7.57 (m, 2H), 7.65-7.70 (m, 4H), 7.82-7.86 (m, 2H), 7.92-7.96 (d, 1H), 8.06-8.08 (d, 1H); MS: m/z 502.9, 504.9 (MH$^+$).

Compound 172

N-(3-Bromo-benzo[b]thiophen-2-yl)-N-(2-trifluoromethoxy-benzyl)-benzenesulfonamide. $^1$H-NMR (CDCl$_3$): δ 5.00 (s, 2H), 7.10-7.14 (m, 1H), 7.23-7.28 (m, 2H), 7.35-7.42 (m, 2H), 7.50-7.56 (m, 2H), 7.62-7.71 (m, 4H), 7.76-7.78 (m, 2H); MS: m/z 541.9, 543.9 (MH$^+$).

Compound 173

N-(3-Bromo-benzo[b]thiophen-2-yl)-N-(3-trifluoromethoxy-benzyl)-benzenesulfonamide. $^1$H-NMR (CDCl$_3$): δ 4.85 (s, 2H), 7.07-7.09 (m, 1H), 7.14 (s, 1H), 7.21-7.27 (m, 2H), 7.37-7.42 (m, 2H), 7.51-7.55 (m, 2H), 7.62-7.72 (m, 3H), 7.86-7.89 (m, 2H); MS: m/z 542.0, 543.9 (MH$^+$).

Compound 174

N-(3-Bromo-benzo[b]thiophen-2-yl)-N-(4-trifluoromethoxy-benzyl)-benzenesulfonamide. $^1$H-NMR (CDCl$_3$): δ 4.85 (s, 2H), 7.07-7.08 (d, 2H), 7.30-7.32 (m, 2H), 7.37-7.42 (m, 2H), 7.51-7.55 (d, 2H), 7.62-7.72 (m, 3H), 7.85-7.87 (m, 2H); MS: m/z 542.0 (MH$^+$).

Compound 175

N-(Benzyl)-N-(3-bromo-benzo[b]thiophen-2-yl)-benzenesulfonamide. $^1$H-NMR (CDCl$_3$): δ 4.85 (s, 2H), 7.20-7.29 (m, 5H), 7.35-7.40 (m, 2H), 7.51-7.55 (m, 2H), 7.61-7.70 (m, 3H), 7.87-7.89 (d, 2H); MS: m/z 458.0, 460.0 (MH$^+$).

Compound 176

N-(3-Bromo-benzo[b]thiophen-2-yl)-N-(4-fluoro-3-methoxy-benzyl)-benzenesulfonamide. $^1$H-NMR (CDCl$_3$): δ 3.79 (s, 3H), 4.79 (s, 2H), 6.65-6.70 (m, 1H), 6.84-6.89 (m, 1H), 6.98-6.99 (m, 1H), 7.36-7.42 (m, 2H), 7.52-7.55 (m, 2H), 7.63-7.72 (m, 3H), 7.86-7.89 (d, 2H); MS: m/z 506.0 (MH$^+$).

Compound 177

N-(3-Bromo-benzo[b]thiophen-2-yl)-N-(4-fluoro-3-trifluoromethyl-benzyl)-benzenesulfonamide. $^1$H-NMR (DMSO-d$_6$): δ 4.84 (s, 2H), 7.04-7.09 (m, 1H), 7.39-7.44 (m, 2H), 7.47-7.57 (m, 4H), 7.65-7.73 (m, 3H), 7.85-7.88 (m, 2H); MS: m/z 544.0 (MH$^+$).

Compound 178

N-(3-Bromo-benzo[b]thiophen-2-yl)-N-(2-methyl-benzyl)-benzenesulfonamide. $^1$H-NMR (CDCl$_3$): δ 2.40 (s, 3H), 4.89 (s, 2H), 6.92-6.95 (m, 1H), 7.07-7.09 (m, 3H), 7.35-7.39 (m, 2H), 7.51-7.55 (m, 2H), 7.59-7.68 (m, 3H), 7.87-7.90 (d, 2H); MS: m/z 472.0 (MH$^+$).

Compound 179

N-(3-Bromo-benzo[b]thiophen-2-yl)-N-(3-methyl-benzyl)-benzenesulfonamide. $^1$H-NMR (CDCl$_3$): δ 2.23 (s, 3H), 4.82 (s, 2H), 6.99-7.11 (m, 4H), 7.35-7.39 (m, 2H), 7.49-7.57 (m, 2H), 7.61-7.72 (m, 3H), 7.86-7.88 (d, 2H); MS: m/z 472.0 (MH$^+$).

Compound 180

N-(3-Chloro-benzo[b]thiophen-2-yl)-N-(4-fluoro-3-trifluoromethyl-benzyl)-3-methoxy-benzenesulfonamide. $^1$H-NMR (DMSO-d$_6$): δ 3.89 (s, 3H), 4.87 (s, 2H), 7.17-7.21 (d, 2H), 7.40-7.47 (m, 1H), 7.49-7.53 (m, 2H), 7.62-7.73 (m, 3H), 7.83-7.87 (d, 2H), 7.94-8.00 (m, 1H); MS: m/z 530.0 (MH$^+$).

Compound 181

N-(3-Chloro-benzo[b]thiophen-2-yl)-N-(4-fluoro-3-trifluoromethyl-benzyl)-4-methoxy-benzenesulfonamide. $^1$H-NMR (DMSO-d$_6$): δ 3.84 (s, 3H), 4.90 (s, 2H), 7.38-7.54 (m, 6H), 7.58-7.75 (m, 4H), 7.97-8.01 (m, 1H); MS: m/z 530.0 (MH$^+$).

Compound 182

N-(3-Bromo-benzo[b]thiophen-2-yl)-N-(4-fluoro-3-trifluoromethyl-benzyl)-4-methoxy-benzenesulfonamide. $^1$H-NMR (DMSO-d$_6$): δ 3.89 (s, 3H), 4.86 (s, 2H), 7.18-7.22 (d, 2H), 7.39-7.52 (m, 3H), 7.61-7.71 (m, 3H), 7.83-7.87 (d, 2H), 7.95-7.99 (m, 1H); MS: m/z 574.0 (MH$^+$).

Compound 183

N-(3-Bromo-benzo[b]thiophen-2-yl)-N-(4-fluoro-3-trifluoromethyl-benzyl)-ethanesulfonamide. $^1$H-NMR (DMSO-d$_6$): δ 1.36-1.41 (t, 3H), 3.50-3.57 (q, 2H), 4.96 (s, 2H), 7.43-7.54 (m, 3H), 7.66-7.76 (m, 3H), 7.96-7.99 (m, 1H); MS: m/z 495.9 (MH$^+$).

Compound 184

N-(3-Bromo-benzo[b]thiophen-2-yl)-N-(4-fluoro-3-trifluoromethyl-benzyl)-thiophene-2-sulfonamide. $^1$H-NMR (DMSO-d$_6$): δ 4.93 (s, 2H), 7.34-7.38 (m, 1H), 7.41-7.47 (m, 1H), 7.48-7.53 (m, 2H), 7.65-7.72 (m, 3H), 7.90-7.91 (m, 1H), 7.98-8.02 (m, 1H), 8.19-8.21 (m, 1H); MS: m/z 549.9 (MH$^+$).

Compound 185

N-(3-Bromo-benzo[b]thiophen-2-yl)-N-(4-fluoro-3-trifluoromethyl-benzyl)-3-methoxy-benzenesulfonamide.

¹H-NMR (DMSO-d₆): δ 3.64 (s, 3H), 4.91 (s, 2H), 7.37-7.53 (m, 6H), 7.59-7.72 (m, 4H), 7.97-7.99 (m, 1H); MS: m/z 574.0 (MH⁺).

Compound 186

N-(3-Bromo-benzo[b]thiophen-2-yl)-N-(4-fluoro-3-trifluoromethyl-benzyl)-thien-3-yl-sulfonamide. ¹H-NMR (DMSO-d₆): δ 4.92 (s, 2H), 7.41-7.54 (m, 4H), 7.64-7.71 (m, 3H), 7.91-7.99 (m, 2H), 8.46-8.47 (m, 1H); MS: m/z 549.9 (MH⁺).

Compound 187

N-(3-Chloro-benzo[b]thiophen-2-yl)-N-(4-fluoro-3-trifluoromethyl-benzyl)-thien-3-yl-sulfonamide. ¹H-NMR (DMSO-d₆): δ 4.93 (s, 2H), 7.42-7.56 (m, 4H), 7.64-7.76 (m, 3H), 7.91-8.00 (m, 2H), 8.46-8.47 (m, 1H); MS: m/z 506.0 (MH⁺).

Compound 188

N-(3-Bromo-benzo[b]thiophen-2-yl)-N-(4-fluoro-3-trifluoromethyl-benzyl)-pyridin-3-yl-sulfonamide. ¹H-NMR (DMSO-d₆): δ 4.99 (s, 2H), 7.43-7.53 (m, 3H), 7.67-7.76 (m, 4H), 7.96-8.02 (m, 1H), 8.32-8.36 (m, 1H), 8.98-9.01 (m, 1H), 9.08-9.09 (m, 1H); MS: m/z 545.0 (MH⁺).

Compound 189

N-(3-Chloro-benzo[b]thiophen-2-yl)-N-(4-fluoro-3-trifluoromethyl-benzyl)-pyridin-3-yl-sulfonamide. ¹H-NMR (DMSO-d₆): δ 5.01 (s, 2H), 7.43-7.53 (m, 3H), 7.67-7.76 (m, 4H), 7.98-8.03 (m, 1H), 8.32-8.36 (m, 1H), 8.97-9.02 (m, 1H), 9.06-9.09 (m, 1H); MS: m/z 501.0 (MH⁺).

Compound 190

N-(3-Chloro-benzo[b]thiophen-2-yl)-N-(4-fluoro-3-trifluoromethyl-benzyl)-ethanesulfonamide. ¹H-NMR (DMSO-d₆): δ 1.22-1.44 (t, 3H), 3.49-3.57 (q, 2H), 4.97 (s, 2H), 7.44-7.54 (m, 3H), 7.67-7.79 (m, 3H), 7.96-8.03 (m, 1H); MS: m/z 452.0 (MH⁺).

Compound 191

N-(3-Chloro-benzo[b]thiophen-2-yl)-N-(4-fluoro-3-trifluoromethyl-benzyl)-thiophene-2-sulfonamide. ¹H-NMR (DMSO-d₆): δ 4.93 (s, 2H), 7.34-7.36 (m, 2H), 7.43-7.57 (m, 3H), 7.66-7.76 (m, 2H), 7.89-7.92 (m, 1H), 7.97-8.03 (m, 1H), 8.19-8.23 (m, 1H); MS: m/z 528.0 (MH⁺).

Compound 192

N-(3-Bromo-benzo[b]thiophen-2-yl)-N-(4-fluoro-3-trifluoromethyl-benzyl)-4-carbomethoxy-benzenesulfonamide. ¹H-NMR (DMSO-d₆): δ 3.93 (s, 3H), 4.96 (s, 2H), 7.42-7.52 (m, 3H), 7.63-7.71 (m, 3H), 7.95-7.99 (m, 1H), 8.06-8.08 (dd, 2H), 8.20-8.23 (dd, 2H); MS: m/z 601.8 (MH⁺).

Compound 193

N-(3-Bromo-benzo[b]thiophen-2-yl)-N-(4-fluoro-3-trifluoromethyl-benzyl)-3-carbomethoxy-benzenesulfonamide. ¹H-NMR (DMSO-d₆): δ 3.89 (s, 3H), 4.96 (s, 2H), 7.41-7.49 (m, 1H), 7.50-7.54 (m, 2H), 7.63-7.72 (m, 3H), 7.84-7.88 (t, 1H), 7.98-8.01 (m, 1H), 8.19-8.22 (m, 1H), 8.32-8.36 (m, 2H); MS: m/z 603.9 (MH⁺).

Compound 194

N-(3-Chloro-benzo[b]thiophen-2-yl)-N-(4-fluoro-3-trifluoromethyl-benzyl)-4-carbomethoxy-benzenesulfonamide. ¹H-NMR (DMSO-d₆): δ 3.93 (s, 3H), 4.96 (s, 2H), 7.43-7.54 (m, 3H), 7.65-7.74 (m, 3H), 7.96-7.99 (m, 1H), 8.06-8.08 (dd, 2H), 8.20-8.23 (dd, 2H); MS: m/z 558.0 (MH⁺).

Compound 195

N-(3-Chloro-benzo[b]thiophen-2-yl)-N-(4-fluoro-3-trifluoromethyl-benzyl)-3-carbomethoxy-benzenesulfonamide. ¹H-NMR (DMSO-d₆): δ 3.89 (s, 3H), 4.96 (s, 2H), 7.42-7.47 (t, 1H), 7.49-7.54 (m, 2H), 7.64-7.68 (m, 2H), 7.72-7.74 (m, 1H), 7.85-7.89 (m, 1H), 7.98-8.02 (m, 1H), 8.19-8.22 (m, 1H), 8.31-8.36 (m, 2H); MS: m/z 558.0 (MH⁺).

Compound 196

N-(3-Chloro-benzo[b]thiophen-2-yl)-N-(4-fluoro-3-trifluoromethyl-benzyl)-2-carbomethoxy-benzenesulfonamide. ¹H-NMR (DMSO-d₆): δ 3.64 (s, 3H), 5.04 (s, 2H), 7.44-7.54 (m, 3H), 7.69-7.78 (m, 5H), 7.83-7.91 (m, 2H), 7.95-7.99 (m, 1H); MS: m/z 558.0 (MH⁺).

Compound 197

N-(3-Bromo-benzo[b]thiophen-2-yl)-N-(4-fluoro-3-trifluoromethyl-benzyl)-2-carbomethoxy-benzenesulfonamide. ¹H-NMR (DMSO-d₆): δ 3.65 (s, 3H), 5.05 (s, 2H), 7.43-7.51 (m, 3H), 7.64-7.77 (m, 5H), 7.84-7.90 (m, 2H), 7.97-7.99 (m, 1H); MS: m/z 603.9 (MH⁺).

Compound 312

N-(3-Bromo-benzo[b]thiophen-2-yl)-N-(4-fluoro-3-trifluoromethyl-benzyl)-4-acetyl-benzenesulfonamide. ¹H-NMR (DMSO-d₆): δ 2.67 (s, 3H), 4.95 (s, 2H), 7.44-7.51 (m, 3H), 7.67-7.72 (m, 3H), 7.80-8.07 (m, 3H), 8.19-8.21 (m, 2H); MS: m/z 585.9 (MH⁺).

Compound 317

N-(3-Bromo-benzo[b]thiophen-2-yl)-N-(4-fluoro-3-trifluoromethyl-benzyl)-N',N'-dimethylsulfamide. ¹H-NMR (DMSO-d₆): δ 2.94 (s, 6H), 4.87 (s, 2H), 7.41-7.52 (m, 3H), 7.64-7.73 (m, 3H), 7.96-7.99 (m, 1H); MS: m/z 511, 513.1 (MH⁺).

Compound 345

N-(3-Bromobenzo[b]thiophen-2-yl)-N-(butyl)-pyridin-3-yl-sulfonamide. ¹H-NMR (DMSO-d₆): δ 0.83 (t, 3H), 1.49-1.29 (m, 4H), 3.70 (t, 2H), 7.60-7.50 (m, 2H), 7.74-7.68 (m, 1H), 7.81-7.75 (m, 1H), 8.06-7.98 (m, 1H), 8.29-8.23 (m, 1H), 9.00-8.92 (m, 2H); MS: m/z 425.0 (MH⁺).

Compound 350

N-(3-Bromo-benzo[b]thiophen-2-yl)-N-(4-fluoro-3-trifluoromethyl-benzyl)-C-methanesulfonyl-methanesulfonamide. MS: m/z 560, 562.0 (MH⁺), 582, 584.0 (MNa⁺).

Compound 576

N-(3-Bromo-benzo[b]thiophen-2-yl)-N-(4-fluoro-3-trifluoromethyl-benzyl)-3-(1H-tetrazol-5-yl)-benzenesulfonamide. $^1$H-NMR (DMSO-d$_6$): δ 4.98 (s, 2H), 7.38-7.55 (m, 3H), 7.61-7.74 (m, 3H), 7.90-8.01 (m, 2H), 8.14 (d, 1H), 8.48 (d, 1H), 8.55 (s, 1H); MS: m/z 612, 614.0 (MH$^+$).

Compound 578

N-(3-Chloro-benzo[b]thiophen-2-yl)-N-(4-fluoro-3-trifluoromethyl-benzyl)-3-(1H-tetrazol-5-yl)-benzenesulfonamide. $^1$H-NMR (DMSO-d$_6$): δ 4.98 (s, 2H), 7.35-7.58 (m, 3H), 7.63-7.78 (m, 3H), 7.90-8.03 (m, 2H), 8.14 (d, 1H), 8.49 (d, 1H), 8.55 (s, 1H); MS: m/z 567.6 (MH$^+$).

Compound 594

N-(3-Bromo-benzo[b]thiophen-2-yl)-N-(2-cyclopropyl-ethyl)-4-(1H-tetrazol-5-yl)-benzenesulfonamide. $^1$H-NMR (DMSO-d$_6$): δ 0.014-0.065 (m, 3H), 0.343-0.388 (m, 2H), 0.713-0.813 (m, 1H), 1.35-1.40 (m, 2H), 3.72-3.76 (t, 2H), 7.51-7.57 (m, 2H), 7.73-7.79 (m, 1H), 7.96-8.03 (m, 1H), 8.06-8.08 (d, 2H), 8.30-8.32 (d, 2H); MS: m/z 505.6 (MH$^+$).

Compound 595

N-(3-Bromo-benzo[b]thiophen-2-yl)-N-(3,3,3-trifluoropropyl)-4-(1H-tetrazol-5-yl)-benzenesulfonamide. $^1$H-NMR (DMSO-d$_6$): δ 2.57-2.67 (m, 2H), 3.96-4.02 (t, 2H), 7.53-7.57 (m, 2H), 7.74-7.77 (m, 1H), 8.00-8.04 (m, 1H), 8.07-8.09 (d, 2H), 8.29-8.31 (m, 2H); MS: m/z 533.5 (MH$^+$).

Compound 635

N-(3-Chloro-benzo[b]thiophen-2-yl)-N-(2-cyclopropyl-ethyl)-4-(1H-tetrazol-5-yl)-benzenesulfonamide. $^1$H-NMR (DMSO-d$_6$): δ 0.008-0.034 (m, 3H), 0.346-0.392 (m, 2H), 0.719-0.794 (m, 1H), 1.35-1.40 (m, 2H), 3.72-3.75 (t, 2H), 7.52-7.57 (m, 2H), 7.77-7.82 (m, 1H), 7.98-8.01 (m, 1H), 8.02-8.09 (m, 2H), 8.29-8.32 (m, 2H); MS: m/z 459.7 (MH$^+$).

Compound 636

N-(3-Chloro-benzo[b]thiophen-2-yl)-N-(3,3,3-trifluoropropyl)-4-(1H-tetrazol-5-yl)-benzenesulfonamide. $^1$H-NMR (DMSO-d$_6$): δ 2.55-2.67 (m, 2H), 3.97-4.01 (t, 2H), 7.52-7.58 (m, 2H), 7.76-7.82 (m, 1H), 8.00-8.05 (m, 1H), 8.07-8.09 (d, 2H), 8.29-8.31 (d, 2H); MS: m/z 487.6 (MH$^+$).

Compound 702

N-(3-Bromo-benzo[b]thiophen-2-yl)-N-(4-fluoro-3-trifluoromethyl-benzyl)-2,2,2-trifluoro-ethanesulfonamide. $^1$H-NMR (CDCl$_3$): δ 4.07 (q, 2H), 4.96 (s, 2H), 7.12 (t, 1H), 7.42-7.55 (m, 4H), 7.65-7.76 (m, 1H), 7.76-7.86 (m, 1H); MS: m/z 573.9 (MNa$^+$).

Compound 703

N-(3-Chloro-benzo[b]thiophen-2-yl)-N-(4-fluoro-3-trifluoromethyl-benzyl)-2,2,2-trifluoro-ethanesulfonamide. MS: m/z 528.0 (MNa$^+$).

Compound 706

N-(3-Bromo-benzo[b]thiophen-2-yl)-N-(cyclopropyl-ethyl)-4-(5-oxo-4,5-dihydro-[1,2,4]thiadiazol-3-yl)-benzenesulfonamide. $^1$H-NMR (DMSO-d$_6$): δ 0.013-0.050 (m, 2H), 0.314-0.376 (m, 2H), 0.695-0.794 (m, 1H), 1.33-1.38 (m, 2H), 3.70-3.74 (m, 2H), 7.50-7.56 (m, 2H), 7.73-7.78 (m, 1H), 7.96-7.98 (m, 1H), 8.00-8.01 (d, 2H), 8.18-8.20 (d, 2H), 13.69 (s, 1H); MS: m/z 538.0 (MH$^+$).

Compound 707

N-(3-Bromo-benzo[b]thiophen-2-yl)-N-(5,5,5-trifluoro-pentyl)-2-fluoro-4-carboxy-benzenesulfonamide. $^1$H-NMR (DMSO-d$_6$): δ 1.58-1.75 (m, 4H), 2.18-2.28 (m, 2H), 3.85-3.87 (m, 2H), 7.51-7.55 (m, 2H), 7.72-7.76 (m, 1H), 7.85-7.90 (m, 2H), 7.94-8.04 (m, 2H), 13.88 (s, 1H); MS: m/z 555.9 (MH$^+$).

Compound 708

N-(3-Bromo-benzo[b]thiophen-2-yl)-N-(3,3,3-trifluoropropyl)-4-(5-oxo-4,5-dihydro-[1,2,4]thiadiazol-3-yl)-benzenesulfonamide. $^1$H-NMR (DMSO-d$_6$): δ 2.55-2.66 (m, 2H), 3.98-4.01 (t, 2H), 7.53-7.57 (m, 2H), 7.74-7.78 (m, 1H), 8.00-8.04 (m, 3H), 8.18-8.20 (d, 2H), 13.70 (s, 1H); MS: m/z 566.0 (MH$^+$).

Compound 709

N-(3-Bromo-benzo[b]thiophen-2-yl)-N-(2-cyclopropyl-ethyl)-2-fluoro-4-carboxy-benzenesulfonamide. $^1$H-NMR (DMSO-d$_6$): δ 0.000-0.005 (m, 2H), 0.292-0.373 (m, 2H), 0.670-0.769 (m, 1H), 1.36-1.41 (m, 2H), 3.84-3.87 (t, 2H), 7.47-7.52 (m, 2H), 7.68-7.74 (m, 1H), 7.81-7.86 (m, 2H), 7.91-7.99 (m, 2H), 13.84 (s, 1H); MS: m/z 500.0 (MH$^+$).

Compound 710

N-(3-Bromo-benzo[b]thiophen-2-yl)-N-(3,3,3-trifluoropropyl)-2-fluoro-4-carboxy-benzenesulfonamide. $^1$H-NMR (DMSO-d$_6$): δ 2.58-2.68 (m, 2H), 4.12-4.16 (t, 2H), 7.51-7.57 (m, 2H), 7.71-7.77 (m, 1H), 7.83-7.89 (m, 2H), 7.96-8.06 (m, 2H), 13.89 (s, 1H); MS: m/z 528.0 (MH$^+$).

Compound 711

N-(3-Bromo-benzo[b]thiophen-2-yl)-N-(4-fluoro-3-trifluoromethyl-benzyl)-2-fluoro-4-carboxy-benzenesulfonamide. $^1$H-NMR (DMSO-d$_6$): δ 5.08 (s, 2H), 7.45-7.52 (m, 3H), 7.65-7.69 (m, 3H), 7.89-8.01 (m, 4H), 13.92 (s, 1H); MS: m/z 608.0 (MH$^+$).

Compound 712

N-(3-Bromo-benzo[b]thiophen-2-yl)-N-(5,5,5-trifluoro-pentyl)-4-(5-oxo-4,5-dihydro-[1,2,4]thiadiazol-3-yl)-benzenesulfonamide. $^1$H-NMR (DMSO-d$_6$): δ 1.52-1.63 (m, 4H), 2.21-2.28 (m, 2H), 3.70 (m, 2H), 7.51-7.58 (m, 2H), 7.77-7.80 (m, 1H), 7.98-8.02 (m, 3H), 8.19-8.21 (m, 2H), 13.70 (s, 1H); MS: m/z 594.0 (MH$^+$).

Compound 785

N-(3-Methyl-benzo[b]thiophen-2-yl)-N-(4-trifluoromethoxy-benzyl)-4-(1H-tetrazol-5-yl)-benzenesulfonamide. $^1$H-NMR (DMSO-d$_6$): δ 1.93 (s, 3H), 4.68-4.96 (s, 2H), 7.23-7.35 (m, 2H), 7.36-7.42 (m, 4H), 7.65-7.68 (m, 1H), 7.80-7.84 (m, 1H), 8.10-8.12 (d, 2H), 8.31-8.33 (d, 2H); MS: m/z 546.0 (MH⁺).

Example 12

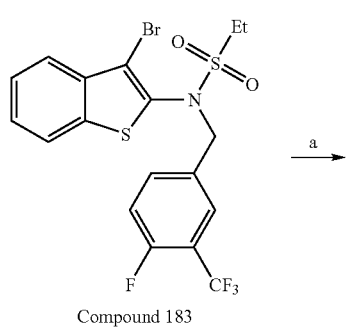

Compound 183

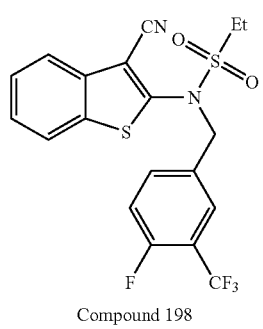

Compound 198 a) CuCN, DMF.

Compound 198

N-(3-Cyano-benzo[b]thiophen-2-yl)-N-(4-fluoro-3-trifluoromethyl-benzyl)-ethanesulfonamide. A mixture of compound 183 (97 mg, 0.195 mmol) and CuCN (44 mg, 0.496 mmol) in DMF (3 mL) was heated at reflux for 6 h. The mixture was cooled, an additional portion of CuCN (55 mg, 0.614 mmol) was added, and the reaction heated overnight. The mixture was cooled, and the inorganics were removed by filtration. The resultant solution was partitioned between ethyl acetate and water. The organic layer was separated, washed with water (3×), brine, dried over sodium sulfate, filtered, and the solvent was evaporated in vacuo. The crude residue was purified by HPLC (C₁₈) eluting with a acetonitrile-water (0.1% TFA) (10-40%) gradient, to afford compound 198 as an oil (40 mg, 46%). ¹H-NMR (DMSO-d₆): δ 1.39 (t, 3H), 3.62 (q, 2H), 5.09 (s, 2H), 7.49 (t, 1H), 7.54-7.61 (m, 2H), 7.68-7.72 (m, 1H), 7.78-7.83 (m, 2H), 8.09-8.13 (m, 1H); MS: m/z 443.1 (MH⁺).

Example 13

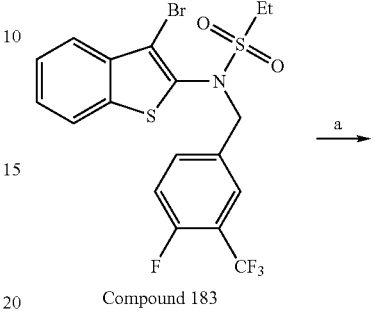

Compound 183

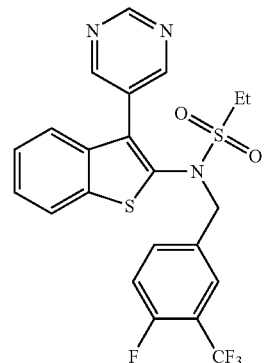

Compound 199 a) 5-Pyrimidineboronic acid, Na₂CO₃(aq), Pd(118), dioxane.

Compound 199

N-(4-Fluoro-3-trifluoromethyl-benzyl)-N-(3-pyrimidin-5-yl-benzo[b]thiophen-2-yl)-ethanesulfonamide. A solution of compound 183 (140 mg, 0.28 mmol) and 5-pyrimidineboronic acid (42 mg, 0.34 mmol) in dioxane (2 mL) was treated with 2 M sodium carbonate (352 μL, 0.705 mmol) and palladium catalyst (Johnson Matthey Pd(118), 10 mg, 0.015 mmol). Dioxane was added, the tube was purged with argon, sealed and heated to 80° C. for 2 h. The solvent was evaporated in vacuo, and the residue partitioned between dichloromethane and water. The organic layer was separated, dried over sodium sulfate, filtered, and the solvent evaporated in vacuo. The residue was purified by HPLC (C₁₈) eluting with an acetonitrile-water (0.1% TFA) (30-90%) to afford compound 199 as a brown oil (19 mg, 14%). ¹H-NMR (DMSO-d₆): δ 1.35 (t, 3H), 3.58 (q, 2H), 4.77 (s, 2H), 7.24-7.42 (m, 5H), 7.49-7.56 (m, 1H), 8.09 (d, 1H), 8.50 (s, 2H), 9.15 (s, 1H); MS: m/z 496.2 (MH⁺).

Following the procedure described above for example 13 and substituting the appropriate reagents, starting materials and purification methods known to those skilled in the art, the following compounds of the present invention were prepared:

Compound 200

N-[3-(2-Fluoro-phenyl)-benzo[b]thiophen-2-yl]-N-(4-fluoro-3-trifluoromethyl-benzyl)-ethanesulfonamide.

$^1$H-NMR (DMSO-d$_6$): δ 1.26 (t, 3H), 3.44 (q, 2H), 4.61 (d, 1H), 4.86 (d, 1H), 7.09-7.19 (m, 2H), 7.23-7.30 (m, 2H), 7.33-7.51 (m, 6H), 8.00 (d, 1H); MS: m/z 512.3 (MH$^+$).

Compound 201

N-[3-(4-Fluoro-phenyl)-benzo[b]thiophen-2-yl]-N-(4-fluoro-3-trifluoromethyl-benzyl)-ethanesulfonamide. $^1$H-NMR (DMSO-d$_6$): δ 1.30 (t, 3H), 3.47 (q, 2H), 4.71 (s, 2H), 7.15-7.40 (m, 9H), 7.44-7.50 (m, 1H), 8.00 (d, 1H); MS: m/z 512.2 (MH$^+$).

Compound 202

N-(4-Fluoro-3-trifluoromethyl-benzyl)-N-(3-thiophen-3-yl-benzo[b]thiophen-2-yl)-ethanesulfonamide. $^1$H-NMR (DMSO-d$_6$): δ 1.27 (t, 3H), 3.39 (q, 2H), 4.76 (s, 2H), 7.06 (d, 1H), 7.28 (t, 1H), 7.36-7.52 (m, 5H), 7.55-7.58 (m, 1H), 7.62-7.65 (m, 1H), 7.97 (d, 1H); MS: m/z 500.1 (MH$^+$).

Example 14

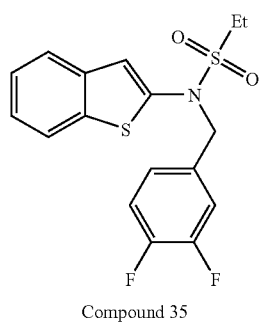

Compound 35

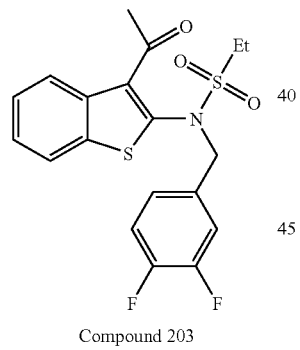

Compound 203 a) SnCl$_4$, acetyl chloride, DCM.

Compound 203

N-(4-Fluoro-3-trifluoromethyl-benzyl)-N-(3-formyl-benzo[b]thiophen-2-yl)-4-carbomethoxybenzenesulfonamide. A solution of acetylchloride (16 μL, 0.224 mmol) in dichloromethane (3 mL), at 0° C., was treated with tin(IV) chloride (26 μL, 0.224 mmol) and the resultant solution was stirred at 0° C. for 15 min. Compound 35 (75 mg, 0.204 mmol) was added to the solution and the mixture stirred at ambient temperature overnight. The reaction mixture was washed with 2 N HCl, dried over sodium sulfate, filtered, and the solvent evaporated under reduced pressure. The crude residue was purified by flash column chromatography (SiO$_2$) eluting with an ethyl acetate-heptane (10-80%) gradient. The product was further purified by HPLC (C$_{18}$) eluting with an acetonitrile-water (0.1% TFA) (40-90%) gradient to afford compound 203 as a colorless solid (25 mg, 30%). $^1$H-NMR (DMSO-d$_6$): δ 1.31 (t, 3H), 2.30 (s, 3H), 3.47 (q, 2H), 4.98 (s, 2H), 7.17 (m, 1H), 7.35 (m, 4H), 7.94-8.03 (m, 2H); MS: m/z 410.1 (MH$^+$).

Following the procedure described above for example 14 and substituting the appropriate reagents, starting materials and purification methods known to those skilled in the art, the following compounds of the present invention were prepared:

Compound 204

N-(3-Acetyl-benzo[b]thiophen-2-yl)-N-(3,4-difluoro-benzyl)-benzenesulfonamide. $^1$H-NMR (DMSO-d$_6$): δ 2.37 (s, 3H), 4.86 (br s, 2H), 7.16-7.24 (m, 1H), 7.33-7.49 (m, 4H), 7.65-7.73 (m, 2H), 7.82-7.86 (m, 3H), 7.90-7.96 (m, 1H), 7.99-8.04 (m, 1H); MS: m/z 458.3 (MH$^+$).

Compound 833

N-(3-Acetyl-benzo[b]thiophen-2-yl)-N-(3-fluoro-propyl)-benzenesulfonamide. $^1$H-NMR (CDCl$_3$): δ 2.08-2.21 (m, 2H), 2.79 (s, 3H), 3.81 (s, 2H), 4.48 (t, 1H), 4.61 (t, 1H), 7.41-7.78 (m, 8H), 8.25 (m, 1H).

Example 15

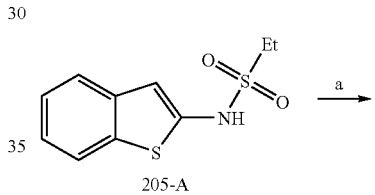

205-A

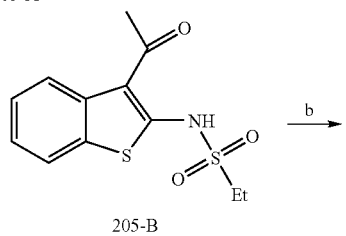

205-B

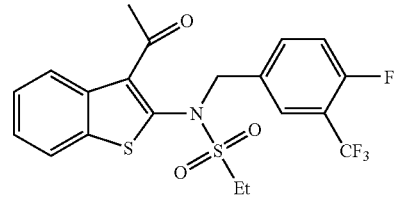

Compound 205 a) Acetyl chloride, SnCl$_4$, DCM; b) NaH, 15-Crown-5, 4-fluoro-3-trifluoromethylbenzyl bromide.

Compound 205-A was prepared from compound 1-C and 4-ethanesulfonyl chloride, following the procedure used to prepare compound 1-D.

N-(3-Acetyl-benzo[b]thiophen-2-yl)-ethanesulfonamide (205-B). Tin(IV) chloride (173 μL, 1.48 mmol) was added to a solution of acetyl chloride (124 μL, 1.75 mmol) in dichloromethane (10 mL), at 0° C., and the solution was stirred for 5 min. To the reaction mixture was added a solution of compound 205-A (325 mg, 1.35 mmol) in dichloromethane (2 mL) at 0° C. The resultant solution was allowed to warm to ambient temperature and stirred overnight. The solution was treated with water (10 mL), the organic layer separated, dried over sodium sulfate, filtered, and the solvent evaporated in vacuo to afford compound 205-B as a colorless solid (355 mg, 93%). $^1$H-NMR (DMSO-d$_6$): δ 1.25 (t, 3H), 2.71 (s, 3H), 3.39 (q, 2H), 7.34-7.48 (m, 2H), 7.94 (d, 1H), 8.10 (d, 1H); MS: m/z 284.1 (MH$^+$).

Compound 205

N-(3-Acetyl-benzo[b]thiophen-2-yl)-N-(4-fluoro-3-trifluoromethyl-benzyl)-ethanesulfonamide. Sodium hydride (60% in oil, 46 mg, 1.15 mmol) was added to a solution of compound 205-B (310 mg, 1.09 mmol) in DMF (4 mL), at 0° C. The resultant mixture was stirred at 0° C. for 15 min, to which was added 4-fluoro-3-trifluoromethylbenzyl bromide (253 µL, 1.33 mmol) and the resultant mixture was stirred at ambient temperature for 2 h. 15-Crown-5 (220 µL, 1.33 mmol) and an additional equivalent of 4-fluoro-3-trifluoromethylbenzyl bromide was added to the reaction mixture. The resultant solution was stirred at ambient temperature overnight, water added, and the product extracted into ethyl acetate. The organic phase was washed with water (3x), brine, dried over sodium sulfate, filtered, and the solvent evaporated in vacuo. The crude residue was purified by flash column chromatography (SiO$_2$), eluting with an ethyl acetate-heptane gradient to afford compound 205 as an off-white solid (285 mg, 57%). $^1$H-NMR (DMSO-d$_6$): δ 1.32 (t, 3H), 2.29 (s, 3H), 3.49 (q, 2H), 5.08 (s, 2H), 7.41-7.52 9m, 3H), 7.70-7.77 (m, 2H), 7.93-8.03 (m, 2H); MS: m/z 460.2 (MH$^+$).

Following the procedure described above for example 15 and substituting the appropriate reagents, starting materials and purification methods known to those skilled in the art, the following compounds of the present invention were prepared:

Compound 313

N-(3-Acetyl-benzo[b]thiophen-2-yl)-N-(4-fluoro-3-trifluoromethyl-benzyl)-4-carbomethoxy-benzenesulfonamide. $^1$H-NMR (DMSO-d$_6$): δ 2.36 (s, 3H), 3.92 (s, 3H), 4.99 (s, 2H), 7.41-7.48 (m, 3H), 7.67-7.73 (m, 2H), 7.91-8.00 (m, 4H), 8.21 (d, 2H); MS: m/z 566.2 (MH$^+$).

Compound 314

N-(3-Acetyl-benzo[b]thiophen-2-yl)-N-(4-fluoro-3-trifluoromethyl-benzyl)-benzenesulfonamide. $^1$H-NMR (DMSO-d$_6$): δ 2.38 (s, 3H), 4.95 (s, 2H), 7.41-7.48 (m, 3H), 7.68-7.75 (m, 4H), 7.80-7.87 (m, 3H), 7.91-7.96 (m, 1H), 8.00-8.04 (m, 1H); MS: m/z 508.2 (MH$^+$).

Compound 837

N-(3-Acetyl-benzo[b]thiophen-2-yl)-N-(4-fluoro-3-methoxy-benzyl)-ethanesulfonamide. $^1$H-NMR (CDCl$_3$): δ 1.46 (t, 3H), 2.36 (s, 3H), 3.19 (q, 2H), 3.81 (s, 3H), 4.91 (s, 2H), 6.82-6.86 (m, 1H), 6.97 (dd, 1H), 7.03 (dd, 1H), 7.40-7.44 (m, 2H), 7.72-7.75 (m, 1H), 8.07-8.11 (m, 1H); MS: m/z 444.1 (MNa$^+$).

Example 16

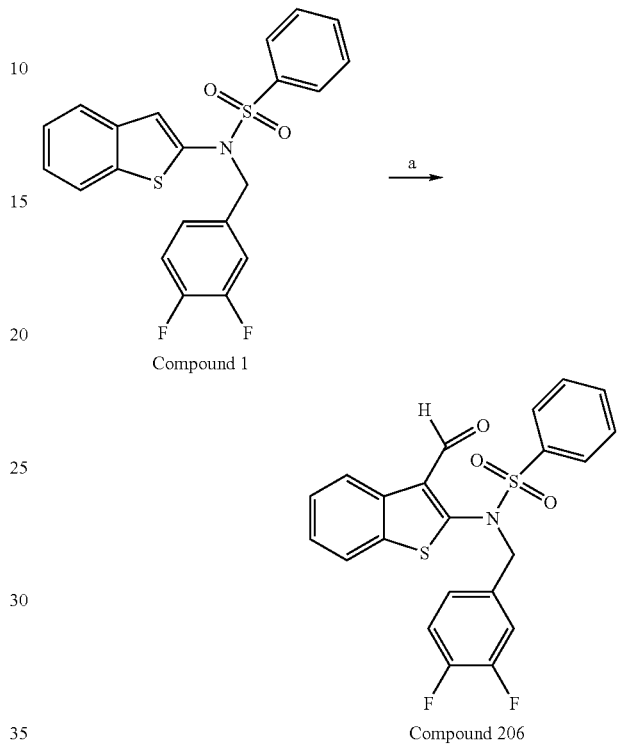

a) TiCl$_4$, α,α-dichloromethylmethyl ether, DCM.

Compound 206

N-(3,4-Difluoro-benzyl)-N-(3-formyl-benzo[b]thiophen-2-yl)-benzenesulfonamide. A solution of titanium(IV) chloride (1.0 M in dichloromethane, 0.94 mL, 0.94 mmol) was added to a solution of compound 1 (270 mg, 0.65 mmol) in dichloromethane (6 mL), at −5° C. The resultant solution was stirred at −5° C. for 15 min to which was added α,α-dichloromethylmethyl ether (75 mL, 0.845 mmol) and the reaction mixture was stirred at ambient temperature overnight. The solution was treated with 2N HCl (10 mL), the organic layer separated, dried over sodium sulfate, filtered, and the solvent evaporated in vacuo. The crude residue was purified by flash column chromatography (SiO$_2$), eluting with an ethyl acetate-heptane gradient (10-40%) to afford compound 206 as a colorless solid (180 mg, 62%). $^1$H-NMR (DMSO-d$_6$): δ 4.94 (s, 2H), 7.15-7.25 (m, 1H), 7.33-7.55 (m, 4H), 7.68-7.72 (m, 2H), 7.83-7.87 (m, 3H), 7.98-8.01 (m, 1H), 8.43-8.46 (m, 1H), 9.87 (s, 1H); MS: m/z 444.1 (MH$^+$).

Following the procedure described above for example 16 and substituting the appropriate reagents, starting materials and purification methods known to those skilled in the art, the following compounds of the present invention were prepared:

Compound 207

N-(4-Fluoro-3-trifluoromethyl-benzyl)-N-(3-formyl-benzo[b]thiophen-2-yl)-benzenesulfonamide. $^1$H-NMR (DMSO-d$_6$): δ 5.06 (br s, 2H), 7.43-7.55 (m, 3H), 7.68-7.79 (m, 4H), 7.83-7.89 (m, 3H), 7.98-8.03 (m, 1H), 8.42-8.47 (m, 1H), 9.84 (s, 1H); MS: m/z 494.1 (MH$^+$).

Compound 208

N-(4-Fluoro-3-trifluoromethyl-benzyl)-N-(3-formyl-benzo[b]thiophen-2-yl)-methanesulfonamide. $^1$H-NMR (DMSO-d$_6$): δ 3.45 (s, 3H), 5.11 (s, 2H), 7.44-7.55 (m, 3H), 7.73-7.79 (m, 2H), 8.04-8.09 (m, 1H), 8.42-8.46 (m, 1H), 9.91 (s, 1H); MS: m/z 432.0 (MH$^+$).

Compound 209

N-(3,4-Difluoro-benzyl)-N-(3-formyl-benzo[b]thiophen-2-yl)-methanesulfonamide. $^1$H-NMR (DMSO-d$_6$): δ 3.43 (s, 3H), 5.00 (s, 2H), 7.19-7.26 (m, 1H), 7.33-7.55 (m, 4H), 8.03-8.09 (m, 1H), 8.42-8.47 (m, 1H), 9.91 (s, 1H); MS: m/z 382.2 (MH$^+$).

Compound 210

N-(4-Fluoro-3-trifluoromethyl-benzyl)-N-(3-formyl-benzo[b]thiophen-2-yl)-ethanesulfonamide. $^1$H-NMR (DMSO-d$_6$): δ 1.36 (t, 3H), 3.61 (q, 2H), 5.15 (s, 2H), 7.45-7.55 (m, 3H), 7.71-7.78 (m, 2H), 8.03-8.10 (m, 1H), 8.40-8.47 (m, 1H), 9.83 (s, 1H); MS: m/z 446.1 (MH$^+$).

Compound 211

N-(3-Formyl-benzo[b]thiophen-2-yl)-N-(4-fluoro-3-trifluoromethyl-benzyl)-4-carbomethoxy-benzenesulfonamide. $^1$H-NMR (DMSO-d$_6$): δ 3.93 (s, 3H), 5.08 (s, 2H), 7.44-7.55 (m, 3H), 7.70-7.81 (m, 2H), 7.99-8.05 (m, 3H), 8.22 (d, 2H), 8.42-8.46 (m, 1H), 9.85 (s, 1H); MS: m/z 552.2 (MH$^+$).

Compound 212

N-(3,4-Difluoro-benzyl)-N-(3-formyl-benzo[b]thiophen-2-yl)-ethanesulfonamide. $^1$H-NMR (DMSO-d$_6$): δ 1.36 (t, 3H), 3.61 (q, 2H), 5.04 (s, 2H), 7.17-7.24 (m, 1H), 7.34-7.46 (m, 2H), 7.48-7.54 (m, 2H), 8.03-8.08 (m, 1H), 8.40-8.46 (m, 1H), 9.83 (s, 1H); MS: m/z 396.1 (MH$^+$).

Compound 419

N-(Butyl)-N-(3-formyl-benzo[b]thiophene-2-yl)-4-carbomethoxy-benzenesulfonamide. MS: m/z 432.1 (MH$^+$).

Example 17

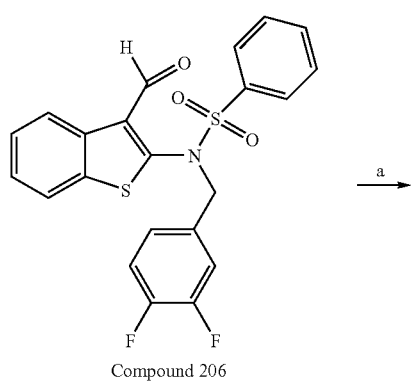

Compound 206 a

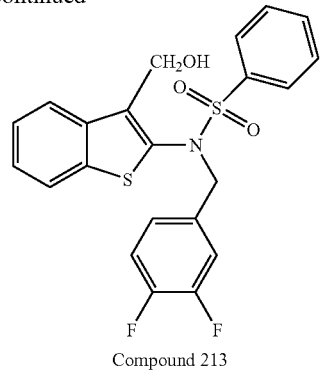

Compound 213 a) NaBH$_4$, EtOH.

Compound 213

N-(3,4-Difluoro-benzyl)-N-(3-hydroxymethyl-benzo[b]thiophen-2-yl)-benzenesulfonamide. Sodium borohydride (25 mg, 0.66 mmol) was added to a solution of compound 206 (50 mg, 0.112 mmol) in ethanol (2 mL), and the mixture was stirred at rt for 3 h. The solvent was evaporated, the residue partitioned between dichloromethane and water, the organic layer separated, dried over sodium sulfate, filtered, and the solvent evaporated in vacuo. The residue was purified by flash column chromatography (SiO$_2$), eluting with an ethyl acetate-heptane (10-40%) gradient to afford compound 213 as a colorless solid (42 mg, 84%). $^1$H-NMR (DMSO-d$_6$): δ 4.26 (d, 2H, collapses to singlet with D$_2$O), 4.80 (s, 2H), 5.01 (t, 1H, exchanges with D$_2$O), 7.10-7.14 (m, 1H), 7.25-7.40 (m, 4H), 7.67 (t, 2H), 7.78-7.86 (m, 4H), 7.90-7.96 (m, 1H); MS: m/z 428.0 (M-OH)$^+$, 468.0 (MNa$^+$).

Following the procedure described above for example 17 and substituting the appropriate reagents, starting materials and purification methods known to those skilled in the art, the following compounds of the present invention were prepared:

Compound 214

N-(4-Fluoro-3-trifluoromethyl-benzyl)-N-(3-hydroxymethyl-benzo[b]thiophen-2-yl)-benzenesulfonamide.
$^1$H-NMR (DMSO-d$_6$): δ 4.29 (d, 2H), 4.90 (s, 2H), 5.02 (t, 1H), 7.35-7.45 (m, 3H), 7.61-7.71 (m, 4H), 7.78-7.87 (m, 4H), 7.90-7.95 (m, 1H); MS: m/z 478.0 [(M-OH)$^+$], 518 (MNa$^+$).

Compound 215

N-(4-Fluoro-3-trifluoromethyl-benzyl)-N-(3-hydroxymethyl-benzo[b]thiophen-2-yl)-methanesulfonamide.
$^1$H-NMR (DMSO-d$_6$): δ 3.32 (s, 3H), 4.55 (d, 2H), 4.92 (s, 2H), 5.10 (t, 1H), 7.36-7.50 (m, 3H), 7.65-7.72 (m, 2H), 7.84-7.90 (m, 1H), 7.93-7.98 (m, 1H); MS: m/z 416.1 (M-OH)$^+$, 456.1 (MNa$^+$).

Compound 216

N-(3,4-Difluoro-benzyl)-N-(3-hydroxymethyl-benzo[b]thiophen-2-yl)-methanesulfonamide. $^1$H-NMR (CDCl$_3$): δ 2.49 (t, 1H), 3.11 (s, 3H), 4.44 (d, 2H), 4.77 (br s, 2H), 7.02-7.20 (m, 3H), 7.40-7.46 (m, 2H), 7.74-7.80 (m, 1H), 7.88-7.94 (m, 1H); MS: m/z 366.1 (M-OH)$^+$, 406.0 (MNa$^+$).

Compound 217

N-(4-Fluoro-3-trifluoromethyl-benzyl)-N-(3-hydroxymethyl-benzo[b]thiophen-2-yl)-ethanesulfonamide. $^1$H-NMR (DMSO-d$_6$): δ 1.33 (t, 3H), 3.47 (q, 2H), 4.53 (d, 2H), 4.93 (s, 2H), 5.09 (t, 1H), 7.36-7.50 (m, 3H), 7.62-7.71 (m, 2H), 7.83-7.90 (m, 1H), 7.92-7.98 (m, 1H); MS: m/z 430.2 (M-OH)$^+$, 470.1 (MNa$^+$).

Compound 218

N-(3-Hydroxymethyl-benzo[b]thiophen-2-yl)-N-(4-fluoro-3-trifluoromethyl-benzyl)-4-carboxy-benzenesulfonamide. $^1$H-NMR (DMSO-d$_6$): δ 2.98 (br s, 1H), 4.29 (s, 2H), 4.93 (s, 2H), 7.34-7.48 (m, 3H), 7.59-7.68 (m, 2H), 7.82-7.87 (m, 1H), 7.91-8.00 (m, 1H) superimposed on 7.98 (d, 2H), 8.18 (d, 2H), 13.63 (br s, 1H); MS: m/z 522.2 (M-OH)$^+$, 562.2 (MNa$^+$).

Compound 219

N-(3,4-Difluoro-benzyl)-N-(3-hydroxymethyl-benzo[b]thiophen-2-yl)-ethanesulfonamide. $^1$H-NMR (DMSO-d$_6$): δ 1.33 (t, 3H), 3.46 (q, 2H), 4.54 (d, 2H), 4.84 (s, 2H), 5.09 (t, 1H), 7.10-7.17 (m, 1H), 7.29-7.42 (m, 4H), 7.83-7.89 (m, 1H), 7.93-7.98 (m, 1H); MS: m/z 380.1 (M-OH)$^+$, 420.1 (MNa$^+$).

Compound 220

N-(4-Fluoro-3-trifluoromethyl-benzyl)-N-[3-(1-hydroxyethyl)-benzo[b]thiophen-2-yl]-ethanesulfonamide. $^1$H-NMR (CDCl$_3$): δ 1.08 (br s, 3H), 1.50 (t, 3H), 3.27 (q, 2H), 4.42 (d, 1H), 4.94 (q, 1H), 5.29 (d, 1H), 7.13 (t, 1H), 7.35-7.40 (m, 2H), 7.49-7.54 (m, 2H), 7.58 (d, 1H), 7.74-7.77 (m, 1H), 8.12 (br d, 1H); MS: m/z 444.1 (M-OH)$^+$, 484.2 (MNa$^+$). Compound 220 (143 mg) was separated by chiral HPLC (Chiralpak TA) eluting with 100% MeOH to afford 54.4 mg of compound 534 and 48.0 mg of compound 535 as clear oils.

Compound 534

N-(4-Fluoro-3-trifluoromethyl-benzyl)-(S)—N-[3-(1-hydroxy-ethyl)-(benzo[b]thiophen-2-yl)-ethyl-sulfonamide. $^1$H-NMR (DMSO-d$_6$): δ 1.32-1.36 (t, 3H), 3.16-3.17 (d, 1H), 3.44-3.50 (m, 2H), 4.05-4.09 (m, 1H), 4.85-4.98 (m, 4H), 5.11 (s, 1H), 7.32-7.39 (m, 2H), 7.43-7.48 (m, 1H), 7.64-7.70 (m, 2H), 7.85-7.87 (m, 1H), 8.14-8.16 (m, 1H); MS: m/z 444.0 (M-OH)$^+$.

Compound 535

N-(4-Fluoro-3-trifluoromethyl-benzyl)-(R)—N-[3-(1-hydroxy-ethyl)-(benzo[b]thiophen-2-yl)-ethyl-sulfonamide. $^1$H-NMR (DMSO-d$_6$): δ 1.32-1.36 (t, 3H), 3.16-3.17 (d, 1H), 3.45-3.50 (m, 2H), 4.08 (m, 1H), 4.85-5.02 (m, 4H), 5.11 (s, 1H), 7.33-7.39 (m, 2H), 7.43-7.48 (m, 1H), 7.64-7.71 (m, 2H), 7.85-7.87 (m, 1H), 8.14-8.17 (m, 1H); MS: m/z 444.0 (M-OH)$^+$.

Compound 221

N-(3,4-Difluoro-benzyl)-N-[3-(1-hydroxy-ethyl)-benzo[b]thiophen-2-yl]-ethanesulfonamide. $^1$H-NMR (DMSO-d$_6$) δ: 1.02-1.55 (br s, 3H) superimposed on 1.34 (t, 3H), 3.46 (q, 2H), 4.78 (br s, 2H), 4.94-5.04 (m, 1H), 5.12 (s, 1H), 7.11-7.19 (m, 1H), 7.30-7.42 (m, 4H), 7.84-7.89 (m, 1H), 8.13-8.20 (m, 1H); MS: m/z 394.2 (M-OH)$^+$, 434.1 (MNa$^+$).

Compound 335

N-(4-Fluoro-3-trifluoromethyl-benzyl)-N-[3-(1-hydroxyethyl)-benzo[b]thiophen-2-yl]-4-carboxybenzenesulfonamide. $^1$H-NMR (CDCl$_3$): δ 1.15 (d, 3H), 5.03-5.47 (m, 3H), 7.18 (t, 1H), 7.32-7.70 (m, 5H), 7.87-8.00 (m, 2H), 8.12-8.20 (m, 1H), 8.27 (d, 2H); MS: m/z 536 (M-OH)$^+$, 576 (MNa$^+$).

Compound 821

N-(3-Fluoropropyl)-N-(3-hydroxymethyl-benzo[b]thiophen-2-yl)-benzenesulfonamide. $^1$H-NMR (CDCl$_3$): δ 1.95 (dtt, 2H), 2.96 (t, 1H), 3.51-3.91 (br, 2H), 4.52 (dt, 2H), 4.89 (br d, 2H), 7.41 (dt, 1H), 7.48 (dt, 1H), 7.55 (t, 2H), 7.68-7.72 (m, 2H), 7.75-7.77 (m, 2H), 8.02-8.04 (m, 1H); MS: m/z 402.0 (MNa$^+$).

Compound 834

2,5-Dibromo-N-(3,4-difluoro-benzyl)-N-(3-hydroxymethyl-benzo[b]thiophen-2-yl)-benzenesulfonamide. MS: m/z 624.2, 626.2, 628.2 (MNa$^+$).

Example 18

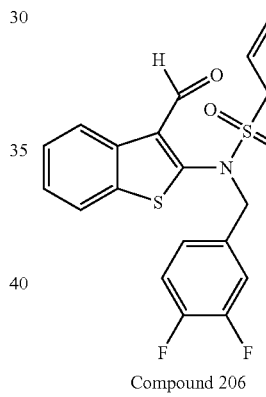

Compound 206

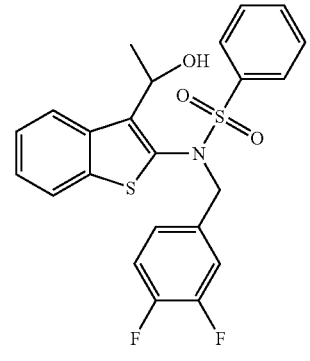

a) MeMgBr, THF.

Compound 222

Compound 222

N-(3,4-Difluoro-benzyl)-N-[3-(1-hydroxy-ethyl)-benzo[b]thiophen-2-yl]-benzenesulfonamide. A solution of methylmagnesium bromide in THF/toluene (1.4 M, 0.31 mL, 0.41 mmol) was added to a solution of compound 206 (120 mg, 0.270 mmol) in THF (3 mL) at 0° C. The resultant solution was stirred at ambient temperature for 3 h, then treated with a saturated aqueous solution of ammonium chloride. The product was extracted into ethyl acetate, washed with brine, dried over sodium sulfate, filtered, and the solvent evaporated in vacuo. The crude residue was purified by flash column chromatography (SiO$_2$), eluting with an ethyl acetate-heptane (10-40%) gradient to afford compound 222 as a colorless solid (103 mg, 83%). $^1$H-NMR (DMSO-d$_6$): δ 0.65-1.50 (br m, 3H), 4.53-4.73 (br s, 1h), 4.75-4.97 (br s, 2H), 5.08 (d, 1H, exchanges with D$_2$O), 7.01-7.12 (m, 1H), 7.19-7.40 (m, 4H), 7.68 (t, 2H), 7.78-7.82 (d of d, 2H), 7.90 (d, 2H), 8.12-8.16 (m, 1 h); MS: m/z 442 (M-OH)$^+$, 482.1 (MNa$^+$).

Following the procedure described above for example 18 and substituting the appropriate reagents, starting materials and purification methods known to those skilled in the art, the following compounds of the present invention were prepared.

Compound 223

N-(4-Fluoro-3-trifluoromethyl-benzyl)-N-[3-(1-hydroxyethyl)-benzo[b]thiophen-2-yl]-benzenesulfonamide.
$^1$H-NMR (CDCl$_3$): δ 1.10-1.28 (m, 3H), 2.64 (br s, 1H, exchanges with D$_2$O), 4.06-4.21 (m, 1H), 5.05-5.34 (m, 2H), 7.09 (t, 1H), 7.31-7.39 (m, 2H), 7.43-7.50 (m, 1H), 7.52-7.85 (m, 7H), 8.11-8.19 (m, 1H); MS: m/z 492.0 [(M-OH)$^+$], 532.0 (MNa$^+$).

Compound 224

N-(4-Fluoro-3-trifluoromethyl-benzyl)-N-[3-(1-hydroxyethyl)-benzo[b]thiophen-2-yl]-methanesulfonamide.
$^1$H-NMR (CDCl$_3$): δ 1.06-1.29 (br m, 3H), 2.53 (br s, 1H), 3.10 (s, 3H), 4.38 (br d, 1H), 4.98-5.30 (br m, 2H), 7.14 (t, 1H), 7.34-7.42 (m, 2H), 7.49-7.56 (m, 1H), 7.56-7.62 (m, 1H), 7.73-7.79 (m, 1H), 8.09-8.16 (m, 1H); MS: m/z 430 [(M-OH)$^+$], 470.2 (MNa$^+$).

Compound 225

N-(3,4-Difluoro-benzyl)-N-[3-(1-hydroxy-ethyl)-benzo[b]thiophen-2-yl]-methanesulfonamide. $^1$H-NMR (CDCl$_3$): δ 1.06-1.63 (br m, 3H), 2.52 (br s, 1H), 4.32 (br d, 1H), 3.08 (s, 3H), 4.95-5.24 (br m, 2H), 7.01-7.24 (m, 3H), 7.34-7.41 (m, 2H), 7.73-7.79 (m, 1H), 8.09-8.17 (m, 1H); MS: m/z 380.1 [(M-OH)$^+$], 420.1 (MNa$^+$).

Compound 316

N-(4-Fluoro-3-trifluoromethyl-benzyl)-N-[3-(1-hydroxy-1-methyl-ethyl)-benzo[b]thiophen-2-yl]-benzenesulfonamide. $^1$H-NMR (DMSO-d$_6$): δ 1.35 (s, 3H), 1.62 (s, 3H), 4.53-4.61 (m, 1H), 5.04-5.61 (m, 2H), 7.30-7.50 (m, 5H), 7.65-7.90 (m, 6H), 8.40 (s, 1H); MS: m/z 506.2 (M-OH)$^+$.

Compound 821

N-(3-Fluoropropyl)-N-[3-(1-hydroxyethyl)-benzo[b]thiophen-2-yl]-benzenesulfonamide. $^1$H-NMR (CDCl$_3$): δ 1.60-2.10 (m, 5H), 2.71 (br s, 1H), 3.12-3.20 (m, 1H), 4.02-4.15 (m, 1H), 4.34-4.56 (m, 2H), 5.38-5.46 (m, 1H), 7.26-7.36 m, 2H), 7.43-7.47 (m, 2H), 7.57-7.61 (m, 2H), 7.65-7.72 (m, 2H), 8.16-8.21 (m, 1H); MS: m/z 416.0 (MNa$^+$).

Compound 827

N-(4-Fluoro-3-methoxybenzyl)-N-[3-(1-hydroxyethyl)-benzo[b]thiophen-2-yl]-ethanesulfonamide. $^1$H-NMR (CDCl$_3$): δ 1.10 (br s, 3H), 1.52 (t, 3H), 2.65 (br s, 1H), 3.27 (br q, 2H), 3.86 (br s, 3H), 4.35-4.39 (br m, 1H), 4.95-5.00 (m, 1H), 5.21-5.25 (m, 1H), 6.73-6.77 (m, 1H), 6.95 (dd, 1H), 7.02 (dd, 1H), 7.35-7.42 (m, 2H), 7.75-7.78 (m, 1H), 8.12-8.14 (m, 1H); MS: m/z 446.4 (MNa$^+$).

Compound 835

N-(2-Fluoropyridin-4-ylmethyl)-N-[3-(1-hydroxyethyl)-benzo[b]thiophen-2-yl]-ethanesulfonamide. MS: m/z 395.2 (MH$^+$).

Example 19

Compound 203 a) MeMgBr, THF.

Compound 226

Compound 226

N-(3,4-Difluoro-benzyl)-N-[3-(1-hydroxy-1-methyl-ethyl)-benzo[b]thiophen-2-yl]-ethanesulfonamide. A solution of methylmagnesium bromide in THF/toluene (1.4 M, 0.21 mL, 0.29 mmol) was added to a solution of compound 203 (0.10 g, 0.24 mmol) in THF (2 mL), at 0° C. and the resultant solution was stirred at ambient temperature for 2 h. An additional portion of methylmagnesium bromide in THF/toluene (1.4 M, 0.21 mL, 0.29 mmol) was added, and the resultant solution stirred at rt for an additional 18 h, and the solution was quenched with a saturated aqueous solution of ammonium chloride. The product was extracted into ethyl acetate, washed with brine and dried over sodium sulfate, filtered, and the solvent evaporated in vacuo. The crude residue was purified by flash column chromatography (SiO$_2$), eluting with an ethyl acetate-heptane (10-30%) gradient to afford compound 226 as a colorless solid (66 mg, 65%). $^1$H-NMR (DMSO-d$_6$): δ 1.30 (t, 3H), 1.41 (s, 3H), 1.60 (s, 3H), 3.31-3.45 (m, 2H), 4.74 (d, 1H), 4.86 (d, 1H), 5.14 (s, 1H), 7.11-7.17 (m, 1H), 7.31-7.45 (m, 4H) 7.79-7.85 (m, 1H), 8.31-8.36 (m, 1H); MS: m/z 408.1 [(M-OH)⁺], 448.2 (MNa⁺).

Following the procedure described above for example 19 and substituting the appropriate reagents, starting materials and purification methods known to those skilled in the art, the following compounds of the present invention were prepared.

Compound 227

N-(4-Fluoro-3-trifluoromethyl-benzyl)-N-[3-(1-hydroxy-1-methyl-ethyl)-benzo[b]thiophen-2-yl]-ethanesulfonamide. ¹H-NMR (CDCl₃): δ 1.41 (t, 3H), 1.49 (s, 3H), 1.75 (s, 3H), 3.16-3.36 (m, 2H), 3.65 (s, 1H), 4.87 (d, 1H), 4.98 (d, 1H), 7.12 (t, 1H), 7.34-7.40 (m, 2H), 7.55-7.72 (m, 3H), 7.87-7.92 (m, 1H); MS: m/z 458.1 [(M-OH)⁺], 498.1 (MNa⁺).

Compound 776

N-(2-Fluoro-3-methoxy-benzyl)-N-[3-(1-hydroxy-1-methyl-ethyl)-benzo[b]thiophen-2-yl]-ethanesulfonamide. ¹H-NMR (CDCl₃): δ 1.45 (t, 3H), 1.61 (s, 3H), 1.76 (s, 3H), 3.25-3.40 (m, 2H), 3.54 (s, 1H), 3.82-3.89 (m, 3H), 4.90-5.14 (m, 2H), 6.82-6.99 (m, H), 7.28-7.38 (m, 2H), 7.60-7.68 (m, 1H), 7.88-7.97 (m, 1H); MS: m/z 420.1 (M-OH)⁺.

Compound 802

N-[3-(1-Hydroxy-1-methyl-ethyl)-benzo[b]thiophen-2-yl]-N-(2,4,5-trifluoro-3-methoxy-benzyl)-ethanesulfonamide. ¹H-NMR (CDCl₃): δ 1.45 (t, 3H), 1.59 (s, 3H), 1.79 (s, 3H), 3.31 (qd, 2H), 3.73 (s, 1H), 3.97 (s, 3H), 4.96 (s, 2H), 6.95 (ddd, 1H), 7.31-7.43 (m, 2H), 7.63-7.73 (m, 1H), 7.85-7.94 (m, 1H); MS: m/z 456.03 (M-OH)⁺.

Compound 830

N-(3-Fluoropropyl)-N-[3-(1-hydroxy-1-methyl-ethyl)-benzo[b]thiophen-2-yl]-benzenesulfonamide. ¹H-NMR (CDCl₃): δ 1.79 (s, 3H), 1.92 (s, 3H), 1.94-2.21 (m, 2H), 3.44-3.52 (m, 1H), 3.59 (s, 1H), 4.14-4.22 (m, 1H), 4.45-4.75 (m, 2H), 7.33-7.42 (m, 2H), 7.54 (t, 2H), 7.61-7.63 (m, 1H), 7.69 (t, 1H), 7.79-7.81 (m, 2H), 8.03 (d, 1H); MS: m/z 430.0 (MNa⁺).

Compound 836

N-(2-Fluoro-pyridin-4-ylmethyl)-N-[3-(1-hydroxy-1-methyl-ethyl)-benzo[b]thiophen-2-yl]-ethanesulfonamide. ¹H-NMR (CDCl₃): δ 1.43 (t, 3H), 1.57 (s, 3H), 1.80 (s, 3H), 3.22-3.38 (m, 2H), 3.77 (s, 1H), 4.90-4.95 (m, 2H), 7.05 (s, 1H), 7.26-7.28 (m, 1H), 7.35-7.40 (m, 2H), 7.67-7.71 (m, 1H), 7.87-7.90 (m, 1H), 8.16 (d, 1H). MS: m/z 409.4 (MH⁺).

Compound 838

N-(4-Fluoro-3-methoxybenzyl)-N-[3-(1-hydroxy-1-methyl-ethyl)-benzo[b]thiophen-2-yl]-ethanesulfonamide. ¹H-NMR (CDCl₃): δ 1.41 (t, 3H), 1.52 (s, 3H), 1.72 (s, 3H), 3.16-3.32 (m, 2H), 3.48 (s, 1H), 3.82 (s, 3H), 4.78 (d, 1H), 4.92 (d, 1H), 6.77-6.81 (m, 1H), 6.93 (dd, 1H), 7.09 (dd, 1H), 7.33-7.38 (m, 2H), 7.68-7.71 (m, 1H), 7.92-7.96 (m, 1H); MS: m/z 897.2 (M₂Na⁺).

Example 20

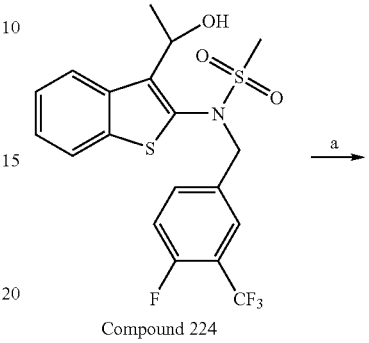

Compound 224

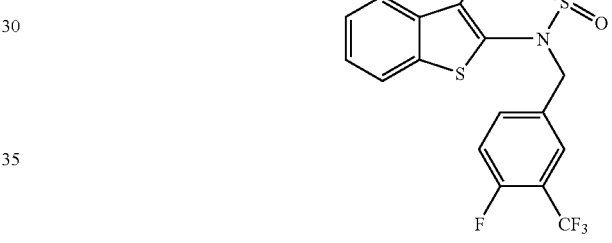

a) PCC, DCM.

Compound 228

Compound 228

N-(3-Acetyl-benzo[b]thiophen-2-yl)-N-(4-fluoro-3-trifluoromethyl-benzyl)-methanesulfonamide. Pyridinium chlorochromate (0.205 g, 0.955 mmol) was added to a solution of compound 224 (0.285 g, 0.637 mmol) in dichloromethane (10 mL) and stirred at rt for 18 h. The mixture was washed with water, absorbed onto silica gel, and the product isolated by flash column chromatography (SiO₂), eluting with an ethyl acetate-heptane (10-70%) gradient to afford compound 228 as a colorless solid (0.228 g, 80%). ¹H-NMR (DMSO-d₆): δ 2.31 (s, 3H), 3.34 (s, 3H), 5.03 (s, 2H), 7.43-7.52 (m, 3H), 7.70-7.78 (m, 2H), 7.97-8.03 (m, 2H); MS: m/z 446.1 (MH⁺).

Following the procedure described above for example 20 and substituting the appropriate reagents, starting materials and purification methods known to those skilled in the art, the following compounds of the present invention were prepared.

Compound 229

N-(3-Acetyl-benzo[b]thiophen-2-yl)-N-(3,4-difluoro-benzyl)-methanesulfonamide. ¹H-NMR (DMSO-d₆): δ 2.31

Example 21

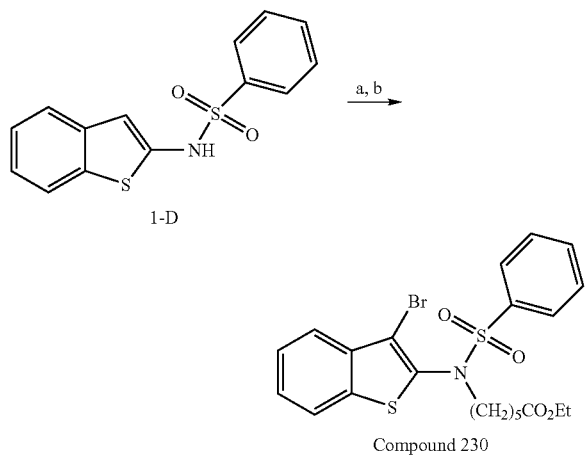

a) PPh₃, DEAD, 6-hydroxy-hexanoic acid ethyl ester, THF, toluene; b) NBS, DCE, AcOH.

Compound 230

N-(3-Bromo-benzo[b]thiophen-2-yl)-N-(5-carboethoxy-pentyl)benzenesulfonamide. To a stock solution of Ph₃P in THF (1.0 mL, 0.375 M, 0.375 mmol) was added THF (2 mL) and a solution of DEAD (0.17 mL, 40% in toluene, 0.38 mmol). After stirring for a few minutes, compound 1-D (0.072 g, 0.25 mmol) was added followed by 6-hydroxy-hexanoic acid ethyl ester (0.049 mL, 0.30 mmol), and the reaction mixture was stirred overnight. The reaction mixture was evaporated in vacuo and the crude residue was dissolved in 1:1 dichloroethane/acetic acid (2 mL), to which was added NBS (0.053 g, 0.30 mmol). After stirring for 6 h the reaction mixture was evaporated in vacuo and purified by reverse-phase chromatography (25-95% acetonitrile/water+0.1% TFA) to afford compound 230 as a waxy tan solid (0.090 g, 0.18 mmol). $^1$H-NMR (DMSO-$d_6$): δ 1.14 (t, 3H), 1.28-1.52 (m, 6H), 2.21 (t, 2H), 3.59 (br t, 2H), 4.01 (q, 2H), 7.50-7.59 (m, 2H), 7.66 (t, 2H), 7.75-7.82 (m, 2H), 7.85 (d, 2H), 7.96-8.03 (m, 1H); MS: m/z 510.1 (MH⁺).

Following the procedure described above for example 21 and substituting the appropriate reagents, starting materials and purification methods known to those skilled in the art, the following compounds of the present invention were prepared.

Compound 231

N-(3-Bromo-benzo[b]thiophen-2-yl)-N-(butyl)-benzenesulfonamide. $^1$H-NMR (DMSO-$d_6$): δ 0.81 (t, 3H), 1.28-1.45 (m, 4H), 3.60 (br t, 2H), 7.49-7.58 (m, 2H), 7.67 (t, 2H), 7.75-7.82 (m, 2H), 7.85 (dd, 2H), 7.97-8.02 (m, 1H); MS: m/z 424.1 (MH⁺).

Compound 232

N-(3-Bromo-benzo[b]thiophen-2-yl)-N-(cyclohexylmethyl)-benzenesulfonamide. $^1$H-NMR (DMSO-$d_6$): δ 0.87-1.00 (m, 2H), 1.01-1.16 (m, 3H), 1.23-1.35 (m, 1H), 1.52-1.67 (m, 3H), 1.77 (br s, 2H), 3.44 (br s, 2H), 7.49-7.58 (m, 2H), 7.65 (t, 2H), 7.73-7.85 (m, 4H), 7.96-8.02 (m, 1H); MS: m/z 464.0 (MH⁺).

Compound 233

N-(3-Bromo-benzo[b]thiophen-2-yl)-N-(phenethyl)-benzenesulfonamide. $^1$H-NMR (DMSO-$d_6$): δ 2.81 (t, 2H), 3.86 (t, 2H), 7.13-7.29 (m, 5H), 7.50-7.58 (m, 2H), 7.64 (t, 2H), 7.73-7.86 (m, 4H), 7.79-8.04 (m, 1H); MS: m/z 472.1 (MH⁺).

Compound 234

N-(3-Bromo-benzo[b]thiophen-2-yl)-N-(2-tert-butoxy-ethyl)-benzenesulfonamide. $^1$H-NMR (DMSO-$d_6$): δ 0.98 (s, 9H), 3.41 (t, 2H), 3.79 (t, 2H), 7.48-7.56 (m, 2H), 7.64 (t, 2H), 7.71-7.79 (m, 2H), 7.83-7.89 (m, 2H), 7.97-8.02 (m, 1H); MS: m/z 490.0 (MNa⁺).

Compound 235

(R)—N-(3-Bromo-benzo[b]thiophen-2-yl)-N-(2,3-dihydroxy-propyl)-benzenesulfonamide. MS: m/z 464.0 (MNa⁺).

Compound 236

N-(3-Bromo-benzo[b]thiophen-2-yl)-N-[2-(2-oxo-pyrrolidin-1-yl)-ethyl]-benzenesulfonamide. $^1$H-NMR (DMSO-$d_6$): δ 1.84 (p, 2H), 2.14 (t, 2H), 3.29-3.38 (m, 4H), 3.78 (br t, 2H), 7.49-7.58 (m, 2H), 7.66 (t, 2H), 7.72-7.87 (m, 4H), 7.98-8.04 (m, 1H); MS: m/z 479.0 (MH⁺).

Compound 237

N-(3-Bromo-benzo[b]thiophen-2-yl)-N-(2-morpholin-4-yl-ethyl)-benzenesulfonamide. $^1$H-NMR (DMSO-$d_6$): δ 3.07-3.20 (m, 2H), 3.32-3.42 (m, 2H), 3.44-3.56 (m, 2H), 3.61-3.78 (m, 2H), 3.88-3.99 (m, 2H), 4.03-4.18 (m, 2H), 7.53-7.60 (m, 2H), 7.69 (t, 2H), 7.76-7.86 (m, 2H), 7.90 (d, 2H), 8.01-8.06 (m, 1H), 10.75 (br s, 1H); MS: m/z 481.0 (MH⁺).

Compound 238

N-(3-Bromo-benzo[b]thiophen-2-yl)-N-(2-dimethylamino-ethyl)-benzenesulfonamide. $^1$H-NMR (DMSO-$d_6$): δ 2.85 (s, 6H), 3.33 (br t, 2H), 4.02 (br t, 2H), 7.53-7.60 (m, 2H), 7.69 (t, 2H), 7.75-7.80 (m, 1H), 7.83 (t, 1H), 7.89 (d, 2H), 8.01-8.07 (m, 1H), 9.59 (br s, 1H); MS: m/z 439.1 (MH⁺).

Compound 239

N-(3-Bromo-benzo[b]thiophen-2-yl)-N-(2-methanesulfonyl-ethyl)-benzenesulfonamide. $^1$H-NMR (DMSO-$d_6$): δ 3.06 (s, 3H), 3.43 (br t, 2H), 4.05 (br t, 2H), 7.51-7.60 (m, 2H), 7.69 (t, 2H), 7.75-7.85 (m, 2H), 7.88 (dd, 2H), 8.00-8.06 (m, 1H); MS: m/z 495.9 (MNa⁺).

Compound 240

N-(3-Bromo-benzo[b]thiophen-2-yl)-N-[2-(2-oxo-imidazolidin-1-yl)-ethyl]-benzenesulfonamide. $^1$H-NMR (DMSO-$d_6$): δ 3.13 (t, 2H), 3.19 (t, 2H), 3.31 (t, 2H), 3.76 (t, 2H), 6.36 (br s, 1H), 7.50-7.58 (m, 2H), 7.66 (t, 2H), 7.72-7.81 (m, 2H), 7.85 (dd, 2H), 7.97-8.04 (m, 1H); MS: m/z 480.0 (MH⁺).

Compound 241

(S)—N-(3-Bromo-benzo[b]thiophen-2-yl)-N-(1-methyl-pyrrolidin-2-ylmethyl)-benzenesulfonamide. MS: m/z 465.0 (MH$^+$).

Compound 242

N-(3-Bromo-benzo[b]thiophen-2-yl)-N-(2,2-difluoro-ethyl)-benzenesulfonamide. $^1$H-NMR (DMSO-d$_6$): δ 4.16 (dt, 2H), 6.23 (tt, 1H), 7.50-7.57 (m, 2H), 7.65 (t, 2H), 7.71-7.76 (m, 1H), 7.79 (t, 1H), 7.86 (d, 2H), 7.98-8.04 (m, 1H); MS: m/z 432.1 (MH$^+$).

Compound 243

N-(3-Bromo-benzo[b]thiophen-2-yl)-N-(carbomethoxymethyl)-benzenesulfonamide. $^1$H-NMR (DMSO-d$_6$): δ 3.62 (s, 3H), 4.63 (s, 2H), 7.48-7.56 (m, 2H), 7.62 (t, 2H), 7.68-7.72 (m, 1H), 7.75 (t, 1H), 7.84 (dd, 2H), 7.97-8.03 (m, 1H); MS: m/z 440.1 (MH$^+$).

Compound 244

N-(3-Bromo-benzo[b]thiophen-2-yl)-N-[2(S)-methyl-2-carbomethoxy-ethyl]-benzenesulfonamide. $^1$H-NMR (DMSO-d$_6$): δ 1.17 (d, 3H), 2.60 (q, 1H), 3.46 (s, 3H), 3.75 (br s, 1H), 3.86 (br s, 1H), 7.50-7.58 (m, 2H), 7.66 (t, 2H), 7.72-7.86 (m, 4H), 7.97-8.03 (m, 1H); MS: m/z 468.1 (MH$^+$).

Compound 245

N-(3-Bromo-benzo[b]thiophen-2-yl)-N-[2(R)-methyl-2-carbomethoxy-ethyl]-benzenesulfonamide. $^1$H-NMR (DMSO-d$_6$): δ 1.17 (d, 3H), 2.60 (q, 1H), 3.46 (s, 3H), 3.74 (br s, 1H), 3.86 (br s, 1H), 7.50-7.57 (m, 2H), 7.66 (t, 2H), 7.73-7.86 (m, 4H), 7.97-8.03 (m, 1H); MS: m/z 468.1 (MH$^+$).

Compound 246

N-(3-Bromo-benzo[b]thiophen-2-yl)-N-(3-phenyl-propyl)-benzenesulfonamide. $^1$H-NMR (DMSO-d$_6$): δ 1.71 (p, 2H), 2.65 (br t, 2H), 3.64 (br t, 2H), 7.09-7.19 (m, 3H), 7.23 (t, 2H), 7.50-7.59 (m, 2H), 7.67 (t, 2H), 7.75-7.86 (m, 4H), 7.97-8.03 (m, 1H); MS: m/z 486.1 (MH$^+$).

Compound 247

N-(3-Bromo-benzo[b]thiophen-2-yl)-N-(ethyl)-benzenesulfonamide. $^1$H-NMR (DMSO-d$_6$): δ 1.08 (t, 3H), 3.66 (q, 2H), 7.50-7.59 (m, 2H), 7.67 (t, 2H), 7.75-7.82 (m, 2H), 7.86 (dd, 2H), 7.98-8.03 (m, 1H); MS: m/z 396.0 (MH$^+$).

Compound 248

N-(3-Bromo-benzo[b]thiophen-2-yl)-N-(hexyl)-benzenesulfonamide. $^1$H-NMR (DMSO-d$_6$): δ 0.81 (t, 3H), 1.11-1.25 (m, 4H), 1.26-1.36 (m, 2H), 1.36-1.46 (m, 2H), 3.59 (br t, 2H), 7.50-7.58 (m, 2H), 7.67 (t, 2H), 7.75-7.82 (m, 2H), 7.85 (d, 2H), 7.97-8.03 (m, 1H); MS: m/z 452.1 (MH$^+$).

Compound 249

N-(Adamant-1-ylmethyl)-N-(3-bromo-benzo[b]thiophen-2-yl)-benzenesulfonamide. $^1$H-NMR (DMSO-d$_6$): δ 1.42 (d, 3H), 1.53 (d, 6H), 1.62 (d, 3H), 1.87 (s, 3H), 3.06 (d, 1H), 3.62 (d, 1H), 7.48-7.56 (m, 2H), 7.62 (t, 2H), 7.73-7.80 (m, 4H), 7.94-8.00 (m, 1H); MS: m/z 516.2 (MH$^+$).

Compound 250

N-(3-Bromo-benzo[b]thiophen-2-yl)-N-(3,3,3-trifluoro-propyl)-benzenesulfonamide. $^1$H-NMR (DMSO-d$_6$): δ 2.51-2.66 (m, 2H), 3.93 (t, 2H), 7.52-7.58 (m, 2H), 7.66 (t, 2H), 7.74-7.83 (m, 2H), 7.85 (dd, 2H), 8.00-8.04 (m, 1H); MS: m/z 464.0 (MH$^+$).

Compound 251

N-(3-Bromo-benzo[b]thiophen-2-yl)-N-(pent-3-ynyl)-benzenesulfonamide. $^1$H-NMR (DMSO-d$_6$): δ 1.59 (t, 3H), 2.33-2.40 (m, 2H), 3.74 (t, 2H), 7.50-7.57 (m, 2H), 7.66 (t, 2H), 7.74-7.81 (m, 2H), 7.86 (dd, 2H), 7.98-8.03 (m, 1H); MS: m/z 434.0 (MH$^+$).

Compound 252

N-(3-Bromo-benzo[b]thiophen-2-yl)-N-(2-methoxy-ethyl)-benzenesulfonamide. $^1$H-NMR (DMSO-d$_6$): δ 3.13 (s, 3H), 3.40 (t, 2H), 3.82 (t, 2H), 7.49-7.56 (m, 2H), 7.65 (t, 2H), 7.73-7.80 (m, 2H), 7.85 (d, 2H), 7.97-8.02 (m, 1H); MS: m/z 426.1 (MH$^+$).

Compound 253

N-(3-Bromo-benzo[b]thiophen-2-yl)-N-(4-oxo-pentyl)-benzenesulfonamide. $^1$H-NMR (DMSO-d$_6$): δ 1.59 (p, 2H), 2.04 (s, 3H), 2.58 (t, 2H), 3.57 (br t, 2H), 7.50-7.58 (m, 2H), 7.67 (t, 2H), 7.75-7.86 (m, 4H), 7.97-8.03 (m, 1H); MS: m/z 452.0 (MH$^+$).

Compound 254

N-(3-Bromo-benzo[b]thiophen-2-yl)-N-(dimethoxyphos-phinoyl-ethyl)-benzenesulfonamide. $^1$H-NMR (DMSO-d$_6$): δ 2.02-2.13 (m, 2H), 3.58 (s, 3H), 3.61 (s, 3H), 3.76-3.86 (m, 2H), 7.51-7.58 (m, 2H), 7.68 (t, 2H), 7.74-7.87 (m, 4H), 7.98-8.04 (m, 1H); MS: m/z 504.1 (MH$^+$).

Compound 255

N-(3-Bromo-benzo[b]thiophen-2-yl)-N-(cyclopropylm-ethyl)-benzenesulfonamide. $^1$H-NMR (DMSO-d$_6$): δ 0.06-0.11 (m, 2H), 0.35-0.41 (m, 2H), 0.83-0.95 (m, 1H), 3.52 (dd, 2H), 7.50-7.57 (m, 2H), 7.66 (t, 2H), 7.74-7.80 (m, 2H), 7.83-7.88 (m, 2H), 7.97-8.02 (m, 1H); MS: m/z 422.0 (MH$^+$).

Compound 256

N-(3-Bromo-benzo[b]thiophen-2-yl)-N-(2-piperidin-1-yl-ethyl)-benzenesulfonamide. $^1$H-NMR (DMSO-d$_6$): δ 1.27-1.38 (m, 1H), 1.50-1.71 (m, 3H), 1.75-1.84 (m, 2H), 2.88-3.01 (m, 2H), 3.26-3.34 (m, 2H), 3.46-3.55 (m, 2H), 3.99-4.08 (m, 2H), 7.53-7.59 (m, 2H), 7.69 (t, 2H), 7.76-7.80 (m, 1H), 7.83 (t, 1H), 7.88 (dd, 2H), 8.01-8.06 (m, 1H), 9.16 (br s, 1H); MS: m/z 479.0 (MH$^+$).

Compound 257

N-(3-Bromo-benzo[b]thiophen-2-yl)-N-[2-(2,5-dioxo-pyrrolidin-1-yl)-ethyl]-benzenesulfonamide. $^1$H-NMR (DMSO-d$_6$): δ 2.54 (s, 4H), 3.56 (t, 2H), 3.82 (t, 2H), 7.52-7.57 (m, 2H), 7.66 (t, 2H), 7.72-7.81 (m, 4H), 8.01-8.06 (m, 1H); MS: m/z 492.9 (MH$^+$).

Compound 258

(R)—N-(3-Bromo-benzo[b]thiophen-2-yl)-N-(5-oxo-pyrrolidin-2-ylmethyl)-benzenesulfonamide. $^1$H-NMR (DMSO-d$_6$): δ 1.87-2.00 (m, 1H), 2.02-2.25 (m, 3H), 3.45-3.75 (m, 3H), 7.46 (br s, 1H), 7.51-7.57 (m, 2H), 7.67 (t, 2H), 7.74-7.83 (m, 2H), 7.86 (d, 2H), 7.98-8.03 (m, 1H); MS: m/z 464.9 (MH$^+$).

Compound 259

(S)—N-(3-Bromo-benzo[b]thiophen-2-yl)-N-(5-oxo-pyrrolidin-2-ylmethyl)-benzenesulfonamide. $^1$H-NMR (DMSO-d$_6$): δ 1.85-1.99 (m, 1H), 2.02-2.25 (m, 3H), 3.44-3.76 (m, 3H), 4.76 (br s, 1H), 7.51-7.57 (m, 2H), 7.67 (t, 2H), 7.74-7.83 (m, 2H), 7.86 (d, 2H), 7.98-8.03 (m, 1H); MS: m/z 465.0 (MH$^+$).

Compound 260

N-(3-Bromo-benzo[b]thiophen-2-yl)-N-(2-methylsulfanyl-ethyl)-benzenesulfonamide. $^1$H-NMR (DMSO-d$_6$): δ 2.02 (s, 3H), 2.62 (t, 2H), 3.83 (t, 2H), 7.51-7.57 (m, 2H), 7.66 (t, 2H), 7.73-7.82 (m, 2H), 7.87 (d, 2H), 7.98-8.04 (m, 1H); MS: m/z 441.9 (MH$^+$).

Compound 261

N-(3-Bromo-benzo[b]thiophen-2-yl)-N-(butyl)-ethanesulfonamide. $^1$H-NMR (DMSO-d$_6$): δ 0.84 (t, 3H), 1.30-1.41 (m, 5H), 1.47 (p, 2H), 3.38 (q, 2H), 3.69 (t, 2H), 7.51-7.60 (m, 2H), 7.77-7.83 (m, 1H), 7.99-8.05 (m, 1H); MS: m/z 376.0 (MH$^+$).

Compound 262

N-(3-Bromo-benzo[b]thiophen-2-yl)-N-(cyclopropylmethyl)-ethanesulfonamide. $^1$H-NMR (DMSO-d$_6$): δ 0.11-0.17 (m, 2H), 0.40-0.46 (m, 2H), 0.92-1.03 (m, 1H), 1.34 (t, 3H), 3.38 (q, 2H), 3.57 (d, 2H), 7.51-7.59 (m, 2H), 7.77-7.83 (m, 1H), 8.00-8.05 (m, 1H); MS: m/z 374.0 (MH$^+$).

Compound 263

N-(3-Bromo-benzo[b]thiophen-2-yl)-N-(2,2-difluoro-ethyl)-ethanesulfonamide. $^1$H-NMR (DMSO-d$_6$): δ 1.35 (t, 3H), 3.47 (q, 2H), 4.17 (dt, 2H), 6.22 (tt, 1H), 7.52-7.59 (m, 2H), 7.77-7.83 (m, 1H), 8.01-8.06 (m, 1H); MS: m/z 384.1 (MH$^+$).

Compound 264

N-(3-Bromo-benzo[b]thiophen-2-yl)-N-(2-tert-butoxy-ethyl)-ethanesulfonamide. $^1$H-NMR (DMSO-d$_6$): δ 1.10 (s, 9H), 1.35 (t, 3H), 3.38-3.47 (m, 4H), 3.81 (t, 2H), 7.50-7.58 (m, 2H), 7.76-7.81 (m, 1H), 7.99-8.06 (m, 1H); MS: m/z 442.0 (MNa$^+$).

Compound 265

N-(3-Bromo-benzo[b]thiophen-2-yl)-N-(butyl)-N',N'-dimethylsulfamide. $^1$H-NMR (DMSO-d$_6$): δ 0.84 (t, 3H), 1.34 (h, 2H), 1.45 (p, 2H), 2.89 (s, 6H), 3.58 (t, 2H), 7.50-7.58 (m, 2H), 7.76-7.81 (m, 1H), 7.98-8.04 (m, 1H); MS: m/z 391.0 (MH$^+$).

Compound 266

N-(3-Bromo-benzo[b]thiophen-2-yl)-N-(cyclopropylmethyl)-N',N'-dimethylsulfamide. $^1$H-NMR (DMSO-d$_6$): δ 0.08-0.14 (m, 2H), 0.37-0.44 (m, 2H), 0.89-1.01 (m, 1H), 2.87 (s, 6H), 3.48 (d, 2H), 7.50-7.57 (m, 2H), 7.76-7.82 (m, 1H), 7.98-8.04 (m, 1H); MS: m/z 389.0 (MH$^+$).

Compound 267

N-(3-Bromo-benzo[b]thiophen-2-yl)-N-(2-tert-butoxy-ethyl)-N',N'-dimethylsulfamide. $^1$H-NMR (DMSO-d$_6$): δ 1.08 (s, 9H), 2.91 (s, 6H), 3.42 (t, 2H), 3.72 (t, 2H), 7.49-7.56 (m, 2H), 7.75-7.80 (m, 1H), 7.98-8.03 (m, 1H); MS: m/z 435.1 (MH$^+$).

Compound 268

N-(3-Bromo-benzo[b]thiophen-2-yl)-N-(2,2-difluoro-ethyl)-N',N'-dimethylsulfamide. $^1$H-NMR (DMSO-d$_6$): δ 2.89 (s, 6H), 4.07 (dt, 2H), 6.21 (tt, 1H), 7.51-7.58 (m, 2H), 7.76-7.82 (m, 1H), 8.00-8.06 (m, 1H); MS: m/z 399.0 (MH$^+$).

Compound 269

N-(3-Bromo-benzo[b]thiophen-2-yl)-N-(3,3,3-trifluoro-propyl)-N',N'-dimethylsulfamide. $^1$H-NMR (DMSO-d$_6$): δ 2.54-2.68 (m, 2H), 2.89 (s, 6H), 3.87 (t, 2H), 7.52-7.59 (m, 2H), 7.77-7.84 (m, 1H), 8.01-8.07 (m, 1H); MS: m/z 431.0 (MH$^+$).

Example 22

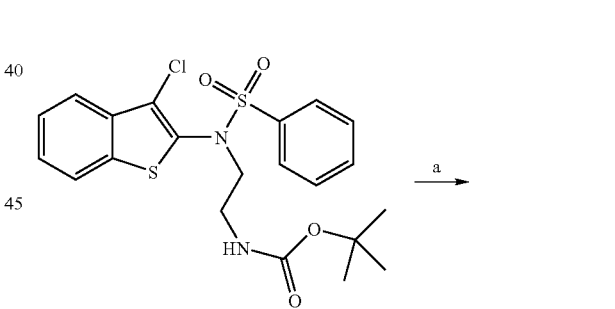

Compound 86

Compound 270 a) TFA, CH$_2$Cl$_2$.

Compound 270

N-(2-Amino-ethyl)-N-(3-chloro-benzo[b]thiophen-2-yl)-benzenesulfonamide. To compound 86 (0.035 g, 0.075 mmol), dissolved in CH₂Cl₂ (1 mL), was added trifluoroacetic acid (1 mL) and the reaction mixture was stirred at room temperature for 3 h. The reaction mixture was evaporated in vacuo, and the residue triturated with hexanes (2 mL) to afford compound 270 as a brown solid (0.031 g, 86%). $^1$H-NMR (CDCl₃): δ 3.17-3.28 (t, 2H), 3.58-3.62 (t, 2H), 7.34-7.55 (m, 4H), 7.58-7.70 (m, 5H); MS: m/z 367.1 (MH⁺).

Example 23

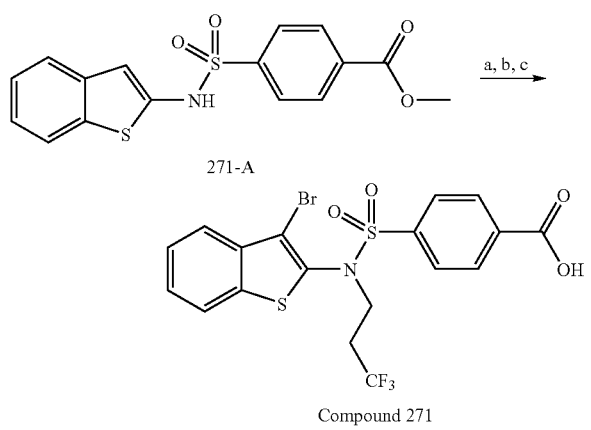

a) Ph₃P, DEAD, 3,3,3-trifluoropropan-1-ol, THF; b). aq NaOH; c) NBS, DCE, HOAc.

Compound 271

N-(3-Bromo-benzo[b]thiophen-2-yl)-N-(3,3,3-trifluoropropyl)-4-carboxy-benzenesulfonamide. To a solution of Ph₃P (0.888 g, 3.39 mmol) in THF (27 mL) was added a solution of DEAD (1.50 mL, 3.38 mmol). After stirring for 2 min, compound 271-A (0.782 g, 2.25 mmol) was added. To a portion (0.25 mmol of 271-A) of the aforementioned reaction mixture was added 3,3,3-trifluoropropan-1-ol (0.025 mL, 0.30 mmol). The reaction was stirred for 2 days, 1N NaOH (0.5 mL, 0.5 mmol) was added, and the reaction was evaporated in vacuo. The crude residue was re-dissolved in 1:1 dichloroethane/acetic acid (2 mL), and NBS (0.053 g, 0.30 mmol) was added. After stirring overnight an additional portion of NBS (0.041 g, 0.23 mmol) was added, and the reaction stirred for an additional 4 h. The reaction mixture was evaporated in vacuo and purified by reverse-phase chromatography (25-95% acetonitrile/water+0.1% TFA) to afford compound 271 as a tan powder (0.069 g, 0.14 mmol). $^1$H-NMR (DMSO-d₆): δ 2.54-2.68 (m, 2H), 3.98 (t, 2H), 7.52-7.59 (m, 2H), 7.73-7.79 (m, 1H), 7.97 (d, 2H), 8.00-8.06 (m, 1H), 8.16 (d, 2H), 13.60 (br s, 1H); MS: m/z 507.9 (MH⁺).

Following the procedure described above for example 23 and substituting the appropriate reagents, starting materials and purification methods known to those skilled in the art, the following compounds of the present invention were prepared.

Compound 272

N-(3-Bromo-benzo[b]thiophen-2-yl)-N-(butyl)-4-carboxy-benzenesulfonamide. $^1$H-NMR (DMSO-d₆): δ 0.83 (t, 3H), 1.30-1.47 (m, 4H), 3.65 (brt, 2H), 7.50-7.58 (m, 2H), 7.75-7.80 (m, 1H), 7.96 (d, 2H), 7.99-8.03 (m, 1H), 8.17 (d, 2H), 13.58 (s, 1H); MS: m/z 468.0 (MH⁺).

Compound 273

N-(3-Bromo-benzo[b]thiophen-2-yl)-N-(cyclopropylmethyl)-4-carboxy-benzenesulfonamide. $^1$H-NMR (DMSO-d₆): δ 0.06-0.15 (m, 2H), 0.36-0.43 (m, 2H), 0.85-0.97 (m, 1H), 3.56 (d, 2H), 7.50-7.58 (m, 2H), 7.74-7.80 (m, 1H), 7.97 (d, 2H), 7.99-8.03 (m, 1H), 8.16 (d, 2H), 13.58 (br s, 1H); MS: m/z 465.9 (MH⁺).

Compound 274

N-(3-Bromo-benzo[b]thiophen-2-yl)-N-(2-methoxyethyl)-4-carboxy-benzenesulfonamide. $^1$H-NMR (DMSO-d₆): δ 3.14 (s, 3H), 3.41 (t, 2H), 3.87 (t, 2H), 7.50-7.57 (m, 2H), 7.72-7.78 (m, 1H), 7.96 (d, 2H), 7.99-8.03 (m, 1H), 8.15 (d, 2H), 13.57 (s, 1H); MS: m/z 470.0 (MH⁺).

Compound 275

N-(3-Bromo-benzo[b]thiophen-2-yl)-N-(2-tert-butoxyethyl)-4-carboxy-benzenesulfonamide. $^1$H-NMR (DMSO-d₆): δ 0.98 (s, 9H), 3.42 (t, 2H), 3.84 (t, 2H), 7.49-7.56 (m, 2H), 7.71-7.78 (m, 1H), 7.95-8.03 (m, 3H), 8.15 (d, 2H), 13.56 (br s, 1H); MS: m/z 512.0 (MH⁺).

Compound 276

N-(3-Bromo-benzo[b]thiophen-2-yl)-N-(2,2-difluoroethyl)-4-carboxy-benzenesulfonamide. $^1$H-NMR (DMSO-d₆) δ: 4.19 (dt, 2H), 6.24 (tt, 1H), 7.51-7.58 (m, 2H), 7.71-7.77 (m, 1H), 7.98 (d, 2H), 8.01-8.05 (m, 1H), 8.15 (d, 2H), 13.61 (s, 1H); MS: m/z 475.9 (MH⁺).

Compound 277

N-(3-Bromo-benzo[b]thiophen-2-yl)-N-(2-morpholin-4-yl-ethyl)-4-carboxy-benzenesulfonamide. $^1$H-NMR (CD₃OD): δ 3.38 (br s, 4H), 3.46 (t, 2H), 3.91 (br s, 4H), 4.20 (t, 2H), 7.49-7.56 (m, 2H), 7.76-7.82 (m, 1H), 7.84-7.90 (m, 1H), 7.97 (d, 2H), 8.23 (d, 2H); MS: m/z 525.0 (MH⁺).

Compound 278

N-(3-Bromo-benzo[b]thiophen-2-yl)-N-(adamant-1-yl-methyl)-4-carboxy-benzenesulfonamide. $^1$H-NMR (DMSO-d₆): δ 1.40-1.48 (m, 3H), 1.50-1.58 (m, 6H), 1.58-1.66 (m, 3H), 1.88 (br s, 3H), 3.12 (d, 1H), 3.65 (d, 1H), 7.48-7.56 (m, 2H), 7.74-7.79 (m, 1H), 7.88 (d, 2H), 7.96-8.01 (m, 1H), 8.13 (d, 2H), 13.57 (s, 1H); MS: m/z 560.0 (MH⁺).

Compound 279

N-(3-Bromo-benzo[b]thiophen-2-yl)-N-(cyclohexylmethyl)-4-carboxy-benzenesulfonamide. $^1$H-NMR (DMSO-d₆): δ 0.89-1.02 (m, 2H), 1.02-1.19 (m, 3H), 1.25-1.38 (m, 1H), 1.52-1.60 (m, 1H), 1.60-1.94 (m, 4H), 3.49 (br s, 2H), 7.50-7.58 (m, 2H), 7.73-7.80 (m, 1H), 7.94 (d, 2H), 7.97-8.03 (m, 1H), 8.15 (d, 2H), 13.58 (br s, 1H); MS: m/z 508.0 (MH⁺).

Compound 390

N-(3-Bromo-benzo[b]thiophen-2-yl)-N-(ethyl)-4-carboxy-benzenesulfonamide. MS: m/z 438.1 (M-H)⁻.

Compound 391

N-(3-Bromo-benzo[b]thiophen-2-yl)-N-(propyl)-4-carboxy-benzenesulfonamide. MS: m/z 452.1 (M-H)⁻.

Compound 392

N-(3-Bromo-benzo[b]thiophen-2-yl)-N-(pentyl)-4-carboxy-benzenesulfonamide. ¹H-NMR (DMSO-$d_6$): δ 0.80 (t, 3H), 1.37-1.15 (m, 4H), 1.50-1.38 (m, 2H), 3.64 (t, 2H), 7.59-7.50 (m, 2H), 7.81-7.74 (m, 1H), 8.03-7.93 (m, 3H), 8.17 (d, 2H), 13.59 (s, 1H); MS: m/z 480.1 (M-H)⁻.

Compound 393

N-(3-Bromo-benzo[b]thiophen-2-yl)-N-(hexyl)-4-carboxy-benzenesulfonamide. ¹H-NMR (DMSO-$d_6$): δ 0.81 (t, 3H), 1.25-1.12 (m, 4H), 1.49-1.26 (m, 4H), 3.64 (t, 2H), 7.59-7.50 (m, 2H), 7.81-7.74 (m, 1H), 8.04-7.94 (m, 3H), 8.17 (d, 2H), 13.59 (s, 1H); MS: m/z 494 (M-H)⁻.

Compound 394

N-(3-Bromo-benzo[b]thiophen-2-yl)-N-(4,4,4-trifluoro-butyl)-4-carboxy-benzenesulfonamide. ¹H-NMR (DMSO-$d_6$): δ 1.76-1.64 (m, 2H), 2.48-2.34 (m, 2H), 3.74 (t, 2H), 7.60-7.51 (m, 2H), 7.82-7.76 (m, 1H), 7.97 (d, 2H), 8.06-8.00 (m, 1H), 8.18 (d, 2H), 13.62 (s, 1H); MS: m/z 520 (M-H)⁻.

Compound 395

N-(3-Bromo-benzo[b]thiophen-2-yl)-N-(5,5,5-trifluoro-pentyl)-4-carboxy-benzenesulfonamide. ¹H-NMR (DMSO-$d_6$): δ 1.65-1.46 (m, 4H), 2.34-2.14 (m, 2H), 3.68 (br t, 2H), 7.59-7.50 (m, 2H), 7.82-7.74 (m, 1H), 8.04-7.95 (m, 3H), 8.17 (d, 2H), 13.59 (s, 1H); MS: m/z 534.1 (M-H)⁻.

Compound 396

N-(3-Bromo-benzo[b]thiophen-2-yl)-N-(2-cyclopropyl-ethyl)-4-carboxy-benzenesulfonamide. ¹H-NMR (DMSO-$d_6$): δ 0.03-0.04 (m, 2H), 0.39-0.31 (m, 2H), 0.81-0.68 (m, 1H), 1.39 (q, 2H), 3.72 (t, 2H), 7.58-7.49 (m, 2H), 7.79-7.74 (m, 1H), 8.03-7.94 (m, 3H), 8.17 (d, 2H), 13.59 (s, 1H); MS: m/z 478.1 (M-H)⁻.

Compound 397

N-(3-Bromo-benzo[b]thiophen-2-yl)-N-(3-tert-butox-ypropyl)-4-carboxy-benzenesulfonamide. ¹H-NMR (DMSO-$d_6$): δ 1.06 (s, 9H), 1.60 (p, 2H), 3.32 (t, 2H), 3.71 (br t, 2H), 7.59-7.49 (m, 2H), 7.81-7.75 (m, 1H), 7.96 (d, 2H), 8.04-7.98 (m, 1H), 8.17 (d, 2H), 13.59 (br s, 1H); MS: m/z 524 (M-H)⁻.

Compound 437

N-(3-Bromo-benzo[b]thiophen-2-yl)-N-(cyclobutylm-ethyl)-4-carboxy-benzenesulfonamide. ¹H-NMR (DMSO-$d_6$): δ 1.71-1.60 (m, 2H), 1.83-1.72 (m, 2H), 1.95-1.85 (m, 2H), 2.40-2.31 (m, 1H), 3.68 (br s, 2H), 7.57-7.50 (m, 2H), 7.79-7.73 (m, 1H), 8.02-7.94 (m, 3H), 8.17 (d, 2H), 13.59 (s, 1H); MS: m/z 478 (M-H)⁻.

Compound 438

N-(3-Bromo-benzo[b]thiophen-2-yl)-N-(cyclopentylm-ethyl)-4-carboxy-benzenesulfonamide. ¹H-NMR (DMSO-$d_6$): δ 1.29 (br s, 2H), 1.49-1.39 (m, 2H), 1.60-1.50 (m, 2H), 1.73-1.60 (br m, 2H), 1.89 (p, 1H), 3.73-334 (br m, 2H), 7.58-7.50 (m, 2H), 7.79-7.74 (m, 1H), 7.95 (d, 2H), 8.02-7.97 (m, 1H), 8.16 (d, 2H), 13.59 (s, 1H); MS: m/z 492.2 (M-H)⁻.

Compound 439

RS,RS—N-(Bicyclo[2.2.1]heptan-2-ylmethyl)-N-(3-bromobenzo[b]thiophen-2-yl)-4-carboxy-benzenesulfonamide. ¹H-NMR (DMSO-$d_6$): δ 2.21-0.62 (m, 1H), 3.63 (br s, 2H), 7.58-7.49 (m, 2H), 7.80-7.74 (m, 1H), 8.02-7.93 (m, 3H), 8.18-8.13 (m, 2H), 13.59 (br s, 1H); MS: m/z 518.2 (M-H)⁻.

Compound 440

N-(3-Bromo-benzo[b]thiophen-2-yl)-N-((tetrahydro-2H-pyran-4-yl)methyl)-4-carboxy-benzenesulfonamide. ¹H-NMR (DMSO-$d_6$): δ 1.23 (m, 2H), 1.84-1.52 (m, 3H), 3.23-3.13 (m, 2H), 3.55 (br s, 2H), 3.85-3.76 (m, 2H), 7.58-7.50 (m, 2H), 7.80-7.74 (m, 1H), 7.95 (d, 2H), 8.03-7.98 (m, 1H), 8.16 (d, 2H), 13.59 (s, 1H); MS: m/z 508.1 (M-H)⁻.

Compound 441

N-(3-Bromo-benzo[b]thiophen-2-yl)-N-(2-(dimethylamino)ethyl)-4-carboxy-benzenesulfonamide. MS: m/z 481 (M-H)⁻.

Compound 452

N-(3-Bromo-benzo[b]thiophen-2-yl)-N-(isobutyl)-4-carboxy-benzenesulfonamide. ¹H-NMR (DMSO-$d_6$): δ 0.93 (d, 6H), 1.66-1.54 (m, 1H), 3.38 (br s, 2H), 7.57-7.50 (m, 2H), 7.79-7.74 (m, 1H), 7.94 (d, 2H), 8.02-7.97 (m, 1H), 8.15 (d, 2H), 13.58 (s, 1H); MS: m/z 466.1 (M-H)⁻.

Compound 453

N-(3-Bromo-benzo[b]thiophen-2-yl)-N-(2-(cyclohexy-loxy)ethyl)-4-carboxy-benzenesulfonamide. ¹H-NMR (DMSO-$d_6$): δ 1.16-0.97 (m, 5H), 1.42-1.33 (m, 1H), 1.56-1.47 (m, 2H), 1.66-1.57 (m, 2H), 3.14-3.07 (m, 1H), 3.46 (t, 2H), 3.86 (t, 2H), 7.56-7.49 (m, 2H), 7.78-7.73 (m, 1H), 8.03-7.96 (m, 3H), 8.15 (d, 2H), 13.55 (s, 1H); MS: m/z 536.2 (M-H)⁻.

Compound 454

N-(3-Bromo-benzo[b]thiophen-2-yl)-N-(3-methoxy-3-methylbutyl)-4-carboxy-benzenesulfonamide. ¹H-NMR (DMSO-$d_6$): δ 1.05 (s, 6H), 1.72-1.65 (m, 2H), 2.98 (s, 3H), 3.73-3.64 (m, 2H), 7.58-7.51 (m, 2H), 7.80-7.75 (m, 1H), 7.97 (d, 2H), 8.03-7.99 (m, 1H), 8.18 (d, 2H), 13.59 (s, 1H); MS: m/z 510.2 (M-H)⁻.

Compound 523

N-(3-Methyl-benzo[b]thiophen-2-yl)-N—(C-benzo[1,3]dioxol-5-yl-methyl)-4-carboxy-benzenesulfonamide. ¹H-NMR (DMSO-$d_6$) δ 1.82-2.03 (m, 3H), 4.67 (br s, 2H), 5.97 (s, 2H), 6.67 (dd, 1H), 6.78 (d, 2H), 7.25-7.44 (m, 2H), 7.61-7.73 (m, 1H), 7.73-7.88 (m, 1H), 7.98 (m, 2H), 8.17 (m, 2H), 13.60 (br s, 1H); MS: m/z 504.0 (MH⁺).

Compound 524

N-(3-Methyl-benzo[b]thiophen-2-yl)-N—(C-(2,2-difluoro-benzo[1,3]dioxol-5-yl)-methyl)-4-carboxy-benzenesulfonamide. $^1$H-NMR (DMSO-d$_6$) δ 1.95 (s, 3H), 4.81 (br s, 2H), 7.11 (dd, 1H), 7.22-7.48 (m, 4H), 7.57-7.73 (m, 1H), 7.76-7.92 (m, 1H), 7.99 (m, 2H), 8.18 (m, 2H), 13.61 (br s, 1H); MS: m/z 540.0 (MH$^+$).

Compound 525

N-(3-Methyl-benzo[b]thiophen-2-yl)-N-(3,4-dimethoxybenzyl)-4-carboxy-benzenesulfonamide. $^1$H-NMR (DMSO-d$_6$) δ 1.97 (s, 3H), 3.31 (s, 4H), 3.62-3.75 (m, 3H), 4.66 (br s, 1H), 6.61-6.74 (m, 1H), 6.74-6.89 (m, 2H), 7.25-7.44 (m, 2H), 7.61-7.72 (m, 1H), 7.72-7.85 (m, 1H), 7.99 (m, 2H), 8.18 (m, 2H), 13.59 (s, 1H); MS: m/z 520.0 (MH$^+$).

Example 24

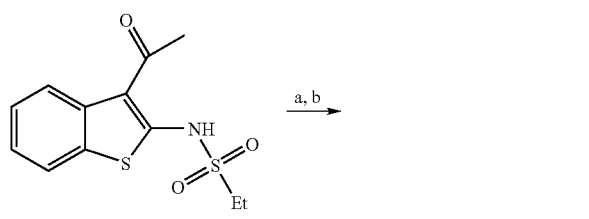

a) PPh$_3$, DEAD, n-BuOH, THF, toluene; b) NaBH$_4$, MeOH.

Compound 280

N-(Butyl)-N-[3-(1-hydroxy-ethyl)-benzo[b]thiophen-2-yl]-ethanesulfonamide. To a solution of Ph$_3$P (0.494 g, 1.88 mmol) in THF (15 mL) was added a solution of DEAD (0.84 mL, 1.89 mmol). After stirring for a few minutes, compound 205-B (0.354 g, 1.25 mmol) was added. To a portion of the aforementioned reaction mixture (0.25 mmol of 205-B) was added n-butan-1-ol (0.027 mL, 0.30 mmol) and the reaction stirred for 2 days. Methanol (0.50 mL) was added followed by NaBH$_4$ (0.019 g, 0.50 mmol) and the reaction was stirred for 3 h. The reaction mixture was evaporated in vacuo and purified by reverse-phase chromatography (25-95% acetonitrile/water+0.1% TFA) to afford compound 280 as a tan semi-solid (0.053 g, 0.16 mmol). $^1$H-NMR (DMSO-d$_6$): δ 0.86 (t, 3H), 1.22-1.37 (m, 5H), 1.44-1.57 (m, 5H), 3.26-3.41 (m, 2H), 3.46 (br s, 1H), 3.70 (br s, 1H), 5.09-5.18 (br d, 1H), 5.26 (br s, 1H), 7.37-7.43 (m, 2H), 7.87-7.93 (m, 1H), 8.22-8.27 (m, 1H); MS: m/z 364.0 (MH$^+$).

Following the procedure described above for example 24 and substituting the appropriate reagents, starting materials and purification methods known to those skilled in the art, the following compounds of the present invention were prepared.

Compound 281

N-(Cyclopropylmethyl)-N-(3-(1-hydroxyethyl)benzo[b]thiophen-2-yl)-ethanesulfonamide. $^1$H-NMR (DMSO-d$_6$): δ 0.15-0.26 (m, 2H), 0.48 (d, 2H), 1.01 (br s, 1H), 1.30 (t, 3H), 1.54 (d, 3H), 3.26-3.39 (m, 2H), 3.39-3.57 (m, 2H), 5.17-5.27 (m, 2H), 7.37-7.43 (m, 2H), 7.39-7.88 (m, 1H), 8.22-8.28 (m, 1H); MS: m/z 362.1 (MNa$^+$).

Compound 282

N-(3-(1-Hydroxyethyl)benzo[b]thiophen-2-yl)-N-(3,3,3-trifluoro-propyl)-ethanesulfonamide. $^1$H-NMR (DMSO-d$_6$): δ 1.30 (t, 3H), 1.54 (d, 3H), 2.57-2.73 (m, 2H), 3.32-3.53 (m, 2H), 3.67 (br s, 1H), 4.07 (br s, 1H), 5.10 (br s, 1H), 5.34 (br s, 1H), 7.40-7.46 (m, 2H), 7.91-7.96 (m, 1H), 8.23-8.29 (m, 1H); MS: m/z 404.1 (MNa$^+$).

Compound 283

N-(2-tert-Butoxyethyl)-N-(3-(1-hydroxyethyl)benzo[b]thiophen-2-yl)-ethanesulfonamide. $^1$H-NMR (DMSO-d$_6$): δ 1.16 (s, 9H), 1.31 (t, 3H), 1.53 (d, 3H), 3.36-3.52 (m, 4H), 3.73 (m, 2H), 5.11 (br s, 1H), 5.30 (br s, 1H), 7.37-7.44 (m, 2H), 7.88-7.93 (m, 1H), 8.21-8.26 (m, 1H); MS: m/z 408.1 (MNa$^+$).

Compound 284

N-(3-(1-Hydroxyethyl)benzo[b]thiophen-2-yl)-N-(2-morpholinoethyl)-ethanesulfonamide. MS: m/z 399.1 (MH$^+$).

Example 25

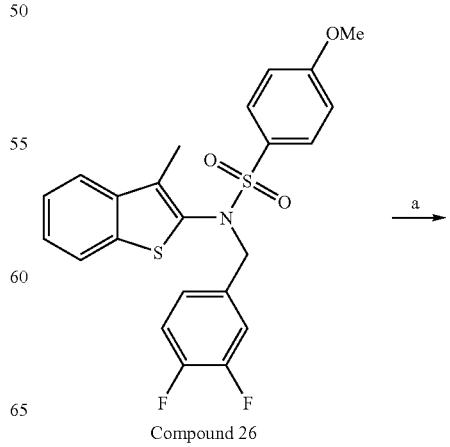

Compound 26

-continued

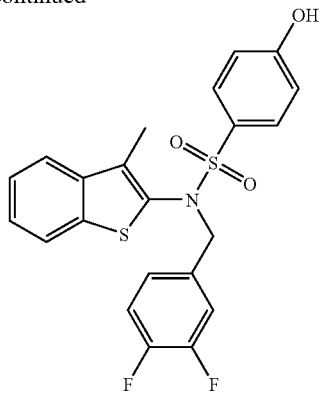

a) BBr₃, DCM.

Compound 285

Compound 285

N-(3,4-Difluoro-benzyl)-N-(3-methyl-benzo[b]thiophen-2-yl)-4-hydroxy-benzenesulfonamide. A solution of boron tribromide (1.0 M in dichloromethane, 1.57 mL, 1.57 mmol) was added to a solution of compound 26 (180 mg, 0.392 mmol) in dichloromethane (10 mL), at 0° C. The resultant solution was stirred at 0° C. for 1 h, then treated with 2 N hydrochloric acid. The organic layer was separated, dried over sodium sulfate, filtered, and the solvent evaporated in vacuo. The residue was purified by HPLC ($C_{18}$) eluting with an acetonitrile-water (0.1% TFA) gradient (40-90%). The resulting residue was further purified by flash column chromatography ($SiO_2$), eluting with an ethyl acetate-heptane gradient to afford compound 285 as a colorless solid (33 mg, 19%). $^1$H-NMR (DMSO-$d_6$): δ 1.98 (s, 3H), 4.67 (br s, 2H), 6.96 (d, 2H), 7.11-7.14 (m, 1H), 7.25-7.40 (m, 4H), 7.64-7.68 (m, 3H), 7.80-7.85 (m, 1H), 10.73 (br s, 1H); MS: m/z 446.1 (MH$^+$).

Following the procedure described above for example 25 and substituting the appropriate reagents, starting materials and purification methods known to those skilled in the art, the following compounds of the present invention were prepared.

Compound 286

N-(3,4-Difluoro-benzyl)-N-(3-methyl-benzo[b]thiophen-2-yl)-3-hydroxy-benzenesulfonamide. $^1$H-NMR (DMSO-$d_6$): δ 1.97 (s, 3H), 4.71 (s, 2H), 7.09-7.17 (m, 3H), 7.26-7.40 (m, 5H), 7.49 (t, 1H), 7.65-7.70 (m, 1H), 7.81-7.86 (m, 1H), 10.24 (br s, 1H); MS: m/z 446.1 (MH$^+$).

Compound 287

N-(Benzo[b]thiophen-2-yl)-N-(3-hydroxy-benzyl)-benzenesulfonamide. $^1$H-NMR (CDCl$_3$): δ 4.75 (s, 2H), 6.69-6.71 (m, 1H), 6.85-6.87 (m, 2H) 7.01 (s, 1H), 7.10-7.14 (t, 1H), 7.26-7.29 (m, 2H), 7.48-7.52 (m, 2H), 7.60-7.63 (m, 3H), 7.76-7.78 (d, 2H); MS: m/z 396.0 (MH$^+$).

Compound 288

N-(3-Chloro-benzo[b]thiophen-2-yl)-N-(4-fluoro-3-trifluoromethyl-benzyl)-3-hydroxy-benzenesulfonamide. $^1$H-NMR (DMSO-$d_6$): δ 4.83 (s, 2H), 6.97-6.99 (d, 2H), 7.40-7.51 (m, 3H), 7.63-7.73 (m, 5H), 7.96-7.98 (m, 1H), 10.76 (s, 1H); MS: m/z 516.0 (MH$^+$).

Compound 289

N-(3-Chloro-benzo[b]thiophen-2-yl)-N-(4-fluoro-3-trifluoromethyl-benzyl)-4-hydroxy-benzenesulfonamide. $^1$H-NMR (DMSO-$d_6$): δ 4.88 (s, 2H), 7.15-7.22 (m, 2H), 7.35-7.52 (m, 4H), 7.63-7.73 (m, 3H), 7.97-8.01 (m, 1H), 10.27 (s, 1H); MS: m/z 516.0 (MH$^+$).

Compound 290

N-(3-Bromo-benzo[b]thiophen-2-yl)-N-(4-fluoro-3-trifluoromethyl-benzyl)-4-hydroxy-benzenesulfonamide. $^1$H NMR (DMSO-$d_6$): δ 4.83 (s, 2H), 6.96-6.99 (d, 2H), 7.37-7.52 (m, 3H), 7.60-7.74 (m, 5H), 7.95-7.98 (m, 1H), 10.75 (s, 1H); MS: m/z 561.9 (MH$^+$), 584.0 (MNa$^+$).

Compound 291

N-(3-Bromo-benzo[b]thiophen-2-yl)-N-(4-fluoro-3-trifluoromethyl-benzyl)-3-hydroxy-benzenesulfonamide. $^1$H-NMR (DMSO-$d_6$): δ 4.87 (s, 2H), 7.14-7.23 (m, 2H), 7.35-7.52 (m, 5H), 7.59-7.71 (m, 3H), 7.96-7.99 (m, 1H), 10.26 (s, 1H); MS: m/z 561.9 (MH$^+$).

Compound 780

N-(3-Chloro-benzo[b]thiophen-2-yl)-N-(4-fluoro-3-trifluoromethyl-benzyl)-2-hydroxy-4-methanesulfonylamino-benzenesulfonamide. MS: m/z 608.89 (MH$^+$).

Example 26

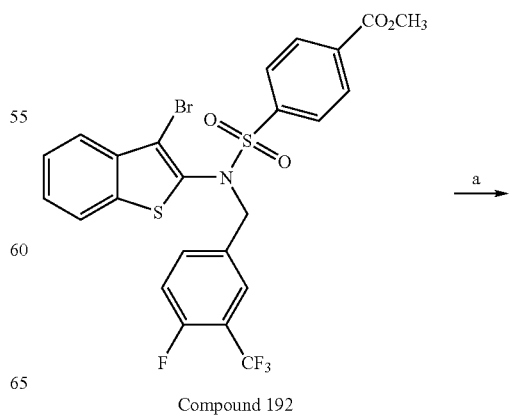

Compound 192

-continued

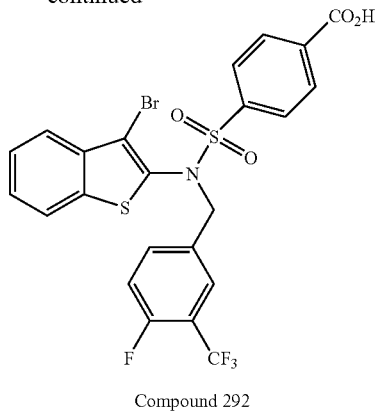

Compound 292 a) MeOH, 3N NaOH.

Compound 292

N-(3-Bromo-benzo[b]thiophen-2-yl)-N-(4-fluoro-3-trifluoromethyl-benzyl)-4-carboxy-benzenesulfonamide. To a solution of compound 192 (87.1 mg, 0.145 mmol) in MeOH (2 mL) was added 3N NaOH (73 μL, 0.218 mmol) and the reaction was refluxed for 18 h. The reaction was cooled to ambient temperature and the solvent evaporated under reduced pressure. The residue was dissolved in H$_2$O, cooled to 0° C., and acidified with 1N HCl. The precipitate was filtered, washed extensively with H$_2$O, and dried under vacuo to afford compound 292 as a white solid (0.063 g, 74%). $^1$H-NMR (CD$_3$OD): δ 4.94 (s, 2H), 7.16-7.21 (t, 1H), 7.42-7.46 (m, 2H), 7.52-7.56 (m, 1H), 7.61-7.63 (m, 1H), 7.68-7.70 (m, 1H), 7.75-7.77 (m, 1H), 7.99-8.01 (d, 2H), 8.22-8.25 (d, 2H); MS: m/z 588.0 (MH$^+$).

Following the procedure described above for example 26 and substituting the appropriate reagents, starting materials and purification methods known to those skilled in the art, the following compounds of the present invention were prepared:

Compound 293

N-(3-Bromo-benzo[b]thiophen-2-yl)-N-(4-fluoro-3-trifluoromethyl-benzyl)-3-carboxy-benzenesulfonamide. $^1$H-NMR (CD$_3$OD): δ 4.93 (s, 2H), 7.16-7.21 (t, 1H), 7.42-7.45 (m, 2H), 7.45-7.52 (m, 1H), 7.53-7.56 (m, 1H), 7.60-7.79 (m, 3H), 8.08-8.10 (d, 1H), 8.34-8.36 (d, 1H), 8.48 (s, 1H); MS: m/z 588.0 (MH$^+$).

Compound 294

N-(3-Chloro-benzo[b]thiophen-2-yl)-N-(4-fluoro-3-trifluoromethyl-benzyl)-4-carboxy-benzenesulfonamide. $^1$H-NMR (DMSO-d$_6$): δ 4.95 (s, 2H), 7.42-7.53 (m, 3H), 7.65-7.74 (m, 3H), 7.97-7.99 (m, 2H), 8.03-8.05 (m, 2H), 8.18-8.20 (m, 1H), 13.64 (s, 1H); MS: m/z 544.0 (MH$^+$).

Compound 295

N-(Benzo[b]thiophen-2-yl)-N-(4-fluoro-3-trifluoromethyl-benzyl)-3-carboxy-benzenesulfonamide. $^1$H-NMR (DMSO-d$_6$): δ 5.01 (s, 2H), 7.20 (s, 1H), 7.31-7.35 (m, 2H), 7.45-7.50 (t, 1H), 7.69-7.73 (m, 3H), 7.78-7.85 (m, 2H), 8.05-8.08 (m, 1H), 8.25-8.30 (m, 2H), 13.59 (s, 1H); MS: m/z 510.0 (MH$^+$).

Compound 296

N-(Benzo[b]thiophen-2-yl)-N-(4-fluoro-3-trifluoromethyl-benzyl)-4-carboxy-benzenesulfonamide. $^1$H-NMR (DMSO-d$_6$): δ 5.01 (s, 2H), 7.19 (s, 1H), 7.30-7.35 (m, 2H), 7.45-7.50 (t, 1H), 7.69-7.73 (m, 3H), 7.82-7.84 (m, 2H), 7.94-7.96 (m, 2H), 8.15-8.17 (m, 2H), 13.60 (s, 1H); MS: m/z 510.0 (MH$^+$).

Compound 297

N-(3-Chloro-benzo[b]thiophen-2-yl)-N-(4-fluoro-3-trifluoromethyl-benzyl)-2-carboxy-benzenesulfonamide. $^1$H-NMR (DMSO-d$_6$): δ 5.06 (s, 2H), 7.42-7.53 (m, 3H), 7.61-7.82 (m, 7H), 7.95-7.99 (m, 1H), 13.81 (s, 1H); MS: m/z 543.9 (MH$^+$).

Compound 298

N-(3-Bromo-benzo[b]thiophen-2-yl)-N-(4-fluoro-3-trifluoromethyl-benzyl)-2-carboxy-benzenesulfonamide. $^1$H-NMR (DMSO-d$_6$): δ 5.08 (s, 2H), 7.40-7.51 (m, 3H), 7.59-7.81 (m, 7H), 7.95-7.98 (m, 1H), 13.86 (s, 1H); MS: m/z 590.0 (MH$^+$).

Compound 299

N-(3-Formyl-benzo[b]thiophen-2-yl)-N-(4-fluoro-3-trifluoromethyl-benzyl)-4-carboxy-benzenesulfonamide. $^1$H-NMR (DMSO-d$_6$): δ 5.08 (br s, 2H), 7.42-7.54 (m, 3H), 7.69-7.80 (m, 2H), 7.97-8.04 (m, 3H), 8.20 (d, 2H), 8.42-8.47 (m, 1H), 9.85 (s, 1H), 13.70 (br s, 1H); MS: m/z 538.2 (MH$^+$).

Compound 305

N-(3-Methyl-benzo[b]thiophen-2-yl)-N-(4-fluoro-3-trifluoromethyl-benzyl)-3-carboxy-benzenesulfonamide. $^1$H-NMR (DMSO-d$_6$): δ 1.96 (s, 3H), 3.89 (s, 3H), 4.88 (br s, 2H), 7.38-7.42 (m, 3H), 7.69-7.72 (m, 1H), 7.84-7.88 (m, 2H), 8.16-8.18 (m, 1H), 8.27-8.28 (t, 1H), 8.33-8.35 (m, 1H).

Compound 306

N-(3-Methyl-benzo[b]thiophen-2-yl)-N-(4-fluoro-3-trifluoromethyl-benzyl)-4-carboxy-benzenesulfonamide. $^1$H-NMR (DMSO-d$_6$): δ 2.00 (s, 3H), 4.89 (s, 2H), 7.40-7.45 (m, 2H), 7.47-7.52 (m, 1H), 7.68-7.74 (m, 3H), 7.80-7.82 (d, 2H), 7.87-7.90 (m, 1H), 8.09-8.11 (d, 2H); MS: m/z 524.0 (MH$^+$).

Compound 307

N-(3-Chloro-benzo[b]thiophen-2-yl)-N-(4-fluoro-3-trifluoromethyl-benzyl)-3-carboxy-benzenesulfonamide. $^1$H-NMR (DMSO-d$_6$): δ 4.95 (s, 2H), 7.41-7.55 (m, 3H), 7.64-7.76 (m, 3H), 7.82-7.86 (m, 1H), 7.97-8.00 (m, 1H), 8.16-8.19 (m, 1H), 8.31-8.34 (m, 2H), 13.61 (s, 1H); MS: m/z 543.9 (MH$^+$).

Compound 318

N-(3-Acetyl-benzo[b]thiophen-2-yl)-N-(4-fluoro-3-trifluoromethyl-benzyl)-4-carboxy-benzenesulfonamide. $^1$H-NMR (DMSO-d$_6$): δ 2.38 (s, 3H), 5.00 (s, 2H), 7.42-7.50 (m, 3H), 7.68-7.75 (m, 2H), 7.93-7.97 (m, 3H), 8.01-8.05 (m, 1H), 8.18 (d, 2H); MS: m/z 552.2 (MH$^+$).

Compound 376

N-(6-Fluoro-3-methyl-benzo[b]thiophen-2-yl)-N-(4-fluoro-3-trifluoromethyl-benzyl)-3-carboxy-benzenesulfonamide. $^1$H-NMR (DMSO-d$_6$): δ 1.94 (s, 3H), 4.87 (s, 2H), 7.23-7.35 (m, 1H), 7.42-7.49 (m, 1H), 7.61-7.86 (m, 5H), 8.12-8.15 (d, 1H), 8.27-8.33 (m, 2H), 13.61 (s, 1H); MS: m/z 542.0 (MH$^+$).

Compound 423

N-(Butyl)-N-(3-methoxy-benzo[b]thiophen-2-yl)-4-carboxy-benzenesulfonamide. $^1$H-NMR (DMSO-d$_6$): δ 0.83 (t, 3H), 1.26-1.38 (m, 2H), 1.42-1.52 (m, 2H), 3.56 (t, 2H), 3.97 (s, 3H), 7.39-7.46 (m, 2H), 7.75-7.84 (m, 2H), 7.96 (d, 2H), 8.15 (d, 2H), 13.58 (br s, 1H); MS: m/z 420.1 (MH$^+$).

Compound 426

N-(6-Fluoro-3-methyl-benzo[b]thiophen-2-yl)-N-(4,4,4-trifluoro-butyl)-4-carboxy-benzenesulfonamide. $^1$H-NMR (DMSO-d$_6$): δ 1.65-1.69 (m, 2H), 2.21 (s, 3H), 2.30-2.40 (m, 2H), 3.66 (m, 2H), 7.30-7.35 (m, 1H), 7.81-7.84 (m, 2H), 7.85-7.91 (m, 2H), 8.15-8.17 (d, 1H), 13.62 (s, 1H); MS: m/z 476.0 (MH$^+$).

Compound 427

N-(6-Fluoro-3-methyl-benzo[b]thiophen-2-yl)-N-(4-fluoro-3-trifluoromethyl-benzyl)-4-carboxy-benzenesulfonamide. $^1$H-NMR (DMSO-d$_6$): δ 1.91 (s, 3H), 4.89 (s, 2H), 7.22-7.27 (m, 1H), 7.42-7.47 (t, 1H), 7.63-7.80 (m, 6H), 8.03-8.05 (d, 1H), 13.62 (s, 1H); MS: m/z 542.0 (MH$^+$).

Compound 432

N-(Butyl)-N-(1,1-dioxo-1H-benzo[b]thiophen-2-yl)-4-carboxy-benzenesulfonamide. $^1$H-NMR (DMSO-d$_6$): δ 0.87 (t, 3H), 1.16-1.41 (m, 2H), 1.49-1.67 (m, 2H), 3.72 (t, 2H), 7.56-7.76 (m, 4H), 7.80 (d, 1H), 8.01 (d, 2H), 8.12 (d, 2H); MS: m/z 422.1 (MH$^+$).

Compound 450

N-(6-Fluoro-3-methyl-benzo[b]thiophen-2-yl)-N-(butyl)-4-carboxy-benzenesulfonamide. $^1$H-NMR (DMSO-d$_6$): δ 0.828-0.864 (t, 3H), 1.28-1.44 (m, 4H), 2.22 (s, 3H), 3.51-3.56 (m, 2H), 7.28-7.33 (m, 1H), 7.79-7.82 (m, 2H), 7.83-7.90 (m, 2H), 8.13-8.15 (m, 2H), 13.62 (s, 1H); MS: m/z 422.1 (MH$^+$).

Compound 451

N-(Benzo[b]thiophen-2-yl)-N-(4,4,4-trifluoro-butyl)-4-carboxy-benzenesulfonamide. MS: m/z 444.0 (MH$^+$).

Compound 456

N-(Benzo[b]thiophen-2-yl)-N-(3,3,3-trifluoro-propyl)-4-carboxy-benzenesulfonamide. MS: m/z 430.0 (MH$^+$).

Compound 468

N-(Butyl)-N-(3-carbamoyl-benzo[b]thiophen-2-yl)-4-carboxy-benzenesulfonamide. MS: m/z 433.0 (MH$^+$).

Compound 469

N-(Butyl)-N-(3-dimethylcarbamoyl-benzo[b]thiophen-2-yl)-4-carboxy-benzenesulfonamide. MS: m/z 461.1 (MH$^+$).

Compound 486

N-(3-Methyl-benzo[b]thiophen-2-yl)-N-(benzyl)-4-carboxy-benzenesulfonamide. $^1$H-NMR (CDCl$_3$) δ 1.98 (s, 3H), 3.50 (br s, 2H), 7.24 (d, 5H), 7.29-7.40 (m, 2H), 7.52-7.61 (m, 1H), 7.61-7.70 (m, 1H), 7.95 (m, 2H), 8.26 (m, 2H); MS: m/z 452.5 (MH$^+$).

Compound 487

N-(3-Methyl-benzo[b]thiophen-2-yl)-N-(4-fluoro-benzyl)-4-carboxy-benzenesulfonamide. $^1$H-NMR (CDCl$_3$) δ 1.98 (s, 3H), 3.50 (br s, 2H), 6.83-7.00 (m, 2H), 7.20-7.25 (m, 2H), 7.30-7.40 (m, 2H), 7.55-7.69 (m, 2H), 7.94 (m, 2H), 8.26 (m, 2H); MS: m/z 456.0 (MH$^+$).

Compound 488

N-(3-Methyl-benzo[b]thiophen-2-yl)-N-(3,4-difluoro-benzyl)-4-carboxy-benzenesulfonamide. $^1$H-NMR (CDCl$_3$) δ 2.00-2.09 (m, 3H), 4.67 (br s, 1H), 6.91-7.08 (m, 2H), 7.08-7.21 (m, 1H), 7.31-7.43 (m, 2H), 7.53-7.71 (m, 2H), 7.94 (m, 2H), 8.27 (m, 2H); MS: m/z 474.0 (MH$^+$).

Compound 489

N-(3-Methyl-benzo[b]thiophen-2-yl)-N-(4-fluoro-3-chloro-benzyl)-4-carboxy-benzenesulfonamide. $^1$H-NMR (CDCl$_3$) δ 2.06 (s, 3H), 4.67 (br s, 1H), 7.00 (t, 1H), 7.12 (m, 1H), 7.30-7.44 (m, 3H), 7.54-7.71 (m, 2H), 7.94 (m, 2H), 8.27 (m, 2H); MS: m/z 490.0 (MH$^+$).

Compound 490

N-(3-Methyl-benzo[b]thiophen-2-yl)-N-(4-difluoromethoxy-benzyl)-4-carboxy-benzenesulfonamide. $^1$H-NMR (CDCl$_3$) δ 2.00 (s, 3H), 4.71 (br s, 2H), 6.2-6.7 (m, 1H), 6.99 (d, 2H), 7.24-7.26 (m, 2H), 7.30-7.44 (m, 2H), 7.52-7.74 (m, 2H), 7.95 (m, 2H), 8.27 (m, 2H); MS: m/z 504.0 (MH$^+$).

Compound 491

N-(3-Methyl-benzo[b]thiophen-2-yl)-N-(3-trifluoromethyl-benzyl)-4-carboxy-benzenesulfonamide. $^1$H-NMR (CDCl$_3$) δ 2.04 (s, 3H), 4.77 (br s, 2H), 7.31-7.40 (m, 3H), 7.44 (d, 1H), 7.51 (d, 1H), 7.54-7.62 (m, 2H), 7.62-7.68 (m, 1H), 7.95 (m, 2H), 8.28 (m, 2H); MS: m/z 506.1 (MH$^+$).

Compound 492

N-(3-Methyl-benzo[b]thiophen-2-yl)-N-(4-methylsulfone-benzyl)-4-carboxy-benzenesulfonamide. MS: m/z 538.0 (MH$^+$).

Compound 493

N-(3-Methyl-benzo[b]thiophen-2-yl)-N-(2,3,4,5,6-pentafluoro-benzyl)-4-carboxy-benzenesulfonamide. $^1$H-NMR (CDCl$_3$) δ 2.03-2.20 (m, 3H), 3.50 (br s, 2H), 7.31-7.45 (m, 2H), 7.58-7.73 (m, 2H), 7.95 (m, 2H), 8.26 (m, 2H); MS: m/z 528.0 (MH$^+$).

Compound 494

N-(3-Methyl-benzo[b]thiophen-2-yl)-N-(4-trifluoromethylsulfone-benzyl)-4-carboxy-benzenesulfonamide. $^1$H-NMR (CDCl$_3$) δ 2.00 (s, 3H), 3.50 (br s, 2H), 7.30-7.46 (m, 2H), 7.51-7.72 (m, 4H), 7.94 (dd, 4H), 8.15-8.33 (m, 2H); MS: m/z 570.0 (MH$^+$).

Compound 495

N-(3-Methyl-benzo[b]thiophen-2-yl)-N-(pyridin-3-ylmethyl)-4-carboxy-benzenesulfonamide. MS: m/z 439.0 (MH$^+$).

Compound 496

N-(3-Methyl-benzo[b]thiophen-2-yl)-N-(4-trifluoromethoxy-benzyl)-4-carboxy-benzenesulfonamide. $^1$H-NMR (CDCl$_3$) δ 1.98 (s, 3H), 4.70 (br s, 2H), 7.27-7.33 (m, 2H), 7.33-7.40 (m, 2H), 7.53-7.64 (m, 1H), 7.64-7.72 (m, 1H), 7.95 (m, 2H), 8.27 (m, 2H); MS: m/z 522.0 (MH$^+$). Anal. (C$_{24}$H$_{17}$F$_3$NO$_5$S$_2$·Na·H$_2$O) C, H, N, F, S, Na, KF.

Compound 497

N-(3-Methyl-benzo[b]thiophen-2-yl)-N-(3-fluoro-4-trifluoromethyl-benzyl)-4-carboxy-benzenesulfonamide. $^1$H-NMR (CDCl$_3$) δ 2.10 (s, 3H), 4.74 (br s, 2H), 7.12-7.23 (m, 2H), 7.32-7.44 (m, 2H), 7.50 (t, 1H), 7.57-7.72 (m, 2H), 7.94 (m, 2H), 8.28 (m, 2H); MS: m/z 524.0 (MH$^+$).

Compound 502

N-(3-Cyclopentyl-benzo[b]thiophen-2-yl)-N-(4-fluoro-3-trifluoromethyl-benzyl)-4-carboxy-benzenesulfonamide. $^1$H-NMR (DMSO-d$_6$): δ 0.69 (s, 1H), 1.25-1.63 (m, 3H), 1.63-1.91 (m, 4H), 3.05 (d, 1H), 4.35 (d, 1H), 5.24 (d, 1H), 7.13-7.48 (m, 3H), 7.49-7.70 (m, 3H), 7.75-7.87 (m, 1H), 7.97 (d, 2H), 8.13 (d, 2H); MS: m/z 578.1 (MH$^+$).

Compound 517

N-(3-Methyl-benzo[b]thiophen-2-yl)-N-(3,4,5-trifluorobenzyl)-4-carboxy-benzenesulfonamide. $^1$H-NMR (DMSO-d$_6$) δ 2.00 (s, 3H), 4.80 (br s, 2H), 7.25 (dd, 2H), 7.34-7.49 (m, 2H), 7.70 (dd, 1H), 7.78-7.91 (m, 1H), 7.99 (m, 2H), 8.18 (m, 2H), 13.62 (s, 1H); MS: m/z 492.5 (MH$^+$).

Compound 518

N-(3-Methyl-benzo[b]thiophen-2-yl)-N-(4-trifluoromethyl-benzyl)-4-carboxy-benzenesulfonamide. $^1$H-NMR (DMSO-d$_6$) δ 1.94 (s, 3H), 4.89 (br s, 2H), 7.24-7.46 (m, 2H), 7.52 (d, 2H), 7.61-7.78 (m, 3H), 7.83 (dd, 1H), 8.00 (m, 2H), 8.18 (m, 2H), 13.61 (s, 1H); MS: m/z 506.1 (MH$^+$).

Compound 519

N-(3-Methyl-benzo[b]thiophen-2-yl)-N-(2-fluoro-5-trifluoromethyl-benzyl)-4-carboxy-benzenesulfonamide. $^1$H-NMR (DMSO-d$_6$) δ 1.92 (s, 3H), 4.96 (br s, 2H), 7.33-7.44 (m, 3H), 7.58-7.64 (m, 1H), 7.64-7.70 (m, 1H), 7.76 (br. s., 1H), 7.80-7.92 (m, 1H), 8.00 (m, 2H), 8.19 (m, 2H), 13.62 (s, 1H); MS: m/z 524.0 (MH$^+$).

Compound 520

N-(3-Methyl-benzo[b]thiophen-2-yl)-N-(2,5-dichlorobenzyl)-4-carboxy-benzenesulfonamide. $^1$H-NMR (DMSO-d$_6$) δ 1.94 (s, 3H), 4.93 (br s, 2H), 7.22-7.51 (m, 5H), 7.62-7.75 (m, 1H), 7.75-7.91 (m, 1H), 7.99 (m, 2H), 8.18 (m, 2H), 13.62 (br s, 1H); MS: m/z 528.0 (MH$^+$).

Compound 521

N-(3-Methyl-benzo[b]thiophen-2-yl)-N-(4-chloro-3-fluoro-benzyl)-4-carboxy-benzenesulfonamide. $^1$H-NMR (DMSO-d$_6$) δ 1.97 (s, 3H), 4.80 (br s, 2H), 7.18 (dd, 1H), 7.30 (dd, 1H), 7.38 (dd, 2H), 7.54 (t, 1H), 7.62-7.76 (m, 1H), 7.76-7.91 (m, 1H), 7.99 (d, 2H), 8.18 (d, 2H), 13.62 (br s, 1H); MS: m/z 490.0 (MH$^+$).

Compound 522

N-(3-Methyl-benzo[b]thiophen-2-yl)-N-(4-fluoro-2-trifluoromethyl-benzyl)-4-carboxy-benzenesulfonamide. $^1$H-NMR (DMSO-d$_6$) δ 1.87 (s, 3H), 4.99 (br s, 2H), 7.23-7.45 (m, 2H), 7.45-7.75 (m, 4H), 7.75-7.93 (m, 1H), 7.99 (m, 2H), 8.18 (m, 2H), 13.63 (br s, 1H); MS: m/z 524.0 (MH$^+$).

Compound 526

N-(3-Methyl-benzo[b]thiophen-2-yl)-N-(4-trifluoromethylsulfanyl-benzyl)-4-carboxy-benzenesulfonamide. $^1$H-NMR (DMSO-d$_6$) δ 1.90 (s, 3H), 4.85 (br s, 2H), 7.32-7.46 (m, 4H), 7.65 (d, 3H), 7.73-7.89 (m, 1H), 7.99 (m, 2H), 8.18 (m, 2H), 13.60 (s, 1H); MS: m/z 538.0 (MH$^+$).

Compound 527

N-(3-Methyl-benzo[b]thiophen-2-yl)-N-(4-fluoro-3-trifluoromethyl-benzyl)-4-carboxy-thien-2-ylsulfonamide. $^1$H-NMR (DMSO-d$_6$) δ 2.02 (s, 4H), 4.93 (br s, 2H), 7.35-7.51 (m, 4H), 7.58-7.79 (m, 4H), 7.79-7.95 (m, 1H), 8.04 (d, 1H), 8.74 (d, 1H), 13.36 (s, 1H); MS: m/z 530.0 (MH$^+$).

Compound 528

N-(3-Methyl-benzo[b]thiophen-2-yl)-N-(4-fluoro-3-trifluoromethyl-benzyl)-(5-carboxy-3-methyl-thien-2-yl)-sulfonamide. $^1$H-NMR (DMSO-d$_6$) δ 2.01 (s, 3H), 2.19 (s, 3H), 4.94 (br s, 2H), 7.28-7.54 (m, 3H), 7.54-7.80 (m, 4H), 7.80-8.03 (m, 1H), 13.91 (br s, 1H); MS: m/z 544.0 (MH$^+$).

Compound 529

N-(3-Methyl-benzo[b]thiophen-2-yl)-N-(4-fluoro-3-trifluoromethyl-benzyl)-5-carboxy-furan-2-yl-sulfonamide. MS: m/z 514.0 (MH$^+$).

Compound 556

N-(Benzo[b]thiophen-2-yl)-N-(butyl)-4-carboxy-benzenesulfonamide. MS m/z 390.0 (MH$^+$).

Compound 557

N-(3-Methyl-6-trifluoromethyl-benzo[b]thiophen-2-yl)-N-(4-fluoro-3-trifluoromethyl-benzyl)-4-carboxy-benzenesulfonamide. $^1$H-NMR (CD$_3$OD): δ 2.03 (s, 3H), 7.19-7.24 (t, 1H), 7.53-7.55 (m, 3H), 7.80-7.82 (d, 1H), 7.95-7.98 (d, 2H), 8.09 (s, 1H), 8.23-8.25 (d, 2H).

Compound 558

N-(3-Methyl-6-trifluoromethyl-benzo[b]thiophen-2-yl)-N-(butyl)-4-carboxy-benzenesulfonamide. MS: m/z 472.0 (MH$^+$).

Compound 566

N-(4-Fluoro-3-trifluoromethyl-benzyl)-N-(3-isopropyl-benzo[b]thiophen-2-yl)-4-carboxy-benzenesulfonamide. $^1$H-NMR (CDCl$_3$): δ 0.78 (d, 3H), 1.43 (d, 3H), 3.28 (q, 1H), 4.17 (d, 1H), 5.24 (d, 1H), 7.07 (t, 1H), 7.27-7.38 (m, 2H), 7.38-7.46 (m, 1H), 7.59 (dd, 1H), 7.62-7.71 (m, 1H), 7.85-7.93 (m, 1H), 7.98 (d, 2H), 8.30 (d, 2H).

Compound 567

N-(2-Cyclopropyl-ethyl)-N-(3-isopropyl-benzo[b]thiophen-2-yl)-4-carboxy-benzenesulfonamide. $^1$H-NMR (CDCl$_3$): δ −0.08-0.07 (m, 2H), 0.37-0.49 (m, 2H), 0.57-0.74 (m, 1H), 1.19 (m, 1H), 1.42 (d, 3H), 1.52 (d, 3H), 1.57-1.72 (m, 1H), 3.18-3.32 (m, 1H), 3.55-3.69 (m, 1H), 3.87-4.08 (m, 1H), 7.29-7.40 (m, 2H), 7.63-7.71 (m, 1H), 7.95 (d, 2H), 7.98-8.06 (m, 1H), 8.26 (d, 2H); MS: m/z 444.1 (MH$^+$).

Compound 568

N-(5,5,5-Trifluoro-pentyl)-N-(3-isopropyl-benzo[b]thiophen-2-yl)-4-carboxy-benzenesulfonamide. $^1$H-NMR (CDCl$_3$): δ 1.43 (d, 3H), 1.53 (d, 3H), 1.53-1.78 (m, 4H), 1.94-2.19 (m, 2H), 3.14-3.30 (m, 1H), 3.62 (q, 1H), 3.80-4.00 (m, 1H), 7.31-7.42 (m, 2H), 7.64-7.73 (m, 1H), 7.92 (d, 2H), 7.98-8.08 (m, 1H), 8.26 (d, 2H); MS: m/z 500.1 (MH$^+$).

Compound 675

N-(3-Cyclopropyl-benzo[b]thiophen-2-yl)-N-(4-fluoro-3-trifluoromethyl-benzyl)-4-carboxy-benzenesulfonamide. $^1$H-NMR (DMSO-d$_6$): δ 0.59 (m, 4H), 1.38-1.63 (m, 1H), 4.24-5.37 (m, 2H), 7.36 (d, 3H), 7.54-7.67 (m, 2H), 7.70-7.90 (m, 4H), 8.04 (d, 2H); MS: m/z 550.0 (MH$^+$).

Compound 698

N-(3-Cyclobutyl-benzo[b]thiophen-2-yl)-N-(4-fluoro-3-trifluoromethyl-benzyl)-4-carboxy-benzenesulfonamide. $^1$H-NMR (DMSO-d$_6$): δ 1.59-2.44 (m, 6H), 3.67 (q, 1H), 4.44 (d, 1H), 5.26 (d, 1H), 7.26-7.54 (m, 3H), 7.54-7.67 (m, 2H), 7.80-7.93 (m, 1H), 7.95-8.11 (m, 3H), 8.19 (d, 2H), 13.64 (s, 1H); MS: m/z 562 (M-H)$^-$.

Compound 755

N-(3-Cyclopropyl-benzo[b]thiophen-2-yl)-N-(4-trifluoromethoxyl-benzyl)-4-carboxy-benzenesulfonamide. $^1$H-NMR (DMSO-d$_6$): δ 0.30-0.80 (m, 4H), 1.42-1.66 (m, 1H), 4.26-5.32 (m., 2H), 7.22-7.44 (m, 6H), 7.69-7.79 (m, 1H), 7.80-7.89 (m, 1H), 8.02 (d, 2H), 8.12-8.27 (m, 2H), 13.62 (s, 1H), MS: m/z 546.2 (M-H)$^-$.

Compound 756

N-(3-Cyclobutyl-benzo[b]thiophen-2-yl)-N-(4-trifluoromethoxy-benzyl)-4-carboxy-benzenesulfonamide. $^1$H-NMR (DMSO-d$_6$): δ 1.57-2.38 (m, 6H), 3.66 (t, 1H), 4.29 (d, 1H), 5.26 (d, 1H), 7.29-7.42 (m, 6H), 7.82-7.90 (m, 1H), 7.95-8.06 (m, 3H), 8.18 (d, 2H), 13.63 (s., 1H); MS: m/z 560.1 (M-H)$^-$.

Compound 765

N-(4-Fluoro-3-trifluoromethyl-benzyl)-N-(3-methyl-benzo[b]thiophen-2-yl)-3-carboxy-propanesulfonamide. $^1$H-NMR (CDCl$_3$): δ 2.05 (s, 3H), 2.24 (q, 2H), 2.63 (t, 2H), 3.26-3.40 (m, 2H), 4.82 (s, 2H), 7.09 (t, 1H), 7.34-7.42 (m, 2H), 7.44-7.51 (m, 1H), 7.53-7.64 (m, 2H), 7.69-7.77 (m, 1H); MS: m/z 490.0 (MH$^+$).

Compound 792

N-(4-Fluoro-3-trifluoromethyl-benzyl)-N-(3-methyl-benzo[b]thiophen-2-yl)-carboxy-methanesulfonamide. $^1$H-NMR (DMSO-d$_6$): δ 2.00 (s, 3H), 4.54 (s, 2H), 4.90 (s, 2H), 7.32-7.52 (m, 3H), 7.57-7.75 (m, 3H), 7.86-7.96 (m, 1H), 13.64 (s, 1H); MS: m/z 462.0 (MH$^+$).

Example 27

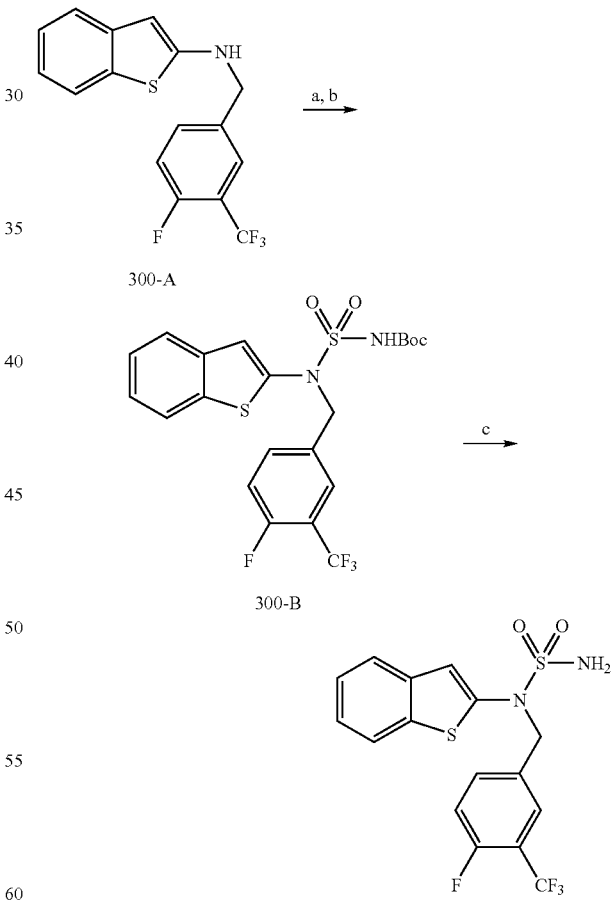

a) Chlorosulfonyl isocyanate, CH$_2$Cl$_2$, t-BuOH;
b) CH$_2$Cl$_2$, pyridine;
c) 4H HCl.

Compound 300-A was prepared from compound 1-C, following the procedure used to prepare compound 127-D.

N-(4-Fluoro-3-trifluorobenzyl)-N-(benzo[b]thiophen-2-yl)-[N'-tert-butyloxycarbonyl]-sulfonamide (300-B). To a solution of chlorosulfonyl isocyanate (200 mg, 1.41 mmol) in CH$_2$Cl$_2$ (2 mL) was added tert-butanol (0.135 mL, 1.41 mmol) and the reaction was stirred at ambient temperature for 2 h. This solution was added drop-wise to a cooled (0° C.) solution of compound 300-A (485 mg; 1.34 mmol) in CH$_2$Cl$_2$ (2.5 mL) and pyridine (2.5 mL). The reaction mixture was stirred at ambient temperature for 18 h, diluted with EtOAc, washed with 1N HCl (2×), H$_2$O, brine, dried over Na$_2$SO$_4$, filtered, and the solvent was evaporated under reduced pressure. The crude residue was purified by flash column chromatography (SiO$_2$) eluting with a heptane-EtOAc gradient to afford compound 300-B as a yellow solid (0.389 g, 58%). $^1$H-NMR (DMSO-d$_6$): δ 1.48 (s, 9H), 5.13 (s, 2H), 7.30 (s, 1H), 7.34-7.37 (m, 2H), 7.47-7.52 (m, 1H), 7.70-7.79 (m, 3H), 7.88-7.91 (m, 1H), 11.77 (s, 1H).

Compound 300

N-(Benzo[b]thiophen-2-yl)-N-(4-fluoro-3-trifluoromethyl-benzyl)-sulfamide. To compound 300-B (167 mg, 0.331 mmol) was added solution of 1N HCl in dioxane (6 mL) and the reaction was stirred at ambient temperature for 18 h. The reaction mixture was evaporated under reduced pressure, the residue dried under vacuo, and purified by flash column chromatography (SiO$_2$) eluting with a heptane-EtOAc gradient to afford compound 300 as a pink oil (0.097 g, 73%). $^1$H-NMR (DMSO-d$_6$): δ 4.88 (s, 2H), 7.22 (s, 1H), 7.28-7.33 (m, 2H), 7.44-7.49 (m, 1H), 7.69-7.83 (m, 6H); MS: m/z 405.0 (MH$^+$).

Example 28

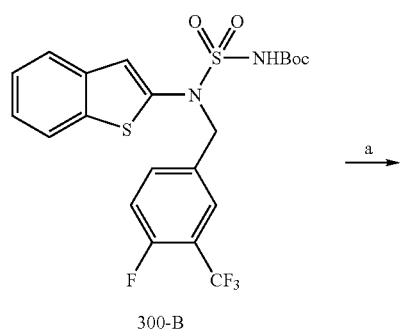

300-B a →

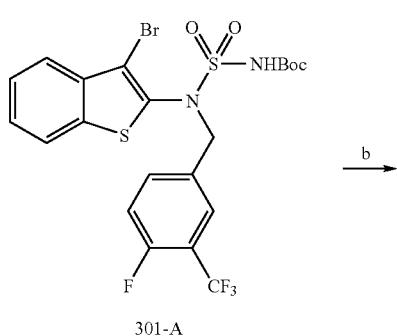

301-A b →

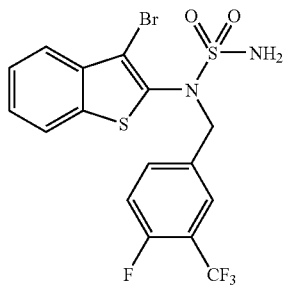

Compound 301 a) DCE, NBS;
b) 4N HCl.

N-(4-Fluoro-3-trifluorobenzyl)-N-(3-bromo-benzo[b]thiophen-2-yl)-[N'-tert-butyloxycarbonyl]-sulfonamide (301-A). To a solution compound 300-B (306 mg; 0.606 mmol) in DCE (3 mL) was added N-bromosuccinimide (119 mg, 0.666 mmol) and the reaction was allowed to stir at ambient temperature for 2 h. The resultant solution was evaporated under reduced pressure and the crude residue purified by flash column chromatography (SiO$_2$) eluting with a heptane-EtOAc gradient to afford compound 301-A as a beige solid (0.254 mg, 72%). $^1$H-NMR (DMSO-d$_6$): δ 1.51 (s, 9H), 5.06 (s, 1H), 7.41-7.46 (t, 1H), 7.49-7.54 (m, 2H), 7.62-7.66 (m, 1H), 7.70-7.77 (m, 2H), 8.00-8.03 (m, 1H), 11.81 (s, 1H).

Compound 301

N-(3-Bromo-benzo[b]thiophen-2-yl)-N (4-fluoro-3-trifluoromethyl-benzyl)-sulfamide. To compound 301-B (200 mg, 0.342 mmol) was added solution of 1N HCl in dioxane (6 mL) and the reaction was stirred at ambient temperature for 18 h. The reaction mixture was evaporated under reduced pressure, the residue dried under vacuo, and purified by flash column chromatography (SiO$_2$) eluting with a heptane-EtOAc gradient to afford compound 301 as a light purple oil (0.117 g, 71%). $^1$H-NMR (DMSO-d$_6$): δ 3.16-3.17 (d, 2H), 4.80 (s, 2H), 7.39-7.49 (m, 3H), 7.67-7.82 (m, 3H), 7.96-7.98 (m, 1H); MS: m/z 483 (MH$^+$).

Following the procedure described above for example 28 and substituting the appropriate reagents, starting materials and purification methods known to those skilled in the art, the following compounds of the present invention were prepared:

Compound 302

N-(3-Chloro-benzo[b]thiophen-2-yl)-N-(4-fluoro-3-trifluoromethyl-benzyl)-sulfamide. $^1$H-NMR (DMSO-d$_6$): δ

3.33 (s, 2H), 4.81 (s, 2H), 7.44-7.47 (t, 1H), 7.40-7.49 (m, 3H), 7.69-7.72 (m, 2H), 7.78-7.82 (m, 3H), 7.96-7.98 (m, 1H); MS: m/z 439.0 (MH⁺).

Example 29

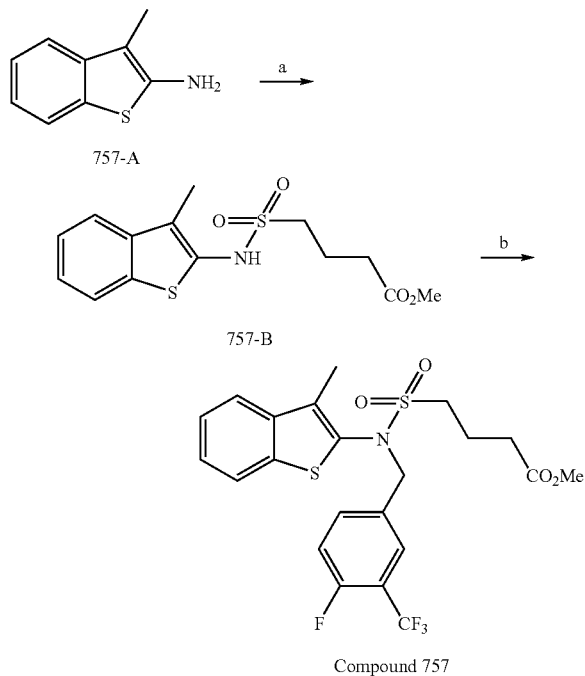

a) ClSO₂(CH₂)₃CO₂Me, pyridine, DCM;
b) KO-t-Bu, 4-fluoro-3-trifluoromethybenzyl bromide, DMF.

Compound 757-A, was prepared by the method used to synthesize compound 1-C in Example 1, steps A and B. MS: m/z 164.1 (MH⁺).

N-(3-Methyl-benzo[b]thiophen-2-yl)-3-carbomethoxy-propanesulfonamide (757-B). To a solution of compound 757-A (1.45 g, 7.25 mmol) and pyridine (1.42 mL, 17.6 mmol) in dichloromethane (20 mL), cooled to −10° C., was added 4-chlorosulfonyl-butyric acid methyl ester (1.6 g, 7.97 mmol) and the reaction mixture was stirred at ambient temperature for 2 days. The solvent was evaporated in vacuo, and the product was purified by flash column chromatography (SiO₂) eluting with an ethyl acetate (10-50%) in heptane gradient, to afford 1.75 g of compound 757-B as a pale orange solid. ¹H-NMR (DMSO-d₆): δ 1.87-2.10 (m, 2H), 2.32 (s, 3H), 2.42-2.58 (m, 2H), 3.11-3.29 (m, 2H), 3.59 (s, 3H), 7.25-7.48 (m, 2H), 7.71 (d, 1H), 7.77-7.94 (m, 1H), 10.07 (s, 1H); MS: m/z 328.0 (MH⁺).

Compound 757

N-(4-Fluoro-3-trifluoromethyl-benzyl)-N-(3-methyl-benzo[b]thiophen-2-yl)-3-carbomethoxy-propanesulfonamide. To a solution of compound 757-B (0.85 g, 2.59 mmol) in DMF (15 mL), cooled to 0° C., was added a solution of potassium t-butoxide (1.0 M in THF, 2.59 mL, 2.59 mmol) and the reaction mixture was stirred for 15 min. 4-Fluoro-3-trifluorobenzyl bromide (0.75 mL, 3.89 mL) was added in one-portion and the resultant solution was stirred at ambient temperature for 2 days. The reaction was partitioned between H₂O and EtOAc, the organic layer washed with water (3×), brine, dried over sodium sulfate, filtered, and the solvent was evaporated in vacuo. The crude residue was purified by flash column chromatography (SiO₂), eluting with an ethyl acetate (5-40%) in heptane gradient, to afford 1.11 g of compound 757 as an oil. ¹H-NMR (CDCl₃): δ 2.04 (s, 3H), 2.24 (q, 2H), 2.45-2.62 (m, 2H), 3.23-3.43 (m, 2H), 3.71 (s, 3H), 4.82 (s, 2H), 7.09 (t, 1H), 7.32-7.43 (m, 2H), 7.43-7.52 (m, 1H), 7.52-7.65 (m, 2H), 7.73 (dd, 1H); MS: m/z 504.1 (MH⁺).

Following the procedure described above for example 29 and substituting the appropriate reagents, starting materials and purification methods known to those skilled in the art, the following compounds of the present invention were prepared:

Compound 310

N-(Benzo[b]thiophen-2-yl)-N-(4-fluoro-3-trifluoromethyl-benzyl)-2-chloro-pyridin-3-ylsulfonamide. MS: m/z 501.0 (MH⁺).

Compound 311

N-(Benzo[b]thiophen-2-yl)-N-(4-fluoro-3-trifluoromethyl-benzyl)-2-chloro-pyridin-5-ylsulfonamide. MS: m/z 501.0 (MH⁺).

Compound 315

N-(Benzo[b]thiophen-2-yl)-N-(4-fluoro-3-trifluoromethyl-benzyl)-N',N'-dimethlysulfamide. MS: m/z 433.1 (MH⁺).

Compound 319

N-(3-Bromo-benzo[b]thiophen-2-yl)-N-(4-fluoro-3-trifluoromethyl-benzyl)-2-chloro-pyridin-3-ylsulfonamide. ¹H-NMR (CDCl₃) δ 5.27 (s, 2H), 7.14 (t, 1H), 7.30 (dd, 1H), 7.38-7.46 (m, 2H), 7.57 (dd, 2H), 7.62-7.69 (m, 2H), 8.16 (dd, 1H), 8.59 (dd, 1H); MS: m/z 578.8 (MH⁺).

Compound 320

N-(3-Bromo-benzo[b]thiophen-2-yl)-N-(4-fluoro-3-trifluoromethyl-benzyl)-2-chloro-pyridin-5-ylsulfonamide. ¹H-NMR (CDCl₃) δ 4.89 (s, 2H), 7.11 (t, 1H), 7.40-7.47 (m, 2H), 7.47-7.59 (m, 3H), 7.64-7.75 (m, 2H), 8.01 (dd, 1H), 8.83 (d, 1H); MS: m/z 580.9 (MH⁺).

Compound 321

N-(3-Chloro-benzo[b]thiophen-2-yl)-N-(4-fluoro-3-trifluoromethyl-benzyl)-2-chloro-pyridin-3-ylsulfonamide. MS: m/z 537.0 (MH⁺).

Compound 322

N-(3-Bromo-benzo[b]thiophen-2-yl)-N-(3-fluoro-4-trifluoromethyl-benzyl)-pyridin-3-ylsulfonamide. ¹H-NMR (CDCl₃) δ 4.95 (s, 2H), 7.18-7.25 (m, 2H), 7.39-7.49 (m, 2H), 7.49-7.61 (m, 2H), 7.63-7.75 (m, 2H), 8.11-8.19 (m, 1H), 8.91 (dd, 1H), 9.10 (d, 1H); MS: m/z 545.0 (MH⁺).

Compound 323

N-(3-Bromo-benzo[b]thiophen-2-yl)-N-(4-trifluoromethoxy-benzyl)-pyridin-3-ylsulfonamide. ¹H-NMR (CDCl₃) δ 4.86 (s, 2H), 6.97-7.11 (m, 2H), 7.19 (dd, 1H), 7.39-7.48 (m, 2H), 7.58 (dd, 1H), 7.64-7.76 (m, 2H), 8.17 (dt, 1H), 8.90 (dd, 1H), 9.10 (d, 1H); MS: m/z 543.0 (MH$^+$).

Compound 324

N-(3-Bromo-benzo[b]thiophen-2-yl)-N-(2-fluoro-5-chloro-benzyl)-pyridin-3-ylsulfonamide. $^1$H-NMR (CDCl$_3$) δ 4.96 (s, 2H), 6.88 (t, 1H), 7.20 (m, 1H), 7.39-7.48 (m, 3H), 7.51 (dd, 1H), 7.66-7.77 (m, 2H), 8.14 (dt, 1H), 8.88 (dd, 1H), 9.09 (d, 1H); MS: m/z 512.8 (MH$^+$).

Compound 326

N-(3-Methyl-benzo[b]thiophen-2-yl)-N-(4-fluoro-3-trifluoromethyl-benzyl)-5-(2-methyl-5-trifluoromethyl-2H-pyrazol-3-yl)-thien-2-ylsulfonamide. MS: m/z 633.9 (MH$^+$).

Compound 327

N-(3-Methyl-benzo[b]thiophen-2-yl)-N-(4-fluoro-3-trifluoromethyl-benzyl)-5-carbomethoxy-furan-2-yl-sulfonamide. MS: m/z 527.8 (MH$^+$).

Compound 328

N-(3-Methyl-benzo[b]thiophen-2-yl)-N-(4-fluoro-3-trifluoromethyl-benzyl)-1-methyl-3-trifluoromethyl-1H-pyrazol-4-ylsulfonamide. MS: m/z 551.8 (MH$^+$).

Compound 329

N-(3-Methyl-benzo[b]thiophen-2-yl)-N-(4-fluoro-3-trifluoromethyl-benzyl)-5-(5-trifluoromethyl-isoxazol-3-yl)-thien-2-ylsulfonamide. MS: m/z 620.8 (MH$^+$).

Compound 330

N-(3-Methyl-benzo[b]thiophen-2-yl)-N-(4-fluoro-3-trifluoromethyl-benzyl)-5-bromo-6-chloro-pyridin-3-ylsulfonamide. MS: m/z 594.8 (MH$^+$).

Compound 331

N-(3-Methyl-benzo[b]thiophen-2-yl)-N-(4-fluoro-3-trifluoromethyl-benzyl)-5,6-dichloro-pyridin-3-ylsulfonamide. MS: m/z 550.8 (MH$^+$).

Compound 332

N-(3-Methyl-benzo[b]thiophen-2-yl)-N-(4-fluoro-3-trifluoromethyl-benzyl)-4-pyrazol-1-yl-benzenesulfonamide. $^1$H-NMR (CDCl$_3$) δ 2.04-2.12 (m, 4H), 3.51 (br s, 1H), 6.53-6.63 (m, 1H), 7.06 (t, 1H), 7.30-7.40 (m, 2H), 7.40-7.49 (m, 1H), 7.55 (dd, 1H), 7.58-7.70 (m, 2H), 7.83 (d, 1H), 7.86-7.94 (m, 4H), 8.04 (d, 1H); MS: m/z 633.9 (MH$^+$).

Compound 333

N-(3-Methyl-benzo[b]thiophen-2-yl)-N-(4-fluoro-3-trifluoromethyl-benzyl)-3-(5-methyl-[1,3,4]oxadiazol-2-yl)-benzenesulfonamide. $^1$H-NMR (CDCl$_3$) δ 2.07 (s, 3H), 2.63 (s, 3H), 3.50 (s, 2H), 7.07 (t, 1H), 7.32-7.40 (m, 2H), 7.40-7.49 (m, 1H), 7.50-7.57 (m, 1H), 7.58-7.67 (m, 2H), 7.70 (t, 1H), 7.90-7.99 (m, 2H), 8.38 (dt, 1H), 8.41-8.44 (m, 1H); MS: m/z 561.9 (MH$^+$).

Compound 334

N-(3-Methyl-benzo[b]thiophen-2-yl)-N-(4-fluoro-3-trifluoromethyl-benzyl)-3-oxazol-5-yl-benzenesulfonamide. $^1$H-NMR (CDCl$_3$): δ 2.07 (s, 3H), 2.74 (br s, 2H), 7.06 (t, 1H), 7.29-7.41 (m, 2H), 7.41-7.48 (m, 1H), 7.48-7.70 (m, 4H), 7.77-7.86 (m, 2H), 7.86-7.93 (m, 2H), 8.08 (s, 1H); MS: m/z 546.9 (MH$^+$).

Compound 336

N-(3-Methyl-benzo[b]thiophen-2-yl)-N-(4-fluoro-3-trifluoromethyl-benzyl)-(3-chloro-4-acetamide)-benzenesulfonamide. $^1$H-NMR (CDCl$_3$): δ 2.07 (s, 3H), 2.32 (s, 3H), 3.52 (br s, 2H), 7.06 (t, 1H), 7.32-7.39 (m, 2H), 7.42 (d, 1H), 7.53 (dd, 1H), 7.58-7.63 (m, 1H), 7.64-7.69 (m, 1H), 7.72 (dd, 1H), 7.79-7.88 (m, 2H), 8.68 (d, 1H); MS: m/z 570.9 (MH$^+$).

Compound 337

N-(3-Methyl-benzo[b]thiophen-2-yl)-N-(4-fluoro-3-trifluoromethyl-benzyl)-(6-chloro-imidazo[2,1-b]thiazol-5-yl-sulfonamide. $^1$H-NMR (CDCl$_3$): δ 2.06 (s, 3H), 3.53 (br s, 2H), 6.76 (d, 1H), 7.08 (t, 1H), 7.23 (d, 1H), 7.31-7.39 (m, 2H), 7.43-7.50 (m, 1H), 7.55-7.62 (m, 3H); MS: m/z 559.8 (MH$^+$).

Compound 338

N-(3-Chloro-benzo[b]thiophen-2-yl)-N-(4-fluoro-3-trifluoromethyl-benzyl)-4-chloro-pyridin-3-ylsulfonamide. $^1$H-NMR (CDCl$_3$) δ 4.87 (s, 2H), 7.07-7.19 (m, 1H), 7.26 (s, 1H), 7.38-7.63 (m, 4H), 7.63-7.83 (m, 2H), 8.01 (dd, 1H), 8.83 (d, 1H); MS: m/z 536.8 (MH$^+$).

Compound 367

N-(3,4-Difluoro-benzyl)-N-(3-methyl-benzo[b]thiophen-2-yl)-methanesulfonamide. $^1$H-NMR (DMSO-d$_6$): δ 2.10 (s, 3H), 3.29 (s, 3H), 4.77 (s, 2H), 7.12-7.17 (m, 1H), 7.31-7.44 (m, 4H), 7.67-7.73 (m, 1H), 7.87-7.92 (m, 1H); MS: m/z 368.0 (MH$^+$).

Compound 368

N-(4-Fluoro-3-trifluoromethyl-benzyl)-N-(3-methyl-benzo[b]thiophen-2-yl)-methanesulfonamide. $^1$H-NMR (DMSO-d$_6$): δ 2.08 (s, 3H), 3.31 (s, 3H), 4.88 (s, 2H), 7.37-7.49 (m, 3H), 7.65-7.73 (m, 3H), 7.87-7.91 (m, 1H); MS: m/z 417.9 (MH$^+$).

Compound 369

N-(3-Methyl-benzo[b]thiophen-2-yl)-N-(4-trifluoromethoxy-benzyl)-methanesulfonamide. $^1$H-NMR (DMSO-d$_6$): δ 2.04 (s, 3H), 3.29 (s, 3H), 4.81 (s, 2H), 7.29 (d, 2H), 7.35-7.42 (m, 4H), 7.65-7.71 (m, 1H), 7.87-7.92 (m, 1H); MS: m/z 416.0 (MH$^+$).

Compound 379

N-(Benzo[b]thiophen-2-yl)-N-(3-carbomethoxy-benzyl)-pyridin-3-ylsulfonamide. MS: m/z 438.9 (MH$^+$).

Compound 380

N-(Benzo[b]thiophen-2-yl)-N-(4-carbomethoxy-benzyl)-pyridin-3-ylsulfonamide. MS: m/z 438.9 (MH$^+$).

Compound 383

N-(Benzo[b]thiophen-2-yl)-N-(4,4,4-trifluoro-butyl)-pyridin-3-ylsulfonamide. MS: m/z 401.1 (MH$^+$).

Compound 384

N-(3-Methyl-benzo[b]thiophen-2-yl)-N-(4,4,4-trifluoro-butyl)-2-oxo-2,3-dihydro-benzooxazol-6-yl-sulfonamide. $^1$H-NMR (DMSO-d$_6$) δ 1.64 (d, 3H), 2.21-2.31 (m, 3H), 2.38 (m, 3H), 7.30 (d, 1H), 7.39-7.51 (m, 2H), 7.55 (dd, 1H), 7.71 (d, 1H), 7.80 (dd, 1H), 7.84-7.93 (m, 1H), 7.95 (s, 1H), 12.3 (s, 1H); MS: m/z 470.9 (MH$^+$).

Compound 405

N-(3-Bromo-benzo[b]thiophen-2-yl)-N-(3-carbomethoxy-benzyl)-pyridin-3-ylsulfonamide. MS: m/z 518.8 (MH$^+$).

Compound 406

N-(3-Bromo-benzo[b]thiophen-2-yl)-N-(4-carbomethoxy-benzyl)-pyridin-3-ylsulfonamide. MS: m/z 518.8 (MH$^+$).

Compound 407

N-(3-Bromo-benzo[b]thiophen-2-yl)-N-(4,4,4-trifluoro-butyl)-pyridin-3-yl-sulfonamide. MS: m/z 480.8 (MH$^+$).

Compound 408

N-(3-Chloro-benzo[b]thiophen-2-yl)-N-(4,4,4-trifluoro-butyl)-3-pyridin-3-yl-sulfonamide. MS: m/z 434.9 (MH$^+$).

Compound 546

N-(4-Fluoro-3-trifluoromethyl-benzyl)-N-(3-methyl-benzo[b]thiophen-2-yl)-3-cyano-benzenesulfonamide. MS: m/z 505.0 (MH$^+$).

Compound 547

N-(4-Fluoro-3-trifluoromethyl-benzyl)-N-(3-isopropyl-benzo[b]thiophen-2-yl)-benzenesulfonamide. $^1$H-NMR (CDCl$_3$): δ 0.78 (d, 3H), 1.41 (d, 3H), 3.30 (q, 1H), 4.14 (d, 1H), 5.20 (d, 1H), 7.04 (t, 1H), 7.27-7.34 (m, 2H), 7.37-7.45 (m, 1H), 7.52-7.60 (m, 3H), 7.62-7.72 (m, 2H), 7.84-7.91 (m, 3H); MS: m/z 508.0 (MH$^+$).

Compound 669

N-(4-Fluoro-3-trifluoromethyl-benzyl)-N-(3-methyl-benzo[b]thiophen-2-yl)-2,2,2-trifluoro-ethanesulfonamide. MS: m/z 486.0 (MH$^+$).

Compound 697

N-(Benzo[b]thiophen-2-yl)-N-(4-fluoro-3-trifluoromethyl-benzyl)-2,2,2-trifluoro-ethanesulfonamide. MS: m/z 472.0 (MH$^+$).

Compound 700

N-(3-Methyl-benzo[b]thiophen-2-yl)-N-(4-fluoro-3-trifluoromethyl-benzyl)-2-(2,2,2-trifluoro-acetyl)-1,2,3,4-tetrahydro-isoquinoline sulfonamide. MS: m/z 631.1 (MH$^+$).

Compound 760

N-(3-Methyl-benzo[b]thiophen-2-yl)-N-(3-trifluoromethoxy-benzyl)-2-carbomethoxy-ethanesulfonamide. MS: m/z 488.1 (MH$^+$).

Example 30

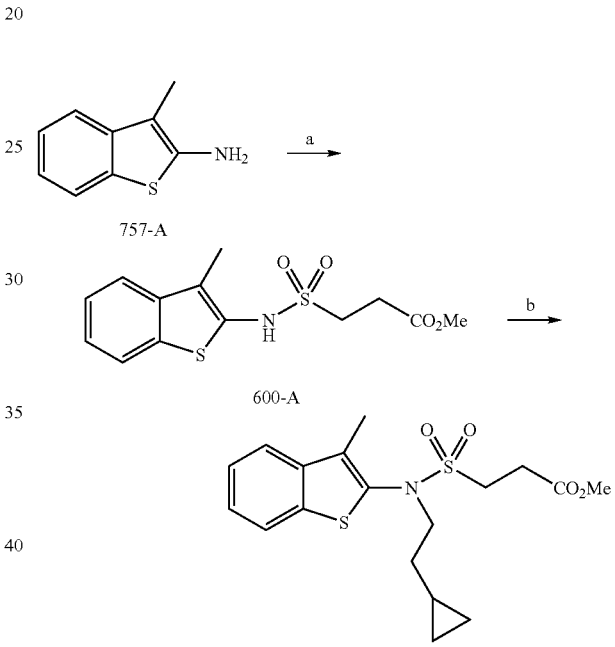

a) DCM, pyridine, ClSO$_2$CH$_2$CH$_2$CO$_2$Me;
b) PPh$_3$, DEAD, HOCH$_2$CH$_2$-c-Pr, THF.

N-(3-Methyl-benzo[b]thiophen-2-yl)-2-carbomethoxy-ethanesulfonamide (600-A). A solution of compound 757-A (1.0 g, 5.01 mmol) and pyridine (851 μL, 10.5 mmol) in dichloromethane (20 mL), cooled to 10° C. was treated with 3-chlorosulfonyl-propionic acid methyl ester (716 μL, 5.25 mmol) and stirred at ambient temperature for 18 h. The solvent was evaporated in vacuo, and the crude residue purified by flash column chromatography (SiO$_2$), eluting with an ethyl acetate (10-50%) in heptane gradient to afford 1.1 g of compound 600-A as an off white solid. $^1$H-NMR (DMSO-d$_6$): δ 2.31 (s, 3H), 2.82 (t, 2H), 3.43 (t, 2H), 3.62 (s, 3H), 7.24-7.50 (m, 2H), 7.58-7.77 (m, 1H), 7.80-7.95 (m, 1H), 10.17 (s, 1H); MS: m/z 314.1 (MH$^+$).

Compound 600

N-(2-Cyclopropyl-ethyl)-N-(3-methyl-benzo[b]thiophen-2-yl)-2-carbomethoxy-ethanesulfonamide. A solution of triphenylphosphine (0.251 g, 0.957 mmol) in THF (3 mL)

was treated with DEAD (40% in toluene, 425 μL, 0.957 mmol) and stirred at ambient temperature for 5 min. Compound 600-A (0.20 g, 0.638 mmol) was added to the solution and stirred for 5 min. 2-Cyclopropyethanol (77 mL, 0.830 mmol) was added to the solution and the reaction mixture was stirred at ambient temperature for 18 h. The solvent was evaporated in vacuo, and the crude residue purified by flash column chromatography (SiO$_2$), eluting with an ethyl acetate (10-40%) in heptane gradient to afford 223 mg of compound 600 as a colorless oil. $^1$H-NMR (CDCl$_3$): δ −0.02-0.06 (m, 2H), 0.35-0.52 (m, 2H), 0.56-0.80 (m, 1H), 1.49 (q, 2H), 2.40 (s, 3H), 2.81-2.97 (m, 2H), 3.41-3.57 (m, 2H), 3.64-3.84 (s superimposed on m, 5H), 7.33-7.49 (m, 2H), 7.59-7.80 (m, 2H); MS: m/z 382.4 (MH$^+$).

Following the procedure described above for example 30 and substituting the appropriate reagents, starting materials and purification methods known to those skilled in the art, the following compounds of the present invention were prepared:

Compound 308

N-(Benzo[b]thiophen-2-yl)-N-(4-fluoro-3-trifluoromethyl-benzyl)-4-acetyl-benzenesulfonamide. MS: m/z 508.0 (MH$^+$).

Compound 351

N-(3-Methyl-benzo[b]thiophen-2-yl)-N-(4,4,4-trifluorobutyl)-4-acetyl-benzenesulfonamide. $^1$H-NMR (DMSO-d$_6$): δ 1.52-1.73 (m, 2H), 2.24 (s, 3H), 2.29-2.46 (m, 2H), 2.67 (s, 3H), 3.49-3.67 (m, 2H), 7.36-7.48 (m, 2H), 7.76-7.94 (m, 5H), 8.16-8.19 (m, 2H); MS: m/z 456.0 (MH$^+$).

Compound 352

N-(3-Methyl-benzo[b]thiophen-2-yl)-N-(4-fluoro-3-trifluoromethyl-benzyl)-4-acetyl-benzenesulfonamide. $^1$H-NMR (DMSO-d$_6$): δ 1.95 (s, 3H), 3.33 (s, 3H), 4.88 (s, 2H), 7.25-7.49 (m, 3H), 7.62-7.71 (m, 3H), 7.81-7.87 (m, 1H), 8.01-8.04 (d, 2H), 8.19-8.22 (d, 2H); MS: m/z 522.0 (MH$^+$).

Compound 353

N-(3-Methyl-benzo[b]thiophen-2-yl)-N-(4-fluoro-3-trifluoromethyl-benzyl)-3-(2-methyl-pyrimidin-4-yl)-benzenesulfonamide. $^1$H-NMR (DMSO-d$_6$): δ 1.97 (s, 3H), 2.66 (s, 3H), 4.91 (s, 2H), 7.36-7.48 (m, 3H), 7.66-7.76 (m, 3H), 7.80-7.89 (m, 2H), 8.02-8.04 (d, 2H), 8.57-8.62 (m, 2H), 8.82-8.84 (d, 1H); MS: m/z 572.0 (MH$^+$).

Compound 354

N-(3-Methyl-benzo[b]thiophen-2-yl)-N-(4,4,4-trifluorobutyl)-3-(2-methyl-pyrimidin-4-yl)-benzenesulfonamide. MS: m/z 506.0 (MH$^+$).

Compound 355

N-(3-Methyl-benzo[b]thiophen-2-yl)-N-(4-fluoro-3-trifluoromethyl-benzyl)-8-methoxy-quinolin-5-ylsulfamide. $^1$H-NMR (DMSO-d$_6$): δ 1.76 (s, 3H), 4.07 (s, 3H), 4.91 (s, 2H), 7.19-7.45 (m, 4H), 7.52-7.63 (m, 4H), 7.59-7.81 (m, 1H), 8.23-8.26 (d, 2H), 8.81-8.84 (dd, 1H), 8.96-8.98 (m, 1H); MS: m/z 561.0 (MH$^+$).

Compound 356

N-(3-Methyl-benzo[b]thiophen-2-yl)-N-(4,4,4-trifluorobutyl)-8-methoxyquinolin-5-ylsulfonamide. MS: m/z 495.0 (MH$^+$).

Compound 370

N-(Benzo[b]thiophen-2-yl)-N-(4-fluoro-3-trifluoromethyl-benzyl)-3-cyano-benzenesulfonamide. $^1$H-NMR (DMSO-d$_6$): δ 5.05 (s, 2H), 7.22 (s, 1H), 7.31-7.37 (m, 2H), 7.46-7.52 (m, 4H), 7.69-7.74 (m, 3H), 7.82-7.92 (m, 2H), 8.04-8.07 (m, 1H), 8.26-8.29 (m, 1H), 8.43-8.44 (m, 1H).

Compound 372

N-(3-Methyl-benzo[b]thiophen-2-yl)-N-(4,4,4-trifluorobutyl)-4-(pyridin-4-yloxy)-benzenesulfonamide. $^1$H-NMR (DMSO-d$_6$): δ 1.53-1.73 (m, 2H), 2.26 (s, 3H), 2.33-2.46 (m, 2H), 4.08 (m, 2H), 7.35-7.37 (m, 2H), 7.40-7.48 (m, 2H), 7.50-7.54 (m, 2H), 7.79-7.82 (m, 1H), 7.84-7.94 (m, 3H), 8.73-8.75 (d, 2H); MS: m/z 507.0 (MH$^+$).

Compound 373

N-(3-Methyl-benzo[b]thiophen-2-yl)-N-(4,4,4-trifluorobutyl)-4-(pyridin-3-yloxy)-benzenesulfonamide. MS: m/z 507.0 (MH$^+$).

Compound 411

N-(Benzo[b]thiophen-2-yl)-N-(4-fluoro-3-trifluoromethyl-benzyl)-4-cyano-benzenesulfonamide. MS: m/z 490.9 (MH$^+$).

Compound 548

N-(2-Cyclopropyl-ethyl)-N-(3-isopropyl-benzo[b]thiophen-2-yl)-benzenesulfonamide. $^1$H-NMR (CDCl$_3$): δ −0.11-0.07 (m, 2H), 0.38-0.44 (m, 2H), 0.65 (m, 1H), 1.06-1.26 (m, 1H), 1.41 (d, 3H), 1.50 (d, 3H), 1.55-1.68 (m, 1H), 3.12-3.32 (m, 1H), 3.54-3.74 (m, 1H), 3.85-4.07 (m, 1H), 7.28-7.38 (m, 2H), 7.48-7.56 (m, 2H), 7.60-7.69 (m, 2H), 7.83 (d, 2H), 8.00 (dd, 1H); MS: m/z 400.0 (MH$^+$).

Compound 549

N-(2-Cyclopropyl-ethyl)-N-(3-methyl-benzo[b]thiophen-2-yl)-3-cyano-benzenesulfonamide. $^1$H-NMR (CDCl$_3$): δ −0.07-0.08 (m, 2H), 0.44 (d, 2H), 0.54-0.77 (m, 1H), 1.32-1.52 (m, 2H), 2.38 (s, 3H), 3.37-3.87 (m, 2H), 7.40 (ddd, 2H), 7.59-7.78 (m, 3H), 7.91 (d, 1H), 7.99 (d, 1H), 8.10 (s, 1H); MS: m/z 397.0 (MH$^+$).

Compound 550

N-(3-Methyl-benzo[b]thiophen-2-yl)-N-(3,3,3-trifluoropropyl)-3-cyano-benzenesulfonamide. $^1$H-NMR (CDCl$_3$): δ 2.27-2.65 (m, 2H) superimposed on 2.38 (s, 3H), 3.61-4.03 (m, 2H), 7.36-7.51 (m, 2H), 7.62-7.80 (m, 3H), 7.94 (d, 1H), 8.00 (d, 1H), 8.08 (s, 1H); MS: m/z 425.1 (MH$^+$).

Compound 551

N-(3-Methyl-benzo[b]thiophen-2-yl)-N-(4,4,4-trifluorobutyl)-3-cyano-benzenesulfonamide. MS: m/z 439.0 (MH$^+$).

Compound 552

N-(3-Methyl-benzo[b]thiophen-2-yl)-N-(5,5,5-trifluoro-pentyl)-3-cyano-benzenesulfonamide. $^1$H-NMR (CDCl$_3$): δ 1.52-1.74 (m, 4H), 1.93-2.20 (m, 2H), 2.39 (s, 3H), 3.23-3.91 (m, 2H), 7.33-7.50 (m, 2H), 7.60-7.79 (m, 3H), 7.91 (d, 1H), 7.97 (d, 1H), 8.07 (s, 1H); MS: m/z 453.0 (MH$^+$).

Compound 573

N-(Benzo[b]thiophen-2-yl)-N-(3,3,3-trifluoro-propyl)-3-cyano-benzenesulfonamide. MS: m/z 410.7 (MH$^+$).

Compound 574

N-(Benzo[b]thiophen-2-yl)-N-(4,4,4-trifluoro-butyl)-3-cyano-benzenesulfonamide. MS: m/z 424.6 (MH$^+$).

Compound 575

N-(Benzo[b]thiophen-2-yl)-N-(2-cyclopropyl-ethyl)-3-cyano-benzenesulfonamide. MS: m/z 382.8 (MH$^+$).

Compound 601

N-(3-Methyl-benzo[b]thiophen-2-yl)-N-(3,3,3-trifluoro-propyl)-2-carbomethoxy-ethanesulfonamide. $^1$H-NMR (CDCl$_3$): δ 2.36-2.57 ((m, 2H) superimposed on 2.42 (s, 3H), 2.81-2.96 (m, 2H), 3.42-3.59 (m, 2H), 3.75 (s, 3H), 3.81-4.00 (m, 2H), 7.43 (q, 2H), 7.68-7.82 (m, 2H); MS: m/z 382.4 (MH$^+$).

Compound 602

N-(3-Methyl-benzo[b]thiophen-2-yl)-N-(4,4,4-trifluoro-butyl)-2-carbomethoxy-ethanesulfonamide. $^1$H-NMR (CDCl$_3$): δ 1.73-1.90 (m, 2H), 2.10-2.33 (m, 2H), 2.42 (s, 3H), 2.77-2.94 (m, 2H), 3.37-3.57 (m, 2H), 3.65-3.84 (s superimposed on m, 5H), 7.32-7.50 (m, 2H), 7.62-7.84 (m, 2H); MS: m/z 424.2 (MH$^+$).

Compound 603

N-(3-Methyl-benzo[b]thiophen-2-yl)-N-(5,5,5-trifluoro-pentyl)-2-carbomethoxy-ethanesulfonamide. $^1$H-NMR (CDCl$_3$): δ 1.65 (m, 4H), 1.94-2.20 (m, 2H), 2.41 (s, 3H), 2.76-2.99 (m, 2H), 3.36-3.56 (m, 2H), 3.69 (br s, 2H), 3.74 (s, 3H), 7.32-7.50 (m, 2H), 7.63-7.82 (m, 2H); MS: m/z 438.3 (MH$^+$).

Compound 614

N-(2-Cyclopropyl-ethyl)-N-(3-methyl-benzo[b]thiophen-2-yl)-benzenesulfonamide. $^1$H-NMR (CDCl$_3$): δ −0.12-0.06 (m, 2H), 0.31-0.47 (m, 2H), 0.53-0.73 (m, 1H), 1.30-1.51 (m, 2H), 2.36 (s, 3H), 3.35-3.86 (m, 2H), 7.30-7.43 (m, 2H), 7.47-7.55 (m, 2H), 7.59-7.72 (m, 3H), 7.79 (d, 2H); MS: m/z 372.1 (MH$^+$).

Compound 615

N-(3-Methyl-benzo[b]thiophen-2-yl)-N-(3,3,3-trifluoro-propyl)-benzenesulfonamide. $^1$H-NMR (CDCl$_3$): δ 2.34 (s, 3H), 2.35-2.50 (m, 2H), 3.53-4.03 (m, 2H), 7.35-7.46 (m, 2H), 7.49-7.57 (m, 2H), 7.62-7.75 (m, 3H), 7.77 (d, 1H), 7.80 (s, 1H); MS: m/z 400.0 (MH$^+$).

Compound 616

N-(3-Methyl-benzo[b]thiophen-2-yl)-N-(4,4,4-trifluoro-butyl)-benzenesulfonamide. $^1$H-NMR (CDCl$_3$): δ 1.70-1.84 (m, 2H), 2.14-2.35 (m, 2H), 2.36 (s, 3H), 3.40-3.78 (m, 2H), 7.32-7.45 (m, 2H), 7.47-7.56 (m, 2H), 7.60-7.74 (m, 3H), 7.77 (d, 2H); MS: m/z 414.0 (MH$^+$).

Compound 617

N-(3-Methyl-benzo[b]thiophen-2-yl)-N-(5,5,5-trifluoro-pentyl)-benzenesulfonamide. $^1$H-NMR (CDCl$_3$): δ 1.51-1.74 (m, 4H), 1.93-2.18 (m, 2H), 2.36 (s, 3H), 3.41-3.69 (m., 2H), 7.32-7.44 (m, 2H), 7.47-7.55 (m, 2H), 7.60-7.73 (m, 3H), 7.74-7.80 (m, 2H); MS: m/z 428.1 (MH$^+$).

Compound 670

N-(2-Cyclopropyl-ethyl)-N-(3-methyl-benzo[b]thiophen-2-yl)-2,2,2-trifluoro-ethanesulfonamide. MS: m/z 378.0 (MH$^+$).

Compound 671

N-(3-Methyl-benzo[b]thiophen-2-yl)-N-(3,3,3-trifluoro-propyl)-2,2,2-trifluoro-ethanesulfonamide. MS: m/z 406.0 (MH$^+$).

Compound 672

N-(3-Methyl-benzo[b]thiophen-2-yl)-N-(4,4,4-trifluoro-butyl)-2,2,2-trifluoro-ethanesulfonamide. MS: m/z 420.0 (MH$^+$).

Compound 673

N-(3-Methyl-benzo[b]thiophen-2-yl)-N-(5,5,5-trifluoro-pentyl)-2,2,2-trifluoro-ethanesulfonamide. MS: m/z 434.1 (MH$^+$).

Compound 721

N-(3-Methyl-benzo[b]thiophen-2-yl)-N-(5,5,5-trifluoro-pentyl)-quinoxalin-5-yl-sulfonamide. $^1$H-NMR (DMSO-d$_6$): δ 1.60-1.65 (m, 2H), 2.17 (s, 3H), 2.22-2.33 (m, 2H), 3.96-4.07 (m, 2H), 7.31-7.39 (m, 2H), 7.69-7.72 (m, 2H), 7.88-7.92 (m, 1H), 8.26-8.28 (m, 1H), 8.42-8.44 (m, 1H), 9.20-9.25 (m, 2H); MS: m/z 480.0 (MH$^+$).

Compound 723

N-(3-Methyl-benzo[b]thiophen-2-yl)-N-(4-fluoro-3-trifluoromethyl-benzyl)-quinoxalin-5-yl-sulfonamide. $^1$H-NMR (DMSO-d$_6$): δ 1.75 (s, 3H), 5.31 (s, 2H), 7.28-7.34 (m, 2H), 7.46-7.51 (m, 1H), 7.58-7.61 (m, 1H), 7.66-7.71 (m, 3H), 7.91-7.95 (m, 1H), 8.31-8.33 (m, 1H), 8.47-8.49 (m, 1H), 9.26-9.32 (m, 2H); MS: m/z 532.0 (MH$^+$).

Compound 761

N-(3-Methyl-benzo[b]thiophen-2-yl)-N-(4-trifluoromethoxy-benzyl)-carbomethoxy-methanesulfonamide. MS: m/z 474.0 (MH$^+$).

Compound 791

N-(4-Fluoro-3-trifluoromethyl-benzyl)-N-(3-methyl-benzo[b]thiophen-2-yl)-carbomethoxy-methanesulfonamide. ¹H-NMR (CDCl₃): δ 1.96 (s, 3H), 3.91 (s, 3H), 4.25 (s, 2H), 4.95 (br s, 2H), 7.08 (t, 1H), 7.33-7.49 (m, 3H), 7.49-7.66 (m, 2H), 7.71-7.85 (m, 1H); MS: m/z 476.1 (MH⁺).

Compound 794

N-(3-Methyl-benzo[b]thiophen-2-yl)-N-(4-trifluoromethoxy-benzyl)-2-carbomethoxy-ethanesulfonamide. ¹H-NMR (CDCl₃): δ 1.96 (s, 3H), 2.85-2.97 (m, 2H), 3.48-3.61 (m, 2H), 3.75 (s, 3H), 4.78 (br s, 2H), 7.11 (d, 2H), 7.28-7.42 (m, 4H), 7.55-7.62 (m, 1H), 7.70-7.77 (m, 1H); MS: m/z 488.1 (MH⁺).

Example 31

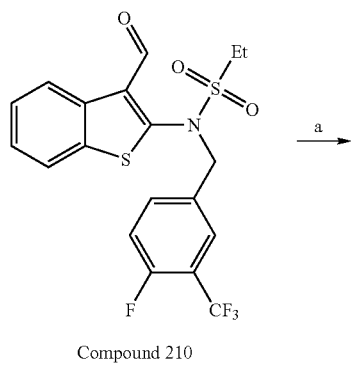

Compound 210

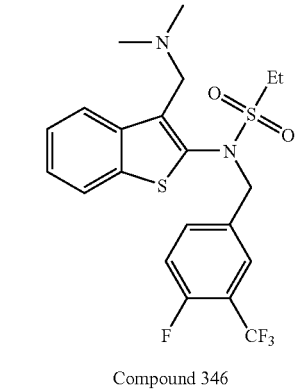

Compound 346 a) (Me)₂NH, Na(OAc)₃BH, DCM.

Compound 346

N-(3-Dimethylaminomethyl-benzo[b]thiophen-2-yl)-N-(4-fluoro-3-trifluoromethyl-benzyl)-ethanesulfonamide. To a solution of compound 210 (0.116 g, 0.26 mmol) in dichloromethane (4 mL) was added dimethylamine (2 M in THF, 195 µL, 0.39 mmol) and the reaction mixture stirred at ambient temperature for 15 min. Sodium triacetoxyborohydride (0.11 g, 0.52 mmol) was added to the reaction mixture and stirred at ambient temperature for 6 h. The solution was treated with saturated aqueous sodium bicarbonate, the organic layer separated, dried over Na₂SO₄, filtered, and the solvent evaporated in vacuo. The crude residue was purified by reverse phase prep HPLC (eluting with an 20-90% acetonitrile in water with 0.1% TFA gradient) to afford the 90 mg of compound 346 as the TFA salt (90 mg, 59%). MS: m/z 475.2 (MH⁺).

Following the procedure described above for example 31 and substituting the appropriate reagents, starting materials and purification methods known to those skilled in the art, the following compounds of the present invention were prepared:

Compound 347

N-(4-Fluoro-3-trifluoromethyl-benzyl)-N-(3-methylaminomethyl-benzo[b]thiophen-2-yl)-ethanesulfonamide. MS: m/z 461.2 (MH⁺).

Compound 348

N-(4-Fluoro-3-trifluoromethyl-benzyl)-N-(3-propylaminomethyl-benzo[b]thiophen-2-yl)-ethanesulfonamide. MS: m/z 489.3 (MH⁺).

Compound 349

N-(4-Fluoro-3-trifluoromethyl-benzyl)-N-(3-pyrrolidin-1-yl-methyl-benzo[b]thiophen-2-yl)-ethanesulfonamide. MS: m/z 501.2 (MH⁺).

Compound 381

N-(4-Fluoro-3-trifluoromethyl-benzyl)-N-(3-pyrrolidin-1-yl-methyl-benzo[b]thiophen-2-yl)-benzenesulfonamide. MS: m/z 549.3 (MH⁺).

Compound 417

N-(4-Fluoro-3-trifluoromethyl-benzyl)-N-(3-methylaminomethyl-benzo[b]thiophen-2-yl)-benzenesulfonamide. MS: m/z 509.1 (MH⁺).

Compound 418

N-(3-Dimethylaminomethyl-benzo[b]thiophen-2-yl)-N-(4-fluoro-3-trifluoromethyl-benzyl)-benzenesulfonamide. MS: m/z 523.2 (MH⁺).

Compound 420

N-(3-Dimethylaminomethyl-benzo[b]thiophen-2-yl)-N-(butyl)-4-carbomethoxy-benzenesulfonamide. MS: m/z 461.27 (MH⁺).

Example 32

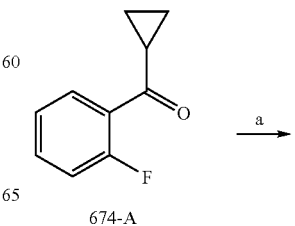

674-A

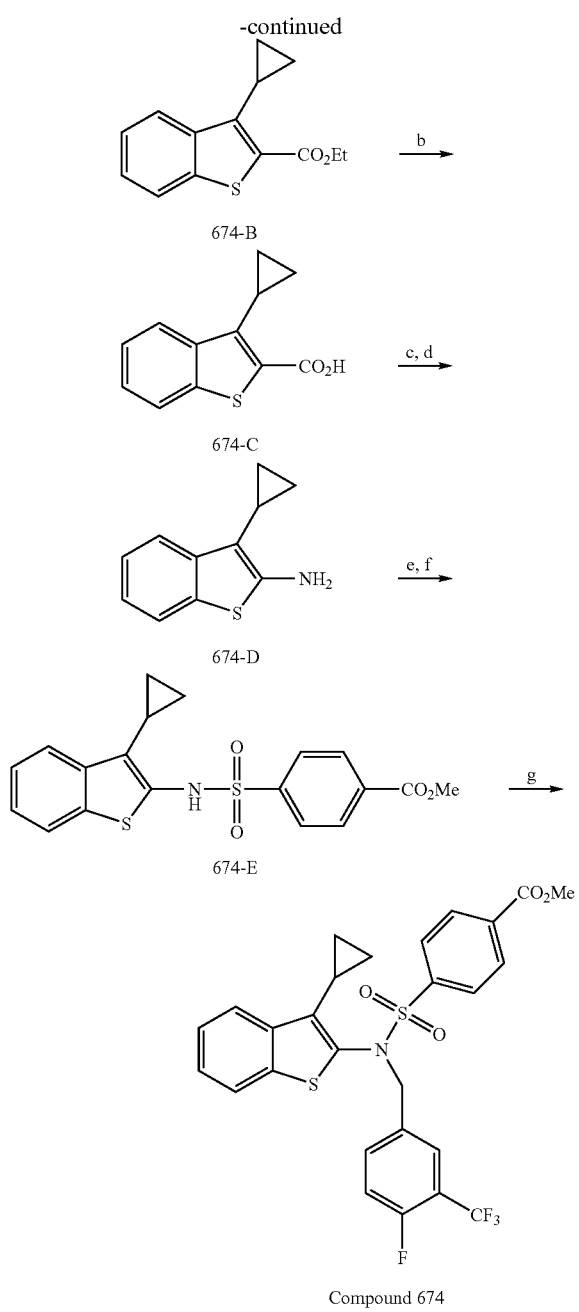

Compound 674 a) NaH, ethylthioglycolate, THF;
b) 3N NaOH, MeOH;
c) DPPA, DiEA, t-BuOH;
d) HCl/dioxane;
e) 4-chlorosulfonylbenzoic acid, pyridine, DCM;
f) MeOH, H$_2$SO$_4$;
g) t-BuOK, 4-fluoro-3-trifluoromethylbenzyl bromide, DMF.

3-Cyclopropyl-benzo[b]thiophene-2-carboxylic acid ethyl ester (674-B). To a suspension of 60% NaH (0.26 g; 7.74 mmol) in THF (10 mL), at ambient temperature, was added ethyl thioglycolate (0.86 g; 7.14 mmol) drop-wise, and the reaction was stirred at ambient temperature for 30 min. Compound 674-A (0.98 g; 5.96 mmol) was added in one-portion. The reaction was allowed to reflux for 18 h, cooled, diluted with EtOAc, washed sequentially with 1N NaOH, H$_2$O, and brine, dried over Na$_2$SO$_4$, filtered, and the filtrate was concentrated under reduced pressure. The crude residue was purified by flash column chromatography (SiO$_2$), eluting with a heptane-EtOAc gradient to afford 0.484 g of compound 674-B as an oil. $^1$H-NMR (DMSO-d$_6$): δ 1.08-1.16 (m, 4H), 1.32-1.36 (t, 3H), 2.36-2.51 (m, 1H), 4.31-4.37 (q, 2H), 7.32-7.54 (m, 2H), 7.64-7.75 (m, 1H), 7.99-8.05 (m, 1H); MS: m/z 247.1 (MH$^+$).

3-Cyclopropyl-benzo[b]thiophene-2-carboxylic acid (674-C). A solution of compound 674-B (2.68 g, 10.9 mmol) in ethanol (30 mL) was treated with 3N aqueous sodium hydroxide (5.4 mL, 16.2 mmol) and refluxed for 2 h. The solution was cooled, and the solvent was evaporated in vacuo. The residue was dissolved in water and washed with dichloromethane. The aqueous phase was acidified with concentrated hydrochloric acid, and the product was extracted into ethyl acetate, washed with brine, dried over Na$_2$SO$_4$, filtered and the solvent was evaporated in vacuo, to afford 1.9 g of compound 674-C as a colorless solid. $^1$H-NMR (DMSO-d$_6$): δ 0.58-1.37 (m, 4H), 2.44-2.47 (m, 1H), 7.13-7.61 (m, 2H), 7.98 (dd, 2H), 13.33 (br s, 1H).

2-Amino-3-cyclopropyl-benzo[b]thiophene (674-D). A solution of compound 647-C (6.9 g, 31.6 mmol) and diisopropylethylamine (6.63 mL, 37.9 mmol) in t-butanol (100 mL) was treated with DPPA (8.2 mL, 37.9 mmol) and refluxed for 4 h. The solvent was evaporated in vacuo, and the crude residue was purified by flash column chromatography (SiO$_2$) eluting an ethyl acetate (0-15%) in heptane gradient, to afford 7.1 g of the BOC-protected amine (MS: m/z 290.1 (MH$^+$)). The BOC-protected amine was dissolved in a solution of 4N HCl in dioxane (100 mL) and stirred at ambient temperature for 4 h. The solid precipitate was collected by filtration, washed with diethyl ether and dried under vacuo to afford 2.36 g of the hydrochloride salt of compound 674-D as a colorless solid. The combined solvents were evaporated in vacuo to afford 3.1 g of additional 674-D as a yellow solid. MS: m/z 190.1 (MH$^+$).

N-(3-Cyclopropyl-benzo[b]thiophen-2-yl)-4-carbomethoxy-benzenesulfonamide (674-E). A solution of compound 674-D (0.60 g, 2.07 mmol) and pyridine (343 µL, 4.25 mmol) in dichloromethane, cooled to −10° C. was treated with 4-chlorosulfonylbenzoic acid (0.480 g, 2.17 mmol) and stirred at ambient temperature for 2 days. The solution was cooled to −10° C. and treated with additional portions of pyridine (120 µL) and 4-chlorosulfonylbenzoic acid (0.16 g) and stirred at ambient temperature for 18 h. The reaction mixture was partitioned between 2N HCl and ethyl acetate, the organic layer washed with brine, dried over sodium sulfate, filtered, and the solvent evaporated under reduced pressure to afford 0.95 g of the crude acid. The crude acid was suspended in methanol (25 mL), treated with sulfuric acid (0.1 mL) and refluxed for 6 h. The yellow solid was filtered, the solution concentrated in vacuo, diluted with water, extracted with ethyl acetate, the organic layer washed with brine, dried over sodium sulfate, filtered and the solvent evaporated under reduced pressure. The crude material was purified by flash column chromatography (SiO$_2$), eluting with an ethyl acetate (10-50%) gradient to afford 0.483 g of compound 674-E as a yellow oil. MS: m/z 388.0 (MH$^+$).

Compound 674

N-(3-Cyclopropyl-benzo[b]thiophen-2-yl)-N-(4-fluoro-3-trifluoromethyl-benzyl)-4-carbomethoxy-benzenesulfonamide. To a solution of compound 674-E (0.176 g, 0.454 mmol) in DMF (3 mL), cooled to 0° C. was added a solution of potassium t-butoxide (1.0 M in THF, 454 µL, 0.454 mmol) and the reaction mixture was stirred for 15 min. 4-Fluoro-3-trifluorobenzyl bromide (131 µL, 0.681 mmol) was added and the solution was stirred at ambient temperature for 18 h. The solution was diluted with water (20 mL), extracted with ethyl acetate, and the organic layer was washed with brine, dried over sodium sulfate, filtered, and the solvent evaporated in vacuo. The crude residue was purified by flash column chromatography (SiO$_2$) eluting with an ethyl acetate-heptane (10-50%) gradient to afford 0.187 g of compound 674 as an oil. $^1$H-NMR (CDCl$_3$): δ 0.65-0.99 (m, 4H), 1.42-1.67 (m, 1H), 3.99 (s, 3H), 4.16-5.33 (m, 2H), 7.05 (t, 1H), 7.30-7.46 (m, 3H), 7.55 (dd, 1H), 7.59-7.70 (m, 1H), 7.70-7.84 (m, 1H), 7.92 (d, 2H), 8.20 (d, 2H); MS: m/z 564.2 (MH$^+$).

Following the procedure described above for example 32 and substituting the appropriate reagents, starting materials and purification methods known to those skilled in the art, the following compounds of the present invention were prepared:

Compound 325

N-(3-Trifluoromethyl-benzo[b]thiophen-2-yl)-N-(4-trifluoromethoxy-benzyl)-benzenesulfonamide. Compound 325 was prepared substituting 2-fluoro-2,2,2,-trifluoroacetopheneone for cyclopropyl-(2-fluoro-phenyl)-methanone, triethylamine for NaH and acetonitrile for THF in Step A of Example 32. $^1$H-NMR (CDCl$_3$): δ 4.57 (br s, 1H), 4.89 (br s, 1H), 7.08 (d, 2H), 7.18-7.35 (m, 2H), 7.37-7.49 (m, 2H), 7.49-7.62 (m, 2H), 7.62-7.75 (m, 2H), 7.83 (d, 3H); MS: m/z 531.9 (MH$^+$).

Compound 501

N-(3-Cyclopentyl-benzo[b]thiophen-2-yl)-N-(4-fluoro-3-trifluoromethyl-benzyl)-4-carbomethoxy-benzenesulfonamide. MS: m/z 564.2 (MH$^+$).

Compound 696

N-(3-Cyclobutyl-benzo[b]thiophen-2-yl)-N-(4-fluoro-3-trifluoromethyl-benzyl)-4-carbomethoxy-benzenesulfonamide. $^1$H-NMR (CDCl$_3$): δ 1.91 (m, 3H), 2.17-2.60 (m, 3H), 3.66-3.89 (m, 1H), 3.99 (s, 3H), 4.11-4.34 (m, 1H), 5.07-5.27 (m, 1H), 6.99-7.15 (m, 1H), 7.37 (dd, 3H), 7.49-7.59 (m, 1H), 7.61-7.71 (m, 1H), 7.88 (d, 2H), 7.99-8.10 (m, 1H), 8.19 (d, 2H); MS: m/z 578.1 (MH$^+$).

Compound 753

N-(3-Cyclopropyl-benzo[b]thiophen-2-yl)-N-(4-trifluoromethoxy-benzyl)-4-carbomethoxy-benzenesulfonamide. $^1$H-NMR (CDCl$_3$): δ 0.44-0.79 (m, 4H), 1.22-1.63 (m, 1H), 3.99 (s, 3H), 4.30-5.15 (m, 2H), 7.08 (d, 2H), 7.25-7.37 (m, 4H), 7.60-7.68 (m, 1H), 7.74-7.83 (m, 1H), 7.91 (d, 2H), 8.15-8.25 (m, 2H); MS: m/z 562.0 (MH$^+$).

Compound 754

N-(3-Cyclobutyl-benzo[b]thiophen-2-yl)-N-(4-trifluoromethoxy-benzyl)-4-carbomethoxy-benzenesulfonamide. $^1$H-NMR (CDCl$_3$): δ 1.59-2.11 (m, 4H), 2.13-2.49 (m, 3H), 3.99 (s, 3H), 4.16 (d, 1H), 5.17 (d, 1H), 7.09 (d, 2H), 7.23-7.43 (m, 4H), 7.60-7.71 (m, 1H), 7.89 (d, 2H), 7.97-8.07 (m, 1H), 8.14-8.26 (m, 2H); MS: m/z 576.2 (MH$^+$).

Example 33

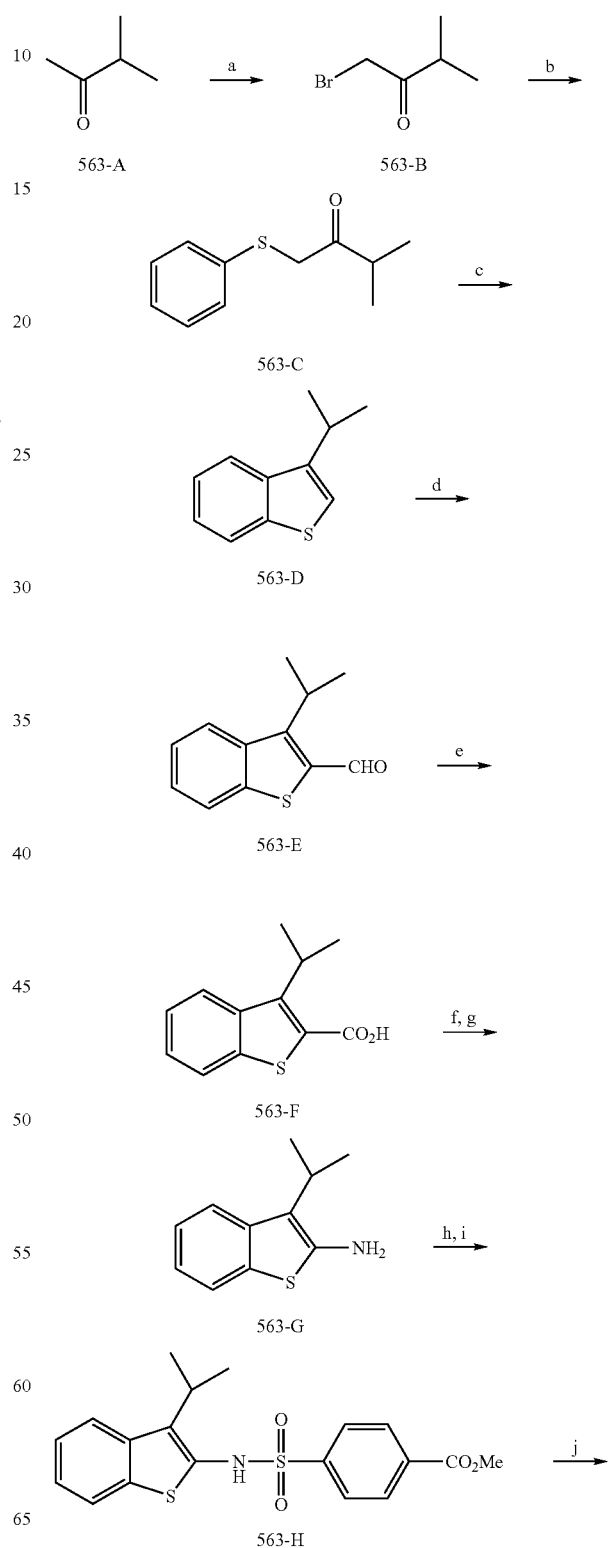

-continued

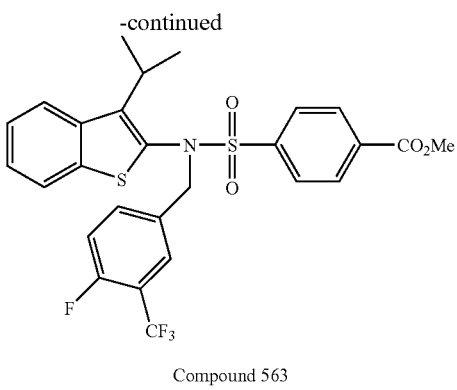

Compound 563 a) Br₂, MeOH;
b) thiophenol, pyridine, Et₂O;
c) PPA, PhCl;
d) n-BuLi, THF, DMF;
e) KMnO₄, acetone, H₂O;
f) DPPA, DiEA, t-BuOH;
g) 4N HCl in dioxane;
h) 4-chlorosulfonyl-benzoic acid, pyridine, DCM;
i) MeOH, H₂SO₄;
j) t-BuOK, 4-fluoro-3-trifluorobenzyl bromide, DMF.

1-Bromo-3-methyl-butan-2-one (563-B). To a solution of compound 563-A (6.0 g; 69.7 mmol) dissolved in MeOH (40 mL) and cooled to 0° C., was added bromine (3.56 mL; 69.7 mmol), at a rate such that the internal temperature did not exceed 10° C. The reaction was allowed to stir for 45 min at 5-10° C., to which was then added H₂O (20 mL) and the reaction was stirred for an additional 18 h at ambient temperature. Water was added to the reaction mixture, which was then extracted with diethyl ether. The combined ether extracts were washed sequentially with 10% aq. NaHCO₃, H₂O, and brine, dried over Na₂SO₄, filtered, and the filtrate was evaporated under reduced pressure to afford compound 563-B as an oil. ¹H-NMR (CDCl₃): δ 1.10-1.17 (d, 6H), 2.95-3.02 (m, 1H), 3.98 (s, 2H).

3-Methyl-1-phenylsulfanyl-butan-2-one (563-C). To a solution of thiophenol (4.44 mL; 43.4 mmol) in diethyl ether (29 mL) was added pyridine (17.2 mL; 0.21 mol), followed by the drop-wise addition of a solution of compound 563-B (7.18 g; 43.5 mmol) in diethyl ether (15 mL), at ambient temperature, and the reaction was stirred for 72 h. The reaction was diluted with EtOAc, washed with 2N HCl, H₂O, brine, dried over Na₂SO₄, filtered and the solvent evaporated under reduced pressure. The crude residue was purified by flash column chromatography (SiO₂) eluting with a heptane-EtOAc gradient to afford compound 563-C as an oil. ¹H-NMR (CDCl₃): δ 1.09-1.10 (d, 6H), 2.90-2.97 (m, 1H), 3.75 (s, 2H), 7.18-7.35 (m, 5H).

3-Isopropyl-benzo[b]thiophene (563-D). To a hot solution (136° C.) of PPA (8.2 g) in chlorobenzene (50 mL) is added a solution of compound 563-C (4.34 g; 22.4 mmol) in chlorobenzene (35 mL). The reaction was stirred at 136° C. for 18 h, cooled to ambient temperature, diluted with EtOAc, quenched with H₂O, and the EtOAc layer was washed with H₂O, brine, dried over Na₂SO₄, filtered and the solvent evaporated under reduced pressure. The crude residue was purified by flash column chromatography (SiO₂), eluting with a heptane-EtOAc gradient to afford compound 563-D as an oil. ¹H-NMR (DMSO-d₆): δ 1.31-1.33 (d, 6H), 3.26-3.31 (m, 1H), 7.33-7.43 (m, 2H), 7.83-7.85 (m, 1H), 7.95-7.97 (m, 1H); MS: m/z 328.0 (MH⁺).

3-Isopropyl-benzo[b]thiophene-2-carboxaldehyde (563-E). To a solution of compound 563-D (3.8 g, 21.5 mmol) in THF (70 mL), cooled to −70 to −78° C. was added a solution of n-butyl lithium (2.5 M in hexanes, 8.6 mL; 21.5 mmol), drop-wise. The reaction mixture was allowed to warm slowly to −20° C., then re-cooled to −73° C. DMF (2.5 mL) was added drop-wise to the solution at −70 to −78° C. The reaction mixture was allowed to warm ambient temperature and stirred for 18 h. The reaction mixture was cooled on an ice bath, and quenched with several ice chips. The reaction mixture was treated with saturated aqueous NH₄Cl, extracted with ethyl acetate, and the organic phase washed with brine, dried over Na₂SO₄, filtered, and the solvent was evaporated in vacuo. The crude residue was purified by flash column chromatography (SiO₂), eluting with an ethyl acetate (0-10%) in heptane gradient, to afford 2.06 g of compound 563-E as a yellow oil. ¹H-NMR (CDCl₃): δ 1.60 (d, 6H), 3.99 (q, 1H), 7.33-7.61 (m, 2H), 7.87 (d, 1H), 8.05 (d, 1H), 10.44 (s, 1H); MS: m/z 205.1 (MH⁺).

3-Isopropyl-benzo[b]thiophene-2-carboxylic acid (563-F). A solution of compound 563-E (1.95 g, 9.5 mmol) in acetone (30 mL) was refluxed for 30 min. A mixture of potassium permanganate (3.02 g, 19.1 mmol) in water (10 mL) was added in portions, and the resultant mixture was refluxed for an additional 30 min. The mixture was cooled to ambient temperature and concentrated in vacuo. A solution of aqueous Na₂SO₃ (1M, 50 mL) was added followed by sulfuric acid (1 M, 50 mL). Two additional portions of Na₂SO₃ (1M, 20 mL) were added followed by sulfuric acid (1 M, 20 mL), which resulted in the disappearance of the dark brown color. The resultant suspension was diluted with H₂O, filtered, washed with H₂O and dried under vacuo to afford 1.52 g of compound 563-F as a yellow solid. MS: m/z 221.1 (MH⁺).

2-Amino-3-isopropyl-benzo[b]thiophene, hydrochloride (563-G). A solution of compound 563-F (1.52 g, 6.90 mmol) and DIEA (1.45 mL, 8.27 mmol) in t-butanol (30 mL) was treated with DPPA (1.8 mL, 8.27 mmol) and refluxed for 6 h. The reaction mixture was cooled and the solvent evaporated in vacuo. The crude residue was purified by flash column chromatography (SiO₂) eluting with an ethyl acetate (0-20%) in heptane gradient, to afford 1.41 g of the BOC-protected amine (not shown). ¹H-NMR (CDCl₃): δ 1.41 (d, 6H), 1.55 (s, 9H), 3.26 (dt, 1H), 6.74 (br s, 1H), 7.12-7.39 (m, 2H), 7.57-7.86 (m, 2H); MS: m/z 292.2 (MH⁺). The BOC-protected amine (1.41 g, 4.84 mmol) was dissolved in 4N HCl in dioxane (20 mL) and stirred at ambient temperature for 6 h. The suspension was diluted with diethyl ether, the solid filtered, washed with diethyl ether, and dried under vacuo to afford 1.09 g of the hydrochloride salt of compound 563-G as a pale yellow solid. ¹H-NMR (DMSO-d₆): δ 1.35 (d, 6H), 3.33 (q, 1H), 7.03-7.20 (m, 1H), 7.27 (t, 1H), 7.73 (dd, 2H), 8.73 (br s, 1H); MS: m/z 192.0 (MH⁺).

N-(3-Isopropyl-benzo[b]thiophen-2-yl)-4-carboxy-benzenesulfonamide. A solution of compound 563-G (0.774 g, 3.40 mmol) and pyridine (577 μL, 7.14 mmol) in dichloromethane, cooled to −10° C., was treated with chlorosulfonyl-benzoic acid (0.787 g, 3.56 mmol) and the reaction mixture was stirred at ambient temperature for 4 h. The solvent was evaporated in vacuo, the residue treated with 2N HCl, the aqueous phase extracted with ethyl acetate, the organic phase washed with brine, dried over Na₂SO₄, filtered, and the solvent evaporated in vacuo to afford 1.16 g of the crude benzoic acid (not shown). ¹H-NMR (DMSO-d₆): δ 1.15 (d, 6H), 3.25 (dt, 1H), 7.25-7.37 (m, 2H), 7.67-7.99 (m, 4H), 8.13 (d, 2H), 10.66 (s, 1H); MS: m/z 192.0 (MH⁺).

N-(3-Isopropyl-benzo[b]thiophen-2-yl)-4-carbomethoxy-benzenesulfonamide (563-H). A solution of the crude benzoic acid (1.1 g, 2.93 mmol) and sulfuric acid (0.15 mL) in methanol (30 mL) was refluxed for 13 h. The solution cooled, concentrated in vacuo, and partitioned between dichloromethane and water. The organic layer was separated, and by flash column chromatography (SiO$_2$) eluting with an ethyl acetate (5-40%) in heptane gradient to afford 0.9 g of compound 563-H as a pale pink solid. $^1$H-NMR (DMSO-d$_6$): δ 1.16 (d, 6H), 3.26 (dt, 1H), 3.89 (s, 3H), 7.28-7.34 (m, 2H), 7.73-7.83 (m, 1H), 7.83-7.95 (m, 3H), 8.15 (d, 2H), 10.67 (s, 1H); MS: m/z 390.1 (MH$^+$).

Compound 563

N-(4-Fluoro-3-trifluoromethyl-benzyl)-N-(3-isopropyl-benzo[b]thiophen-2-yl)-4-carbomethoxy-benzenesulfonamide. A solution of compound 563-H (0.30 g, 0.77 mmol) in DMF (6 mL), at 0° C., was treated with a solution of potassium t-butoxide (1.0 M in THF, 0.81 mL, 0.81 mmol) and stirred for 10 min. 4-Fluoro-3-trifluoromethylbenzyl bromide (293 μL, 1.54 mmol) was added and the resultant solution was stirred at ambient temperature for 18 h. Water was added, the reaction mixture extracted with ethyl acetate, and the organic layer was washed with water (3×), brine, dried over Na$_2$SO$_4$, filtered, and the solvent was evaporated in vacuo. The product was purified by flash column chromatography (SiO$_2$) eluting with an ethyl acetate (1-35%) in heptane gradient to afford 0.29 g of compound 563 as a colorless solid. $^1$H-NMR (CDCl$_3$): δ 0.77 (d, 3H), 1.42 (d, 3H), 3.17-3.35 (m, 1H), 4.00 (s, 3H), 4.14 (d, 1H), 5.23 (d, 1H), 7.06 (t, 1H), 7.28-7.36 (m, 2H), 7.38-7.45 (m, 1H), 7.58 (dd, 1H), 7.65 (dd, 1H), 7.85-7.95 (m, 3H), 8.22 (d, 2H); MS: m/z 566.0 (MH$^+$).

Example 34

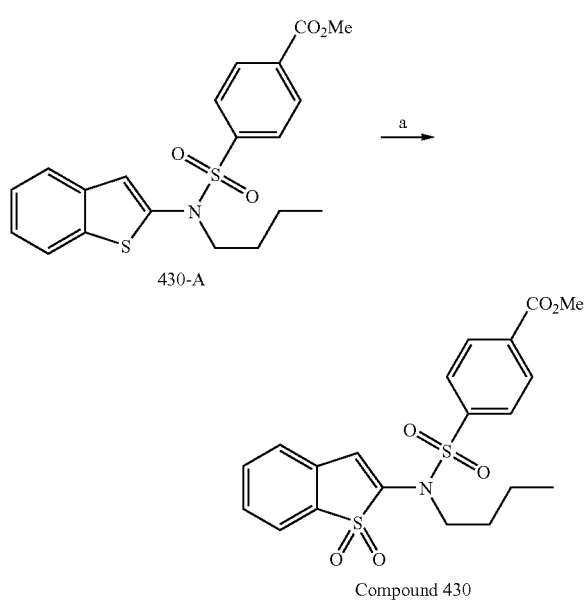

a) mCPBA, CHCl$_3$.

N-(Butyl)-N-(benzo[b]thiophen-2-yl)-4-carbomethoxy-benzenesulfonamide. Compound 430-A was prepared utilizing Compound 1-C, Example 32, steps E and F, and Example 3, step A. MS: m/z 404.2 (MH$^+$).

Compound 430

N-(Butyl)-N-(1,1-dioxo-benzo[b]thiophen-2-yl)-4-carbomethoxy-benzenesulfonamide. A solution of compound 430-A (0.199 g, 0.493 mmol) in chloroform (10 mL) was treated with meta-chloroperbenzoic acid (77%, 0.243 g, 1.08 mmol), and the reaction mixture was stirred at ambient temperature for 18 h. The mixture was washed with saturated aqueous sodium bicarbonate, dried over sodium sulfate, filtered and the solvent evaporated in vacuo. The crude residue was purified flash column chromatography (SiO$_2$), eluting with an ethyl acetate (10-50%) in heptane gradient to afford 0.120 g of compound 430 as a colorless solid. $^1$H-NMR (CDCl$_3$): δ 0.94 (t, 3H), 1.35-1.48 (m, 2H), 1.71-1.82 (m, 2H), 3.81 (t, 2H), 3.93 (s, 3H), 7.24 (s, 1H), 7.36 (d, 1H), 7.44-7.50 (m, 1H), 7.54-7.90 (m, 2H), 7.94 (d, 2H), 8.14 (d, 2H); MS: m/z 436.2 (MH$^+$).

Following the procedure described above for example 34 and substituting the appropriate reagents, starting materials and purification methods known to those skilled in the art, the following compounds of the present invention were prepared:

Compound 421

N-(4-Fluoro-3-trifluoromethyl-benzyl)-N-(1,1-dioxo-benzo[b]thiophen-2-yl)-benzenesulfonamide. MS: m/z 498.1 (MH$^+$).

Compound 431

N-(3-Bromo-1,1-dioxo-benzo[b]thiophen-2-yl)-N-(4-fluoro-3-trifluoromethyl-benzyl)-benzenesulfonamide. The precursor, N-(3-bromo-benzo[b]thiophen-2-yl)-N-(4-fluoro-3-trifluoromethyl-benzyl)-4-carbomethoxy-benzenesulfonamide, was synthesized from N-(benzo[b]thiophen-2-yl)-N-(4-fluoro-3-trifluoromethyl-benzyl)-4-carbomethoxy-benzenesulfonamide as per Example 5, step A. $^1$H-NMR (CDCl$_3$): δ 4.76 (br s, 2H), 7.08 (t, 1H), 7.51-7.72 (m, 8H), 7.76 (dd, 1H), 8.10 (d, 2H); MS: m/z 576 & 578.1 (MH$^+$).

Compound 433

N-(3-Bromo-1,1-dioxo-benzo[b]thiophen-2-yl)-N-(butyl)-4-carbomethoxy-benzenesulfonamide. The precursor, N-(3-bromo-benzo[b]thiophen-2-yl)-N-(butyl)-4-carbomethoxy-benzenesulfonamide, was synthesized from N-(benzo[b]thiophen-2-yl)-N-(butyl)-4-carbomethoxy-benzenesulfonamide as per Example 5, step A. $^1$H-NMR (CDCl$_3$): δ 0.89 (t, 3H), 1.36 (m, 2H), 1.69 (q, 2H), 3.53-3.65 (m, 2H), 3.97 (s, 3H), 7.60-7.76 (m, 4H), 8.12-8.18 (m, 2H), 8.19-8.25 (m, 2H); MS: m/z 514 & 516.0 (MH$^+$).

Compound 460

N-(3-Acetyl-1,1-dioxo-1H-benzo[b]thiophen-2-yl)-N-(4-fluoro-3-trifluoromethyl-benzyl)-benzenesulfonamide. The precursor, N-(3-acetyl-benzo[b]thiophen-2-yl)-N-(4-fluoro-3-trifluoromethyl-benzyl)-4-carbomethoxy-benzenesulfonamide, was synthesized from N-(benzo[b]thiophen-2-yl)-N-(4-fluoro-3-trifluoromethyl-benzyl)-4-carbomethoxy-benzenesulfonamide as per Example 14, step A. $^1$H-NMR (CDCl$_3$): δ 2.27 (s, 3H), 4.96 (s, 2H), 7.19 (t, 1H), 7.48-7.74 (m, 7H), 7.79-7.89 (m, 1H), 7.89-8.00 (m, 3H); MS: m/z 540.2 (MH$^+$), 562.0 (MNa$^+$).

Compound 463

N-(4-Fluoro-3-trifluoromethyl-benzyl)-N-[3-(1-hydroxy-1-methyl-ethyl)-1,1-dioxo-benzo[b]thiophen-2-yl]-benzenesulfonamide. The precursor, N-(4-fluoro-3-trifluoromethyl-benzyl)-N-[3-(1-hydroxy-1-methyl-ethyl)-benzo[b]thiophen-2-yl]-benzenesulfonamide, was synthesized from N-(3-acetyl-benzo[b]thiophen-2-yl)-N-(4-fluoro-3-trifluoromethyl-benzyl)-benzenesulfonamide as per Example 19, step A. $^1$H-NMR (CDCl$_3$): δ 1.46 (s, 3H), 1.78 (s, 3H), 3.52 (br s, 1H), 4.88 (d, 1H), 4.95 (d, 1H), 7.05 (t, 1H), 7.45-7.49 (m, 2H), 7.52-7.68 (m, 3H), 7.69-7.73 (m, 3H), 7.79 (dd, 1H), 7.92 (d, 2H); MS: m/z 538.0 (M-OH)$^+$, 578.1 (MNa$^+$).

Compound 464

N-(3,4-Difluoro-benzyl)-N-[3-(1-hydroxy-ethyl)-1,1-dioxo-benzo[b]thiophen-2-yl]-benzenesulfonamide. The precursor, N-(3,4-difluorobenzyl)-N-[3-(1-hydroxy-1-ethyl)-benzo[b]thiophen-2-yl]benzenesulfonamide, was synthesized from N-(3-acetyl-benzo[b]thiophen-2-yl)-N-(3,4-difluorobenzyl)-benzenesulfonamide as per Example 18, step A. $^1$H-NMR (CDCl$_3$): δ 1.04 (d, 3H), 4.58 (d, 1H), 4.87-4.93 (m, 2H), 7.08-7.18 (m, 1H), 7.41-7.45 (m, 1H), 7.53-7.72 (m, 7H), 7.95 (d, 1H), 8.04 (d, 2H); MS: m/z 474.1 (M-OH)$^+$, 514.0 (MNa$^+$).

Compound 577

N-(3-Bromo-1,1-dioxo-1H-benzo[b]thiophen-2-yl)-N-(2-cyclopropylethyl)-benzenesulfonamide. The precursor, N-(3-bromo-benzo[b]thiophen-2-yl)-N-(2-cyclopropylethyl)-benzenesulfonamide, was synthesized from N-(benzo[b]thiophen-2-yl)-N-(2-cyclopropylethyl)-benzenesulfonamide as per Example 5, step A. $^1$H-NMR (CDCl$_3$): δ −0.02-0.06 (m, 2H), 0.24-0.47 (m, 2H), 0.52-0.75 (m, 1H), 1.47-1.73 (m, 2H), 3.48-3.80 (m, 2H), 7.49-7.79 (m, 7H), 8.03-8.19 (m, 2H); MS: m/z 468 & 470.1 (MH$^+$).

Compound 618

N-(2-Cyclopropyl-ethyl)-N-(3-methyl-1,1-dioxo-benzo[b]thiophen-2-yl)-benzenesulfonamide. $^1$H-NMR (CDCl$_3$): δ 0.02-0.09 (m, 2H), 0.27-0.49 (m, 2H), 0.51-0.74 (m, 1H), 1.45-1.75 (m, 2H), 2.38 (s, 3H), 3.66 (t, 2H), 7.42-7.71 (m, 7H), 7.97-8.30 (m, 2H); MS: m/z 404.1 (MH$^+$).

Compound 619

N-(3-Methyl-1,1-dioxo-benzo[b]thiophen-2-yl)-N-(3,3,3-trifluoro-propyl)-benzenesulfonamide. $^1$H-NMR (CDCl$_3$): δ 2.39 (s, 3H), 2.44-2.70 (m, 2H), 3.86 (t, 2H), 7.47-7.62 (m, 4H), 7.62-7.72 (m, 3H), 8.05 (d, 2H); MS: m/z 432.0 (MH$^+$).

Compound 620

N-(3-Methyl-1,1-dioxo-benzo[b]thiophen-2-yl)-N-(4,4,4-trifluoro-butyl)-benzenesulfonamide. $^1$H-NMR (CDCl$_3$): δ 1.77-2.03 (m, 2H), 2.04-2.31 (m, 2H), 2.40 (s, 3H), 3.67 (t, 2H), 7.49-7.61 (m, 4H), 7.61-7.69 (m, 3H), 8.01-8.05 (m, 2H); MS: m/z 446.1 (MH$^+$).

Compound 621

N-(3-Methyl-1,1-dioxo-benzo[b]thiophen-2-yl)-N-(5,5,5-trifluoro-pentyl)-benzenesulfonamide. $^1$H-NMR (CDCl$_3$): δ 1.36-1.68 (m, 2H), 1.70-1.84 (m, 2H), 1.91-2.20 (m, 2H), 2.39 (s, 3H), 3.60 (t, 2H), 7.47-7.60 (m, 4H), 7.60-7.69 (m, 3H), 8.01-8.07 (m, 2H); MS: m/z 460.0 (MH$^+$).

Compound 622

N-(4-Fluoro-3-trifluoromethyl-benzyl)-N-(3-methyl-1,1-dioxo-benzo[b]thiophen-2-yl)-benzenesulfonamide. MS: m/z 512.0 (MH$^+$).

Compound 632

N-(2-Cyclopropyl-ethyl)-N-(3-methyl-1,1-dioxo-benzo[b]thiophen-2-yl)-4-carboxy-benzenesulfonamide. MS: m/z 447.7 (MH$^+$).

Compound 633

N-(3-Methyl-1,1-dioxo-benzo[b]thiophen-2-yl)-N-(5,5,5-trifluoro-pentyl)-4-carboxy-benzenesulfonamide. MS: m/z 503.7 (MH$^+$).

Compound 634

N-(4-Fluoro-3-trifluoromethyl-benzyl)-N-(3-methyl-1,1-dioxo-benzo[b]thiophen-2-yl)-4-carboxy-benzenesulfonamide. MS: m/z 555.6 (MH$^+$).

Example 35

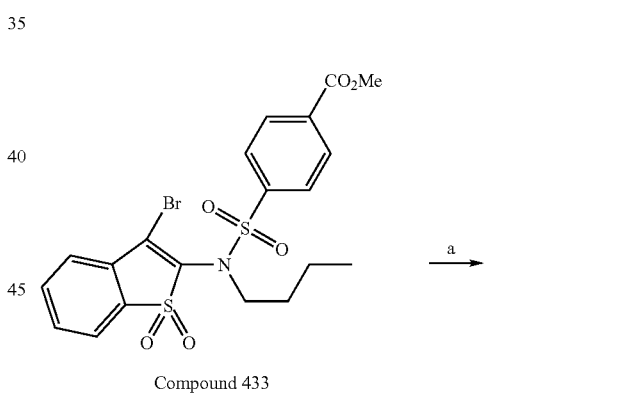

Compound 433

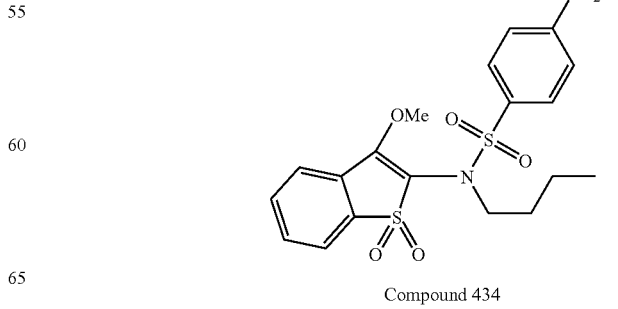

Compound 434

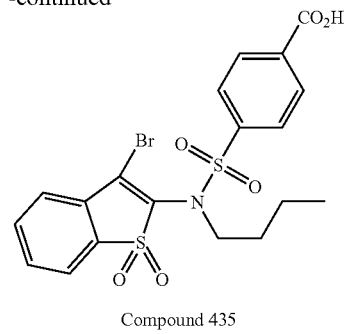

Compound 435

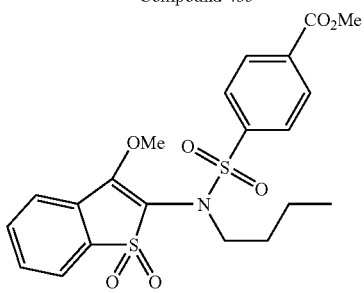

Compound 436 a) 1N NaOH, MEOH.

Compounds 434, 435, 436

N-(Butyl)-N-(3-methoxy-1,1-dioxo-1H-benzo[b]thiophen-2-yl)-4-carboxy-benzenesulfonamide, N-(butyl)-N-(3-bromo-1,1-dioxo-1H-benzo[b]thiophen-2-yl)-4-carboxy-benzenesulfonamide, and N-(butyl)-N-(3-methoxy-1,1-dioxo-1H-benzo[b]thiophen-2-yl)-4-carbomethoxy-benzenesulfonamide. A solution of compound 433 (0.525 g, 1.02 mmol) in methanol (10 mL) was treated with 1N sodium hydroxide (1.3 mL, 1.3 mmol) and refluxed for 30 minutes. The solution was cooled, neutralized with 1N hydrochloric acid the solvent evaporated in vacuo, and the crude residue purified by reverse phase pHPLC ($C_{18}$) using a gradient of acetonitrile (30-90%) in water (0.1% TFA), to afford 0.015 g of compound 434, 0.050 g of compound 435, and 0.15 g of compound 436.

Compound 434

N-(Butyl)-N-(3-methoxy-1,1-dioxo-1H-benzo[b]thiophen-2-yl)-4-carboxy-benzenesulfonamide. $^1$H-NMR (CDCl$_3$): δ 0.94 (t, 3H), 1.33-1.43 (m, 2H), 1.78-1.86 (m, 2H), 3.70 (t, 2H), 4.47 (s, 3H), 7.58-7.70 (m, 4H), 8.17 (d, 2H), 8.30 (d, 2H); MS: m/z 452.1 (MH$^+$).

Compound 435

N-(Butyl)-N-(3-bromo-1,1-dioxo-1H-benzo[b]thiophen-2-yl)-4-carboxy-benzenesulfonamide. $^1$H-NMR (CDCl$_3$): δ 0.90 (t, 3H), 1.33-1.42 (m, 2H), 1.67-1.74 (m, 2H), 3.61 (t, 2H), 7.60-7.74 (m, 4H), 8.19 (d, 2H), 8.28 (d, 2H); MS: m/z 500 & 502.0 (MH$^+$).

Compound 436

N-(Butyl)-N-(3-methoxy-1,1-dioxo-1H-benzo[b]thiophen-2-yl)-4-carbomethoxy-benzenesulfonamide. $^1$H-NMR (CDCl$_3$): δ 0.93 (t, 3H), 1.32-1.41 (m, 2H), 1.74-1.82 (m, 2H), 3.65 (t, 2H), 3.96 (s, 3H), 4.44 (s, 3H), 7.55-7.70 (m, 4H), 8.10 (d, 2H), 8.18 (d, 2H); MS: m/z 466.2 (MH$^+$).

Example 36

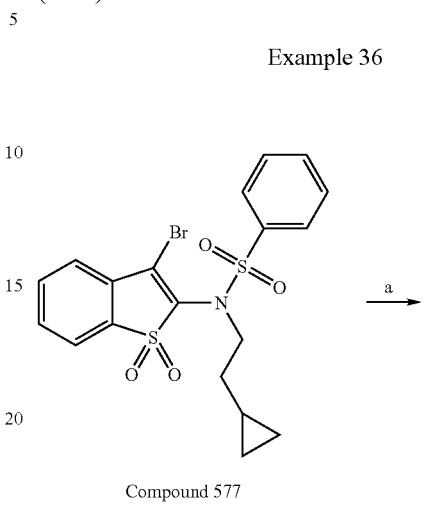

Compound 577 a) THF, MeNH$_2$.

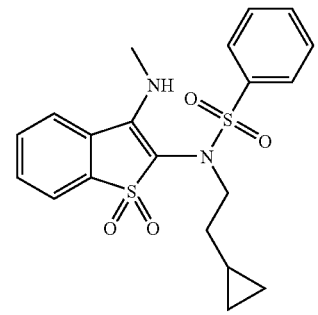

Compound 644

Compound 644

N-(2-Cyclopropylethyl)-N-(3-methylamino-1,1-dioxo-1H-benzo[b]thiophen-2-yl)-benzenesulfonamide. A solution of compound 577 (56 mg, 0.120 mmol) in THF (1 mL) was treated with a solution of methylamine in THF (2.0 M, 1 mL, 2.0 mmol) and stirred at ambient temperature for 1 h. The solvent was evaporated in vacuo and the crude residue purified by reverse phase pHPLC, eluting with an acetonitrile (20-90%) in water (0.1% TFA) gradient to afford 30 mg of compound 644 as a colorless solid. $^1$H-NMR (DMSO-d$_6$): δ −0.01-0.03 (m, 2H), 0.19-0.47 (m, 2H), 0.47-0.77 (m, 1H), 1.20-1.47 (m, 1H), 1.66 (tt, 1H), 3.19 (d, 3H), 3.47 (td, 1H), 3.65 (td, 1H), 7.32-7.89 (m, 7H), 7.84-8.14 (m, 3H); MS: m/z 419.1 (MH$^+$).

Following the procedure described above for example 36 and substituting the appropriate reagents, starting materials and purification methods known to those skilled in the art, the following compounds of the present invention were prepared:

Compound 536

N-(Butyl)-N-(3-dimethylamino-1,1-dioxo-1H-benzo[b]thiophen-2-yl)-4-carboxy-benzenesulfonamide. MS: m/z 465.1 (MH$^+$).

Compound 643

N-(2-Cyclopropylethyl)-N-(3-dimethylamino-1,1-dioxo-1H-benzo[b]thiophen-2-yl)-benzenesulfonamide. $^1$H-NMR (CDCl$_3$): δ −0.02-0.06 (m, 2H), 0.25-0.46 (m, 2H), 0.51-0.74 (m, 1H), 1.47-1.86 (m, 2H), 3.03-3.27 (s, 6H), 3.62 (td, 1H), 3.70-3.90 (m, 1H), 7.42-7.71 (m, 7H), 8.02 (d, 2H); MS: m/z 433.0 (MH$^+$).

Compound 645

N-(2-Cyclopropyl-ethyl)-N-[3-(4-methyl-piperazin-1-yl)-1,1-dioxo-1H-1λ$^6$-benzo[b]thiophen-2-yl]-benzenesulfonamide. MS: m/z 488.1 (MH$^+$).

Compound 646

N-(3-Amino-1,1-dioxo-1H-benzo[b]thiophen-2-yl)-N-(2-cyclopropylethyl)-benzenesulfonamide. MS: m/z 405.1 (MH$^+$).

Compound 647

N-(2-Cyclopropyl-ethyl)-N-(1,1-dioxo-3-piperazin-1-yl-1H-1λ$^6$-benzo[b]thiophen-2-yl)-benzenesulfonamide. MS: m/z 474.1 (MH$^+$).

Compound 648

N-(4-Fluoro-3-trifluoromethyl-benzyl)-N-(3-methylamino-1,1-dioxo-1H-1λ$^6$-benzo[b]thiophen-2-yl)-benzenesulfonamide. MS: m/z 527.1 (MH$^+$).

Compound 649

N-(4-Fluoro-3-trifluoromethyl-benzyl)-N-[3-(4-methyl-piperazin-1-yl)-1,1-dioxo-benzo[b]thiophen-2-yl]-benzenesulfonamide. MS: m/z 596.1 (MH$^+$).

Example 37

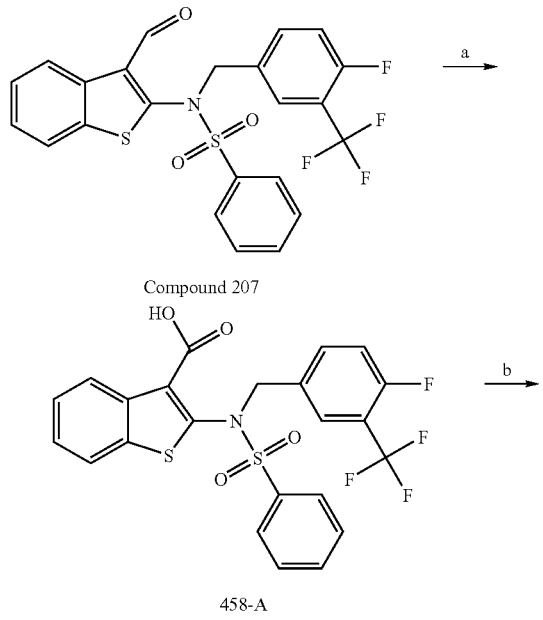

Compound 207

458-A

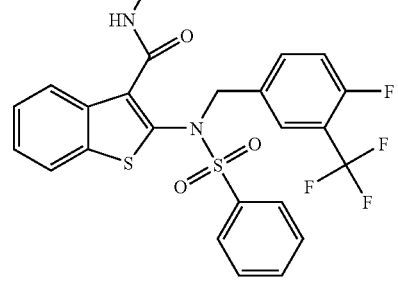

Compound 458 a) KMnO$_4$, acetone, water;
b) HBTU, DIEA, MeNH$_2$, THF, CH$_3$CN.

N-(4-Fluoro-3-trifluoromethyl-benzyl)-N-(3-carboxy-benzo[b]thiophen-2-yl)-benzenesulfonamide (458-A). A solution of compound 207 (0.4 g, 0.81 mmol) in acetone 1 (15 mL) was heated to reflux and treated with a solution of potassium permanganate (0.192 g, 1.21 mmol) in water (~3 mL). The resultant mixture was refluxed for an additional 2 h. The mixture was concentrated in vacuo, diluted with water, treated with 1M Na$_2$SO$_3$ (4 mL) and IM sulfuric acid (4 mL). The clear colorless solution was extracted with dichloromethane, washed with 1N hydrochloric acid, dried over sodium sulfate, filtered and the solvent was evaporated in vacuo to afford 0.41 g of compound 458-A as a colorless solid. $^1$H-NMR (CDCl$_3$): δ 4.88 (s, 2H), 7.04 (t, 1H), 7.30-7.79 (m, 10H), 8.32 (d, 1H); MS: m/z 510.0 (MH$^+$).

Compound 458

N-(3-Methyl-carbamoyl-benzo[b]thiophen-2-yl)-N-(4-fluoro-3-trifluoromethyl-benzyl)-benzenesulfonamide. A solution of compound 458-A (0.41 g, 0.804 mmol) in acetonitrile (12 mL) was treated with diisopropylethylamine (350 μL, 2.01 mmol) and HBTU (0.336 g, 0.885 mmol) and stirred at ambient temperature for 5 min. The resultant solution was split into 3 equal portions. One portion was treated with methylamine (2.0 M in THF, 402 μL, 402 mmol) and stirred for 18 h. The reaction mixture was partitioned between dichloromethane and water, the organic layer dried over sodium sulfate, filtered and the solvent evaporated in vacuo. The crude residue was purified by reverse phase pHPLC (C$_{18}$), eluting with an acetonitrile (30-90%) in water (0.1% TFA) gradient to afford 73 mg of compound 458 as a colorless solid. $^1$H-NMR (CDCl$_3$): δ 2.96 (d, 2H), 4.47 (br s, 1H), 4.74 (br s, 2H), 7.04 (t, 1H), 7.19-7.32 (m, 1H), 7.32-7.46 (m, 2H), 7.49-7.71 (m, 4H), 7.72-7.84 (m, 1H), 7.85-8.01 (m, 3H); MS: m/z 523.2 (MH$^+$).

Following the procedure described above for example 37 and substituting the appropriate reagents, starting materials and purification methods known to those skilled in the art, the following compounds of the present invention were prepared:

Compound 457

N-(3-Dimethyl-carbamoyl-benzo[b]thiophen-2-yl)-N-(4-fluoro-3-trifluoromethyl-benzyl)-benzenesulfonamide. MS: m/z 537.2 (MH$^+$).

Compound 459

N-(3-Carbamoyl-benzo[b]thiophen-2-yl)-N-(4-fluoro-3-trifluoromethyl-benzyl)-benzenesulfonamide. $^1$H-NMR (CDCl$_3$): δ 4.77 (br s, 2H), 6.86 (br s, 1H), 7.04 (t, 1H), 7.32-7.48 (m, 3H), 7.52 (dd, 1H), 7.60-7.68 (m, 2H), 7.70-7.80 (m, 3H), 7.90 (d, 2H), 8.02 (d, 1H); MS: m/z 509.1 (MH$^+$).

Compound 465

N-(Butyl)-N-(3-carbamoyl-benzo[b]thiophen-2-yl)-4-carbomethoxy-benzenesulfonamide. MS: m/z 447.1 (MH$^+$).

Compound 466

N-(Butyl)-N-(3-methyl-carbamoyl-benzo[b]thiophen-2-yl)-4-carbomethoxy-benzenesulfonamide. MS: m/z 461.1 (MH$^+$).

Compound 467

N-(Butyl)-N-(3-dimethyl-carbamoyl-benzo[b]thiophen-2-yl)-4-carbomethoxy-benzenesulfonamide. $^1$H-NMR (CDCl$_3$): δ 0.85 (t, 3H), 1.19-1.37 (m, 2H), 1.43-1.58 (m, 1H), 1.61-1.81 (m, 1H), 2.90 (s, 3H), 3.16 (s, 3H), 3.45 (ddd, 1H), 3.86 (ddd, 1H), 3.98 (s, 3H), 7.34-7.44 (m, 2H), 7.51-7.60 (m, 1H), 7.66-7.75 (m, 1H), 7.90 (d, 2H), 8.19 (d, J=8.67 Hz, 2H); MS: m/z 475.2 (MH$^+$).

Example 38

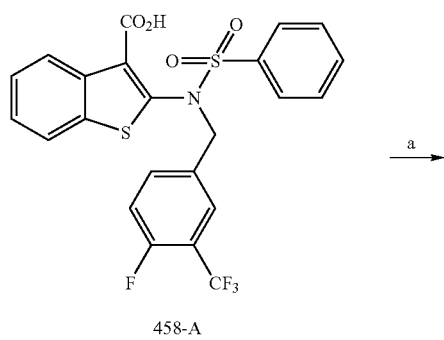
458-A

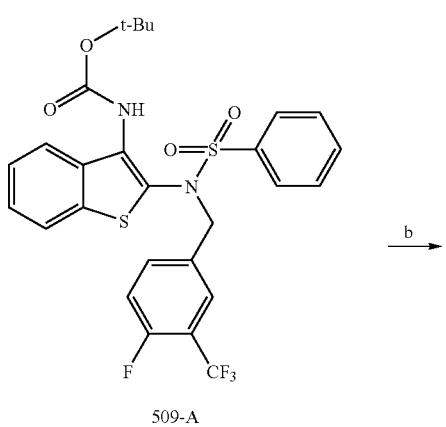
509-A

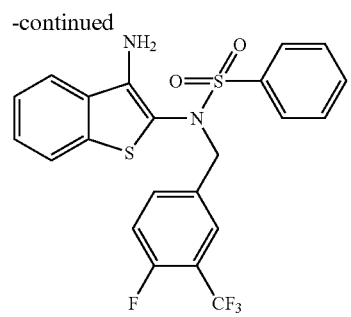
509-B

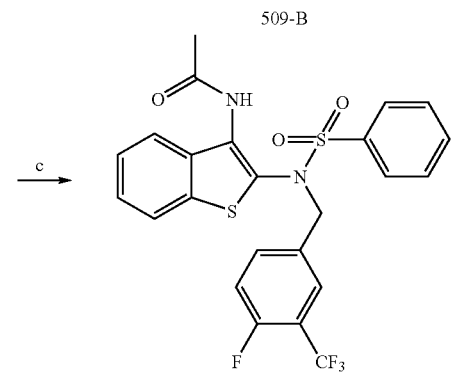
Compound 509 a) DPPA, DIEA, tBuOH;
b) HCl, dioxane;
c) DIEA, CH$_3$COCl, DCM.

{2-[Benzenesulfonyl-(4-fluoro-3-trifluoromethyl-benzyl)-amino]-benzo[b]thiophen-3-yl}-carbamic acid t-butyl ester (509-A). A solution of compound 458-A (1.96 g, 3.85 mmol) and diisopropylethylamine (806 µL, 4.61 mmol) in t-butanol (30 mL) was treated with DPPA (1.0 mL, 4.61 mmol) and refluxed for 6 h. The solvent was evaporated in vacuo, and the crude residue purified by flash column chromatography (SiO$_2$), eluting with an ethyl acetate (10-35%) in heptane gradient, to afford compound 509-A (1.0 g, 45%) as a yellow amorphous solid. $^1$H-NMR (CDCl$_3$): δ 1.48 (br s, 9H), 4.74 (s, 2H), 6.92-7.14 (m, 2H), 7.29-7.39 (m, 2H), 7.43-7.58 (m, 5H), 7.62-7.77 (m, 4 H); MS: m/z 603.0 (MNa$^+$).

N-(3-Amino-benzo[b]thiophen-2-yl)-N-(4-fluoro-3-trifluoromethyl-benzyl)-benzenesulfonamide (509-B). Compound 509-A (1.0 g, 1.72 mmol) was dissolved in 4N HCl in dioxane (20 mL) and stirred at ambient temperature for 18 h. The resultant suspension was diluted with diethyl ether, filtered, washed with diethyl ether and dried under vacuo to afford 0.65 g of compound 509-B. MS: m/z 481.0 (MH$^+$).

Compound 509

N-{2-[Benzenesulfonyl-(4-fluoro-3-trifluoromethyl-benzyl)-amino]-benzo[b]thiophen-3-yl}-acetamide. A solution of compound 509-B (80 mg, 0.155 mmol) and diisopropylethylamine (68 µL, 0.387 mmol) in dichloromethane, cooled to 0° C., was treated with acety chloride (15 µL, 0.201 mmol) and the resultant solution was stirred at ambient temperature for 18 h. An additional portion of acetyl chloride (15 µL, 0.201 mmol) was added, and the solution was stirred an additional hour. The solution was washed with 2N HCl, saturated aqueous sodium bicarbonate, dried over sodium sulfate, filtered and the solvent evaporated in vacuo. The crude residue was purified by reverse phase pHPLC (C$_{18}$), eluting with a gradient of acetonitrile (40-90%) in water (0.1% TFA) to afford crude compound 509. Crude compound 509 was further purified by flash column chromatography (SiO$_2$) eluting with an ethyl acetate (20-70%) in heptane gradient to afford 51 mg of compound 509 an off-white solid. $^1$H-NMR (CDCl$_3$): δ 2.11 (s, 3H), 4.68 (br s, 2H), 6.75-7.08 (m, 1H), 7.11-7.71 (m, 11H), 7.88 (br s, 1H); MS: m/z 523.0 (MH$^+$).

Compound 500

N-(3-Acetylamino-benzo[b]thiophen-2-yl)-N-(butyl)-4-carbomethoxy-benzenesulfonamide. MS: m/z 461.1 (MH$^+$).

Example 39

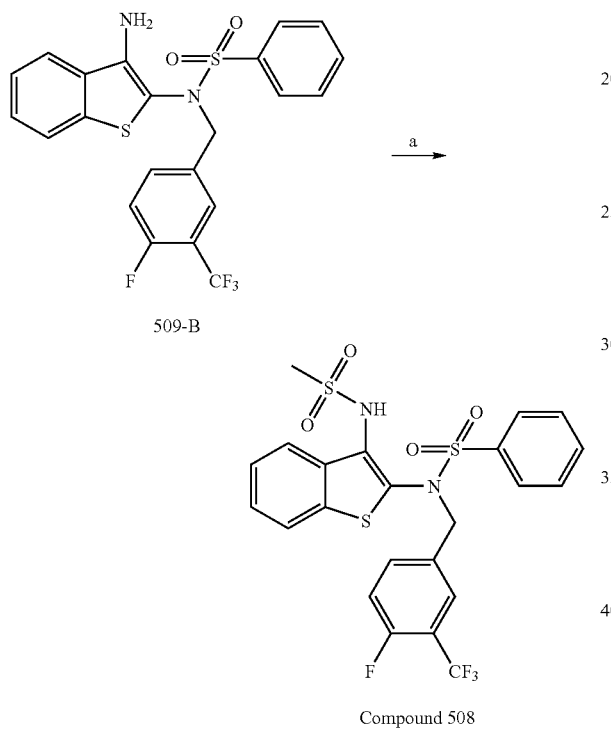

a) pyridine, CH$_3$SO$_2$Cl, DCE, DIEA.

Compound 508

N-(4-Fluoro-3-trifluoromethyl-benzyl)-N-(3-methanesulfonylamino-benzo[b]thiophen-2-yl)-benzenesulfonamide. To a solution of compound 509-B (75 mg, 0.145 mmol) and pyridine (25 μL, 0.304 mmol) in dichloroethane (2 mL), cooled to 0° C., was added a solution of methanesulfonyl chloride IM in dichloromethane (0.145 mL, 0.145 mmol). After stirring the reaction at ambient temperature for 1 h, pyridine (2 mL) was added and the solution cooled on an ice bath. An additional portion of methanesulfonyl chloride (30 μL) was added, and the solution stirred 4 h at ambient temperature. Diisopropylethylamine (60 mL) was added followed by another portion of methanesulfonyl chloride (30 μL), and the reaction mixture stirred for 2 days. The solution was partitioned between dichloromethane and 2N HCl, dried over sodium sulfate filtered, and the solvent was evaporated in vacuo. The crude residue was purified by reverse phase pHPLC, using a gradient of acetonitrile (40-90%) in water (0.1% TFA) to afford 11 mg of compound 508 as a colorless solid. $^1$H-NMR (CDCl$_3$): δ 2.69 (s, 3H), 4.77 (br s, 2H), 7.11 (t, 1H), 7.35-7.47 (m, 3H), 7.50-7.62 (m, 5H), 7.64-7.73 (m, 3H), 8.02 (d, 1H); MS: m/z 559.0 (MH$^+$).

Example 40

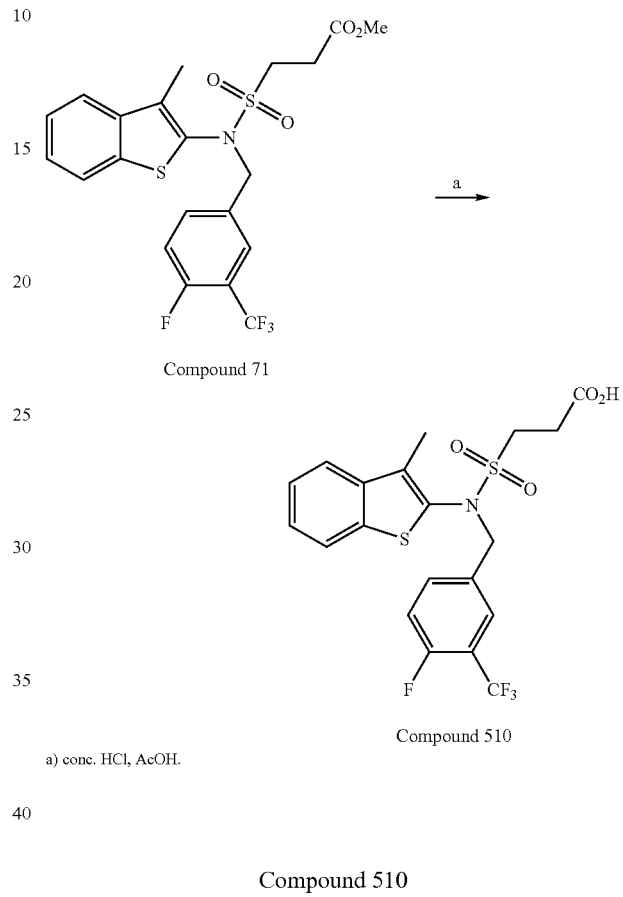

a) conc. HCl, AcOH.

Compound 510

N-(4-Fluoro-3-trifluoromethyl-benzyl)-N-(3-methyl-benzo[b]thiophen-2-yl)-2-carboxy-ethanesulfonamide. A solution of compound 71 (110 mg, 0.225 mmol) in acetic acid (5 mL) and 6N HCl (5 mL) was refluxed for 2 h. The reaction mixture was cooled and the solvent evaporated in vacuo. The crude residue was purified by pHPLC (C$_{18}$), eluting with an acetonitrile (30-90%) in water (0.1% TFA) gradient, to afford 60 mg of compound 510 as a colorless solid. $^1$H-NMR (CDCl$_3$): δ 2.04 (s, 3H), 2.91-3.04 (m, 2H), 3.48-3.63 (m, 2H), 4.82 (br s, 2H), 7.10 (t, 1H), 7.32-7.42 (m, 2H), 7.42-7.51 (m, 1H), 7.51-7.64 (m, 2H), 7.68-7.82 (m, 1H); MS: m/z 476.1 (MH$^+$).

Following the procedure described above for example 40 and substituting the appropriate reagents, starting materials and purification methods known to those skilled in the art, the following compounds of the present invention were prepared:

Compound 604

N-(3-Methyl-benzo[b]thiophen-2-yl)-N-(3,3,3-trifluoropropyl)-2-carboxy-ethanesulfonamide. MS: m/z 396.0 (MH$^+$).

Compound 605

N-(3-Methyl-benzo[b]thiophen-2-yl)-N-(4,4,4-trifluoro-butyl)-2-carboxy-ethanesulfonamide. MS: m/z 410.1 (MH$^+$).

Compound 606

N-(3-Methyl-benzo[b]thiophen-2-yl)-N-(5,5,5-trifluoro-pentyl)-2-carboxy-ethanesulfonamide. MS: m/z 424.0 (MH$^+$).

Compound 762

N-(3-Methyl-benzo[b]thiophen-2-yl)-N-(3-trifluoromethoxy-benzyl)-2-carboxy-ethanesulfonamide.
$^1$H-NMR (CDCl$_3$): δ 2.00 (s, 3H), 2.88-3.06 (m, 2H), 3.55 (t, 2H), 4.81 (br s, 2H), 7.11-7.41 (m, 6H), 7.55-7.62 (m, 1H), 7.70-7.78 (m, 1H); MS: m/z 474.0 (MH$^+$).

Compound 795

N-(3-Methyl-benzo[b]thiophen-2-yl)-N-(4-trifluoromethoxy-benzyl)-2-carboxy-ethanesulfonamide.
$^1$H-NMR (CDCl$_3$): δ 1.98 (s, 3H), 2.77 (t, 2H), 2.67 (t, 2H), 4.83 (br s, 2H), 7.23-7.35 (m, 2H), 7.35-7.46 (m, 4H), 7.62-7.73 (m, 1H), 7.84-7.96 (m, 1H), 12.57 (br s, 1H); MS: m/z 474.0 (MH$^+$).

Example 41

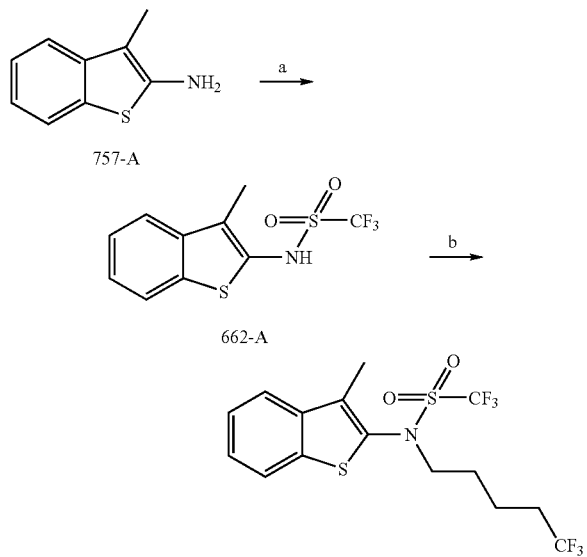

Compound 662 a) 1. (CF$_3$SO$_2$)$_2$O, TEA, DCM; 2. 3N NaOH, MeOH;
b) PPh$_3$, DEAD, HO(CH$_2$)$_4$CF$_3$.

N-(3-Methyl-benzo[b]thiophen-2-yl)-C,C,C-trifluoromethanesulfonamide (662-A). A solution of compound 757-A (0.25 g, 1.25 mmol) and triethylamine (540 μL, 3.88 mmol) in dichloromethane (10 mL,) cooled to −10° C., was treated with trifluoromethanesulfonic anhydride (442 μL, 2.62 mmol). The reaction mixture was stirred at −10° C. for 1 h, washed with 1N HCl, dried over Na$_2$SO$_4$, filtered, and the solvent was evaporated in vacuo to afford crude a bis-sulfonylated by-product. The bis-sulfonylated by-product was dissolved in methanol (4 mL), treated with 4 N NaOH (625 mL, 1.88 mmol) and stirred at ambient temperature for 1 h. The solution was concentrated in vacuo, diluted with H$_2$O, acidified with 2N HCl, extracted with EtOAc, and the organic phase washed with brine, dried over Na$_2$SO$_4$, filtered, and the solvent was evaporated in vacuo to afford 0.35 g of crude compound 662-A. MS: m/z 294.0 (M-H)$^-$.

Compound 662

C,C,C-Trifluoro-N-(3-methyl-benzo[b]thiophen-2-yl)-N-(5,5,5-trifluoro-pentyl)-methanesulfonamide. A solution of triphenylphosphine (0.404 g, 1.54 mmol) in THF (10 mL) was treated with DEAD (40% in toluene, 684 μL, 1.54 mmol) and stirred at ambient temperature for 5 min. Compound 662-A (0.35 g) was added and the reaction mixture stirred for 15 min, to which was added 5,5,5-trifluoropentanol (164 μL, 1.42 mmol), and the resultant solution was stirred at ambient temperature for 4 h. The solvent was evaporated in vacuo, and the crude residue purified by flash column chromatography (SiO$_2$) eluting with an ethyl acetate (1-30%) in heptane gradient to afford crude compound 662. Further purification by pHPLC (C$_{18}$), eluting with an acetonitrile (40-90%) in water (0.1% TFA) gradient, to afford 0.126 g of compound 662 as an oil. $^1$H-NMR (CDCl$_3$): δ 1.58-1.78 (m, 4H), 1.96-2.18 (m, 2H), 2.42 (s, 3H), 3.73-3.90 (m., 2H), 7.35-7.50 (m, 2H), 7.62-7.83 (m, 2H); MS: m/z 420.0 (MH$^+$).

Following the procedure described above for example 41 and substituting the appropriate reagents, starting materials and purification methods known to those skilled in the art, the following compounds of the present invention were prepared:

Compound 664

C,C,C-Trifluoro-N-(4-fluoro-3-trifluoromethyl-benzyl)-N-(3-methyl-benzo[b]thiophen-2-yl)-methanesulfonamide. MS: m/z 472.0 (MH$^+$).

Compound 665

N-(2-Cyclopropyl-ethyl)-C,C,C-trifluoro-N-(3-methyl-benzo[b]thiophen-2-yl)-methanesulfonamide. MS: m/z 364.0 (MH$^+$).

Example 42

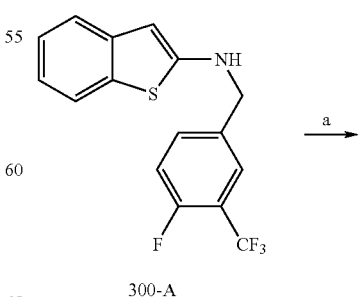

300-A

-continued

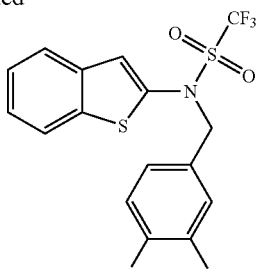

Compound 663 a) TEA, (CF₃SO₂)₂O, DCM.

Compound 663

N-Benzo[b]thiophen-2-yl-N-(4-fluoro-3-trifluoromethyl-benzyl)-C,C,C-trifluoro-methanesulfonamide. A solution of compound 300-A (0.101 g, 0.279 mmol) and triethylamine (86 µL, 0.614 mmol) in dichloromethane (4 mL), cooled to −10° C., was treated with trifluoromethanesulfonic anhydride (52 µL, 0.307 mmol) and stirred at −10° C. for 1 h. The reaction mixture was washed with 2N HCl, dried over Na₂SO₄, filtered, and the solvent evaporated in vacuo. The crude residue was purified by pHPLC ($C_{18}$), eluting with an acetonitrile (30-90%)-water gradient, to afford 40 mg of compound 663 as a brown oil. ¹H-NMR (CDCl₃): δ 4.49 (s, 2H), 7.11-7.26 (m, 3H), 7.36 (t, 1H), 7.47-7.68 (m, 4H).

Example 43

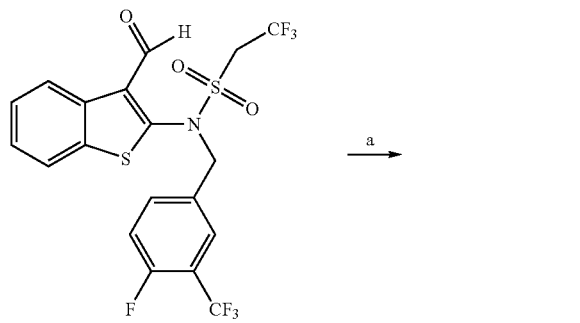

704-A

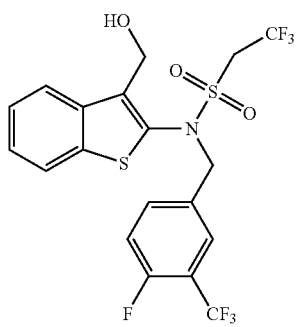

Compound 704 a) LiBH₄, THF.

(4-Fluoro-3-trifluoromethyl-benzyl)-(3-formyl-benzo[b]thiophen-2-yl)-2,2,2-trifluoro-ethanesulfonamide (704-A). Compound 704-A was prepared using the procedure in Example 16, step A, substituting compound 1 with compound 697.

Compound 704

N-(3-Hydroxymethyl-benzo[b]thiophen-2-yl)-N-(4-fluoro-3-trifluoromethyl-benzyl)-2,2,2-trifluoro-ethane-sulfonamide. A solution of compound 704-A (0.16 g, 0.32 mmol) in THF (5 mL) was treated with lithium borohydride (10 mg, 0.46 mmol) and stirred at ambient temperature for 2 h. The reaction mixture was quenched with H₂O, stirred for 2 h and extracted ethyl acetate. The organic phase was washed with brine, dried over Na₂SO₄, filtered, and the solvent was evaporated in vacuo. The crude residue was purified by flash column chromatography (SiO₂), eluting with an ethyl acetate (10-50%) in heptane gradient to afford 70 mg of compound 704 as a colorless solid. ¹H-NMR (CDCl₃): δ 2.21 (t, 1H), 4.03 (q, 2H), 4.22 (d, 2H), 4.87 (s, 2H), 7.13 (t, 1H), 7.39-7.54 (m, 4H), 7.76-7.85 (m, 1H), 7.85-8.01 (m, 1H); MS: m/z 484.0 [M-(OH⁻)]⁺, 524.1 (MNa⁺).

Example 44

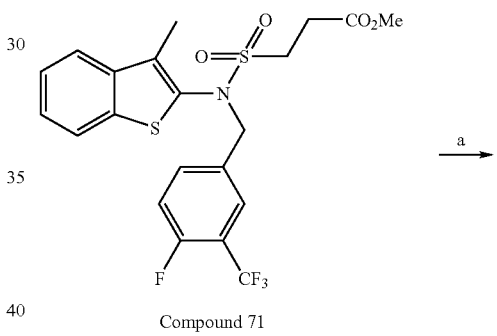

Compound 71

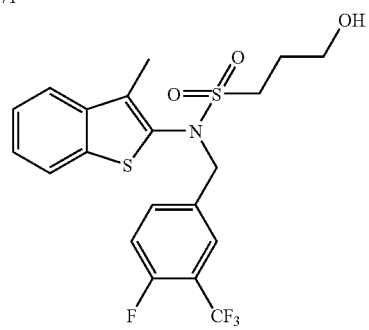

Compound 699 a) LiBH₄, THF.

Compound 699

N-(4-Fluoro-3-trifluoromethyl-benzyl)-N-(3-methyl-benzo[b]thiophen-2-yl)-3-hydroxy-propanesulfonamide. A solution of compound 71 (0.47 g, 0.96 mmol) in THF (5 mL) was treated with lithium borohydride (21 mg, 0.96 mmol) and stirred at ambient temperature for 1 h. An additional portion of lithium borohydride (30 mg, 1.38 mmol) was added and the resultant mixture was stirred at ambient temperature for 2 h.

Water (2 mL) was added, the reaction mixture stirred for 5 min and then partitioned between ethyl acetate and water. The organic layer was washed with brine, dried over $Na_2SO_4$, filtered, and the solvent evaporated in vacuo. The crude residue was purified by flash column chromatography ($SiO_2$) eluting with an ethyl acetate (30-100%) in heptane gradient to afford 0.334 g of compound 699 as a colorless oil. $^1$H-NMR ($CDCl_3$): δ 1.61 (t, 1H), 2.06 (s, 3H), 2.11-2.23 (m, 2H), 3.34-3.44 (m, 2H), 3.83 (q, 2H), 4.82 (br s, 2H), 7.09 (t, 1H), 7.34-7.43 (m, 2H), 7.43-7.53 (m, 1H), 7.52-7.65 (m, 2H), 7.69-7.78 (m, 1H); MS: m/z 462.1 (MH$^+$).

Following the procedure described above for example 44 and substituting the appropriate reagents, starting materials and purification methods known to those skilled in the art, the following compounds of the present invention were prepared:

Compound 758

N-(4-Fluoro-3-trifluoromethyl-benzyl)-N-(3-methyl-benzo[b]thiophen-2-yl)-4-hydroxy-butanesulfonamide. $^1$H-NMR ($CDCl_3$): δ 1.38 (t, 1H), 1.68-1.82 (m, 2H), 1.97-2.15 (m, 2H) superimposed on 2.09 (s, 3H), 3.20-3.36 (m, 2H), 3.72 (q, 2H), 4.82 (br s, 2H), 7.09 (t, 1H), 7.34-7.42 (m, 2H), 7.44-7.51 (m, 1H), 7.53-7.63 (m, 2H), 7.70-7.77 (m, 1H); MS: m/z 476.1 (MH$^+$).

Compound 764

N-(3-Methyl-benzo[b]thiophen-2-yl)-N-(3-trifluormethoxy-benzyl)-3-hydroxy-propanesulfonamide. $^1$H-NMR ($CDCl_3$): δ 1.64 (t, 1H), 2.02 (s, 3H), 2.10-2.25 (m, 2H), 3.29-3.43 (m, 2H), 3.82 (q, 2H), 4.81 (br s, 2H), 7.10-7.41 (m, 6H), 7.59 (dd, 1H), 7.68-7.76 (m, 1H); MS: m/z 460.0 (MH$^+$).

Compound 793

N-(4-Fluoro-3-trifluoromethyl-benzyl)-N-(3-methyl-benzo[b]thiophen-2-yl)-2-hydroxy-ethanesulfonamide. $^1$H-NMR ($CDCl_3$): δ 2.04 (s, 3H), 2.45 (t, 1H), 3.41-3.56 (m, 2H), 4.08-4.25 (m, 2H), 4.83 (br s, 2H), 7.10 (t, 1H), 7.34-7.43 (m, 2H), 7.43-7.51 (m, 1H), 7.53-7.64 (m, 2H), 7.69-7.77 (m, 1H); MS: m/z 448.0 (MH$^+$).

Example 45

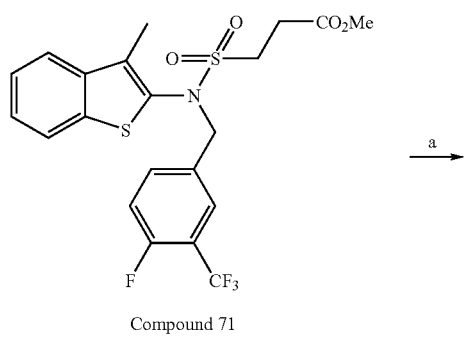

Compound 71

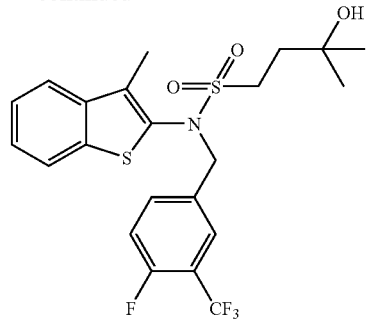

Compound 725 a) MeMgBr, THF.

Compound 725

N-(4-Fluoro-3-trifluoromethyl-benzyl)-N-(3-methyl-benzo[b]thiophen-2-yl)-3-hydroxy-3-methyl-butane-1-sulfonamide. A solution of compound 71 (0.11 g, 0.225 mmol) in THF (4 mL) cooled to −10° C., was treated with methylmagnesium bromide (3 M in $Et_2O$, 2 mL, 6 mmol) and stirred at −10° C. for 1 h. Saturated aqueous ammonium chloride (0.5 mL) was added, the mixture partitioned between $H_2O$ and EtOAc, the organic layer washed with brine, and dried over $Na_2SO_4$, filtered, and the solvent evaporated under reduced pressure. The crude residue was purified by flash column chromatography ($SiO_2$) eluting with an ethyl acetate (10-60%) in heptane gradient to afford 73 mg of compound 725 as a colorless oil. $^1$H-NMR ($CDCl_3$): δ 1.18-1.33 (br s, 1H) superimposed on 1.30 (s, 6H), 1.98-2.11 (m, 2H) superimposed on 2.06 (s, 3H), 3.33-3.44 (m, 2H), 4.82 (br s, 2H), 7.09 (t, 1H), 7.35-7.42 (m, 2H), 7.44-7.51 (m, 1H), 7.54-7.63 (m, 2H), 7.70-7.77 (m, 1H); MS: m/z 490.0 (MH$^+$).

Following the procedure described above for example 45 and substituting the appropriate reagents, starting materials and purification methods known to those skilled in the art, the following compounds of the present invention were prepared:

Compound 371

N-(3-Methyl-benzo[b]thiophen-2-yl)-N-(4,4,4-trifluoro-butyl)-4-(1-hydroxy-1-methyl-ethyl)-benzenesulfonamide. $^1$H-NMR (DMSO-$d_6$): δ 1.46 (s, 6H), 1.60-1.67 (m, 2H), 2.22 (s, 3H), 2.30-2.39 (m, 2H), 3.16-3.18 (d, 1H), 3.60 (m, 1H), 7.39-7.47 (m, 2H), 7.72 (s, 4H), 7.75-7.80 (m, 1H), 7.82-7.89 (m, 1H); MS: m/z 472.0 (MH$^+$).

Compound 374

N-(3-Methyl-benzo[b]thiophen-2-yl)-N-(4-fluoro-3-trifluoromethyl-benzyl)-4-(1-hydroxy-1-methyl-ethyl)-benzenesulfonamide. $^1$H-NMR (DMSO-$d_6$): δ 1.48 (s, 6H), 1.94 (s, 3H), 4.82 (s, 2H), 5.33 (s, 1H), 7.35-7.47 (m, 3H), 7.61-7.87 (m, 8H); MS: m/z 537.9 (MH$^+$).

Compound 759

N-(4-Fluoro-3-trifluoromethyl-benzyl)-N-(3-methyl-benzo[b]thiophen-2-yl)-4-hydroxy-4-methyl-pentane-1-sulfonamide. $^1$H-NMR ($CDCl_3$): δ 1.23 (s, 1H), 1.26 (s, 6H), 1.57-1.67 (m, 2H), 1.97-2.09 (m, 2H) superimposed on 2.09 (s, 3H), 3.21-3.32 (m, 2H), 4.82 (br s, 2H), 7.09 (t, 1H), 7.35-7.42 (m, 2H), 7.45-7.51 (m, 1H), 7.53-7.63 (m, 2H), 7.67-7.83 (m, 1H); MS: m/z 526.0 (MNa⁺).

Compound 763

N-(3-Methyl-benzo[b]thiophen-2-yl)-N-(3-trifluoromethoxy-benzyl)-3-hydroxy-3-methyl-butane-1-sulfonamide. ¹H-NMR (CDCl₃): δ 1.29 (s, 6H), 1.30 (s, 1H), 1.98-2.10 (m, 2H) superimposed on 2.02 (s, 3H), 3.32-3.45 (m, 2H), 4.81 (br s, 2H), 7.10-7.41 (m, 6H), 7.55-7.62 (m, 1H), 7.73 (dd, 1H); MS: m/z 488.1 (MH⁺).

Compound 796

N-(3-Methyl-benzo[b]thiophen-2-yl)-N-(4-trifluoromethoxy-benzyl)-3-hydroxy-3-methyl-butane-1-sulfonamide. ¹H-NMR (CDCl₃): δ 1.29 (s, 6H) superimposed on 1.33 (br s, 1H), 1.99 (s, 3H), 2.01-2.09 (m, 2H), 3.26-3.49 (m, 2H), 4.80 (br s, 2H), 7.10 (d, 2H), 7.28-7.41 (m, 4H), 7.53-7.63 (m, 1H), 7.68-7.79 (m, 1H); MS: m/z 488.1 (MH⁺).

Example 46

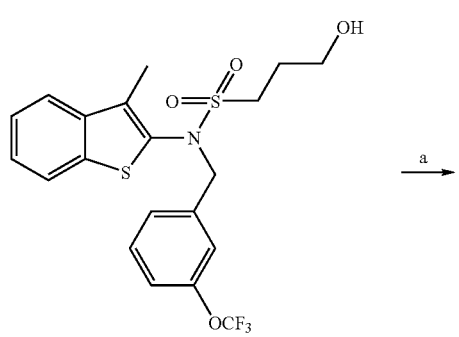

Compound 764

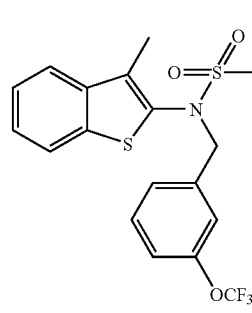

Compound 769 a) DCM, PPh₃, CBr₄.

Compound 769

N-(3-Methyl-benzo[b]thiophen-2-yl)-N-(3-trifluoromethoxy-benzyl)-3-bromo-propane-1-sulfonamide. A solution of compound 764 (0.80 g, 1.7 mmol) and CBr₄ (0.635 g, 1.92 mmol) in dichloromethane (25 mL) was treated with triphenylphosphine (0.503 g, 1.92 mmol) and stirred at ambient temperature for several hours. Additional portions of CBr₄ (0.20 g, 0.6 mmol) and triphenylphosphine (0.15 g, 0.57 mmol) were added and stirred an additional 18 h. The solvent was evaporated and the crude residue purified by flash column chromatography (SiO₂) eluting with an ethyl acetate (1-25%) in heptane gradient to afford 0.90 g of compound 769 as an oil. ¹H-NMR (CDCl₃): δ 2.02 (s, 3H), 2.39-2.51 (m, 2H), 3.34-3.43 (m, 2H), 3.55 (t, 2H), 4.81 (br s, 2H), 7.10-7.41 (m, 6H), 7.55-7.62 (m, 1H), 7.70-7.77 (m, 1H); MS: m/z 522, 524 (MH⁺).

Following the procedure described above for example 46 and substituting the appropriate reagents, starting materials and purification methods known to those skilled in the art, the following compounds of the present invention were prepared:

Compound 771

N-(4-Fluoro-3-trifluoromethyl-benzyl)-N-(3-methyl-benzo[b]thiophen-2-yl)-4-bromo-butane-1-sulfonamide. ¹H-NMR (CDCl₃): δ 1.98-2.20 (m, 4H) superimposed on 2.04 (s, 3H), 3.17-3.31 (m, 2H), 3.45 (t, 2H), 4.83 (br s, 2H), 7.10 (t, 1H), 7.34-7.43 (m, 2H), 7.44-7.51 (m, 1H), 7.53-7.64 (m, 2H), 7.70-7.78 (m, 1H); MS: m/z 538.0, 540.0 (MH⁺).

Compound 797

N-(4-Fluoro-3-trifluoromethyl-benzyl)-N-(3-methyl-benzo[b]thiophen-2-yl)-2-bromo-ethane-1-sulfonamide. ¹H-NMR (CDCl₃): δ 1.97-2.11 (m, 3H), 3.62-3.79 (m, 4H), 4.82 (br s, 2H), 7.10 (t, 1H), 7.36-7.51 (m, 3H), 7.54 (dd, 1H), 7.58-7.64 (m, 1H), 7.72-7.79 (m, 1H); MS: m/z 510, 512.0 (MH⁺).

Example 47

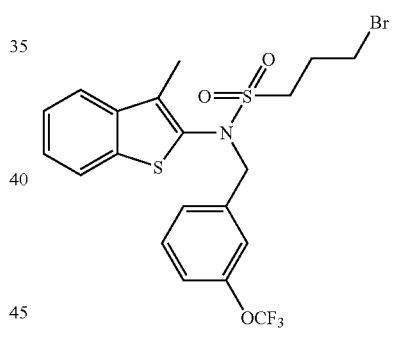

Compound 769

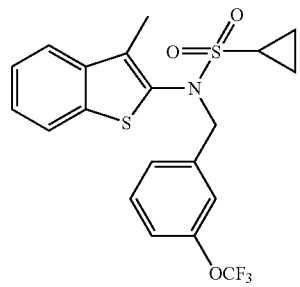

Compound 770 a) sodium imidazolide, DMF.

Compound 770

N-(3-Methyl-benzo[b]thiophen-2-yl)-N-(3-trifluoromethoxy-benzyl)-cyclopropanesulfonamide. A solution of compound 769 (90 mg, 0.172 mmol) in DMF (2 mL) was treated with sodium imidazolide (0.10 g, 1.1 mmol), and the resultant mixture was stirred at ambient temperature for 18 h. The solvent was evaporated, and the crude residue pre-absorbed onto silica gel. The product was isolated by flash column chromatography ($SiO_2$) eluting with an ethyl acetate (5-40%)-heptane gradient to afford 51 mg of compound 770 as an oil. $^1$H-NMR ($CDCl_3$): δ 1.03-1.14 (m, 2H), 1.20-1.32 (m, 2H), 2.05 (s, 3H), 2.61 (tt, 1H), 4.81 (br s, 2H), 7.11 (d, 1H), 7.18-7.31 (m, 3H), 7.31-7.41 (m, 2H), 7.54-7.62 (m, 1H), 7.69-7.76 (m, 1H); MS: m/z 442.0.

Example 48

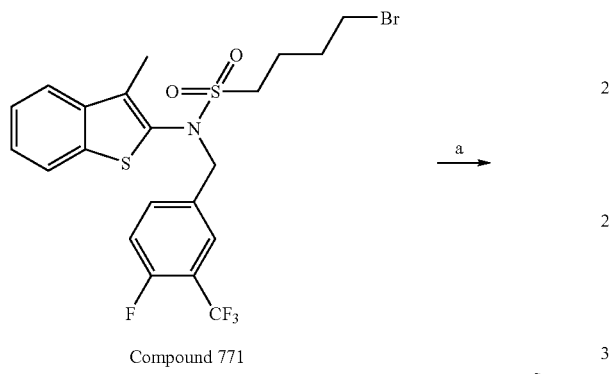

a) imidazole, $CH_3CN$.

Compound 779

N-(4-Fluoro-3-trifluoromethyl-benzyl)-N-(3-methyl-benzo[b]thiophen-2-yl)-4-(imidazol-1-yl)-butane-1-sulfonamide. A solution of compound 771 (96 mg, 0.18 mmol) in acetonitrile (1 mL) was treated with imidazole (0.25 g, 3.7 mmol) and heated at 80° C. for 18 h. The solvent was evaporated in vacuo, and the crude residue was purified by pHPLC ($C_{18}$) eluting with an acetonitrile (20-90%) in water (0.1% TFA) gradient to afford 58 mg of compound 779 as the product as the TFA salt. $^1$H-NMR (DMSO-$d_6$): δ 1.67-1.82 (m, 2H), 1.90-2.06 (m, 2H) superimposed on 2.02 (s, 3H), 3.40-3.61 (m, 2H), 4.27 (t, 2H), 4.86 (br s, 2H), 7.34-7.52 (m, 3H), 7.58-7.76 (m, 4H), 7.81 (t, 1H), 7.84-7.97 (m, 1H), 9.15 (s, 1H); MS: m/z 526.2 ($MH^+$).

Following the procedure described above for example 48 and substituting the appropriate reagents, starting materials and purification methods known to those skilled in the art, the following compounds of the present invention were prepared:

Compound 778

N-(3-Methyl-benzo[b]thiophen-2-yl)-N-(3-trifluoromethoxy-benzyl)-3-imidazol-1-yl-propane-1-sulfonamide. MS: m/z 510.1 ($MH^+$).

Example 49

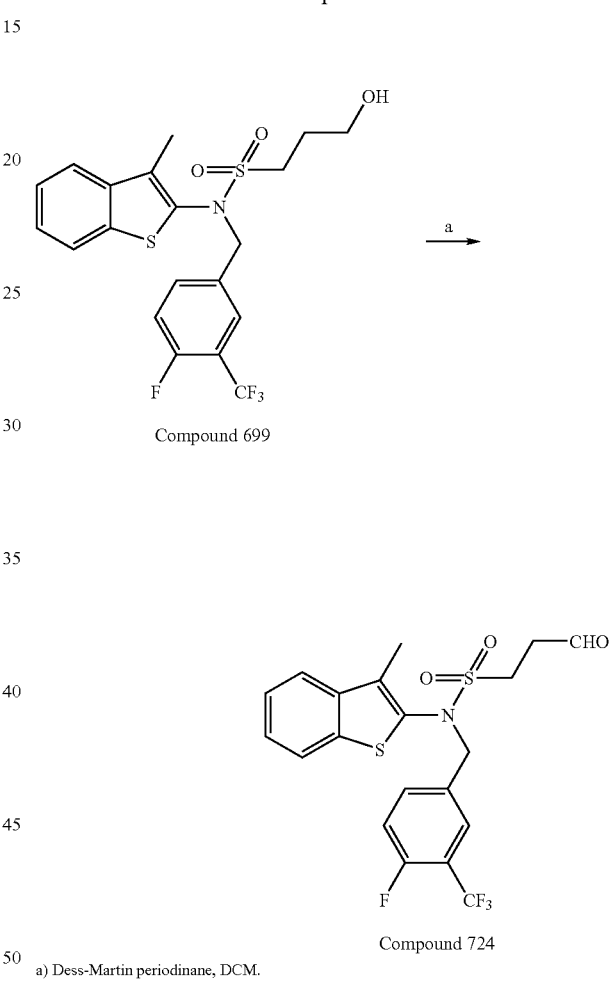

Compound 724

N-(4-Fluoro-3-trifluoromethyl-benzyl)-N-(3-methyl-benzo[b]thiophen-2-yl)-3-oxo-propane-1-sulfonamide. A solution of compound 699 (0.415 g, 0.899 mmol) in dichloromethane (20 mL) was treated with Dess-Martin periodinane (0.57 g, 1.35 mmol) and stirred at ambient temperature for 3 days. The crude residue was preabsorbed onto silica gel and purified by flash column chromatography ($SiO_2$) eluting with an ethyl acetate (10-60%) in heptane gradient to afford 0.255 g of compound 724 as an oil. $^1$H-NMR ($CDCl_3$): δ 2.04 (s, 3H), 3.11 (t, 2H), 3.55 (t, 2H), 4.81 (br s, 2H), 7.10 (t, 1H), 7.34-7.43 (m, 2H), 7.44-7.51 (m, 1H), 7.53-7.63 (m, 2H), 7.70-7.77 (m, 1H), 9.84 (s, 1H); MS: m/z 460.0.

Example 50

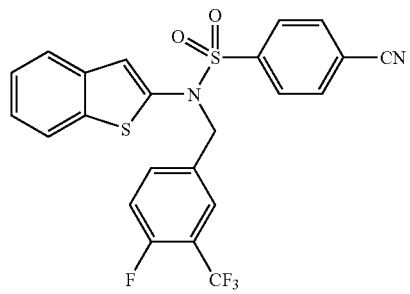

Compound 411

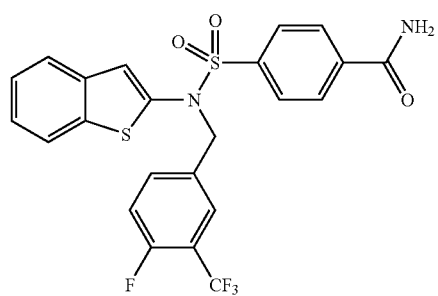

a) MeOH, HCl.

Compound 413

N-(Benzo[b]thiophen-2-yl)-N-(4-fluoro-3-trifluoromethyl-benzyl)-4-carboxamide-benzenesulfonamide. To a pressure vessel containing compound 411 (266 mg; 0.542 mmol) was added methanol (5 mL). The suspension was cooled to 0° C., hydrogen chloride$_g$ was bubbled into the suspension for 10 min, the reaction was sealed and allowed to stir at ambient temperature for 2 h. The reaction was cooled, the pressure released, and the solvent evaporated under reduced pressure. The crude residue was purified by reverse-phase semi-prep HPLC (Gemini, C-18 column; 100×30 mm I.D.; 5μ) eluting with a 55 to 75% gradient to afford 61 mg of compound 413 as a white solid. MS: m/z 509.0 (MH$^+$).

Following the procedure described above for example 50 and substituting the appropriate reagents, starting materials and purification methods known to those skilled in the art, the following compounds of the present invention were prepared:

Compound 414

N-(Benzo[b]thiophen-2-yl)-N-(4,4,4-trifluoro-butyl)-4-carboxamide-benzene-sulfonamide. MS: m/z 443.0 (MH$^+$)

Example 51

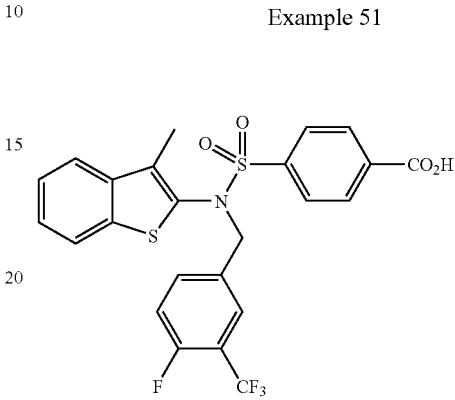

Compound 306

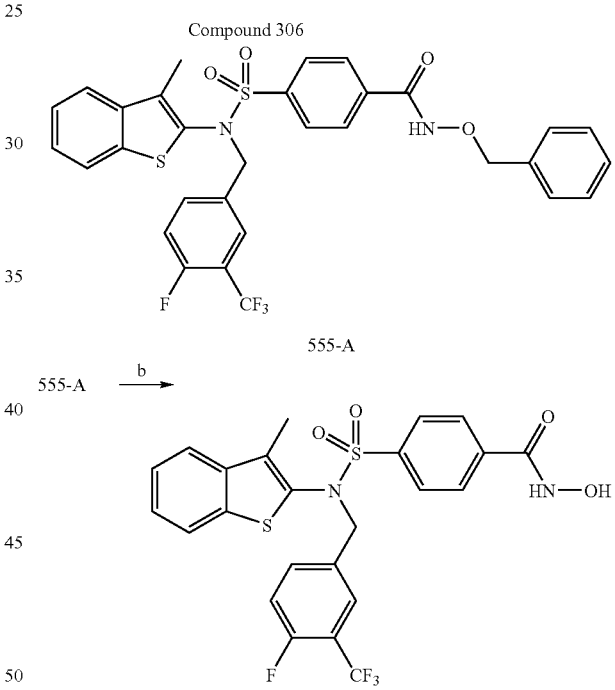

a) DCM, EDC-HCl, H$_2$NOBz;
b) DCM, BBr$_3$.

4-Benzyloxy-4-[4-fluoro-3-trifluoromethyl-benzyl)-(3-methyl-benzo[b]thiophen-2-yl)-sulfamoyl]-benzamide (555-A). To a suspension of compound 306 (127.6 mg; 0.244 mmol) in CH$_2$Cl$_2$ (1 mL) was added H$_2$NOBz (60 mg; 0.488 mmol) followed by EDC-HCl (94 mg; 0.488 mmol) and the reaction was allowed to stir at ambient temperature for 5 h. The reaction mixture was diluted with EtOAc, washed with H$_2$O (2×), brine, dried over Na$_2$SO$_4$, filtered and the solvent evaporated under reduced pressure. The crude residue was purified by flash chromatography (SiO$_2$) eluting with a heptane-EtOAc gradient to afford 118.4 mg of compound 555-A as a white solid. $^1$H-NMR (DMSO-d$_6$): δ 1.94 (s, 3H), 4.97 (s, 4H), 7.37-7.49 (m, 8H), 7.64-7.70 (m, 3H), 7.82-7.85 (m, 1H), 7.99 (s, 5H), 12.10 (s, 1H); MS: m/z 629.1 (MH$^+$).

Compound 555

4-([4-Fluoro-3-trifluoromethyl-benzyl)-(3-methyl-benzo[b]thiophen-2-yl)-sulfamoyl]-N-hydroxy-benzamide. To a solution of compound 555-A (91.6 mg; 0.175 mmol) in CH$_2$Cl$_2$ (2 mL), cooled to 0° C., was added a 1.0M soln of BBr$_3$-CH$_2$Cl$_2$ (0.263 mL) and the reaction was stirred at ambient temperature for 8 h. The solvent was evaporated under reduced pressure and the crude residue purified by reverse-phase semi-prep HPLC (Gemini, C-18 column; 100× 30 mm I.D.; 5μ) eluting with a 50% to 70% MeCN—H$_2$O gradient to afford 46.0 mg of compound 555 as a red oil. $^1$H-NMR (DMSO-d$_6$): δ 1.94 (s, 3H), 4.88 (s, 2H), 7.36-7.40 (m, 2H), 7.43-7.48 (m, 1H), 7.64-7.69 (m, 3H), 7.81-7.86 (m, 1H), 7.95-8.02 (m, 4H), 9.28 (s, 1H), 11.53 (s, 1H); MS: m/z 539.1 (MH$^+$).

Example 52

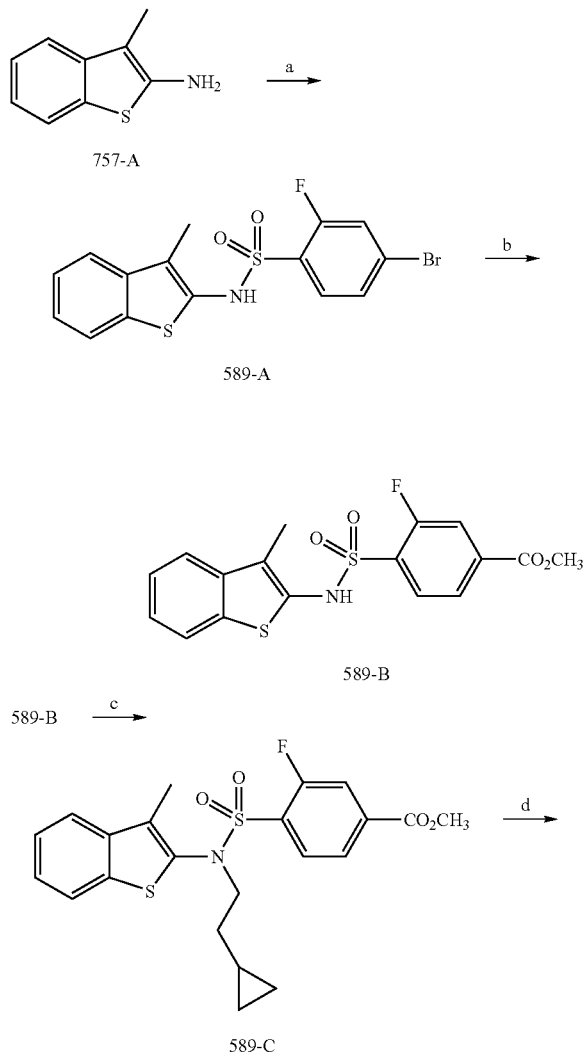

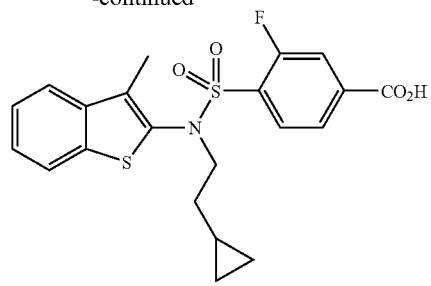

Compound 589 a) DCM, pyridine, 4-bromo-2-fluorobenzene sulfonyl chloride;
b) DMF, MeOH, (PPh$_3$)$_2$PdCl$_2$, CO;
c) THF, DEAD, PPh$_3$, cyclopropylethanol;
d) MeOH, NaOH.

4-Bromo-2-fluoro-N-(3-methyl-benzo[b]thiophen-2-yl)-benzenesulfonamide (589-A). To a suspension of compound 757-A (1.64 g; 8.23 mmol) in CH$_2$Cl$_2$ (10 mL), was added pyridine (1.33 mL; 16.5 mmol) and the reaction was cooled to 5° C. 4-Bromo-2-fluorobenzene sulfonyl chloride (2.5 g; 9.14 mmoL), dissolved in CH$_2$Cl$_2$ (5 mL) was added drop-wise, and the reaction was allowed to stir at ambient temperature for 18 h. The reaction was diluted with EtOAc, washed with 1N HCl, water, brine, dried over Na$_2$SO$_4$, filtered, and the solvent evaporated under reduced pressure. The crude solid was triturated with CH$_2$Cl$_2$-MeOH, filtered, and the solid washed with ether and dried under vacuo to afford 450 mg of compound 589-A as a white solid. The solvent was evaporated and the crude residue dried under vacuo to afford an additional 2.4 g of compound 589-A as a pink solid. MS: m/z 423.9 (MH$^+$+MeCN).

2-Fluoro-4-(3-methyl-benzo[b]thiophen-2-yl)-4-carbomethoxy-benzene-sulfonamide (589-B). To a solution of compound 589-A (2.46 g; 6.14 mmol), in DMF (30 mL) and MeOH (70 mL), was added TEA (2.57 mL; 18.4 mmol), and (PPh$_3$)$_2$PdCl$_2$ (194 mg). The reaction mixture was added to a high pressure vessel, purged with vacuo and CO (3×). Carbon monoxide was added to the vessel to 50 psi, and the reaction was heated at 80° C. for 18 h. An additional 239 mg of palladium catalyst was added, CO added and the reaction heated at 80° C. for an additional 96 h (convenient—over weekend). The reaction was cooled, the pressure carefully released, and the solvent concentrated under reduced pressure. The crude residue was diluted with EtOAc, washed with H$_2$O (2×), brine, dried over Na$_2$SO$_4$, filtered and the solvent evaporated under reduced pressure. The crude residue was purified by flash chromatography (SiO$_2$) eluting with a heptane-EtOAc gradient to afford 1.12 g of compound 589-B as a yellow foam. $^1$H-NMR (DMSO-d$_6$): δ 2.13 (s, 3H), 3.89 (s, 2H), 7.31-7.38 (m, 2H), 7.64-7.66 (m, 1H), 7.78-7.80 (m, 1H), 7.84-7.89 (m, 2H), 7.95-7.98 (m, 1H), 11.05 (s, 1H); MS: m/z 380.1 (MH$^+$).

N-(3-Methyl-benzo[b]thiophen-2-yl)-N-(2-cyclopropyl-ethyl)-2-fluoro-4-carbomethoxy-benzenesulfonamide (589-C). To PPh$_3$ (155 mg; 0.593 mmol) was added THF (3.5 mL) followed by DEAD (0.275 mL; 0.604 mmol) and the reaction mixture was stirred at RT for 3 min, to which was then added compound 589-B (42 mg; 0.482 mmol). The reaction mixture was stirred for 5 min, to which was added cyclopropyl-ethanol and the reaction was stirred for 72 h. The reaction was diluted with EtOAc, washed with H$_2$O, brine, dried over Na$_2$SO$_4$, filtered and the solvent evaporated under reduced pressure to afford compound 589-C, which was used as is in the next step.

Compound 589

N-(3-Methyl-benzo[b]thiophen-2-yl)-N-(2-cyclopropyl-ethyl)-2-fluoro-4-carboxy-benzenesulfonamide. To a solution of compound 589-C (~0.395 mmol) in MeOH (2 mL) was added 3N NaOH (0.198 mL; 0.593 mmol) and the reaction was stirred at 63° C. for 18 h. The reaction was cooled, the solvent evaporated under reduced pressure, and the crude residue partitioned between 1N HCl and EtOAc. The organic layer was washed with $H_2O$, brine, dried over $Na_2SO_4$, filtered, and the solvent evaporated under reduced pressure. The crude residue was purified by reverse-phase semi-prep HPLC (Gemini, C-18 column; 100×30 mm I.D.; 5μ) eluting with a 53 to 73% gradient to afford 109.8 mg of compound 589 as a white solid. $^1$H-NMR (DMSO-$d_6$): δ 0.005-0.03 (t, 3H), 0.366-0.410 (m, 2H), 0.668-0.754 (m, 1H), 1.39-1.40 (m, 2H), 2.23 (s, 3H), 3.77-3.96 (m, 2H), 7.38-7.44 (m, 2H), 7.76-7.88 (m, 4H), 7.96-7.97 (m, 1H), 13.84 (s, 1H); MS: m/z 433.8 (MH$^+$).

Following the procedure described above for example 52 and substituting the appropriate reagents, starting materials and purification methods known to those skilled in the art, the following compounds of the present invention were prepared:

Compound 590

N-(3-Methyl-benzo[b]thiophen-2-yl)-N-(3,3,3-trifluoro-propyl)-2-fluoro-4-carboxy-benzenesulfonamide. $^1$H-NMR (DMSO-$d_6$): δ 2.25 (s, 3H), 2.51-2.67 (m, 2H), 3.91-4.00 (m, 2H), 7.40-7.46 (m, 2H), 7.76-7.88 (m, 4H), 7.96-7.99 (m, 1H), 13.92 (s, 1H); MS: m/z 461.7 (MH$^+$).

Compound 591

N-(3-Methyl-benzo[b]thiophen-2-yl)-N-(5,5,5-trifluoro-pentyl)-2-fluoro-4-carboxy-benzenesulfonamide. $^1$H-NMR (DMSO-$d_6$): δ 1.57 (m, 4H), 2.24 (s, 3H), 3.75 (m, 2H), 7.38-7.45 (m, 2H), 7.76-7.88 (m, 4H), 7.94-7.97 (m, 1H), 13.90 (s, 1H); MS: m/z 489.6 (MH$^+$).

Compound 592

N-(3-Methyl-benzo[b]thiophen-2-yl)-N-(4-fluoro-3-trifluoromethyl-benzyl)-2-fluoro-4-carboxy-benzenesulfonamide. $^1$H-NMR (DMSO-$d_6$): δ 1.90 (s, 3H), 5.00 (m, 2H), 7.35-7.40 (m, 2H), 7.45-7.50 (t, 1H), 7.63-7.69 (m, 3H), 7.82-7.89 (m, 3H), 7.99-8.02 (d, 1H), 13.93 (s, 1H); MS: m/z 541.7 (MH$^+$).

Compound 593

N-(3-Methyl-benzo[b]thiophen-2-yl)-N-(butyl)-2-fluoro-4-carboxy-benzenesulfonamide. $^1$H-NMR (DMSO-$d_6$): δ0.838-0.875 (t, 3H), 1.30-1.39 (m, 2H), 1.42-1.49 (m, 2H), 2.24 (s, 3H), 3.71 (m, 2H), 7.38-7.45 (m, 2H), 7.47-7.87 (m, 4H), 7.94-7.97 (m, 1H), 13.91 (s, 1H); MS: m/z 421.7 (MH$^+$).

Compound 638

N-(3-Benzo[b]thiophen-2-yl)-N-(2-cyclopropyl-ethyl)-2-fluoro-4-carboxy-benzenesulfonamide. MS: m/z 419.7 (MH$^+$).

Compound 639

N-(3-Benzo[b]thiophen-2-yl)-N-(3,3,3-trifluoro-propyl)-2-fluoro-4-carboxy-benzenesulfonamide. MS: m/z 447.7 (MH$^+$).

Compound 685

N-(Benzo[b]thiophen-2-yl)-N-(5,5,5-trifluoro-pentyl)-2-fluoro-4-carboxy-benzenesulfonamide. $^1$H-NMR (DMSO-$d_6$): δ 1.56-1.60 (m, 4H), 2.22-2.35 (m, 2H), 3.83-3.87 (m, 2H), 7.33-7.39 (m, 3H), 7.77-7.80 (m, 1H), 7.84-7.94 (m, 4H), 13.80 (s, 1H); MS: m/z 476.1 (MH$^+$).

Compound 686

N-(Benzo[b]thiophen-2-yl)-N-(4-fluoro-3-trifluoromethyl-benzyl)-2-fluoro-4-carboxy-benzenesulfonamide. $^1$H-NMR (DMSO-$d_6$): δ 5.14 (s, 2H), 7.25 (s, 1H), 7.30-7.35 (m, 2H), 7.47-7.54 (t, 1H), 7.69-7.75 (m, 3H), 7.81-7.88 (m, 1H), 7.91-8.00 (m, 4H), 13.97 (s, 1H); MS: m/z 528.0 (MH$^+$).

Compound 774

N-(3-Methyl-benzo[b]thiophen-2-yl)-N-(4-trifluoromethoxy-benzyl)-3-fluoro-4-carboxy-benzenesulfonamide. $^1$H-NMR (DMSO-$d_6$): δ 1.93 (s, 3H), 4.62-4.93 (s, 2H), 7.14-7.16 (m, 2H), 7.23-7.44 (m, 4H), 7.48-7.54 (m, 2H), 7.57-7.67 (m, 2H), 7.85-7.88 (m, 1H), 13.92 (s, 1H); MS: m/z 540.0 (MH$^+$).

Compound 775

N-(3-Methyl-benzo[b]thiophen-2-yl)-N-(4-fluoro-3-trifluoromethyl-benzyl)-3-fluoro-4-carboxy-benzenesulfonamide. $^1$H-NMR (DMSO-$d_6$): δ 4.71-4.86 (m, 2H), 7.36-7.51 (m, 6H), 7.59-7.69 (m, 3H), 7.85-7.88 (m, 1H), 12.84 (s, 1H); MS: m/z 542.1 (MH$^+$).

Example 53

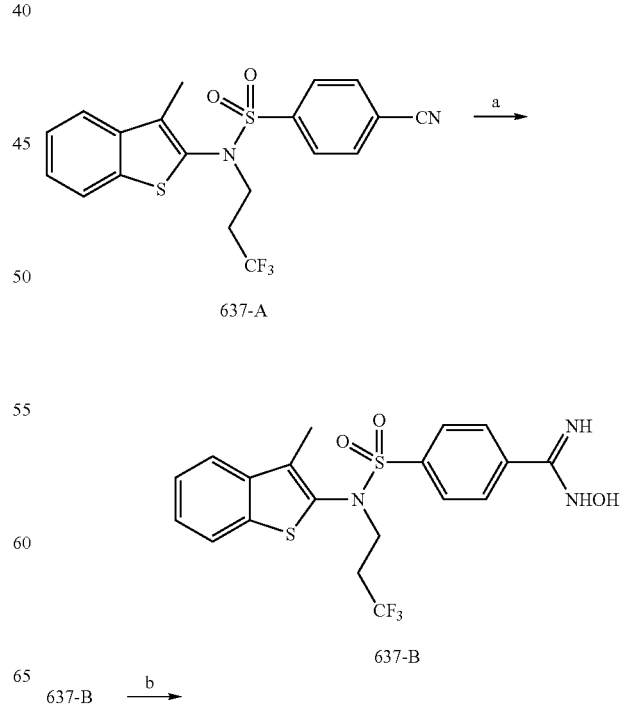

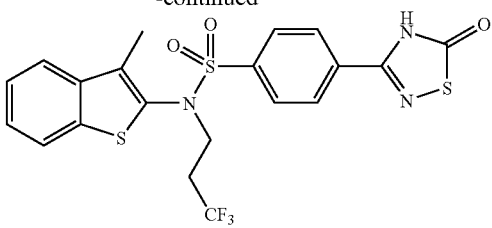

Compound 637 a) DMSO, H₂NOH·HCl, TEA;
b) 1. TCDI; 2. BF₃·OEt.

Compound 637-A was prepared as per Example 1, step A, substituting 3-methyl-benzo[b]thiophene-2-carboxylic acid for benzo[b]thiophene-2-carboxylic acid, step C, substituting 4-cyanobenzenesulfonyl chloride for benzenesulfonyl chloride, and Example 3, step A, substituting trifluoropropan-1-ol for cyclohexylmethanol.

N-Hydroxy-4-[(3-methyl-benzo[b]thiophen-2-yl)-N-(3,3,3-trifluoro-propyl)-benzenesulfonamide (637-B). To a solution of compound 637-A (354 mg; 0.834 mmol) in DMSO (4 mL), purged with N₂, was added hydroxylamine hydrochloride (290 mg; 4.17 mmol) followed by TEA (581 μL; 4.17 mmol) and the reaction was heated under microwave irradiation at 100° C. for 10 min. The reaction was partitioned between H₂O and EtOAc, the layers separated, the organic phase washed with H₂O, brine, dried over MgSO₄, filtered and the solvent evaporated under reduced pressure to afford 410.2 mg of compound 637-B as a white foam. ¹H-NMR (DMSO-d₆): δ 2.23 (s, 3H), 2.52-2.59 (m, 2H), 3.85 (s, 2H), 6.03 (s, 2H), 7.39-7.46 (m, 2H), 7.77-7.80 (m, 3H), 7.86-7.93 (m, 3H), 10.04 (s, 1H); MS: m/z 457.6 (MH⁺).

Compound 637

N-(3-Methyl-benzo[b]thiophen-2-yl)-N-(3,3,3-trifluoro-propyl)-4-(5-oxo-4,5-dihydro-[1,2,4]thiadiazol-3-yl)-benzenesulfonamide. A mixture of compound 637-B (403 mg; 0.882 mmol) and TCDI (90%; 259 mg; 1.32 mmol) in THF (3.5 mL) was stirred at rt for 30 min. The reaction was diluted with water and extracted with EtOAc. The extract was washed with H₂O, brine, dried over Na₂SO₄, filtered and the solvent evaporated under reduced pressure to afford an off-white foam. The solid was dissolved in THF (3.5 mL) to which was added boron trifluoride diethyl etherate (332 μL; 2.64 mmol) and the reaction stirred at room temperature for 1 h. The reaction mixture was partitioned between H₂O and EtOAc, the layers separated, the organic phase washed with H₂O, brine, dried over Na₂SO₄, filtered and evaporated under reduced pressure. The solid was triturated with MeOH, filtered, washed to MeOH and dried under vacuo to afford 274 mg of compound 637 as a white solid. ¹H-NMR (DMSO-d₆): δ 2.23 (s, 3H), 2.52-2.59 (m, 2H), 3.89 (s, 2H), 7.40-7.47 (m, 2H), 7.78-7.79 (m, 1H), 7.80-7.82 (m, 1H), 7.85-7.87 (m, 2H), 7.95-8.19 (m, 2H), 13.68 (s, 1H); MS: m/z 499.6 (MH⁺).

Following the procedure described above for example 53 and substituting the appropriate reagents, starting materials and purification methods known to those skilled in the art, the following compounds of the present invention were prepared:

Compound 640

N-(3-Methyl-benzo[b]thiophen-2-yl)-N-(5,5,5-trifluoro-pentyl)-4-(5-oxo-4,5-dihydro-[1,2,4]thiadiazol-3-yl)-benzenesulfonamide. ¹H-NMR (DMSO-d₆): δ 1.54-1.56 (m, 4H), 2.22-2.31 (m, 5H), 3.63-3.74 (m, 2H), 7.38-7.47 (m, 2H), 7.78-7.80 (m, 1H), 7.81-7.87 (m, 1H), 7.93-7.96 (m, 2H), 8.16-8.19 (m, 2H), 13.70 (s, 1H); MS: m/z 527.7 (MH⁺).

Compound 641

N-(3-Methyl-benzo[b]thiophen-2-yl)-N-(cyclopropyl-ethyl)-4-(5-oxo-4,5-dihydro-[1,2,4]thiadiazol-3-yl)-benzenesulfonamide. ¹H-NMR (DMSO-d₆): δ 0.000-0.074 (m, 3H), 0.353-0.412 (m, 2H), 0.685-0.751 (m, 1H), 1.35-1.36 (m, 2H), 2.25 (s, 3H), 3.63 (m, 2H), 7.38-7.46 (m, 2H), 7.76-7.82 (m, 1H), 7.83-7.86 (m, 1H), 7.93-7.95 (m, 2H), 8.17-8.19 (m, 1H), 13.69 (s, 1H); MS: m/z 471.7 (MH⁺).

Compound 642

N-(Benzo[b]thiophen-2-yl)-N-(cyclopropyl-ethyl)-4-(5-oxo-4,5-dihydro-[1,2,4]thiadiazol-3-yl)-benzenesulfonamide. MS: m/z 457.7 (MH⁺).

Compound 684

N-(Benzo[b]thiophen-2-yl)-N-(3,3,3-trifluoro-propyl)-4-(5-oxo-4,5-dihydro-[1,2,4]thiadiazol-3-yl)-benzenesulfonamide. MS: m/z 486.0 (MH⁺).

Compound 687

N-(Benzo[b]thiophen-2-yl)-N-(5,5,5-trifluoro-pentyl)-4-(5-oxo-4,5-dihydro-[1,2,4]thiadiazol-3-yl)-benzenesulfonamide. MS: m/z 514.0 (MH⁺).

Compound 784

N-(3-Methyl-benzo[b]thiophen-2-yl)-N-(4-fluoro-3-trifluoromethyl-benzyl)-4-(5-oxo-4,5-dihydro-[1,2,4]thiadiazol-3-yl)-benzenesulfonamide. ¹H-NMR (DMSO-d₆): δ 1.95 (s, 3H), 4.87-4.88 (m, 2H), 7.25-7.54 (m, 3H), 7.59-7.68 (m, 4H), 7.83-7.85 (m, 3H), 8.20-8.22 (d, 2H); MS: m/z 580.0 (MH⁺).

Compound 810

N-(3-Methyl-benzo[b]thiophen-2-yl)-N-(4-trifluoromethoxy-benzyl)-4-(5-oxo-4,5-dihydro-[1,2,4]thiadiazol-3-yl)-benzenesulfonamide. ¹H-NMR (DMSO-d₆): δ 1.91 (s, 3H), 4.80-4.85 (m, 2H), 7.28-7.34 (m, 2H), 7.35-7.41 (m, 4H), 7.63-7.66 (m, 1H), 7.81-7.84 (m, 3H), 8.20-8.22 (d, 2H); MS: m/z 578.0 (MH⁺).

Example 54

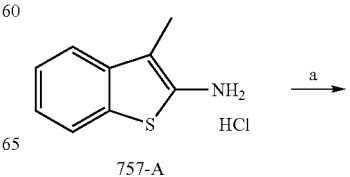

757-A

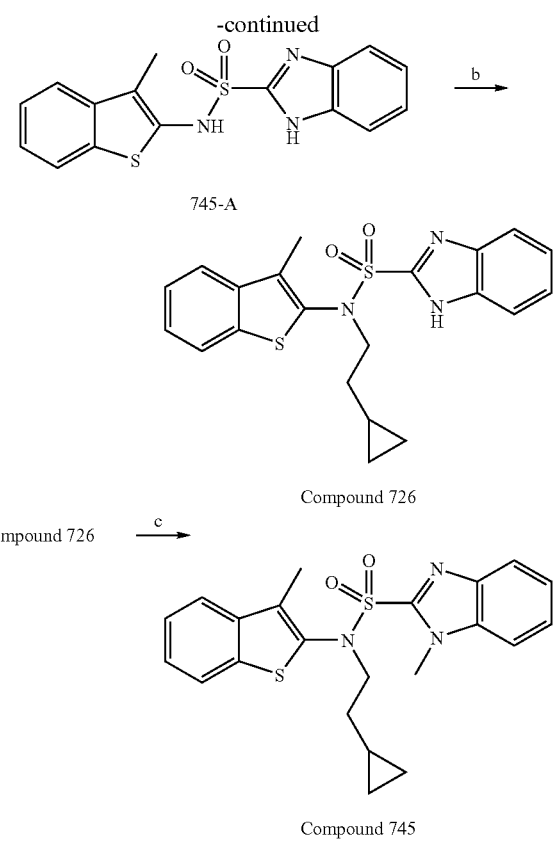

a) DCM, pyridine, compound Int-5;
b) THF, DEAD, PPh₃, cyclopropyl-ethanol;
c) DMF, DBU, (MeO₂)SO₂.

(3-Methyl-benzo[b]thiophen-2-yl)-1H-benzoimidazole-2-sulfonamide. To a suspension of compound 757A (1.89 g; 9.45 mmol) in DCM (20 mL), cooled to 0° C., was added pyridine (1.68 mL; 20.8 mmol), followed by the addition of compound Int-5 (2.2 g; 10.1 mmol) in one-portion. The reaction mixture was allowed to stir at ambient temperature for 4 h, diluted with CH₂Cl₂, washed with H₂O (2×), dried over Na₂SO₄, filtered, the solvent evaporated under reduced pressure and the crude residue purified by flash column chromatography (SiO₂) eluting with a heptane-EtOAc gradient to afford 1.72 g of compound 745A as an off-white solid. ¹H-NMR (DMSO-d₆): δ 2.13 (s, 3H), 7.31-7.38 (m, 4H), 7.66-7.68 (m, 2H), 7.77-7.79 (m, 2H), 11.18 (s, 1H), 13.63 (s, 1H); MS: m/z 344.0 (MH⁺).

Compound 726

N-(Cyclopropyl-ethyl)-N-(3-methyl-benzo[b]thiophen-2-yl)-1H-benzimidazole-2-sulfonamide. To PPh₃ (0.462 g; 1.76 mmol) was added THF (10 mL) followed by DEAD (40%; 815 μL; 1.79 mmol) and the reaction mixture was stirred at ambient temperature for 3 min, to which was added compound 745-A (0.403 g; 1.17 mmol). The reaction mixture was stirred for 5 min, to which was added cyclopropyl ethanol (0.123 g; 1.43 mmol) and the reaction was stirred for an additional 18 h. The reaction was diluted with EtOAc, washed with H₂O, brine, dried over Na₂SO₄, filtered and the solvent evaporated under reduced pressure. The crude oil was purified by reverse-phase semi-prep HPLC (Gemini, C-18 column; 100×30 mm I.D.; 5μ) eluting with a 55% to 75% gradient to afford 189 mg of compound 726 as an off-white solid. ¹H-NMR (DMSO-d₆): δ 0.008-0.056 (m, 2H), 0.394-0.438 (m, 2H), 0.727-0.802 (m, 1H), 1.45 (m, 2H), 2.28 (s, 3H), 3.83-3.91 (m, 2H), 7.36-7.57 (m, 4H), 7.77-7.82 (m, 4H), 13.78 (s, 1H); MS: m/z 412.0 (MH⁺).

Compound 745

N-(Cyclopropyl-ethyl)-N-(3-methyl-benzo[b]thiophen-2-yl)-1-methyl-1H-benzimidazole-2-sulfonamide. To a solution of compound 726 (0.125 g; 0.132 mmol) in DMF (2 mL) was added DBU (99 μL; 0.666 mmol) followed by dimethyl sulfate (32 μL; 0.332 mmol) and the reaction was stirred at 67° C. for 18 h. An additional portion of DBU (226 μL; 1.51 mmol) and dimethyl sulfate (144 μL; 1.51 mmol) was added and the reaction mixture was stirred at 67° C. for an additional 18 h. The reaction mixture was cooled, diluted with H₂O, extracted with EtOAc, the layers separated, and the organic phase washed with H₂O, brine, dried over Na₂SO₄, filtered and the solvent evaporated under reduced pressure. The crude oil was purified by reverse-phase semi-prep HPLC (Gemini, C-18 column; 100×30 mm I.D.; 5μ) eluting with a 55% to 75% gradient to afford 107 mg of compound 745 as an oil. ¹H-NMR (DMSO-d₆): δ 0.008-0.013 (m, 2H), 0.346-0.391 (m, 2H), 0.685-0.759 (m, 1H), 1.43 (m, 2H), 2.31 (s, 3H), 3.79 (s, 3H), 3.84-3.97 (m, 2H), 7.33-7.38 (m, 3H), 7.39-7.49 (m, 1H), 7.69-7.72 (d, 1H), 7.75-7.81 (m, 2H), 7.88-7.90 (d, 1H); MS: m/z 426.1 (MH⁺).

Following the procedure described above for example 54 and substituting the appropriate reagents, starting materials and purification methods known to those skilled in the art, the following compounds of the present invention were prepared:

Compound 720

N-(3-Methyl-benzo[b]thiophen-2-yl)-N-(5,5,5-trifluoropentyl)-1H-benzimidazole-2-sulfonamide. ¹H-NMR (DMSO-d₆): δ 1.48-1.75 (m, 4H), 2.13-2.27 (m, 5H), 3.40-387 (m, 2H), 7.37-7.47 (m, 4H), 7.60-7.83 (m, 4H), 13.83 (s, 1H); MS: m/z 468.1 (MH⁺).

Compound 722

N-(3-Methyl-benzo[b]thiophen-2-yl)-N-(4-fluoro-3-trifluoromethyl-benzyl)-1-methyl-1H-benzimidazole-2-sulfonamide. MS: m/z 534.2 (MH⁺).

Compound 728

N-(3-Methyl-benzo[b]thiophen-2-yl)-N-(4-fluoro-3-trifluoromethyl-benzyl)-1H-benzimidazole-2-sulfonamide. MS: m/z 520.0 (MH⁺).

Compound 729

N-(3-Methyl-benzo[b]thiophen-2-yl)-N-(4-trifluoromethoxy-benzyl)-1H-benzimidazole-2-sulfonamide. MS: m/z 518.1 (MH⁺).

Compound 746

N-(3-Methyl-benzo[b]thiophen-2-yl)-N-(4-trifluoromethoxy-benzyl)-1-methyl-1H-benzimidazole-2-sulfonamide. MS: m/z 532.0 (MH$^+$).

Example 55

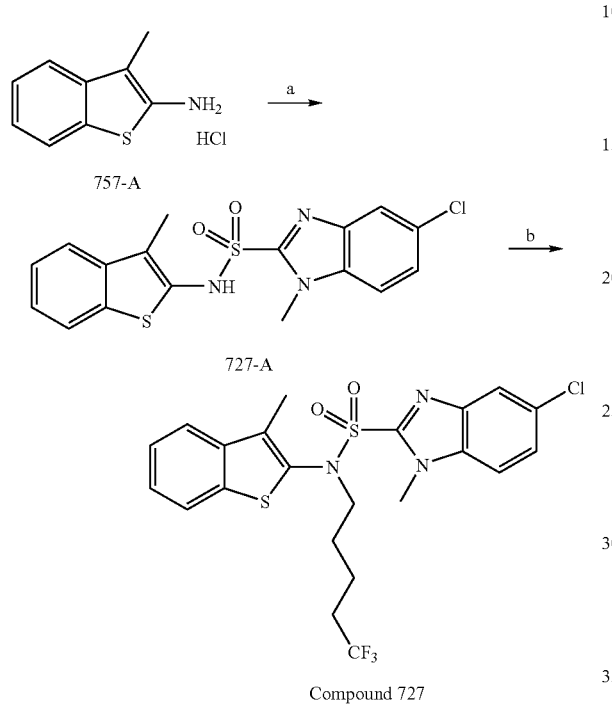

Compound 727 a) DCM, pyridine, compound Int-7;
b) THF, PPh$_3$, DEAD, 5,5,5-trifluoro-pentan-1-ol.

(3-Methyl-benzo[b]thiophen-2-yl)-1H-benzimidazole-2-sulfonamide (727-A). To a suspension of compound 757-A (0.589 g; 2.95 mmol) in DCM (20 mL), cooled to 0° C., was added pyridine (525 μL; 6.49 mmol), followed by the addition of compound Int-7 (0.5 g; 1.88 mmol) in one-portion. The reaction was allowed to stir at ambient temperature for 4 h, diluted with CH$_2$Cl$_2$, washed with H$_2$O (2×), dried over Na$_2$SO$_4$, filtered, the solvent evaporated under reduced pressure and the crude residue purified by flash column chromatography (SiO$_2$) eluting with a heptane-EtOAc gradient to afford crude compound 727-A. Compound 727-A was further purified by reverse-phase semi-prep HPLC (Gemini, C-18 column; 100×30 mm I.D.; 5μ) eluting with a 60% to 80% gradient to afford 131 mg of compound 727-A as a white solid. MS: m/z 392.0 (MH$^+$).

Compound 727

N-(3-Methyl-benzo[b]thiophen-2-yl)-N-(5,5,5,-trifluoropentyl)-1H-benzimidazole-2-sulfonamide. To PPh$_3$ (0.068 g; 0.258 mmol) was added THF (1.5 mL) followed by DEAD (40%; 120 μL; 0.263 mmol) and the reaction mixture was stirred at ambient temperature for 3 min, to which was then added compound 727-A (0.067 g; 0.172 mmol). The reaction mixture was stirred for 5 min, to which was added 5,5,5-trifluoro-pentan-1-ol (0.03 g; 0.210 mmol) and the reaction was stirred for an additional 18 h. The reaction mixture was diluted with EtOAc, washed with H$_2$O, brine, dried over Na$_2$SO$_4$, filtered and the solvent evaporated under reduced pressure. The crude oil was purified by reverse-phase semi-prep HPLC (Gemini, C-18 column; 100×30 mm I.D.; 5μ) eluting with a 65% to 85% gradient to afford 34 mg of compound 727 as a white solid. MS: m/z 516.2 (MH$^+$).

Example 56

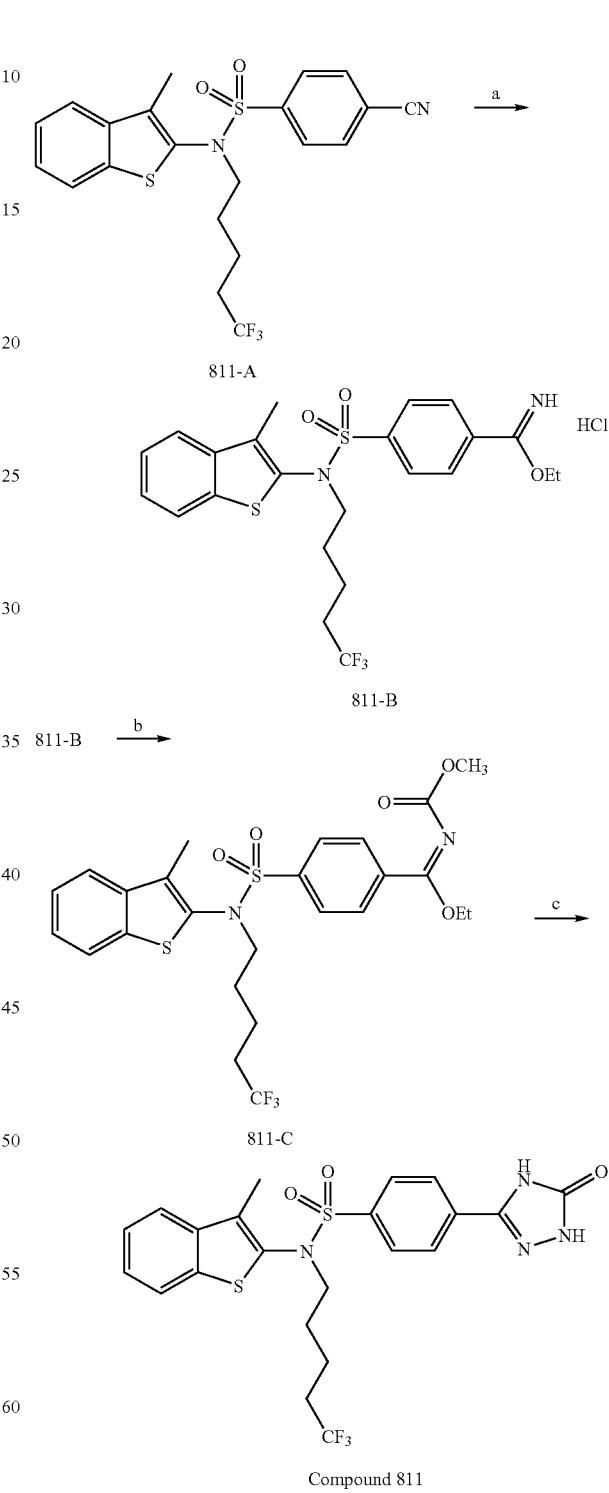

Compound 811 a) EtOH, HCl;
b) methyl chloroformate, CHCl$_3$, 2,4,6-collidine;
c) CCl$_4$, H$_2$NNH$_2$.

Compound 811-A, was prepared by the method used to synthesize compound 600 in Example 30, steps A and B.

4-[(3-Methyl-benzo[b]thiophen-2-yl)-(5,5,5-trifluoro-pentyl)-sulfamoyl)]-benzimidic acid ethyl ester (811-B). To a solution of compound 811-A (706 mg; 1.56 mmol), cooled to 0° C. was bubbled HCl(g) for 15 min. The reaction was sealed and allowed to stir 18 h at ambient temperature. The solvent was evaporated under reduced pressure and the solid dried to afford 777 mg of compound 811-B as a white solid.

(Ethoxy-{4-[(3-methyl-benzo[b]thiophen-2-yl)-(5,5,5-trifluoro-pentyl)-sulfamoyl]-phenyl}-methylene)-carbamic acid methyl ester (811-C). To a suspension of compound 811-B (777 mg; 1.45 mmol), in CHCl₃ (1 mL), was added 2,4,6-collidine (275 µL; 1.93 mmol), followed by methyl chloroformate (115 µL; 2.18 mmol) and the reaction was stirred at ambient temperature for 72 h. TEA (200 µL) was added to the reaction, followed by another 1.5 equiv of methyl chloroformate and the reaction was stirred at ambient temperature for 18 h. The reaction was diluted with CH₂Cl₂, washed with H₂O, dried over Na₂SO₄, filtered, and the solvent evaporated under reduced pressure to afford crude compound 811-C.

Compound 811

N-(3-Methyl-benzo[b]thiophen-2-yl)-N-(5,5,5-trifluoro-pentyl)-4-(5-oxo-4,5-dihydro-1H-[1,2,4]triazol-3-yl)-benzenesulfonamide. To a solution of compound 811-C (403 mg; 0.775 mmol), in carbontetrachloride (3.5 mL), was added hydrazine (25 µL; 797 mmol) and the reaction was refluxed in a sealed tube for 18 h. The reaction was cooled and the solvent evaporated. The crude reaction was purified by reverse-phase semi-prep HPLC (Gemini, C-18 column; 100×30 mm I.D.; 5µ) eluting with a 50 to 70% gradient to afford 75 mg of compound 811 as a white solid. ¹H-NMR (DMSO-d₆): δ 1.52-1.55 (m, 4H), 2.19-2.22 (m, 5H), 3.50-3.69 (m, 2H), 7.39-7.46 (m, 2H), 7.78-7.79 (m, 1H), 7.80-7.90 (m, 3H), 8.00-8.02 (d, 2H), 11.97 (s, 1H), 12.29 (s, 1H); MS: m/z 511.0 (MH⁺).

Compound 812

N-(3-Methyl-benzo[b]thiophen-2-yl)-N-(5,5,5-trifluoro-pentyl)-4-(1-methyl-5-oxo-4,5-dihydro-1H-[1,2,4]triazol-3-yl)-benzenesulfonamide. ¹H-NMR (DMSO-d₆): δ 1.36-1.40 (m, 4H), 1.92-2.06 (m, 5H), 3.23 (s, 3H), 3.28-3.42 (m, 2H), 7.22-7.29 (m, 2H), 7.61-7.62 (m, 1H), 7.63-7.70 (m, 1H), 7.72-7.74 (d, 2H), 7.83-7.85 (d, 2H), 12.32 (s, 1H); MS: m/z 525.0 (MH⁺).

Example 57

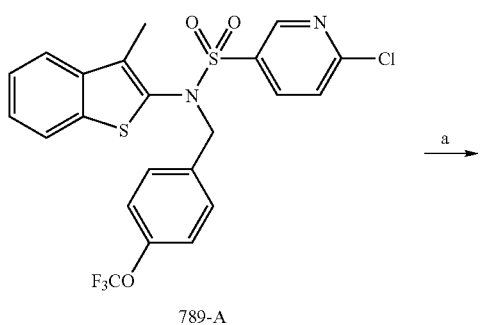

789-A

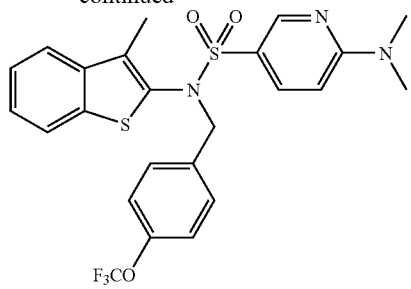

Compound 789 a) DMSO, dimethylamine.

Compound 789-A, was prepared by the method used to synthesize compound 757 in Example 29.

Compound 789

N-(3-Methyl-benzo[b]thiophen-2-yl)-N-(4-trifluoromethoxy-benzyl)-4-dimethylamino-3-pyridylsulfonamide. To a solution of compound 789-A (0.07 g, 0.14 mmol) in DMSO (1 mL) was added a solution of 2.0 M dimethylamine-tetrahydrofuran (0.205 mL, 0.41 mmol) and the reaction mixture was stirred at ambient temperature for 18 h. The crude reaction was purified by reverse-phase semi-prep HPLC (Gemini, C₁₈ column; 100×30 mm I.D.; 5µ) to afford 0.06 g of compound 789 as a white solid. ¹H NMR (DMSO-d₆) δ 1.98 (s, 3H), 3.16 (s, 6H), 4.72 (br s, 2H), 6.79 (d, 1H), 7.28 (d, 2H), 7.33-7.47 (m, 4H), 7.60-7.71 (m, 1H), 7.76-7.94 (m, 2H), 8.42 (d, 1H); MS: m/z 522.2 (MH⁺).

Following the procedure described above for example 57 and substituting the appropriate reagents, starting materials and purification methods known to those skilled in the art, the following compounds of the present invention were prepared:

Compound 786

N-(3-Methyl-benzo[b]thiophen-2-yl)-N-(cyclopropyl-ethyl)-4-dimethylamino-3-pyridyl-sulfonamide. ¹H-NMR (DMSO-d₆): δ –0.10-0.07 (m, 2H), 0.27-0.47 (m, 2H), 0.61-0.82 (m, 1H), 1.34 (br s, 2H), 2.31 (s, 3H), 3.16 (s, 6H), 3.40-3.67 (m, 2H), 6.78 (d, 1H), 7.34-7.55 (m, 2H), 7.67-7.85 (m, 2H), 7.85-7.96 (m, 1H), 8.34 (d, 1H); MS: m/z 416.1 (MH⁺).

Compound 787

N-(3-Methyl-benzo[b]thiophen-2-yl)-N-(5,5,5-trifluoro-pentyl)-4-dimethylamino-3-pyridyl-sulfonamide. ¹H-NMR (DMSO-d₆) δ 1.51 (br s, 4H), 2.30 (s, 6H), 2.4-2.5 (m, 2H), 3.14 (s, 6H), 6.76 (d, 1H), 7.32-7.52 (m, 2H), 7.72 (dd, 1H), 7.79 (dd, 1H), 7.88 (dd, 1H), 8.34 (d, 1H); MS: m/z 472.0 (MH⁺).

Compound 788

N-(3-Methyl-benzo[b]thiophen-2-yl)-N-(5,5,5-trifluoro-pentyl)-4-morpholino-3-pyridyl-sulfonamide. ¹H NMR (DMSO-d₆): δ 1.51 (br s, 5H), 2.31 (s, 6H), 3.57 (s, 2H), 3.61-3.82 (m, 9H), 6.97 (d, 1H), 7.35-7.56 (m, 2H), 7.69-7.84 (m, 2H), 7.84-7.94 (m, 1H), 8.39 (d, 1H); MS: m/z 514.0 (MH⁺).

Compound 790

N-(3-Methyl-benzo[b]thiophen-2-yl)-N-(4-trifluoromethoxy-benzyl)-4-morpholino-3-pyridyl-sulfonamide. $^1$H NMR (DMSO-d$_6$): δ 1.99 (s, 3H), 3.65-3.87 (m, 8H), 4.72 (br s, 2H), 7.00 (d, 1H), 7.29 (d, 2H), 7.33-7.50 (m, 4H), 7.60-7.74 (m, 1H), 7.79-7.94 (m, 2H), 8.46 (d, 1H); MS: m/z 564.0 (MH$^+$).

Compound 798

N-(3-Methyl-benzo[b]thiophen-2-yl)-N-(cyclopropylethyl)-4-morpholino-3-pyridyl-sulfonamide. MS: m/z 451.8 (MH$^+$).

Example 58

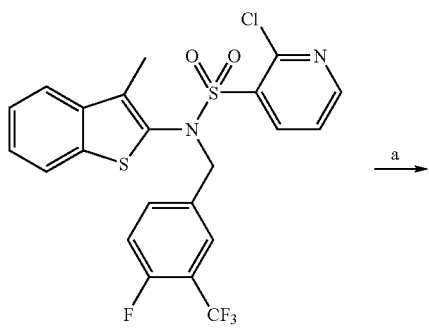

Compound 77

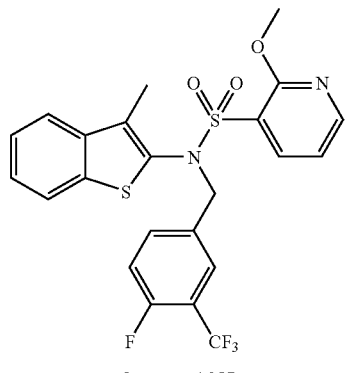

Compound 357 a) Toluene, sodium methoxide 0.5M in MeOH.

Compound 357

N-(3-Methyl-benzo[b]thiophen-2-yl)-N-(4-fluoro-3-trifluoromethyl-benzyl)-2-methoxy-pyridin-3-ylsulfonamide. To a solution of compound 77 (0.07 g, 0.14 mmol) in toluene (1 mL) was added a solution of 0.5M solution of sodium methoxide in MeOH (0.82 mL, 0.41 mmol) and the reaction mixture was refluxed for 2 h. The reaction mixture was cooled, diluted with H$_2$O, extracted with EtOAc, washed with H$_2$O, brine, dried over Na$_2$SO$_4$, filtered, and the solvent evaporated in vacuo. The crude residue was purified by reverse-phase semi-prep HPLC (Gemini, C$_{18}$ column; 100× 30 mm I.D.; 5μ) to afford 0.06 g of compound 357 as a white solid. $^1$H-NMR (CDCl$_3$) δ 1.78-1.97 (s, 3H), 4.23 (s, 3H), 5.02 (br s, 2H), 6.93 (dd, 1H), 7.10 (t, 1H), 7.30-7.36 (m, 2H), 7.42-7.67 (m, 4H), 8.00 (dd, 1H), 8.38 (dd, 1H); MS: m/z 510.9 (MH$^+$).

Following the procedure described above for example 58 and substituting the appropriate reagents, starting materials and purification methods known to those skilled in the art, the following compounds of the present invention were prepared:

Compound 358

N-(3-Methyl-benzo[b]thiophen-2-yl)-N-(4-fluoro-3-trifluoromethyl-benzyl)-2-dimethylamino-pyridin-3-yl-sulfonamide. $^1$H-NMR (CDCl$_3$) δ 1.88 (s, 3H), 3.07 (s, 6H), 4.95 (br s, 2H), 6.93 (dd, 1H), 7.07 (t, 1H), 7.28-7.36 (m, 2H), 7.37-7.47 (m, 1H), 7.47-7.55 (m, 2H), 7.55-7.62 (m, 1H), 8.02 (dd, 1H), 8.47 (dd, 1H); MS: m/z 524.0 (MH$^+$).

Compound 359

N-(3-Methyl-benzo[b]thiophen-2-yl)-N-(4-fluoro-3-trifluoromethyl-benzyl)-4-methoxy-pyridin-3-yl-sulfonamide. $^1$H-NMR (CDCl$_3$) δ 2.04-2.15 (m, 3H), 4.05 (s, 3H), 4.68 (br s, 2H), 6.85 (d, 1H), 7.07 (t, 1H), 7.30-7.50 (m, 3H), 7.50-7.75 (m, 3H), 7.88 (dd, 1H), 8.62 (d, 1H); MS: m/z 510.9 (MH$^+$).

Compound 360

N-(3-Methyl-benzo[b]thiophen-2-yl)-N-(4-fluoro-3-trifluoromethyl-benzyl)-4-dimethylamino-pyridin-3-yl-sulfonamide. MS: m/z 524.0 (MH$^+$).

Compound 377

N-(3-Methyl-benzo[b]thiophen-2-yl)-N-(4-fluoro-3-trifluoromethyl-benzyl)-2-thiomethyl-pyridin-3-yl-sulfonamide. MS: m/z 527.0 (MH$^+$).

Compound 378

N-(3-Methyl-benzo[b]thiophen-2-yl)-N-(4-fluoro-3-trifluoromethyl-benzyl)-4-thiomethyl-pyridin-3-yl-sulfonamide. MS: m/z 527.0 (MH$^+$).

Compound 448

N-(3-Methyl-benzo[b]thiophen-2-yl)-N-(butyl)-2-dimethylamino-pyridin-3-yl-sulfonamide. $^1$H-NMR (CDCl$_3$) δ 0.89 (t, 3H), 1.37 (m, 2H), 1.45-1.62 (m, 2H), 2.38 (s, 3H), 3.17 (s, 6H), 3.72 (m., 2H), 6.99 (dd, 1H), 7.37 (m, 2H), 7.59-7.80 (m, 2H), 8.14-8.29 (m, 1H), 8.37-8.50 (m, 1H); MS: m/z 404.1 (MH$^+$).

Example 59

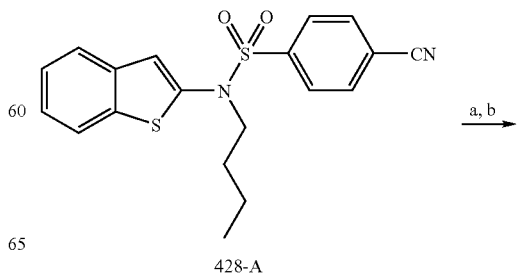

428-A

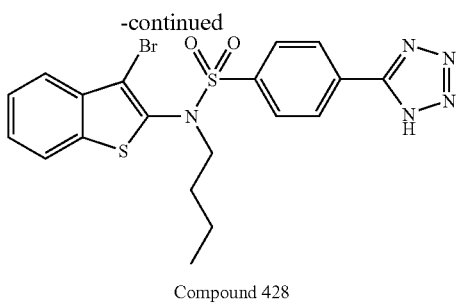

Compound 428 a) NaN₃, NH₄Cl, DMF; b) NBS, DMF.

Compound 428-A, was prepared by the method used to synthesize compound 600 in Example 30, steps A and B.

Compound 428

N-(3-Bromo-benzo[b]thiophen-2-yl)-N-(butyl)-4-(1H-tetrazol-5-yl)-benzenesulfonamide. Dimethylformamide (2 mL), sodium azide (0.098 g, 1.5 mmol), ammonium chloride (0.08 g, 1.5 mmol) and compound 428-A (0.185 g, 0.5 mmol) were added to a microwave vessel with stir bar, sealed, and heated in a 300 watt microwave reactor to 160° C. for 10 min. The solution was decanted, N-bromosuccinimide (0.356 g, 2.0 mmol) was added to the solution and stirred for 3 h at ambient temperature. The solution was diluted with H₂O, extracted with EtOAc, washed with H₂O, brine, dried over Na₂SO₄, filtered, and the solvent was evaporated in vacuo. The crude residue was purified by reverse-phase semi-prep HPLC (Gemini, $C_{18}$ column; 100×30 mm I.D.; 5μ) to afford 0.124 g of compound 428 as a white solid. ¹H-NMR (CD₃OD) δ 0.91 (t, 3H), 1.48 (it, 4H), 3.74 (t, 2H), 7.35-7.59 (m, 2H), 7.73-7.88 (m, 2H), 7.93 (m, 2H), 8.26 (m, 2H); MS: m/z 492.0 (MH⁺).

Following the procedure described above for example 59 and substituting the appropriate reagents, starting materials and purification methods known to those skilled in the art, the following compounds of the present invention were prepared:

Compound 424

N-(Benzo[b]thiophen-2-yl)-N-(4-fluoro-3-trifluoromethyl-benzyl)-4-(1H-tetrazol-5-yl)-benzenesulfonamide. ¹H-NMR (DMSO-d₆): δ 4.98 (s, 2H), 7.16 (s, 1H), 7.25-7.29 (m, 2H), 7.41-7.46 (t, 1H), 7.65-7.69 (m, 3H), 7.76-7.79 (m, 1H), 8.00-8.02 (d, 2H), 8.24-8.26 (d, 2H); MS: m/z 534.0 (MH⁺).

Compound 425

N-(Benzo[b]thiophen-2-yl)-N-(4,4,4-trifluoro-butyl)-4-(1H-tetrazol-5-yl)-benzenesulfonamide. MS: m/z 468.0 (MH⁺).

Compound 429

N-(3-Bromo-benzo[b]thiophen-2-yl)-N-(5,5,5-trifluoro-butyl)-4-(1H-tetrazol-5-yl)-benzenesulfonamide. ¹H-NMR (CD₃OD) δ 1.82 (br s, 2H), 2.41 (br s, 2H), 3.83 (s, 2H), 7.44-7.60 (m, 2H), 7.77-7.89 (m, 2H), 7.93 (m, 2H), 8.27 (m, 2H); MS: m/z 546.0 (MH⁺).

Compound 449

N-(Benzo[b]thiophen-2-yl)-N-(butyl)-4-(1H-tetrazol-5-yl)-benzenesulfonamide. MS: m/z 414.0 (MH⁺).

Compound 455

N-(3-Methyl-benzo[b]thiophen-2-yl)-N-(4-fluoro-3-trifluoromethyl-benzyl)-3-(1H-tetrazol-5-yl)-benzenesulfonamide. MS: m/z 548.0 (MH⁺).

Compound 474

N-(3-Bromo-benzo[b]thiophen-2-yl)-N-(cyclopropylmethyl)-4-(1H-tetrazol-5-yl)-benzenesulfonamide. ¹H-NMR (DMSO-d₆) δ 0.05-0.17 (m, 2H), 0.38 (d, 2H), 0.90 (br s, 1H), 3.55 (br s, 2H), 7.40-7.63 (m, 2H), 7.72-7.81 (m, 1H), 7.85 (m, 2H), 7.94-8.08 (m, 1H), 8.20 (m, 2H); MS: m/z 490.0 (MH⁺).

Compound 475

N-(3-Bromo-benzo[b]thiophen-2-yl)-N-(4-fluoro-3-trifluoromethyl-benzyl)-4-(1H-tetrazol-5-yl)-benzenesulfonamide. ¹H-NMR (DMSO-d₆) δ 4.92 (br s, 2H), 7.35-7.54 (m, 3H), 7.60-7.80 (m, 3H), 7.85-8.03 (m, 3H), 8.24 (d, 2H); MS: m/z 612.0 (MH⁺).

Compound 539

N-(3-Methyl-benzo[b]thiophen-2-yl)-N-(butyl)-4-(1H-tetrazol-5-yl)-benzenesulfonamide. ¹H-NMR (CDCl₃) δ 0.89 (t, 3H), 1.28-1.45 (m, 2H), 1.45-1.59 (m, 2H), 2.39 (s, 3H), 3.54 (s, 2H), 7.30-7.48 (m, 2H), 7.58-7.77 (m, 2H), 7.93 (m, 2H), 8.27 (m, 2H); MS: m/z 428.1 (MH⁺).

Compound 542

N-(3-Methyl-benzo[b]thiophen-2-yl)-N-(4-fluoro-3-trifluoromethyl-benzyl)-4-(1H-tetrazol-5-yl)-benzenesulfonamide. ¹H-NMR (CDCl₃) δ 2.07 (s, 3H), 3.53 (br s, 2H), 7.01-7.14 (m, 1H), 7.30-7.41 (m, 2H), 7.45 (dd, 1H), 7.55 (dd, 1H), 7.57-7.68 (m, 2H), 7.98 (m, 2H), 8.34 (m, 2H); MS: m/z 548.1 (MH⁺).

Compound 569

N-(Benzo[b]thiophen-2-yl)-N-(2-cyclopropyl-ethyl)-4-(1H-tetrazol-5-yl)-benzenesulfonamide. MS: m/z 425.7 (MH⁺).

Compound 570

N-(3-Methyl-benzo[b]thiophen-2-yl)-N-(cyclopropyl-ethyl)-4-(1H-tetrazol-5-yl)-benzenesulfonamide. ¹H-NMR (DMSO-d₆) δ −0.12-0.09 (m, 2H), 0.25-0.47 (m, 2H), 0.59-0.84 (m, 1H), 1.34 (br s, 2H), 2.26 (s, 3H), 3.62 (br s, 2H), 7.31-7.51 (m, 2H), 7.69-7.83 (m, 3H), 7.83-7.92 (m, 1H), 8.20 (d, 2H); MS: m/z 440.1 (MH⁺).

Compound 571

N-(Benzo[b]thiophen-2-yl)-N-(3,3,3-trifluoro-propyl)-4-(1H-tetrazol-5-yl)-benzenesulfonamide. MS: m/z 453.7 (MH⁺).

Compound 572

N-(3-Methyl-benzo[b]thiophen-2-yl)-N-(3,3,3-trifluoro-propyl)-4-(1H-tetrazol-5-yl)-benzenesulfonamide. ¹H-NMR (DMSO-d$_6$): δ 2.25 (s, 3H), 2.51-2.67 (m, 2H), 3.90 (m, 2H), 7.40-7.47 (m, 2H), 7.78-7.82 (dd, 1H), 7.84-7.88 (m, 1H), 8.02-8.04 (d, 2H), 8.28-8.30 (d, 2H); MS: m/z 467.7 (MH$^+$).

Compound 579

N-(3-Bromo-benzo[b]thiophen-2-yl)-N-(5,5,5-trifluoro-pentyl)-4-(1H-tetrazol-5-yl)-benzenesulfonamide. ¹H-NMR (DMSO-d$_6$) δ 1.56 (d, 4H), 2.10-2.33 (m, 2H), 3.71 (br s, 2H), 7.43-7.60 (m, 2H), 7.72-7.85 (m, 1H), 7.94-8.06 (m, 1H), 8.09 (m, 2H), 8.31 (m, 2H); MS: m/z 561.6 (MH$^+$).

Compound 580

N-(3-Chloro-benzo[b]thiophen-2-yl)-N-(5,5,5-trifluoro-pentyl)-4-(1H-tetrazol-5-yl)-benzenesulfonamide. ¹H-NMR (DMSO-d$_6$) δ 1.41-1.69 (m, 4H), 2.15-2.36 (m, 2H), 3.66 (t, 2H), 7.42-7.64 (m, 2H), 7.74-7.92 (m, 3H), 7.94-8.09 (m, 1H), 8.21 (d, 2H); MS: m/z 516.0 (MH$^+$).

Compound 804

N-(3-Methyl-benzo[b]thiophen-2-yl)-N-(cyclopropyl-ethyl)-4-(1H-tetrazol-5-yl)-pyridin-3-ylsulfonamide. Compound 804 was prepared using the procedure in Example 59, step A, substituting compound 428-A with compound Int-9. ¹H-NMR (DMSO-d$_6$) δ −0.01 (q, 2H), 0.22-0.45 (m, 2H), 0.57-0.80 (m, 1H), 1.37 (br s, 2H), 2.27 (s, 3H), 3.67 (br s, 2H), 7.31-7.53 (m, 2H), 7.79 (dd, 1H), 7.81-7.93 (m, 1H), 8.33-8.57 (m, 2H), 9.04 (d, 1H); MS: m/z 441.0 (MH$^+$).

Compound 805

N-(3-Methyl-benzo[b]thiophen-2-yl)-N-(4-trifluoromethoxy-benzyl)-4-(1H-tetrazol-5-yl)-pyridin-3-ylsulfonamide. Compound 805 was prepared using the procedure in Example 59, step A, substituting compound 428-A with compound Int-9. ¹H-NMR (DMSO-d$_6$) δ 1.83-2.01 (m, 3H), 4.88 (br s, 2H), 7.32 (d, 2H), 7.34-7.52 (m, 4H), 7.61-7.74 (m, 1H), 7.80-7.96 (m, 1H), 8.50 (d, 1H), 8.57 (dd, 1H), 9.18 (d, 1H); MS: m/z 547.0 (MH$^+$).

Compound 806

N-(3-Methyl-benzo[b]thiophen-2-yl)-N-(5,5,5-trifluoro-pentyl)-4-(1H-tetrazol-5-yl)-pyridin-3-ylsulfonamide. Compound 806 was prepared using the procedure in Example 59, step A, substituting compound 428-A with compound LMR-2-B. ¹H-NMR (DMSO-d$_6$) δ 1.45 (d, 5H), 2.10 (br s, 3H), 2.13-2.22 (m, 3H), 7.16-7.42 (m, 2H), 7.71 (dd, 1H), 7.77 (dd, 1H), 8.24-8.44 (m, 2H), 8.97 (d, 1H); MS: m/z 497.1 (MH$^+$).

Example 60

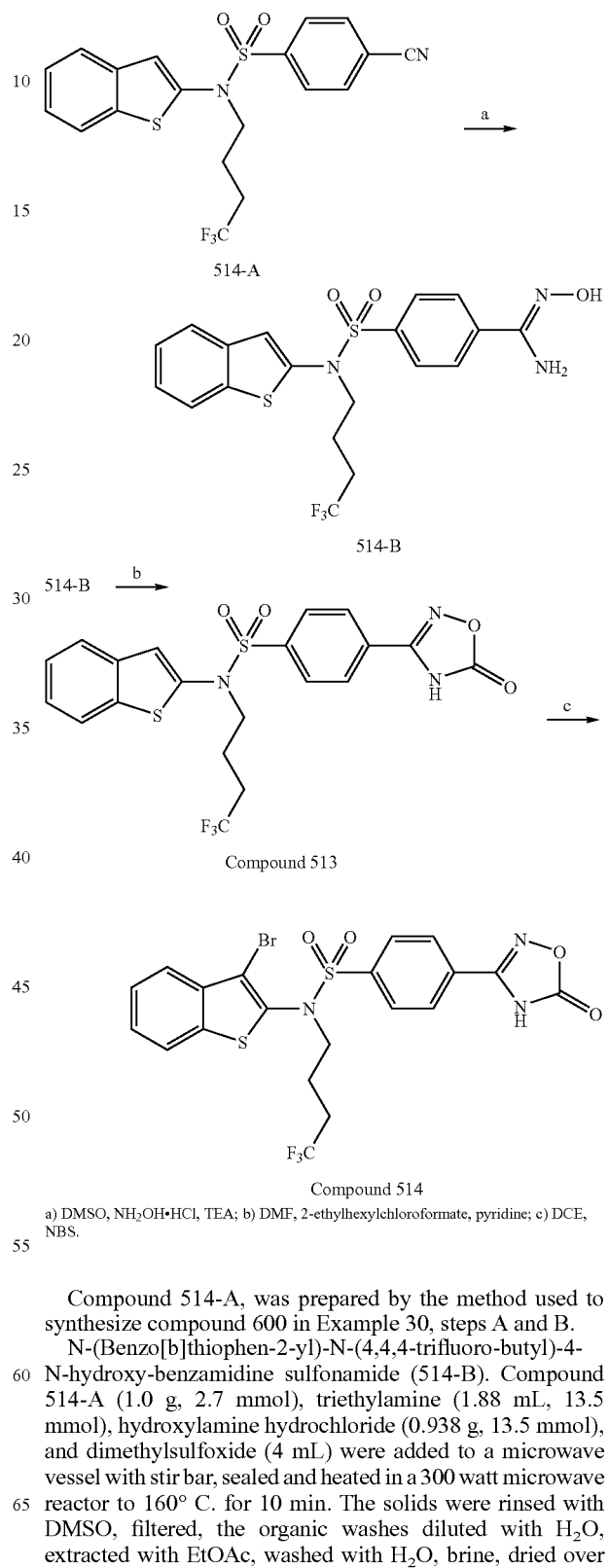

a) DMSO, NH$_2$OH•HCl, TEA; b) DMF, 2-ethylhexylchloroformate, pyridine; c) DCE, NBS.

Compound 514-A, was prepared by the method used to synthesize compound 600 in Example 30, steps A and B.

N-(Benzo[b]thiophen-2-yl)-N-(4,4,4-trifluoro-butyl)-4-N-hydroxy-benzamidine sulfonamide (514-B). Compound 514-A (1.0 g, 2.7 mmol), triethylamine (1.88 mL, 13.5 mmol), hydroxylamine hydrochloride (0.938 g, 13.5 mmol), and dimethylsulfoxide (4 mL) were added to a microwave vessel with stir bar, sealed and heated in a 300 watt microwave reactor to 160° C. for 10 min. The solids were rinsed with DMSO, filtered, the organic washes diluted with H$_2$O, extracted with EtOAc, washed with H$_2$O, brine, dried over Na$_2$SO$_4$, filtered, and the solvent evaporated in vacuo. Crude compound 514-B crystallized to afford 1.0 g of an off white solid. MS: m/z 458.0 (MH$^+$).

Compound 513

N-(Benzo[b]thiophen-2-yl)-N-(4,4,4-trifluoro-butyl)-4-(5-oxo-4,5-dihydro-[1,2,4]oxadiazol-3-yl)-benzenesulfonamide. To an ice-cooled solution of pyridine (0.10 mL, 1.24 mmol) and compound 514-B (0.50 g, 1.24 mmol), sealed in a microwave vessel, under N$_2$, was added 2-ethylhexylchloroformate (0.239 g, 1.24 mmol), drop-wise. The reaction mixture was stirred at 0° C. for 30 mins and heated at 140° C. for 30 min in a 300 watt microwave. The solution was diluted with H$_2$O, extracted with EtOAc, washed with H$_2$O, brine, Na$_2$SO$_4$, filtered, and the solvent evaporated in vacuo. The crude residue was purified by reverse-phase semi-prep HPLC (Gemini, C$_{18}$ column; 100×30 mm I.D.; 5µ) to afford 0.175 g of compound 513 as a white solid. $^1$H-NMR (DMSO-d$_6$) δ 1.66-1.82 (m, 2H), 2.26-2.45 (m, 2H), 3.78 (t, 2H), 7.25-7.37 (m, 1H), 7.37-7.46 (m, 2H), 7.77-7.84 (m, 1H), 7.86-7.93 (m, 1H), 7.96 (m, 2H), 8.04 (m, 2H), 13.21 (br s, 1H); MS: m/z 484.1 (MH$^+$).

Compound 514

N-(3-Bromo-benzo[b]thiophen-2-yl)-N-(4,4,4-trifluoro-butyl)-4-(5-oxo-4,5-dihydro-[1,2,4]oxadiazol-3-yl)-benzenesulfonamide. N-Bromosuccinimide (0.037 g, 0.21 mmol) was added to a solution of dichloroethane (2 mL), and compound 513 (0.10 g, 0.21 mmol) and the reaction mixture was stirred at ambient temperature for 18 h. The solution was diluted with H$_2$O, extracted with EtOAc, washed with H$_2$O, brine, Na$_2$SO$_4$, filtered, and the solvent evaporated in vacuo. The crude residue was purified by reverse-phase semi-prep HPLC (Gemini, C$_{18}$ column; 100×30 mm I.D.; 5µ) to afford 0.024 g of compound 514 as a white solid. $^1$H-NMR (DMSO-d$_6$): δ1.60-1.79 (m, 2H), 2.24-2.45 (m, 2H), 3.68-3.83 (m, 2H), 7.45-7.66 (m, 2H), 7.69-7.92 (m, 1H), 7.92-8.17 (m, 5H), 13.25 (br s, 1H); MS: m/z 562.8 (MH$^+$).

Following the procedure described above for example 60 and substituting the appropriate reagents, starting materials and purification methods known to those skilled in the art, the following compounds of the present invention were prepared:

Compound 442

N-(Benzo[b]thiophen-2-yl)-N-(butyl)-4-(5-oxo-4,5-dihydro-[1,2,4]oxadiazol-3-yl)-benzenesulfonamide. MS: m/z 430.0 (MH$^+$).

Compound 443

N-(3-Bromo-benzo[b]thiophen-2-yl)-N-(butyl)-4-(5-oxo-4,5-dihydro-[1,2,4]oxadiazol-3-yl)-benzenesulfonamide. $^1$H-NMR (CD$_3$OD) δ 0.91 (t, 3H), 1.32-1.60 (m, 4H), 3.63-3.83 (m, 2H), 7.46-7.62 (m, 2H), 7.74-7.88 (m, 2H), 7.90 (m, 2H), 8.00 (s, 2H), 8.06 (m, 2H); MS: m/z 507.9 (MH$^+$).

Compound 471

N-(Benzo[b]thiophen-2-yl)-N-(butyl)-4-N-hydroxy-benzamidinesulfonamide. MS: m/z 404.1 (MH$^+$).

Compound 473

N-(3-Bromo-benzo[b]thiophen-2-yl)-N-(butyl)-4-N-hydroxy-benzamidinesulfonamide. $^1$H-NMR (DMSO-d$_6$) δ 0.73-0.89 (m, 3H), 1.30-1.46 (m, 4H), 3.64 (br s, 2H), 7.46-7.61 (m, 3H), 7.74-7.84 (m, 1H), 7.92 (d, 2H), 7.97-8.03 (m, 1H), 8.09 (d, 2H), 8.24 (s, 1H); MS: m/z 484.4 (MH$^+$).

Compound 482

N-(Benzo[b]thiophen-2-yl)-N-(4-fluoro-3-trifluoromethyl-benzyl)-4-N-hydroxy-benzamidinesulfonamide. $^1$H-NMR (DMSO-d$_6$) δ 5.03 (s, 2H), 7.19 (s, 1H), 7.29-7.38 (m, 2H), 7.50 (t, 1H), 7.66-7.78 (m, 3H), 7.78-7.88 (m, 1H), 7.95 (s, 4H); MS: m/z 524.5 (MH$^+$).

Compound 483

N-(Benzo[b]thiophen-2-yl)-N-(4-fluoro-3-trifluoromethyl-benzyl)-4-(5-oxo-4,5-dihydro-[1,2,4]oxadiazol-3-yl)-benzenesulfonamide. $^1$H-NMR (DMSO-d$_6$) δ 5.03 (s, 2H), 7.21 (s, 1H), 7.26-7.39 (m, 2H), 7.41-7.59 (m, 1H), 7.62-7.78 (m, 3H), 7.78-7.93 (m, 1H), 7.98-8.16 (m, 4H), 13.24 (br s, 1H); MS: m/z 550.1 (MH$^+$).

Compound 511

N-(3-Bromo-benzo[b]thiophen-2-yl)-N-(4-fluoro-3-trifluoromethyl-benzyl)-4-(5-oxo-4,5-dihydro-[1,2,4]oxadiazol-3-yl)-benzenesulfonamide. $^1$H-NMR (CDCl$_3$) δ 4.91 (s, 2H), 7.05-7.17 (m, 1H), 7.35-7.48 (m, 2H), 7.48-7.57 (m, 2H), 7.71 (dd, 2H), 7.95 (m, 2H), 8.03 (m, 2H); MS: m/z 628.0 (MH$^+$).

Compound 512

N-(3-Chloro-benzo[b]thiophen-2-yl)-N-(4-fluoro-3-trifluoromethyl-benzyl)-4-(5-oxo-4,5-dihydro-[1,2,4]oxadiazol-3-yl)-benzenesulfonamide. Compound 512 was synthesized as per compound 514 of Example 60, substituting NBS with NCS. $^1$H-NMR (CDCl$_3$) δ 4.89 (s, 2H), 7.12 (d, 1H), 7.39-7.48 (m, 2H), 7.53 (d, 2H), 7.63-7.76 (m, 2H), 7.94 (m, 2H), 8.03 (m, 2H); MS: m/z 584.0 (MH$^+$).

Compound 515

N-(3-Chloro-benzo[b]thiophen-2-yl)-N-(4,4,4-trifluoro-butyl)-4-(5-oxo-4,5-dihydro-[1,2,4]oxadiazol-3-yl)-benzenesulfonamide. Compound 515 was synthesized as per compound 514 of Example 60, substituting NBS with NCS. MS: m/z 515.8 (MH$^+$).

Compound 541

N-(3-Methyl-benzo[b]thiophen-2-yl)-N-(butyl)-4-(5-oxo-4,5-dihydro-[1,2,4]oxadiazol-3-yl)-benzenesulfonamide. $^1$H-NMR (CDCl$_3$) δ 0.89 (t, 3H), 1.31-1.44 (m, 2H), 1.5-1.6 (m, 2H), 2.40 (s, 3H), 3.55 (br s, 2H), 7.31-7.49 (m, 2H), 7.58-7.79 (m, 2H), 7.84-8.04 (m, 4H), 10.72 (s, 1H); MS: m/z 444.1 (MH$^+$).

Compound 544

N-(3-Methyl-benzo[b]thiophen-2-yl)-N-(4-fluoro-3-trifluoromethyl-benzyl)-4-(5-oxo-4,5-dihydro-[1,2,4]oxadiazol-3-yl)-benzenesulfonamide. $^1$H-NMR (CDCl$_3$) δ 2.02-2.19 (m, 3H), 4.76 (br s, 2H), 7.08 (t, 1H), 7.34-7.41 (m, 2H), 7.42-7.48 (m, 1H), 7.54 (dd, 1H), 7.58-7.68 (m, 2H), 7.99 (m, 4H), 11.25 (br s, 1H); MS: m/z 564.0 (MH$^+$).

Compound 583

N-(3-Bromo-benzo[b]thiophen-2-yl)-N-(5,5,5-trifluoro-pentyl)-4-(5-oxo-4,5-dihydro-[1,2,4]oxadiazol-3-yl)-benzenesulfonamide. ¹H-NMR (DMSO-d₆) δ 1.40-1.68 (m, 4H), 2.12-2.34 (m, 2H), 3.70 (br s, 2H), 7.39-7.64 (m, 2H), 7.64-7.86 (m, 1H), 7.98-8.04 (m, 1H), 8.07 (s, 4H), 13.24 (br s, 1H); MS: m/z 577.6 (MH⁺).

Compound 584

N-(3-Chloro-benzo[b]thiophen-2-yl)-N-(5,5,5-trifluoro-pentyl)-4-(5-oxo-4,5-dihydro-[1,2,4]oxadiazol-3-yl)-benzenesulfonamide. Compound 584 was synthesized as per compound 514 of Example 60, substituting NBS with NCS. ¹H-NMR (DMSO-d₆) δ 1.57-1.62 (m 4H) 2.18-2.39 (m, 2H) 3.57-3.86 (m, 2H) 7.46-7.65 (m, 2H) 7.68-7.87 (m, 1H) 7.98-8.04 (m, 1H) 8.07 (s, 4H) 13.24 (br s, 1H); MS: m/z 531.6 (MH⁺).

Compound 597

N-(Benzo[b]thiophen-2-yl)-N-(3,3,3-trifluoro-propyl)-4-(5-oxo-4,5-dihydro-[1,2,4]oxadiazol-3-yl)-benzenesulfonamide. MS: m/z 496.6 (MH⁺).

Compound 599

N-(3-Methyl-benzo[b]thiophen-2-yl)-N-(3,3,3-trifluoro-propyl)-4-(5-oxo-4,5-dihydro-[1,2,4]oxadiazol-3-yl)-benzenesulfonamide. ¹H-NMR (DMSO-d₆) δ 2.24 (s, 3H), 2.54-2.63 (m, 2H), 3.88 (br s, 2H), 7.35-7.56 (m, 2H), 7.78-7.83 (m, 1H), 7.84-7.90 (m, 1H), 7.99-8.08 (m, 4H), 13.23 (br s, 1H); MS: m/z 483.6 (MH⁺).

Compound 608

N-(3-Bromo-benzo[b]thiophen-2-yl)-N-(3,3,3-trifluoro-propyl)-4-(5-oxo-4,5-dihydro-[1,2,4]oxadiazol-3-yl)-benzenesulfonamide. ¹H-NMR (DMSO-d₆) δ 2.54-2.77 (m, 2H), 4.00 (t, 2H), 7.44-7.64 (m, 2H), 7.68-7.85 (m, 1H), 7.94-8.21 (m, 5H), 13.25 (br s, 1H); MS: m/z 549.6 (MH⁺).

Compound 609

N-(3-Chloro-benzo[b]thiophen-2-yl)-N-(3,3,3-trifluoro-propyl)-4-(5-oxo-4,5-dihydro-[1,2,4]oxadiazol-3-yl)-benzenesulfonamide. Compound 609 was synthesized as per compound 514 of Example 60, substituting NBS with NCS. MS: m/z 503.7 (MH⁺).

Compound 612

N-(Benzo[b]thiophen-2-yl)-N-(cyclopropyl-ethyl)-4-(5-oxo-4,5-dihydro-[1,2,4]oxadiazol-3-yl)-benzenesulfonamide. MS: m/z 441.7 (MH⁺).

Compound 613

N-(3-Methyl-benzo[b]thiophen-2-yl)-N-(cyclopropyl-ethyl)-4-(5-oxo-4,5-dihydro-[1,2,4]oxadiazol-3-yl)-benzenesulfonamide. ¹H-NMR (DMSO-d₆) δ 0.1-0.2 (m, 2H), 0.4-0.48 (m, 2H), 0.52-0.77 (m, 1H), 1.36 (br s, 2H), 2.26 (s, 3H), 3.65 (br s, 2H), 7.26-7.55 (m, 2H), 7.74-7.82 (m, 1H), 7.82-7.89 (m, 1H), 8.00 (m, 2H), 8.06 (m, 2H), 13.24 (br s, 1H); MS: m/z 455.7 (MH⁺).

Compound 626

N-(3-Bromo-benzo[b]thiophen-2-yl)-N-(cyclopropyl-ethyl)-4-(5-oxo-4,5-dihydro-[1,2,4]oxadiazol-3-yl)-benzenesulfonamide. ¹H-NMR (DMSO-d₆) δ 0.1-0.2 (m, 2H), 0.30-0.54 (m, 2H), 0.69-0.91 (m, 1H), 1.39 (br s, 2H), 3.64-3.89 (m, 2H), 7.55 (dd, 2H), 7.70-7.93 (m, 1H), 7.94-8.24 (m, 5H), 13.25 (br s, 1H); MS: m/z 520.1 (MH⁺).

Compound 627

N-(3-Chloro-benzo[b]thiophen-2-yl)-N-(cyclopropyl-ethyl)-4-(5-oxo-4,5-dihydro-[1,2,4]oxadiazol-3-yl)-benzenesulfonamide. Compound 627 was synthesized as per compound 514 of Example 60, substituting NBS with NCS. ¹H-NMR (DMSO-d₆) δ 0.1-0.2 (m, 2H), 0.26-0.43 (m, 2H,) 0.69-0.80 (m, 1H), 1.38 (q, 2H), 3.73 (t, 2H), 7.47-7.61 (m, 2H,) 7.68-7.85 (m, 1H), 7.89-8.18 (m, 5H), 13.25 (br s, 1H); MS: m/z 476.6 (MH⁺).

Compound 801

N-(3-Methyl-benzo[b]thiophen-2-yl)-N-(4-trifluoromethoxy-benzyl)-4-(5-oxo-4,5-dihydro-[1,2,4]oxadiazol-3-yl)-benzenesulfonamide. ¹H-NMR (DMSO-d₆) δ 1.92 (s, 3H), 4.83 (br s, 2H), 7.26-7.35 (m, 2H), 7.35-7.45 (m, 4H), 7.63-7.72 (m, 1H), 7.83 (dd, 1H), 8.09 (s, 4H), 13.27 (br s, 1H); MS: m/z 562.0 (MH⁺).

Compound 807

N-(3-Methyl-benzo[b]thiophen-2-yl)-N-(cyclopropyl-ethyl)-4-(5-oxo-4,5-dihydro-[1,2,4]oxadiazol-3-yl)-pyrid-3-ylsulfonamide. Compound 807 was prepared using the procedure in Example 60, step A, substituting compound 514-A with compound Int-9. ¹H-NMR (DMSO-d₆) δ −0.16-0.13 (m, 2H), 0.23-0.46 (m, 2H), 0.72 (br s, 1H), 1.3-1.4 (m, 2H), 3.61 (br s, 2H), 7.29-7.54 (m, 2H), 7.81 (dd, 1H), 7.88 (dd, 1H), 8.24 (d, 1H), 8.46 (dd, 1H), 9.02 (d, 1H), 13.49 (s, 1H); MS: m/z 457.0 (MH⁺).

Compound 808

N-(3-Methyl-benzo[b]thiophen-2-yl)-N-(4-trifluoromethoxy-benzyl)-4-(5-oxo-4,5-dihydro-[1,2,4]oxadiazol-3-yl)-pyrid-3-ylsulfonamide. Compound 808 was prepared using the procedure in Example 60, step A, substituting compound 514-A with compound Int-9. ¹H-NMR (DMSO-d₆) δ 1.79-2.08 (m, 3H), 4.90 sa(br s, 2H), 7.32 (d, 2H), 7.35-7.48 (m, 4H), 7.59-7.78 (m, 1H), 7.78-7.91 (m, 1H), 8.27 (d, 1H), 8.53 (dd, 1H), 9.14 (d, 1H), 13.46-13.57 (m, 1H); MS: m/z 563.0 (MH⁺).

Compound 809

N-(3-Methyl-benzo[b]thiophen-2-yl)-N-(5,5,5-trifluoro-pentyl)-4-(5-oxo-4,5-dihydro-[1,2,4]oxadiazol-3-yl)-pyrid-3-ylsulfonamide. Compound 809 was prepared using the procedure in Example 60, step A, substituting compound 514-A with compound Int-9. ¹H-NMR (DMSO-d₆) δ 1.43-1.63 (m, 5H), 2.24 (br s, 3H), 2.27-2.37 (m, 3H), 7.30-7.57 (m, 2H), 7.82 (dd, 1H), 7.87-8.00 (m, 1H), 8.24 (d, 1H), 8.46 (dd, 1H), 9.04 (d, 1H), 13.49 (br s, 1H); MS: m/z 513.0 (MH+).

Example 61

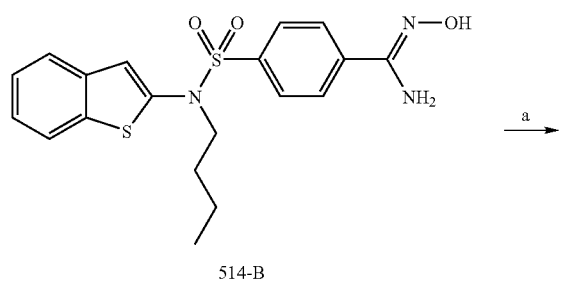

514-B

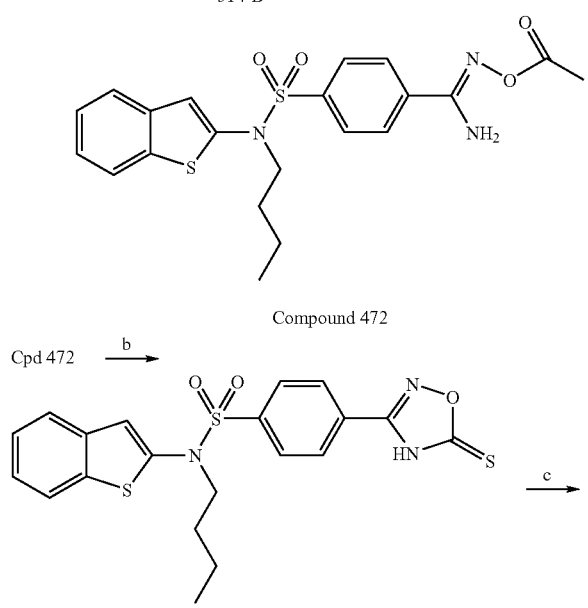

a) DCM, acetic anhydride, TEA; b) DMF, CS₂, NaH; c) DMF, DCE, NBS.

Compound 472

N-(Benzo[b]thiophen-2-yl)-N-(butyl)-4-N-hydroxy-acetyl-benzamidine sulfonamide. A solution of compound 514-B (0.5 g 1.24 mmol), DCM (5 mL), acetic anhydride (0.126 g 1.24 mmol), and triethylamine (0.125 g 1.24 mmol) was stirred at ambient temperature for 18 h. The solution was diluted with H₂O, extracted with EtOAc, washed with H₂O, brine, dried over Na₂SO₄, filtered, and the solvent evaporated in vacuo. The crude residue was purified by reverse-phase semi-prep HPLC (Gemini, C₁₈ column; 100×30 mm I.D.; 5μ) to afford 0.340 g of compound 472 as a white solid. MS: m/z 446.1 (MH+).

N-Benzo[b]thiophen-2-yl-N-(butyl)-4-(5-thioxo-4,5-di-hydro-[1,2,4]oxadiazol-3-yl)-benzenesulfonamide (481-B). To an ice-cooled mixture of compound 472 (0.220 g, 0.494 mmol) and carbon disulfide (0.113 mL, 1.88 mmol) in DMF was added sodium hydride (0.036 g, 1.48 mmol) and the reaction mixture was stirred at 0° C. and allowed to warm to ambient temperature over 18 h. The reaction mixture was diluted with 1N hydrochloric acid, the aqueous phase extracted with EtOAc, washed with H₂O, brine, dried over Na₂SO₄, filtered, and the solvent evaporated in vacuo. The crude residue was purified by reverse-phase semi-prep HPLC (Gemini, C₁₈ column; 100×30 mm I.D.; 5μ) to afford 0.110 g of compound 481-B as a pale, yellow solid. $^1$H-NMR (DMSO-d₆) δ 0.86 (t, 3H), 1.25-1.42 (m, 2H), 1.42-1.58 (m, 2H), 3.68 (t, 4H), 7.25 (s, 1H), 7.29-7.45 (m, 2H), 7.72-7.83 (m, 1H), 7.83-7.94 (m, 3H), 8.08 (d, 2H); MS: m/z 446.1 (MH+).

Compound 481

N-(3-Bromo-benzo[b]thiophen-2-yl)-N-(butyl)-4-(5-thioxo-4,5-dihydro-[1,2,4]oxadiazol-3-yl)-benzenesulfonamide. N-Bromosuccinimide (0.048, 0.27 mmol) was added to a solution of dichloroethane (2 mL), dimethylformamide (2 mL) and compound 481-B (0.120 g, 0.27 mmol) and stirred at ambient temperature for 18 h. The reaction mixture was diluted with H₂O, the aqueous phase extracted with EtOAc, washed with H₂O, brine, dried over Na₂SO₄, filtered, and the solvent evaporated in vacuo. The crude residue was purified by reverse-phase semi-prep HPLC (Gemini, C₁₈ column; 100×30 mm I.D.; 5μ) to afford 0.019 g of compound 481 pale, pink solid. $^1$H-NMR (DMSO-d₆) δ 0.83 (t, 3H), 1.24-1.51 (m, 4H), 3.66 (br s, 3H), 7.44-7.60 (m, 2H), 7.69-7.83 (m, 1H), 7.94-8.07 (m, 3H), 8.07-8.21 (m, 2H); MS: m/z 525.1 (MH+).

Example 62

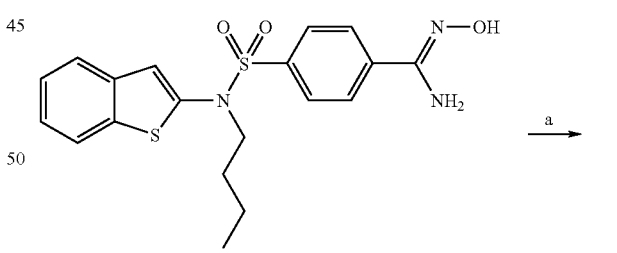

514-B

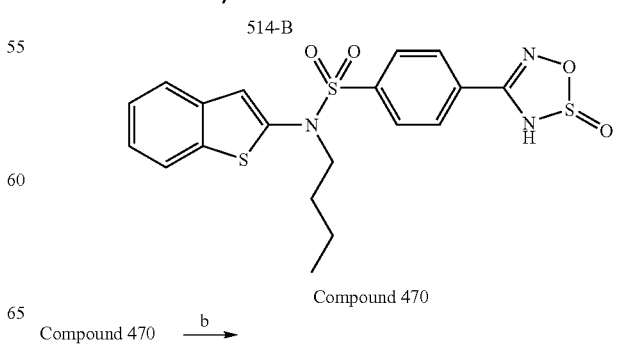

Compound 470

Compound 470 →ᵇ

-continued

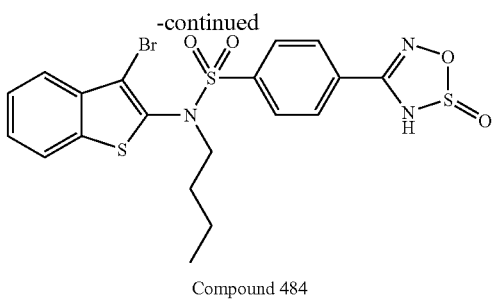

Compound 484 a) THF, pyridine, SOCl$_2$; b) DCE, DMF, NBS.

Compound 470

N-(Benzo[b]thiophen-2-yl)-N-(butyl)-4-(3H-[1,2,3,5]oxathiadiazole-2-oxide)-benzenesulfonamide. To an ice-cooled solution of compound 514-B (0.250 g, 0.62 mmol), pyridine (0.098 g, 1.24 mmol) and THF (4 mL) was added, drop-wise, a solution of thionyl chloride (0.073 g, 0.62 mmol) in DCM (1 mL), and the resulting mixture was stirred for 30 min at 0° C. The solvent was evaporated in vacuo, the residue dissolved in water and extracted with CHCl$_3$. The solvent was evaporated in vacuo and the crude residue purified by reverse-phase semi-prep HPLC (Gemini, C$_{18}$ column; 100×30 mm I.D.; 5µ) to afford 0.224 g of compound 470 as a white solid. MS: m/z 450.0 (MH$^+$).

Compound 484

N-(3-Bromo-benzo[b]thiophen-2-yl)-N-(butyl)-4-(3H-[1,2,3,5]oxathiadiazole-2-oxide)-benzenesulfonamide. To a solution of compound 470 (0.130 g, 0.289 mmol), DCE (2 mL), and DMF (2 mL) was added N-bromosuccinimide (0.051 g, 0.289 mmol) and the reaction mixture was stirred at ambient temperature for 18 h. The reaction mixture was washed with H$_2$O, the organics separated, and the solvent was evaporated in vacuo. The crude residue was purified by reverse-phase semi-prep HPLC (Gemini, C$_{18}$ column; 100×30 mm I.D.; 5µ) to afford 0.084 g of compound 484 as a white solid. $^1$H-NMR (DMSO-d$_6$) δ 0.73-0.93 (m, 3H), 1.27-1.53 (m, 4H), 3.59-3.81 (m, 2H), 7.44-7.62 (m, 2H), 7.73-7.85 (m, 1H), 7.93-8.07 (m, 3H), 8.07-8.21 (m, 2H); MS: m/z 529.4 (MH$^+$).

Following the procedure described above for example 62 and substituting the appropriate reagents, starting materials and purification methods known to those skilled in the art, the following compounds of the present invention were prepared:

Compound 485

N-(3-Chloro-benzo[b]thiophen-2-yl)-N-(butyl)-4-(3H-[1,2,3,5]oxathiadiazole-2-oxide)-benzenesulfonamide. Compound 485 was synthesized as per compound 484 of Example 62, substituting NBS with NCS. $^1$H-NMR (DMSO-d$_6$) δ 0.75-0.91 (m, 3H), 1.26-1.52 (m, 4H), 3.67 (t, 2H), 7.45-7.61 (m, 2H), 7.75-7.89 (m, 1H), 7.95-8.07 (m, 3H), 8.07-8.20 (m, 2H); MS: m/z 485.4 (MH$^+$).

Compound 540

N-(3-Methyl-benzo[b]thiophen-2-yl)-N-(butyl)-4-(3H-[1,2,3,5]oxathiadiazole-2-oxide)-benzenesulfonamide. $^1$H-NMR (CDCl$_3$) δ 0.89 (t, 3H), 1.28-1.44 (m, 2H), 1.44- 1.59 (m, 2H), 2.38 (s, 3H), 3.51 (s, 2H), 7.30-7.46 (m, 2H), 7.60-7.76 (m, 2H), 7.78-7.91 (m, 3H), 7.99 (s, 1H); MS: m/z 464.1 (MH$^+$).

Compound 543

N-(3-Methyl-benzo[b]thiophen-2-yl)-N-(4-fluoro-3-trifluoromethyl-benzyl)-4-(3H-[1,2,3,5]oxathiadiazole-2-oxide)-benzenesulfonamide. $^1$H-NMR (CDCl$_3$) δ 2.02-2.12 (s, 3H), 4.67 (br s, 2H), 7.08 (t, 1H), 7.31-7.38 (m, 2H), 7.44 (dt, 1H), 7.49-7.57 (m, 1H), 7.57-7.73 (m, 2H), 7.82-7.99 (m, 4H); MS: m/z 548.1 (MH$^+$).

Compound 581

N-(3-Bromo-benzo[b]thiophen-2-yl)-N-(5,5,5-trifluoropentyl)-4-(3H-[1,2,3,5]oxathiadiazole-2-oxide)-benzenesulfonamide. $^1$H-NMR (DMSO-d$_6$) δ 1.57 (m, 4H), 2.10-2.36 (m, 2H), 3.71 (br s, 2H), 7.43-7.66 (m, 2H), 7.74-7.85 (m, 1H), 7.94-8.09 (m, 3H), 8.09-8.21 (m, 2H); MS: m/z 597.1 (MH$^+$).

Compound 582

N-(3-Chloro-benzo[b]thiophen-2-yl)-N-(5,5,5-trifluoropentyl)-4-(3H-[1,2,3,5]oxathiadiazole-2-oxide)-benzenesulfonamide. Compound 582 was synthesized as per compound 484 of Example 62, substituting NBS with NCS. MS: m/z 551.5 (MH$^+$).

Compound 596

N-(Benzo[b]thiophen-2-yl)-N-(3,3,3-trifluoro-propyl)-4-(3H-[1,2,3,5]oxathiadiazole-2-oxide)-benzenesulfonamide. MS: m/z 489.6 (MH$^+$).

Compound 598

N-(3-Methyl-benzo[b]thiophen-2-yl)-N-(3,3,3-trifluoropropyl)-4-(3H-[1,2,3,5]oxathiadiazole-2-oxide)-benzenesulfonamide. $^1$H-NMR (DMSO-d$_6$) δ 2.15-2.30 (s, 3H), 2.54-2.64 (m, 2H), 3.41 (br s, 2H), 7.36-7.53 (m, 2H), 7.75-7.83 (m, 1H), 7.83-7.94 (m, 1H), 8.00 (m, 2H), 8.10 (m, 2H); MS: m/z 503.7 (MH$^+$).

Compound 607

N-(3-Bromo-benzo[b]thiophen-2-yl)-N-(3,3,3-trifluoropropyl)-4-(3H-[1,2,3,5]oxathiadiazole-2-oxide)-benzenesulfonamide. MS: m/z 569.9 (MH$^+$).

Compound 610

N-(Benzo[b]thiophen-2-yl)-N-(cyclopropyl-ethyl)-4-(3H-[1,2,3,5]oxathiadiazole-2-oxide)-benzenesulfonamide. MS: m/z 461.7 (MH$^+$).

Compound 611

N-(3-Methyl-benzo[b]thiophen-2-yl)-N-(cyclopropylethyl)-4-(3H-[1,2,3,5]oxathiadiazole-2-oxide)-benzenesulfonamide. $^1$H-NMR (DMSO-d$_6$) δ 0.1-0.2 (m, 2H) 0.28-0.43 (m, 2H) 0.70 (d, 1H) 1.36 (br s, 2H) 2.26 (s, 3H) 3.64 (br s, 2H) 7.28-7.51 (m, 2H) 7.70-7.83 (m, 1H) 7.83-7.93 (m, 1H) 7.99 (d, 2H) 8.04-8.19 (m, 2H); MS: m/z 475.6 (MH$^+$).

Compound 624

N-(3-Bromo-benzo[b]thiophen-2-yl)-N-(cyclopropylethyl)-4-(3H-[1,2,3,5]oxathiadiazole-2-oxide)-benzenesulfonamide. ¹H-NMR (DMSO-d₆) δ 0.1-0.2 (m, 2H), 0.29-0.46 (m, 2H), 0.63-0.86 (m, 1H), 1.38 (q, 2H), 3.74 (t, 2H), 7.44-7.62 (m, 2H), 7.71-7.84 (m, 1H), 7.93-8.07 (m, 3H), 8.07-8.20 (m, 2H); MS: m/z 539.4 (MH⁺).

Compound 625

N-(3-Chloro-benzo[b]thiophen-2-yl)-N-(cyclopropyl-ethyl)-4-(3H-[1,2,3,5]oxathiadiazole-2-oxide)-benzene-sulfonamide. Compound 625 was synthesized as per compound 484 of Example 62, substituting NBS with NCS. ¹H-NMR (DMSO-d₆) δ 0.1-0.2 (m, 2H) 0.29-0.43 (m, 2H) 0.68-0.83 (m, 1H) 1.38 (q, 2H) 3.74 (t, 2H) 7.47-7.60 (m, 2H) 7.72-7.87 (m, 1H) 7.96-8.07 (m, 3H) 8.07-8.18 (m, 2H); MS: m/z 495.5 (MH⁺).

Example 63

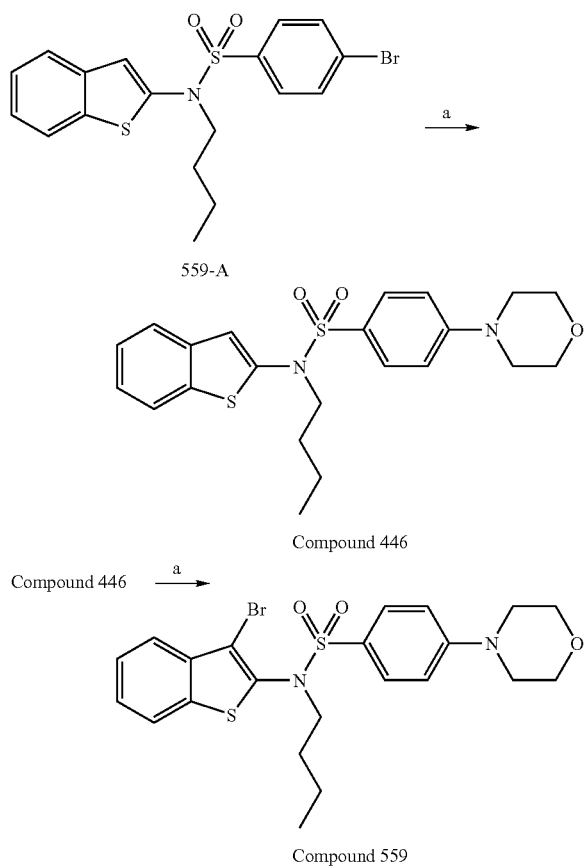

a) KO-tBu, Pd₂(dba), 9,9-dimethyl-4,5-bis(diphenylphosphino)xanthine, morpholine, dioxane.

Compound 559-A, was prepared by the method used to synthesize compound 600 in Example 30, steps A and B.

Compound 446

N-Benzo[b]thiophen-2-yl-N-(butyl)-4-morpholin-4-yl-benzenesulfonamide. Compound 559-A (0.10 g, 0.236 mmol), 1.0 M potassium t-butoxide-THF (1.41 mL, 1.41 mmol), Pd(dba) (0.01 g, 0.011 mmol), 9,9-dimethyl-4,5-bis(diphenylphosphino)xanthine, (0.006 g, 0.011 mmol), morpholine (0.04 mL, 0.47 mmol) and dioxane (4 mL) were added to a microwave vessel with stir bar and heated at 100° C. for 30 min in a 300 watt microwave reactor. The reaction mixture was diluted with H₂O, extracted with EtOAc, and the solvent evaporated under reduced pressure. The crude residue was dissolved in acetonitrile, the solution filtered and purified by reverse-phase semi-prep HPLC (Gemini, C₁₈ column; 100×30 mm I.D.; 5µ) to afford 0.021 g of compound 446 as a dark, viscous oil. ¹H-NMR (CDCl₃) δ 0.89 (t, 3H), 1.29-1.46 (m, 2H), 1.50-1.63 (m, 2H), 3.23-3.34 (m, 4H), 3.57 (t, 2H), 3.81-3.93 (m, 4H), 6.84 (m, 2H), 7.13 (s, 1H), 7.29-7.40 (m, 2H), 7.57 (m, 2H), 7.63-7.73 (m, 2H); MS: m/z 431.1 (MH⁺).

Compound 559

N-(3-Bromo-benzo[b]thiophen-2-yl)-N-(butyl)-4-morpholine-benzenesulfonamide. N-Bromosuccinimide (0.030 g, 0.167 mmol) was added to a solution of dichloroethane (2 mL), and compound 446 (0.072 g, 0.167 mmol) and stirred at ambient temperature for 2 h. The reaction mixture was diluted with H₂O, extracted with EtOAc, and the solvent evaporated under reduced pressure. The crude residue was purified by reverse-phase semi-prep HPLC (Gemini, C₁₈ column; 100×30 mm I.D.; 5µ) to afford 0.050 g of compound 559 as a dark, green gum. ¹H-NMR (CDCl₃): δ 0.86 (t, 3H), 1.29-1.45 (m, 2H), 1.45-1.59 (m, 2H), 3.23-3.38 (m, 4H), 3.60 (t, 2H), 3.82-3.98 (m, 4H), 6.78-6.95 (m, 2H), 7.34-7.49 (m, 2H), 7.63-7.75 (m, 3H), 7.75-7.84 (m, 1H); MS: m/z 511.0 (MH⁺).

Following the procedure described above for example 63 and substituting the appropriate reagents, starting materials and purification methods known to those skilled in the art, the following compounds of the present invention were prepared:

Compound 444

N-(Benzo[b]thiophen-2-yl)-N-(butyl)-4-dimethylamino-benzenesulfonamide. MS: m/z 389.1 (MH⁺).

Compound 445

N-(Benzo[b]thiophen-2-yl)-N-(butyl)-4-pyrrolidin-1-yl-benzenesulfonamide. MS: m/z 415.0 (MH⁺).

Compound 447

N-(Benzo[b]thiophen-2-yl)-N-(butyl)-4-(4-methyl-piperazin-1-yl)-benzenesulfonamide. MS: m/z 444.1 (MH⁺).

Compound 560

N-(3-Bromo-benzo[b]thiophen-2-yl)-N-(butyl)-4-dimethylamino-benzenesulfonamide. MS: m/z 467.0 (MH⁺).

Compound 561

N-(3-Chloro-benzo[b]thiophen-2-yl)-N-(butyl)-4-dimethylamino-benzenesulfonamide. Compound 561 was synthesized as per compound 559 of Example 63, substituting NBS with NCS. ¹H-NMR (CDCl₃) δ 0.86 (t, 3H) 1.28-1.44 (m, 2H) 1.44-1.55 (m, 2H) 3.06 (s, 6H) 3.57 (t, 2H) 6.65 (m, 2H) 7.35-7.50 (m, 2H) 7.65 (m, 2H) 7.67-7.74 (m, 1H) 7.75-7.86 (m, 1H); MS: m/z 423.0 (MH⁺).

Compound 562

N-(3-Chloro-benzo[b]thiophen-2-yl)-N-(butyl)-4-morpholin-4-yl-benzenesulfonamide. Compound 562 was synthesized as per compound 559 of Example 63, substituting NBS with NCS. MS: m/z 465.0 (MH⁺).

Compound 738

N-(3-Methyl-benzo[b]thiophen-2-yl)-N-(cyclopropyl-ethyl)-4-dimethylamino-benzenesulfonamide. $^1$H-NMR (DMSO-d$_6$) δ −0.11-0.05 (m, 2H), 0.31-0.46 (m, 2H), 0.59-0.81 (m, 1H), 1.34 (br s, 2H), 2.31 (s, 3H), 3.08 (s, 6H), 3.52 (br s, 2H), 6.76-6.93 (m, 2H), 7.35-7.51 (m, 2H), 7.51-7.63 (m, 2H), 7.73-7.84 (m, 1H), 7.84-7.97 (m, 1H); MS: m/z 415.2 (MH⁺).

Compound 739

N-(3-Methyl-benzo[b]thiophen-2-yl)-N-(cyclopropyl-ethyl)-4-diethylamino-benzenesulfonamide. $^1$H-NMR (DMSO-d$_6$) δ −0.11-0.06 (m, 2H), 0.31-0.50 (m, 2H), 0.62-0.80 (m, 1H), 1.36 (br s, 2H), 2.27 (s, 3H), 3.01 (br s, 4H), 3.62 (br s, 3H), 3.80 (br s, 3H), 3.98 (s, 1H), 7.36-7.58 (m, 2H), 7.65-7.76 (m, 2H), 7.76-7.84 (m, 1H), 7.84-7.98 (m, 3H); MS: m/z 443.3 (MH⁺).

Compound 740

N-(3-Methyl-benzo[b]thiophen-2-yl)-N-(cyclopropyl-ethyl)-4-thiomorpholin-4-yl-benzenesulfonamide. MS: m/z 473.2 (MH⁺).

Compound 741

N-(3-Methyl-benzo[b]thiophen-2-yl)-N-(cyclopropyl-ethyl)-4-morpholino-benzenesulfonamide. $^1$H-NMR (DMSO-d$_6$) δ −0.09-0.11 (m, 2H), 0.26-0.47 (m, 2H), 0.72 (d, 1H), 1.34 (br s, 2H), 2.19-2.35 (m, 3H), 3.24-3.44 (m, 4H), 3.53 (br s, 2H), 3.69-3.89 (m, 4H), 7.12 (d, 2H), 7.36-7.50 (m, 2H), 7.52-7.66 (m, 2H), 7.75-7.86 (m, 1H), 7.86-7.97 (m, 1H); MS: m/z 457.2 (MH⁺).

Compound 742

N-(3-Methyl-benzo[b]thiophen-2-yl)-N-(cyclopropyl-ethyl)-4-(piperazin-1-yl)-benzenesulfonamide. MS: m/z 456.2 (MH⁺).

Compound 748

N-(3-Methyl-benzo[b]thiophen-2-yl)-N-(5,5,5-trifluoro-pentyl)-4-dimethylamino-benzenesulfonamide. $^1$H-NMR (DMSO-d$_6$) δ 1.49 (br s, 4H), 2.27 (s, 6H), 3.03 (s, 6H), 6.79 (d, 2H), 7.32-7.46 (m, 2H), 7.46-7.55 (m, 2H), 7.73-7.82 (m, 1H), 7.84-7.93 (m, 1H); MS: m/z 471.2 (MH⁺).

Compound 749

N-(3-Methyl-benzo[b]thiophen-2-yl)-N-(5,5,5-trifluoro-pentyl)-4-thiomorpholin-4-yl-benzenesulfonamide. MS: m/z 526.2 (MH⁺).

Compound 750

N-(3-Methyl-benzo[b]thiophen-2-yl)-N-(5,5,5-trifluoro-pentyl)-4-morpholino-benzenesulfonamide. $^1$H-NMR (DMSO-d$_6$) δ 1.35-1.64 (m, 4H), 2.13-2.35 (m, 5H), 2.99 (br s, 2H), 3.21-3.39 (m, 4H), 3.48 (br s, 2H), 3.53 (br s, 2H), 3.67-3.91 (m, 4H), 7.07 (d, 2H), 7.33-7.52 (m, 2H), 7.56 (d, 2H), 7.78 (dd, 1H), 7.83-8.00 (m, 1H); MS: m/z 513.2 (MH⁺).

Compound 751

N-(3-Methyl-benzo[b]thiophen-2-yl)-N-(cyclopropyl-ethyl)-4-piperidin-1-yl-benzenesulfonamide. MS: m/z 455.2 (MH⁺).

Compound 752

N-(3-Methyl-benzo[b]thiophen-2-yl)-N-(5,5,5-trifluoro-pentyl)-4-piperidine-benzenesulfonamide. MS: m/z 511.16 (MH⁺).

Example 64

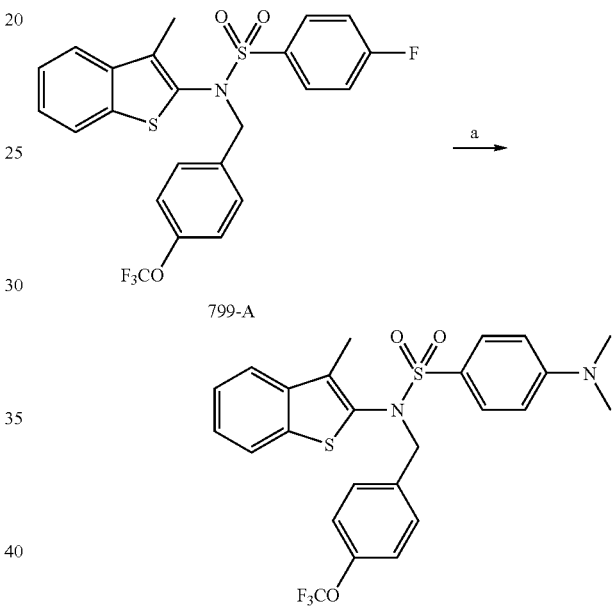

a) DMSO, dimethylamine.

Compound 799-A, was prepared by the method used to synthesize compound 757 in Example 29, steps A and B.

Compound 799

N-(3-Methyl-benzo[b]thiophen-2-yl)-N-(4-trifluoromethoxy-benzyl)-4-dimethylamino-benzenesulfonamide. To a solution of compound 799-A (0.07 g, 0.14 mmol) in dimethylsulfoxide (2 mL) was added a 2.0 M solution of dimethylamine-THF (0.42 mmol), the reaction mixture was sealed and heated at 100° C. in a 300 W microwave. The crude solution was purified by reverse-phase semi-prep HPLC (Gemini, C$_{18}$ column; 100×30 mm I.D.; 5μ) to afford 0.053 g of compound 799 as an off-white solid. $^1$H-NMR (DMSO-d$_6$) δ 1.96 (s, 3H), 3.05 (s, 6H), 4.65 (br s, 2H), 6.76-6.87 (m, 2H), 7.27 (d, 2H), 7.31-7.45 (m, 4H), 7.52-7.62 (m, 2H), 7.62-7.70 (m, 1H), 7.76-7.91 (m, 1H); MS: m/z 521.1 (MH⁺).

Following the procedure described above for example 64 and substituting the appropriate reagents, starting materials and purification methods known to those skilled in the art, the following compounds of the present invention were prepared:

Compound 800

N-(3-Methyl-benzo[b]thiophen-2-yl)-N-(4-trifluoromethoxy-benzyl)-4-morpholino-benzenesulfonamide. $^1$H-NMR (DMSO-d$_6$) δ 1.96 (s, 3H), 3.24-3.39 (m, 4H) 3.65-3.85 (m, 4H), 4.68 (br s, 2H), 7.11 (d, 2H), 7.28 (d, 2H), 7.32-7.46 (m, 4H), 7.58-7.73 (m, 3H), 7.76-7.89 (m, 1H); MS: m/z 563.1 (MH$^+$).

Example 65

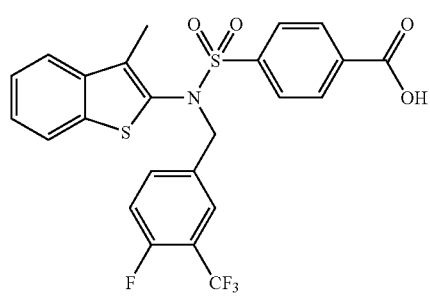

Compound 306

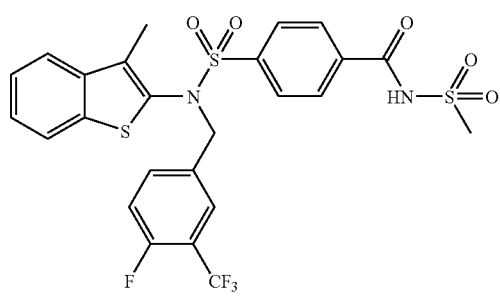

Compound 623
a) THF, CDI; b) MeSO$_2$NH$_2$, DBU, DMAP.

Compound 623

N-(3-Methyl-benzo[b]thiophen-2-yl)-N-(4-fluoro-3-trifluoromethyl-benzyl)-4-methanesulfonylaminocarbonyl-benzenesulfonamide. To a solution of compound 306 (0.50 g, 0.96 mmol) in THF (30 mL) was added CDI (0.232 g, 1.43 mmol) and the reaction mixture was refluxed for 5 h. Methyl sulfonamide (0.136 g, 1.43 mmol), DBU (0.218 g, 1.43 mmol) and DMAP (0.012 g, 0.096 mmol) were added to the reaction mixture and the reaction was refluxed for 1 h. The solution was diluted with H$_2$O, extracted with EtOAc, washed with brine, dried over Na$_2$SO$_4$, filtered, and the solvent evaporated in vacuo. The crude residue was purified by reverse-phase semi-prep HPLC (Gemini, C$_{18}$ column; 100×30 mm I.D.; 5µ) to afford 0.2 g of compound 623 as a white solid. $^1$H-NMR (DMSO-d$_6$) δ 1.93 (s, 3H), 3.40 (s, 3H), 4.91 (br s, 2H), 7.34-7.43 (m, 2H), 7.47 (t, 1H), 7.57-7.75 (m, 3H), 7.75-7.89 (m, 1H), 8.02 (m, 2H), 8.18 (m, 2H); MS: m/z 601.0 (MH$^+$).

Example 66

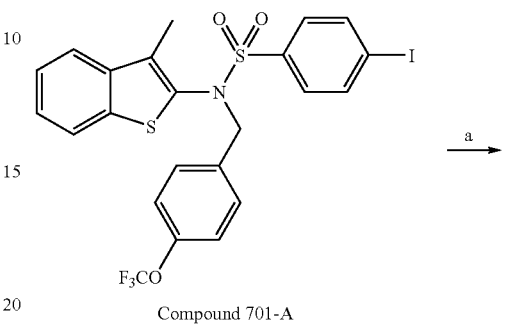

Compound 701-A

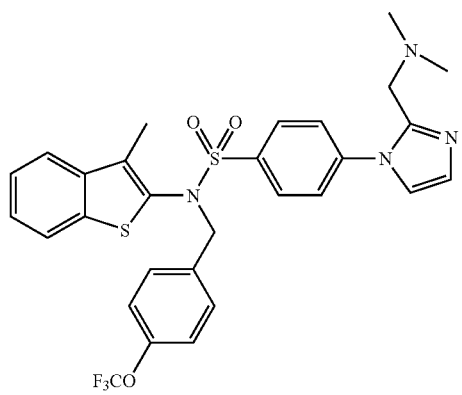

Compound 701
a) DMSO, CuI, K$_2$CO$_3$, compound Int-16.

Compound 701-A, was prepared by the method used to synthesize compound 757 in Example 29, steps A and B.

Compound 701

4-(2-Dimethylaminomethyl-imidazol-1-yl)-N-(3-methyl-benzo[b]thiophen-2-yl)-N-(4-trifluoromethoxy-benzyl)-benzenesulfonamide. A solution of compound 701-A (0.250 g, 0.414 mmol), DMSO (3 mL), CuI (0.016 g, 0.083 mmol), and K$_2$CO$_3$ (0.115 g, 0.828 mmol) was stirred at ambient temperature for 15 min. Compound Int-16 (0.078 g, 0.628 mmol) was added, the reaction mixture refluxed for 18 h, cooled to ambient temperature, and partitioned between H$_2$O and EtOAc. The aqueous phase was extracted with chloroform, the organics combined, dried over MgSO$_4$, filtered, and the solvent evaporated in vacuo. The crude residue was purified by reverse-phase semi-prep HPLC (Gemini, C$_{18}$ column; 100×30 mm I.D.; 5µ) to afford 0.10 g of compound 701 as a yellow oil. $^1$H-NMR (DMSO-d$_6$) δ 1.89-2.01 (m, 3H), 2.80 (s, 5H), 3.17 (s, 3H), 4.49 (s, 2H), 4.85 (br s, 2H), 7.32 (d, 3H), 7.36-7.50 (m, 4H), 7.69 (dd, 1H), 7.75 (s, 1H), 7.80-7.91 (m, 3H), 8.01-8.15 (m, 2H); MS: m/z 601.2 (MH⁺).

Example 67

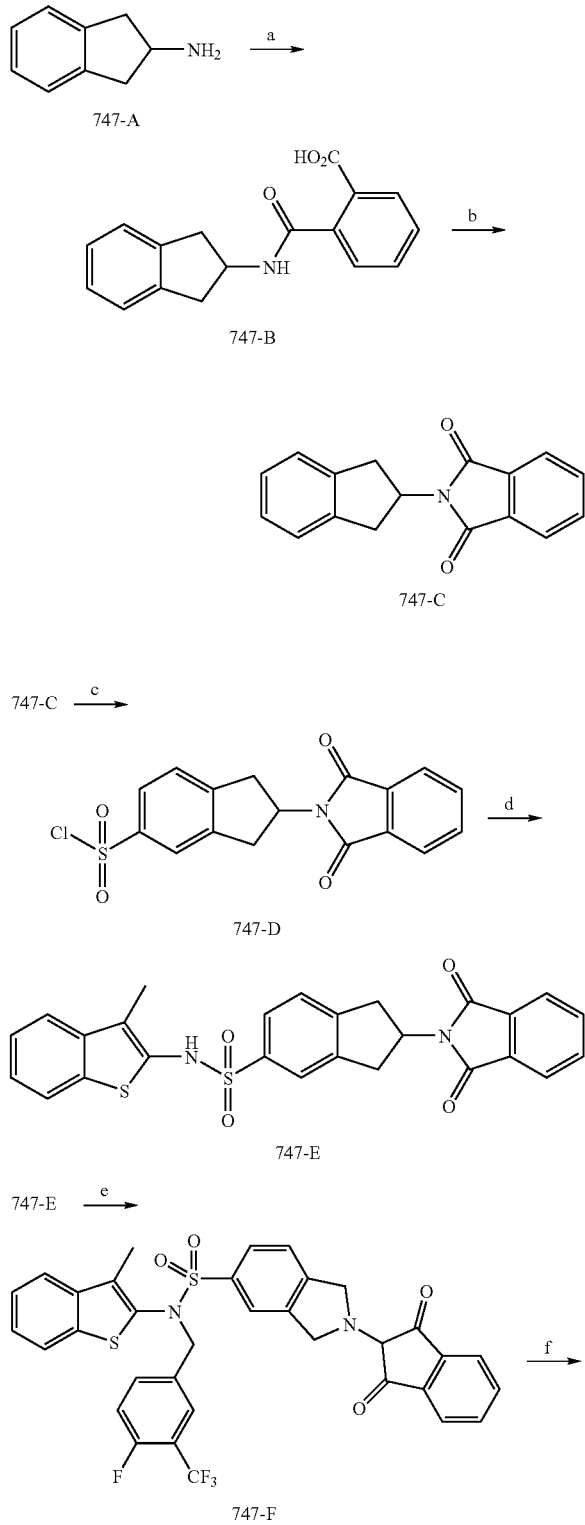

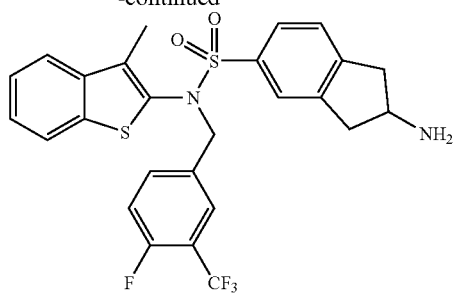

Compound 747 a) CHCl₃, phthalic anhydride; b) DMF, DMAP; c) MeCN, ClSO₃H;
d) DCM, pyridine, compound 757-A; e) DMF, K₂CO₃, 4-fluoro-3-trifluoromethylbenzyl bromide; f) MeOH, H₂NNH₂.

N-Indan-2-yl-phthalamic acid (747-B). To a solution of compound 747-A (1.5 g, 11.3 mmol) in CHCl₃ (100 mL) was added phthalic anhydride (2.25 g, 15.2 mmol) and the reaction mixture was heated at 70° C. for 18 h. The reaction mixture was cooled, the solvent evaporated under reduced pressure, H₂O added to the residue, and the residue was extracted with EtOAc, the organic extracts combined, and concentrated in vacuo. The crude residue was triturated with MeOH, the solid filtered and dried under vacuo to afford 2.0 g of compound 747-B as an amber, crystalline solid. MS: m/z 282.1 (MH⁺).

2-Indan-2-yl-isoindole-1,3-dione (747-C). To a solution of compound 747-B (1.8 g, 0.74 mmol) in DMF (20 mL) was added DMAP (0.782 g; 0.74 mmol) and the reaction mixture was heated at 120° C. for 18 h. The reaction mixture was cooled, diluted with H₂O, and the precipitate filtered and dried under vacuo to afford 1.2 g of compound 747-C as a light brown solid. ¹H-NMR (CDCl₃) δ 3.18 (dd, 2H), 3.63 (dd, 2H), 5.16 (q, 1H), 7.14-7.24 (m, 4H), 7.68-7.77 (m, 2H), 7.79-7.90 (m, 2H); MS: m/z 264.1 (MH⁺).

2-(1,3-Dioxo-1,3-dihydro-isoindol-2-yl)-indan-5-sulfonyl chloride (747-D). To a solution of compound 747-C (0.72 g, 2.7 mmol) in MeCN (50 mL) was added chlorosulfonic acid (3.72 g, 32.4 mmol), drop-wise, and the reaction mixture was stirred at ambient temperature for 48 h. The reaction mixture was diluted with H₂O, extracted with CH₂Cl₂, dried over Na₂SO₄, filtered, and dried to afford 0.976 g of compound 747-D as a brown solid. ¹H-NMR (CDCl₃) δ 3.26-3.43 (m, 2H,) 3.60-3.78 (m, 2H), 5.26 (t, 1H), 7.46 (d, 1H), 7.68-7.79 (m, 2H), 7.79-7.93 (m, 4H); MS: m/z 384.1 (MNa⁺).

2-(1,3-Dioxo-1,3-dihydro-isoindol-2-yl)-indan-N-(3-methyl-benzo[b]thiophen-2-yl)-N-sulfonamide (747-E). To a solution of compound 757-A (0.449 g, 2.25 mmol) in DCM (5 mL) and pyridine (0.355 g, 4.5 mmol), cooled to 0° C., was added compound 747-D (0.976 g; 2.7 mmol) in DCM (2 mL) and the reaction mixture was stirred at ambient temperature for 48 h. The reaction mixture was diluted with H₂O, extracted with EtOAc, washed with brine, dried over Na₂SO₄, filtered and the solvent evaporated in vacuo. The crude residue was purified by reverse-phase semi-prep HPLC (Gemini, C₁₈ column; 100×30 mm I.D.; 5µ) to afford 0.73 g of compound 747-E as a brown solid. MS: m/z 489.1 (MH⁺).

2-(1,3-Dioxo-1,3-dihydro-isoindol-2-yl)-indan-N-(3-methyl-benzo[b]thiophen-2-yl)-N-(4-fluoro-3-trifluoromethylbenzyl)-N-sulfonamide (747-F). To a solution of compound 747-E (0.73 g, 1.49 mmol) in DMF (10 mL) was added K₂CO₃ (0.248 g; 1.79 mmol) and the reaction mixture was stirred for 30 min. A solution of 4-fluoro-3-trifluoromethylbenzyl bromide (0.460 g, 1.79 mmol) in DMF (2 mL) was added drop-wise and the reaction mixture stirred at ambient temperature for 18 h. The reaction mixture was diluted with H₂O, extracted with EtOAc, washed with brine, dried over Na₂SO₄, filtered and the solvent was evaporated in vacuo to afford 0.94 g of crude compound 747-F as a white solid. ¹H-NMR (DMSO-d₆) δ 1.99 (s, 3H), 3.47 (m, 4H), 4.86 (br s, 2H), 5.14 (s, 1H), 7.31-7.56 (m, 4H), 7.58-7.75 (m, 4H), 7.79 (s, 1H), 7.82-7.99 (m, 5H); MS: m/z 665.1 (MH⁺). MS: m/z 663.1 (MH⁺).

Compound 747

2-Amino-indan-N-(3-methyl-benzo[b]thiophen-2-yl)-N-(4-fluoro-3-trifluoromethyl-benzyl)-N-sulfonamide. Compound 747-F (0.91 g, 1.37 mmol) was added a 0.2M hydrazine-methanol solution (20 mL) and the reaction mixture was stirred for 2 h at ambient temperature. The solvent was evaporated in vacuo and the crude residue purified by reverse-phase semi-prep HPLC (Gemini, C₁₈ column; 100×30 mm I.D.; 5μ) to afford 0.4 g of compound 747 as an orange gum. ¹H-NMR (DMSO-d₆) δ 1.78-1.92 (m, 3H), 2.85-3.03 (m, 2H), 3.22-3.43 (m, 2H), 4.00 (br s, 1H), 4.71 (br s, 2H), 7.20-7.42 (m, 3H), 7.42-7.65 (m, 5H), 7.65-7.81 (m, 2H), 7.97 (br s, 2H); MS: m/z 535.1 (MH⁺).

Example 68

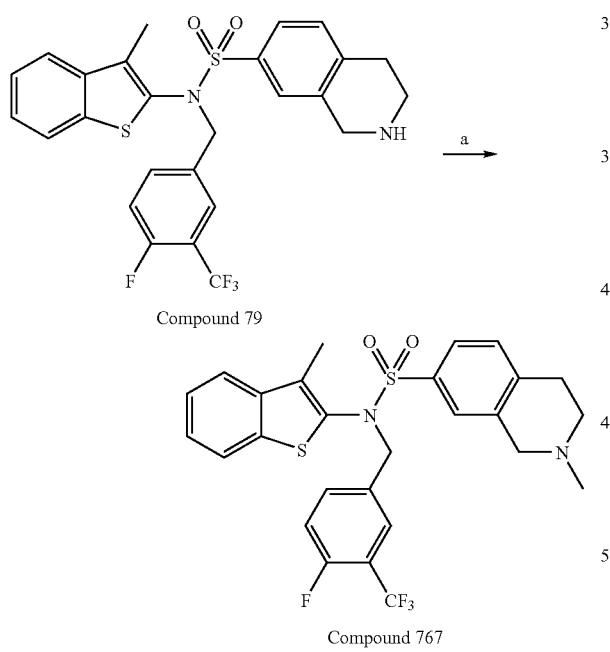

Compound 79

Compound 767 a) HCO₂H, 37% HCHO.

Compound 767

2-Methyl-N-(4-fluoro-3-trifluoromethyl-benzyl)-N-(3-methyl-benzo[b]thiophen-2-yl)-1,2,3,4-tetrahydroisoquinolin-7-yl-sulfonamide. To compound 79 (0.10 g, 0.19 mmol) was added 37% aqueous formaldehyde (0.3 mL) and concentrated formic acid (0.4 mL) and the reaction mixture was heated at 50° C. for 7 days. The reaction mixture was cooled, diluted with H₂O, extracted with EtOAc, washed with brine, dried over Na₂SO₄, filtered, and the solvent evaporated in vacuo. The crude residue was purified by reverse-phase semi-prep HPLC (Gemini, C₁₈ column; 100×30 mm I.D.; 5μ) to afford 0.02 g of compound 767 as a clear, viscous oil. ¹H-NMR (DMSO-d₆) δ 1.83-2.02 (m, 3H), 2.96 (s, 3H), 3.13-3.29 (m, 2H), 3.41 (br s, 1H), 3.73 (br s, 1H), 4.40 (br s, 1H), 4.62 (br s, 1H), 4.84 (br s, 2H), 7.33-7.44 (m, 2H), 7.48 (t, 1H), 7.59 (d, 1H), 7.61-7.74 (m, 3H), 7.74-7.92 (m, 3H); MS: m/z 549.2 (MH⁺).

Example 69

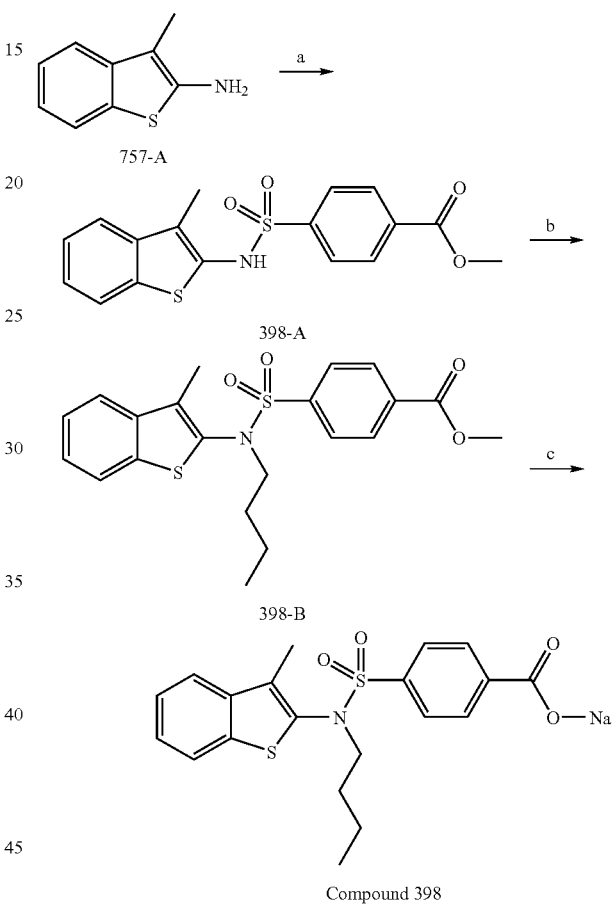

Compound 398 a) 1. 4-(Chlorosulfonyl)benzoic acid, pyridine, DCM; 2. MeOH, H₂SO₄; b) Ph₃P, DEAD, butan-1-ol, THF; c) 1. LiOH•H₂O, THF, H₂O; 2. aq HCl; 3. aq. NaOH.

N-(3-Methylbenzo[b]thiophen-2-yl)-4-carbomethoxy-benzenesulfonamide (398-A). To a stirred solution of compound 757-A (4.99 g, 25.0 mmol) in pyridine (50 mL) and methylene chloride (25 mL), cooled on an ice bath, was added 4-(chlorosulfonyl)benzoic acid (5.52 g, 25.0 mmol), portion-wise, for 4 min, and the reaction was allowed to stir at ambient temperature for 4 days. The reaction mixture was concentrated under reduced pressure, the residue stirred with 1N HCl (100 mL), the resulting solid filtered, washed with 1N HCl and air dried. The crude product was triturated with MeOH (15 mL), filtered, rinsed with MeOH (2×5 mL) and air-dried to afford crude benzoic acid (not shown). The benzoic acid was suspended in MeOH (100 mL), treated with concentrated H₂SO₄ (0.1 mL) and the reaction mixture refluxed for 5 days. The reaction mixture was cooled, the solvent evaporated under reduced pressure, and the residue was triturated with MeOH (15 mL), filtered, washed with methanol (2×5 mL)

and once with another portion of methanol (10 mL). The solid was dried to afford 6.31 g of compound 398-A as a tan-yellow powder. $^1$H-NMR (DMSO-$d_6$) δ: 2.02 (s, 3H), 3.89 (s, 3H), 7.40-7.29 (m, 2H), 7.67-7.61 (m, 1H), 7.83-7.77 (m, 1H), 7.89 (d, 2H), 8.14 (d, 2H), 10.66 (s, 1H); MS: m/z 360.2 (M-H$^+$).

N-(Butyl)-N-(3-methylbenzo[b]thiophen-2-yl)-4-carbomethoxy-benzenesulfonamide (398-B). To a solution of triphenyl phosphine (0.396 g, 1.51 mmol) in THF (10 mL) was added 40% DEAD in toluene solution (0.67 mL, 1.51 mmol) and the reaction mixture was stirred at ambient temperature for 2 min. Compound 398-A (0.361 g, 1.00 mmol) was added in one-portion and the reaction stirred for an additional 5 min. n-Butanol (0.11 mL, 1.20 mmol) was added and the reaction mixture was stirred for 18 h at ambient temperature. The reaction mixture was concentrated under reduced pressure and the crude material purified by flash column chromatography (SiO$_2$) eluting with an EtOAc-heptane gradient to afford 0.372 g of compound 398-B as a viscous, colorless oil. $^1$H-NMR (DMSO-$d_6$) δ: 0.84 (t, 3H), 1.48-1.27 (m, 4H), 2.24 (s, 3H), 3.57 (s, 2H), 3.92 (s, 3H), 7.48-7.37 (m, 2H), 7.82-7.76 (m, 1H), 7.88-7.83 (m, 1H), 7.93 (d, 2H), 8.17 (d, 2H); MS: m/z 418.3 (MH$^+$).

Compound 398

Sodium, N-(Butyl)-N-(3-methylbenzo[b]thiophen-2-yl)-4-carboxy-benzenesulfonamide. To a solution of compound 398-B (0.371 g, 0.89 mmol) in a 5:1 THF/water mixture (10 mL) was added LiOH.H$_2$O (0.042 g, 1.00 mmol), the reaction mixture was stirred for 18 h, and the organics were evaporated in vacuo. The crude residue was diluted with H$_2$O (10 mL), acidified with 1N HCl (1.00 mL), the solid filtered, washed with H$_2$O and dried under vacuum. The benzoic acid (0.337 g, 0.84 mmol) was dissolved in a mixture of H$_2$O (10 mL) and 1N NaOH (0.84 mL, 0.84 mmol), with gentle heating. The turbid solution was filtered, frozen and lyophilized to afford 0.359 g of the sodium salt of compound 398 as an off-white solid. $^1$H-NMR (DMSO-$d_6$) δ: 0.83 (t, 3H), 1.43-1.27 (m, 4H), 2.24 (s, 3H), 3.51 (br s, 2H), 7.45-7.37 (m, 2H), 7.64 (d, 2H), 7.79-7.75 (m, 1H), 7.87-7.83 (m, 1H), 7.99 (d, 2H); MS: m/z 402.3 (M-H)$^-$.

Following the procedure described above for example 69 and substituting the appropriate reagents, starting materials and purification methods known to those skilled in the art, the following compounds of the present invention were prepared:

Compound 399

N-(3-Methyl-benzo[b]thiophen-2-yl)-N-(cyclopropylmethyl)-4-carboxy-benzenesulfonamide. MS: m/z 401.9 (MH$^+$).

Compound 400

Sodium, N-(2-Cyclopropylethyl)-N-(3-methylbenzo[b]thiophen-2-yl)-4-carboxy-benzenesulfonamide. $^1$H-NMR (DMSO-$d_6$): δ 0.01-0.06 (m, 2H), 0.40-0.32 (m, 2H), 0.74-0.63 (m, 1H), 1.38-1.26 (br m, 2H), 2.23 (s, 3H), 3.58 (br s, 2H), 7.45-7.36 (m, 2H), 7.63 (d, 2H), 7.79-7.74 (m, 1H), 7.87-7.83 (m, 1H), 7.98 (d, 2H); MS: m/z 414.2 (M-H)$^-$.

Compound 401

N-(3-Methyl-benzo[b]thiophen-2-yl)-N-(2-tert-butoxy-ethyl)-4-carboxy-benzenesulfonamide. $^1$H-NMR (DMSO-$d_6$) δ 0.91-1.14 (m, 9H), 2.22 (s, 3H), 3.22-3.49 (m, 4H), 7.34-7.51 (m, 2H), 7.71-7.83 (m, 1H), 7.83-7.89 (m, 1H), 7.92 (m, 2H), 8.14 (m, 2H); MS: m/z 447.9 (MH$^+$).

Compound 402

N-(3-Methyl-benzo[b]thiophen-2-yl)-N-(ethyl)-4-carbomethoxy-benzenesulfonamide. MS: m/z 389.9 (MH$^+$).

Compound 403

N-(3-Methyl-benzo[b]thiophen-2-yl)-N-(ethyl)-4-carboxy-benzenesulfonamide. MS: m/z 375.9 (MH$^+$).

Compound 404

N-(3-Methyl-benzo[b]thiophen-2-yl)-N-(propyl)-4-carboxy-benzenesulfonamide. MS: m/z 398.9 (MH$^+$).

Compound 409

Sodium, N-(3-Methylbenzo[b]thiophen-2-yl)-N-(3,3,3-trifluoro-propyl)-4-carboxy-benzenesulfonamide. $^1$H-NMR (DMSO-$d_6$): δ 2.22 (s, 3H), 2.58-2.45 (m, 2H), 3.81 (br s, 2H), 7.46-7.37 (m, 2H), 7.66 (d, 2H), 7.81-7.75 (m, 1H), 7.89-7.83 (m, 1H), 8.00 (d, 2H); MS: m/z 442.2 (M-H)$^-$.

Compound 410

N-(3-Methyl-benzo[b]thiophen-2-yl)-N-(4,4,4-trifluoro-butyl)-4-carboxy-benzenesulfonamide. $^1$H-NMR (DMSO-$d_6$) δ 1.68 (q, 2H), 2.23 (s, 3H), 2.29-2.45 (m, 2H), 3.67 (br s, 2H), 7.28-7.57 (m, 2H), 7.71-8.02 (m, 4H), 8.16 (d, 2H), 13.62 (br s, 1H); MS: m/z 458.0 (MH$^+$).

Compound 416

N-(3-Methyl-benzo[b]thiophen-2-yl)-N-(3-tert-butoxy-propyl)-4-carbomethoxy-benzenesulfonamide. $^1$H-NMR (DMSO-$d_6$) δ 1.08 (s, 9H), 1.59 (t, 2H), 2.26 (s, 3H), 3.21-3.43 (m, 2H), 3.67 (br s, 2H), 3.92 (s, 3H), 7.31-7.54 (m, 2H), 7.79 (dd, 1H), 7.82-7.89 (m, 1H), 7.92 (m, 2H), 8.18 (m, 2H); MS: m/z 476.0 (MH$^+$).

Compound 477

N-(3-Chloro-benzo[b]thiophen-2-yl)-N-(butyl)-4-carboxy-benzenesulfonamide. $^1$H NMR (DMSO-$d_6$) δ 0.71-0.93 (m, 3H), 1.23-1.50 (m, 4H), 3.58 (t, 2H), 7.43-7.64 (m, 2H), 7.72 (d, 2H), 7.77-7.88 (m, 1H), 7.94-8.13 (m, 3H); MS: m/z 423.9 (MH$^+$).

Compound 478

N-(3-Chloro-benzo[b]thiophen-2-yl)-N-(cyclopropylmethyl)-4-carboxy-benzenesulfonamide. $^1$H-NMR (DMSO-$d_6$) δ −0.14-0.07 (m, 2H), 0.19-0.39 (m, 2H), 0.67-0.94 (m, 1H), 3.40 (d, 2H), 7.33-7.55 (m, 2H), 7.64 (d, 2H), 7.68-7.82 (m, 1H), 7.82-8.07 (m, 3H); MS: m/z 421.8 (MH$^+$).

Compound 479

N-(3-Chloro-benzo[b]thiophen-2-yl)-N-2-(cyclopropyl) ethyl)-4-carboxy-benzenesulfonamide. $^1$H-NMR (DMSO-$d_6$) δ −0.01 (q, 2H), 0.22-0.45 (m, 2H), 0.64-0.84 (m, 1H), 1.34 (q, 2H), 3.66 (t, 2H), 7.46-7.64 (m, 2H), 7.67-7.90 (m, 3H), 7.91-8.17 (m, 3H); MS: m/z 435.9 (MH$^+$).

Compound 480

N-(3-Chloro-benzo[b]thiophen-2-yl)-N-(3,3,3-trifluoro-propyl)-4-carboxy-benzenesulfonamide. $^1$H-NMR (DMSO-d$_6$) δ 2.54-2.70 (m, 2H), 3.90 (t, 2H), 7.45-7.61 (m, 2H), 7.74 (d, 2H), 7.79 (dd, 1H), 7.96-8.17 (m, 3H); MS: m/z 464.0 (MH$^+$).

Compound 530

N-(3-Chloro-benzo[b]thiophen-2-yl)-N-(4,4,4-trifluoro-butyl)-4-carbomethoxy-benzenesulfonamide. MS: m/z 491.9 (MH$^+$).

Compound 531

N-(3-Chloro-benzo[b]thiophen-2-yl)-N-(5,5,5-trifluoro-pentyl)-4-carbomethoxy-benzenesulfonamide. MS: m/z 506.0 (MH$^+$).

Compound 537

N-(3-Chloro-benzo[b]thiophen-2-yl)-N-(4,4,4-trifluoro-butyl)-4-carboxy-benzenesulfonamide. $^1$H NMR (DMSO-d$_6$) δ 1.67 (q, 2H), 2.26-2.45 (m, 2H), 3.68 (t, 2H), 7.48-7.61 (m, 2H), 7.73 (d, 2H), 7.78-7.92 (m, 1H), 7.94-8.13 (m, 3H); MS: m/z 477.9 (MH$^+$).

Compound 538

N-(3-Chloro-benzo[b]thiophen-2-yl)-N-(5,5,5-trifluoro-pentyl)-4-carboxy-benzenesulfonamide. $^1$H-NMR (DMSO-d$_6$) δ 1.35-1.70 (m, 4H), 2.07-2.36 (m, 2H), 3.62 (t, 2H), 7.45-7.63 (m, 2H), 7.73 (d, 2H), 7.76-7.86 (m, 1H), 7.92-8.14 (m, 3H); MS: m/z 492.0 (MH$^+$).

Compound 545

Sodium, N-(3-Methylbenzo[b]thiophen-2-yl)-N-(5,5,5-trifluoro-pentyl)-4-carboxy-benzenesulfonamide. $^1$H-NMR (DMSO-d$_6$): δ 1.62-1.45 (m, 4H), 2.32-2.17 (m, 5H), 3.56 (br s, 2H), 7.45-7.37 (m, 2H), 7.66 (d, 2H), 7.80-7.75 (m, 1H), 7.88-7.83 (m, 1H), 8.00 (m, 2H); MS: m/z 470.2 (M-H)$^-$.

Example 70

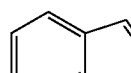

1-C $\xrightarrow{a}$

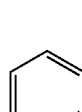

361-A $\xrightarrow{b}$

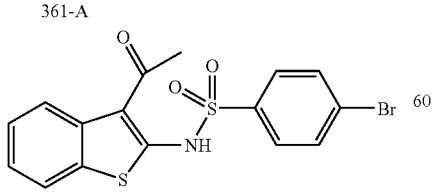

361-B

361-B  $\xrightarrow{c}$

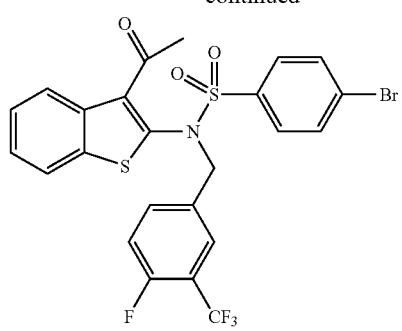

Compound 386

$\xrightarrow{d}$

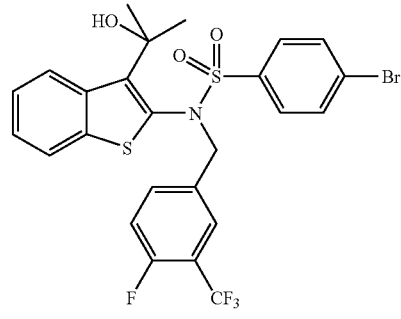

Compound 388

Compound 388 $\xrightarrow{e}$

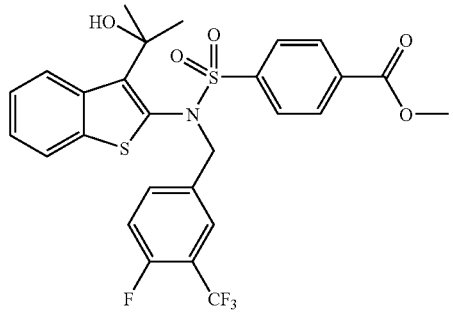

Compound 415

$\xrightarrow{f}$

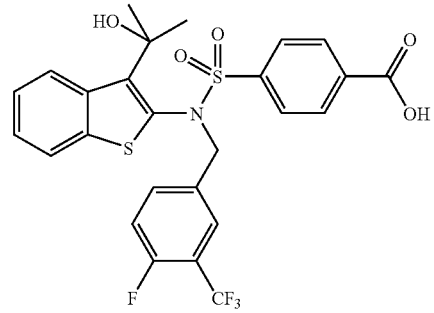

Compound 361

Compound 361 $\xrightarrow{g}$

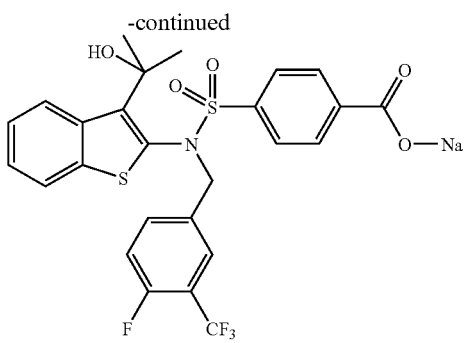

361 (Na)

a) 4-Bromobenzene-1-sulfonyl chloride, pyridine, DCM; b) AcCl, SnCl₄, DCM;
c) 4-(bromomethyl)-1-fluoro-2-(trifluoromethyl)benzene, KOtBu, 18-C-6, DMF;
d) MeMgCl, THF; e) CO, Pd catalyst, iPr₂NEt, MeOH, DMF; f) 1. LiOH•H₂O, THF, H₂O; 2. aq. HCl; g) aq. NaOH.

N-(Benzo[b]thiophen-2-yl)-4-bromobenzenesulfonamide (361-A). To a stirred solution of compound 1-C (9.28 g, 49.9 mmol) in pyridine (100 mL) and methylene chloride (50 mL), cooled on an ice bath, was added 4-bromobenzene-1-sulfonyl chloride (12.8 g, 49.9 mmol), portion-wise over a period of 4 minutes. The reaction mixture was allowed to warm to ambient temperature and stirred for 18 h. The reaction mixture was concentrated under reduced pressure, the crude residue partitioned between EtOAc (500 mL) and 1N HCl (250 mL), the layers separated, the organic phase washed with 1N HCl (125 mL), brine, dried over MgSO₄, filtered and evaporated in vacuo. The crude residue was purified by flash column chromatography (SiO₂) eluting with an EtOAc-Heptane gradient to afford 13.5 g of compound 361-A as a tan powder. ¹H-NMR (DMSO-d₆) δ: 6.89 (s, 1H), 7.33-7.20 (m, 2H), 7.75-7.64 (m, 3H), 7.84-7.76 (m, 3H), 11.30 (s, 1H); MS: m/z 366.1 (M-H)⁻.

N-(3-Acetyl-benzo[b]thiophen-2-yl)-4-bromobenzenesulfonamide (361-B). To a suspension of compound 361-A (9.21 g, 25.0 mmol) in DCM (50 mL), cooled in an ice-bath, was added an ice-cold solution of acetyl chloride (2.30 mL, 32.3 mmol), followed by SnCl₄ (27.9 mmol) in DCM (200 mL). The reaction mixture was allowed to warm to ambient temperature and stirred for 18 h. The reaction mixture was quenched with saturated NH₄Cl solution (125 mL), filtered over a pad of celite, dried over MgSO₄, filtered and concentrated under vacuum. The residue was dissolved in refluxing EtOAc (75 mL), filtered hot and the filtrate allowed to cool. The solid was filtered and washed EtOAc (10 mL). Another batch of product was obtained by evaporation of the mother liquor, dissolving the residue in refluxing EtOAc (25 mL), filtering hot and allowing the filtrate to cool. The solid was filtered and washed with EtOAc (2 mL). The combined batches of solid were air-dried to afford 8.54 g of compound 361-B as a tan-orange powder. ¹H-NMR (DMSO-d₆) δ: 2.57 (s, 3H), 7.40-7.24 (m, 2H), 7.83-7.70 (m, 5H), 8.14 (d, 1H); MS: m/z 408.1 (M-H)⁻.

Compound 386

N-(3-Acetyl-benzo[b]thiophen-2-yl)-4-bromo-N-(4-fluoro-3-trifluoromethyl-benzyl)benzenesulfonamide. To a solution compound 361-B (8.54 g, 20.8 mmol) in DMF (125 mL) was added KOtBu solution (23.0 mL, 1M in THF) and the reaction was stirred for 5 minutes. 18-Crown-6 (5.51 g, 20.8 mmol) and 4-(bromomethyl)-1-fluoro-2-(trifluoromethyl)-benzene (9.60 mL, 62.0 mmol) were added and the reaction was stirred for 18 h. An additional portion of KOtBu solution (10.0 mL, 1M in THF) and 18-crown-6 (2.42 g, 9.14 mmol) were added to the reaction mixture and the reaction was stirred for an additional 3 days. The reaction mixture was concentrated in vacuo and the crude material purified by flash column chromatography (SiO₂) eluting with an EtOAc-heptane gradient to afford compound 386 as a semi-pure material. The solid was triturated with EtOAc (10 mL), filtered, washed with an additional EtOAc (10 mL) and air-dried to afford 6.92 g of compound 386 as a white crystalline powder. ¹H-NMR (DMSO-d₆) δ: 2.38 (s, 3H), 4.97 (s, 2H), 7.41-7.50 (m, 3H), 7.66-7.70 (m, 4H), 7.92 (d, 2H), 7.94-7.98 (m, 1H), 7.98-8.03 (m, 1H); MS: m/z 586.1 (M-H)⁻.

Compound 388

4-Bromo-N-(4-fluoro-3-trifluoromethylbenzyl)-N-(1-hydroxy-1-methyl-ethyl)-benzo[b]thiophen-2-yl)benzenesulfonamide. To a solution of compound 386 (6.89 g, 11.76 mmol) in THF (120 mL) was added MeMgCl (15.6 mL, 3M in THF) and the reaction was stirred for 18 h at ambient temperature. The crude reaction was quenched with saturated NH₄Cl solution (40 mL), the layers separated, and the organic phase washed with brine (40 mL), dried over MgSO₄, filtered and evaporated in vacuo. The crude residue was purified by flash column chromatography (SiO₂) eluting with an EtOAc-heptane gradient to afford 6.29 g of compound 388 as a glassy yellow-orange solid. ¹H-NMR (DMSO-d₆): δ 1.34 (s, 3H), 1.62 (s, 3H), 4.61 (d, 1H), 5.11-5.04 (m, 2H), 7.37-7.30 (m, 2H), 7.45-7.38 (m, 1H), 7.54-7.45 (m, 2H), 7.83-7.78 (m, 3H), 7.91-7.86 (m, 2H), 8.41-8.35 (m, 1H); MS: m/z 584 (M-OH)⁺.

Compound 415

N-(4-Fluoro-3-trifluoromethylbenzyl)-N-(3-(1-hydroxy-1-methyl-ethyl)-benzo[b]thiophen-2-yl)-4-carbomethoxybenzenesulfonamide. A solution of compound 388 (5.67 g, 9.41 mmol) in a 1:1 mixture of DMF and MeOH (100 mL) was treated with iPr₂NEt (3.3 mL, 18.9 mmol) and (1,1'-bis(di-tert-butylphosphino)ferrocene)palladium(II) chloride (0.311 g, 0.48 mmol) and the reaction mixture was heated at 80° C. under a pressure of 50-60 psi carbon monoxide for 18 h, cooled and the reaction mixture was concentrated in vacuo. The crude residue was purified by flash column chromatography (SiO₂) eluting with an EtOAc-heptane gradient to afford 4.33 g of compound 415 as an orange-tan glassy solid. ¹H-NMR (DMSO-d₆): δ 1.35 (s 3H), 1.63 (s, 3H), 3.94 (s, 3H), 4.66 (d, 1H), 5.14-5.06 (m, 2H), 7.55-7.29 (m, 5H), 7.83-7.76 (m, 1H), 8.02 (d, 2H), 8.19 (d, 2H), 8.41-8.33 (m, 1H); MS: m/z 564.2 (M-OH)⁺.

Compound 361

N-(4-Fluoro-3-trifluoromethylbenzyl)-N-(3-(1-hydroxy-1-methyl-ethyl)-benzo[b]thiophen-2-yl)-4-carboxy-benzenesulfonamide. To a solution of compound 415 (5.33 g, 7.44 mmol) in a 5:1 THF/water mixture (100 mL) was added LiOH.H₂O (0.420 g, 10.0 mmol) and the reaction was stirred for 18 h at ambient temperature. An additional portion of LiOH.H₂O (0.084 g, 2.0 mmol) was added, the reaction was stirred for an additional 18 h, and the organics were evaporated in vacuo. The crude residue was diluted with water (100 mL), acidified with 1N HCl (12.0 mL), the precipitate filtered, washed with water and dried under vacuum to afford 4.10 g of compound 361 as a white solid. ¹H-NMR (DMSO-d₆): δ 1.36 (s, 3H), 1.63 (s, 3H), 4.66 (d, 1H), 5.15-5.04 (m, 2H), 7.55-7.29 (m, 5H), 7.84-7.76 (m, 1H), 7.99 (d, 2H), 8.16 (d, 2H), 8.42-8.34 (m, 1H), 13.63 (br s, 1H); MS: m/z 566.2 (M-H)⁻.

Compound 361, Sodium Salt

Sodium, N-(4-Fluoro-3-trifluoromethylbenzyl)-N-(3-(1-hydroxy-1-methyl-ethyl)-benzo[b]thiophen-2-yl)-4-carboxy-benzenesulfonamide. To a suspension of compound 361 (4.10 g, 7.22 mmol) in water (50 mL) was added 1N NaOH (7.10 mL, 7.10 mmol) and the reaction mixture was refluxed briefly and cooled back to ambient temperature. The turbid reaction was filtered, the filtrate frozen and lyophilized to afford a fluffy product. The product was stirred with hexanes (100 mL), filtered, and the powder dried under vacuum at 50° C. to afford 4.18 g of the sodium salt of compound 361 as a cream-colored powder. ¹H-NMR (DMSO-d₆): δ 1.26 (s, 3H), 1.61 (s, 3H), 4.46 (d, 1H), 5.05 (s, 1H), 5.13 (d, 1H), 7.35-7.28 (m, 2H), 7.43-7.36 (m, 1H), 7.52-7.46 (m, 1H), 7.57-7.53 (m, 1H), 7.75 (d, 2H), 7.81-7.70 (m, 1H), 8.01 (d, 2H), 8.41-8.36 (m, 1H); MS: m/z 566.2 (M-H)⁻.

Following the procedure described above for example 70 and substituting the appropriate reagents, starting materials and purification methods known to those skilled in the art, the following compounds of the present invention were prepared:

Compound 730

N-(3-Acetyl-benzo[b]thiophen-2-yl)-4-bromo-N-(4-fluoro-benzyl)benzene-sulfonamide. ¹H-NMR (DMSO-d₆): δ 2.30 (s, 3H), 4.86 (br s, 2H), 7.19-7.11 (m, 2H), 7.40-7.33 (m, 2H), 7.47-7.41 (m, 2H), 7.75-7.70 (m, 2H), 7.93-7.88 (m, 2H), 7.98-7.93 (m, 1H), 8.05-7.99 (m, 1H); MS: m/z 517.9 (MH⁺).

Compound 731

N-(3-Acetyl-benzo[b]thiophen-2-yl)-4-bromo-N-(4-(trifluoromethoxy)-benzyl)benzenesulfonamide. ¹H-NMR (DMSO-d₆): δ 2.28 (s, 3H), 4.91 (br s, 2H), 7.33 (d, 2H), 7.49-7.42 (m, 4H), 7.75-7.70 (m, 2H), 7.93-7.88 (m, 2H), 7.98-7.93 (m, 1H), 8.05-7.99 (m, 1H); MS: m/z 583.9 (MH⁺).

Compound 732

N-(3-Acetyl-benzo[b]thiophen-2-yl)-N-(benzyl)-4-bromobenzenesulfonamide. ¹H-NMR (DMSO-d₆): δ 2.28 (s, 3H), 4.86 (br s, 2H), 7.35-7.28 (m, 5H), 7.46-7.41 (m, 2H), 7.74-7.70 (m, 2H), 7.92-7.88 (m, 2H), 7.97-7.92 (m, 1H), 8.05-7.99 (m, 1H); MS: m/z 500.0 (MH⁺).

Compound 733

N-(3-Acetyl-benzo[b]thiophen-2-yl)-4-bromo-N-(3-chloro-4-fluoro-benzyl)benzenesulfonamide. ¹H-NMR (DMSO-d₆): δ 2.37 (s, 3H), 4.88 (br s, 2H), 7.41-7.33 (m, 2H), 7.48-7.43 (m, 2H), 7.53 (dd, 1H), 7.76-7.77 (m, 2H), 7.93-7.89 (m, 2H), 7.99-7.94 (m, 1H), 8.05-7.99 (m, 1H); MS: m/z 552.0 (MH⁺).

Compound 734

N-(4-Fluorobenzyl)-N-(3-(1-hydroxy-1-methyl-ethyl)-benzo[b]thiophen-2-yl)-4-bromo-benzenesulfonamide. ¹H-NMR (DMSO-d₆): δ 1.17 (s, 3H), 1.63 (s, 3H), 4.34 (d, 1H), 5.11-5.02 (m, 2H), 7.22-7.04 (m, 4H), 7.38-7.27 (m, 2H), 7.84-7.76 (m, 3H), 7.90 (d, 2H), 8.44-8.36 (m, 1H); MS: m/z 516 (M-OH)⁺.

Compound 735

N-(3-(1-Hydroxy-1-methyl-ethyl)-benzo[b]thiophen-2-yl)-N-(4-trifluoromethoxybenzyl)-4-bromo-benzenesulfonamide. ¹H-NMR (DMSO-d₆): δ 1.10 (s, 3H), 1.63 (s, 3H), 4.38 (d, 1H), 5.08 (s, 1H), 5.12 (d, 1H), 7.38-7.25 (m, 6H), 7.84-7.77 (m, 3H), 7.89 (d, 2H), 8.43-8.35 (m, 1H); MS: m/z 582.0 (M-OH)⁺.

Compound 736

N-(Benzyl)-N-(3-(1-hydroxy-1-methyl-ethyl)-benzo[b]thiophen-2-yl)-4-bromo-benzenesulfonamide. ¹H-NMR (DMSO-d₆): δ 1.09 (s, 3H), 1.64 (s, 3H), 4.33 (d, 1H), 5.12-5.03 (m, 2H), 7.17-7.09 (m, 2H), 7.37-7.20 (m, 5H), 7.84-7.75 (m, 3H), 7.89 (d, 2H), 8.43-8.36 (m, 1H); MS: m/z 498.0 (M-OH)⁺.

Compound 737

N-(3-Chloro-4-fluorobenzyl)-N-(3-(1-hydroxy-1-methyl-ethyl)-benzo[b]thiophen-2-yl)-4-bromo-benzenesulfonamide. ¹H-NMR (DMSO-d₆): δ 1.33 (s, 3H), 1.63 (s, 3H), 4.97 (d, 1H), 5.02 (d, 1H), 5.11 (s, 1H), 7.20-7.12 (m, 1H), 7.39-7.25 (m, 4H), 7.84-7.76 (m, 3H), 7.90 (d, 2H), 8.43-8.35 (m, 1H); MS: m/z 550.0 (M-OH)⁺.

Compound 781

Sodium, N-(3-(1-Hydroxy-1-methyl-ethyl)-benzo[b]thiophen-2-yl)-N-(4-trifluoromethoxy)benzyl-4-carboxy-benzenesulfonamide. ¹H-NMR (DMSO-d₆): δ 1.06 (s, 3H), 1.63 (s, 3H), 4.27 (d, 1H), 5.05 (s, 1H), 5.13 (d, 1H), 7.35-7.22 (m, 6H), 7.75 (d, 2H), 7.81-7.77 (m, 1H), 8.01 (d, 2H), 8.43-8.39 (m, 1H); MS: m/z 564.1 (M-H)⁻.

Example 71

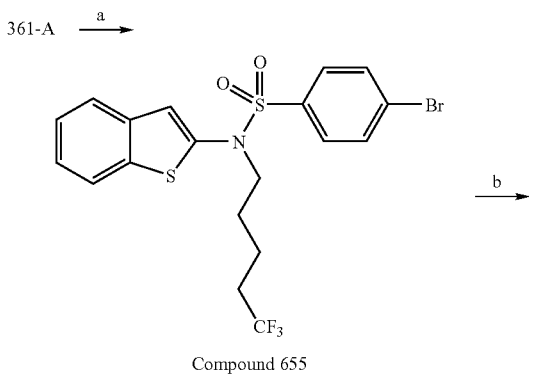

Compound 655

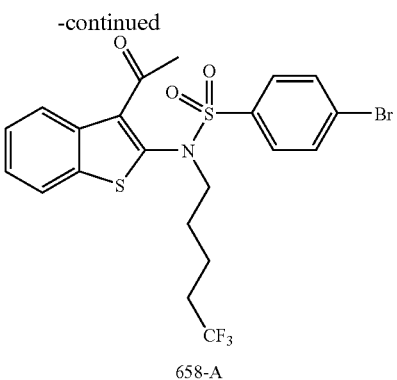

658-A

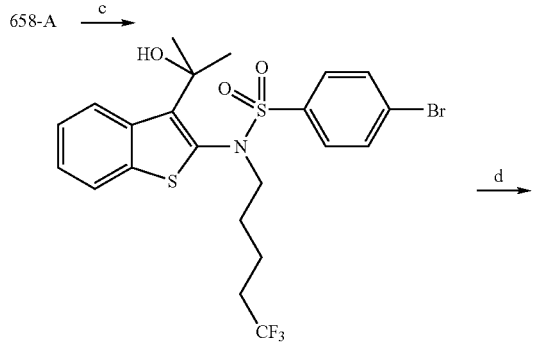

Compound 656

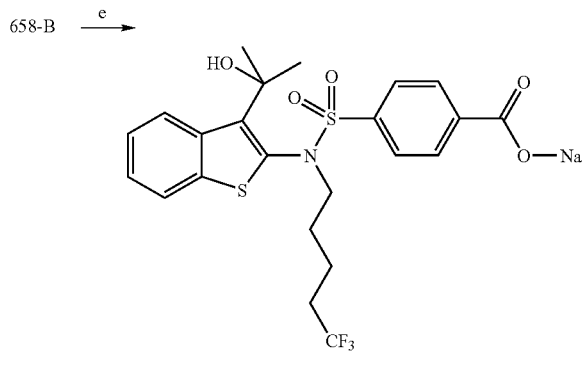

Compound 658 a) Ph₃P, DEAD, 5,5,5-trifluoropentan-1-ol, THF; b) Ac₂O, H₃PO₄; c) MeMgCl, THF; d) CO, Pd catalyst, iPr₂NEt, MeOH, DMF; e) 1. LiOH·H₂O, THF, H₂O; 2. aq HCl; 3. aq NaOH.

Compound 655

N-(Benzo[b]thiophen-2-yl)-4-bromo-N-(5,5,5-trifluoropentyl)-benzenesulfonamide. To a solution of triphenyl phosphine (1.97 g, 7.50 mmol) in THF (50 mL) was added 40% DEAD in toluene solution (3.40 mL, 7.65 mmol) and the reaction mixture was stirred for 2 min. Compound 361-A (1.84 g, 5.00 mmol) was added, the reaction mixture stirred an additional 5 min, to which was added 5,5,5-trifluoropentan-1-ol (0.62 mL, 5.99 mmol) and the reaction mixture was stirred for 18 h. The reaction mixture was concentrated in vacuo and the crude material purified by flash column chromatography (SiO₂) eluting with an EtOAc-heptane gradient to afford 2.19 g of compound 655 as a tan powder. ¹H-NMR (DMSO-d₆): δ 1.64-1.49 (m, 4H), 2.37-2.17 (m, 2H), 3.71-3.64 (m, 2H), 7.27 (s, 1H), 7.47-7.34 (m, 2H), 7.69-7.63 (m, 2H), 7.92-7.77 (m, 4H).

N-(3-Acetylbenzo[b]thiophen-2-yl)-4-bromo-N-(5,5,5-trifluoro-pentyl)-benzenesulfonamide (658-A). To compound 655 (2.16 g, 4.39 mmol) was added acetic anhydride (50 mL) and 85% H₃PO₄ (0.50 mL) and the reaction was refluxed for 18 h, cooled, and the reaction mixture concentration under reduced pressure. The crude residue was partitioned between EtOAc (250 mL) and saturated NaHCO₃ (50 mL). Insoluble material was filtered, the organic layer washed with brine (50 mL), dried over MgSO₄, filtered and concentrated in vacuo. The crude residue was purified by flash column chromatography (SiO₂) eluting with an EtOAc-heptane gradient to afford 1.26 g of compound 658-A as a thick, colorless oil. ¹H-NMR (DMSO-d₆): δ 1.64-1.50 (m, 2H), 1.78-1.64 (m, 2H), 2.37-2.18 (m, 2H), 2.66 (s, 3H), 3.67 (br s, 2H), 7.53-7.42 (m, 2H), 7.67-7.60 (m, 2H), 7.90-7.83 (m, 2H), 7.99-7.92 (m, 1H), 8.17-8.10 (m, 1H); MS: m/z 534 (MH⁺).

Compound 656

4-Bromo-N-(3-(1-hydroxy-1-methyl-ethyl)-benzo[b]thiophen-2-yl)-N-(5,5,5-trifluoro-pentyl)-benzenesulfonamide. To a solution of compound 658-A (1.26 g, 2.35 mmol) in THF (25 mL) was added MeMgCl (3.95 mL, 3M in THF) and the reaction was stirred for 18 h. The reaction was quenched with a saturated NH₄Cl solution (10 mL), the organics were washed with brine (10 mL), dried with MgSO₄, filtered and evaporated in vacuo. The crude residue was purified by flash column chromatography (SiO₂) eluting with an EtOAc-heptane gradient to afford 0.865 g of compound 656 as a colorless glass. ¹H-NMR (DMSO-d₆): δ 1.55-1.37 (m, 3H), 1.74-1.65 (m, 4H), 1.78 (s, 3H), 2.29-2.14 (m, 2H), 3.26-3.17 (m, 1H), 3.89-3.79 (m, 1H), 5.26 (s, 1H), 7.39-7.32 (m, 2H), 7.83-7.74 (m, 3H), 7.91-7.85 (m, 2H), 8.53-8.47 (m, 1H); MS: m/z 532.2 (M-OH)⁺.

N-(3-(1-Hydroxy-1-methyl-ethyl)-benzo[b]thiophen-2-yl)-N-(5,5,5-trifluoro-pentyl)-4-carbomethoxy-benzenesulfonamide (658-B). A solution of compound 656 (0.828 g, 1.50 mmol) in a 1:1 mixture of DMF and MeOH (50 mL) was treated with iPr₂NEt (0.53 mL, 3.04 mmol) and (1,1'-bis(di-tert-butylphosphino)ferrocene)palladium(II) chloride (0.050 g, 0.08 mmol) and the reaction mixture was heated at 80° C. under a pressure of 50-60 psi carbon monoxide for two days. The reaction mixture was cooled, concentrated in vacuo and the material was purified by flash column chromatography (SiO₂) eluting with an EtOAc-heptane gradient to afford 0.514 g of compound 658-B. ¹H-NMR (DMSO-d₆): δ 1.55-1.37 (m, 3H), 1.75-1.63 (m, 4H), 1.79 (s, 3H), 2.29-2.14 (m, 2H), 3.30-3.21 (m, 1H), 3.91-3.82 (m, 1H), 3.93 (s, 3H), 5.27 (s, 1H), 7.40-7.32 (m, 2H), 7.81-7.75 (m, 1H), 8.02-7.98 (m, 2H), 8.21-8.16 (m, 2H), 8.53-8.47 (m, 1H); MS: m/z 512.2 (M-OH)⁺.

Compound 658

Sodium, N-(3-(1-Hydroxy-1-methyl-ethyl)-benzo[b]thiophen-2-yl)-N-(5,5,5-trifluoro-pentyl)-4-carboxy-benzenesulfonamide. To compound 658-B (0.506 g, 0.96 mmol) in a 5:1 THF/water mixture (25 mL) was added LiOH.H$_2$O (0.084 g, 2.00 mmol) and the reaction mixture was stirred for 18 h at ambient temperature. The solvent was evaporated in vacuo, the residue dissolved in H$_2$O (10 mL) and acidified with 1N HCl (2.0 mL). The precipitate was filtered, washed with H$_2$O, and dried under vacuum to afford the 0.460 g of the carboxylic acid of compound 658. product. Water (10 mL) was added followed by 1N NaOH (0.88 mL, 0.88 mmol), the turbid reaction filtered, and the filtrate frozen and lyophilized to afford 0.478 g of the sodium salt of compound 658 as a cream-colored powder. $^1$H-NMR (DMSO-d$_6$): δ 1.58-1.36 (m, 3H), 1.76-1.62 (m, 4H), 1.80 (s, 3H), 2.31-2.11 (m, 2H), 3.21-3.09 (m, 1H), 3.91-3.78 (m, 1H), 5.27 (s, 1H), 7.38-7.29 (m, 2H), 7.70 (d, 2H), 7.82-7.75 (m, 1H), 8.00 (d, 2H), 8.56-8.47 (m, 1H); MS: m/z 514.2 (M-H)$^-$.

Following the procedure described above for example 71 and substituting the appropriate reagents, starting materials and purification methods known to those skilled in the art, the following compounds of the present invention were prepared:

Compound 504

N-(3-(1-Hydroxy-1-methyl-ethyl)-benzo[b]thiophen-2-yl)-N-(3,3,3-trifluoro-propyl)-4-carbomethoxy-benzenesulfonamide. $^1$H-NMR (DMSO-d$_6$): δ 1.68 (s, 3H), 1.77 (s, 3H), 2.51-2.42 (m, 1H), 2.88-2.73 (m, 1H), 3.50-3.41 (m, 1H), 3.92 (s, 3H), 4.18-4.09 (m, 1H), 5.26 (s, 1H), 7.41-7.34 (m, 2H), 7.84-7.78 (m, 1H), 7.99 (d, 2H), 8.20 (d, 2H), 8.49-8.42 (m, 1H); MS: m/z 484.2 (M-OH)$^+$.

Compound 505

Sodium, N-(3-(1-Hydroxy-1-methyl-ethyl)-benzo[b]thiophen-2-yl)-N-(3,3,3-trifluoro-propyl)-4-carboxy-benzenesulfonamide. $^1$H-NMR (DMSO-d$_6$): δ 1.68 (s, 3H), 1.80 (s, 3H), 2.49-2.38 (m, 1H), 2.85-2.72 (m, 1H), 3.40-3.31 (m, 1H), 4.13-4.03 (m, 1H), 5.28 (s, 1H), 7.40-7.32 (m, 2H), 7.70 (d, 2H), 7.84-7.79 (m, 1H), 8.02 (d, 2H), 8.53-8.46 (m, 1H); MS: m/z 486.2 (M-H)$^-$.

Compound 654

N-(Benzo[b]thiophen-2-yl)-N-(2-cyclopropyl-ethyl)-4-bromo-benzenesulfonamide. $^1$H-NMR (DMSO-d$_6$): δ 0.05-0.02 (m, 2H), 0.42-0.35 (m, 2H), 0.78-0.64 (m, 1H), 1.41 (q, 2H), 3.71 (t, 2H), 7.26 (s, 1H), 7.41-7.32 (m, 2H), 7.69-7.62 (m, 2H), 7.90-7.76 (m, 4H).

Compound 657

Sodium, N-(2-Cyclopropyl-ethyl)-N-(3-(1-hydroxy-1-methyl-ethyl)-benzo[b]thiophen-2-yl)-4-carboxy-benzenesulfonamide. $^1$H-NMR (DMSO-d$_6$): δ −0.02−−0.16 (m, 2H), 0.40-0.31 (m, 2H), 0.68-0.56 (m, 1H), 1.27-1.08 (m, 1H), 1.66-1.52 (m, 1H), 1.70 (s, 3H), 1.79 (s, 3H), 3.24-3.11 (m, 1H), 3.93-3.80 (m, 1H), 5.28 (s, 1H), 7.38-7.30 (m, 2H), 7.68 (d, 2H), 7.83-7.75 (m, 1H), 8.01 (d, 2H), 8.56-8.48 (m, 1H); MS: m/z 458.2 (M-H)$^-$.

Example 72

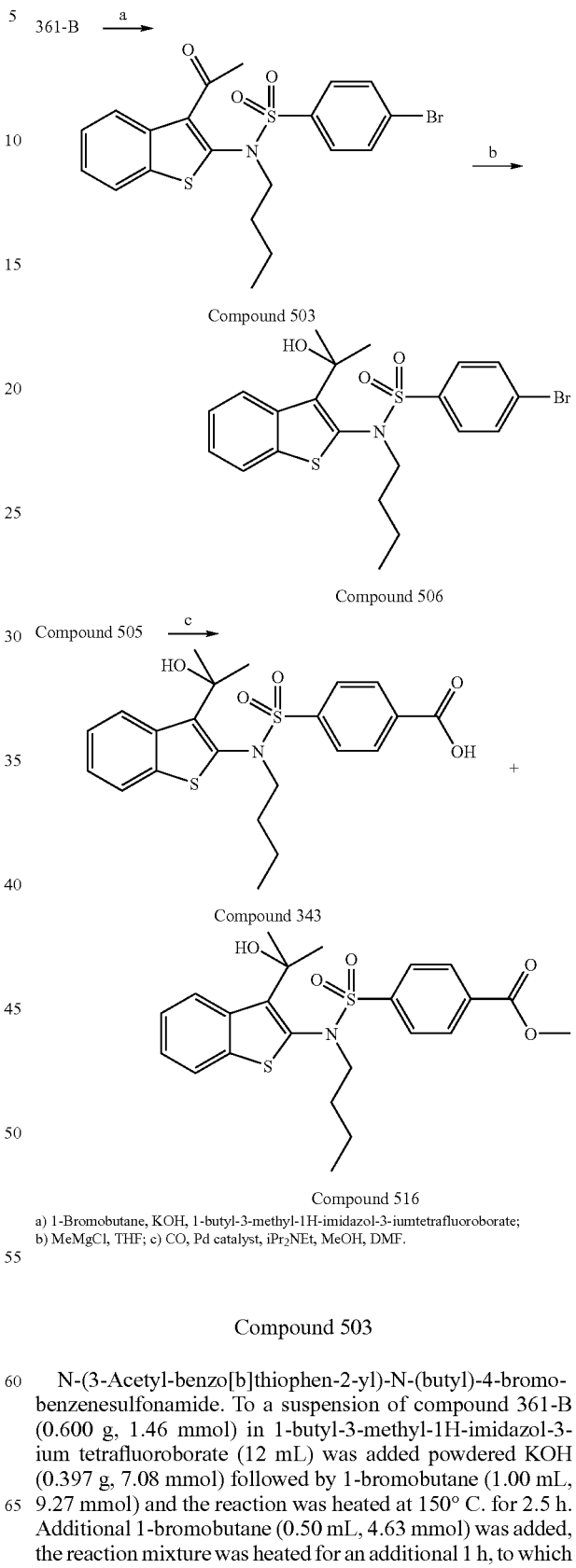

a) 1-Bromobutane, KOH, 1-butyl-3-methyl-1H-imidazol-3-iumtetrafluoroborate;
b) MeMgCl, THF; c) CO, Pd catalyst, iPr$_2$NEt, MeOH, DMF.

Compound 503

N-(3-Acetyl-benzo[b]thiophen-2-yl)-N-(butyl)-4-bromo-benzenesulfonamide. To a suspension of compound 361-B (0.600 g, 1.46 mmol) in 1-butyl-3-methyl-1H-imidazol-3-ium tetrafluoroborate (12 mL) was added powdered KOH (0.397 g, 7.08 mmol) followed by 1-bromobutane (1.00 mL, 9.27 mmol) and the reaction was heated at 150° C. for 2.5 h. Additional 1-bromobutane (0.50 mL, 4.63 mmol) was added, the reaction mixture was heated for an additional 1 h, to which was added additional KOH (0.198 g, 3.53 mmol), and the reaction mixture was heated at 150° C. for 2 days. The reaction mixture was cooled to ambient temperature, diluted with H$_2$O (100 mL), extracted with EtOAc (200 mL), the organic extract washed with H$_2$O (2×100 mL), brine (100 mL), dried over MgSO$_4$, filtered and concentrated in vacuo. The crude residue was purified by flash column chromatography (SiO$_2$) eluting with an EtOAc-heptane gradient to afford 0.347 g of compound 503 as a tan semi-solid. $^1$H-NMR (DMSO-d$_6$): δ 0.86 (t, 3H), 1.35 (h, 2H), 1.60 (p, 2H), 2.66 (s, 3H), 3.63 (br s, 2H), 7.51-7.43 (m, 2H), 7.64-7.59 (m, 2H), 7.88-7.84 (m, 2H), 7.97-7.93 (m, 1H), 8.16-8.11 (m, 1H); MS: m/z 466.1 (MH$^+$).

Compound 506

N-(Butyl)-N-(3-(1-hydroxy-1-methyl-ethyl)-benzo[b]thiophen-2-yl)-4-bromo-benzenesulfonamide. To a solution of compound 503 (0.330 g, 0.71 mmol) in THF (10 mL) was added MeMgCl (1.20 mL, 3M in THF) and the reaction mixture was stirred for 18 h. The reaction mixture was quenched with saturated NH$_4$Cl solution (5 mL), brine (5 mL), dried over MgSO$_4$, filtered and evaporated in vacuo. The material was purified by flash column chromatography (SiO$_2$) eluting with an EtOAc-heptane gradient to afford 0.22 g of compound 506 as an off-white powder. $^1$H-NMR (DMSO-d$_6$): δ 0.82 (t, 3H), 1.42-1.15 (m, 3H), 1.67-1.53 (m, 1H), 1.71 (s, 3H), 3.21-3.12 (m, 1H), 3.84-3.74 (m, 1H), 5.28 (s, 1H), 7.38-7.32 (m, 2H), 7.77-7.73 (m, 2H), 7.82-7.77 (m, 1H), 7.90-7.85 (m, 2H), 8.54-8.49 (m, 1H); MS: m/z 464 (M-OH)$^-$.

Compounds 343 and 516

N-(Butyl)-N-(3-(1-hydroxy-1-methyl-ethyl)-benzo[b]thiophen-2-yl)-4-carboxy-benzenesulfonamide (Cpd 343) and N-(Butyl)-N-(3-(1-hydroxy-1-methyl-ethyl)-benzo[b]thiophen-2-yl)-4-carbomethoxy-benzenesulfonamide (Cpd 516). To a solution of compound 506 (0.201 g, 0.42 mmol) in DMF (5 mL) and MeOH (2 mL) was added iPr$_2$NEt (0.15 mL, 0.86 mmol) followed by (1,1'-bis(diphenylphosphino)ferrocene)palladium(II) chloride (0.035 g, 0.04 mmol). The reaction mixture was degassed with argon, cooled on a dry-ice acetone bath and charged with carbon monoxide. The reaction vessel was sealed and heated at 60° C. for 18 h. The reaction was cooled to ambient temperature, iPr$_2$NEt (0.15 mL, 0.86 mmol) and (1,1'-bis(diphenylphosphino)ferrocene)palladium(II) chloride (0.035 g, 0.04 mmol) were added, the reaction mixture was cooled on a dry-ice acetone bath, charged with carbon monoxide, the reaction vessel sealed and heated at 60° C. for 7 h. This step was repeated once more and heated at 60° C. for 5 days. The reaction mixture was cooled, concentrated in vacuo, dissolved in MeOH, filtered, and the filtrate concentrated in vacuo. The crude residue was chromatographed reverse-phase (25-95% acetonitrile/water+ 0.1% TFA) and lyophilized to afford 0.009 g of compound 343 and 0.015 g of compound 516.

Compound 343

N-(Butyl)-N-(3-(1-hydroxy-1-methyl-ethyl)-benzo[b]thiophen-2-yl)-4-carboxy-benzenesulfonamide. $^1$H-NMR (DMSO-d$_6$): δ 0.81 (t, 3H), 1.43-1.15 (m, 3H), 1.62-1.54 (m, 1H), 1.72 (s, 3H), 1.80 (s, 3H), 3.24-3.15 (m, 1H), 3.87-3.77 (m, 1H), 5.29 (br s, 1H), 7.39-7.32 (m, 2H), 7.80-7.75 (m, 1H), 7.95 (d, 2H), 8.17 (d, 2H), 8.55-8.48 (m, 1H), 13.58 (s, 1H); MS: m/z 446.3 (M-H)$^-$.

Compound 516

N-(Butyl)-N-(3-(1-hydroxy-1-methyl-ethyl)-benzo[b]thiophen-2-yl)-4-carbomethoxy-benzenesulfonamide. $^1$H-NMR (DMSO-d$_6$): δ 0.81 (t, 3H), 1.43-1.15 (m, 3H), 1.67-1.53 (m, 1H), 1.71 (s, 3H), 1.80 (s, 3H), 3.24-3.15 (m, 1H), 3.87-3.77 (m, 1H), 3.92 (s, 3H), 5.28 (br s, 1H), 7.39-7.32 (m, 2H), 7.80-7.74 (m, 1H), 7.97 (d, 2H), 8.19 (d, 2H), 8.54-8.48 (m, 1H); MS: m/z 444.3 (M-OH)$^+$.

Example 73

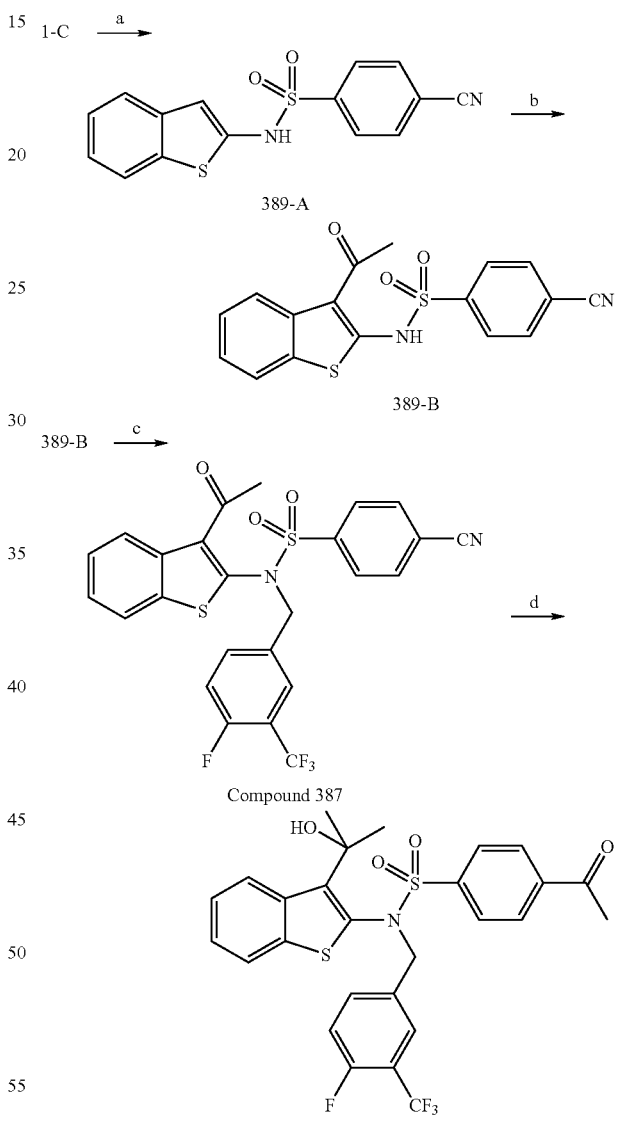

a) 4-Cyanobenzene-1-sulfonyl chloride, pyridine, DCM; b) AcCl, SnCl$_4$, DCM; c) 4-(bromomethyl)-1-fluoro-2-(trifluoromethyl)benzene, KOtBu, 18-C-6, DMF; d) MeMgCl, THF.

N-(Benzo[b]thiophen-2-yl)-4-cyanobenzenesulfonamide (389-A). To a stirred solution of compound 1-C (0.927 g, 5.0 mmol) in pyridine (10 mL) and methylene chloride (5 mL), cooled on an ice bath, was added 4-cyanobenzene-1-sulfonyl chloride (1.01 g, 5.0 mmol) portion-wise over 3 min. The reaction was allowed to warm slowly to ambient temperature and allowed to stir for 72 h. The reaction mixture was concentrated under reduced pressure, the crude residue was partitioned between EtOAc (100 mL) and 1N HCl (25 mL), the layers separated, the organic phase washed with brine (25 mL), dried over MgSO$_4$, filtered and evaporated in vacuo. The crude residue was purified by flash column chromatography (SiO$_2$) eluting with an EtOAc-heptane gradient to afford 1.22 g of compound 389-A as a tan-brown powder. $^1$H-NMR (DMSO-d$_6$): δ 6.91 (s, 1H), 7.33-7.21 (m, 2H), 7.69-7.64 (m, 1H), 7.82-7.76 (m, 1H), 7.99-7.93 (m, 2H), 8.11-8.05 (m, 2H), 11.49 (br s, 1H); MS: m/z 313.1 (M-H)$^-$.

N-(3-Acetyl-benzo[b]thiophen-2-yl)-4-cyanobenzenesulfonamide (389-B). To a suspension of compound 389-A (1.22 g, 3.88 mmol) in DCM (10 mL), cooled in an ice bath, was added a pre-mixed (5 min) solution of ice-cold acetyl chloride (0.36 mL, 5.06 mmol) and SnCl$_4$ (0.51 mL, 4.32 mmol) in DCM (25 mL). The reaction mixture was allowed to warm slowly to ambient temperature and stir for 18 h. The reaction mixture was quenched with a saturated NH$_4$Cl solution (25 mL), filtered through a pad of celite, the organics dried over MgSO$_4$, filtered and concentrated under vacuum to afford 1.62 g of compound 389-B as a semi-pure product. $^1$H-NMR (DMSO-d$_6$): δ 2.55 (s, 3H), 7.22-7.14 (m, 1H), 7.31-7.24 (m, 1H), 7.67 (d, 1H), 8.04-7.92 (m, 4H), 8.21 (d, 1H); MS: m/z 355.1 (M-H)$^-$.

Compound 387

N-(3-Acetyl-benzo[b]thiophen-2-yl)-4-cyano-N-(4-fluoro-3-trifluoromethyl-benzyl)-benzenesulfonamide. To a solution of compound 389-B (assume 3.88 mmol) in DMF (25 mL) was added a KOtBu solution (4.30 mL, 1M in THF), the reaction was stirred for 5 min, to which was added then 18-C-6 (1.03 g, 3.89 mmol) and 4-(bromomethyl)-1-fluoro-2-(trifluoromethyl)benzene (1.80 mL, 11.63 mmol). The reaction mixture was stirred for 4 days, concentrated in vacuo, and the material was purified by flash column chromatography (SiO$_2$) eluting with an EtOAc-heptane gradient to afford 1.59 g of compound 387 as a tan glass. $^1$H-NMR (DMSO-d$_6$): δ 2.37 (s, 3H), 5.02 (br s, 2H), 7.52-7.42 (m, 3H), 7.74-7.66 (m, 2H), 8.05-7.92 (m, 4H), 8.22-8.16 (m, 2H).

Compound 389

4-Acetyl-N-(4-fluoro-3-trifluoromethylbenzyl)-N-(3-(1-hydroxy-1-methyl-ethyl)-benzo[b]thiophen-2-yl)-benzenesulfonamide. To a solution of compound 387 (0.267 g, 0.50 mmol) in THF (5 mL) was added MeMgCl (1.90 mL, 3M in THF), portion-wise over 5 h, and the reaction was stirred for an additional 30 min. The reaction was quenched with a saturated NH$_4$Cl solution (5 mL), the layers partitioned, the organic phase dried over MgSO$_4$, filtered and evaporated in vacuo. The crude residue was purified by flash column chromatography (SiO$_2$) eluting with an EtOAc-heptane gradient to afford 0.075 g of compound 389 as a glassy yellow solid. $^1$H-NMR (DMSO-d$_6$): δ 1.35 (s, 3H), 1.63 (s, 3H), 2.68 (s, 3H), 4.64 (d, 1H), 5.15-5.06 (m, 2H), 7.53-7.30 (m, 5H), 7.83-7.76 (m, 1H), 8.02 (d, 2H), 8.19 (d, 2H), 8.42-8.35 (m, 1H); MS: m/z 548.2 (M-OH)$^+$.

Following the procedure described above for example 73 and substituting the appropriate reagents, starting materials and purification methods known to those skilled in the art, the following compounds of the present invention were prepared:

Compound 772

N-(3-Acetyl-benzo[b]thiophen-2-yl)-N-(4-trifluoromethoxy-benzyl)-4-cyano-benzenesulfonamide. $^1$H-NMR (DMSO-d$_6$): δ 2.27 (s, 3H), 4.95 (s, 2H), 7.32-7.34 (d, 2H), 7.43-7.49 (m, 5H), 7.93-8.03 (m, 5H), 8.16-8.18 (m, 2H); MS: m/z 531.0 (MH$^+$).

Compound 773

N-(3-Acetyl-benzo[b]thiophen-2-yl)-N-(5,5,5-trifluoropentyl)-4-cyano-benzenesulfonamide. MS: m/z 481.0 (MH$^+$).

Example 74

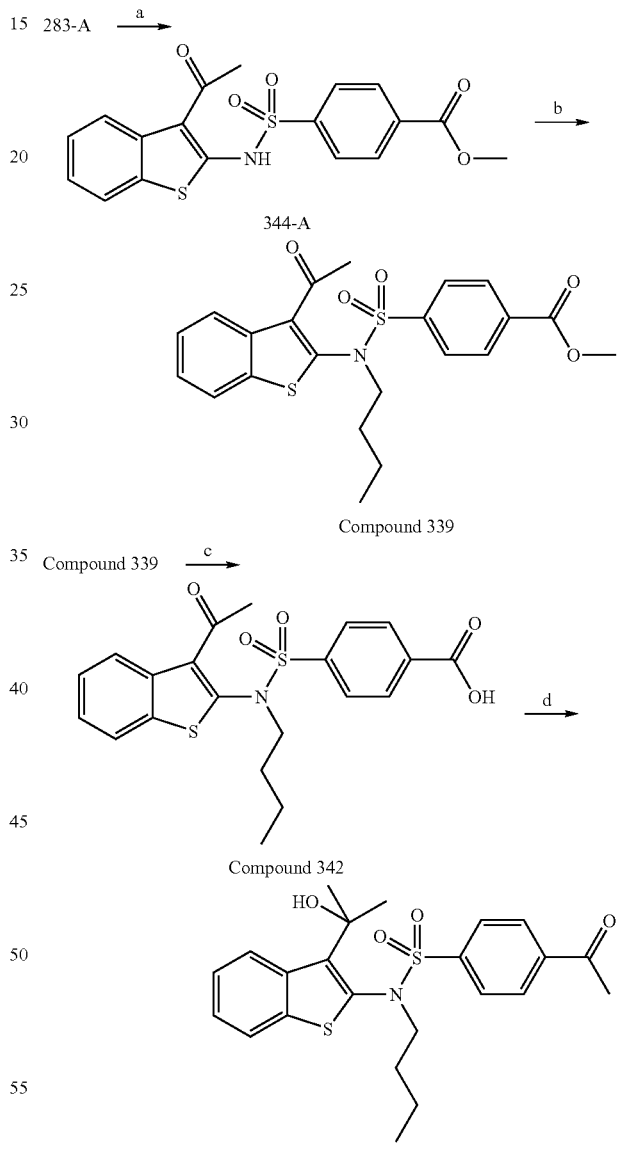

a) AcCl, SnCl$_4$, DCM; b) Ph$_3$P, DEAD, butan-1-ol, THF; c) 1. LiOH•H$_2$O, THF, H$_2$O; 2. aq HCl; d) MeMgCl, THF.

N-(3-Acetyl-benzo[b]thiophen-2-yl)-4-carbomethoxy-benzenesulfonamide (344-A). To a suspension of compound 283-A (1.05 g, 3.01 mmol) in DCM (4 mL), in an ice bath, was added a pre-mixed (5 min) solution of acetyl chloride (0.28 mL, 3.93 mmol) and SnCl$_4$ (0.39 mL, 3.31 mmol) in DCM (20 mL). The reaction mixture was allowed to warm slowly to ambient temperature and stir for 18 h. The reaction mixture was quenched with a saturated NH₄Cl solution (25 mL), filtered through a pad of celite, the organics dried over MgSO₄, filtered and concentrated under vacuum. The residue was triturated with EtOAc (4 mL), filtered and air dried to afford 0.925 g of compound 344-A as a tan powder. ¹H-NMR (DMSO-d₆): δ 2.55 (s, 3H), 3.86 (s, 3H), 7.24 (t, 1H), 7.32 (t, 1H), 7.73 (d, 1H), 7.94 (d, 2H), 8.11 (d, 2H), 8.16 (d, 1H); MS: m/z 390.0 (MH⁺).

Compound 339

N-(3-Acetyl-benzo[b]thiophen-2-yl)-N-(butyl)-4-carbomethoxy-benzenesulfonamide. To a solution of triphenyl phosphine (0.933 g, 3.56 mmol) in THF (30 mL) was added a 40% DEAD-toluene solution (1.60 mL, 3.60 mmol), the reaction mixture was stirred for 2 min, compound 344-A (0.924 g, 2.37 mmol) was added, the reaction mixture was stirred for an additional 5 min, to which was added n-butanol (0.26 mL, 2.84 mmol) and the reaction was stirred for 4 days. The reaction mixture was concentrated in vacuo and the crude residue purified by flash column chromatography (SiO₂) eluting with an EtOAc-heptane gradient to afford 0.624 g of compound 339 as a white foam. ¹H-NMR (DMSO-d₆): δ 0.86 (t, 3H), 1.35 (h, 2H), 1.61 (p, 2H), 2.67 (s, 3H), 3.65 (br s, 2H), 3.91 (s, 3H), 7.52-7.43 (m, 2H), 7.87-7.83 (m, 2H), 7.94-7.91 (m, 1H), 8.18-8.11 (m, 3H); MS: m/z 446.1 (MH⁺).

Compound 342

N-(3-Acetyl-benzo[b]thiophen-2-yl)-N-(butyl)-4-carboxy-benzenesulfonamide. To compound 339 (0.361 g, 0.81 mmol) in a 5:1 THF/water mixture (10 mL) was added LiOH.H₂O (0.042 g, 1.00 mmol) and the reaction mixture was stirred for 2.5 h. The solvent was evaporated in vacuo, the residue diluted with H₂O (5 mL), acidified with 1N HCl (1.0 mL), the precipitate filtered, washed with H₂O, and dried under vacuum to afford 0.334 g of compound 342 as a white powder. ¹H-NMR (DMSO-d₆): δ 0.86 (t, 3H), 1.35 (h, 2H), 1.61 (p, 2H), 2.67 (s, 3H), 3.65 (br s, 2H), 7.53-7.41 (m, 2H), 7.82 (d, 2H), 7.96-7.90 (m, 1H), 8.18-8.10 (m, 3H), 13.63 (s, 1H); MS: m/z 430.2 (M-H)⁻.

Compound 344

N-(Butyl)-N-(3-(1-hydroxy-1-methyl-ethyl)-benzo[b]thiophen-2-yl)-4-acetyl-benzenesulfonamide. To a solution of MeMgCl (0.37 mL, 3M in THF) in THF (2.5 mL) was added a solution of compound 342 (0.216 g, 0.50 mmol) in THF (2.5 mL), drop-wise, over was 2 min. Additional MeMgCl (0.54 mL, 3M in THF) was added in three portions over 4 h, and the reaction mixture was stirred for an additional 45 min. The reaction was quenched with a saturated NH₄Cl solution (5 mL), the organic layer were dried over MgSO₄, filtered, and concentrated in vacuo. The crude residue was purified by reverse-phase (25-95% acetonitrile/water+0.1% TFA), the product fractions combined, treated with poly(vinylpyridine), filtered, frozen and lyophilized to afford 0.047 g of compound 344 as a cream-colored powder. ¹H-NMR (DMSO-d₆): δ 0.81 (t, 3H), 1.50-1.14 (m, 3H), 1.68-1.53 (m, 1H), 1.72 (s, 3H), 1.80 (s, 3H), 2.68 (s, 3H), 3.24-3.12 (m, 1H), 3.89-3.77 (m, 1H), 5.31 (s, 1H), 7.40-7.32 (m, 2H), 7.81-7.74 (m, 1H), 7.97 (d, 2H), 8.91 (d, 2H), 8.56-8.48 (m, 1H); MS: m/z 428.2 (M-OH)⁺.

Example 75

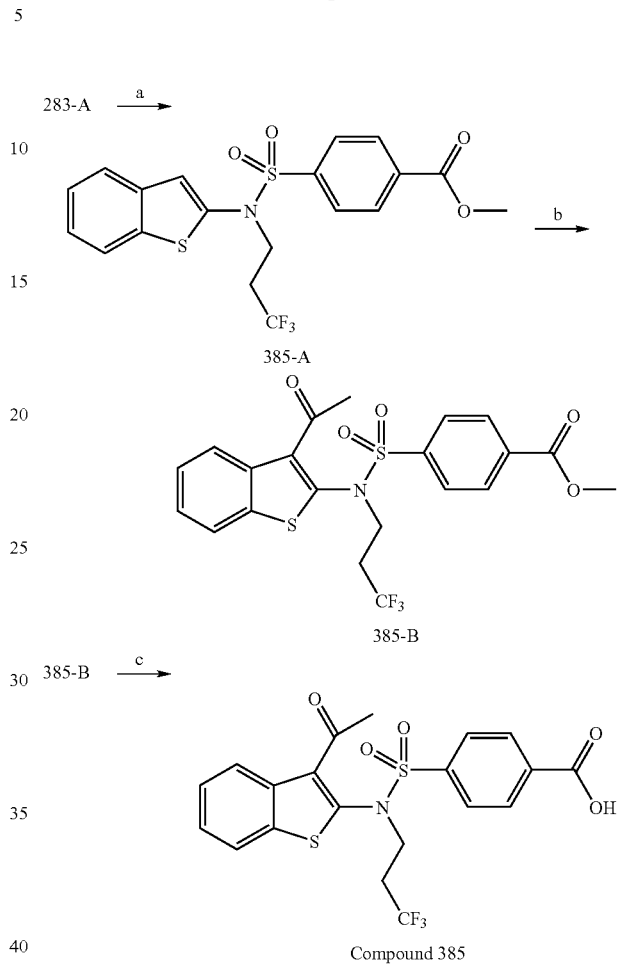

Compound 385 a) Ph₃P, DEAD, 3,3,3-trifluoropropan-1-ol, THF; b) Ac₂O, H₃PO₄; c) 1. LiOH•H₂O, THF, H₂O; 2. aq HCl.

N-(Benzo[b]thiophen-2-yl)-N-(3,3,3-trifluoropropyl)-4-carbomethoxy-benzenesulfonamide (385-A). To a solution of triphenyl phosphine (2.27 g, 8.64 mmol) in THF (60 mL) was added a 40% DEAD-toluene solution (3.85 mL, 8.67 mmol), the reaction mixture was stirred for 2 min, compound 283-A (2.0 g, 5.76 mmol) was added, the reaction mixture was stirred for an additional 5 min, to which was added 3,3,3-trifluoropropan-1-ol (0.61 mL, 6.90 mmol) and the reaction was stirred for 18 h. The reaction mixture was concentrated in vacuo and the crude residue purified by flash column chromatography (SiO₂) eluting with an EtOAc-heptane gradient to afford 2.16 g of compound 385-A as a tan solid. ¹H-NMR (DMSO-d₆): δ 2.68-2.50 (m, 2H), 3.90 (s, 3H), 3.97 (t, 2H), 7.28 (s, 1H), 7.42-7.34 (m, 2H), 7.84-7.76 (m, 1H), 7.94-7.86 (m, 3H), 8.18-8.11 (m, 2H); MS: m/z 444.1 (MH⁺).

N-(3-Acetyl-benzo[b]thiophen-2-yl)-N-(3,3,3-trifluoropropyl)-4-carbomethoxy-benzenesulfonamide (385-B). To compound 385-A (0.388 g, 0.87 mmol) was added acetic anhydride (10 mL) and 85% H₃PO₄ (0.10 mL), and the reaction was heated at 100° C. for three days. Additional acetic anhydride (10 mL) was added, the reaction mixture heated for an additional 4 more days. The reaction mixture was cooled, concentrated under vacuum, partitioned between EtOAc (100 mL) and saturated NaHCO$_3$ (50 mL), filtered, the organic layer washed with brine (50 mL), dried over MgSO$_4$, filtered, and concentrated in vacuo. The crude residue was purified by flash column chromatography (SiO$_2$) eluting with an EtOAc-heptane gradient to afford 0.197 g of compound 385-B as a colorless oil. $^1$H-NMR (DMSO-d$_6$): δ 2.64 (s, 3H), 2.91-2.72 (m, 2H), 4.01-3.87 (m, 5H), 7.54-7.43 (m, 2H), 7.87 (d, 2H), 7.99-7.92 (m, 1H), 8.19-8.08 (m, 3H); MS: m/z 486.1 (MH$^+$).

Compound 385

N-(3-Acetyl-benzo[b]thiophen-2-yl)-N-(3,3,3-trifluoro-propyl)-4-carboxy-benzenesulfonamide. To compound 385-B (0.190 g, 0.39 mmol) in a 5:1 THF/water mixture (5 mL) was added LiOH.H$_2$O (0.021 g, 0.50 mmol) and the reaction mixture was stirred for 18 h at ambient temperature. The solvent was evaporated in vacuo, the crude residue dissolved in warm H$_2$O (5 mL), acidified with 1N HCl (0.5 mL), the precipitate filtered, washed with H$_2$O, and dried under vacuum to afford 0.166 g of compound 385 as a white powder. $^1$H-NMR (DMSO-d$_6$): δ 2.64 (s, 3H), 2.91-2.73 (m, 2H), 4.02-3.85 (m, 2H), 7.54-7.43 (m, 2H), 7.84 (d, 2H), 7.99-7.91 (m, 1H), 8.17-8.08 (m, 3H), 13.65 (s, 1H); MS: m/z 470.1 (M-H)$^-$.

Example 76

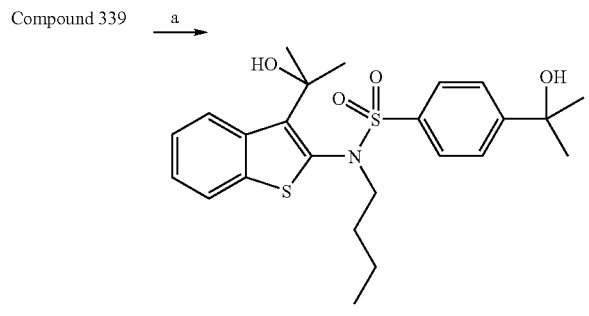

Compound 341 a) MeMgCl, THF.

Compound 341

N-(Butyl)-N-(3-(1-hydroxy-1-methyl-ethyl)-benzo[b]thiophen-2-yl)-4-(2-1-hydroxy-1-methyl-ethyl)-benzenesulfonamide. A solution of compound 339 (0.232 g, 0.52 mmol) in THF (2.5 mL) was added to a solution of MeMgCl (0.20 mL, 3M in THF) in THF (1 mL). Additional MeMgCl (0.70 mL, 3M in THF) was added to the reaction mixture over 18 h, portion-wise, the reaction was quenched with a saturated NH$_4$Cl solution (5 mL), the layers separated, the organic layer dried over MgSO$_4$, filtered, and concentrated in vacuo. The crude residue was purified by reverse-phase (25-95% acetonitrile/water+0.1% TFA), the product fractions combined, treated with poly(vinylpyridine), filtered, frozen and lyophilized to afford 0.087 g of compound 341 as an off-white powder. $^1$H-NMR (DMSO-d$_6$): δ 0.80 (t, 3H), 1.39-1.13 (m, 3H), 1.47 (s, 6H), 1.66-1.52 (m, 1H), 1.70 (s, 3H), 1.80 (s, 3H), 3.18-3.05 (m, 1H), 3.81-3.68 (m, 1H), 5.39-5.22 (br m, 2H), 7.39-7.31 (m, 2H), 7.82-7.70 (m, 5H), 8.57-8.49 (m, 1H); MS: m/z 444.2 (M-OH)$^+$.

Example 77

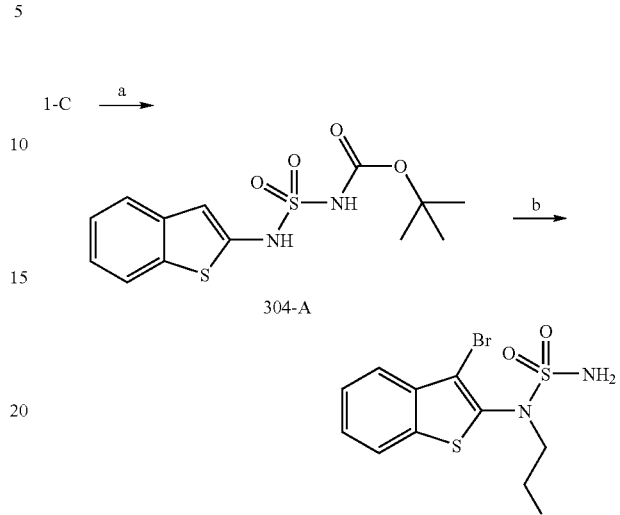

a) 1. DCM, pyridine; 2. ClSO$_2$NCO, t-BuOH, DCM; b) 1. Ph$_3$P, DEAD, 3,3,3-trifluoropropan-1-ol, THF; 2. NBS, DCE, HOAc; 3. TFA.

tert-Butyl N-(benzo[b]thiophen-2-yl)-sulfamoylcarbamate (304-A). To a solution of chlorosulfonyl isocyanate (0.52 mL, 5.96 mmol) in DCM (5 mL) was added t-butanol (0.57 mL, 6.00 mmol), drop-wise over 1-2 min and the reaction mixture was stirred at ambient temperature for 2 h. A suspension of compound 1-C (0.928 g, 5.00 mmol) in DCM (10 mL) was treated with pyridine (1 mL), the resulting solution cooled on an ice bath and the aforementioned reaction mixture was added drop-wise over 4 min. The reaction mixture was allowed to slowly warm to ambient temperature and stirred for 18 h. The reaction mixture was concentrated in vacuo, the residue dissolved in DCM (100 mL), washed with 1N HCl (25 mL), saturated NaHCO$_3$ (25 mL), brine (25 mL), the organic phase dried over MgSO$_4$, filtered, and evaporated under vacuum. The crude solid was triturated with DCM (10 mL), filtered, washed with DCM (2 mL) and air-dried to afford 0.602 g of compound 304-A as an off-white powder. $^1$H-NMR (DMSO-d$_6$): δ 1.39 (s, 9H), 6.98 (s, 1H), 7.37-7.24 (m, 2H), 7.72 (d, 1H), 7.84 (d, 1H), 11.11 (s, 1H), 11.40 (s, 1H); MS: m/z 351.1 (MNa$^+$).

Compound 304

N-(3-Bromo-benzo[b]thiophen-2-yl)-N-(3,3,3-trifluoro-propyl)-sulfamide. To a solution of Ph$_3$P (0.492 g, 1.88 mmol) in THF (15 mL) was added a 40% DEAD-toluene solution (0.84 mL, 1.89 mmol), the reaction mixture was stirred for 2 min, compound 304-A (0.352 g, 1.07 mmol) was added, and the reaction mixture was then split equally into 5-portions. 3,3,3-Trifluoro-propan-1-ol (0.025 mL, 0.30 mmol) was added to one-portion of the aforementioned reaction mixture, the reaction stirred for 18 h, and the solvent evaporated in vacuo. The crude residue dissolved 1:1 dichloroethane/acetic acid (2 mL), NBS (0.053 g, 0.30 mmol) was added, and the reaction mixture was stirred for 1 h. Additional NBS (0.011 g, 0.06 mmol) was added, the reaction mixture was stirred for 30 min, trifluoroacetic acid (0.50 mL) was added, and the reaction mixture was stirred for 3 days. The solvent was evaporated in vacuo, the crude residue purified by reverse-phase (25-95% acetonitrile/water+0.1% TFA), and the product fractions frozen and lyophilized to afford 0.012 g of compound 304. $^1$H-NMR (DMSO-d$_6$): δ 2.64-2.54 (m, 2H), 3.80 (t, 2H), 7.58-7.50 (m, 2H), 7.67 (s, 2H), 7.82-7.76 (m, 1H), 8.05-8.00 (m, 1H); MS: m/z 403 (MH$^+$).

Following the procedure described above for example 77 and substituting the appropriate reagents, starting materials and purification methods known to those skilled in the art, the following compounds of the present invention were prepared:

Compound 303

N-(3-Bromo-benzo[b]thiophen-2-yl)-N-(cyclopropylmethyl)-sulfamide. MS m/z 361.0 (MH$^+$).

Compound 849

N-(3-Bromo-benzo[b]thiophen-2-yl)-N,N'-bis-butyl-sulfamide. MS: m/z 419.1 (MH$^+$)

Example 78

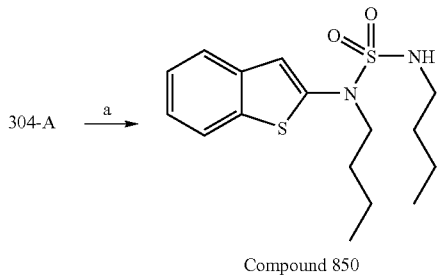

Compound 850 a) 1. Ph$_3$P, DEAD, butan-1-ol, THF; 2. TFA, DCM.

Compound 850

N-Benzo[b]thiophen-2-yl-N,N'-bis-butyl-sulfamide. To a solution of Ph$_3$P (0.100 g, 1.88 mmol) in THF (3 mL) was added a 40% DEAD-toluene solution (0.17 mL, 0.38 mmol), the reaction mixture was stirred for 2 min, compound 304-A (0.083 g, 1.07 mmol) was added, the reaction mixture stirred for 5 min, the butan-1-ol (0.027 mL, 0.29 mmol) was added, and the reaction mixture stirred for 18 h. Trifluoroacetic acid (0.50 mL) was added, the reaction mixture stirred for 1 h, and the solvent evaporated under reduced pressure. DCM (2 mL) and TFA (1 mL) were added to the residue, the reaction mixture stirred for 3 days, the solvent evaporated in vacuo, the crude residue purified by reverse-phase chromatography (25-95% acetonitrile/water+0.1% TFA), and the product fractions frozen and lyophilized to afford 0.02 g of compound 850. $^1$H-NMR (DMSO-d$_6$): δ 0.89-0.80 (m, 6H), 1.36-1.22 (m, 4H), 1.44-1.36 (m, 2H), 1.54-1.44 (m, 2H), 2.92 (q, 2H), 3.60 (t, 2H), 7.27 (s, 1H), 7.39-7.30 (m, 2H), 7.71 (t, 1H), 7.80-7.76 (m, 1H), 7.89-7.85 (m, 1H); MS: m/z 341.2 (MH$^+$).

Example 79

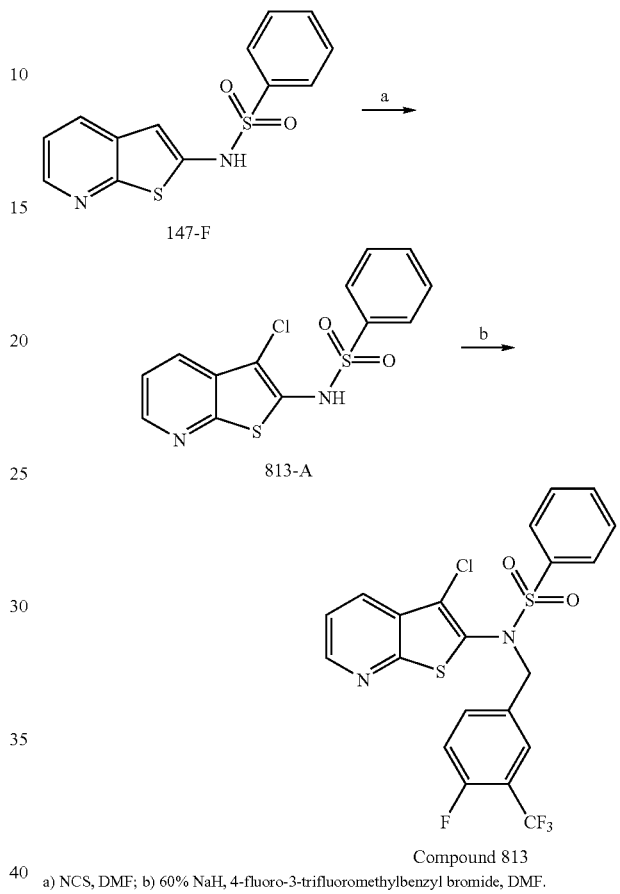

Compound 813
a) NCS, DMF; b) 60% NaH, 4-fluoro-3-trifluoromethylbenzyl bromide, DMF.

N-(3-Chloro-thieno[2,3-b]pyridin-2-yl)-benzenesulfonamide (813-A). To compound 147-F (0.26 g, 0.643 mmol) in DMF (1 mL) under argon at ambient temperature was added N-chlorosuccinimide (94.4 mg, 0.707 mmol) and the reaction mixture was stirred for 16 h. Ethyl acetate was added, the mixture washed with H$_2$O (2×), brine, evaporated under reduced pressure and purified by reverse phase pHPLC (C$_{18}$) to afford 0.072 g of compound 813-A as a tan solid. $^1$H-NMR (DMSO-d$_6$): δ 7.50 (dd, 1H), 7.56-7.65 (m, 2H), 7.65-7.74 (m, 1H), 7.81-7.89 (m, 2H), 8.00 (dd, 1H), 8.58 (dd, 1H).

Compound 813

N-(3-Chloro-thieno[2,3-b]pyridin-2-yl)-N-(4-fluoro-3-trifluoromethyl-benzyl)-benzenesulfonamide. To a solution of compound 813-A (72.1 mg, 0.222 mmol) in DMF (1 mL) under argon was added 60% NaH (9.3 mg, 0.233 mmol) and the reaction mixture was stirred for 15 min at ambient temperature. 4-Fluoro-3-trifluoromethylbenzyl bromide (0.034 mL, 0.222 mmol) was added and the reaction mixture was stirred for six days at ambient temperature. Saturated NaHCO$_3$ was added, the solution was extracted with EtOAc, washed with brine, dried over K$_2$CO$_3$, filtered, and evaporated under reduced pressure. The crude residue was purified by flash column chromatography (SiO$_2$) eluting with CH$_2$Cl$_2$, the pure fractions combined, excess 1M ethereal hydrogen chloride added, and the mixture evaporated under reduced pressure to afford 80 mg of compound 813 as a white solid. $^1$H-NMR (DMSO-d$_6$): δ 4.93 (s, 2H), 7.40-7.51 (m, 1H), 7.58 (dd, 1H), 7.63-7.78 (m, 4H), 7.80-7.90 (m, 1H), 7.95 (d, 2H), 8.15 (d, 1H), 8.65-8.76 (m, 1H); MS: m/z 501.04 (MH$^+$).

Example 80

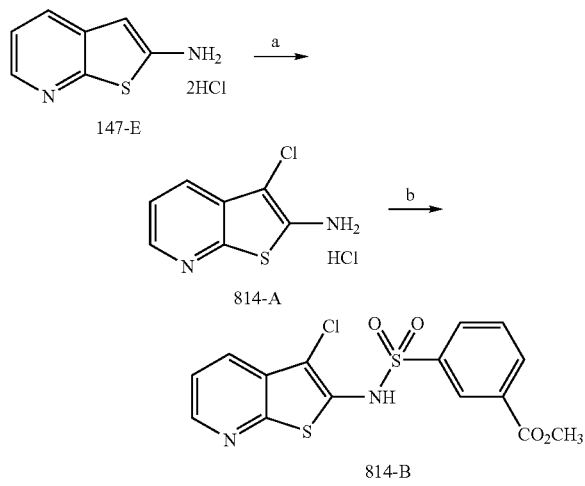

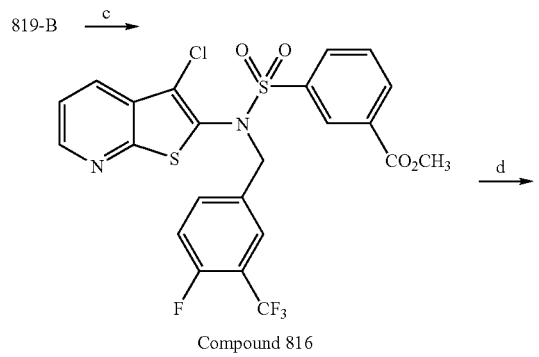

a) NCS, DMF; b) 3-chlorosulfonyl-benzoic acid methyl ester, pyridine; c) 60% NaH, 4-fluoro-3-trifluoromethylbenzyl bromide, DMF; d) 3N NaOH, MeOH.

3-(Chloro-thieno[2,3-b]pyridin-2-yl)-amine (814-A). To a homogeneous solution of compound 147-E (0.30 g, 1.34 mmol) in DMF (4 mL) under argon at ambient temperature was added N-chlorosuccinimide (0.22 g, 1.65 mmol), the reaction mixture was stirred for seven days, EtOAc was added, and the precipitate filtered to afford 0.12 g of compound 814-A as a white solid. MS: m/z 185 (MH$^+$).

3-(Chloro-thieno[2,3-b]pyridin-2-yl)-3-carbomethoxy-benzenesulfonamide (814-B). To a solution of compound 814-A (0.17 g, 0.654 mmol) in pyridine (1.7 mL) under argon at ambient temperature was added 3-chlorosulfonyl-benzoic acid methyl ester (0.153 g, 0.654 mmol) and the reaction mixture was stirred at ambient temperature for 24 h. An additional portion of 3-chlorosulfonyl-benzoic acid methyl ester (0.03 g, 0.128 mmol) was added and the reaction mixture was stirred for an additional 48 h, at which time another portion of 3-chlorosulfonyl-benzoic acid methyl ester (0.043 g, 0.183 mmol) was added and the reaction mixture was allowed to stir for 18 h. The solvent was evaporated under reduced pressure and the crude residue purified by flash column chromatography (SiO$_2$) eluting with 1:1 heptane: CH$_2$Cl$_2$, CH$_2$Cl$_2$, and 1:3 acetone:CH$_2$Cl$_2$ to afford 0.12 g of compound 814-B. MS: m/z 383.05 (MH$^+$).

Compound 816

N-(3-Chloro-thieno[2,3-b]pyridin-2-yl)-N-(4-fluoro-3-trifluoromethyl-benzyl)-3-carbomethoxy-benzenesulfonamide. To a solution of Compound 814-B (0.12 g, 0.313 mmol) in DMF (2 mL) under argon was added 60% NaH (13.8 mg, 0.345 mmol) and the reaction mixture was stirred at ambient temperature for 15 min. 4-Fluoro-3-trifluoromethylbenzyl bromide (0.048 mL, 0.329 mmol) was added, the reaction mixture stirred for five days, water added, the solution extracted with EtOAc, washed with brine, dried with K$_2$CO$_3$, filtered, evaporated under reduced pressure, and purified by reverse phase pHPLC (C$_{18}$) to afford 0.06 g of compound 816 as a clear oil. MS: m/z 559.0 (MH$^+$).

Compound 814

N-(3-Chloro-thieno[2,3-b]pyridin-2-yl)-N-(4-fluoro-3-trifluoromethyl-benzyl)-3-carboxy-benzenesulfonamide. To a solution of compound 816 (0.055 g, 0.0983 mmol) in methanol (5.5 mL) was added 3N NaOH (0.066 ml, 0.197 mmol) and the reaction mixture was stirred at ambient temperature for six days, the solvent evaporated under reduced pressure, the residue dissolved in 0.1% TFA in acetonitrile/DMSO, and purified by reverse phase pHPLC (C$_{18}$) to afford 0.04 g of compound 814 as a white solid. MS: m/z 545.07 (MH$^+$).

Example 81

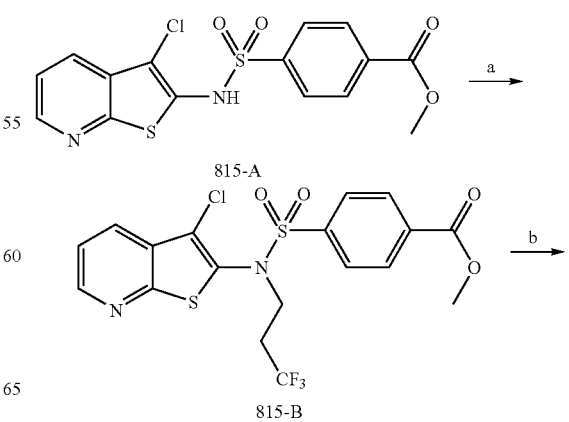

-continued

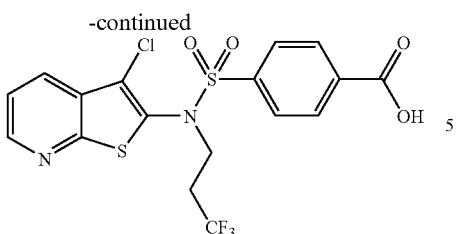

Compound 815 a) PPh₃, DEAD, 3,3,3-trifluoro-propan-1-ol, THF, toluene; b) 3N NaOH, MeOH.

Compound 815-A was prepared by the method used to synthesize compound 814-B in Example 80, steps A and B.

N-(3-Chloro-thieno[2,3-b]pyridin-2-yl)-N-(3,3,3-trifluoro-propyl)-4-carbomethoxy-benzenesulfonamide (815-B). To a flask under argon was added Ph₃P (0.268 g, 0.101 mmol), THF (7 mL), and 40% DEAD in toluene (0.449 mL, 0.101 mmol) and the reaction mixture was stirred for 2 min. Compound 815-A (0.258 g, 0.674 mmol) was added, the reaction mixture stirred for five min, to which was added 3,3,3-trifluoro-propan-1-ol (0.095 g, 0.809 mmol) in THF (3 mL) and the reaction mixture stirred at ambient temperature for six days. The solvent was evaporated under reduced pressure and the residue purified by reverse phase pHPLC ($C_{18}$) to afford 0.167 g of compound 815-B. MS: m/z 479.1 (MH⁺).

Compound 815

N-(3-Chloro-thieno[2,3-b]pyridin-2-yl)-N-(3,3,3-trifluoro-propyl)-4-carboxy-benzenesulfonamide. To a solution of compound 815-B (0.167 g, 0.348 mmol) in methanol (12 mL), under argon, was added 3N NaOH (0.116 mL, 0.348 mmol) and the reaction mixture was stirred at ambient temperature 18 h. An additional portion of 3N NaOH (0.116 mL, 0.348 mmol) was added and the reaction mixture was stirred for six days. 1N HCl (0.804 mL, 0.804 mmol) was added to the reaction and the precipitate filtered to afford 0.115 g of compound 815 as a white solid. MS: m/z 465.0 (MH⁺).

Example 82

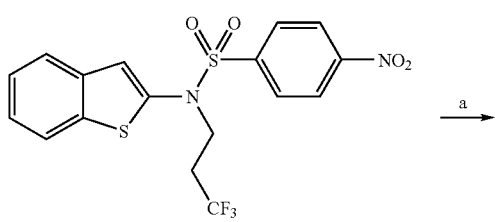

Compound 498

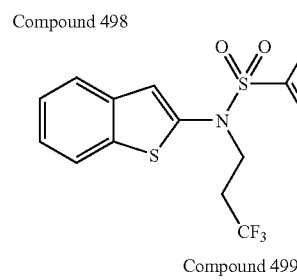

Compound 499

Compound 499 —b→

-continued

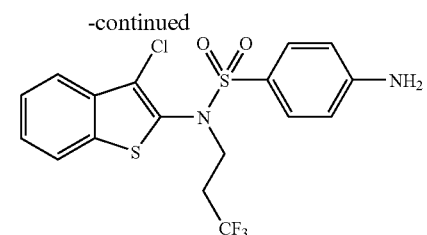

Compound 585 a) 5% sulfided Pd/C, H₂, MeOH; b) NCS, DMF.

Compound 499

4-Amino-N-(benzo[b]thiophen-2-yl)-N-(3,3,3-trifluoro-propyl)-benzenesulfonamide. A Paar flask containing 5% sulfided Pd/C (0.05 g, 10% w/w), compound 498 (0.49 g, 1.14 mmol) and methanol (20 mL) was reacted under hydrogen atmosphere for 3 days. The catalyst was filtered through a pad of celite and the filtrate evaporated under reduced pressure to afford 0.49 g of compound 499 as an off-white greenish solid. ¹H-NMR (CDCl₃): δ 2.48 (m, 2H), 3.78-3.87 (m, 2H), 6.63 (d, 2H), 7.14 (s, 1H), 7.30-7.40 (m, 2H), 7.48 (d, 2H), 7.65-7.75 (m, 2H); MS: m/z 401.19 (MH⁺).

Compound 585

4-Amino-N-(3-chloro-benzo[b]thiophen-2-yl)-N-(3,3,3-trifluoro-propyl)-benzenesulfonamide. To a solution of compound 499 (0.18 g, 0.450 mmol) in DMF (2.5 mL) was added N-chlorosuccinimide (0.084 g, 0.494 mmol) and the reaction mixture stirred at ambient temperature for 3 days. Ether was added to the reaction mixture, the organics washed with H₂O, brine, and the solvent evaporated under reduced pressure. The crude residue was purified by reverse phase pHPLC ($C_{18}$) to afford 0.036 g of compound 585 as an amber gum. ¹H-NMR (CDCl₃): δ 2.42-2.60 (m, 2H), 3.81-3.87 (m, 2H), 6.65-6.72 (m, 2H), 7.42-7.50 (m, 2H), 7.57-7.63 (m, 2H), 7.69-7.75 (m, 1H), 7.77-7.84 (m, 1H); MS: m/z 435.14 (MH⁺).

Following the procedure described above for example 82 and substituting the appropriate reagents, starting materials and purification methods known to those skilled in the art, the following compounds of the present invention were prepared:

Compound 586

4-Amino-N-(benzo[b]thiophen-2-yl)-3-chloro-N-(3,3,3-trifluoro-propyl)-benzenesulfonamide. ¹H-NMR (CDCl₃): δ 2.40-2.58 (m, 2H), 3.79-3.88 (m, 2H), 6.73 (d, 1H), 7.17 (s, 1H), 7.30-7.43 (m, 3H), 7.65 (d, 1H), 7.68-7.76 (m, 2H); MS: m/z 435.14 (MH⁺).

Compound 587

4-Amino-N-(3-bromo-benzo[b]thiophen-2-yl)-N-(3,3,3-trifluoro-propyl)-benzenesulfonamide. Compound 587 was prepared using the methodology in Example 82, step B, substituting NBS for NCS. ¹H-NMR (CDCl₃): δ 2.43-2.61 (m, 2H), 3.80-3.89 (m, 2H), 6.65-6.73 (m, 2H), 7.42-7.50 (m, 2H), 7.58-7.65 (m, 2H), 7.70-7.76 (m, 1H), 7.77-7.83 (m, 1H); MS: m/z 479.23 (MH⁺).

Compound 588

4-Amino-3-bromo-N-(3-bromo-benzo[b]thiophen-2-yl)-N-(3,3,3-trifluoro-propyl)-benzenesulfonamide. Compound 588 was isolated as a by-product from the synthesis of compound 587, prepared by using the methodology in Example 82, step B, substituting NBS for NCS. ¹H-NMR (CDCl₃): δ 2.44-2.62 (m, 2H), 3.82-3.90 (m, 2H), 6.76 (d, 1H), 7.44-7.51 (m, 2H), 7.54 (dd, 1H), 7.72-7.77 (m, 1H), 7.78-7.84 (m, 1H), 7.91 (d, 1H); MS: m/z 558.92 (MH⁺).

Compound 650

4-Amino-N-(3-bromo-benzo[b]thiophen-2-yl)-N-(4-fluoro-3-trifluoromethyl-benzyl)-benzenesulfonamide. Compound 650 was prepared using the methodology in Example 1, steps C and D, and Example 82, steps A and B. ¹H-NMR (CDCl₃): δ 4.78 (s, 2H), 6.65-6.74 (m, 2H), 7.01-7.10 (m, 1H), 7.36-7.44 (m, 2H), 7.45-7.56 (m, 2H), 7.59-7.69 (m, 3H), 7.70-7.74 (m, 1H); MS: m/z 559.08 (MH⁺).

Compound 651

4-Amino-3-bromo-N-(3-bromo-benzo[b]thiophen-2-yl)-N-(4-fluoro-3-trifluoromethyl-benzyl)-benzenesulfonamide. Compound 651 was isolated as a by-product from the synthesis of compound 650, prepared by using the methodology in Example 82, step B, substituting NBS for NCS. ¹H-NMR (CDCl₃): δ 4.79 (s, 2H), 6.77 (d, 1H), 7.07 (t, 1H), 7.37-7.58 (m, 5H), 7.64-7.76 (m, 2H), 7.92 (d, 1H); MS: m/z 638.85 (MH⁺).

Compound 653

4-Amino-N-(benzo[b]thiophen-2-yl)-N-(4-fluoro-3-trifluoromethyl-benzyl)-benzenesulfonamide. Compound 653 was prepared using the methodology in Example 1, steps C and D, and Example 82, step A. ¹H-NMR (CDCl₃): δ 4.76 (s, 2H), 6.62-6.70 (m, 2H), 7.02 (s, 1H), 7.05-7.14 (m, 1H), 7.27-7.35 (m, 2H), 7.49-7.58 (m, 4H), 7.63 (td, 2H); MS: m/z 481.2 (MH⁺).

Compound 666

4-Amino-N-(3-chloro-benzo[b]thiophen-2-yl)-N-(5,5,5-trifluoro-pentyl)-benzenesulfonamide. Compound 666 was prepared using the methodology in Example 1, step C, Example 3, step A, and Example 82, steps A and B. ¹H-NMR (CDCl₃): δ 1.52-1.75 (m, 4H), 1.96-2.15 (m, 2H), 3.61 (t, 2H), 6.64-6.71 (m, 2H), 7.40-7.49 (m, 2H), 7.55-7.63 (m, 2H), 7.66-7.74 (m, 1H), 7.76-7.84 (m, 1H); MS: m/z 463.11 (MH⁺).

Compound 667

4-Amino-3-chloro-N-(3-chloro-benzo[b]thiophen-2-yl)-N-(5,5,5-trifluoro-pentyl)-benzenesulfonamide. Compound 667 was isolated as a by-product from the synthesis of compound 585, prepared by using the methodology in Example 82, step B. MS: m/z 497.02 (MH⁺).

Compound 668

4-Amino-N-(3-bromo-benzo[b]thiophen-2-yl)-N-(5,5,5-trifluoro-pentyl)-benzenesulfonamide. Compound 668 was prepared using the methodology in Example 1, step C, Example 3, step A, and Example 82, steps A and B, substituting N-bromosuccinimide for N-chlorosuccinimide. ¹H-NMR (CDCl₃): δ 1.52-1.75 (m, 4H), 1.96-2.14 (m, 2H), 3.62 (t, 2H), 6.64-6.73 (m, 2H), 7.39-7.49 (m, 2H), 7.56-7.64 (m, 2H), 7.68-7.74 (m, 1H), 7.80 (dd, 1H); MS: m/z 508.90 (MH⁺).

Example 83

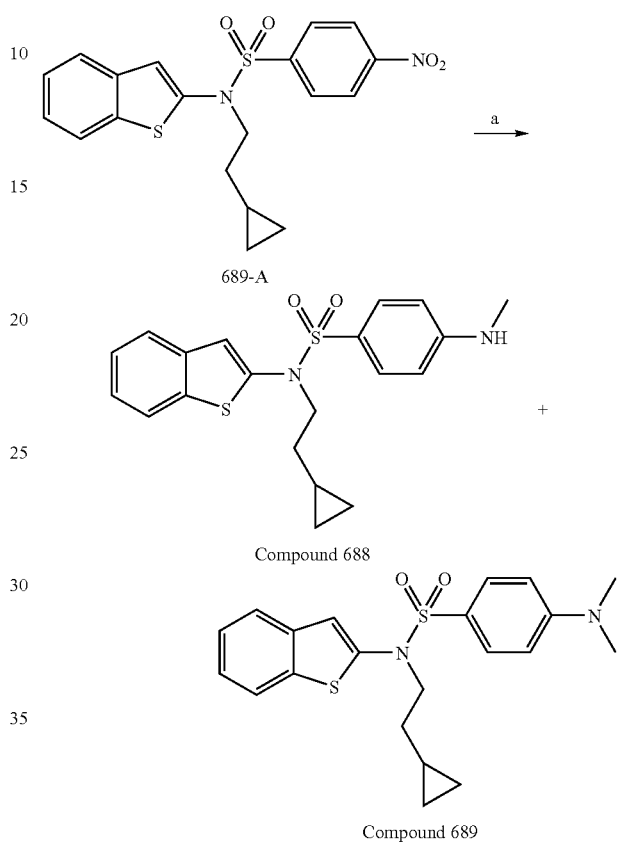

a) 10% Pd/C, H₂, MeOH/HCHO.

Compound 689-A was prepared by the method in Example 1, step C, and Example 3, step A.

Compound 688 and Compound 689

N-(Benzo[b]thiophen-2-yl)-N-(2-cyclopropyl-ethyl)-4-methylamino-benzenesulfonamide (Cpd 688) and N-(benzo[b]thiophen-2-yl)-N-(2-cyclopropyl-ethyl)-4-dimethylamino-benzenesulfonamide (Cpd 689). A Paar flask containing 10% Pd/C (0.15 g, 24% w/w), and compound 689-A (0.62 g, 1.54 mmol) in methanol (100 mL), contaminated with some formaldehyde, was reacted under hydrogen atmosphere for two days. The catalyst was filtered through a pad of celite and the filtrate evaporated under reduced pressure to afford 0.42 g of a mixture of compound 688 and compound 689. The crude mixture was purified by reverse phase pHPLC (C₁₈) to afford 0.016 g of compound 688 as a white solid and 0.028 g of compound 689 as an off-white solid.

Compound 688

N-(Benzo[b]thiophen-2-yl)-N-(2-cyclopropyl-ethyl)-4-methylamino-benzenesulfonamide. MS: m/z 387 (MH⁺).

Compound 689

N-(Benzo[b]thiophen-2-yl)-N-(2-cyclopropyl-ethyl)-4-dimethylamino-benzenesulfonamide. MS: m/z 401 (MH⁺).

Following the procedure described above for example 83 and substituting the appropriate reagents, starting materials and purification methods known to those skilled in the art, the following compounds of the present invention were prepared:

Compound 690

N-(3-Chloro-benzo[b]thiophen-2-yl)-N-(2-cyclopropyl-ethyl)-4-methylamino-benzenesulfonamide. Compound 690 was prepared using the methodology in Example 82, step B. $^1$H-NMR (CDCl$_3$): δ −0.04-0.00 (m, 6H), 0.34-0.46 (m, 7H), 0.61-0.76 (m, 3H), 1.43 (q, 7H), 2.94 (s, 3H), 3.6-3.72 (m, 2H), 6.71 (d, 2H), 7.38-7.49 (m, 2H), 7.63-7.74 (m, 3H), 7.75-7.83 (m, 1H); MS: m/z 421.1 (MH⁺).

Compound 691

3-Chloro-N-(3-chloro-benzo[b]thiophen-2-yl)-N-(2-cyclopropyl-ethyl)-4-methylamino-benzenesulfonamide. Compound 691 was isolated as a by-product during the synthesis of compound 690, prepared by using the methodology in Example 82, step B. $^1$H-NMR (CDCl$_3$): δ 0.00-0.05 (m, 6H), 0.36-0.45 (m, 8H), 0.63-0.77 (m, 4H), 1.38-1.49 (m, 8H), 2.98 (s, 3H), 3.62-3.72 (m, 2H), 6.63 (d, 1H), 7.38-7.50 (m, 2H), 7.61 (dd, 1H), 7.76-7.84 (m, 1H); MS: m/z 455.09 (MH⁺).

Compound 692

3-Bromo-N-(3-bromo-benzo[b]thiophen-2-yl)-N-(2-cyclopropyl-ethyl)-4-methylamino-benzenesulfonamide. Compound 692 was isolated as a by-product during the synthesis of compound 693, prepared by using the methodology in Example 82, step B, substituting NBS for NCS. $^1$H-NMR (CDCl$_3$): δ 0.00-0.04 (m, 6H), 0.37-0.45 (m, 7H), 0.61-0.78 (m, 3H), 1.38-1.51 (m, 8H), 2.98 (s, 3H), 3.63-3.73 (m, 2H), 6.60 (d, 1H), 7.38-7.49 (m, 2H), 7.65 (dd, 1H), 7.71 (dd, 1H), 7.76-7.84 (m, 1H), 7.91 (d, 1H); MS: m/z 544.97 (MH⁺).

Compound 693

N-(3-Bromo-benzo[b]thiophen-2-yl)-N-(2-cyclopropyl-ethyl)-4-methylamino-benzenesulfonamide. Compound 693 was prepared using the methodology in Example 82, step B, substituting NBS for NCS. $^1$H-NMR (CDCl$_3$): δ −0.05-0.02 (m, 9H), 0.34-0.46 (m, 2H), 0.61-0.75 (m, 1H), 1.37-1.52 (m, 2H), 2.96 (s, 3H), 3.63-3.73 (m, 2H), 6.83 (d, 2H), 7.38-7.48 (m, 2H), 7.65-7.74 (m, 3H), 7.75-7.82 (m, 1H); MS: m/z 465.07 (MH⁺).

Example 84

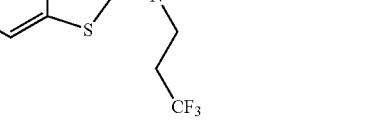

Compound 499

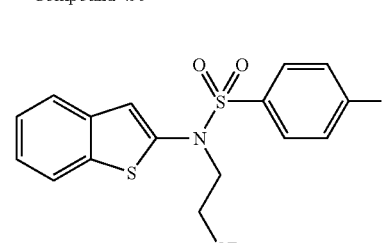

Compound 507

Compound 507 →$^b$

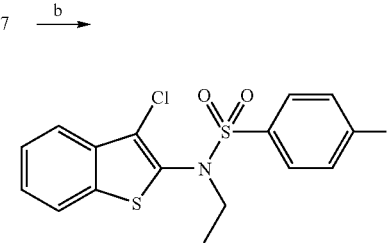

Compound 676 a) CH$_3$SO$_2$Cl, DIEA, THF; b) NCS, DMF.

Compound 507

N-(Benzo[b]thiophen-2-yl)-4-methanesulfonylamino-N-(3,3,3-trifluoro-propyl)-benzenesulfonamide. To a flask under argon was added compound 499 (52.1 mg, 0.013 mmol), THF (3 mL), DIEA (0.027 mL, 0.016 mmol) and methanesulfonyl chloride (0.010 mL, 0.013 mmol). The reaction mixture was heated at 70° C. for seven days, the solvent evaporated under reduced pressure and the crude residue purified by flash column chromatography (SiO$_2$) eluting with DCM, followed by reverse phase pHPLC (C$_{18}$) to afford 7.2 mg of compound 507 as a yellow solid. MS: m/z 479.1 (MH⁺).

Compound 676

N-(3-Chloro-benzo[b]thiophen-2-yl)-4-methanesulfonylamino-N-(3,3,3-trifluoro-propyl)-benzenesulfonamide. To N-chlorosuccinimide (55.2 mg, 0.414 mmol) under argon was added compound 507 (0.22 g, 0.460 mmol) in DMF (5 mL). The reaction mixture was stirred at ambient temperature for 18 h, another portion of N-chlorosuccinimide (55.2 mg, 0.414 mmol) was added and the reaction mixture was stirred for an additional 18 h. Ethyl acetate was added to the reaction mixture, the organics washed with water (2×), the solvent evaporated under reduced pressure and the crude residue purified by reverse phase pHPLC ($C_{18}$) to afford 119 mg of compound 676 as a white solid. $^1$H-NMR (CDCl$_3$): δ 2.45-2.62 (m, 2H), 3.13 (s, 3H), 3.85-3.93 (m, 2H), 6.93 (s, 1H), 7.28-7.34 (m, 2H), 7.45-7.53 (m, 2H), 7.72-7.86 (m, 4H); MS: m/z 512.96 (MH$^+$).

Following the procedure described above for example 84 and substituting the appropriate reagents, starting materials and purification methods known to those skilled in the art, the following compounds of the present invention were prepared:

Compound 652

N-(Benzo[b]thiophen-2-yl)-N-(4-fluoro-3-trifluoromethyl-benzyl)-4-methanesulfonylamino-benzenesulfonamide. Compound 652 was prepared using the methodology in Example 1, steps C and D, and Example 82, step A, and Example 84, step A. MS: m/z 559.07 (MH$^+$).

Compound 659

N-(3-Chloro-benzo[b]thiophen-2-yl)-N-(4-fluoro-3-trifluoromethyl-benzyl)-4-methanesulfonylamino-benzenesulfonamide. Compound 659 was prepared from compound 652 using the methodology in Example 1, steps C and D, Example 82, step A, and Example 84, steps A and B. $^1$H-NMR (CDCl$_3$): δ 3.14 (s, 3H), 4.83 (s, 2H), 6.96 (s, 1H), 7.09 (t, 1H), 7.28-7.36 (m, 2H), 7.39-7.47 (m, 2H), 7.47-7.57 (m, 2H), 7.64-7.76 (m, 2H), 7.83 (d, 2H); MS: m/z 593.05 (MH$^+$).

Compound 660

N-(3-Bromo-benzo[b]thiophen-2-yl)-N-(4-fluoro-3-trifluoromethyl-benzyl)-4-methanesulfonylamino-benzenesulfonamide. Compound 660 was prepared from compound 652 using the methodology in Example 1, steps C and D, Example 82, step A, and Example 84, steps A and B, substituting NBS for NCS. $^1$H-NMR (CDCl$_3$): δ 3.14 (s, 3H), 4.84 (s, 2H), 7.01-7.14 (m, 2H), 7.28-7.36 (m, 2H), 7.38-7.58 (m, 4H), 7.62-7.77 (m, 2H); MS: m/z 639.08 (MH$^+$).

Compound 661

3-Bromo-N-(3-bromo-benzo[b]thiophen-2-yl)-N-(4-fluoro-3-trifluoromethyl-benzyl)-4-methanesulfonylamino-benzenesulfonamide. Compound 661 was isolated as a by-product during the synthesis of compound 660. $^1$H-NMR (CDCl$_3$): δ 3.14 (s, 3H), 4.86 (s, 2H), 7.10 (t, 1H), 7.19 (s, 1H), 7.45 (dd, 2H), 7.47-7.57 (m, 2H), 7.71 (ddd, 2H), 7.78-7.81 (m, 2H), 7.78-7.81 (m, 2H), 8.05 (s, 1H).

Compound 677

N-(3-Bromo-benzo[b]thiophen-2-yl)-N-(3,3,3-trifluoropropyl)-4-methanesulfonylamino-benzenesulfonamide. Compound 677 was prepared from compound 507 using the methodology in Example 1, steps C and D, Example 3, step A, Example 82, step A, and Example 84, steps A and B, substituting NBS for NCS. $^1$H-NMR (CDCl$_3$): δ 2.42-2.63 (m, 2H), 3.11-3.44 (m, 3H), 3.84-3.94 (m, 2H), 6.88-0.24 (m, 1H), 7.30 (d, 1H), 7.36-7.44 (m, 1H), 7.45-7.52 (m, 1H), 7.64-7.97 (m, 4H); MS: m/z 558.93 (MH$^+$).

Compound 678

N-(Benzo[b]thiophen-2-yl)-4-methanesulfonylamino-N-(5,5,5-trifluoro-pentyl)-benzenesulfonamide. $^1$H-NMR (CDCl$_3$): δ 1.65-1.73 (m, 4H), 1.99-2.18 (m, 2H), 3.11 (s, 3H), 3.57-3.68 (m, 2H), 6.87 (s, 1H), 7.20 (d, 2H), 7.31-7.42 (m, 2H), 7.64-7.76 (m, 4H); MS: m/z 507.02 (MH$^+$).

Compound 679

N-(3-Chloro-benzo[b]thiophen-2-yl)-4-methanesulfonylamino-N-(5,5,5-trifluoro-pentyl)-benzenesulfonamide. MS: m/z 541.02 (MH$^+$).

Compound 680

N-(3-Bromo-benzo[b]thiophen-2-yl)-4-methanesulfonylamino-N-(5,5,5-trifluoro-pentyl)-benzenesulfonamide. Compound 680 was prepared using the methodology in Example 84, steps A and B, substituting N-bromosuccinimide for N-chlorosuccinimide. MS: m/z 586.93 (MH$^+$).

Compound 681

3,5-Dichloro-N-(3-chloro-benzo[b]thiophen-2-yl)-4-methanesulfonylamino-N-(3,3,3-trifluoro-propyl)-benzenesulfonamide. Compound 681 was isolated as a by-product during the synthesis of compound 676 using the methodology in Example 1, steps C and D, Example 82, step A, and Example 84, steps A and B. MS: m/z 580.84 (MH$^+$).

Compound 682

3,5-Dichloro-N-(3-chloro-benzo[b]thiophen-2-yl)-4-methanesulfonylamino-N-(5,5,5-trifluoro-pentyl)-benzenesulfonamide. Compound 682 was isolated as a by-product during the synthesis of compound 679 using the methodology in Example 1, steps C and D, Example 82, step A, and Example 84, steps A and B. MS: m/z 610.79 (MH$^+$).

Compound 683

3-Bromo-N-(3-bromo-benzo[b]thiophen-2-yl)-4-methanesulfonylamino-N-(3,3,3-trifluoro-propyl)-benzenesulfonamide. Compound 683 was isolated as a by-product during the synthesis of compound 677 using the methodology in Example 1, steps C and D, Example 82, step A, and Example 84, steps A and B. $^1$H-NMR (CDCl$_3$): δ 2.47-2.65 (m, 2H), 3.11-3.45 (m, 3H), 3.87-3.96 (m, 2H), 7.18 (s, 1H), 7.46-7.54 (m, 2H), 7.73-7.84 (m, 4H), 8.04-8.09 (m, 1H).

Compound 713

N-(Benzo[b]thiophen-2-yl)-3-methanesulfonylamino-N-(3,3,3-trifluoro-propyl)-benzenesulfonamide. MS: m/z 479.00 (MH$^+$).

Compound 714

N-(3-Chloro-benzo[b]thiophen-2-yl)-3-methanesulfonylamino-N-(3,3,3-trifluoro-propyl)-benzenesulfonamide. $^1$H-NMR (CDCl$_3$): δ 2.45-2.62 (m, 2H), 2.96 (s, 3H), 3.88-3.98 (m, 2H), 6.76 (s, 1H), 7.44-7.52 (m, 2H), 7.53-7.63 (m, 3H), 7.63-7.69 (m, 1H), 7.71-7.81 (m, 2H); MS: m/z 512.99 (MH$^+$).

Compound 715

N-(3-Bromo-benzo[b]thiophen-2-yl)-3-methanesulfonylamino-N-(3,3,3-trifluoro-propyl)-benzenesulfonamide. Compound 715 was prepared using the methodology in Example 84, steps A and B, substituting NBS for NCS. ¹H-NMR (300 MHz, CDCl₃): δ 2.46-2.64 (m, 9H), 2.96 (s, 3H), 3.90-3.99 (m, 2H), 6.70 (s, 1H), 7.45-7.53 (m, 2H), 7.64-7.70 (m, 1H), 7.71-7.81 (m, 2H); MS: m/z 558.85 (MH⁺).

Compound 716

N-(3-Chloro-benzo[b]thiophen-2-yl)-N-(2-cyclopropyl-ethyl)-4-methanesulfonylamino-benzenesulfonamide. ¹H-NMR (CDCl₃): δ 0.00-0.06 (m, 8H), 0.37-0.47 (m, 8H), 0.61-0.77 (m, 4H), 1.40-1.52 (m, 8H), 3.12 (s, 3H), 3.67-3.76 (m, 6H), 6.97 (s, 3H), 7.27-7.33 (m, 7H), 7.41-7.51 (m, 6H), 7.68-7.88 (m, 12H); MS: m/z 485.04 (MH⁺).

Compound 717

N-(3-Bromo-benzo[b]thiophen-2-yl)-N-(2-cyclopropyl-ethyl)-4-methanesulfonylamino-benzenesulfonamide. Compound 717 was prepared from compound 716 using the methodology in Example 84, steps A and B, substituting NBS for NCS. ¹H-NMR (CDCl₃): δ 0.01-0.07 (m, 7H), 0.37-0.47 (m, 7H), 0.69 (t, 4H), 1.41-1.54 (m, 7H), 3.12 (s, 3H), 3.68-3.78 (m, 2H), 6.84 (s, 1H), 7.29 (d, 2H), 7.41-7.49 (m, 2H), 7.69-7.87 (m, 4H); MS: m/z 528.89 (MH⁺).

Compound 718

N-(3-Chloro-benzo[b]thiophen-2-yl)-4-cyclopropane-sulfonylamino-N-(2-cyclopropyl-ethyl)-benzenesulfona-mide. MS: m/z 511.02 (MH⁺).

Compound 719

N-(3-Bromo-benzo[b]thiophen-2-yl)-4-cyclopropane-sulfonylamino-N-(2-cyclopropyl-ethyl)-benzenesulfona-mide. Compound 719 was prepared using the methodology in Example 84, steps A and B, substituting NBS for NCS. ¹H-NMR (CDCl₃): δ 0.01-0.06 (m, 6H), 0.38-0.46 (m, 2H), 0.69 (s, 1H), 1.00-1.10 (m, 2H), 1.21-1.31 (m, 2H), 1.42-1.52 (m, 2H), 2.51-2.63 (m, 1H), 3.68-3.80 (m, 2H), 6.75 (s, 1H), 7.29-7.37 (m, 2H), 7.40-7.50 (m, 2H), 7.68-7.86 (m, 4H); MS: m/z 555.02 (MH⁺).

Compound 743

N-(Benzo[b]thiophen-2-yl)-N-(4-fluoro-3-trifluorom-ethyl-benzyl)-4-methanesulfonylamino-2-methoxy-benze-nesulfonamide. Compound 743 was prepared using the methodology in Example 1, steps C and D, Example 82, step A, and Example 84, step A. MS: m/z 589.03 (MH⁺).

Compound 744

N-(3-Chloro-benzo[b]thiophen-2-yl)-N-(4-fluoro-3-trif-luoromethyl-benzyl)-4-methanesulfonylamino-2-methoxy-benzenesulfonamide. Compound 744 was prepared from compound 743 using the methodology in Example 84, step B. MS: m/z 622.90 (MH⁺).

Compound 766

5-Chloro-N-(3-chloro-benzo[b]thiophen-2-yl)-N-(4-fluoro-3-trifluoromethyl-benzyl)-4-methanesulfonylamino-2-methoxy-benzenesulfonamide. Compound 766 was isolated as a by-product during the synthesis of compound 744. ¹H-NMR (CDCl₃): δ 3.10 (s, 3H), 4.07 (s, 3H), 5.07 (s, 2H), 7.05 (s, 1H), 7.11 (t, 1H), 7.41 (dd, 2H), 7.47 (s, 1H), 7.53 (dd, 2H), 7.60-7.73 (m, 2H), 7.84 (s, 1H); MS: m/z 657.0 (MH⁺).

Example 85

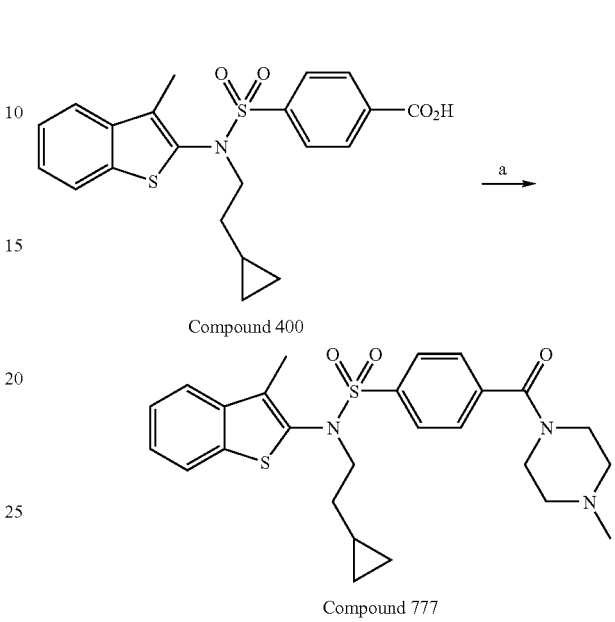

Compound 400

Compound 777 a) HATU, DIEA, DMF, 1-methyl-piperazine.

Compound 777

N-(2-Cyclopropyl-ethyl)-N-(3-methyl-benzo[b]thiophen-2-yl)-4-(4-methyl-piperazine-1-carbonyl)-benzenesulfona-mide. To a solution of compound 400 (0.100 g, 0.241 mmol) in DMF (1.5 mL) was added DIEA (0.0838 mL, 0.481 mmol), 1-methyl-piperazine (0.027 mL, 0.241 mmol) and HATU (0.110 g, 0.289 mmol) and the reaction mixture stirred at ambient temperature for 18 h. Ethyl acetate was added and the organics washed with water, brine, and evaporated under reduced pressure. The crude residue was purified by reverse phase pHPLC (C₁₈) to afford 0.108 g of compound 777 as a white solid. MS: m/z 498.18 (MH⁺).

Following the procedure described above for example 85 and substituting the appropriate reagents, starting materials and purification methods known to those skilled in the art, the following compounds of the present invention were prepared:

Compound 782

(S)-4-[(2-Cyclopropyl-ethyl)-(3-methyl-benzo[b] thiophen-2-yl)-sulfamoyl]-N-pyrrolidin-3-yl-benzamide. MS: m/z 484.16 (MH⁺).

Compound 783

(R)-4-[(2-Cyclopropyl-ethyl)-(3-methyl-benzo[b] thiophen-2-yl)-sulfamoyl]-N-pyrrolidin-3-yl-benzamide. MS: m/z 484.16 (MH⁺).

Example 86

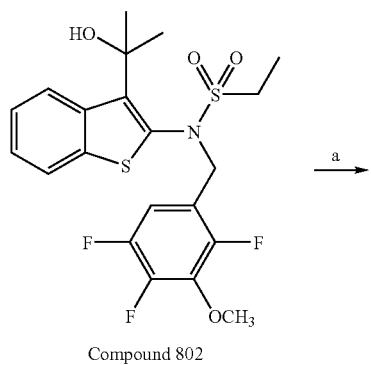

Compound 802 a →

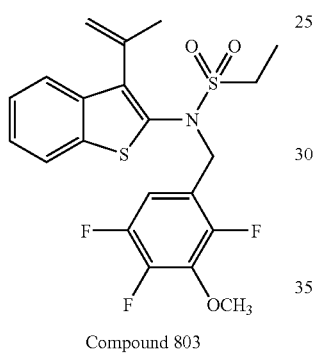

Compound 803 a) 0.1% TFA in CH₃CN/H₂O.

Compound 803

N-(3-Isopropenyl-benzo[b]thiophen-2-yl)-N-(2,4,5-trifluoro-3-methoxy-benzyl)-ethanesulfonamide. Compound 802 was purified by reverse phase pHPLC ($C_{18}$) eluting with 0.1% TFA in $CH_3CN/H_2O$. The pure fractions were lyophilized affording complete conversion of compound 802 to compound 803 as a white solid. $^1$H-NMR ($CDCl_3$): δ 1.48 (t, 3H), 2.04 (s, 3H), 3.30 (q, 2H), 3.95 (s, 3H), 4.84 (s, 2H), 4.94 (s, 1H), 5.40 (s, 1H), 6.94 (ddd, 1H), 7.31-7.42 (m, 2H), 7.61-7.74 (m, 2H); MS: m/z 456.01 (MH$^+$).

Following the procedure described above for example 86 and substituting the appropriate reagents, starting materials and purification methods known to those skilled in the art, the following compounds of the present invention were prepared:

Compound 768

N-(4-Chloro-2-fluoro-5-methoxy-benzyl)-N-(3-isopropenyl-benzo[b]thiophen-2-yl)-ethanesulfonamide. $^1$H-NMR ($CDCl_3$): δ 1.48 (t, 3H), 2.02 (s, 3H), 3.29 (q, 2H), 3.73 (s, 3H), 4.86 (s, 2H), 4.93 (s, 1H), 5.38 (d, 1H), 6.95 (d, 1H), 7.04 (d, 1H), 7.31-7.40 (m, 2H), 7.61-7.73 (m, 2H); MS: m/z 454.12 (MH$^+$).

Example 87

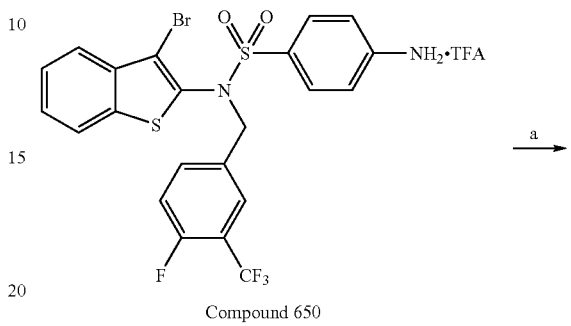

Compound 650 a →

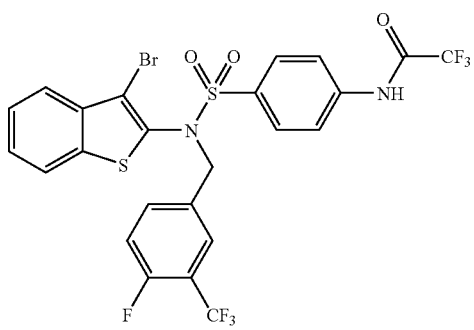

Compound 695 a) $CH_3SO_2Cl$, pyridine.

Compound 695

N-(3-Bromo-benzo[b]thiophen-2-yl)-N-(4-fluoro-3-trifluoromethyl-benzyl)-4-trifluoroacetamido-benzenesulfonamide. To a solution of compound 650 (0.074 g, 0.136 mmol) in pyridine (1 mL), under argon, was added methanesulfonyl chloride (0.053 mL, 0.680 mmol) and the reaction mixture was stirred at ambient temperature for 18 h. The solvent was evaporated under reduced pressure and the crude residue purified by reverse phase pHPLC ($C_{18}$) to afford 0.029 g of compound 695 as a white solid. $^1$H-NMR ($CDCl_3$): δ 4.85 (s, 2H), 7.04-7.14 (m, 1H), 7.38-7.57 (m, 4H), 7.63-7.74 (m, 2H), 7.76-7.82 (m, 2H), 7.85-7.93 (m, 2H), 8.12 (s, 1H); MS: m/z 654.9 (MH+).

Compound 694

N-(3-Chloro-benzo[b]thiophen-2-yl)-N-(2-cyclopropyl-ethyl)-4-trifluoroacetamido-benzenesulfonamide. MS: m/z 503.05 (MH+).

Example 88

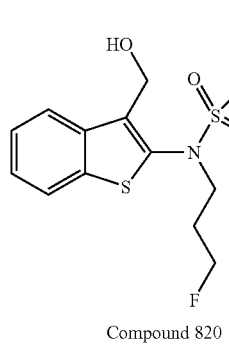

Compound 820

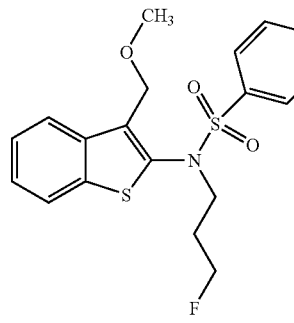

Compound 832 a) NaH, THF, MeI.

Compound 832

N-(3-Fluoro-propyl)-N-(3-methoxymethyl-benzo[b]thiophen-2-yl)-benzenesulfonamide. To a solution of compound 820 (38 mg, 0.10 mmol) in THF (3 mL), was added sodium hydride (16 mg, 0.40 mmol) followed by iodomethane (28 mg, 0.20) at room temperature and the reaction mixture was stirred for 2 h. The reaction mixture was quenched with water, extracted with EtOAc, the layers separated, and the organic phase dried over Na$_2$SO$_4$, filtered, and the solvent evaporated under reduced pressure. The crude residue was purified by flash column chromatography (SiO$_2$) eluting with 15% ethyl acetate in hexanes, to afford 36 mg of compound 832. MS: m/z 416.2 (MNa+).

Following the procedure described above for Example 88 and substituting the appropriate reagents, starting materials and purification methods known to those skilled in the art, the following compounds of the present invention were prepared:

Compound 822

N-(3-Fluoro-propyl)-N-[3-(1-methoxy-ethyl)-benzo[b]thiophen-2-yl]-benzenesulfonamide. MS: m/z 430.0 (MNa+).

Compound 839

N-(4-Fluoro-3-trifluoromethyl-benzyl)-N-[3-(1-methoxy-ethyl)-benzo[b]thiophen-2-yl]-ethanesulfonamide.
$^1$H-NMR (CDCl$_3$): δ 1.51 (t, 3H), 1.55 (s, 3H), 2.38-2.55 (br, 2H), 3.22-3.31 (br, 3H), 4.41-4.61 (br, 2H), 5.10-5.15 (br, 1H), 7.11-7.16 (m, 1H), 7.34-7.41 (m, 2H), 7.55-7.59 (m, 2H), 7.74-7.76 (m, 1H), 8.14-8.16 (m, 1H); MS: m/z 498.1 (MNa+).

Example 89

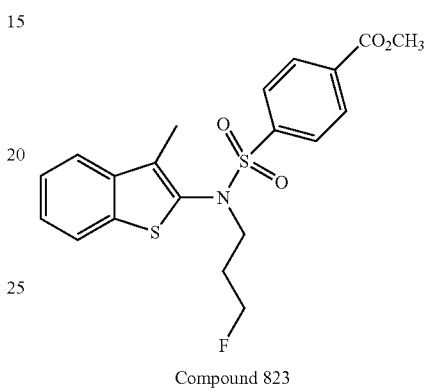

Compound 823

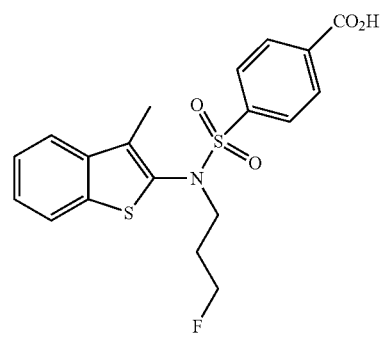

Compound 824 a) LiOH·H$_2$O, THF, MeOH, H$_2$O.

Compound 824

N-(3-Fluoropropyl)-N-(3-methyl-benzo[b]thiophen-2-yl)-4-carboxy-benzenesulfonamide. To a solution of compound 823 (100 mg, 0.237 mmol) in THF (9 mL), was added lithium hydroxide monohydrate (60 mg, 1.43 mmol) in water (3 mL), followed methanol (1 mL) at room temperature and the reaction mixture was stirred for 3 h. The reaction mixture was concentrated, triturated with 2N HCl, filtered, and the solids were washed three times with water, and the solid was dried under vacuum to afford 42 mg of compound 824. MS: m/z 408.0 (MH+).

Example 90

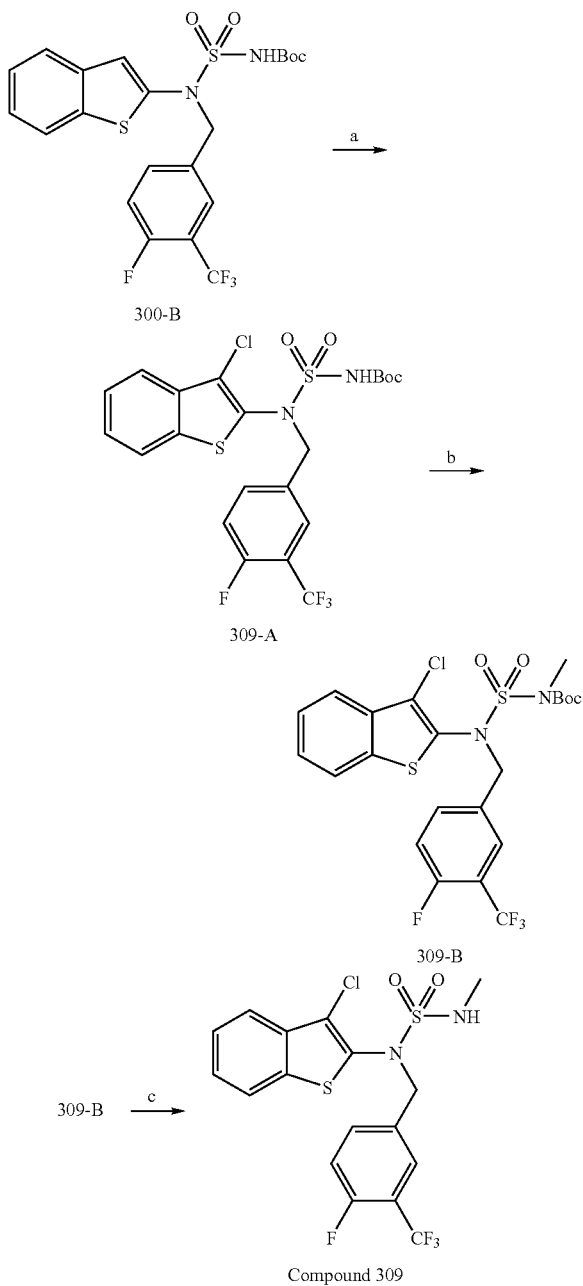

300-B

309-A

309-B

309-B →c→ Compound 309 a) DCE, NCS; b) DMF, NaH, MeI; c) 4N HCl.

N-(4-Fluoro-3-trifluorobenzyl)-N-(3-chloro-benzo[b]thiophen-2-yl)-[N'-tert-butyloxycarbonyl]-sulfonamide (309-A). To a solution of compound 300-B (595 mg; 1.17 mmol) in DCE (6 mL), at ambient temperature, was added NCS (173 mg; 1.29 mmol), and the reaction mixture was allowed to stir at ambient temperature for 2 h. The reaction mixture was concentrated under reduced pressure and the crude residue purified by flash column chromatography (SiO$_2$) eluting with a heptane/EtOAc gradient to afford 528 mg of compound 309-A as a yellow solid. $^1$H-NMR (DMSO-d$_6$): δ 1.51 (s, 9H), 5.07 (s, 2H), 7.42-7.47 (q, 1H), 7.51-7.55 (m, 2H), 7.64-7.68 (m, 1H), 7.75-7.79 (m, 2H), 8.01-8.03 (m, 1H), 11.83 (s, 1H).

N-(4-Fluoro-3-trifluorobenzyl)-N-(3-chloro-benzo[b]thiophen-2-yl)-N'-methyl-N-(tert-butyloxycarbonyl)-sulfonamide (309-B). To a solution of compound 309-A (334 mg; 0.619 mmol) in DMF (3 mL), at ambient temperature, was added 60% NaH (31 mg; 0.805 mmol), and the suspension was allowed to stir at ambient temperature for 30 min. Methyl iodide (46 μL; 0.743 mmol) in DMF (0.1 mL), was added drop-wise, and the reaction was allowed to stir for 72 h at ambient temperature. The reaction mixture was diluted with EtOAc, washed with H$_2$O, brine, dried over Na$_2$SO$_4$, filtered, and the solvent evaporated under reduced pressure. The crude residue was purified by flash column chromatography (SiO$_2$) eluting with a heptane/EtOAc gradient to afford 303 mg of compound 309-B as a yellow oil. $^1$H-NMR (DMSO-d$_6$): δ 1.54 (s, 9H), 3.02 (s, 3H), 5.10 (s, 2H), 7.44-7.49 (q, 1H), 7.52-7.55 (m, 2H), 7.65-7.69 (m, 1H), 7.76-7.79 (m, 2H), 8.02-8.04 (m, 1H); MS: m/z 453.0 ((M-Boc)+H+).

Compound 309

N-(3-Chloro-benzo[b]thiophen-2-yl)-N-(4-fluoro-3-trifluoromethyl-benzyl)-N'-methyl-sulfamide. To compound 309-B (303 mg, 0.548 mmol) was added solution of 1N HCl in dioxane (6 mL) and the reaction was stirred at ambient temperature for 18 h. The reaction mixture was evaporated under reduced pressure, the residue dried under vacuo, and purified by flash column chromatography (SiO$_2$) eluting with a heptane-EtOAc gradient to afford 211 mg of compound 309 as an oil. $^1$H-NMR (DMSO-d$_6$): δ 2.72 (s, 3H), 4.81 (s, 2H), 7.44-7.56 (m, 3H), 7.64-7.78 (m, 3H), 7.99-8.04 (m, 2H); MS: m/z 453.0 (MH+).

Following the procedure described above for Example 90 and substituting the appropriate reagents, starting materials and purification methods known to those skilled in the art, the following compounds of the present invention were prepared:

Compound 532

N-(Benzo[b]thiophen-2-yl)-N-(butyl)-N'-methyl-sulfamide. MS: m/z 299.1 (MH+).

Compound 533

N-(4-Fluoro-3-trifluoromethyl-benzyl)-N-(3-methyl-benzo[b]thiophen-2-yl)-N'-methyl-sulfamide. MS: m/z 433.0 (MH+).

Compound 553

N-(3-Chloro-benzo[b]thiophen-2-yl)-N-(butyl)-N'-methyl-sulfamide. MS: m/z 333.0 (MH+).

Compound 554

N-(3-Bromo-benzo[b]thiophen-2-yl)-N-(butyl)-N'-methyl-sulfamide. Compound 554 was synthesized from Example 90, step C, substituting NBS for NCS. MS: m/z 378.9 (MH+).

Compound 705

N-(3-Bromo-benzo[b]thiophen-2-yl)-N-(4-fluoro-3-trifluoromethyl-benzyl)-N'-methyl-sulfamide. Compound 705 was synthesized from Example 90, step C, substituting NBS for NCS. $^1$H-NMR (CD$_3$OD): δ 2.83 (s, 3H), 7.16-7.20 (m, 1H), 7.41-7.79 (m, 6H); MS: m/z 499.0 (MH$^+$).

Example 91

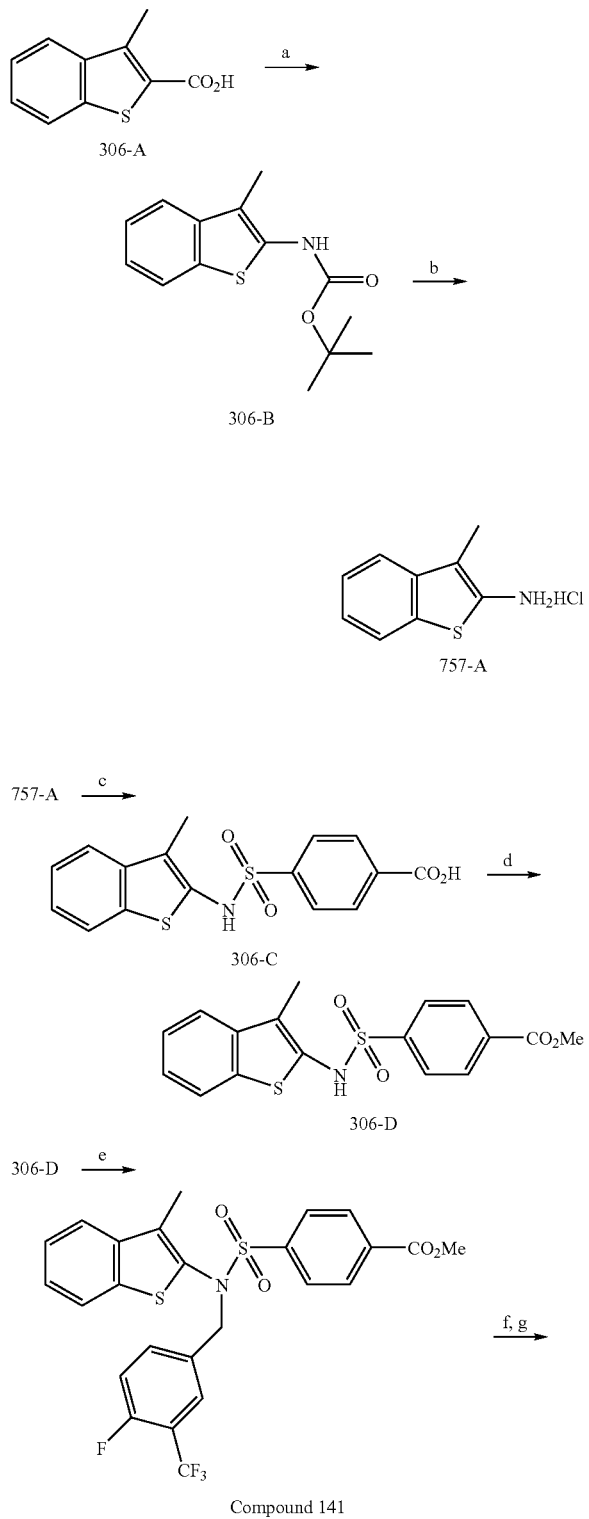

Compound 306, Na a) DPPA, t-BuOH; b) 4N HCl, dioxane; c) THF, pyridine, 4-chlorosulfonylbenzoic acid; d) MeOH, H$_2$SO$_4$; e) DMF, K$_2$CO$_3$, 4-fluoro-3-trifluoromethyl benzyl bromide; f) 1. MeOH, NaOH; 2. HCl; g) IPA, NaOMe, MeOH.

tert-Butyl-3-methylbenzo[b]thiophen-2-ylcarbamate (306-B). A 5-L 4-neck flask equipped with an overhead mechanical stirrer, N$_2$ inlet/outlet adapter, reflux condenser, heating mantle and thermocouple was charged with t-butyl alcohol (2.11 L), compound 306-A (225.0 g, 1.17 mol), and diisopropylethylamine (225 mL, 1.29 mol). Diphenylphosphorylazide (304 mL, 1.4 mol) was premixed with toluene (300 mL) and then added drop-wise over 10 min. The reaction mixture was refluxed with stirring for 21 h, cooled to 22° C. and then evaporated in vacuo. The residue was dissolved in CH$_2$Cl$_2$ (1 L), washed with 1N NaOH (500 mL), brine (500 mL), the organic layer separated, dried over MgSO$_4$, filtered, and evaporated in vacuo to afford a dark orange oil (557 g). The crude residue was purified by the flash column chromatography (SiO$_2$) eluting with heptane-EtOAc to afford 265 g of compound 306-B as a pale yellow solid.

$^1$H-NMR (CDCl$_3$): δ 7.71 (d, 1H), 7.54 (d, 1H), 7.36-7.31 (m, 1H), 7.30-7.20 (m, 1H), 6.75 (br s, 1H), 2.23 (s, 3H), 1.55 (s, 9H).

3-Methylbenzo[b]thiophen-2-amine hydrochloride (757-A). A 5-L 3-neck flask equipped with an overhead mechanical stirrer, N$_2$ inlet/outlet adapter, and thermocouple was charged with 4M HCl in dioxane (3.1 L), compound 306-B (265 g, 1.0 mol) and stirred for 18 h at 22° C. The white precipitate was collected by filtration, washed with diethyl ether (3×500 mL), and dried under house vacuum at 40° C. for 48 h to afford 174 g of compound 757-A as a white solid. $^1$H-NMR (DMSO-d$_6$): δ 8.7 (br s, 3H), 7.71 (d, 1H), 7.44 (d, 1H), 7.29 (t, 1H), 7.14 (t, 1H), 2.184 (s, 3H).

N-(3-Methylbenzo[b]thiophen-2-yl)-4-carboxy-benzenesulfonamide (306-C). A 12-L 4-neck flask equipped with an overhead mechanical stirrer, N$_2$ inlet/outlet adapter, and thermocouple was charged with THF (3.26 L) and compound 757-A (326 g, 1.6 mol) followed by pyridine (265 mL, 3.3 mol). The reaction mixture was cooled to 5° C. using a ice bath, to which was added a solution of 4-(chlorosulfonyl) benzoic acid (396 g, 1.8 mol) dissolved in THF (2.44 L), drop-wise. The reaction was allowed to stir at ambient temperature for 72 h, diluted with EtOAc (4 L), washed with 1N HCl (1 L), brine (1 L), the organic layer dried over Na$_2$SO$_4$, filtered and evaporated under reduced pressure. The crude residue was purified by triturating with EtOAc/heptane (1:1/1 L). The slurry was filtered, washed with heptane (2×250 mL) and dried in a vacuum oven at 40° C. for 18 h to afford 470 g of compound 306-C as a white solid. $^1$H-NMR (DMSO-d$_6$): δ 13.51 (br s, 1H), 10.65 (br s, 1H), 8.12 (d, 2H), 7.86 (d, 2H), 7.83-7.79 (m, 1H), 7.66-7.63 (m, 1H), 7.37-7.33 (m, 1H), 2.03 (s, 3H).

N-(3-Methylbenzo[b]thiophen-2-yl)-4-carbomethoxy-benzenesulfonamide (306-D). A 12-L 4-neck flask equipped with an overhead mechanical stirrer, N$_2$ inlet/outlet adapter, and thermocouple was charged with MeOH (7.5 L) and compound 306-C (470 g, 1.35 mol). Sulfuric acid (24 mL, 0.45 mol) was added to the reaction mixture and the reaction was refluxed for 18 h. The reaction was cooled, diluted with EtOAc (4 L), washed with 1N NaOH (2 L), and H$_2$O (6 L). The aqueous layer with extracted with EtOAc (4×4 L), the combined organic extracts washed with brine (1 L), dried over Na$_2$SO$_4$, filtered and evaporated under reduced pressure to afford 306-D (crude material) as a red, thick oil. $^1$H-NMR (DMSO-d$_6$): δ 7.89 (d, 2H), 7.81 (d, 2H), 7.41 (d, 1H), 7.16 (d, 1H), 7.09-7.04 (m, 1H), 6.91-6.85 (m, 1H), 3.82 (s, 3H), 1.99 (s, 3H).

A 5-L 3-neck flask equipped with an overhead mechanical stirrer, N$_2$ inlet/outlet adapter, and thermocouple was charged with the crude residue in H$_2$O (4 L). The solution was acidified with 1N HCl (200 mL) until the pH=1 and the reaction mixture allowed to stir for 30 min at ambient temperature. The solid was filtered, washed with H$_2$O (2×250 mL) and dried in a vacuum oven at 50° C. for 72 h to afford 302 g of compound 306-D as a white solid. $^1$H-NMR (DMSO-d$_6$): δ 10.67 (br s, 1H), 8.13 (d, 2H), 8.00 (d, 2H), 7.90-7.77 (m, 1H), 7.64-7.61 (m, 1H), 7.36-7.32 (m, 2H), 3.89 (s, 3H), 2.02 (s, 3H).

Compound 141

N-[4-Fluoro-3-(trifluoromethyl)-benzyl]-N-(3-methyl-benzo[b]thiophen-2-yl)-4-carbomethoxy-benzenesulfonamide. A 12-L 4-neck flask equipped with an overhead mechanical stirrer, N$_2$ inlet/outlet adapter, and thermocouple was charged with DMF (4.9 L), compound 306-D (245 g, 0.68 mol) and K$_2$CO$_3$ (112 g, 0.81 mol). 4-Fluoro-3-(trifluoromethyl)benzyl bromide (210 mL, 0.81 mol) was added drop-wise over 15 min and the reaction was stirred for 18 h at room temperature. The reaction mixture was poured into cold H$_2$O (10 L), stirred for 30 min, to which was added EtOAc (4 L). The layers were separated and the aqueous phase was extracted with EtOAc (2×μL). The combined EtOAc layers were washed with brine (1 L), dried over Na$_2$SO$_4$, filtered and evaporated under reduced pressure. The crude product was purified using flash column chromatography (SiO$_2$) eluting with heptane-EtOAc to afford 269 g of compound 141 as a white solid. $^1$H-NMR (DMSO-d$_6$) δ 8.21 (d, 2H), 8.03 (d, 2H), 7.86-7.83 (m, 1H), 7.71-7.63 (m, 3H), 7.45-7.37 (m, 3H), 4.89 (br s, 2H), 3.93 (s, 3H), 1.94 (s, 3H).

N-[4-Fluoro-3-(trifluoromethyl)-benzyl]-N-(3-methyl-benzo[b]thiophen-2-yl)-4-carboxy-benzenesulfonamide (not shown). A 3-L 4-neck flask equipped with an overhead mechanical stirrer, N$_2$ inlet/outlet adapter, condenser and thermocouple was charged with MeOH (1.9 L) and compound 141 (190 g, 0.35 mol) followed by 3M NaOH (412 mL, 1.2 mol) and the reaction mixture was refluxed for 2 h. The reaction mixture was cooled to room temperature, diluted with EtOAc (2 L) and 1N HCl (2 L), the layers separated and the aqueous phase extracted with EtOAc (2 L). The organic extracts were combined, washed with brine (1.5 L), dried over Na$_2$SO$_4$, filtered and evaporated under reduced pressure. The yellow solid was placed in vacuum oven for 18 h at 50° C. to afford 158 g of the titled compound (not shown) as a yellow solid. $^1$H-NMR (DMSO-d$_6$): δ 13.63 (s, 1H), 8.19 (d, 2H), 8.01 (d, 2H), 7.86-7.83 (m, 1H), 7.71-7.63 (m, 3H), 7.49-7.37 (M, 3H), 4.89 (br s, 1H), 1.95 (s, 3H).

Compound 306, Sodium Salt

Sodium N-[4-Fluoro-3-(trifluoromethyl)-benzyl]-N-(3-methylbenzo[b]thiophen-2-yl)-4-carboxy-benzenesulfonamide To a 5-L 4-neck flask equipped with an overhead mechanical stirrer, N$_2$ inlet/outlet adapter, and thermocouple, charged with MeOH (3.1 L) and the benzoic acid (310 g, 0.59 mol), was added 0.5M NaOMe in MeOH (1.25 L, 0.62 mol), the reaction was stirred for 1 h at ambient temperature and evaporated under reduced pressure to afford the crude sodium salt as a yellow solid. A 5-L 4-neck flask equipped with overhead mechanical stirrer, N$_2$ inlet/outlet adapter, condenser, and thermocouple, charged with crude sodium salt and IPA (3.3 L) was refluxed for 1 h and cooled to room temperature overnight. The resulting solid was filtered, washed with cold IPA (250 mL) and dried in a vacuum oven at 60° C. for 18 h, followed by 100° C. for 72 h to afford 250 g of compound 306 as a white solid. $^1$H-NMR (DMSO-d$_6$): δ 8.04 (d, 2H), 7.85-7.82 (m, 1H), 7.76 (d, 2H), 7.69-7.63 (m, 3H), 7.48-7.41 (m, 1H), 7.40-7.35 (m, 2H), 4.83 (br s, 1H), 1.94 (s, 3H). Anal. Calcd for C$_{24}$H$_{16}$F$_4$NNaO$_4$S$_2$: C, 52.84; H, 2.96; N, 2.57; F, 13.93; S, 11.76; Na, 4.21. Found: C, 51.62; H, 2.70; N, 2.38; F, 13.73; S, 11.50; Na, 4.44; KF, 0.61.

Example 92

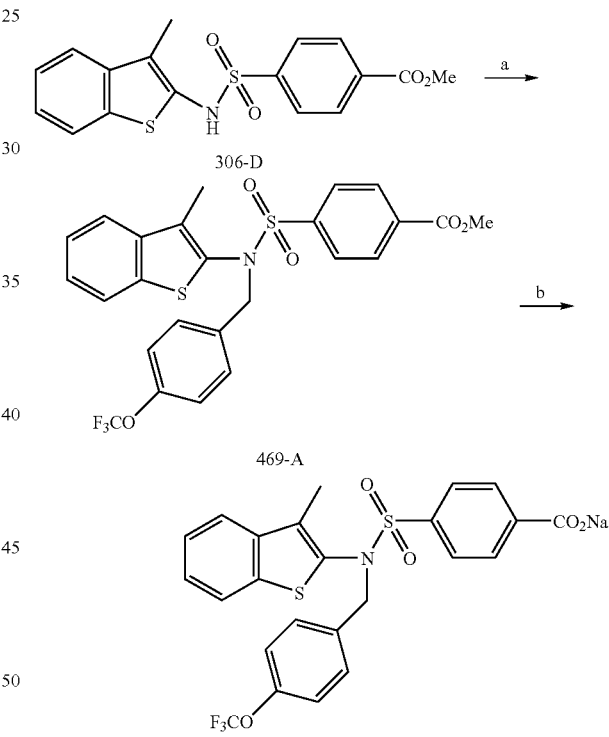

Compound 496, Na
a) DMF, K$_2$CO$_3$, 4-trifluoromethoxy benzyl bromide; b) 1. MeOH, NaOH; 2) IPA.

N-(3-Methyl-benzo[b]thiophen-2-yl)-N-(4-trifluoromethoxy-benzyl)-4-carbomethoxy-benezenesulfonamide (496-A). A 12-L 4-neck flask equipped with an overhead mechanical stirrer, N$_2$ inlet/outlet adapter, and thermocouple was charged with DMF (6.7 L), compound 306-D (334 g, 0.92 mol) and K$_2$CO$_3$ (153 g, 1.11 mol). 1-(Bromomethyl)-4-(trifluoromethoxy)benzene (178 mL, 1.11 mol) was added drop-wise over 15 min and the reaction mixture stirred for 5 h at room temperature. The reaction mixture was poured into cold H$_2$O (13 L) and stirred for 18 h. The resultant solid was filtered, washed with heptane (3×1 L), dried under vacuo for 18 h at 50° C., triturated with IPA (500 mL), filtered and dried under vacuo at 50° C. for 18 h to afford 318 g of compound 496-A as a white solid. ¹H-NMR (DMSO-d₆): δ 8.20 (d, 2H), 8.02 (d, 2H), 7.84-7.81 (m, 1H), 7.69-7.65 (m, 1H), 7.41-7.36 (m, 4H), 7.30 (d, 2H), 4.81 (br s, 2H), 3.93 (s, 3H), 1.90 (s, 3H). Anal. Calcd for $C_{25}H_{20}F_3NO_5S_2$: C, 56.07; H, 3.76; N, 2.62; F, 10.64; S, 11.97. Found: C, 55.85; H, 3.69; N, 2.72; F, 10.57; S, 11.65.

Compound 496, Sodium Salt

Sodium N-(3-Methyl-benzo[b]thiophen-2-yl)-N-(4-trifluoromethoxy-benzyl)-4-carboxy-benezenesulfonamide. To a 3-L 4-neck flask equipped with an overhead mechanical stirrer, N₂ inlet/outlet adapter, and thermocouple, charged with MeOH (1.0 L) and compound 496-A (100 g, 0.19 mol) was added 3M NaOH (68 mL, 0.21 mol) and the reaction was stirred for 1 h at 65° C. The reaction mixture was cooled and evaporated under reduced pressure to afford the sodium salt as a crude yellow solid. To the crude sodium salt was added IPA (250 mL) and the suspension heated (via a heat gun) until the mixture is homogeneous. The solution was allowed to cool slowly to ambient temperature, seeded with a previous batch of sodium compound 496, the resultant solid filtered, washed with cold IPA (150 mL) and dried in a vacuum oven at 60° C. for 18 h to afford 75 g of the sodium salt of compound 496 as a white solid. ¹H-NMR (DMSO-d₆): δ 8.03 (d, 2H), 7.84-7.81 (m, 1H), 7.74 (d, 2H), 7.67-7.64 (m, 1H), 7.40-7.33 (m, 4H), 7.30-7.27 (d, 2H), 4.76 (br s, 2H), 1.91 (s, 3H). Anal. Calcd for $C_{24}H_{19}F_3NNaO_6S_2$: C, 51.34; H, 3.41; N, 2.49; F, 10.15; S, 11.42; Na, 4.09; KF, 3.21. Found: C, 50.98; H, 3.10; N, 2.50; F, 9.25; S, 11.36; Na, 4.32; KF, 3.15.

Preparation of Intermediates

Example 93

Preparation of Sulfonyl Chlorides

Example 93A

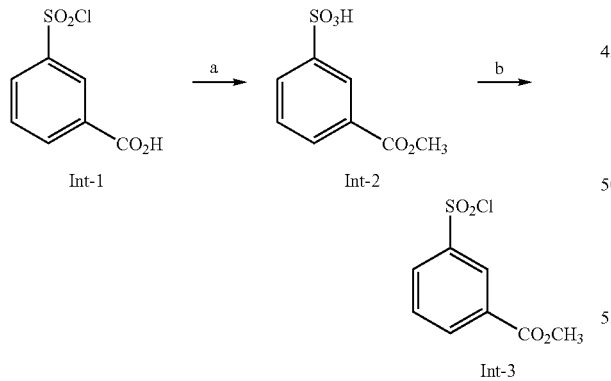

a) 1. DCM, (COCl)₂, cat. DMF; 2) MeOH; b) C₆H₅N, SOCl₂.

3-Sulfo-benzoic acid methyl ester (Int-2). To a suspension of compound Int-1 (5.09 g; 23.0 mmol) in DCM (50 mL), at ambient temperature, was added oxalyl chloride (2.41 mL; 27.6 mmol) in one-portion, followed by 1 drop of DMF and the reaction was stirred for 18 h at ambient temperature. MeOH was added to the reaction mixture and the reaction was allowed to stir for 72 h. The reaction solvent was evaporated under reduced pressure and the residue dried under vacuo to afford 4.97 grams of compound Int-2 as an oil.

3-Chlorosulfonyl-benzoic acid methyl ester (Int-3). To compound Int-2 (4.97 g; 23.0 mmol) was added pyridine (20 mL) and the solution was stirred under N₂ for 60 min. Thionyl chloride (4.2 mL; 57.5 mmol) was added, drop-wise at ambient temperature, and the reaction was stirred at 55° C. for 2 h. The reaction was cooled, the solvent concentrated under reduced pressure and the liquid diluted with EtOAc. The organic phase was washed with 1 N HCl (3×), H₂O, brine, dried over Na₂SO₄, filtered and the solvent evaporated under reduced pressure to afford 4.89 g of compound Int-3 as a white solid. ¹H-NMR (DMSO-d₆): 3.87 (s, 3H), 7.44-7.58 (m, 1H), 7.81-7.98 (m, 2H), 8.17-8.27 (m, 1H), 14.50 (s, 1H).

Example 93B

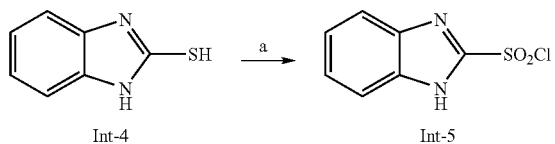

a) H₂O, AcOH, Cl₂.

1H-Benzimidazole-2-sulfonyl chloride (Int-5). A suspension of 1H-benzimidazole-2-thiol, compound Int-4 (1.58 g; 10.5 mmol) in 20% v/v acetic acid water (30/90 mL) was cooled to 0° C. Chlorine gas was bubbled through the mixture until saturation, the reaction mixture was stirred for 1 h at 0° C., filtered, washed with ice-cold water and air dried to afford 2.2 g of compound Int-5 as an off-white solid.

Example 93C

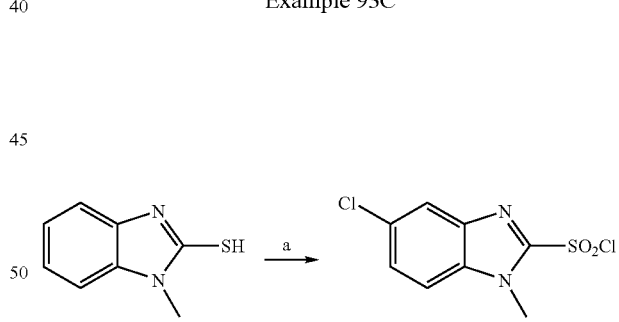

a) CCl₄, H₂O, Cl₂.

5-Chloro-1-methyl-1H-benzimidazole-2-sulfonyl chloride (Int-7). A suspension of 1-methyl-1H-benzimidazole-2-thiol, compound Int-6 (0.538 g; 3.27 mmol) in 20% v/v CCl₄/water (30/90 mL) was cooled to 0° C. Chlorine gas was bubbled through the mixture until saturation, the reaction

Example 94

General 4-cyanopyridyl Intermediates

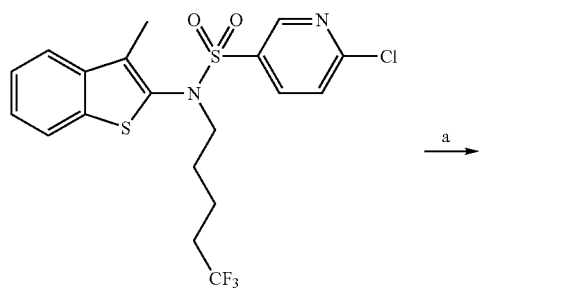

Int-8

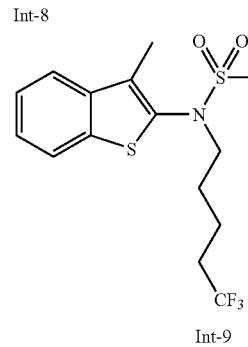

Int-9 a) DMF, KCN, 18-C-6.

Compound Int-8, was prepared by the method used to synthesize Cpd 757 in Example 30, step A, and Example 3, step A.

N-(3-Methyl-benzo[b]thiophen-2-yl)-N-(5,5,5-trifluoropentyl)-4-cyano-pyridin-3-ylsulfonamide (Int-9). A solution of compound Int-8 (0.250 g, 0.54 mmol), dimethylformamide (2 mL), potassium cyanide (0.07 g, 1.08 mmol), and 18-crown-6 ether (0.006 g, 0.022 mmol) was refluxed for 4 h. The reaction mixture was cooled, poured over ice-water and extracted with EtOAc. The solvent was evaporated in vacuo, and the crude residue concentrated to afford 0.25 g of compound Int-9 as a dark gum. MS: m/z 454.0 (MH+).

Example 95

General Synthesis of Benzyl Bromide Intermediates

Example 95A

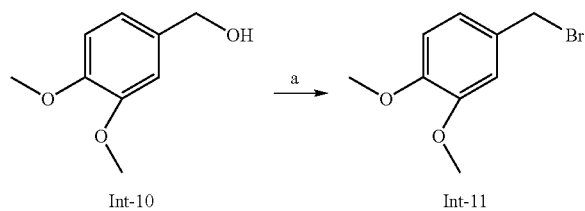

Int-10 Int-11 a) DCM, PBr₃.

4-Bromomethyl-1,2-dimethoxy-benzene (Int-11). To a stirred solution of Int-10 (1.0 g, 5.95 mmol) in dichloromethane (10 mL), cooled to 0° C., was added phosphorous tribromide (1.93 g, 7.13 mmol), drop-wise, and the reaction was stirred for 2 h. The reaction was quenched with aqueous NH₄Cl, the organic phase separated, dried over Na₂SO₄, filtered, and the solvent evaporated in vacuo to afford 1.0 g of compound Int-11. ¹H-NMR (DMSO-d₆) δ 3.74 (s, 3H), 3.72 (s, 3H), 4.41 (d, 2H), 6.83 (d, 1H), 6.85-6.94 (m, 2H).

Example 95B

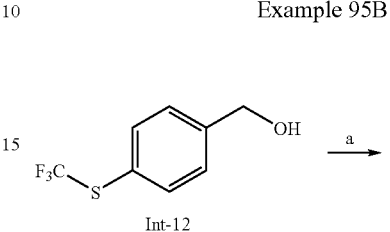

Int-12

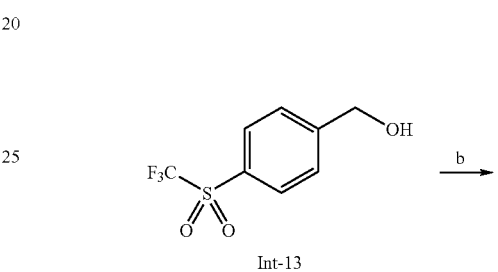

Int-13

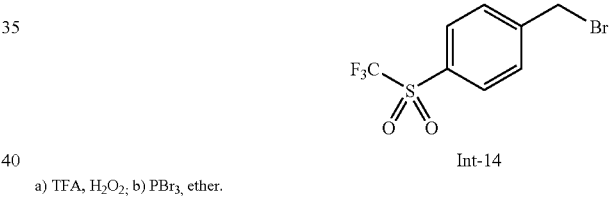

Int-14 a) TFA, H₂O₂; b) PBr₃, ether.

(4-Trifluoromethanesulfonyl-phenyl)-methanol (Int-13). To a solution of compound Int-12 (2.08 g, 10.0 mmol) in trifluoroacetic acid (25 mL) was added a 30% H₂O₂ (5 mL) solution. After stirring at ambient temperature for 5 days, the reaction mixture was diluted with ice-water (125 mL). A scoop of 10% Pd/C was added to consume the excess H₂O₂ present and allowed to stir overnight. The mixture was extracted with diethyl ether (3×50 mL), the combined organics washed times with saturated NaHCO₃ solution (4×50 mL) then treated with solid NaHCO₃ until neutralized. The layers were separated and the organic phase was washed with a 10% Na₂SO₃ solution (50 mL), brine (50 mL), dried with Na₂SO₄, filtered, and evaporated in vacuo to afford 2.19 g of compound Int-13 as a white solid. ¹H-NMR (DMSO-d₆) δ 4.70 (s, 2H), 5.62 (br s, 1H), 7.80 (d, 2H), 8.10 (d, 2H).

1-Bromomethyl-4-trifluoromethanesulfonyl-benzene (Int-14). To a solution of compound Int-13 (2.18 g, 9.05 mmol) in diethyl ether (25 mL) was added PBr₃ (1.3 mL, 13.7 mmol). The reaction was stirred under a nitrogen atmosphere for 3 days, diluted with diethyl ether (100 mL) and washed with H₂O (2×50 mL), saturated NaHCO₃ solution (50 mL), brine (50 mL), dried over Na₂SO₄, filtered and evaporated in vacuo to afford 2.65 g of compound Int-14 as an off-white solid. ¹H-NMR (CDCl₃): δ 4.53 (s, 2H), 7.69 (d, 2H), 8.03 (d, 2H).

Example 96

Preparation of 1-(1H-imidazol-2-yl)-N,N-dimethylmethanamine Intermediate

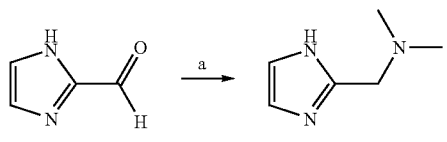

Int-15  Int-16 a) MeOH, H$_2$O, HN(CH$_3$)$_2$, NaBH$_4$.

1-(1H-imidazol-2-yl)-N,N-dimethylmethanamine (Int-16). A solution of compound Int-15 (5.0 g, 52.03 mmole), MeOH (10 mL), H$_2$O (15 mL), and dimethylamine (25 mL, 50 mmole) was stirred at 22° C. for 2 h. The reaction mixture was cooled to 0° C., stirred for 20 min, to which was added NaBH$_4$ (5.0 g, 139.9 mmole) in one-portion and the reaction was heated at 56° C. for 3 h. The reaction mixture was cooled, quenched with brine (100 mL), extracted with CH$_2$Cl$_2$ (100 mL), dried over MgSO$_4$, filtered, and the solvent evaporated in vacuo to afford 4.0 g of compound Int-16 as a yellow waxy solid. $^1$H-NMR (CDCl$_3$): δ 2.20 (s, 6H), 3.50 (s, 2H), 6.90 (s, 2H), 10.10 (br s, 1H); MS: m/z 125.2 (MH$^+$).

Example 97

General Sodium Salt Preparation

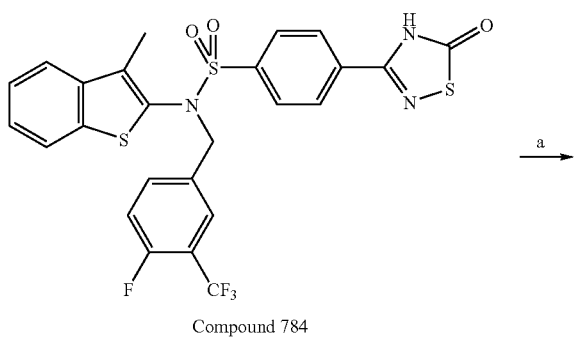

Compound 784 a

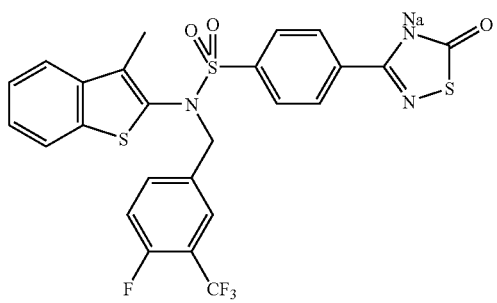

Compound 784, Na a) MeOH, 0.117M NaOMe.

Compound 784, Sodium Salt

Sodium, N-(3-Methyl-benzo[b]thiophen-2-yl)-N-(4-fluoro-3-trifluoromethyl-benzyl-4-(5-oxo-4,5-dihydro-[1,2,4]thiadiazol-3-yl)-benzenesulfonamide. To a solution of compound 784 (335.7 mg; 0.579 mmol) suspended in MeOH (10 mL) was added a solution of 0.117 M NaOMe (5.2 mL) and the solution was stirred for 30 min. The solvent was evaporated under reduced pressure and dried under vacuo at 50° C. to afford 353.8 mg of the sodium salt of compound 784 as a white solid. $^1$H-NMR (DMSO-d$_6$): δ 3.34 (s, 3H), 4.88 (br s, 2H), 7.35-7.43 (m, 2H), 7.45-7.47 (t, 1H), 7.54-7.68 (m, 4H), 7.83-7.85 (m, 3H), 8.20-8.22 (d, 2H); MS: m/z 580.0 (MH$^+$).

Using the methods described in the schemes and specific examples, and adaptations thereof, compounds of Formula (I) shown in Table 1 were prepared.

TABLE 1

| Cpd No. | G | Y | R$^1$ | R$^2$ | R$^3$ | R$^4$ | R$^5$ | R$^6$ | A | B |
|---|---|---|---|---|---|---|---|---|---|---|
| 1 | S | H | phenyl | 3,4-difluorophenylmethyl | H | H | H | H | CR$^5$ | CR$^6$ |
| 2 | S | methyl | 1-methyl-1H-imidazol-4-yl | 3,4-difluorophenylmethyl | H | H | H | H | CR$^5$ | CR$^6$ |
| 3 | S | H | phenyl | 3-fluorophenylmethyl | H | H | H | H | CR$^5$ | CR$^6$ |
| 4 | S | Cl | phenyl | 4-fluorophenylmethyl | H | H | H | H | CR$^5$ | CR$^6$ |
| 5 | S | Cl | phenyl | quinolin-8-ylmethyl | H | H | H | H | CR$^5$ | CR$^6$ |
| 6 | S | Cl | phenyl | 4-trifluoromethoxyphenylmethyl | H | H | H | H | CR$^5$ | CR$^6$ |
| 7 | S | Cl | phenyl | 4-fluoro-3-trifluoromethylphenylmethyl | H | H | H | H | CR$^5$ | CR$^6$ |
| 8 | S | Cl | phenyl | 4-trifluoromethylphenylmethyl | H | H | H | H | CR$^5$ | CR$^6$ |
| 9 | S | H | pyridin-2-yl | 3,4-difluorophenylmethyl | H | H | H | H | CR$^5$ | CR$^6$ |
| 10 | S | methyl | 1-methyl-1H-imidazol-4-yl | quinolin-8-ylmethyl | H | H | H | H | CR$^5$ | CR$^6$ |

TABLE 1-continued

| Cpd No. | G | Y | R¹ | R² | R³ | R⁴ | R⁵ | R⁶ | A | B |
|---|---|---|---|---|---|---|---|---|---|---|
| 11 | S | methyl | 1-methyl-1H-imidazol-4-yl | 4-trifluoromethoxyphenylmethyl | H | H | H | H | CR⁵ | CR⁶ |
| 12 | S | methyl | pyridin-3-yl | 3,4-difluorophenylmethyl | H | H | H | H | CR⁵ | CR⁶ |
| 13 | S | methyl | pyridin-3-yl | 4-trifluoromethoxyphenylmethyl | H | H | H | H | CR⁵ | CR⁶ |
| 14 | S | methyl | pyridin-3-yl | quinolin-8-ylmethyl | H | H | H | H | CR⁵ | CR⁶ |
| 15 | S | methyl | thien-3-yl | 3,4-difluorophenylmethyl | H | H | H | H | CR⁵ | CR⁶ |
| 16 | S | methyl | thien-3-yl | 4-trifluoromethoxyphenylmethyl | H | H | H | H | CR⁵ | CR⁶ |
| 17 | S | methyl | thien-3-yl | quinolin-8-ylmethyl | H | H | H | H | CR⁵ | CR⁶ |
| 18 | S | methyl | benzo[b]thiophen-2-yl | 3,4-difluorophenylmethyl | H | H | H | H | CR⁵ | CR⁶ |
| 19 | S | methyl | benzo[b]thiophen-2-yl | quinolin-8-ylmethyl | H | H | H | H | CR⁵ | CR⁶ |
| 20 | S | methyl | quinolin-8-yl | 3,4-difluorophenylmethyl | H | H | H | H | CR⁵ | CR⁶ |
| 21 | S | methyl | quinolin-8-yl | 4-trifluoromethoxyphenylmethyl | H | H | H | H | CR⁵ | CR⁶ |
| 22 | S | methyl | quinolin-8-yl | quinolin-8-ylmethyl | H | H | H | H | CR⁵ | CR⁶ |
| 23 | S | Cl | phenyl | 3-fluorophenylmethyl | H | H | H | H | CR⁵ | CR⁶ |
| 24 | S | Cl | phenyl | 3,4-difluorophenylmethyl | H | H | H | H | CR⁵ | CR⁶ |
| 25 | S | methyl | 3-methoxyphenyl | 3,4-difluorophenylmethyl | H | H | H | H | CR⁵ | CR⁶ |
| 26 | S | methyl | 4-methoxyphenyl | 3,4-difluorophenylmethyl | H | H | H | H | CR⁵ | CR⁶ |
| 27 | S | methyl | isoquinolin-5-yl | 3,4-difluorophenylmethyl | H | H | H | H | CR⁵ | CR⁶ |
| 28 | S | methyl | isoquinolin-5-yl | 4-trifluoromethoxyphenylmethyl | H | H | H | H | CR⁵ | CR⁶ |
| 29 | S | methyl | isoquinolin-5-yl | quinolin-8-ylmethyl | H | H | H | H | CR⁵ | CR⁶ |
| 30 | S | methyl | quinolin-6-yl | 3,4-difluorophenylmethyl | H | H | H | H | CR⁵ | CR⁶ |
| 31 | S | methyl | quinolin-6-yl | 4-trifluoromethoxyphenylmethyl | H | H | H | H | CR⁵ | CR⁶ |
| 32 | S | methyl | quinolin-6-yl | quinolin-8-ylmethyl | H | H | H | H | CR⁵ | CR⁶ |
| 33 | S | H | pyridin-3-yl | 3,4-difluorophenylmethyl | H | H | H | H | CR⁵ | CR⁶ |
| 34 | S | H | methyl | 3,4-difluorophenylmethyl | H | H | H | H | CR⁵ | CR⁶ |
| 35 | S | H | ethyl | 3,4-difluorophenylmethyl | H | H | H | H | CR⁵ | CR⁶ |
| 36 | S | H | n-propyl | 3,4-difluorophenylmethyl | H | H | H | H | CR⁵ | CR⁶ |
| 37 | S | H | n-butyl | 3,4-difluorophenylmethyl | H | H | H | H | CR⁵ | CR⁶ |
| 38 | S | methyl | thien-2-yl | 4-trifluoromethyl-3-fluorophenylmethyl | H | H | H | H | CR⁵ | CR⁶ |
| 39 | S | methyl | pyridin-3-yl | 4-fluoro-3-trifluoromethylphenylmethyl | H | H | H | H | CR⁵ | CR⁶ |
| 40 | S | methyl | ethyl | 4-fluoro-3-trifluoromethylphenylmethyl | H | H | H | H | CR⁵ | CR⁶ |
| 41 | S | methyl | ethyl | 3,4-difluorophenylmethyl | H | H | H | H | CR⁵ | CR⁶ |
| 42 | S | methyl | ethyl | 4-trifluoromethoxyphenylmethyl | H | H | H | H | CR⁵ | CR⁶ |
| 43 | S | H | ethyl | 4-fluoro-3-trifluoromethylphenylmethyl | H | H | H | H | CR⁵ | CR⁶ |
| 44 | S | methyl | dimethylamino | 3,4-difluorophenylmethyl | H | H | H | H | CR⁵ | CR⁶ |
| 45 | S | H | methyl | 4-fluoro-3-trifluoromethylphenylmethyl | H | H | H | H | CR⁵ | CR⁶ |
| 46 | S | H | phenyl | 4-chlorophenylmethyl | H | H | H | H | CR⁵ | CR⁶ |
| 47 | S | H | phenyl | 2-methoxyphenylmethyl | H | H | H | H | CR⁵ | CR⁶ |
| 48 | S | H | phenyl | 3-methoxyphenylmethyl | H | H | H | H | CR⁵ | CR⁶ |
| 49 | S | H | phenyl | 4-methoxyphenylmethyl | H | H | H | H | CR⁵ | CR⁶ |
| 50 | S | H | phenyl | 2-fluorophenylmethyl | H | H | H | H | CR⁵ | CR⁶ |
| 51 | S | H | phenyl | 3-nitrophenylmethyl | H | H | H | H | CR⁵ | CR⁶ |
| 52 | S | H | phenyl | pyridin-2-ylmethyl | H | H | H | H | CR⁵ | CR⁶ |
| 53 | S | H | phenyl | pyridin-3-ylmethyl | H | H | H | H | CR⁵ | CR⁶ |
| 54 | S | H | phenyl | pyridin-4-ylmethyl | H | H | H | H | CR⁵ | CR⁶ |
| 55 | S | H | phenyl | 2-nitrophenylmethyl | H | H | H | H | CR⁵ | CR⁶ |
| 56 | S | H | phenyl | 2-trifluoromethoxyphenylmethyl | H | H | H | H | CR⁵ | CR⁶ |
| 57 | S | H | phenyl | 3-trifluoromethoxyphenylmethyl | H | H | H | H | CR⁵ | CR⁶ |
| 58 | S | H | phenyl | 4-trifluoromethoxyphenylmethyl | H | H | H | H | CR⁵ | CR⁶ |
| 59 | S | H | phenyl | phenylmethyl | H | H | H | H | CR⁵ | CR⁶ |
| 60 | S | H | phenyl | 4-fluoro-3-methoxyphenylmethyl | H | H | H | H | CR⁵ | CR⁶ |
| 61 | S | H | phenyl | 4-fluoro-3-trifluoromethylphenylmethyl | H | H | H | H | CR⁵ | CR⁶ |
| 62 | S | H | phenyl | 2-methylphenylmethyl | H | H | H | H | CR⁵ | CR⁶ |
| 63 | S | H | phenyl | 3-methylphenylmethyl | H | H | H | H | CR⁵ | CR⁶ |
| 64 | S | methyl | 4-methoxy-3-fluorophenyl | 4-fluoro-3-trifluoromethylphenylmethyl | H | H | H | H | CR⁵ | CR⁶ |
| 65 | S | methyl | benzothiazol-6-yl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 66 | S | methyl | 2-oxo-2,3-dihydro-benzooxazol-6-yl | 4-fluoro-3-trifluoromethylphenylmethyl | H | H | H | H | CR⁵ | CR⁶ |
| 67 | S | methyl | 3-oxo-3,4-dihydro-2H-benzo[1,4]oxazin-6-yl | 4-fluoro-3-trifluoromethylphenylmethyl | H | H | H | H | CR⁵ | CR⁶ |
| 68 | S | methyl | 4-methyl-3,4-dihydro-2H-benzo[1,4]oxazin-7-yl | 4-fluoro-3-trifluoromethylphenylmethyl | H | H | H | H | CR⁵ | CR⁶ |
| 69 | S | methyl | 4-[1,2,3]thiadiazol-4-yl-phenyl | 4-fluoro-3-trifluoromethylphenylmethyl | H | H | H | H | CR⁵ | CR⁶ |
| 70 | S | methyl | 3-phenoxyphenyl | 4-fluoro-3-trifluoromethylphenylmethyl | H | H | H | H | CR⁵ | CR⁶ |
| 71 | S | methyl | 2-(methoxycarbonyl)ethyl | 4-fluoro-3-trifluoromethylphenylmethyl | H | H | H | H | CR⁵ | CR⁶ |
| 72 | S | methyl | 2,4-dihydroxy-6-methyl-pyrimidin-5-yl | 4-fluoro-3-trifluoromethylphenylmethyl | H | H | H | H | CR⁵ | CR⁶ |
| 73 | S | methyl | 2-(2,2,2-trifluoro-acetyl)-1,2,3,4-tetrahydro-isoquinolin-8-yl | 4-fluoro-3-trifluoromethylphenylmethyl | H | H | H | H | CR⁵ | CR⁶ |
| 74 | S | methyl | 1,3,5-trimethyl-1H-pyrazol-4-yl | 4-fluoro-3-trifluoromethylphenylmethyl | H | H | H | H | CR⁵ | CR⁶ |
| 75 | S | methyl | 2,4-dimethyl-thiazol-5-yl | 4-fluoro-3-trifluoromethylphenylmethyl | H | H | H | H | CR⁵ | CR⁶ |
| 76 | S | methyl | 2-chloropyridin-5-yl | 4-fluoro-3-trifluoromethylphenylmethyl | H | H | H | H | CR⁵ | CR⁶ |
| 77 | S | methyl | 2-chloropyridin-3-yl | 4-fluoro-3-trifluoromethylphenylmethyl | H | H | H | H | CR⁵ | CR⁶ |
| 78 | S | H | thien-3-yl | 4-fluoro-3-trifluoromethylphenylmethyl | H | H | H | H | CR⁵ | CR⁶ |
| 79 | S | methyl | 1,2,3,4-tetrahydro-isoquinolin-8-yl | 4-fluoro-3-trifluoromethylphenylmethyl | H | H | H | H | CR⁵ | CR⁶ |
| 80 | S | Cl | phenyl | cyclohexylmethyl | H | H | H | H | CR⁵ | CR⁶ |
| 81 | S | Cl | phenyl | 2-(tert-butoxy)ethyl | H | H | H | H | CR⁵ | CR⁶ |
| 82 | S | Cl | phenyl | 2-(2-oxo-pyrrolidin-1-yl)ethyl | H | H | H | H | CR⁵ | CR⁶ |
| 83 | S | Cl | phenyl | n-butyl | H | H | H | H | CR⁵ | CR⁶ |
| 84 | S | Cl | phenyl | allyl | H | H | H | H | CR⁵ | CR⁶ |
| 85 | S | Cl | phenyl | 2-(phenyl)ethyl | H | H | H | H | CR⁵ | CR⁶ |
| 86 | S | Cl | phenyl | 2-(tert-butoxycarbonylamino)ethyl | H | H | H | H | CR⁵ | CR⁶ |
| 87 | S | Cl | phenyl | 2-(dimethylamino)ethyl | H | H | H | H | CR⁵ | CR⁶ |
| 88 | S | Cl | phenyl | 2-(methanesulfonyl)ethyl | H | H | H | H | CR⁵ | CR⁶ |
| 89 | S | Cl | phenyl | (N-tert-butoxycarbonylpyrrolidin-2-yl)methyl | H | H | H | H | CR⁵ | CR⁶ |
| 90 | S | Cl | phenyl | (N-tert-butoxycarbonylpiperidin-4-yl)methyl | H | H | H | H | CR⁵ | CR⁶ |
| 91 | S | Cl | phenyl | 2-(2-oxo-imidazolidin-1-yl)ethyl | H | H | H | H | CR⁵ | CR⁶ |
| 92 | S | Cl | phenyl | 2-(morpholin-4-yl)ethyl | H | H | H | H | CR⁵ | CR⁶ |
| 93 | S | methyl | phenyl | 2-(methoxycarbonyl)-2(R)-methylethyl | H | H | H | H | CR⁵ | CR⁶ |
| 94 | S | methyl | phenyl | 2-(methoxycarbonyl)-2(S)-methylethyl | H | H | H | H | CR⁵ | CR⁶ |
| 95 | S | methyl | phenyl | 2-(morpholin-4-yl)ethyl | H | H | H | H | CR⁵ | CR⁶ |
| 96 | S | methyl | phenyl | 2-(piperidin-1-yl)ethyl | H | H | H | H | CR⁵ | CR⁶ |
| 97 | S | methyl | phenyl | cyclopropylmethyl | H | H | H | H | CR⁵ | CR⁶ |
| 98 | S | methyl | phenyl | 2-(methylsulfanyl)ethyl | H | H | H | H | CR⁵ | CR⁶ |
| 99 | S | methyl | phenyl | 2-methoxyethyl | H | H | H | H | CR⁵ | CR⁶ |
| 100 | S | methyl | phenyl | 2-(tert-butoxy)ethyl | H | H | H | H | CR⁵ | CR⁶ |
| 101 | S | methyl | phenyl | methoxycarbonylmethyl | H | H | H | H | CR⁵ | CR⁶ |
| 102 | S | methyl | phenyl | 2,2-difluoroethyl | H | H | H | H | CR⁵ | CR⁶ |
| 103 | S | methyl | phenyl | (N-tert-butoxycarbonylpyrrolidin-2-yl)methyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 104 | S | methyl | phenyl | 2-phenylethyl | H | H | H | H | CR⁵ | CR⁶ |
| 105 | S | methyl | ethyl | 2-methoxyethyl | H | H | H | H | CR⁵ | CR⁶ |
| 106 | S | methyl | ethyl | 3,3,3-trifluoropropyl | H | H | H | H | CR⁵ | CR⁶ |
| 107 | S | methyl | ethyl | pent-3-ynyl | H | H | H | H | CR⁵ | CR⁶ |
| 108 | S | methyl | ethyl | 2-(methylsulfanyl)ethyl | H | H | H | H | CR⁵ | CR⁶ |
| 109 | S | methyl | ethyl | 2-oxo-pyrrolidin-5(S)-ylmethyl | H | H | H | H | CR⁵ | CR⁶ |
| 110 | S | methyl | ethyl | 2-(tert-butoxy)ethyl | H | H | H | H | CR⁵ | CR⁶ |
| 111 | S | methyl | ethyl | 2,2-difluoroethyl | H | H | H | H | CR⁵ | CR⁶ |
| 112 | S | methyl | ethyl | cyclopropylmethyl | H | H | H | H | CR⁵ | CR⁶ |
| 113 | S | methyl | ethyl | 2-(morpholin-4-yl)ethyl | H | H | H | H | CR⁵ | CR⁶ |
| 114 | S | methyl | ethyl | (N-tert-butoxycarbonylpyrrolidin-2-yl)methyl | H | H | H | H | CR⁵ | CR⁶ |
| 115 | S | H | phenyl | 2-phenylethyl | H | H | H | H | CR⁵ | CR⁶ |
| 116 | S | H | phenyl | allyl | H | H | H | H | CR⁵ | CR⁶ |
| 117 | S | H | phenyl | n-butyl | H | H | H | H | CR⁵ | CR⁶ |
| 118 | S | H | phenyl | cyclohexylmethyl | H | H | H | H | CR⁵ | CR⁶ |
| 119 | S | H | phenyl | cyclohexyl | H | H | H | H | CR⁵ | CR⁶ |
| 120 | S | H | phenyl | 2-(methylsulfanyl)ethyl | H | H | H | H | CR⁵ | CR⁶ |
| 121 | S | acetyl | ethyl | n-butyl | H | H | H | H | CR⁵ | CR⁶ |
| 122 | S | acetyl | ethyl | cyclopropylmethyl | H | H | H | H | CR⁵ | CR⁶ |
| 123 | S | acetyl | ethyl | 2-(tert-butoxy)ethyl | H | H | H | H | CR⁵ | CR⁶ |
| 124 | S | acetyl | ethyl | 2-(morpholin-4-yl)ethyl | H | H | H | H | CR⁵ | CR⁶ |
| 125 | S | methyl | phenyl | 3,4-difluorophenylmethyl | H | H | H | H | CR⁵ | CR⁶ |
| 126 | S | methyl | phenylmethyl | 3,4-difluorophenylmethyl | H | H | H | H | CR⁵ | CR⁶ |
| 127 | S | methyl | 3-fluorophenyl | 3,4-difluorophenylmethyl | H | H | H | H | CR⁵ | CR⁶ |
| 128 | S | methyl | 2-fluorophenyl | 3,4-difluorophenylmethyl | H | H | H | H | CR⁵ | CR⁶ |
| 129 | S | methyl | thien-2-yl | 3,4-difluorophenylmethyl | H | H | H | H | CR⁵ | CR⁶ |
| 130 | S | H | 1-methyl-1H-imidazol-4-yl | 3,4-difluorophenylmethyl | H | H | H | H | CR⁵ | CR⁶ |
| 131 | S | H | 3-fluorophenyl | 3,4-difluorophenylmethyl | H | H | H | H | CR⁵ | CR⁶ |
| 132 | S | H | 4-trifluoromethylphenyl | 3,4-difluorophenylmethyl | H | H | H | H | CR⁵ | CR⁶ |
| 133 | S | H | methanesulfonylmethyl | 3,4-difluorophenylmethyl | H | H | H | H | CR⁵ | CR⁶ |
| 134 | S | H | 4-methoxyphenyl | 4-fluoro-3-trifluoromethylphenylmethyl | H | H | H | H | CR⁵ | CR⁶ |
| 135 | S | H | 4-methoxycarbonylphenyl | 4-fluoro-3-trifluoromethylphenylmethyl | H | H | H | H | CR⁵ | CR⁶ |
| 136 | S | H | 3-methoxycarbonylphenyl | 4-fluoro-3-trifluoromethylphenylmethyl | H | H | H | H | CR⁵ | CR⁶ |
| 137 | S | methyl | 3-methoxycarbonylphenyl | 4-fluoro-3-trifluoromethylphenylmethyl | H | H | H | H | CR⁵ | CR⁶ |
| 138 | S | methyl | 4-methoxycarbonylphenyl | 4-fluoro-3-trifluoromethylphenylmethyl | H | H | H | H | CR⁵ | CR⁶ |
| 139 | S | H | 2-methoxycarbonylphenyl | 4-fluoro-3-trifluoromethylphenylmethyl | H | H | H | H | CR⁵ | CR⁶ |
| 140 | S | Br | phenyl | 4-fluorophenylmethyl | H | H | H | H | CR⁵ | CR⁶ |
| 141 | S | Br | pyridin-3-yl | 3,4-difluorophenylmethyl | H | OCH₃ | H | H | CR⁵ | CR⁶ |
| 142 | S | H | phenyl | 3,4-difluorophenylmethyl | H | H | H | OCH₃ | CR⁵ | CR⁶ |
| 143 | S | Cl | phenyl | 3,4-difluorophenylmethyl | H | H | H | OCH₃ | CR⁵ | CR⁶ |
| 144 | S | Cl | phenyl | 3,4-difluorophenylmethyl | H | Cl | H | OCH₃ | CR⁵ | CR⁶ |
| 145a | S | Br | phenyl | 3,4-difluorophenylmethyl | H | H | NA | H | N | CR⁶ |
| 145b | S | Cl | phenyl | 3,4-difluorophenylmethyl | H | H | NA | H | N | CR⁶ |
| 146 | S | H | phenyl | 4-fluoro-3-trifluoromethylphenylmethyl | H | H | NA | H | N | CR⁶ |
| 147 | S | H | phenyl | 3,4-difluorophenylmethyl | H | H | H | NA | CR⁵ | CR⁶ |
| 148 | S | Br | phenyl | 3,4-difluorophenylmethyl | H | H | H | H | CR⁵ | CR⁶ |
| 149 | S | Br | pyridin-3-yl | 3,4-difluorophenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 150 | S | Br | 1-methyl-1H-imidazol-4-yl | 3,4-difluorophenylmethyl | H | H | H | H | CR⁵ | CR⁶ |
| 151 | S | Br | methyl | 3,4-difluorophenylmethyl | H | H | H | H | CR⁵ | CR⁶ |
| 152 | S | Br | ethyl | 3,4-difluorophenylmethyl | H | H | H | H | CR⁵ | CR⁶ |
| 153 | S | Br | n-propyl | 3,4-difluorophenylmethyl | H | H | H | H | CR⁵ | CR⁶ |
| 154 | S | Br | n-butyl | 3,4-difluorophenylmethyl | H | H | H | H | CR⁵ | CR⁶ |
| 155 | S | Br | 3-fluorophenyl | 3,4-difluorophenylmethyl | H | H | H | H | CR⁵ | CR⁶ |
| 156 | S | Br | 4-trifluoromethylphenyl | 3,4-difluorophenylmethyl | H | H | H | H | CR⁵ | CR⁶ |
| 157 | S | Br | methyl | 4-fluoro-3-trifluoromethylphenylmethyl | H | H | H | H | CR⁵ | CR⁶ |
| 158 | S | Cl | phenyl | 4-chlorophenylmethyl | H | H | H | H | CR⁵ | CR⁶ |
| 159 | S | Br | phenyl | 4-chlorophenylmethyl | H | H | H | H | CR⁵ | CR⁶ |
| 160 | S | Br | phenyl | 2-methoxyphenylmethyl | H | H | H | H | CR⁵ | CR⁶ |
| 161 | S | Br | phenyl | 5-bromo-2-methoxyphenylmethyl | H | H | H | H | CR⁵ | CR⁶ |
| 162 | S | Br | phenyl | 3-methoxyphenylmethyl | H | H | H | H | CR⁵ | CR⁶ |
| 163 | S | Br | phenyl | 2-bromo-5-methoxyphenylmethyl | H | H | H | H | CR⁵ | CR⁶ |
| 164 | S | Br | phenyl | 4-methoxyphenylmethyl | H | H | H | H | CR⁵ | CR⁶ |
| 165 | S | Br | phenyl | 4-methoxy-3-bromophenylmethyl | H | H | H | H | CR⁵ | CR⁶ |
| 166 | S | Br | phenyl | 2-fluorophenylmethyl | H | H | H | H | CR⁵ | CR⁶ |
| 167 | S | Br | phenyl | 3-nitrophenylmethyl | H | H | H | H | CR⁵ | CR⁶ |
| 168 | S | Br | phenyl | pyridin-2-ylmethyl | H | H | H | H | CR⁵ | CR⁶ |
| 169 | S | Br | phenyl | pyridin-3-ylmethyl | H | H | H | H | CR⁵ | CR⁶ |
| 170 | S | Br | phenyl | pyridin-4-ylmethyl | H | H | H | H | CR⁵ | CR⁶ |
| 171 | S | Br | phenyl | 2-nitrophenylmethyl | H | H | H | H | CR⁵ | CR⁶ |
| 172 | S | Br | phenyl | 2-trifluoromethoxyphenylmethyl | H | H | H | H | CR⁵ | CR⁶ |
| 173 | S | Br | phenyl | 3-trifluoromethoxyphenylmethyl | H | H | H | H | CR⁵ | CR⁶ |
| 174 | S | Br | phenyl | 4-trifluoromethoxyphenylmethyl | H | H | H | H | CR⁵ | CR⁶ |
| 175 | S | Br | phenyl | phenylmethyl | H | H | H | H | CR⁵ | CR⁶ |
| 176 | S | Br | phenyl | 4-fluoro-3-methoxyphenylmethyl | H | H | H | H | CR⁵ | CR⁶ |
| 177 | S | Br | phenyl | 4-fluoro-3-trifluoromethylphenylmethyl | H | H | H | H | CR⁵ | CR⁶ |
| 178 | S | Br | phenyl | 2-methylphenylmethyl | H | H | H | H | CR⁵ | CR⁶ |
| 179 | S | Br | phenyl | 3-methylphenylmethyl | H | H | H | H | CR⁵ | CR⁶ |
| 180 | S | Cl | 3-methoxyphenyl | 4-fluoro-3-trifluoromethylphenylmethyl | H | H | H | H | CR⁵ | CR⁶ |
| 181 | S | Cl | 4-methoxyphenyl | 4-fluoro-3-trifluoromethylphenylmethyl | H | H | H | H | CR⁵ | CR⁶ |
| 182 | S | Br | 4-methoxyphenyl | 4-fluoro-3-trifluoromethylphenylmethyl | H | H | H | H | CR⁵ | CR⁶ |
| 183 | S | Br | ethyl | 4-fluoro-3-trifluoromethylphenylmethyl | H | H | H | H | CR⁵ | CR⁶ |
| 184 | S | Br | thien-2-yl | 4-fluoro-3-trifluoromethylphenylmethyl | H | H | H | H | CR⁵ | CR⁶ |
| 185 | S | Br | 3-methoxyphenyl | 4-fluoro-3-trifluoromethylphenylmethyl | H | H | H | H | CR⁵ | CR⁶ |
| 186 | S | Br | thien-3-yl | 4-fluoro-3-trifluoromethylphenylmethyl | H | H | H | H | CR⁵ | CR⁶ |
| 187 | S | Cl | thien-3-yl | 4-fluoro-3-trifluoromethylphenylmethyl | H | H | H | H | CR⁵ | CR⁶ |
| 188 | S | Br | pyridin-3-yl | 4-fluoro-3-trifluoromethylphenylmethyl | H | H | H | H | CR⁵ | CR⁶ |
| 189 | S | Cl | pyridin-3-yl | 4-fluoro-3-trifluoromethylphenylmethyl | H | H | H | H | CR⁵ | CR⁶ |
| 190 | S | Cl | ethyl | 4-fluoro-3-trifluoromethylphenylmethyl | H | H | H | H | CR⁵ | CR⁶ |
| 191 | S | Cl | thien-2-yl | 4-fluoro-3-trifluoromethylphenylmethyl | H | H | H | H | CR⁵ | CR⁶ |
| 192 | S | Br | 4-methoxycarbonylphenyl | 4-fluoro-3-trifluoromethylphenylmethyl | H | H | H | H | CR⁵ | CR⁶ |
| 193 | S | Br | 3-methoxycarbonylphenyl | 4-fluoro-3-trifluoromethylphenylmethyl | H | H | H | H | CR⁵ | CR⁶ |
| 194 | S | Cl | 4-methoxycarbonylphenyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 195 | S | Cl | 3-methoxycarbonylphenyl | 4-fluoro-3-trifluoromethylphenylmethyl | H | H | H | H | CR⁵ | CR⁶ |
| 196 | S | Cl | 2-methoxycarbonylphenyl | 4-fluoro-3-trifluoromethylphenylmethyl | H | H | H | H | CR⁵ | CR⁶ |
| 197 | S | Br | 2-methoxycarbonylphenyl | 4-fluoro-3-trifluoromethylphenylmethyl | H | H | H | H | CR⁵ | CR⁶ |
| 198 | S | cyano | ethyl | 4-fluoro-3-trifluoromethylphenylmethyl | H | H | H | H | CR⁵ | CR⁶ |
| 199 | S | pyrimidin-5-yl | ethyl | 4-fluoro-3-trifluoromethylphenylmethyl | H | H | H | H | CR⁵ | CR⁶ |
| 200 | S | 2-fluorophenyl | ethyl | 4-fluoro-3-trifluoromethylphenylmethyl | H | H | H | H | CR⁵ | CR⁶ |
| 201 | S | 4-fluorophenyl | ethyl | 4-fluoro-3-trifluoromethylphenylmethyl | H | H | H | H | CR⁵ | CR⁶ |
| 202 | S | thien-3-yl | ethyl | 4-fluoro-3-trifluoromethylphenylmethyl | H | H | H | H | CR⁵ | CR⁶ |
| 203 | S | acetyl | ethyl | 3,4-difluorophenylmethyl | H | H | H | H | CR⁵ | CR⁶ |
| 204 | S | acetyl | phenyl | 3,4-difluorophenylmethyl | H | H | H | H | CR⁵ | CR⁶ |
| 205 | S | acetyl | ethyl | 4-fluoro-3-trifluoromethylphenylmethyl | H | H | H | H | CR⁵ | CR⁶ |
| 206 | S | formyl | phenyl | 3,4-difluorophenylmethyl | H | H | H | H | CR⁵ | CR⁶ |
| 207 | S | formyl | phenyl | 4-fluoro-3-trifluoromethylphenylmethyl | H | H | H | H | CR⁵ | CR⁶ |
| 208 | S | formyl | methyl | 4-fluoro-3-trifluoromethylphenylmethyl | H | H | H | H | CR⁵ | CR⁶ |
| 209 | S | formyl | methyl | 3,4-difluorophenylmethyl | H | H | H | H | CR⁵ | CR⁶ |
| 210 | S | formyl | ethyl | 4-fluoro-3-trifluoromethylphenylmethyl | H | H | H | H | CR⁵ | CR⁶ |
| 211 | S | formyl | 4-methoxycarbonylphenyl | 4-fluoro-3-trifluoromethylphenylmethyl | H | H | H | H | CR⁵ | CR⁶ |
| 212 | S | formyl | ethyl | 3,4-difluorophenylmethyl | H | H | H | H | CR⁵ | CR⁶ |
| 213 | S | hydroxymethyl | phenyl | 3,4-difluorophenylmethyl | H | H | H | H | CR⁵ | CR⁶ |
| 214 | S | hydroxymethyl | phenyl | 4-fluoro-3-trifluoromethylphenylmethyl | H | H | H | H | CR⁵ | CR⁶ |
| 215 | S | hydroxymethyl | methyl | 4-fluoro-3-trifluoromethylphenylmethyl | H | H | H | H | CR⁵ | CR⁶ |
| 216 | S | hydroxymethyl | methyl | 3,4-difluorophenylmethyl | H | H | H | H | CR⁵ | CR⁶ |
| 217 | S | hydroxymethyl | ethyl | 4-fluoro-3-trifluoromethylphenylmethyl | H | H | H | H | CR⁵ | CR⁶ |
| 218 | S | hydroxymethyl | 4-carboxyphenyl | 4-fluoro-3-trifluoromethylphenylmethyl | H | H | H | H | CR⁵ | CR⁶ |
| 219 | S | hydroxymethyl | ethyl | 3,4-difluorophenylmethyl | H | H | H | H | CR⁵ | CR⁶ |
| 220 | S | 1-hydroxyethyl | ethyl | 4-fluoro-3-trifluoromethylphenylmethyl | H | H | H | H | CR⁵ | CR⁶ |
| 221 | S | 1-hydroxyethyl | ethyl | 3,4-difluorophenylmethyl | H | H | H | H | CR⁵ | CR⁶ |
| 222 | S | 1-hydroxyethyl | phenyl | 3,4-difluorophenylmethyl | H | H | H | H | CR⁵ | CR⁶ |
| 223 | S | 1-hydroxyethyl | phenyl | 4-fluoro-3-trifluoromethylphenylmethyl | H | H | H | H | CR⁵ | CR⁶ |
| 224 | S | 1-hydroxy-ethyl | methyl | 4-fluoro-3-trifluoromethylphenylmethyl | H | H | H | H | CR⁵ | CR⁶ |
| 225 | S | 1-hydroxy-ethyl | methyl | 3,4-difluorophenylmethyl | H | H | H | H | CR⁵ | CR⁶ |
| 226 | S | 1-hydroxy-1-methyl-ethyl | ethyl | 3,4-difluorophenylmethyl | H | H | H | H | CR⁵ | CR⁶ |
| 227 | S | 1-hydroxy-1-methyl-ethyl | ethyl | 4-fluoro-3-trifluoromethylphenylmethyl | H | H | H | H | CR⁵ | CR⁶ |
| 228 | S | acetyl | methyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 229 | S | acetyl | methyl | 3,4-difluorophenylmethyl | H | H | H | H | CR⁵ | CR⁶ |
| 230 | S | Br | phenyl | 5-(ethoxycarbonyl)pentyl | H | H | H | H | CR⁵ | CR⁶ |
| 231 | S | Br | phenyl | n-butyl | H | H | H | H | CR⁵ | CR⁶ |
| 232 | S | Br | phenyl | cyclohexylmethyl | H | H | H | H | CR⁵ | CR⁶ |
| 233 | S | Br | phenyl | 2-phenylethyl | H | H | H | H | CR⁵ | CR⁶ |
| 234 | S | Br | phenyl | 2-(tert-butoxy)ethyl | H | H | H | H | CR⁵ | CR⁶ |
| 235 | S | Br | phenyl | 2(R)-3-dihydroxy-propyl | H | H | H | H | CR⁵ | CR⁶ |
| 236 | S | Br | phenyl | 2-(2-oxo-pyrrolidin-1-yl)ethyl | H | H | H | H | CR⁵ | CR⁶ |
| 237 | S | Br | phenyl | 2-(morpholin-4-yl)ethyl | H | H | H | H | CR⁵ | CR⁶ |
| 238 | S | Br | phenyl | 2-(dimethylamino)ethyl | H | H | H | H | CR⁵ | CR⁶ |
| 239 | S | Br | phenyl | 2-(methanesulfonyl)ethyl | H | H | H | H | CR⁵ | CR⁶ |
| 240 | S | Br | phenyl | 2-(2-oxo-imidazolidin-1-yl)-ethyl | H | H | H | H | CR⁵ | CR⁶ |
| 241 | S | Br | phenyl | N-methylpyrrolidin-2(S)-ylmethyl | H | H | H | H | CR⁵ | CR⁶ |
| 242 | S | Br | phenyl | 2,2-difluoroethyl | H | H | H | H | CR⁵ | CR⁶ |
| 243 | S | Br | phenyl | methoxycarbonylmethyl | H | H | H | H | CR⁵ | CR⁶ |
| 244 | S | Br | phenyl | 2(S)-methoxycarbonyl-2-methylethyl | H | H | H | H | CR⁵ | CR⁶ |
| 245 | S | Br | phenyl | 2(R)-methoxycarbonyl-2-methylethyl | H | H | H | H | CR⁵ | CR⁶ |
| 246 | S | Br | phenyl | 3-phenylpropyl | H | H | H | H | CR⁵ | CR⁶ |
| 247 | S | Br | phenyl | ethyl | H | H | H | H | CR⁵ | CR⁶ |
| 248 | S | Br | phenyl | n-hexyl | H | H | H | H | CR⁵ | CR⁶ |
| 249 | S | Br | phenyl | adamant-1-ylmethyl | H | H | H | H | CR⁵ | CR⁶ |
| 250 | S | Br | phenyl | 3,3,3-trifluoropropyl | H | H | H | H | CR⁵ | CR⁶ |
| 251 | S | Br | phenyl | pent-3-ynyl | H | H | H | H | CR⁵ | CR⁶ |
| 252 | S | Br | phenyl | 2-methoxyethyl | H | H | H | H | CR⁵ | CR⁶ |
| 253 | S | Br | phenyl | 3-(methylcarbonyl)propyl | H | H | H | H | CR⁵ | CR⁶ |
| 254 | S | Br | phenyl | 2-(dimethylphospho)ethyl | H | H | H | H | CR⁵ | CR⁶ |
| 255 | S | Br | phenyl | cyclopropylmethyl | H | H | H | H | CR⁵ | CR⁶ |
| 256 | S | Br | phenyl | 2-(piperidin-1-yl)ethyl | H | H | H | H | CR⁵ | CR⁶ |
| 257 | S | Br | phenyl | 2-(2,5-dioxo-pyrrolidin-1-yl)ethyl | H | H | H | H | CR⁵ | CR⁶ |
| 258 | S | Br | phenyl | 2-oxo-pyrrolidin-5(R)-ylmethyl | H | H | H | H | CR⁵ | CR⁶ |
| 259 | S | Br | phenyl | 2-oxo-pyrrolidin-5(S)-ylmethyl | H | H | H | H | CR⁵ | CR⁶ |
| 260 | S | Br | phenyl | 2-(methylsulfanyl)ethyl | H | H | H | H | CR⁵ | CR⁶ |
| 261 | S | Br | ethyl | n-butyl | H | H | H | H | CR⁵ | CR⁶ |
| 262 | S | Br | ethyl | cyclopropylmethyl | H | H | H | H | CR⁵ | CR⁶ |
| 263 | S | Br | ethyl | 2,2-difluoroethyl | H | H | H | H | CR⁵ | CR⁶ |
| 264 | S | Br | ethyl | 2-(tert-butoxy)ethyl | H | H | H | H | CR⁵ | CR⁶ |
| 265 | S | Br | dimethylamino | n-butyl | H | H | H | H | CR⁵ | CR⁶ |
| 266 | S | Br | dimethylamino | cyclopropylmethyl | H | H | H | H | CR⁵ | CR⁶ |
| 267 | S | Br | dimethylamino | 2-(tert-butoxy)ethyl | H | H | H | H | CR⁵ | CR⁶ |
| 268 | S | Br | dimethylamino | 2,2-difluoroethyl | H | H | H | H | CR⁵ | CR⁶ |
| 269 | S | Br | dimethylamino | 3,3,3-trifluoropropyl | H | H | H | H | CR⁵ | CR⁶ |
| 270 | S | Cl | phenyl | 2-aminoethyl | H | H | H | H | CR⁵ | CR⁶ |
| 271 | S | Br | 4-carboxyphenyl | 3,3,3-trifluoropropyl | H | H | H | H | CR⁵ | CR⁶ |
| 272 | S | Br | 4-carboxyphenyl | n-butyl | H | H | H | H | CR⁵ | CR⁶ |
| 273 | S | Br | 4-carboxyphenyl | cyclopropylmethyl | H | H | H | H | CR⁵ | CR⁶ |
| 274 | S | Br | 4-carboxyphenyl | 2-methoxyethyl | H | H | H | H | CR⁵ | CR⁶ |
| 275 | S | Br | 4-carboxyphenyl | 2-(tert-butoxy)ethyl | H | H | H | H | CR⁵ | CR⁶ |
| 276 | S | Br | 4-carboxyphenyl | 2,2-difluoroethyl | H | H | H | H | CR⁵ | CR⁶ |
| 277 | S | Br | 4-carboxyphenyl | 2-(morpholin-4-yl)ethyl | H | H | H | H | CR⁵ | CR⁶ |
| 278 | S | Br | 4-carboxyphenyl | adamant-1-ylmethyl | H | H | H | H | CR⁵ | CR⁶ |
| 279 | S | Br | 4-carboxyphenyl | cyclohexylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 280 | S | 1-hydroxyethyl | ethyl | n-butyl | H | H | H | H | CR⁵ | CR⁶ |
| 281 | S | 1-hydroxyethyl | ethyl | cyclopropylmethyl | H | H | H | H | CR⁵ | CR⁶ |
| 282 | S | 1-hydroxyethyl | ethyl | 3,3,3-trifluoropropyl | H | H | H | H | CR⁵ | CR⁶ |
| 283 | S | 1-hydroxyethyl | ethyl | 2-(tert-butoxy)ethyl | H | H | H | H | CR⁵ | CR⁶ |
| 284 | S | 1-hydroxyethyl | ethyl | 2-(morpholin-4-yl)ethyl | H | H | H | H | CR⁵ | CR⁶ |
| 285 | S | methyl | 4-hydroxyphenyl | 3,4-difluorophenylmethyl | H | H | H | H | CR⁵ | CR⁶ |
| 286 | S | methyl | 3-hydroxyphenyl | 3,4-difluorophenylmethyl | H | H | H | H | CR⁵ | CR⁶ |
| 287 | S | H | phenyl | 3-hydroxyphenylmethyl | H | H | H | H | CR⁵ | CR⁶ |
| 288 | S | Cl | 3-hydroxyphenyl | 4-fluoro-3-trifluoromethylphenylmethyl | H | H | H | H | CR⁵ | CR⁶ |
| 289 | S | Cl | 4-hydroxyphenyl | 4-fluoro-3-trifluoromethylphenylmethyl | H | H | H | H | CR⁵ | CR⁶ |
| 290 | S | Br | 4-hydroxyphenyl | 4-fluoro-3-trifluoromethylphenylmethyl | H | H | H | H | CR⁵ | CR⁶ |
| 291 | S | Br | 3-hydroxyphenyl | 4-fluoro-3-trifluoromethylphenylmethyl | H | H | H | H | CR⁵ | CR⁶ |
| 292 | S | Br | 4-carboxyphenyl | 4-fluoro-3-trifluoromethylphenylmethyl | H | H | H | H | CR⁵ | CR⁶ |
| 293 | S | Br | 3-carboxyphenyl | 4-fluoro-3-trifluoromethylphenylmethyl | H | H | H | H | CR⁵ | CR⁶ |
| 294 | S | Cl | 4-carboxyphenyl | 4-fluoro-3-trifluoromethylphenylmethyl | H | H | H | H | CR⁵ | CR⁶ |
| 295 | S | H | 3-carboxyphenyl | 4-fluoro-3-trifluoromethylphenylmethyl | H | H | H | H | CR⁵ | CR⁶ |
| 296 | S | H | 4-carboxyphenyl | 4-fluoro-3-trifluoromethylphenylmethyl | H | H | H | H | CR⁵ | CR⁶ |
| 297 | S | Cl | 2-carboxyphenyl | 4-fluoro-3-trifluoromethylphenylmethyl | H | H | H | H | CR⁵ | CR⁶ |
| 298 | S | Br | 2-carboxyphenyl | 4-fluoro-3-trifluoromethylphenylmethyl | H | H | H | H | CR⁵ | CR⁶ |
| 299 | S | formyl | 4-carboxyphenyl | 4-fluoro-3-trifluoromethylphenylmethyl | H | H | H | H | CR⁵ | CR⁶ |
| 300 | S | H | amino | 4-fluoro-3-trifluoromethylphenylmethyl | H | H | H | H | CR⁵ | CR⁶ |
| 301 | S | Br | amino | 4-fluoro-3-trifluoromethylphenylmethyl | H | H | H | H | CR⁵ | CR⁶ |
| 302 | S | Cl | amino | 4-fluoro-3-trifluoromethylphenylmethyl | H | H | H | H | CR⁵ | CR⁶ |
| 303 | S | bromo | amino | cyclopropylmethyl | H | H | H | H | CR⁵ | CR⁶ |
| 304 | S | bromo | amino | 3,3,3-trifluoropropyl | H | H | H | H | CR⁵ | CR⁶ |
| 305 | S | methyl | 3-carboxyphenyl | 4-fluoro-3-trifluoromethylphenylmethyl | H | H | H | H | CR⁵ | CR⁶ |
| 306 | S | methyl | 4-carboxyphenyl | 4-fluoro-3-trifluoromethylphenylmethyl | H | H | H | H | CR⁵ | CR⁶ |
| 307 | S | chloro | 3-carboxyphenyl | 4-fluoro-3-trifluoromethylphenylmethyl | H | H | H | H | CR⁵ | CR⁶ |
| 308 | S | H | 4-methylcarbonylphenyl | 4-fluoro-3-trifluoromethylphenylmethyl | H | H | H | H | CR⁵ | CR⁶ |
| 309 | S | chloro | methylamino | 4-fluoro-3-trifluoromethylphenylmethyl | H | H | H | H | CR⁵ | CR⁶ |
| 310 | S | H | 2-chloropyridin-3-yl | 4-fluoro-3-trifluoromethylphenylmethyl | H | H | H | H | CR⁵ | CR⁶ |
| 311 | S | H | 6-chloro-pyridin-3-yl | 4-fluoro-3-trifluoromethylphenylmethyl | H | H | H | H | CR⁵ | CR⁶ |
| 312 | S | bromo | 4-methylcarbonylphenyl | 4-fluoro-3-trifluoromethylphenylmethyl | H | H | H | H | CR⁵ | CR⁶ |
| 313 | S | methylcarbonyl | 4-methoxycarbonylphenyl | 4-fluoro-3-trifluoromethylphenylmethyl | H | H | H | H | CR⁵ | CR⁶ |
| 314 | S | methylcarbonyl | phenyl | 4-fluoro-3-trifluoromethylphenylmethyl | H | H | H | H | CR⁵ | CR⁶ |
| 315 | S | H | dimethylamino | 4-fluoro-3-trifluoromethylphenylmethyl | H | H | H | H | CR⁵ | CR⁶ |
| 316 | S | 1-hydroxy-1-methyl-ethyl | phenyl | 4-fluoro-3-trifluoromethylphenylmethyl | H | H | H | H | CR⁵ | CR⁶ |
| 317 | S | bromo | dimethylamino | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 318 | S | methylcarbonyl | 4-carboxyphenyl | 4-fluoro-3-trifluoromethylphenylmethyl | H | H | H | H | CR⁵ | CR⁶ |
| 319 | S | bromo | 2-chloropyridin-3-yl | 4-fluoro-3-trifluoromethylphenylmethyl | H | H | H | H | CR⁵ | CR⁶ |
| 320 | S | bromo | 6-chloro-pyridin-3-yl | 4-fluoro-3-trifluoromethylphenylmethyl | H | H | H | H | CR⁵ | CR⁶ |
| 321 | S | chloro | 2-chloropyridin-3-yl | 4-fluoro-3-trifluoromethylphenylmethyl | H | H | H | H | CR⁵ | CR⁶ |
| 322 | S | bromo | pyridin-3-yl | 3-fluoro-4-trifluoromethylphenylmethyl | H | H | H | H | CR⁵ | CR⁶ |
| 323 | S | bromo | pyridin-3-yl | 4-trifluoromethoxyphenylmethyl | H | H | H | H | CR⁵ | CR⁶ |
| 324 | S | bromo | pyridin-3-yl | 3-chloro-6-fluorophenylmethyl | H | H | H | H | CR⁵ | CR⁶ |
| 325 | S | trifluoromethyl | phenyl | 4-trifluoromethoxyphenylmethyl | H | H | H | H | CR⁵ | CR⁶ |
| 326 | S | methyl | 5-(2-methyl-5-trifluoromethyl-2H-pyrazol-3-yl)-thien-2-yl | 4-fluoro-3-trifluoromethylphenylmethyl | H | H | H | H | CR⁵ | CR⁶ |
| 327 | S | methyl | 5-methoxycarbonyl-furan-2-yl | 4-fluoro-3-trifluoromethylphenylmethyl | H | H | H | H | CR⁵ | CR⁶ |
| 328 | S | methyl | 1-methyl-3-trifluoromethyl-1H-pyrazol-4-yl | 4-fluoro-3-trifluoromethylphenylmethyl | H | H | H | H | CR⁵ | CR⁶ |
| 329 | S | methyl | 5-(5-trifluoromethyl-isoxazol-3-yl)-thien-2-yl | 4-fluoro-3-trifluoromethylphenylmethyl | H | H | H | H | CR⁵ | CR⁶ |
| 330 | S | methyl | 5-bromo-6-chloro-pyridin-3-yl | 4-fluoro-3-trifluoromethylphenylmethyl | H | H | H | H | CR⁵ | CR⁶ |
| 331 | S | methyl | 5,6-dichloro-pyridin-3-yl | 4-fluoro-3-trifluoromethylphenylmethyl | H | H | H | H | CR⁵ | CR⁶ |
| 332 | S | methyl | 4-(pyrazol-1-yl)phenyl | 4-fluoro-3-trifluoromethylphenylmethyl | H | H | H | H | CR⁵ | CR⁶ |
| 333 | S | methyl | 3-(5-methyl-[1,3,4]oxadiazol-2-yl)phenyl | 4-fluoro-3-trifluoromethylphenylmethyl | H | H | H | H | CR⁵ | CR⁶ |
| 334 | S | methyl | 4-(oxazol-5-yl)phenyl | 4-fluoro-3-trifluoromethylphenylmethyl | H | H | H | H | CR⁵ | CR⁶ |
| 335 | S | 1-hydroxy-ethyl | 4-carboxyphenyl | 4-fluoro-3-trifluoromethylphenylmethyl | H | H | H | H | CR⁵ | CR⁶ |
| 336 | S | methyl | 3-chloro-4-methylcarbonylamino-phenyl | 4-fluoro-3-trifluoromethylphenylmethyl | H | H | H | H | CR⁵ | CR⁶ |
| 337 | S | methyl | 6-chloro-imidazo[2,1-b]thiazol-5-yl | 4-fluoro-3-trifluoromethylphenylmethyl | H | H | H | H | CR⁵ | CR⁶ |
| 338 | S | chloro | 6-chloro-pyridin-3-yl | 4-fluoro-3-trifluoromethylphenylmethyl | H | H | H | H | CR⁵ | CR⁶ |
| 339 | S | methylcarbonyl | 4-methoxycarbonylphenyl | n-butyl | H | H | H | H | CR⁵ | CR⁶ |
| 340 | S | H | pyridin-3-yl | n-butyl | H | H | H | H | CR⁵ | CR⁶ |
| 341 | S | 1-hydroxy-1-methyl-ethyl | 4-(1-hydroxy-1-methyl-ethyl)phenyl | n-butyl | H | H | H | H | CR⁵ | CR⁶ |
| 342 | S | methylcarbonyl | 4-carboxyphenyl | n-butyl | H | H | H | H | CR⁵ | CR⁶ |
| 343 | S | 1-hydroxy-1-methyl-ethyl | 4-carboxyphenyl | n-butyl | H | H | H | H | CR⁵ | CR⁶ |
| 344 | S | 1-hydroxy-1-methyl-ethyl | 4-methylcarbonylphenyl | n-butyl | H | H | H | H | CR⁵ | CR⁶ |
| 345 | S | bromo | pyridin-3-yl | n-butyl | H | H | H | H | CR⁵ | CR⁶ |
| 346 | S | dimethylamino-methyl | ethyl | 4-fluoro-3-trifluoromethylphenylmethyl | H | H | H | H | CR⁵ | CR⁶ |
| 347 | S | methylamino-methyl | ethyl | 4-fluoro-3-trifluoromethylphenylmethyl | H | H | H | H | CR⁵ | CR⁶ |
| 348 | S | n-propylamino-methyl | ethyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 349 | S | pyrrolidin-1-ylmethyl | ethyl | 4-fluoro-3-trifluoromethylphenylmethyl | H | H | H | H | CR⁵ | CR⁶ |
| 350 | S | bromo | methanesulfonylmethyl | 4-fluoro-3-trifluoromethylphenylmethyl | H | H | H | H | CR⁵ | CR⁶ |
| 351 | S | methyl | 4-methylcarbonylphenyl | 4,4,4-trifluorobutyl | H | H | H | H | CR⁵ | CR⁶ |
| 352 | S | methyl | 4-methylcarbonylphenyl | 4-fluoro-3-trifluoromethylphenylmethyl | H | H | H | H | CR⁵ | CR⁶ |
| 353 | S | methyl | 3-(2-methyl-pyrimidin-4-yl)phenyl | 4-fluoro-3-trifluoromethylphenylmethyl | H | H | H | H | CR⁵ | CR⁶ |
| 354 | S | methyl | 3-(2-methyl-pyrimidin-4-yl)phenyl | 4,4,4-trifluorobutyl | H | H | H | H | CR⁵ | CR⁶ |
| 355 | S | methyl | 8-methoxy-quinolin-5-yl | 4-fluoro-3-trifluoromethylphenylmethyl | H | H | H | H | CR⁵ | CR⁶ |
| 356 | S | methyl | 8-methoxy-quinolin-5-yl | 4,4,4-trifluorobutyl | H | H | H | H | CR⁵ | CR⁶ |
| 357 | S | methyl | 2-methoxypyridin-3-yl | 4-fluoro-3-trifluoromethylphenylmethyl | H | H | H | H | CR⁵ | CR⁶ |
| 358 | S | methyl | 2-dimethylaminopyridin-3-yl | 4-fluoro-3-trifluoromethylphenylmethyl | H | H | H | H | CR⁵ | CR⁶ |
| 359 | S | methyl | 6-methoxypyridin-3-yl | 4-fluoro-3-trifluoromethylphenylmethyl | H | H | H | H | CR⁵ | CR⁶ |
| 360 | S | methyl | 6-dimethylamino-pyridin-3-yl | 4-fluoro-3-trifluoromethylphenylmethyl | H | H | H | H | CR⁵ | CR⁶ |
| 361 | S | 1-hydroxy-1-methyl-ethyl | 4-carboxyphenyl | 4-fluoro-3-trifluoromethylphenylmethyl | H | H | H | H | CR⁵ | CR⁶ |
| 362 | S | H | methanesulfonylmethyl | 4-fluoro-3-trifluoromethylphenylmethyl | H | H | H | H | CR⁵ | CR⁶ |
| 363 | S | methyl | methyl | n-butyl | H | H | H | H | CR⁵ | CR⁶ |
| 364 | S | methyl | methyl | 3,3,3-trifluoropropyl | H | H | H | H | CR⁵ | CR⁶ |
| 365 | S | methyl | methyl | cyclopropylmethyl | H | H | H | H | CR⁵ | CR⁶ |
| 366 | S | methyl | methyl | 2-t-butoxyethyl | H | H | H | H | CR⁵ | CR⁶ |
| 367 | S | methyl | methyl | 3,4-difluorophenylmethyl | H | H | H | H | CR⁵ | CR⁶ |
| 368 | S | methyl | methyl | 4-fluoro-3-trifluoromethylphenylmethyl | H | H | H | H | CR⁵ | CR⁶ |
| 369 | S | methyl | methyl | 4-trifluoromethoxyphenylmethyl | H | H | H | H | CR⁵ | CR⁶ |
| 370 | S | H | 3-cyanophenyl | 4-fluoro-3-trifluoromethylphenylmethyl | H | H | H | H | CR⁵ | CR⁶ |
| 371 | S | methyl | 4-(1-hydroxy-1-methyl-ethyl)phenyl | 4,4,4-trifluorobutyl | H | H | H | H | CR⁵ | CR⁶ |
| 372 | S | methyl | 4-(pyridin-4-yloxy)phenyl | 4,4,4-trifluorobutyl | H | H | H | H | CR⁵ | CR⁶ |
| 373 | S | methyl | 4-(pyridin-3-yloxy)phenyl | 4,4,4-trifluorobutyl | H | H | H | H | CR⁵ | CR⁶ |
| 374 | S | methyl | 4-(1-hydroxy-1-methyl-ethyl)phenyl | 4-fluoro-3-trifluoromethylphenylmethyl | H | H | H | H | CR⁵ | CR⁶ |
| 375 | S | methyl | 3-methoxycarbonylphenyl | 4-fluoro-3-trifluoromethylphenylmethyl | H | F | H | H | CR⁵ | CR⁶ |
| 376 | S | methyl | 3-carboxyphenyl | 4-fluoro-3-trifluoromethylphenylmethyl | H | F | H | H | CR⁵ | CR⁶ |
| 377 | S | methyl | 2-methylthio-pyridin-3-yl | 4-fluoro-3-trifluoromethylphenylmethyl | H | H | H | H | CR⁵ | CR⁶ |
| 378 | S | methyl | 6-methylthiopyridin-3-yl | 4-fluoro-3-trifluoromethylphenylmethyl | H | H | H | H | CR⁵ | CR⁶ |
| 379 | S | H | pyridin-3-yl | 3-methoxycarbonylphenylmethyl | H | H | H | H | CR⁵ | CR⁶ |
| 380 | S | H | pyridin-3-yl | 4-methoxycarbonylphenylmethyl | H | H | H | H | CR⁵ | CR⁶ |
| 381 | S | pyrrolidin-1-ylmethyl | phenyl | 4-fluoro-3-trifluoromethylphenylmethyl | H | H | H | H | CR⁵ | CR⁶ |
| 382 | S | H | methyl | n-butyl | H | H | H | H | CR⁵ | CR⁶ |
| 383 | S | H | pyridin-3-yl | 4,4,4-trifluorobutyl | H | H | H | H | CR⁵ | CR⁶ |
| 384 | S | methyl | 2-oxo-2,3-dihydro-benzooxazol-6-yl | 4,4,4-trifluorobutyl | H | H | H | H | CR⁵ | CR⁶ |
| 385 | S | methylcarbonyl | 4-carboxyphenyl | 3,3,3-trifluoropropyl | H | H | H | H | CR⁵ | CR⁶ |
| 386 | S | methylcarbonyl | 4-bromophenyl | 4-fluoro-3-trifluoromethylphenylmethyl | H | H | H | H | CR⁵ | CR⁶ |
| 387 | S | methylcarbonyl | 4-cyanophenyl | 4-fluoro-3-trifluoromethylphenylmethyl | H | H | H | H | CR⁵ | CR⁶ |
| 388 | S | 1-hydroxy-1- | 4-bromophenyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 389 | S | 1-hydroxy-1-methyl-ethyl methyl-ethyl | 4-methylcarbonylphenyl | 4-fluoro-3-trifluoromethylphenylmethyl | H | H | H | H | CR⁵ | CR⁶ |
| 390 | S | bromo | 4-carboxyphenyl | ethyl | H | H | H | H | CR⁵ | CR⁶ |
| 391 | S | bromo | 4-carboxyphenyl | propyl | H | H | H | H | CR⁵ | CR⁶ |
| 392 | S | bromo | 4-carboxyphenyl | pentyl | H | H | H | H | CR⁵ | CR⁶ |
| 393 | S | bromo | 4-carboxyphenyl | hexyl | H | H | H | H | CR⁵ | CR⁶ |
| 394 | S | bromo | 4-carboxyphenyl | 4,4,4-trifluorobutyl | H | H | H | H | CR⁵ | CR⁶ |
| 395 | S | bromo | 4-carboxyphenyl | 5,5,5-trifluoropentyl | H | H | H | H | CR⁵ | CR⁶ |
| 396 | S | bromo | 4-carboxyphenyl | 2-(cyclopropyl)ethyl | H | H | H | H | CR⁵ | CR⁶ |
| 397 | S | bromo | 4-carboxyphenyl | 3-t-butoxypropyl | H | H | H | H | CR⁵ | CR⁶ |
| 398 | S | methyl | 4-carboxyphenyl | n-butyl | H | H | H | H | CR⁵ | CR⁶ |
| 399 | S | methyl | 4-carboxyphenyl | cyclopropylmethyl | H | H | H | H | CR⁵ | CR⁶ |
| 400 | S | methyl | 4-carboxyphenyl | 2-(cyclopropyl)ethyl | H | H | H | H | CR⁵ | CR⁶ |
| 401 | S | methyl | 4-carboxyphenyl | 2-t-butoxyethyl | H | H | H | H | CR⁵ | CR⁶ |
| 402 | S | methyl | 4-methoxycarbonylphenyl | ethyl | H | H | H | H | CR⁵ | CR⁶ |
| 403 | S | methyl | 4-carboxyphenyl | ethyl | H | H | H | H | CR⁵ | CR⁶ |
| 404 | S | methyl | 4-carboxyphenyl | propyl | H | H | H | H | CR⁵ | CR⁶ |
| 405 | S | bromo | pyridin-3-yl | 3-methoxycarbonylphenylmethyl | H | H | H | H | CR⁵ | CR⁶ |
| 406 | S | bromo | pyridin-3-yl | 4-methoxycarbonylphenylmethyl | H | H | H | H | CR⁵ | CR⁶ |
| 407 | S | bromo | pyridin-3-yl | 4,4,4-trifluorobutyl | H | H | H | H | CR⁵ | CR⁶ |
| 408 | S | chloro | pyridin-3-yl | 4,4,4-trifluorobutyl | H | H | H | H | CR⁵ | CR⁶ |
| 409 | S | methyl | 4-carboxyphenyl | 3,3,3-trifluoropropyl | H | H | H | H | CR⁵ | CR⁶ |
| 410 | S | methyl | 4-carboxyphenyl | 4,4,4-trifluorobutyl | H | H | H | H | CR⁵ | CR⁶ |
| 411 | S | H | 4-cyanophenyl | 4-fluoro-3-trifluoromethylphenylmethyl | H | H | H | H | CR⁵ | CR⁶ |
| 412 | S | methyl | 4-methoxycarbonylphenyl | 4,4,4-trifluorobutyl | H | F | H | H | CR⁵ | CR⁶ |
| 413 | S | H | 4-aminocarbonylphenyl | 4-fluoro-3-trifluoromethylphenylmethyl | H | H | H | H | CR⁵ | CR⁶ |
| 414 | S | H | 4-aminocarbonylphenyl | 4,4,4-trifluorobutyl | H | H | H | H | CR⁵ | CR⁶ |
| 415 | S | 1-hydroxy-1-methyl-ethyl | 4-methoxycarbonylphenyl | 4-fluoro-3-trifluoromethylphenylmethyl | H | H | H | H | CR⁵ | CR⁶ |
| 416 | S | methyl | 4-methoxycarbonylphenyl | 3-t-butoxypropyl | H | H | H | H | CR⁵ | CR⁶ |
| 417 | S | methylamino-methyl | phenyl | 4-fluoro-3-trifluoromethylphenylmethyl | H | H | H | H | CR⁵ | CR⁶ |
| 418 | S | dimethylamino-methyl | phenyl | 4-fluoro-3-trifluoromethylphenylmethyl | H | H | H | H | CR⁵ | CR⁶ |
| 419 | S | formyl | 4-methoxycarbonylphenyl | n-butyl | H | H | H | H | CR⁵ | CR⁶ |
| 420 | S | dimethylamino-methyl | 4-methoxycarbonylphenyl | n-butyl | H | H | H | H | CR⁵ | CR⁶ |
| 421 | S(O₂) | H | phenyl | 4-fluoro-3-trifluoromethylphenylmethyl | H | H | H | H | CR⁵ | CR⁶ |
| 422 | S | methoxy | 4-methoxycarbonylphenyl | n-butyl | H | H | H | H | CR⁵ | CR⁶ |
| 423 | S | methoxy | 4-carboxyphenyl | n-butyl | H | H | H | H | CR⁵ | CR⁶ |
| 424 | S | H | 4-(1H-tetrazol-5-yl)phenyl | 4-fluoro-3-trifluoromethylphenylmethyl | H | H | H | H | CR⁵ | CR⁶ |
| 425 | S | H | 4-(1H-tetrazol-5-yl)phenyl | 4,4,4-trifluorobutyl | H | H | H | H | CR⁵ | CR⁶ |
| 426 | S | methyl | 4-carboxyphenyl | 4,4,4-trifluorobutyl | H | F | H | H | CR⁵ | CR⁶ |
| 427 | S | methyl | 4-carboxyphenyl | 4-fluoro-3-trifluoromethylphenylmethyl | H | F | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 428 | S | bromo | 4-(1H-tetrazol-5-yl)phenyl | n-butyl | H | H | H | H | CR⁵ | CR⁶ |
| 429 | S | bromo | 4-(1H-tetrazol-5-yl)phenyl | 4,4,4-trifluorobutyl | H | H | H | H | CR⁵ | CR⁶ |
| 430 | S(O₂) | H | 4-methoxycarbonylphenyl | n-butyl | H | H | H | H | CR⁵ | CR⁶ |
| 431 | S(O₂) | bromo | phenyl | 4-fluoro-3-trifluoromethylphenylmethyl | H | H | H | H | CR⁵ | CR⁶ |
| 432 | S(O₂) | H | 4-carboxyphenyl | n-butyl | H | H | H | H | CR⁵ | CR⁶ |
| 433 | S(O₂) | bromo | 4-methoxycarbonylphenyl | n-butyl | H | H | H | H | CR⁵ | CR⁶ |
| 434 | S(O₂) | methoxy | 4-carboxyphenyl | n-butyl | H | H | H | H | CR⁵ | CR⁶ |
| 435 | S(O₂) | bromo | 4-carboxyphenyl | n-butyl | H | H | H | H | CR⁵ | CR⁶ |
| 436 | S(O₂) | methoxy | 4-methoxycarbonylphenyl | n-butyl | H | H | H | H | CR⁵ | CR⁶ |
| 437 | S | bromo | 4-carboxyphenyl | cyclobutylmethyl | H | H | H | H | CR⁵ | CR⁶ |
| 438 | S | bromo | 4-carboxyphenyl | cyclopentylmethyl | H | H | H | H | CR⁵ | CR⁶ |
| 439 | S | bromo | 4-carboxyphenyl | bicyclo[2.2.1]hept-2-ylmethyl | H | H | H | H | CR⁵ | CR⁶ |
| 440 | S | bromo | 4-carboxyphenyl | tetrahydropyran-4-ylmethyl | H | H | H | H | CR⁵ | CR⁶ |
| 441 | S | bromo | 4-carboxyphenyl | 2-(dimethylamino)ethyl | H | H | H | H | CR⁵ | CR⁶ |
| 442 | S | H | 4-(5-oxo-4,5-dihydro-[1,2,4]oxadiazol-3-yl)phenyl | n-butyl | H | H | H | H | CR⁵ | CR⁶ |
| 443 | S | bromo | 4-(5-oxo-4,5-dihydro-[1,2,4]oxadiazol-3-yl)phenyl | n-butyl | H | H | H | H | CR⁵ | CR⁶ |
| 444 | S | H | 4-dimethylaminophenyl | n-butyl | H | H | H | H | CR⁵ | CR⁶ |
| 445 | S | H | 4-(pyrrolidin-1-yl)phenyl | n-butyl | H | H | H | H | CR⁵ | CR⁶ |
| 446 | S | H | 4-(morpholin-4-yl)phenyl | n-butyl | H | H | H | H | CR⁵ | CR⁶ |
| 447 | S | H | 4-(1-methyl-piperazin-4-yl)phenyl | n-butyl | H | H | H | H | CR⁵ | CR⁶ |
| 448 | S | methyl | 2-dimethylaminopyridin-3-yl | n-butyl | H | H | H | H | CR⁵ | CR⁶ |
| 449 | S | H | 4-(1H-tetrazol-5-yl)phenyl | n-butyl | H | H | H | H | CR⁵ | CR⁶ |
| 450 | S | methyl | 4-carboxyphenyl | n-butyl | H | F | H | H | CR⁵ | CR⁶ |
| 451 | S | H | 4-carboxyphenyl | 4,4,4-trifluorobutyl | H | H | H | H | CR⁵ | CR⁶ |
| 452 | S | bromo | 4-carboxyphenyl | isobutyl | H | H | H | H | CR⁵ | CR⁶ |
| 453 | S | bromo | 4-carboxyphenyl | 2-(cyclohexyloxy)ethyl | H | H | H | H | CR⁵ | CR⁶ |
| 454 | S | bromo | 4-carboxyphenyl | 3-methoxy-3-methyl-butyl | H | H | H | H | CR⁵ | CR⁶ |
| 455 | S | methyl | 3-(2H-tetrazol-5-yl)phenyl | 4-fluoro-3-trifluoromethylphenylmethyl | H | H | H | H | CR⁵ | CR⁶ |
| 456 | S | H | 4-carboxyphenyl | 3,3,3-trifluoropropyl | H | H | H | H | CR⁵ | CR⁶ |
| 457 | S | dimethyl-aminocarbonyl | phenyl | 4-fluoro-3-trifluoromethylphenylmethyl | H | H | H | H | CR⁵ | CR⁶ |
| 458 | S | methyl-aminocarbonyl | phenyl | 4-fluoro-3-trifluoromethylphenylmethyl | H | H | H | H | CR⁵ | CR⁶ |
| 459 | S | aminocarbonyl | phenyl | 4-fluoro-3-trifluoromethylphenylmethyl | H | H | H | H | CR⁵ | CR⁶ |
| 460 | S(O₂) | methylcarbonyl | phenyl | 4-fluoro-3-trifluoromethylphenylmethyl | H | H | H | H | CR⁵ | CR⁶ |
| 461 | S | H | 3-dimethylaminosulfonylphenyl | 3,3,3-trifluoropropyl | H | H | H | H | CR⁵ | CR⁶ |
| 462 | S | H | 3-dimethylaminosulfonylphenyl | 4-fluoro-3-trifluoromethylphenylmethyl | H | H | H | H | CR⁵ | CR⁶ |
| 463 | S(O₂) | 1-hydroxy-1-methyl-ethyl | phenyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 464 | S(O₂) | 1-hydroxy-ethyl | phenyl | 3,4-difluorophenylmethyl | H | H | H | H | CR⁵ | CR⁶ |
| 465 | S | aminocarbonyl | 4-methoxycarbonylphenyl | n-butyl | H | H | H | H | CR⁵ | CR⁶ |
| 466 | S | methyl-aminocarbonyl | 4-methoxycarbonylphenyl | n-butyl | H | H | H | H | CR⁵ | CR⁶ |
| 467 | S | dimethyl-amino-carbonyl | 4-methoxycarbonylphenyl | n-butyl | H | H | H | H | CR⁵ | CR⁶ |
| 468 | S | aminocarbonyl | 4-carboxyphenyl | n-butyl | H | H | H | H | CR⁵ | CR⁶ |
| 469 | S | dimethyl-amino-carbonyl | 4-carboxyphenyl | n-butyl | H | H | H | H | CR⁵ | CR⁶ |
| 470 | S | H | 4-(2-oxo-2,3-dihydro-2λ4-[1,2,3,5]oxathiadiazol-4-yl)phenyl | n-butyl | H | H | H | H | CR⁵ | CR⁶ |
| 471 | S | H | 4-(N-hydroxy-acetamidinyl)phenyl | n-butyl | H | H | H | H | CR⁵ | CR⁶ |
| 472 | S | H | 4-(N-(methylcarbonyloxy)-acetamidinyl)phenyl | n-butyl | H | H | H | H | CR⁵ | CR⁶ |
| 473 | S | bromo | 4-(N-hydroxy-acetamidinyl)phenyl | n-butyl | H | H | H | H | CR⁵ | CR⁶ |
| 474 | S | bromo | 4-(1H-tetrazol-5-yl)phenyl | cyclopropylmethyl | H | H | H | H | CR⁵ | CR⁶ |
| 475 | S | bromo | 4-(1H-tetrazol-5-yl)phenyl | 4-fluoro-3-trifluoromethylphenylmethyl | H | H | H | H | CR⁵ | CR⁶ |
| 476 | S | H | 4-bromophenyl | 3,3,3-trifluoropropyl | H | H | H | H | CR⁵ | CR⁶ |
| 477 | S | chloro | 4-carboxyphenyl | n-butyl | H | H | H | H | CR⁵ | CR⁶ |
| 478 | S | chloro | 4-carboxyphenyl | cyclopropylmethyl | H | H | H | H | CR⁵ | CR⁶ |
| 479 | S | chloro | 4-carboxyphenyl | 2-(cyclopropyl)ethyl | H | H | H | H | CR⁵ | CR⁶ |
| 480 | S | chloro | 4-carboxyphenyl | 3,3,3-trifluoropropyl | H | H | H | H | CR⁵ | CR⁶ |
| 481 | S | bromo | 4-(5-thioxo-4,5-dihydro-[1,2,4]oxadiazol-3-yl)phenyl | n-butyl | H | H | H | H | CR⁵ | CR⁶ |
| 482 | S | H | 4-(N-hydroxy-acetamidinyl)phenyl | 4-fluoro-3-trifluoromethylphenylmethyl | H | H | H | H | CR⁵ | CR⁶ |
| 483 | S | H | 4-(5-oxo-4,5-dihydro-[1,2,4]oxadiazol-3-yl)phenyl | 4-fluoro-3-trifluoromethylphenylmethyl | H | H | H | H | CR⁵ | CR⁶ |
| 484 | S | bromo | 4-(2-oxo-2,3-dihydro-2λ4-[1,2,3,5]oxathiadiazol-4-yl)phenyl | n-butyl | H | H | H | H | CR⁵ | CR⁶ |
| 485 | S | chloro | 4-(2-oxo-2,3-dihydro-2λ4-[1,2,3,5]oxathiadiazol-4-yl)phenyl | n-butyl | H | H | H | H | CR⁵ | CR⁶ |
| 486 | S | methyl | 4-carboxyphenyl | phenylmethyl | H | H | H | H | CR⁵ | CR⁶ |
| 487 | S | methyl | 4-carboxyphenyl | 4-fluorophenylmethyl | H | H | H | H | CR⁵ | CR⁶ |
| 488 | S | methyl | 4-carboxyphenyl | 3,4-difluorophenylmethyl | H | H | H | H | CR⁵ | CR⁶ |
| 489 | S | methyl | 4-carboxyphenyl | 3-chloro-4-fluorophenylmethyl | H | H | H | H | CR⁵ | CR⁶ |
| 490 | S | methyl | 4-carboxyphenyl | 4-difluoromethoxyphenylmethyl | H | H | H | H | CR⁵ | CR⁶ |
| 491 | S | methyl | 4-carboxyphenyl | 3-trifluoromethylphenylmethyl | H | H | H | H | CR⁵ | CR⁶ |
| 492 | S | methyl | 4-carboxyphenyl | 4-methanesulfonylphenylmethyl | H | H | H | H | CR⁵ | CR⁶ |
| 493 | S | methyl | 4-carboxyphenyl | pentafluorophenylmethyl | H | H | H | H | CR⁵ | CR⁶ |
| 494 | S | methyl | 4-carboxyphenyl | 4-trifluoromethylsulfonylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 495 | S | methyl | 4-carboxyphenyl | pyridin-2-ylmethyl | H | H | H | H | CR⁵ | CR⁶ |
| 496 | S | methyl | 4-carboxyphenyl | 4-trifluoromethoxyphenylmethyl | H | H | H | H | CR⁵ | CR⁶ |
| 497 | S | methyl | 4-carboxyphenyl | 3-fluoro-4-trifluoromethylphenylmethyl | H | H | H | H | CR⁵ | CR⁶ |
| 498 | S | H | 4-nitrophenyl | 3,3,3-trifluoropropyl | H | H | H | H | CR⁵ | CR⁶ |
| 499 | S | H | 4-aminophenyl | 3,3,3-trifluoropropyl | H | H | H | H | CR⁵ | CR⁶ |
| 500 | S | methylcarbonylamino | 4-methoxycarbonylphenyl | n-butyl | H | H | H | H | CR⁵ | CR⁶ |
| 501 | S | cyclopentyl | 4-methoxycarbonylphenyl | 4-fluoro-3-trifluoromethylphenylmethyl | H | H | H | H | CR⁵ | CR⁶ |
| 502 | S | cyclopentyl | 4-carboxyphenyl | 4-fluoro-3-trifluoromethylphenylmethyl | H | H | H | H | CR⁵ | CR⁶ |
| 503 | S | methylcarbonyl | 4-bromophenyl | n-butyl | H | H | H | H | CR⁵ | CR⁶ |
| 504 | S | 1-hydroxy-1-methyl-ethyl | 4-methoxycarbonylphenyl | 3,3,3-trifluoropropyl | H | H | H | H | CR⁵ | CR⁶ |
| 505 | S | 1-hydroxy-1-methyl-ethyl | 4-carboxyphenyl | 3,3,3-trifluoropropyl | H | H | H | H | CR⁵ | CR⁶ |
| 506 | S | 1-hydroxy-1-methyl-ethyl | 4-bromophenyl | n-butyl | H | H | H | H | CR⁵ | CR⁶ |
| 507 | S | H | 4-(methanesulfonylamino)phenyl | 3,3,3-trifluoropropyl | H | H | H | H | CR⁵ | CR⁶ |
| 508 | S | methanesulfonylamino | phenyl | 4-fluoro-3-trifluoromethylphenylmethyl | H | H | H | H | CR⁵ | CR⁶ |
| 509 | S | methylcarbonylamino | phenyl | 4-fluoro-3-trifluoromethylphenylmethyl | H | H | H | H | CR⁵ | CR⁶ |
| 510 | S | methyl | 2-carboxyethyl | 4-fluoro-3-trifluoromethylphenylmethyl | H | H | H | H | CR⁵ | CR⁶ |
| 511 | S | bromo | 4-(5-oxo-4,5-dihydro-[1,2,4]oxadiazol-3-yl)phenyl | 4-fluoro-3-trifluoromethylphenylmethyl | H | H | H | H | CR⁵ | CR⁶ |
| 512 | S | chloro | 4-(5-oxo-4,5-dihydro-[1,2,4]oxadiazol-3-yl)phenyl | 4-fluoro-3-trifluoromethylphenylmethyl | H | H | H | H | CR⁵ | CR⁶ |
| 513 | S | H | 4-(5-oxo-4,5-dihydro-[1,2,4]oxadiazol-3-yl)phenyl | 4,4,4-trifluorobutyl | H | H | H | H | CR⁵ | CR⁶ |
| 514 | S | bromo | 4-(5-oxo-4,5-dihydro-[1,2,4]oxadiazol-3-yl)phenyl | 4,4,4-trifluorobutyl | H | H | H | H | CR⁵ | CR⁶ |
| 515 | S | chloro | 4-(5-oxo-4,5-dihydro-[1,2,4]oxadiazol-3-yl)phenyl | 4,4,4-trifluorobutyl | H | H | H | H | CR⁵ | CR⁶ |
| 516 | S | 1-hydroxy-1-methyl-ethyl | 4-methoxycarbonylphenyl | n-butyl | H | H | H | H | CR⁵ | CR⁶ |
| 517 | S | methyl | 4-carboxyphenyl | 3,4,5-trifluorophenylmethyl | H | H | H | H | CR⁵ | CR⁶ |
| 518 | S | methyl | 4-carboxyphenyl | 4-trifluoromethylphenylmethyl | H | H | H | H | CR⁵ | CR⁶ |
| 519 | S | methyl | 4-carboxyphenyl | 2-fluoro-5-trifluoromethylphenylmethyl | H | H | H | H | CR⁵ | CR⁶ |
| 520 | S | methyl | 4-carboxyphenyl | 2,5-dichlorophenylmethyl | H | H | H | H | CR⁵ | CR⁶ |
| 521 | S | methyl | 4-carboxyphenyl | 4-chloro-3-fluorophenylmethyl | H | H | H | H | CR⁵ | CR⁶ |
| 522 | S | methyl | 4-carboxyphenyl | 4-fluoro-2-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 523 | S | methyl | 4-carboxyphenyl | benzo[1,3]dioxol-5-ylmethyl | H | H | H | H | CR⁵ | CR⁶ |
| 524 | S | methyl | 4-carboxyphenyl | 2,2-difluoro-benzo[1,3]dioxol-5-ylmethyl | H | H | H | H | CR⁵ | CR⁶ |
| 525 | S | methyl | 4-carboxyphenyl | 3,4-dimethoxyphenylmethyl | H | H | H | H | CR⁵ | CR⁶ |
| 526 | S | methyl | 4-carboxyphenyl | 4-trifluoromethylthiophenylmethyl | H | H | H | H | CR⁵ | CR⁶ |
| 527 | S | methyl | 4-carboxythien-2-yl | 4-fluoro-3-trifluoromethylphenylmethyl | H | H | H | H | CR⁵ | CR⁶ |
| 528 | S | methyl | 5-carboxy-3-methyl-thien-2-yl | 4-fluoro-3-trifluoromethylphenylmethyl | H | H | H | H | CR⁵ | CR⁶ |
| 529 | S | methyl | 5-carboxyfuran-2-yl | 4-fluoro-3-trifluoromethylphenylmethyl | H | H | H | H | CR⁵ | CR⁶ |
| 530 | S | chloro | 4-methoxycarbonylphenyl | 4,4,4-trifluorobutyl | H | H | H | H | CR⁵ | CR⁶ |
| 531 | S | chloro | 4-methoxycarbonylphenyl | 5,5,5-trifluoropentyl | H | H | H | H | CR⁵ | CR⁶ |
| 532 | S | H | methylamino | n-butyl | H | H | H | H | CR⁵ | CR⁶ |
| 533 | S | methyl | methylamino | 4-fluoro-3-trifluoromethylphenylmethyl | H | H | H | H | CR⁵ | CR⁶ |
| 534 | S | 1S*-hydroxy-ethyl | ethyl | 4-fluoro-3-trifluoromethylphenylmethyl | H | H | H | H | CR⁵ | CR⁶ |
| 535 | S | 1R*-hydroxy-ethyl | ethyl | 4-fluoro-3-trifluoromethylphenylmethyl | H | H | H | H | CR⁵ | CR⁶ |
| 536 | S(O₂) | dimethylamino | 4-carboxyphenyl | n-butyl | H | H | H | H | CR⁵ | CR⁶ |
| 537 | S | chloro | 4-carboxyphenyl | 4,4,4-trifluorobutyl | H | H | H | H | CR⁵ | CR⁶ |
| 538 | S | chloro | 4-carboxyphenyl | 5,5,5-trifluoropentyl | H | H | H | H | CR⁵ | CR⁶ |
| 539 | S | methyl | 4-(1H-tetrazol-5-yl)phenyl | n-butyl | H | H | H | H | CR⁵ | CR⁶ |
| 540 | S | methyl | 4-(2-oxo-2,3-dihydro-2λ4-[1,2,3,5]oxathiadiazol-4-yl)phenyl | n-butyl | H | H | H | H | CR⁵ | CR⁶ |
| 541 | S | methyl | 4-(5-oxo-4,5-dihydro-[1,2,4]oxadiazol-3-yl)phenyl | n-butyl | H | H | H | H | CR⁵ | CR⁶ |
| 542 | S | methyl | 4-(1H-tetrazol-5-yl)phenyl | 4-fluoro-3-trifluoromethylphenylmethyl | H | H | H | H | CR⁵ | CR⁶ |
| 543 | S | methyl | 4-(2-oxo-2,3-dihydro-2λ4-[1,2,3,5]oxathiadiazol-4-yl)phenyl | 4-fluoro-3-trifluoromethylphenylmethyl | H | H | H | H | CR⁵ | CR⁶ |
| 544 | S | methyl | 4-(5-oxo-4,5-dihydro-[1,2,4]oxadiazol-3-yl)phenyl | 4-fluoro-3-trifluoromethylphenylmethyl | H | H | H | H | CR⁵ | CR⁶ |
| 545 | S | methyl | 4-carboxyphenyl | 5,5,5-trifluoropentyl | H | H | H | H | CR⁵ | CR⁶ |
| 546 | S | methyl | 3-cyanophenyl | 4-fluoro-3-trifluoromethylphenylmethyl | H | H | H | H | CR⁵ | CR⁶ |
| 547 | S | isopropyl | phenyl | 4-fluoro-3-trifluoromethylphenylmethyl | H | H | H | H | CR⁵ | CR⁶ |
| 548 | S | isopropyl | phenyl | 2-(cyclopropyl)ethyl | H | H | H | H | CR⁵ | CR⁶ |
| 549 | S | methyl | 3-cyanophenyl | 2-(cyclopropyl)ethyl | H | H | H | H | CR⁵ | CR⁶ |
| 550 | S | methyl | 3-cyanophenyl | 3,3,3-trifluoropropyl | H | H | H | H | CR⁵ | CR⁶ |
| 551 | S | methyl | 3-cyanophenyl | 4,4,4-trifluorobutyl | H | H | H | H | CR⁵ | CR⁶ |
| 552 | S | methyl | 3-cyanophenyl | 5,5,5-trifluoropentyl | H | H | H | H | CR⁵ | CR⁶ |
| 553 | S | chloro | methylamino | n-butyl | H | H | H | H | CR⁵ | CR⁶ |
| 554 | S | bromo | methylamino | n-butyl | H | H | H | H | CR⁵ | CR⁶ |
| 555 | S | methyl | 4-(hydroxyaminocarbonyl)phenyl | 4-fluoro-3-trifluoromethylphenylmethyl | H | H | H | H | CR⁵ | CR⁶ |
| 556 | S | H | 4-carboxyphenyl | n-butyl | H | H | H | H | CR⁵ | CR⁶ |
| 557 | S | methyl | 4-carboxyphenyl | 4-fluoro-3-trifluoromethylphenylmethyl | H | CF₃ | H | H | CR⁵ | CR⁶ |
| 558 | S | methyl | 4-carboxyphenyl | n-butyl | H | CF₃ | H | H | CR⁵ | CR⁶ |
| 559 | S | bromo | 4-(morpholin-4-yl)phenyl | n-butyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 560 | S | bromo | 4-dimethylaminophenyl | n-butyl | H | H | H | H | CR⁵ | CR⁶ |
| 561 | S | chloro | 4-dimethylaminophenyl | n-butyl | H | H | H | H | CR⁵ | CR⁶ |
| 562 | S | chloro | 4-(morpholin-4-yl)phenyl | n-butyl | H | H | H | H | CR⁵ | CR⁶ |
| 563 | S | isopropyl | 4-methoxycarbonylphenyl | 4-fluoro-3-trifluoromethylphenylmethyl | H | H | H | H | CR⁵ | CR⁶ |
| 564 | S | isopropyl | 4-methoxycarbonylphenyl | 2-(cyclopropyl)ethyl | H | H | H | H | CR⁵ | CR⁶ |
| 565 | S | isopropyl | 4-methoxycarbonylphenyl | 5,5,5-trifluoropentyl | H | H | H | H | CR⁵ | CR⁶ |
| 566 | S | isopropyl | 4-carboxyphenyl | 4-fluoro-3-trifluoromethylphenylmethyl | H | H | H | H | CR⁵ | CR⁶ |
| 567 | S | isopropyl | 4-carboxyphenyl | 2-(cyclopropyl)ethyl | H | H | H | H | CR⁵ | CR⁶ |
| 568 | S | isopropyl | 4-carboxyphenyl | 5,5,5-trifluoropentyl | H | H | H | H | CR⁵ | CR⁶ |
| 569 | S | H | 4-(1H-tetrazol-5-yl)phenyl | 2-(cyclopropyl)ethyl | H | H | H | H | CR⁵ | CR⁶ |
| 570 | S | methyl | 4-(1H-tetrazol-5-yl)phenyl | 2-(cyclopropyl)ethyl | H | H | H | H | CR⁵ | CR⁶ |
| 571 | S | H | 4-(1H-tetrazol-5-yl)phenyl | 3,3,3-trifluoropropyl | H | H | H | H | CR⁵ | CR⁶ |
| 572 | S | methyl | 4-(1H-tetrazol-5-yl)phenyl | 3,3,3-trifluoropropyl | H | H | H | H | CR⁵ | CR⁶ |
| 573 | S | H | 3-cyanophenyl | 3,3,3-trifluoropropyl | H | H | H | H | CR⁵ | CR⁶ |
| 574 | S | H | 3-cyanophenyl | 4,4,4-trifluorobutyl | H | H | H | H | CR⁵ | CR⁶ |
| 575 | S | H | 3-cyanophenyl | 2-(cyclopropyl)ethyl | H | H | H | H | CR⁵ | CR⁶ |
| 576 | S | bromo | 3-(1H-tetrazol-5-yl)phenyl | 4-fluoro-3-trifluoromethylphenylmethyl | H | H | H | H | CR⁵ | CR⁶ |
| 577 | S(O₂) | bromo | phenyl | 2-(cyclopropyl)ethyl | H | H | H | H | CR⁵ | CR⁶ |
| 578 | S | chloro | 3-(1H-tetrazol-5-yl)phenyl | 4-fluoro-3-trifluoromethylphenylmethyl | H | H | H | H | CR⁵ | CR⁶ |
| 579 | S | bromo | 4-(1H-tetrazol-5-yl)phenyl | 5,5,5-trifluoropentyl | H | H | H | H | CR⁵ | CR⁶ |
| 580 | S | chloro | 4-(1H-tetrazol-5-yl)phenyl | 5,5,5-trifluoropentyl | H | H | H | H | CR⁵ | CR⁶ |
| 581 | S | bromo | 4-(2-oxo-2,3-dihydro-2λ4-[1,2,3,5]oxathiadiazol-4-yl)phenyl | 5,5,5-trifluoropentyl | H | H | H | H | CR⁵ | CR⁶ |
| 582 | S | chloro | 4-(2-oxo-2,3-dihydro-2λ4-[1,2,3,5]oxathiadiazol-4-yl)phenyl | 5,5,5-trifluoropentyl | H | H | H | H | CR⁵ | CR⁶ |
| 583 | S | bromo | 4-(5-oxo-4,5-dihydro-[1,2,4]oxadiazol-3-yl)phenyl | 5,5,5-trifluoropentyl | H | H | H | H | CR⁵ | CR⁶ |
| 584 | S | chloro | 4-(5-oxo-4,5-dihydro-[1,2,4]oxadiazol-3-yl)phenyl | 5,5,5-trifluoropentyl | H | H | H | H | CR⁵ | CR⁶ |
| 585 | S | chloro | 4-aminophenyl | 3,3,3-trifluoropropyl | H | H | H | H | CR⁵ | CR⁶ |
| 586 | S | H | 4-amino-3-chlorophenyl | 3,3,3-trifluoropropyl | H | H | H | H | CR⁵ | CR⁶ |
| 587 | S | bromo | 4-aminophenyl | 3,3,3-trifluoropropyl | H | H | H | H | CR⁵ | CR⁶ |
| 588 | S | bromo | 4-amino-3-bromophenyl | 3,3,3-trifluoropropyl | H | H | H | H | CR⁵ | CR⁶ |
| 589 | S | methyl | 4-carboxy-2-fluorophenyl | 2-(cyclopropyl)ethyl | H | H | H | H | CR⁵ | CR⁶ |
| 590 | S | methyl | 4-carboxy-2-fluorophenyl | 3,3,3-trifluoropropyl | H | H | H | H | CR⁵ | CR⁶ |
| 591 | S | methyl | 4-carboxy-2-fluorophenyl | 5,5,5-trifluoropentyl | H | H | H | H | CR⁵ | CR⁶ |
| 592 | S | methyl | 4-carboxy-2-fluorophenyl | 4-fluoro-3-trifluoromethylphenylmethyl | H | H | H | H | CR⁵ | CR⁶ |
| 593 | S | methyl | 4-carboxy-2-fluorophenyl | n-butyl | H | H | H | H | CR⁵ | CR⁶ |
| 594 | S | bromo | 4-(1H-tetrazol-5-yl)phenyl | 2-(cyclopropyl)ethyl | H | H | H | H | CR⁵ | CR⁶ |
| 595 | S | bromo | 4-(1H-tetrazol-5-yl)phenyl | 3,3,3-trifluoropropyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 596 | S | H | 4-(2-oxo-2,3-dihydro-2λ4-[1,2,3,5]oxathiadiazol-4-yl)phenyl | 3,3,3-trifluoropropyl | H | H | H | H | CR⁵ | CR⁶ |
| 597 | S | H | 4-(5-oxo-4,5-dihydro-[1,2,4]oxadiazol-3-yl)phenyl | 3,3,3-trifluoropropyl | H | H | H | H | CR⁵ | CR⁶ |
| 598 | S | methyl | 4-(2-oxo-2,3-dihydro-2λ4-[1,2,3,5]oxathiadiazol-4-yl)-phenyl | 3,3,3-trifluoropropyl | H | H | H | H | CR⁵ | CR⁶ |
| 599 | S | methyl | 4-(5-oxo-4,5-dihydro-[1,2,4]oxadiazol-3-yl)phenyl | 3,3,3-trifluoropropyl | H | H | H | H | CR⁵ | CR⁶ |
| 600 | S | methyl | 2-(methoxycarbonyl)ethyl | 2-(cyclopropyl)ethyl | H | H | H | H | CR⁵ | CR⁶ |
| 601 | S | methyl | 2-(methoxycarbonyl)ethyl | 3,3,3-trifluoropropyl | H | H | H | H | CR⁵ | CR⁶ |
| 602 | S | methyl | 2-(methoxycarbonyl)ethyl | 4,4,4-trifluorobutyl | H | H | H | H | CR⁵ | CR⁶ |
| 603 | S | methyl | 2-(methoxycarbonyl)ethyl | 5,5,5-trifluoropentyl | H | H | H | H | CR⁵ | CR⁶ |
| 604 | S | methyl | 2-carboxyethyl | 3,3,3-trifluoropropyl | H | H | H | H | CR⁵ | CR⁶ |
| 605 | S | methyl | 2-carboxyethyl | 4,4,4-trifluorobutyl | H | H | H | H | CR⁵ | CR⁶ |
| 606 | S | methyl | 2-carboxyethyl | 5,5,5-trifluoropentyl | H | H | H | H | CR⁵ | CR⁶ |
| 607 | S | bromo | 4-(2-oxo-2,3-dihydro-2λ4-[1,2,3,5]oxathiadiazol-4-yl)phenyl | 3,3,3-trifluoropropyl | H | H | H | H | CR⁵ | CR⁶ |
| 608 | S | bromo | 4-(5-oxo-4,5-dihydro-[1,2,4]oxadiazol-3-yl)phenyl | 3,3,3-trifluoropropyl | H | H | H | H | CR⁵ | CR⁶ |
| 609 | S | chloro | 4-(5-oxo-4,5-dihydro-[1,2,4]oxadiazol-3-yl)phenyl | 3,3,3-trifluoropropyl | H | H | H | H | CR⁵ | CR⁶ |
| 610 | S | H | 4-(2-oxo-2,3-dihydro-2λ4-[1,2,3,5]oxathiadiazol-4-yl)-phenyl | 2-(cyclopropyl)ethyl | H | H | H | H | CR⁵ | CR⁶ |
| 611 | S | methyl | 4-(2-oxo-2,3-dihydro-2λ4-[1,2,3,5]oxathiadiazol-4-yl)phenyl | 2-(cyclopropyl)ethyl | H | H | H | H | CR⁵ | CR⁶ |
| 612 | S | H | 4-(5-oxo-4,5-dihydro-[1,2,4]oxadiazol-3-yl)phenyl | 2-(cyclopropyl)ethyl | H | H | H | H | CR⁵ | CR⁶ |
| 613 | S | methyl | 4-(5-oxo-4,5-dihydro-[1,2,4]oxadiazol-3-yl)phenyl | 2-(cyclopropyl)ethyl | H | H | H | H | CR⁵ | CR⁶ |
| 614 | S | methyl | phenyl | 2-(cyclopropyl)ethyl | H | H | H | H | CR⁵ | CR⁶ |
| 615 | S | methyl | phenyl | 3,3,3-trifluoropropyl | H | H | H | H | CR⁵ | CR⁶ |
| 616 | S | methyl | phenyl | 4,4,4-trifluorobutyl | H | H | H | H | CR⁵ | CR⁶ |
| 617 | S | methyl | phenyl | 5,5,5-trifluoropentyl | H | H | H | H | CR⁵ | CR⁶ |
| 618 | S(O₂) | methyl | phenyl | 2-(cyclopropyl)ethyl | H | H | H | H | CR⁵ | CR⁶ |
| 619 | S(O₂) | methyl | phenyl | 3,3,3-trifluoropropyl | H | H | H | H | CR⁵ | CR⁶ |
| 620 | S(O₂) | methyl | phenyl | 4,4,4-trifluorobutyl | H | H | H | H | CR⁵ | CR⁶ |
| 621 | S(O₂) | methyl | phenyl | 5,5,5-trifluoropentyl | H | H | H | H | CR⁵ | CR⁶ |
| 622 | S(O₂) | methyl | phenyl | 4-fluoro-3-trifluoromethylphenylmethyl | H | H | H | H | CR⁵ | CR⁶ |
| 623 | S | methyl | 4-(methanesulfonyl-aminocarbonyl)phenyl | 4-fluoro-3-trifluoromethylphenylmethyl | H | H | H | H | CR⁵ | CR⁶ |
| 624 | S | bromo | 4-(2-oxo-2,3-dihydro-2λ4-[1,2,3,5]oxathiadiazol-4-yl)phenyl | 2-(cyclopropyl)ethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 625 | S | chloro | 4-(2-oxo-2,3-dihydro-2λ4-[1,2,3,5]oxathiadiazol-4-yl)phenyl | 2-(cyclopropyl)ethyl | H | H | H | H | CR⁵ | CR⁶ |
| 626 | S | bromo | 4-(5-oxo-4,5-dihydro-[1,2,4]oxadiazol-3-yl)phenyl | 2-(cyclopropyl)ethyl | H | H | H | H | CR⁵ | CR⁶ |
| 627 | S | chloro | 4-(5-oxo-4,5-dihydro-[1,2,4]oxadiazol-3-yl)phenyl | 2-(cyclopropyl)ethyl | H | H | H | H | CR⁵ | CR⁶ |
| 628 | S | methyl | 4-methoxycarbonylphenyl | 2-(cyclopropyl)ethyl | H | H | H | H | CR⁵ | CR⁶ |
| 629 | S | methyl | 4-methoxycarbonylphenyl | 3,3,3-trifluoropropyl | H | H | H | H | CR⁵ | CR⁶ |
| 630 | S | methyl | 4-methoxycarbonylphenyl | 4,4,4-trifluorobutyl | H | H | H | H | CR⁵ | CR⁶ |
| 631 | S | methyl | 4-methoxycarbonylphenyl | 5,5,5-trifluoropentyl | H | H | H | H | CR⁵ | CR⁶ |
| 632 | S(O₂) | methyl | 4-carboxyphenyl | 2-(cyclopropyl)ethyl | H | H | H | H | CR⁵ | CR⁶ |
| 633 | S(O₂) | methyl | 4-carboxyphenyl | 5,5,5-trifluoropentyl | H | H | H | H | CR⁵ | CR⁶ |
| 634 | S(O₂) | methyl | 4-carboxyphenyl | 4-fluoro-3-trifluoromethylphenylmethyl | H | H | H | H | CR⁵ | CR⁶ |
| 635 | S | chloro | 4-(1H-tetrazol-5-yl)phenyl | 2-(cyclopropyl)ethyl | H | H | H | H | CR⁵ | CR⁶ |
| 636 | S | chloro | 4-(1H-tetrazol-5-yl)phenyl | 3,3,3-trifluoropropyl | H | H | H | H | CR⁵ | CR⁶ |
| 637 | S | methyl | 4-(5-oxo-4,5-dihydro-[1,2,4]thiadiazol-3-yl)phenyl | 3,3,3-trifluoropropyl | H | H | H | H | CR⁵ | CR⁶ |
| 638 | S | H | 4-carboxy-2-fluorophenyl | 2-(cyclopropyl)ethyl | H | H | H | H | CR⁵ | CR⁶ |
| 639 | S | H | 4-carboxy-2-fluorophenyl | 3,3,3-trifluoropropyl | H | H | H | H | CR⁵ | CR⁶ |
| 640 | S | methyl | 4-(5-oxo-4,5-dihydro-[1,2,4]thiadiazol-3-yl)phenyl | 5,5,5-trifluoropentyl | H | H | H | H | CR⁵ | CR⁶ |
| 641 | S | methyl | 4-(5-oxo-4,5-dihydro-[1,2,4]thiadiazol-3-yl)phenyl | 2-(cyclopropyl)ethyl | H | H | H | H | CR⁵ | CR⁶ |
| 642 | S | H | 4-(5-oxo-4,5-dihydro-[1,2,4]thiadiazol-3-yl)phenyl | 2-(cyclopropyl)ethyl | H | H | H | H | CR⁵ | CR⁶ |
| 643 | S(O₂) | dimethylamino | phenyl | 2-(cyclopropyl)ethyl | H | H | H | H | CR⁵ | CR⁶ |
| 644 | S(O₂) | methylamino | phenyl | 2-(cyclopropyl)ethyl | H | H | H | H | CR⁵ | CR⁶ |
| 645 | S(O₂) | 4-methyl-piperazin-1-yl | phenyl | 2-(cyclopropyl)ethyl | H | H | H | H | CR⁵ | CR⁶ |
| 646 | S(O₂) | amino | phenyl | 2-(cyclopropyl)ethyl | H | H | H | H | CR⁵ | CR⁶ |
| 647 | S(O₂) | piperazin-1-yl | phenyl | 2-(cyclopropyl)ethyl | H | H | H | H | CR⁵ | CR⁶ |
| 648 | S(O₂) | methylamino | phenyl | 4-fluoro-3-trifluoromethylphenylmethyl | H | H | H | H | CR⁵ | CR⁶ |
| 649 | S(O₂) | 4-methyl-piperazin-1-yl | phenyl | 4-fluoro-3-trifluoromethylphenylmethyl | H | H | H | H | CR⁵ | CR⁶ |
| 650 | S | bromo | 4-aminophenyl | 4-fluoro-3-trifluoromethylphenylmethyl | H | H | H | H | CR⁵ | CR⁶ |
| 651 | S | bromo | 4-amino-3-bromophenyl | 4-fluoro-3-trifluoromethylphenylmethyl | H | H | H | H | CR⁵ | CR⁶ |
| 652 | S | H | 4-methanesulfonylaminophenyl | 4-fluoro-3-trifluoromethylphenylmethyl | H | H | H | H | CR⁵ | CR⁶ |
| 653 | S | H | 4-aminophenyl | 4-fluoro-3-trifluoromethylphenylmethyl | H | H | H | H | CR⁵ | CR⁶ |
| 654 | S | H | 4-bromophenyl | 2-(cyclopropyl)ethyl | H | H | H | H | CR⁵ | CR⁶ |
| 655 | S | H | 4-bromophenyl | 5,5,5-trifluoropentyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 656 | S | 1-hydroxy-1-methyl-ethyl | 4-bromophenyl | 5,5,5-trifluoropentyl | H | H | H | H | CR⁵ | CR⁶ |
| 657 | S | 1-hydroxy-1-methyl-ethyl | 4-carboxyphenyl | 2-(cyclopropyl)ethyl | H | H | H | H | CR⁵ | CR⁶ |
| 658 | S | 1-hydroxy-1-methyl-ethyl | 4-carboxyphenyl | 5,5,5-trifluoropentyl | H | H | H | H | CR⁵ | CR⁶ |
| 659 | S | chloro | 4-(methanesulfonylamino)phenyl | 4-fluoro-3-trifluoromethylphenylmethyl | H | H | H | H | CR⁵ | CR⁶ |
| 660 | S | bromo | 4-(methanesulfonylamino)phenyl | 4-fluoro-3-trifluoromethylphenylmethyl | H | H | H | H | CR⁵ | CR⁶ |
| 661 | S | bromo | 3-bromo-4-(methanesulfonylamino)phenyl | 4-fluoro-3-trifluoromethylphenylmethyl | H | H | H | H | CR⁵ | CR⁶ |
| 662 | S | methyl | trifluoromethyl | 5,5,5-trifluoropentyl | H | H | H | H | CR⁵ | CR⁶ |
| 663 | S | H | trifluoromethyl | 4-fluoro-3-trifluoromethylphenylmethyl | H | H | H | H | CR⁵ | CR⁶ |
| 664 | S | methyl | trifluoromethyl | 4-fluoro-3-trifluoromethylphenylmethyl | H | H | H | H | CR⁵ | CR⁶ |
| 665 | S | methyl | trifluoromethyl | 2-(cyclopropyl)ethyl | H | H | H | H | CR⁵ | CR⁶ |
| 666 | S | chloro | 4-aminophenyl | 5,5,5-trifluoropentyl | H | H | H | H | CR⁵ | CR⁶ |
| 667 | S | chloro | 4-amino-3-chloro-phenyl | 5,5,5-trifluoropentyl | H | H | H | H | CR⁵ | CR⁶ |
| 668 | S | bromo | 4-aminophenyl | 5,5,5-trifluoropentyl | H | H | H | H | CR⁵ | CR⁶ |
| 669 | S | methyl | 2,2,2-trifluoroethyl | 4-fluoro-3-trifluoromethylphenylmethyl | H | H | H | H | CR⁵ | CR⁶ |
| 670 | S | methyl | 2,2,2-trifluoroethyl | 2-(cyclopropyl)ethyl | H | H | H | H | CR⁵ | CR⁶ |
| 671 | S | methyl | 2,2,2-trifluoroethyl | 3,3,3-trifluoropropyl | H | H | H | H | CR⁵ | CR⁶ |
| 672 | S | methyl | 2,2,2-trifluoroethyl | 4,4,4-trifluorobutyl | H | H | H | H | CR⁵ | CR⁶ |
| 673 | S | methyl | 2,2,2-trifluoroethyl | 5,5,5-trifluoropentyl | H | H | H | H | CR⁵ | CR⁶ |
| 674 | S | cyclopropyl | 4-methoxycarbonylphenyl | 4-fluoro-3-trifluoromethylphenylmethyl | H | H | H | H | CR⁵ | CR⁶ |
| 675 | S | cyclopropyl | 4-carboxyphenyl | 4-fluoro-3-trifluoromethylphenylmethyl | H | H | H | H | CR⁵ | CR⁶ |
| 676 | S | chloro | 4-(methanesulfonylamino)phenyl | 3,3,3-trifluoropropyl | H | H | H | H | CR⁵ | CR⁶ |
| 677 | S | bromo | 4-(methanesulfonylamino)phenyl | 3,3,3-trifluoropropyl | H | H | H | H | CR⁵ | CR⁶ |
| 678 | S | H | 4-(methanesulfonylamino)phenyl | 5,5,5-trifluoropentyl | H | H | H | H | CR⁵ | CR⁶ |
| 679 | S | chloro | 4-(methanesulfonylamino)phenyl | 5,5,5-trifluoropentyl | H | H | H | H | CR⁵ | CR⁶ |
| 680 | S | bromo | 4-(methanesulfonylamino)phenyl | 5,5,5-trifluoropentyl | H | H | H | H | CR⁵ | CR⁶ |
| 681 | S | chloro | 3,5-dichloro-4-methanesulfonylaminophenyl | 3,3,3-trifluoropropyl | H | H | H | H | CR⁵ | CR⁶ |
| 682 | S | chloro | 3,5-dichloro-4-methanesulfonylaminophenyl | 5,5,5-trifluoropentyl | H | H | H | H | CR⁵ | CR⁶ |
| 683 | S | bromo | 3-bromo-4-(methanesulfonylamino)phenyl | 3,3,3-trifluoropropyl | H | H | H | H | CR⁵ | CR⁶ |
| 684 | S | H | 4-(5-oxo-4,5-dihydro-[1,2,4]thiadiazol-3-yl)phenyl | 3,3,3-trifluoropropyl | H | H | H | H | CR⁵ | CR⁶ |
| 685 | S | H | 4-carboxy-2-fluorophenyl | 5,5,5-trifluoropentyl | H | H | H | H | CR⁵ | CR⁶ |
| 686 | S | H | 4-carboxy-2-fluorophenyl | 4-fluoro-3-trifluoromethylphenylmethyl | H | H | H | H | CR⁵ | CR⁶ |
| 687 | S | H | 4-(5-oxo-4,5-dihydro-[1,2,4]thiadiazol-3-yl)-phenyl | 5,5,5-trifluoropentyl | H | H | H | H | CR⁵ | CR⁶ |
| 688 | S | H | 4-methylaminophenyl | 2-(cyclopropyl)ethyl | H | H | H | H | CR⁵ | CR⁶ |
| 689 | S | H | 4-dimethylaminophenyl | 2-(cyclopropyl)ethyl | H | H | H | H | CR⁵ | CR⁶ |
| 690 | S | chloro | 4-methylaminophenyl | 2-(cyclopropyl)ethyl | H | H | H | H | CR⁵ | CR⁶ |
| 691 | S | chloro | 3-chloro-4-methylaminophenyl | 2-(cyclopropyl)ethyl | H | H | H | H | CR⁵ | CR⁶ |
| 692 | S | bromo | 3-bromo-4-methylaminophenyl | 2-(cyclopropyl)ethyl | H | H | H | H | CR⁵ | CR⁶ |
| 693 | S | bromo | 4-methylaminophenyl | 2-(cyclopropyl)ethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 694 | S | chloro | 4-trifluoromethyl-carbonylaminophenyl | 2-(cyclopropyl)ethyl | H | H | H | H | CR⁵ | CR⁶ |
| 695 | S | bromo | 4-trifluoromethyl-carbonylaminophenyl | 4-fluoro-3-trifluoromethylphenylmethyl | H | H | H | H | CR⁵ | CR⁶ |
| 696 | S | cyclobutyl | 4-methoxycarbonylphenyl | 4-fluoro-3-trifluoromethylphenylmethyl | H | H | H | H | CR⁵ | CR⁶ |
| 697 | S | H | 2,2,2-trifluoroethyl | 4-fluoro-3-trifluoromethylphenylmethyl | H | H | H | H | CR⁵ | CR⁶ |
| 698 | S | cyclobutyl | 4-carboxyphenyl | 4-fluoro-3-trifluoromethylphenylmethyl | H | H | H | H | CR⁵ | CR⁶ |
| 699 | S | methyl | 3-hydroxypropyl | 4-fluoro-3-trifluoromethylphenylmethyl | H | H | H | H | CR⁵ | CR⁶ |
| 700 | S | methyl | 2-(2,2,2-trifluoro-acetyl)-1,2,3,4-tetrahydro-isoquinolin-7-yl | 4-fluoro-3-trifluoromethylphenylmethyl | H | H | H | H | CR⁵ | CR⁶ |
| 701 | S | methyl | 4-(2-dimethylaminomethyl-imidazol-1-yl)phenyl | 4-trifluoromethoxyphenylmethyl | H | H | H | H | CR⁵ | CR⁶ |
| 702 | S | bromo | 2,2,2-trifluoroethyl | 4-fluoro-3-trifluoromethylphenylmethyl | H | H | H | H | CR⁵ | CR⁶ |
| 703 | S | chloro | 2,2,2-trifluoroethyl | 4-fluoro-3-trifluoromethylphenylmethyl | H | H | H | H | CR⁵ | CR⁶ |
| 704 | S | hydroxymethyl | 2,2,2-trifluoroethyl | 4-fluoro-3-trifluoromethylphenylmethyl | H | H | H | H | CR⁵ | CR⁶ |
| 705 | S | bromo | methylamino | 4-fluoro-3-trifluoromethylphenylmethyl | H | H | H | H | CR⁵ | CR⁶ |
| 706 | S | bromo | 4-(5-oxo-4,5-dihydro-[1,2,4]thiadiazol-3-yl)phenyl | 2-(cyclopropyl)ethyl | H | H | H | H | CR⁵ | CR⁶ |
| 707 | S | bromo | 4-carboxy-2-fluorophenyl | 5,5,5-trifluoropentyl | H | H | H | H | CR⁵ | CR⁶ |
| 708 | S | bromo | 4-(5-oxo-4,5-dihydro-[1,2,4]thiadiazol-3-yl)phenyl | 3,3,3-trifluoropropyl | H | H | H | H | CR⁵ | CR⁶ |
| 709 | S | bromo | 4-carboxy-2-fluorophenyl | 2-(cyclopropyl)ethyl | H | H | H | H | CR⁵ | CR⁶ |
| 710 | S | bromo | 4-carboxy-2-fluorophenyl | 3,3,3-trifluoropropyl | H | H | H | H | CR⁵ | CR⁶ |
| 711 | S | bromo | 4-carboxy-2-fluorophenyl | 4-fluoro-3-trifluoromethylphenylmethyl | H | H | H | H | CR⁵ | CR⁶ |
| 712 | S | bromo | 4-(5-oxo-4,5-dihydro-[1,2,4]thiadiazol-3-yl)phenyl | 5,5,5-trifluoropentyl | H | H | H | H | CR⁵ | CR⁶ |
| 713 | S | H | 3-methanesulfonylaminophenyl | 3,3,3-trifluoropropyl | H | H | H | H | CR⁵ | CR⁶ |
| 714 | S | chloro | 3-methanesulfonylaminophenyl | 3,3,3-trifluoropropyl | H | H | H | H | CR⁵ | CR⁶ |
| 715 | S | bromo | 3-methanesulfonylaminophenyl | 3,3,3-trifluoropropyl | H | H | H | H | CR⁵ | CR⁶ |
| 716 | S | chloro | 4-methanesulfonylaminophenyl | 2-(cyclopropyl)ethyl | H | H | H | H | CR⁵ | CR⁶ |
| 717 | S | bromo | 4-methanesulfonylaminophenyl | 2-(cyclopropyl)ethyl | H | H | H | H | CR⁵ | CR⁶ |
| 718 | S | chloro | 4-(cyclopropyl-sulfonylamino)phenyl | 2-(cyclopropyl)ethyl | H | H | H | H | CR⁵ | CR⁶ |
| 719 | S | bromo | 4-(cyclopropyl-sulfonylamino)phenyl | 2-(cyclopropyl)ethyl | H | H | H | H | CR⁵ | CR⁶ |
| 720 | S | methyl | benzimidazol-2-yl | 5,5,5-trifluoropentyl | H | H | H | H | CR⁵ | CR⁶ |
| 721 | S | methyl | quinoxalin-5-yl | 5,5,5-trifluoropentyl | H | H | H | H | CR⁵ | CR⁶ |
| 722 | S | methyl | 1-methyl-benzimidazol-2-yl | 4-fluoro-3-trifluoromethylphenylmethyl | H | H | H | H | CR⁵ | CR⁶ |
| 723 | S | methyl | quinoxalin-5-yl | 4-fluoro-3-trifluoromethylphenylmethyl | H | H | H | H | CR⁵ | CR⁶ |
| 724 | S | methyl | 2-formylethyl | 4-fluoro-3-trifluoromethylphenylmethyl | H | H | H | H | CR⁵ | CR⁶ |
| 725 | S | methyl | 3-hydroxy-3-methyl-butyl | 4-fluoro-3-trifluoromethylphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 726 | S | methyl | benzimidazol-2-yl | 2-(cyclopropyl)ethyl | H | H | H | H | CR⁵ | CR⁶ |
| 727 | S | methyl | 5-chloro-1-methyl-benzimidazol-2-yl | 5,5,5-trifluoropentyl | H | H | H | H | CR⁵ | CR⁶ |
| 728 | S | methyl | benzimidazol-2-yl | 4-fluoro-3-trifluoromethylphenylmethyl | H | H | H | H | CR⁵ | CR⁶ |
| 729 | S | methyl | benzimidazol-2-yl | 4-trifluoromethoxyphenylmethyl | H | H | H | H | CR⁵ | CR⁶ |
| 730 | S | methylcarbonyl | 4-bromophenyl | 4-fluorophenylmethyl | H | H | H | H | CR⁵ | CR⁶ |
| 731 | S | methylcarbonyl | 4-bromophenyl | 4-trifluoromethoxyphenylmethyl | H | H | H | H | CR⁵ | CR⁶ |
| 732 | S | methylcarbonyl | 4-bromophenyl | phenylmethyl | H | H | H | H | CR⁵ | CR⁶ |
| 733 | S | methylcarbonyl | 4-bromophenyl | 3-chloro-4-fluorophenylmethyl | H | H | H | H | CR⁵ | CR⁶ |
| 734 | S | 1-hydroxy-1-methyl-ethyl | 4-bromophenyl | 4-fluorophenylmethyl | H | H | H | H | CR⁵ | CR⁶ |
| 735 | S | 1-hydroxy-1-methyl-ethyl | 4-bromophenyl | 4-trifluoromethoxyphenylmethyl | H | H | H | H | CR⁵ | CR⁶ |
| 736 | S | 1-hydroxy-1-methyl-ethyl | 4-bromophenyl | phenylmethyl | H | H | H | H | CR⁵ | CR⁶ |
| 737 | S | 1-hydroxy-1-methyl-ethyl | 4-bromophenyl | 3-chloro-4-fluorophenylmethyl | H | H | H | H | CR⁵ | CR⁶ |
| 738 | S | methyl | 4-dimethylaminophenyl | 2-(cyclopropyl)ethyl | H | H | H | H | CR⁵ | CR⁶ |
| 739 | S | methyl | 4-diethylaminophenyl | 2-(cyclopropyl)ethyl | H | H | H | H | CR⁵ | CR⁶ |
| 740 | S | methyl | 4-(thiomorpholin-4-yl)phenyl | 2-(cyclopropyl)ethyl | H | H | H | H | CR⁵ | CR⁶ |
| 741 | S | methyl | 4-(morpholin-4-yl)phenyl | 2-(cyclopropyl)ethyl | H | H | H | H | CR⁵ | CR⁶ |
| 742 | S | methyl | 4-(piperazin-1-yl)phenyl | 2-(cyclopropyl)ethyl | H | H | H | H | CR⁵ | CR⁶ |
| 743 | S | H | 4-methanesulfonylamino)-2-methoxyphenyl | 4-fluoro-3-trifluoromethylphenylmethyl | H | H | H | H | CR⁵ | CR⁶ |
| 744 | S | chloro | 4-methanesulfonylamino-2-methoxyphenyl | 4-fluoro-3-trifluoromethylphenylmethyl | H | H | H | H | CR⁵ | CR⁶ |
| 745 | S | methyl | 1-methyl-benzimidazol-2-yl | 2-(cyclopropyl)ethyl | H | H | H | H | CR⁵ | CR⁶ |
| 746 | S | methyl | 1-methyl-benzimidazol-2-yl | 4-trifluoromethoxyphenylmethyl | H | H | H | H | CR⁵ | CR⁶ |
| 747 | S | methyl | 2-amino-indan-5-yl | 4-fluoro-3-trifluoromethylphenylmethyl | H | H | H | H | CR⁵ | CR⁶ |
| 748 | S | methyl | 4-dimethylaminophenyl | 5,5,5-trifluoropentyl | H | H | H | H | CR⁵ | CR⁶ |
| 749 | S | methyl | 4-(thiomorpholin-4-yl)phenyl | 5,5,5-trifluoropentyl | H | H | H | H | CR⁵ | CR⁶ |
| 750 | S | methyl | 4-(morpholin-4-yl)phenyl | 5,5,5-trifluoropentyl | H | H | H | H | CR⁵ | CR⁶ |
| 751 | S | methyl | 4-(piperidin-1-yl)phenyl | 2-(cyclopropyl)ethyl | H | H | H | H | CR⁵ | CR⁶ |
| 752 | S | methyl | 4-(piperidin-1-yl)phenyl | 5,5,5-trifluoropentyl | H | H | H | H | CR⁵ | CR⁶ |
| 753 | S | cyclopropyl | 4-methoxycarbonylphenyl | 4-trifluoromethoxyphenylmethyl | H | H | H | H | CR⁵ | CR⁶ |
| 754 | S | cyclobutyl | 4-methoxycarbonylphenyl | 4-trifluoromethoxyphenylmethyl | H | H | H | H | CR⁵ | CR⁶ |
| 755 | S | cyclopropyl | 4-carboxyphenyl | 4-trifluoromethoxyphenylmethyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 756 | S | cyclobutyl | 4-carboxyphenyl | 4-trifluoromethoxyphenylmethyl | H | H | H | H | CR⁵ | CR⁶ |
| 757 | S | methyl | 3-(methoxycarbonyl)propyl | 4-fluoro-3-trifluoromethylphenylmethyl | H | H | H | H | CR⁵ | CR⁶ |
| 758 | S | methyl | 4-hydroxybutyl | 4-fluoro-3-trifluoromethylphenylmethyl | H | H | H | H | CR⁵ | CR⁶ |
| 759 | S | methyl | 4-hydroxy-4-methylpentyl | 4-fluoro-3-trifluoromethylphenylmethyl | H | H | H | H | CR⁵ | CR⁶ |
| 760 | S | methyl | 2-(methoxycarbonyl)ethyl | 3-trifluoromethoxyphenylmethyl | H | H | H | H | CR⁵ | CR⁶ |
| 761 | S | methyl | methoxycarbonylmethyl | 4-trifluoromethoxyphenylmethyl | H | H | H | H | CR⁵ | CR⁶ |
| 762 | S | methyl | 2-carboxyethyl | 3-trifluoromethoxyphenylmethyl | H | H | H | H | CR⁵ | CR⁶ |
| 763 | S | methyl | 3-hydroxy-3-methyl-butyl | 3-trifluoromethoxyphenylmethyl | H | H | H | H | CR⁵ | CR⁶ |
| 764 | S | methyl | 3-hydroxypropyl | 3-trifluoromethoxyphenylmethyl | H | H | H | H | CR⁵ | CR⁶ |
| 765 | S | methyl | 3-carboxypropyl | 4-fluoro-3-trifluoromethylphenylmethyl | H | H | H | H | CR⁵ | CR⁶ |
| 766 | S | chloro | 5-chloro-2-methoxy-4-(methanesulfonylamino)phenyl | 4-fluoro-3-trifluoromethylphenylmethyl | | | | | | |
| 767 | S | methyl | 2-methyl-1,2,3,4-tetrahydro-isoquinolin-7-yl | 4-fluoro-3-trifluoromethylphenylmethyl | H | H | H | H | CR⁵ | CR⁶ |
| 768 | S | isopropenyl | ethyl | 4-chloro-2-fluoro-5-methoxyphenylmethyl | H | H | H | H | CR⁵ | CR⁶ |
| 769 | S | methyl | 3-bromopropyl | 3-trifluoromethoxyphenylmethyl | H | H | H | H | CR⁵ | CR⁶ |
| 770 | S | methyl | cyclopropyl | 3-trifluoromethoxyphenylmethyl | H | H | H | H | CR⁵ | CR⁶ |
| 771 | S | methyl | 4-bromobutyl | 4-fluoro-3-trifluoromethylphenylmethyl | H | H | H | H | CR⁵ | CR⁶ |
| 772 | S | methylcarbonyl | 4-cyanophenyl | 4-trifluoromethoxyphenylmethyl | H | H | H | H | CR⁵ | CR⁶ |
| 773 | S | methylcarbonyl | 4-cyanophenyl | 5,5,5-trifluoropentyl | H | H | H | H | CR⁵ | CR⁶ |
| 774 | S | methyl | 4-carboxy-3-fluorophenyl | 4-trifluoromethoxyphenylmethyl | H | H | H | H | CR⁵ | CR⁶ |
| 775 | S | methyl | 4-carboxy-3-fluorophenyl | 4-fluoro-3-trifluoromethylphenylmethyl | H | H | H | H | CR⁵ | CR⁶ |
| 776 | S | 1-hydroxy-1-methyl-ethyl | ethyl | 2-fluoro-3-methoxyphenylmethyl | H | H | H | H | CR⁵ | CR⁶ |
| 777 | S | methyl | 4-(4-methyl-piperazin-1-ylcarbonyl)phenyl | 2-(cyclopropyl)ethyl | H | H | H | H | CR⁵ | CR⁶ |
| 778 | S | methyl | 3-(imidazol-1-yl)propyl | 3-trifluoromethoxyphenylmethyl | H | H | H | H | CR⁵ | CR⁶ |
| 779 | S | methyl | 4-(imidazol-1-yl)butyl | 4-fluoro-3-trifluoromethylphenylmethyl | H | H | H | H | CR⁵ | CR⁶ |
| 780 | S | chloro | 2-hydroxy-4-(methanesulfonylamino)phenyl | 4-fluoro-3-trifluoromethylphenylmethyl | H | H | H | H | CR⁵ | CR⁶ |
| 781 | S | 1-hydroxy-1-methyl-ethyl | 4-carboxyphenyl | 4-trifluoromethoxyphenylmethyl | H | H | H | H | CR⁵ | CR⁶ |
| 782 | S | methyl | 4-(pyrrolidin-3S-ylaminocarbonyl)-phenyl | 2-(cyclopropyl)ethyl | H | H | H | H | CR⁵ | CR⁶ |
| 783 | S | methyl | 4-(pyrrolidin-3R-ylaminocarbonyl)-phenyl | 2-(cyclopropyl)ethyl | H | H | H | H | CR⁵ | CR⁶ |
| 784 | S | methyl | 4-(5-oxo-4,5-dihydro-[1,2,4]thiadiazol-3-yl)phenyl | 4-fluoro-3-trifluoromethylphenylmethyl | H | H | H | H | CR⁵ | CR⁶ |
| 785 | S | methyl | 4-(1H-tetrazol-5-yl)phenyl | 4-trifluoromethoxyphenylmethyl | H | H | H | H | CR⁵ | CR⁶ |
| 786 | S | methyl | 6-dimethylamino-pyridin-3-yl | 2-(cyclopropyl)ethyl | H | H | H | H | CR⁵ | CR⁶ |
| 787 | S | methyl | 6-(dimethylamino)pyridin-3-yl | 5,5,5-trifluoropentyl | H | H | H | H | CR⁵ | CR⁶ |
| 788 | S | methyl | 6-(morpholin-4-yl)pyridin-3-yl | 5,5,5-trifluoropentyl | H | H | H | H | CR⁵ | CR⁶ |

TABLE 1-continued

| Cpd No. | G | Y | R¹ | R² | R³ | R⁴ | R⁵ | R⁶ | A | B |
|---|---|---|---|---|---|---|---|---|---|---|
| 789 | S | methyl | 6-(dimethylamino)pyridin-3-yl | 4-trifluoromethoxyphenylmethyl | H | H | H | H | CR⁵ | CR⁶ |
| 790 | S | methyl | 6-(morpholin-4-yl)pyridin-3-yl | 4-trifluoromethoxyphenylmethyl | H | H | H | H | CR⁵ | CR⁶ |
| 791 | S | methyl | methoxycarbonylmethyl | 4-fluoro-3-trifluoromethylphenylmethyl | H | H | H | H | CR⁵ | CR⁶ |
| 792 | S | methyl | carboxymethyl | 4-fluoro-3-trifluoromethylphenylmethyl | H | H | H | H | CR⁵ | CR⁶ |
| 793 | S | methyl | 2-hydroxyethyl | 4-fluoro-3-trifluoromethylphenylmethyl | H | H | H | H | CR⁵ | CR⁶ |
| 794 | S | methyl | 2-methoxycarbonylethyl | 4-trifluoromethoxyphenylmethyl | H | H | H | H | CR⁵ | CR⁶ |
| 795 | S | methyl | 2-carboxyethyl | 4-trifluoromethoxyphenylmethyl | H | H | H | H | CR⁵ | CR⁶ |
| 796 | S | methyl | 3-hydroxy-3-methyl-butyl | 4-trifluoromethoxyphenylmethyl | H | H | H | H | CR⁵ | CR⁶ |
| 797 | S | methyl | 2-bromoethyl | 4-fluoro-3-trifluoromethylphenylmethyl | H | H | H | H | CR⁵ | CR⁶ |
| 798 | S | methyl | 6-(morpholin-4-yl)pyridin-3-yl | 2-(cyclopropyl)ethyl | H | H | H | H | CR⁵ | CR⁶ |
| 799 | S | methyl | 4-dimethylaminophenyl | 4-trifluoromethoxyphenylmethyl | H | H | H | H | CR⁵ | CR⁶ |
| 800 | S | methyl | 4-(morpholin-4-yl)phenyl | 4-trifluoromethoxyphenylmethyl | H | H | H | H | CR⁵ | CR⁶ |
| 801 | S | methyl | 4-(5-oxo-4,5-dihydro-[1,2,4]oxadiazol-3-yl)phenyl | 4-trifluoromethoxyphenylmethyl | H | H | H | H | CR⁵ | CR⁶ |
| 802 | S | 1-hydroxy-1-methyl-ethyl | ethyl | 2,4,5-trifluoro-3-methoxyphenylmethyl | H | H | H | H | CR⁵ | CR⁶ |
| 803 | S | isopropenyl | ethyl | 2,4,5-trifluoro-3-methoxyphenylmethyl | H | H | H | H | CR⁵ | CR⁶ |
| 804 | S | methyl | 6-(1H-tetrazol-5-yl)pyridin-3-yl | 2-(cyclopropyl)ethyl | H | H | H | H | CR⁵ | CR⁶ |
| 805 | S | methyl | 6-(1H-tetrazol-5-yl)pyridin-3-yl | 4-trifluoromethoxyphenylmethyl | H | H | H | H | CR⁵ | CR⁶ |
| 806 | S | methyl | 6-(1H-tetrazol-5-yl)pyridin-3-yl | 5,5,5-trifluoropentyl | H | H | H | H | CR⁵ | CR⁶ |
| 807 | S | methyl | 6-(5-oxo-4,5-dihydro-[1,2,4]oxadiazol-3-yl)pyridin-3-yl | 2-(cyclopropyl)ethyl | H | H | H | H | CR⁵ | CR⁶ |
| 808 | S | methyl | 6-(5-oxo-4,5-dihydro-[1,2,4]oxadiazol-3-yl)pyridin-3-yl | 4-trifluoromethoxyphenylmethyl | H | H | H | H | CR⁵ | CR⁶ |
| 809 | S | methyl | 6-(5-oxo-4,5-dihydro-[1,2,4]oxadiazol-3-yl)pyridin-3-yl | 5,5,5-trifluoropentyl | H | H | H | H | CR⁵ | CR⁶ |
| 810 | S | methyl | 4-(5-oxo-4,5-dihydro-[1,2,4]thiadiazol-3-yl)phenyl | 4-trifluoromethoxyphenylmethyl | H | H | H | H | CR⁵ | CR⁶ |
| 811 | S | methyl | 4-(5-oxo-4,5-dihydro-1H-[1,2,4]triazol-3-yl)phenyl | 5,5,5-trifluoropentyl | H | H | H | H | CR⁵ | CR⁶ |
| 812 | S | methyl | 4-(1-methyl-5-oxo-4,5-dihydro-1H-[1,2,4]triazol-3-yl)phenyl | 5,5,5-trifluoropentyl | H | H | H | H | CR⁵ | CR⁶ |
| 813 | S | chloro | phenyl | 4-fluoro-3-trifluoromethylphenylmethyl | H | H | H | NA | CR⁵ | N |
| 814 | S | chloro | 3-carboxyphenyl | 4-fluoro-3-trifluoromethylphenylmethyl | H | H | H | NA | CR⁵ | N |
| 815 | S | chloro | 4-carboxyphenyl | 3,3,3-trifluoropropyl | H | H | H | NA | CR⁵ | N |

TABLE 1-continued

| Cpd No. | G | Y | R¹ | R² | R³ | R⁴ | R⁵ | R⁶ | A | B |
|---|---|---|---|---|---|---|---|---|---|---|
| 816 | S | chloro | 3-methoxycarbonylphenyl | 4-fluoro-3-trifluoromethylphenylmethyl | H | H | H | NA | CR⁵ | N |
| 817 | S | H | phenyl | 3-fluoropropyl | H | H | H | H | CR⁵ | CR⁶ |
| 818 | S | methyl | phenyl | 2-fluoroethyl | H | H | H | H | CR⁵ | CR⁶ |
| 819 | S | methyl | phenyl | 3-fluoropropyl | H | H | H | H | CR⁵ | CR⁶ |
| 820 | S | hydroxymethyl | phenyl | 3-fluoropropyl | H | H | H | H | CR⁵ | CR⁶ |
| 821 | S | 1-hydroxy-ethyl | phenyl | 3-fluoropropyl | H | H | H | H | CR⁵ | CR⁶ |
| 822 | S | 1-methoxy-ethyl | phenyl | 3-fluoropropyl | H | H | H | H | CR⁵ | CR⁶ |
| 823 | S | methyl | 4-methoxycarbonylphenyl | 3-fluoropropyl | H | H | H | H | CR⁵ | CR⁶ |
| 824 | S | methyl | 4-carboxyphenyl | 3-fluoropropyl | H | H | H | H | CR⁵ | CR⁶ |
| 825 | S | methyl | 3,4-difluorophenyl | phenylmethyl | H | H | H | H | CR⁵ | CR⁶ |
| 826 | S | methyl | 3,4-difluorophenyl | 4-fluorophenylmethyl | H | H | H | H | CR⁵ | CR⁶ |
| 827 | S | 1-hydroxy-ethyl | ethyl | 4-fluoro-3-methoxyphenylmethyl | H | H | H | H | CR⁵ | CR⁶ |
| 828 | S | H | ethyl | 4-fluoro-3-methoxyphenylmethyl | H | H | H | H | CR⁵ | CR⁶ |
| 829 | S | methyl | ethyl | 2-fluoropyridin-4-ylmethyl | H | H | H | H | CR⁵ | CR⁶ |
| 830 | S | 1-hydroxy-1-methyl-ethyl | phenyl | 3-fluoropropyl | H | H | H | H | CR⁵ | CR⁶ |
| 831 | S | methyl | 3,4-difluorophenyl | 3-fluoropropyl | H | H | H | H | CR⁵ | CR⁶ |
| 832 | S | methoxymethyl | phenyl | 3-fluoropropyl | H | H | H | H | CR⁵ | CR⁶ |
| 833 | S | methylcarbonyl | phenyl | 3-fluoropropyl | H | H | H | H | CR⁵ | CR⁶ |
| 834 | S | hydroxymethyl | 2,5-dibromophenyl | 3,4-difluorophenylmethyl | H | H | H | H | CR⁵ | CR⁶ |
| 835 | S | 1-hydroxy-ethyl | ethyl | 2-fluoro-pyridin-4-ylmethyl | H | H | H | H | CR⁵ | CR⁶ |
| 836 | S | 1-hydroxy-1-methyl-ethyl | ethyl | 2-fluoropyridin-4-ylmethyl | H | H | H | H | CR⁵ | CR⁶ |
| 837 | S | methylcarbonyl | ethyl | 4-fluoro-3-methoxyphenylmethyl | H | H | H | H | CR⁵ | CR⁶ |
| 838 | S | 1-hydroxy-1-methyl-ethyl | ethyl | 4-fluoro-3-methoxyphenylmethyl | H | H | H | H | CR⁵ | CR⁶ |
| 839 | S | 1-methoxy-ethyl | ethyl | 4-fluoro-3-trifluoromethylphenylmethyl | H | H | H | H | CR⁵ | CR⁶ |
| 840 | S | methyl | ethyl | 2,3,5-trifluoro-pyridin-4-ylmethyl | H | H | H | H | CR⁵ | CR⁶ |
| 841 | S | methyl | 3,4-difluorophenyl | 2-fluoroethyl | H | H | H | H | CR⁵ | CR⁶ |
| 842 | S | H | 4-methoxycarbonylphenyl | 3-fluoropropyl | H | H | H | H | CR⁵ | CR⁶ |
| 843 | S | H | 4-methoxycarbonylphenyl | 2-fluoroethyl | H | H | H | H | CR⁵ | CR⁶ |
| 844 | S | H | phenyl | 2-fluoroethyl | H | H | H | H | CR⁵ | CR⁶ |
| 845 | S | methyl | 3-fluoro-4-(4-fluorophenylmethoxy)phenyl | 4-fluorophenylmethyl | H | H | H | H | CR⁵ | CR⁶ |
| 846 | S | methyl | 3-fluoro-4-(phenylmethoxy)phenyl | phenylmethyl | H | H | H | H | CR⁵ | CR⁶ |
| 847 | S | H | ethyl | 2-fluoropyridin-4-ylmethyl | H | H | H | H | CR⁵ | CR⁶ |
| 848 | S | methylcarbonyl | ethyl | 2-fluoropyridin-4-ylmethyl | H | H | H | H | CR⁵ | CR⁶ |
| 849 | S | bromo | n-butylamino | n-butyl | H | H | H | H | CR⁵ | CR⁶ |
| 850 | S | H | n-butylamino | n-butyl | H | H | H | H | CR⁵ | CR⁶ |

BIOLOGICAL EXAMPLES

Example 1a

In Vitro Canine TRPM8 Functional Assay

The functional activity of compounds of the formula (I) was determined by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

At 24 hrs prior to assay, HEK293 cells stably expressing canine TRPM8 were seeded in culture medium in black wall, clear-base poly-D-lysine coated 384-well plates (BD Biosciences, NJ, USA) and grown overnight in 5% $CO_2$ at 37° C. On assay day, growth media was removed and cells were loaded with Calcium 3 Dye (Molecular Devices) for 35 min at 37° C., under 5% $CO_2$ and then for 25 min at room temperature and atmosphere. Subsequently, cells were tested for agonist-induced increases in intracellular $Ca^{2+}$ levels using FLIPR™ or FDSS. Cells were challenged with a compound of the Formula (I) (at varying concentrations) and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point dose-response studies. Curves were generated using the average of quadruplicate wells for each data point. The resultant data are displayed in Table 2.

TABLE 2

| Cpd No. | $IC_{50}$ (μM) | % Inh @ 0.2 (μM) | % Inh @ 0.5 (μM) |
|---|---|---|---|
| 1 | 0.0240 | | 100 |
| 2 | 0.0163* | | 99 |
| 3 | 0.0350 | | 98 |
| 4 | 0.0040 | | 97 |
| 5 | 0.0630 | | 97 |
| 6 | 0.0113* | | 99 |
| 7 | 0.0073* | | 97 |
| 8 | 0.0100 | | 99 |
| 9 | 0.0470 | | 98 |
| 10 | 0.2290 | | 89 |
| 11 | 0.0330 | | 97 |
| 12 | 0.0060 | | 97 |
| 13 | 0.0030 | | 97 |
| 14 | 0.0189* | | 99 |
| 15 | 0.0050 | | 96 |
| 16 | 0.0060 | | 99 |
| 17 | 0.0220 | | 97 |
| 18 | 0.0810 | | 94 |
| 19 | | | 58 |
| 20 | 0.0060 | | 98 |
| 21 | 0.0150 | | 98 |
| 22 | 0.0320 | | 98 |
| 23 | 0.0260 | | 99 |
| 24 | 0.0088* | | 100 |
| 25 | 0.0210 | | 99 |
| 26 | 0.0200 | | 98 |
| 27 | 0.0200 | | 99 |
| 28 | 0.0320 | | 100 |
| 29 | 0.0330 | | 99 |
| 30 | 0.0120 | | 100 |
| 31 | 0.0220 | | 100 |
| 32 | 0.0370 | | 100 |
| 33 | 0.0574 | | 100 |
| 34 | 0.1841 | | 98 |
| 35 | 0.0608 | | 100 |
| 36 | 0.0771 | | 98 |
| 37 | 0.0983 | | 96 |
| 38 | 0.0030 | | 97 |
| 39 | 0.0039 | | 101 |
| 40 | 0.0137 | | 97 |
| 41 | 0.0054 | | 99 |
| 42 | 0.0106 | | 100 |
| 43 | 0.0250 | | 94 |
| 44 | 0.0070 | | 98 |
| 45 | 0.0520 | 97 | |
| 46 | 0.0840 | | 99 |
| 47 | 0.1120 | | 97 |
| 48 | 0.0790 | | 98 |
| 49 | 0.1700 | | 90 |
| 50 | 0.0660 | | 99 |
| 51 | 0.0780 | | 98 |
| 52 | 0.1160 | | 99 |
| 53 | 0.1640 | | 97 |
| 54 | | | 65 |
| 55 | 0.0655 | | 99 |
| 56 | 0.1031 | | 99 |
| 57 | 0.1080 | | 100 |
| 58 | 0.0455* | | 98 |
| 59 | 0.0445 | | 98 |
| 60 | 0.0283 | | 97 |
| 61 | 0.0524 | | 95 |
| 62 | 0.0581 | | 98 |
| 63 | 0.0740 | | 98 |
| 64 | 0.0190 | 96 | |
| 65 | 0.0170 | 97 | |
| 66 | 0.0040 | 96 | |
| 67 | 0.0550 | 77 | |
| 68 | 0.0020 | 99 | |
| 69 | 0.0030 | 96 | |
| 70 | 0.0070 | 99 | |
| 71 | 0.0180 | 98 | |
| 72 | 0.0260 | 99 | |
| 73 | | 24 | |
| 74 | 0.0210 | 97 | |
| 75 | 0.0180 | 98 | |
| 76 | 0.0210 | 95 | |
| 77 | 0.0220 | 97 | |
| 78 | 0.0225 | 102 | |
| 79 | | 69 | |
| 80 | 0.0290 | | 98 |
| 81 | 0.0150 | | 99 |
| 82 | 0.3190 | | 87 |
| 83 | 0.0480 | | 101 |
| 84 | 0.0350 | | 100 |
| 85 | 0.0240 | | 100 |
| 86 | 0.0530 | | 101 |
| 87 | 0.1700 | | 94 |
| 88 | 0.2610 | | 88 |
| 89 | 0.2050 | | 96 |
| 90 | 0.0210 | | 99 |
| 91 | | | 33 |
| 92 | 0.0682 | 79 | |
| 93 | 0.0110 | 98 | |
| 94 | 0.0180 | 98 | |
| 95 | 0.0060 | 97 | |
| 96 | 0.0040 | 98 | |
| 97 | 0.0140 | 96 | |
| 98 | 0.0150 | 97 | |
| 99 | 0.0180 | 99 | |
| 100 | 0.0068 | 103 | |
| 101 | 0.0305 | 101 | |
| 102 | 0.0402 | 98 | |
| 103 | 0.0908 | 80 | |
| 104 | 0.0089 | 98 | |
| 105 | | 20 | |
| 106 | 0.0190 | 93 | |
| 107 | | 72 | |
| 108 | | 71 | |
| 109 | | 14 | |
| 110 | 0.0072 | 97 | |
| 111 | 0.0920 | 68 | |
| 112 | 0.0302 | 95 | |

TABLE 2-continued

| Cpd No. | IC$_{50}$ (μM) | % Inh @ 0.2 (μM) | % Inh @ 0.5 (μM) |
|---|---|---|---|
| 113 |  | 19 |  |
| 114 | 0.0511* | 93 |  |
| 115 | 0.0795 |  | 95 |
| 116 | 0.1017 |  | 98 |
| 117 | 0.0537 |  | 99 |
| 118 | 0.0480 |  | 100 |
| 119 | 0.1336 |  | 93 |
| 120 | 0.1560 | 75 |  |
| 121 | 0.0350 | 86 |  |
| 122 |  | 23 |  |
| 123 |  | 60 |  |
| 124 |  | 14 |  |
| 125 | 0.0050* |  | 99 |
| 126 |  |  | 45 |
| 127 | 0.0080 |  | 98 |
| 128 | 0.0090 |  | 99 |
| 129 | 0.0028* |  | 101 |
| 130 | 0.1040 |  | 98 |
| 131 | 0.0480 |  | 95 |
| 132 |  |  | 56 |
| 133 | 0.0600 |  | 97 |
| 134 |  | 30 |  |
| 135 |  | 18 |  |
| 136 |  | 40 |  |
| 137 | 0.0080 | 98 |  |
| 138 | 0.0130 | 83 |  |
| 139 | 0.0620 | 91 |  |
| 140 | 0.0020 |  | 98 |
| 141 |  | 18 |  |
| 142 |  |  | 60 |
| 143 |  |  | 48 |
| 144 |  |  | 62 |
| 145 | 0.0141 |  | 100 |
| 146 | 0.0480 |  | 97 |
| 147 | 0.0782 |  | 96 |
| 148 | 0.0021* |  | 98 |
| 149 | 0.0071* | 102 | 101 |
| 150 | 0.0154 |  | 100 |
| 151 | 0.0167 |  | 96 |
| 152 | 0.0026 |  | 95 |
| 153 | 0.0188 |  | 97 |
| 154 | 0.0362 |  | 96 |
| 155 | 0.0040 |  | 99 |
| 156 |  |  | 65 |
| 157 | 0.0140 | 100 |  |
| 158 | 0.0104 |  | 94 |
| 159 | 0.0134 |  | 98 |
| 160 | 0.0358 |  | 97 |
| 161 | 0.0554 |  | 95 |
| 162 | 0.0045 |  | 101 |
| 163 | 0.0639 |  | 92 |
| 164 | 0.0319 |  | 97 |
| 165 | 0.0037 |  | 98 |
| 166 | 0.0114 |  | 94 |
| 167 | 0.0104 |  | 101 |
| 168 | 0.0142 |  | 96 |
| 169 | 0.0214 |  | 98 |
| 170 | 0.0445 |  | 97 |
| 171 | 0.0193 |  | 100 |
| 172 | 0.0111 |  | 98 |
| 173 | 0.0084 |  | 99 |
| 174 | 0.0025 |  | 99 |
| 175 | 0.0046 |  | 97 |
| 176 | 0.0028 |  | 97 |
| 177 | 0.0057 |  | 96 |
| 178 | 0.0355 |  | 96 |
| 179 | 0.0036 |  | 98 |
| 180 | 0.0430 | 96 |  |
| 181 | 0.0840 | 95 |  |
| 182 | 0.0100 |  | 99 |
| 183 | 0.0140 |  | 99 |
| 184 | 0.0039 |  | 97 |
| 185 | 0.0064 | 102 |  |
| 186 | 0.0037 | 103 |  |
| 187 | 0.0060 | 100 |  |
| 188 | 0.0122* | 99 | 101 |
| 189 | 0.0116 | 100 |  |
| 190 | 0.0152 | 101 |  |
| 191 | 0.0060 | 105 |  |
| 192 | 0.0600 | 82 |  |
| 193 | 0.0145 | 101 |  |
| 194 |  | 45 |  |
| 195 | 0.0473 | 88 |  |
| 196 | 0.0080 | 99 |  |
| 197 | 0.0070 | 99 |  |
| 198 | 0.0100 | 95 |  |
| 199 | 0.0130 | 91 |  |
| 200 |  | 29 |  |
| 201 |  | 14 |  |
| 202 |  | 32 |  |
| 203 | 0.0150 |  | 93 |
| 204 | 0.0060 |  | 96 |
| 205 | 0.0030 |  | 96 |
| 206 | 0.0130 | 98 |  |
| 207 | 0.0160 | 98 |  |
| 208 | 0.0120 | 96 |  |
| 209 | 0.0320 | 98 |  |
| 210 | 0.0080 | 91 |  |
| 211 | 0.0300 | 80 |  |
| 212 | 0.0114 | 101 |  |
| 213 | 0.0014 | 95 |  |
| 214 | 0.0021 | 97 |  |
| 215 | 0.0060 | 101 |  |
| 216 | 0.0140 | 100 |  |
| 217 | 0.0030 | 88 |  |
| 218 | 0.0010 | 90 |  |
| 219 | 0.0078 | 101 |  |
| 220 | 0.0012* | 98 | 99 |
| 221 | 0.0050 | 92 |  |
| 222 | 0.0017 | 95 |  |
| 223 | 0.0023 | 96 |  |
| 224 | 0.0010 | 100 |  |
| 225 | 0.0040 | 98 |  |
| 226 | 0.0020 | 99 |  |
| 227 | 0.0006* | 101 |  |
| 228 | 0.0060 | 101 |  |
| 229 | 0.0210 | 99 |  |
| 230 | 0.0129 | 100 |  |
| 231 | 0.0290 |  | 95 |
| 232 | 0.0740 |  | 94 |
| 233 | 0.0220 |  | 93 |
| 234 | 0.0100 |  | 93 |
| 235 |  |  | 51 |
| 236 |  |  | 68 |
| 237 | 0.0248* | 87 | 92 |
| 238 | 0.0930 |  | 96 |
| 239 | 0.0920 |  | 96 |
| 240 |  |  | 43 |
| 241 | 0.1060 |  | 97 |
| 242 | 0.0382 | 95 |  |
| 243 | 0.0380 | 98 |  |
| 244 | 0.0122 | 100 |  |
| 245 | 0.0142 | 102 |  |
| 246 | 0.0088 | 102 |  |
| 247 | 0.0255 | 99 |  |
| 248 | 0.0083 | 98 |  |
| 249 | 0.0009 | 97 |  |
| 250 | 0.0127 | 102 |  |
| 251 | 0.0387 | 95 |  |
| 252 | 0.0171 | 102 |  |
| 253 | 0.0273 | 101 |  |
| 254 | 0.1250 | 58 |  |
| 255 | 0.0860 | 89 |  |
| 256 | 0.0300 | 87 |  |
| 257 |  | 62 |  |
| 258 |  | 25 |  |
| 259 |  | 24 |  |
| 260 | 0.0500 | 86 |  |
| 261 | 0.0126 | 97 |  |
| 262 | 0.0670 | 94 |  |
| 263 | 0.2030 | 52 |  |
| 264 | 0.0341 | 99 |  |

TABLE 2-continued

| Cpd No. | IC$_{50}$ (μM) | % Inh @ 0.2 (μM) | % Inh @ 0.5 (μM) |
|---|---|---|---|
| 265 | 0.0220 | 90 | |
| 266 | 0.0390 | 86 | |
| 267 | 0.0100 | 96 | |
| 268 | | 67 | |
| 269 | 0.0160 | 94 | |
| 270 | 0.3380 | | 75 |
| 271 | 0.0117* | 98 | |
| 272 | 0.0062* | 97 | |
| 273 | 0.0180* | 96 | |
| 274 | 0.0360 | 94 | |
| 275 | 0.0030* | 97 | |
| 276 | 0.0710 | 76 | |
| 277 | 0.0390 | 91 | |
| 278 | 0.0010* | 98 | |
| 279 | 0.0013 | 97 | |
| 280 | 0.0380 | 87 | |
| 281 | | 62 | |
| 282 | 0.0700 | 86 | |
| 283 | 0.0920 | 82 | |
| 284 | | 15 | |
| 285 | 0.0025 | | 100 |
| 286 | 0.0070 | | 99 |
| 287 | 0.0298 | | 96 |
| 288 | 0.0200 | 90 | |
| 289 | 0.0270 | 92 | |
| 290 | 0.0053 | 103 | |
| 291 | 0.0058 | 101 | |
| 292 | 0.0008* | 98 | 100 |
| 293 | 0.0078* | 101 | 101 |
| 294 | 0.0018 | 99 | |
| 295 | 0.0330 | 81 | |
| 296 | 0.0020 | 96 | |
| 297 | | 21 | |
| 298 | | 18 | |
| 299 | 0.0030 | 90 | |
| 300 | | 21 | |
| 301 | | 63 | |
| 302 | | 50 | |
| 303 | | 56 | |
| 304 | | 29 | |
| 305 | 0.0120 | 97 | |
| 306 | 0.0008 | 102 | |
| 307 | 0.0151 | 101 | |
| 308 | 0.0698 | 92 | |
| 309 | 0.0550 | 93 | |
| 310 | | 69 | |
| 311 | 0.1480 | 82 | |
| 312 | 0.0110 | 102 | |
| 313 | 0.0210 | 102 | |
| 314 | 0.0100 | 102 | |
| 315 | 0.0640 | 99 | |
| 316 | 0.0100 | 101 | |
| 317 | 0.0170 | 102 | |
| 318 | 0.0150 | 101 | |
| 319 | 0.0240 | 100 | |
| 320 | 0.0100 | 100 | |
| 321 | 0.0700 | 81 | |
| 322 | 0.0100 | 99 | |
| 323 | 0.0100 | 102 | |
| 324 | 0.0150 | 100 | |
| 325 | 0.0050 | 102 | |
| 326 | | 14 | |
| 327 | 0.0370 | 97 | |
| 328 | 0.0350 | 94 | |
| 329 | | 17 | |
| 330 | 0.0880 | 80 | |
| 331 | 0.0900 | 71 | |
| 332 | 0.0070 | 100 | |
| 333 | 0.0090 | 101 | |
| 334 | 0.0060 | 98 | |
| 335 | 0.0010 | 101 | |
| 336 | 0.0150 | 101 | |
| 337 | 0.0190 | 101 | |
| 338 | 0.0290 | 95 | |
| 339 | 0.0262 | 94 | |
| 340 | | 52 | |
| 341 | 0.0140 | 96 | |
| 342 | 0.0130 | 100 | |
| 343 | 0.0190 | 98 | |
| 344 | 0.0127 | 99 | |
| 345 | 0.0265 | 99 | |
| 346 | 0.0438 | 95 | |
| 347 | 0.0571 | 95 | |
| 348 | | 60 | |
| 349 | | 42 | |
| 350 | | 48 | |
| 351 | 0.0212 | 97 | |
| 352 | 0.0086 | 96 | |
| 353 | 0.0094 | 98 | |
| 354 | 0.1064 | 87 | |
| 355 | 0.0296 | 92 | |
| 356 | 0.0416 | 93 | |
| 357 | 0.0190 | 95 | |
| 358 | 0.0120 | 92 | |
| 359 | 0.0170 | 93 | |
| 360 | 0.0410 | 92 | |
| 361 | 0.0008 | 93 | |
| 362 | | 67 | |
| 363 | 0.0510 | 84 | |
| 364 | 0.0440 | 77 | |
| 365 | | 38 | |
| 366 | 0.0400 | 85 | |
| 367 | 0.0100 | 91 | |
| 368 | 0.0180 | 96 | |
| 369 | 0.0180 | 98 | |
| 370 | | 29 | |
| 371 | 0.0090 | 94 | |
| 372 | 0.0270 | 91 | |
| 373 | 0.1230 | 77 | |
| 374 | 0.0040 | 89 | |
| 375 | 0.0370 | 79 | |
| 376 | 0.0260 | 85 | |
| 377 | | 65 | |
| 378 | 0.0970 | 85 | |
| 379 | | 54 | |
| 380 | | 24 | |
| 381 | | 20 | |
| 382 | | 17 | |
| 383 | | 49 | |
| 384 | 0.0170 | 96 | |
| 385 | | 54 | |
| 386 | 0.0128 | 100.87 | |
| 387 | 0.0310 | 98 | |
| 388 | 0.0190 | 97 | |
| 389 | 0.0100 | 97 | |
| 390 | | 69 | |
| 391 | 0.0470 | 93 | |
| 392 | 0.0070 | 93 | |
| 393 | 0.0050 | 95 | |
| 394 | 0.0090 | 101 | |
| 395 | 0.0030 | 101 | |
| 396 | 0.0050 | 101 | |
| 397 | 0.0080 | 95 | |
| 398 | 0.0060 | 101 | |
| 399 | 0.0360 | 93 | |
| 400 | 0.0050 | 102 | |
| 401 | 0.0050 | 91 | |
| 402 | | 38 | |
| 403 | | 52 | |
| 404 | 0.0530 | 96 | |
| 405 | 0.0360 | 95 | |
| 406 | | 66 | |
| 407 | 0.0430 | 96 | |
| 408 | 0.1220 | 78 | |
| 409 | 0.0100 | 101 | |
| 410 | 0.0170 | 96 | |
| 411 | | 43 | |
| 412 | | 13 | |
| 413 | 0.0460 | 93 | |
| 414 | | 33 | |
| 415 | 0.0050 | 92 | |
| 416 | 0.0120 | 95 | |

TABLE 2-continued

| Cpd No. | IC$_{50}$ (μM) | % Inh @ 0.2 (μM) | % Inh @ 0.5 (μM) |
|---|---|---|---|
| 417 | 0.0620 | 93 | |
| 418 | 0.0690 | 90 | |
| 419 | 0.3450 | 74 | |
| 420 | | 48 | |
| 421 | 0.0640 | 90 | |
| 422 | 0.0180 | 97 | |
| 423 | 0.0070 | 93 | |
| 424 | 0.0070 | 95 | |
| 425 | 0.0790 | 86 | |
| 426 | 0.0300 | 95 | |
| 427 | 0.0050 | 95 | |
| 428 | 0.0100 | 93 | |
| 429 | 0.0170 | 93 | |
| 430 | | 52 | |
| 431 | 0.0200 | 88 | |
| 432 | | 42 | |
| 433 | 0.0330 | 93 | |
| 434 | 0.0170 | 90 | |
| 435 | 0.0330 | 95 | |
| 436 | 0.0040 | 89 | |
| 437 | 0.0090 | 92 | |
| 438 | 0.0020 | 90 | |
| 439 | 0.0020 | 86 | |
| 440 | 0.0140 | 84 | |
| 441 | | 37 | |
| 442 | 0.0670 | 81 | |
| 443 | 0.0140 | 94 | |
| 444 | 0.1220 | 92 | |
| 445 | | 58 | |
| 446 | 0.0960 | 82 | |
| 447 | | 19 | |
| 448 | 0.0120 | 102 | |
| 449 | 0.0880 | 97 | |
| 450 | 0.0290 | 101 | |
| 451 | 0.0680 | 97 | |
| 452 | 0.0180 | 101 | |
| 453 | 0.0020 | 101 | |
| 454 | 0.0040 | 101 | |
| 455 | 0.0360 | 101 | |
| 456 | | 67 | |
| 457 | 0.0470 | 93 | |
| 458 | 0.0120 | 102 | |
| 459 | 0.0090 | 102 | |
| 460 | 0.0080 | 102 | |
| 461 | | 30 | |
| 462 | | 22 | |
| 463 | 0.0260 | 101 | |
| 464 | 0.0070 | 102 | |
| 465 | 0.0630 | 90 | |
| 466 | | 66 | |
| 467 | 0.0200 | 100 | |
| 468 | | 16 | |
| 469 | | 13 | |
| 470 | | 15 | |
| 471 | 0.0590 | 97 | |
| 472 | 0.0400 | 88 | |
| 473 | 0.0090 | 102 | |
| 474 | 0.0080 | 101 | |
| 475 | 0.0020 | 102 | |
| 476 | | 39 | |
| 477 | 0.0120 | 100 | |
| 478 | 0.0250 | 99 | |
| 479 | 0.0080 | 100 | |
| 480 | 0.0130 | 100 | |
| 481 | | 69 | |
| 482 | 0.0240 | 100 | |
| 483 | 0.0090 | 101 | |
| 484 | 0.0210 | 100 | |
| 485 | 0.0210 | 96 | |
| 486 | 0.0040 | 100 | |
| 487 | 0.0020 | 101 | |
| 488 | 0.0010 | 101 | |
| 489 | 0.0006 | 101 | |
| 490 | 0.0010 | 101 | |
| 491 | 0.0010 | 101 | |
| 492 | 0.0620 | 91 | |
| 493 | 0.0008 | 101 | |
| 494 | 0.0009 | 101 | |
| 495 | 0.0550 | 98 | |
| 496 | 0.0008 | 101 | |
| 497 | 0.0004 | 101 | |
| 498 | | 41 | |
| 499 | 0.0150 | 101 | |
| 500 | | 15 | |
| 501 | | 31 | |
| 502 | 0.0100 | 100 | |
| 503 | 0.0470 | 96 | |
| 504 | 0.0180 | 101 | |
| 505 | 0.0240 | 98 | |
| 506 | 0.0310 | 100 | |
| 507 | 0.0340 | 92 | |
| 508 | | 47 | |
| 509 | 0.0320 | 100 | |
| 510 | 0.0110 | 102 | |
| 511 | 0.0030 | 101 | |
| 512 | 0.0040 | 102 | |
| 513 | 0.0210 | 101 | |
| 514 | 0.0460 | 100 | |
| 515 | | 49 | |
| 516 | 0.0190 | 102 | |
| 517 | 0.0020 | 102 | |
| 518 | 0.0007 | 101 | |
| 519 | 0.0060 | 102 | |
| 520 | 0.0090 | 102 | |
| 521 | 0.0020 | 101 | |
| 522 | 0.0040 | 101 | |
| 523 | 0.0020 | 101 | |
| 524 | 0.0020 | 102 | |
| 525 | 0.0060 | 101 | |
| 526 | 0.0010 | 102 | |
| 527 | 0.0050 | 101 | |
| 528 | 0.0160 | 102 | |
| 529 | | 35 | |
| 530 | | 54 | |
| 531 | 0.0460 | 88 | |
| 532 | | 19 | |
| 533 | 0.0320 | 102 | |
| 534 | 0.0020 | 102 | |
| 535 | 0.0010 | 102 | |
| 536 | 0.0770 | 89 | |
| 537 | 0.0082 | 104.64 | |
| 538 | 0.0049 | 104.55 | |
| 539 | 0.0067 | 104.91 | |
| 540 | 0.0122 | 104.6 | |
| 541 | 0.0108 | 104.57 | |
| 542 | 0.0023 | 104.93 | |
| 543 | 0.0072 | 104.46 | |
| 544 | 0.0018 | 105.04 | |
| 545 | 0.0019 | 104.78 | |
| 546 | 0.0683 | 85.683 | |
| 547 | 0.0074 | 104.86 | |
| 548 | 0.0289 | 102.47 | |
| 549 | 0.0159 | 103.68 | |
| 550 | 0.0188 | 103.79 | |
| 551 | 0.0886 | 94.385 | |
| 552 | 0.0251 | 101.3 | |
| 553 | | 38.688 | |
| 554 | | 52.301 | |
| 555 | 0.0219 | 102.49 | |
| 556 | 0.0482 | 99.314 | |
| 557 | | 39.483 | |
| 558 | 0.0994 | 80.935 | |
| 559 | 0.0032 | 104.59 | |
| 560 | 0.0657 | 104.01 | |
| 561 | 0.0284 | 103.38 | |
| 562 | 0.0331 | 102.74 | |
| 563 | 0.0493 | 94.006 | |
| 564 | | 57.717 | |
| 565 | 0.1170 | 74.399 | |
| 566 | 0.0018 | 104.33 | |
| 567 | 0.0103 | 104.13 | |
| 568 | 0.0024 | 103.99 | |

TABLE 2-continued

| Cpd No. | IC$_{50}$ (μM) | % Inh @ 0.2 (μM) | % Inh @ 0.5 (μM) |
|---|---|---|---|
| 569 | 0.0350 | 88 | |
| 570 | 0.0066 | 101 | |
| 571 | | 14 | |
| 572 | 0.0166 | 101 | |
| 573 | | 28 | |
| 574 | | 16 | |
| 575 | | 15 | |
| 576 | 0.0191 | 100 | |
| 577 | 0.0078 | 101 | |
| 578 | 0.0267 | 91 | |
| 579 | 0.0088 | 102 | |
| 580 | 0.0221 | 101 | |
| 581 | 0.0251 | 100 | |
| 582 | 0.0503 | 96 | |
| 583 | 0.0079 | 100 | |
| 584 | 0.0159 | 100 | |
| 585 | 0.0064 | 101 | |
| 586 | 0.0346 | 100 | |
| 587 | 0.0039 | 100 | |
| 588 | 0.0121 | 101 | |
| 589 | 0.0042 | 100 | |
| 590 | 0.0061 | 101 | |
| 591 | 0.0042 | 101 | |
| 592 | 0.0018 | 101 | |
| 593 | 0.0076 | 101 | |
| 594 | 0.0060 | 101 | |
| 595 | 0.0190 | 101 | |
| 596 | | 17 | |
| 597 | | 25 | |
| 598 | 0.0307 | 101 | |
| 599 | 0.0161 | 101 | |
| 600 | 0.0089 | 101 | |
| 601 | 0.0241 | 100 | |
| 602 | 0.0221 | 101 | |
| 603 | 0.0103 | 101 | |
| 604 | | 13 | |
| 605 | | 18 | |
| 606 | 0.0905 | 75 | |
| 607 | 0.0368 | 101 | |
| 608 | 0.0181 | 101 | |
| 609 | 0.0537 | 99 | |
| 610 | | 55 | |
| 611 | 0.0146 | 101 | |
| 612 | 0.0537 | 97 | |
| 613 | 0.0066 | 101 | |
| 614 | 0.0074 | 101 | |
| 615 | 0.0073 | 101 | |
| 616 | 0.0128 | 101 | |
| 617 | 0.0074 | 101 | |
| 618 | 0.0104 | 101 | |
| 619 | 0.0398 | 101 | |
| 620 | 0.0234 | 101 | |
| 621 | 0.0110 | 101 | |
| 622 | 0.0313 | 89 | |
| 623 | 0.0070 | 101 | |
| 624 | 0.0134 | 103 | |
| 625 | 0.0204 | 103 | |
| 626 | 0.0074 | 103 | |
| 627 | 0.0086 | 103 | |
| 628 | 0.0233 | 103 | |
| 629 | 0.0262 | 103 | |
| 630 | 0.0356 | 103 | |
| 631 | 0.0263 | 103 | |
| 632 | | 12 | |
| 633 | | 17 | |
| 634 | | 55 | |
| 635 | 0.0074 | 101 | |
| 636 | 0.0460 | 103 | |
| 637 | 0.0122 | 104 | |
| 638 | 0.0600 | 100 | |
| 639 | 0.1280 | 84 | |
| 640 | 0.0110 | 103 | |
| 641 | 0.0140 | 103 | |
| 642 | 0.0410 | 90 | |
| 643 | 0.0050 | 103 | |
| 644 | | 63 | |
| 645 | | 20 | |
| 646 | | 55 | |
| 647 | | 21 | |
| 648 | | 62 | |
| 649 | | 26 | |
| 650 | 0.0040 | 102 | |
| 651 | 0.0060 | 103 | |
| 652 | 0.0850 | 102 | |
| 653 | 0.0130 | 102 | |
| 654 | | 56 | |
| 655 | | 55 | |
| 656 | 0.0537 | 98 | |
| 657 | 0.0075 | 101 | |
| 658 | 0.0043 | 101 | |
| 659 | 0.0141 | 100 | |
| 660 | 0.0112 | 100 | |
| 661 | 0.0141 | 100 | |
| 662 | | 50.122 | |
| 663 | | 17.113 | |
| 664 | | 53.117 | |
| 665 | | 27.939 | |
| 666 | 0.0081 | 102.6 | |
| 667 | 0.0301 | 102.96 | |
| 668 | 0.0050 | 102.88 | |
| 669 | 0.0512 | 96.422 | |
| 670 | 0.0390 | 99.074 | |
| 671 | 0.0345 | 100.03 | |
| 672 | 0.0749 | 75.3 | |
| 673 | 0.0738 | 94.378 | |
| 674 | 0.0776 | 85.377 | |
| 675 | 0.0024 | 100 | |
| 676 | 0.0259 | 102.32 | |
| 677 | 0.0246 | 101.48 | |
| 678 | | 60.964 | |
| 679 | 0.0579 | 100.43 | |
| 680 | 0.0561 | 96.235 | |
| 681 | 0.0674 | 93.318 | |
| 682 | 0.0317 | 101.01 | |
| 683 | 0.0258 | 100.57 | |
| 684 | 0.1448 | 73.142 | |
| 685 | 0.0119 | 102.25 | |
| 686 | 0.0047 | 104.94 | |
| 687 | 0.0569 | 74.496 | |
| 688 | 0.0602 | 99 | |
| 689 | 0.0528 | 86 | |
| 690 | 0.0161 | 101.25 | |
| 691 | 0.0160 | 101.81 | |
| 692 | 0.0072 | 101.48 | |
| 693 | 0.0252 | 103.39 | |
| 694 | | 42 | |
| 695 | 0.0170 | 101 | |
| 696 | 0.0230 | 97 | |
| 697 | 0.0640 | 92 | |
| 698 | 0.0020 | 102 | |
| 699 | 0.0060 | 103 | |
| 700 | | 37 | |
| 701 | 0.0325 | 95 | |
| 702 | 0.0230 | 99 | |
| 703 | 0.0510 | 80 | |
| 704 | 0.0150 | 102 | |
| 705 | 0.0190 | 101 | |
| 706 | 0.0140 | 102 | |
| 707 | 0.0030 | 102 | |
| 708 | 0.0130 | 102 | |
| 709 | 0.0060 | 102 | |
| 710 | 0.0070 | 102 | |
| 711 | 0.0020 | 102 | |
| 712 | 0.0040 | 102 | |
| 713 | | 47 | |
| 714 | 0.0290 | 96 | |
| 715 | 0.0240 | 101 | |
| 716 | 0.0090 | 101 | |
| 717 | 0.0050 | 102 | |
| 718 | 0.0390 | 96 | |
| 719 | 0.0230 | 100 | |
| 720 | | 52 | |

TABLE 2-continued

| Cpd No. | IC$_{50}$ (μM) | % Inh @ 0.2 (μM) | % Inh @ 0.5 (μM) |
|---|---|---|---|
| 721 | 0.0042 | 102 | |
| 722 | | 28 | |
| 723 | 0.0180 | 102 | |
| 724 | 0.0053 | 102 | |
| 725 | 0.0078 | 102 | |
| 726 | 0.0903 | 69 | |
| 727 | | 16 | |
| 728 | | 44 | |
| 729 | 0.0962 | 75 | |
| 730 | 0.0236 | 100 | |
| 731 | 0.0444 | 87 | |
| 732 | 0.0133 | 100 | |
| 733 | 0.0134 | 100 | |
| 734 | 0.0097 | 102 | |
| 735 | 0.0268 | 101 | |
| 736 | 0.0172 | 101 | |
| 737 | 0.0299 | 101 | |
| 738 | 0.0089 | 102 | |
| 739 | 0.0232 | 90 | |
| 740 | | 57 | |
| 741 | 0.0173 | 101 | |
| 742 | | 66 | |
| 743 | | 32 | |
| 744 | 0.0573 | 99 | |
| 745 | 0.0849 | 74 | |
| 746 | | 31 | |
| 747 | | 48 | |
| 748 | 0.0053 | 101 | |
| 749 | | 64 | |
| 750 | 0.0092 | 101 | |
| 751 | | 54 | |
| 752 | | 65 | |
| 753 | 0.0272 | 69 | |
| 754 | 0.0164 | 82 | |
| 755 | 0.0009 | 101 | |
| 756 | 0.0014 | 101 | |
| 757 | 0.0108 | 101 | |
| 758 | 0.0051 | 101 | |
| 759 | 0.0183 | 101 | |
| 760 | 0.0459 | 94 | |
| 761 | 0.0400 | 79 | |
| 762 | 0.0253 | 101 | |
| 763 | 0.0277 | 102 | |
| 764 | 0.0221 | 101 | |
| 765 | 0.0136 | 101 | |
| 766 | 0.0078 | 101 | |
| 767 | 0.0892 | 77 | |
| 768 | 0.0188 | 93 | |
| 769 | 0.0440 | 85 | |
| 770 | 0.0072 | 95 | |
| 771 | 0.0072 | 96 | |
| 772 | 0.0057 | 95 | |
| 773 | 0.0167 | 94 | |
| 774 | 0.0013 | 95 | |
| 775 | 0.0016 | 95 | |
| 776 | 0.0067 | 95 | |
| 777 | | 56 | |
| 778 | 0.1069 | 87 | |
| 779 | 0.0487 | 79 | |
| 780 | 0.1450 | 72 | |
| 781 | 0.0030 | 102 | |
| 782 | | 33 | |
| 783 | | 38 | |
| 784 | 0.0033 | 102 | |
| 785 | 0.0022 | 102 | |
| 786 | 0.0154 | 102 | |
| 787 | 0.0149 | 102 | |
| 788 | 0.0259 | 100 | |
| 789 | 0.0117 | 102 | |
| 790 | 0.0220 | 101 | |
| 791 | 0.0231 | 95 | |
| 792 | | 23 | |
| 793 | 0.0155 | 102 | |
| 794 | 0.0294 | 101 | |
| 795 | 0.0246 | 100 | |
| 796 | 0.0242 | 101 | |
| 797 | 0.0048 | 102 | |
| 798 | 0.0359 | 102 | |
| 799 | 0.0039 | 102 | |
| 800 | 0.0068 | 102 | |
| 801 | 0.0028 | 102 | |
| 802 | 0.0080 | 101 | |
| 803 | 0.0308 | 101 | |
| 804 | 0.0111 | 102 | |
| 805 | 0.0022 | 103 | |
| 806 | 0.0130 | 102 | |
| 807 | 0.0060 | 103 | |
| 808 | 0.0007 | 102 | |
| 809 | 0.0069 | 103 | |
| 810 | 0.0010 | 102 | |
| 811 | 0.0037 | 103 | |
| 812 | 0.0076 | 103 | |
| 813 | 0.0280 | 90 | |
| 814 | 0.1380 | 80 | |
| 815 | | 44 | |
| 816 | | 15 | |
| 817 | 0.0730 | 80 | |
| 818 | 0.0620 | 92 | |
| 819 | 0.0210 | 98 | |
| 820 | 0.0280 | 102 | |
| 821 | 0.0090 | 102 | |
| 822 | 0.0490 | 97 | |
| 823 | 0.0220 | 102 | |
| 824 | 0.0380 | 98 | |
| 825 | 0.0250 | 89 | |
| 826 | 0.0240 | 97 | |
| 827 | 0.0066 | 101 | |
| 828 | 0.0427 | 88 | |
| 829 | 0.0230 | 100 | |
| 830 | 0.0150 | 102 | |
| 831 | 0.0500 | 91 | |
| 832 | 0.0880 | 76 | |
| 833 | 0.0130 | 102 | |
| 834 | 0.1230 | 87 | |
| 835 | 0.0551 | 89 | |
| 836 | 0.0240 | 96 | |
| 837 | 0.0150 | 103 | |
| 838 | 0.0041 | 101 | |
| 839 | 0.0159 | 101 | |
| 840 | 0.0981 | 71.105 | |
| 841 | | 55 | |
| 842 | | 63 | |
| 843 | | 31 | |
| 844 | | 31 | |
| 845 | | 24 | |
| 846 | | 28 | |
| 847 | | 33 | |
| 848 | | 68 | |
| 849 | | 25 | |
| 850 | | 28 | |

*IC$_{50}$ values are listed as an average of two or more determinations

Example 1b

In Vitro Rat and Human TRPM8 Functional Assay

HEK293 cells are routinely grown as monolayer in Dulbecco's minimum essential medium supplemented with 10% FBS, 1 mM L-glutamine, 100 units/mL penicillin and 100 ug/mL streptomycin. Cells are maintained in 5% CO2 at 37° C.

For functional expression of TRPM8, the full-length cDNA encoding human and rat TRPM8 are subcloned into pCI-NEO mammalian expression vectors. The expression constructs are transiently transfected into HEK293 cells according to the FuGENE 6 transfection Reagent® (ROCHE) instructions. Within twenty-four hours, transiently transfected cells are harvested and either seeded directly into assay plate or cryopreserved for future usage.

Transfected cells may be either cryopreserved or freshly transfected and plated into clearbase poly-D-lysine coated 384-well plates (BD Biosciences, NJ, USA) at a density of 10,000 cells per well in culture medium and grown overnight. The following day, all medium is removed and the cells are incubated with 52 µL of 0.5× Calcium 3 Dye (Molecular Devices) prepared in complete assay buffer containing 20 mM HEPES, 0.1% BSA, and 2.5 mM probenecid at 37° C. for thirty five minutes. The cells are then incubated for an additional fifteen minutes at room temperature before initiating experiments. Following incubation, plates are inserted into a FDSS instrument, where cells were challenged with compounds of the formula (I) (at varying concentrations) and intracellular Ca2+ are measured for 5 min prior to the addition of icilin at the $EC_{80}$ concentration. IC50 values for compounds of the formula (I) are determined from eight point dose-response studies.

Maximal fluorescence intensity (FI) achieved upon addition of icilin is exported from the FDSS and further analyzed using GraphPad Prism 3.02 (Graph Pad Software Inc., CA, U.S.A.) where data is normalized to percent of maximal response. The dose response curves from the average of quadruplicate wells for each data point are analyzed by using nonlinear regression of either sigmoidal dose response or sigmoidal dose response (variable slope). Finally, the IC50 values are calculated with the best-fit dose curve determined by Prism. Results are shown in Table 3.

TABLE 3

| Cpd No | Cell preparation | rTRPM8 $IC_{50}$, nM | hTRPM8 $IC_{50}$, nM |
|---|---|---|---|
| 306 | Freshly transfected | 5.0 | 4.0 |
| 496 | Cryopreserved | 1.8 | 1.4 |

Example 2

TRPM8 Patch Clamp Assays

For patch clamp experiments, HEK293 cells are stably transfected with canine TRPM8 and cultured in DMEM supplemented with 10% fetal bovine serum, 100 units/ml penicillin, 100 µg/ml streptomycin and 1 mg/ml G418. Cells are maintained at 37° C. and in 5% $CO_2$.

The extracellular solution contains (in mM): NaCl, 132; EGTA, 1; KCl, 5.4; $MgCl_2$, 0.8; HEPES, 10; glucose, 10; pH=7.4. Recordings are performed using the conventional whole-cell patch clamp technique, 1-2 days after plating cells onto glass coverslips at densities appropriate for single cell recording. Currents are amplified by a patch clamp amplifier and filtered at 2 kHz (Axopatch 200B, Molecular Devices, Union City, Calif.). Menthol (100 µM) is applied to the cell at 0.5 ml/min via a gravity-fed perfusion system. Recordings involving menthol activation are performed at 22° C.

In experiments where temperatures are varied, temperature ramps are generated by cooling the perfusate in an in-line cooler (Model SC-20, Warner Instruments, Hamden, Conn.) controlled by a temperature controller (Model CL-100, Warner Instruments). The temperature in the vicinity of the recorded cell is measured with a custom-made miniature thermo-microprobe connected to a monitoring thermometer (Model TH-8, Physitemp, Clifton, N.J.), and sampled using Digidata 1322A and pClamp 9.0 (Molecular Devices), as are the currents concurrently measured in the whole-cell patch clamp mode. The current is continuously sampled (at 100 Hz) at a holding potential of −60 mV.

Compounds of the formula (I) are diluted from 10 mM DMSO stocks (stored at −20° C.) into an extracellular solution either containing 100 µM menthol or subjected to cooling. Increasing concentrations of a compound are applied to a cell in a cumulative manner and concentration-dependent responses are measured after steady-state activation is achieved by either 100 µM menthol or cooling to 10° C. A saturating concentration of a reference antagonist is applied at the end of an experiment (either in the presence of 100 µM menthol or 10° C. temperature) to establish the baseline from which all the other measurements are subtracted.

Percentage inhibition by a compound is calculated as follows:

$$100 \times (1 - I_{comp}/I_0);$$

where $I_{comp}$ and $I_0$ are steady-state current amplitudes in either the presence or absence of a concentration of compounds of the formula (I). Concentration-response data are fitted to a logistic function as follows: $R=100/(1+c/IC_{50})^p$; where, R is the percentage inhibition, p is the Hill coefficient and c is the concentration of compounds of the formula (I). Results are shown in Table 4.

TABLE 4

| Cpd | Mode of stimulation | [µM] | % inh | n | $IC_{50}$ (nM) |
|---|---|---|---|---|---|
| 284 | Cold | 0.003 | 24.0 | 2 | 8.0 |
|  |  | 0.01 | 71.0 | 3 |  |
| 306 | menthol | 0.0003 | 11.6 | 3 | 1.1 |
|  |  | 0.001 | 47.3 | 3 |  |
|  |  | 0.003 | 78.0 | 3 |  |
|  |  | 0.01 | 94.9 | 3 |  |
| 306 | cold | 0.001 | 22.4 | 3 | 2.3 |
|  |  | 0.003 | 60.1 | 3 |  |
|  |  | 0.01 | 86.2 | 3 |  |
|  |  | 0.03 | 97.3 | 3 |  |
| 496 | menthol | 0.0001 | 27.5 | 3 | 0.183 |
|  |  | 0.0003 | 68.6 | 3 |  |
|  |  | 0.001 | 95.8 | 3 |  |
|  |  | 0.003 | 99.6 | 3 |  |
| 496 | cold | 0.0003 | 21.6 | 3 | 0.554 |
|  |  | 0.001 | 77.7 | 3 |  |
|  |  | 0.003 | 96.4 | 3 |  |

In Vivo Models

Example 3

Inhibition of Icilin-induced Behaviors in Rodents

Icilin was initially developed as a "super-cooling" compound by Delmar Chemicals Ltd. Subsequently it was shown to be one of the most potent known agonists of TRPM8 (McKemy D D, et al. Nature 2002, 416(6876): 52-8), having an $EC_{50}=0.2$ µM in stimulating calcium ion influx into TRPM8 transfected cells (Behrendt H J et al. Brit J Pharmacol 2004, 141(4): 737-45). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (Wei E T, Seid D A, J Pharm Pharmacol. 1983, 35, 110). The inhibition or reversal of icilin-induced shaking behaviors in rodents provides evidence for the utility of TRPM8 antagonists of the formula (I) in treating or preventing a disease, syndrome, disorder, or condition in a subject in which the disease, syndrome, disorder or condition is affected by the modulation of TRPM8 receptors.

Example 3a

Inhibition of Icilin-induced "Wet-Dog" Shakes in Rats

Male Sprague Dawley rats (220-450 g, Charles River Labs, n=6-9/treatment) were used to evaluate the ability of selected compounds of the formula (I) to block icilin-induced "wet-dog" shakes (WDS). Compounds of the formula (I) were administered in an appropriate vehicle, such as hydroxypropyl-β-cyclodextrin (HPβCD), methocellulose, 10% Solutol, or $H_2O$, or the like, by the appropriate route, i.p. or p.o., 30-120 minutes before icilin. Icilin was administered in PEG-400 or 10% solutol/$H_2O$, at 1.0 or 3.0 mg/kg, i.p. and spontaneous "wet-dog" shakes were counted 10-20 minutes post-icilin. Results are presented as a percent inhibition of shakes, which was calculated as [1−(test compound WDS count/ vehicle WDS count)]×100. Results are shown in Table 5.

TABLE 5

| Cpd | Form | Dose | Route | Vehicle | Pre-icilin min | % Inhibition | ED50, mg/kg |
|---|---|---|---|---|---|---|---|
| 271 | $CO_2^-Na^+$ | 30 | p.o. | Water | 30 | 65 | |
| 271 | $CO_2^-Na^+$ | 1 | p.o. | Water | 30 | 28 | 5.7 |
| | | 3 | | | | 35 | |
| | | 10 | | | | 46 | |
| | | 30 | | | | 88 | |
| 272 | $CO_2^-H$ | 3 | p.o. | methocel | 30 | 26 | |
| | | 10 | | | | 23 | |
| | | 30 | | | | 43 | |
| 272 | $CO_2^-H$ | 30 | p.o. | HPbCD | 30 | 37 | |
| 272 | $CO_2^-Na^+$ | 10 | p.o. | HPbCD | 30 | 0 | |
| | | 30 | | | | 72 | |
| 272 | $CO_2^-Na^+$ | 3 | p.o. | HPbCD | 30 | 0 | 22 |
| | | 10 | | | | 29 | |
| | | 30 | | | | 74 | |
| | | 100 | | | | 75 | |
| 273 | $CO_2^-Na^+$ | 30 | p.o. | HPbCD | 30 | 39 | |
| 273 | $CO_2^-Na^+$ | 10 | p.o. | HPbCD | 30 | 17 | 53 |
| | | 30 | | | | 25 | |
| | | 100 | | | | 71 | |
| 283 | $CO_2^-Na^+$ | 30 | p.o. | HPbCD | 30 | 65 | |
| 283 | $CO_2^-Na^+$ | 3 | p.o. | HPbCD | 30 | 13 | |
| | | 10 | | | | −19 | |
| | | 30 | | | | 13 | |
| | | 100 | | | | 43 | |
| 283 | $CO_2^-Na^+$ | 30 | p.o. | Water | 30 | 71 | |
| 296 | $CO_2^-Na^+$ | 30 | p.o. | HPbCD | 30 | 27 | |
| 306 | $CO_2^-Na^+$ | 30 | p.o. | HPbCD | 60 | 99 | |
| 306 | $CO_2^-Na^+$ | 3 | p.o. | HPbCD | 60 | 63 | |
| | | 10 | | | | 99 | |
| | | 30 | | | | 100 | |
| 306 | $CO_2^-Na^+$ | 0.3 | p.o. | HPbCD | 60 | 39 | 2.5 |
| | | 1 | | | | 9 | |
| | | 3 | | | | 64 | |
| | | 10 | | | | 98 | |
| 306 | $CO_2^-Na^+$ | 10 | p.o. | HPbCD | 60 | 99 | |
| 307 | $CO_2H$ | 30 | p.o. | HPbCD | 30 | 13 | |
| 309 | $CO_2H$ | 30 | p.o. | HPbCD | 30 | 23 | |
| 361 | $CO_2H$ | 30 | p.o. | HPbCD | 30 | 87 | |
| 361 | $CO_2^-Na^+$ | 3 | p.o. | Water | 120 | 38 | 4.5 |
| | | 10 | | | | 74 | |
| | | 30 | | | | 98 | |
| 394 | $CO_2^-Na^+$ | 30 | p.o. | HPbCD | 30 | 63 | |
| 395 | $CO_2^-Na^+$ | 30 | p.o. | HPbCD | 30 | 100 | |
| 395 | $CO_2^-Na^+$ | 1 | p.o. | Water | 60 | 15 | 7.6 |
| | | 3 | | | | 26 | |
| | | 10 | | | | 55 | |
| | | 30 | | | | 88 | |
| 396 | $CO_2^-Na^+$ | 30 | p.o. | HPbCD | 30 | 99 | |
| 398 | $CO_2^-Na^+$ | 30 | p.o. | HPbCD | 30 | 7 | |
| 400 | $CO_2^-Na^+$ | 30 | p.o. | HPbCD | 30 | 84 | |
| 409 | $CO_2^-Na^+$ | 30 | p.o. | HPbCD | 30 | 16 | |
| 427 | $CO_2^-Na^+$ | 30 | p.o. | Water | 30 | 82 | |
| 429 | 1H, Na tetrazole | 30 | p.o. | HPbCD | 30 | 41 | |
| 429 | 1H, Na tetrazole | 30 | p.o. | HPbCD | 60 | 36 | |
| 435 | $CO_2^-Na^+$ | 30 | p.o. | Water | 30 | 41 | |
| 479 | $CO_2^-Na^+$ | 30 | p.o. | HPbCD | 60 | 77 | |
| 480 | $CO_2^-Na^+$ | 30 | p.o. | HPbCD | 60 | 39 | |
| 483 | 1H, Na oxadiazole | 30 | p.o. | Water w/NaOH | 30 | 19 | |
| 486 | $CO_2^-Na^+$ | 10 | p.o. | HPbCD | 60 | 18 | |

TABLE 5-continued

| Cpd | Form | Dose | Route | Vehicle | Pre-icilin min | % Inhibition | ED50, mg/kg |
|---|---|---|---|---|---|---|---|
| 487 | $CO_2^-Na^+$ | 30 | p.o. | HPbCD | 60 | 99 | |
| 488 | $CO_2^-Na^+$ | 10 | p.o. | HPbCD | 60 | 73 | |
| 489 | $CO_2^-Na^+$ | 30 | p.o. | Water | 60 | 99 | |
| 490 | $CO_2^-Na^+$ | 10 | p.o. | HPbCD | 60 | 84 | |
| 496 | $CO_2^-Na^+$ | 30 | p.o. | Water | 60 | 99 | |
| 496 | $CO_2^-Na^+$ | 1 | p.o. | HPbCD | 120 | 74 | |
| | | 3 | | | | 100 | |
| | | 10 | | | | 99 | |
| | | 17.8 | | | | 100 | |
| 496 | $CO_2^-Na^+$ | 0.1 | p.o. | HPbCD | 120 | 43 | 2.5 |
| | | 0.3 | | | | 34 | |
| | | 1 | | | | 79 | |
| | | 3 | | | | 98 | |
| 497 | $CO_2^-Na^+$ | 30 | p.o. | Water | 60 | 96 | |
| 502 | $CO_2^-Na^+$ | 10 | p.o. | HPbCD | 60 | 14 | |
| 505 | $CO_2^-Na^+$ | 30 | p.o. | HPbCD | 60 | 72 | |
| 519 | $CO_2^-Na^+$ | 10 | p.o. | HPbCD | 60 | −6 | |
| 524 | $CO_2^-Na^+$ | 10 | p.o. | HPbCD | 60 | 82 | |
| 537 | $CO_2^-Na^+$ | 30 | p.o. | HPbCD | 60 | 42 | |
| 567 | $CO_2^-Na^+$ | 10 | p.o. | HPbCD | 60 | 55 | |
| 623 | $C(O)NNaSO_2CH_3$ | 10 | p.o. | HPbCD | 60 | 38 | |
| 627 | 1H, Na oxadiazole | 30 | p.o. | HPbCD | 60 | 0 | |
| 635 | 1H, Na tetrazole | 3 | p.o. | HPbCD | 60 | 31 | |
| | | 10 | | | | −8 | |
| | | 30 | | | | 53 | |
| | | 56 | | | | 72 | |
| 640 | 1H, Na oxo-thiadiazole | 30 | p.o. | HPbCD | 60 | 20 | |
| 657 | $CO_2^-Na^+$ | 10 | p.o. | HPbCD | 60 | 32 | |
| 658 | $CO_2^-Na^+$ | 10 | p.o. | HPbCD | 60 | 63 | |
| 755 | $CO_2^-Na^+$ | 10 | p.o. | HPbCD | 60 | 99 | |
| 756 | $CO_2^-Na^+$ | 10 | p.o. | HPbCD | 60 | 100 | |
| 784 | 1H, Na oxo-thiadiazole | 30 | p.o. | HPbCD | 60 | 79 | |

Example 3b

Reversal of Icilin-induced Behaviors in Rats

Male Sprague Dawley rats (225-450 g, Charles River Labs, n=4-6/treatment) were used to evaluate the ability of selected compounds of the formula (I) to reverse icilin-induced "wet-dog" shakes. Icilin was administered in PEG-400 or 10% solutol/$H_2O$, at 1.0 or 3.0 mg/kg, i.p. and spontaneous "wet-dog" shakes (WDS) were counted 10-20 minutes post-icilin. Animals that exhibited 10 or more shakes were randomized into treatment groups and immediately administered compounds of the formula (I) in an appropriate vehicle, such as hydroxypropyl-β-cyclodextrin (HP βCD), methocellulose, 10% Solutol, or $H_2O$, or the like, and by the appropriate route, such as i.p. or p.o. Spontaneous "wet-dog" shakes were counted 60-70 minutes after compound administration. Results are presented as a percent inhibition of shakes, which was calculated as [1−(test compound WDS count/vehicle WDS count)]×100. Results are shown in Table 6.

TABLE 6

| Cpd No. | Dose (mg/kg) | Route | Post-icilin | % Inhibition |
|---|---|---|---|---|
| 2 | 30 | p.o. | 1 h | 18 |
| 7 | 30 | p.o. | 1 h | 65 |
| 13 | 30 | p.o. | 1 h | 28 |
| 14 | 30 | p.o. | 1 h | −16 |
| 15 | 30 | p.o. | 1 h | −18 |
| 125 | 30 | p.o. | 1 h | 39 |
| 148 | 30 | p.o. | 1 h | 33 |

TABLE 6-continued

| Cpd No. | Dose (mg/kg) | Route | Post-icilin | % Inhibition |
|---|---|---|---|---|
| 149 | 30 | p.o. | 1 h | −3 |
| 168 | 30 | p.o. | 1 h | −29 |
| 174 | 30 | p.o. | 1 h | 45 |
| 177 | 30 | p.o. | 1 h | 66 |
| | 3 | p.o. | 1 h | 15 |
| | 10 | p.o. | 1 h | 53 |
| | 16.6 | p.o. | 1 h | 54 |
| | 30 | p.o. | 1 h | 52 |
| | 100 | p.o. | 1 h | 52 |
| 188 | 30 | p.o. | 1 h | 7 |

Example 3c

Rightward Shift of Icilin Dose Effect Curve in Rats

Male Sprague Dawley rats (200-400 g, Charles River Labs, n=6-9/treatment) were administered icilin in a suitable vehicle (e.g. PEG-400, 10% Solutol) at 0.1-30 mg/kg, i.p. Spontaneous "wet-dog" shakes were counted 10-20 minutes post-icilin in order to generate a icilin dose-effect curve. A compound of the present invention was administered orally in hydroxypropyl-β-cyclodextrin 60 minutes before icilin challenge to assess the compound's ability to inhibit spontaneous "wet-dog" shakes (WDS) produced by a range of icilin doses. The ED50 of the icilin dose-effect curve generated in the presence of TRPM8 antagonist may be compared to that generated in the presence of vehicle to determine the magnitude of rightward shift as shown below in Table 7.

TABLE 7

| Cpd | Dose (mg/kg) | Route | Pre-icilin | Icilin ED50, mg/kg, i.p., no pretreatment | Icilin ED50, mg/kg, i.p., compound pretreatment |
|---|---|---|---|---|---|
| 306 | 3 | p.o. | 60 | 0.75 | 2.96 |

Example 4

In Vivo Model of Subacute Inflammatory Pain:
Carrageenan-induced Hyperalgesia

Intraplantar injection of carrageenan into the hind paw of rats causes a robust acute inflammatory response characterized by reddening, swelling and hypersensitivity of the paw to thermal and mechanical stimuli typically peaking 3-6 hours following application and subsiding over the 12-24 hours.

Example 4a

Rat Carrageenan-induced Radiant Heat Hypersensitivity

To assess the effect of test compounds of the formula (I) on inflammatory hyperalgesia radiant heat response latencies were evaluated 3 hours following intraplantar carrageenan (Lambda, Type IV, 200 uL) injection into a single hind paw in male Sprague-Dawley rats. The test compound was administered either 2 hours prior to or 1 hour following carrageenan injection. The intent was to determine whether the compound would prevent or retard the hypersensitivity associated with this inflammogen. Baseline thermal response latencies were determined prior to any treatment and again 3 hours after carrageenan injection. Percent reversal of hyperalgesia relative to vehicle treatment (% R) was calculated for both compound treatment paradigms according to the following formula and is depicted in Table 8:

% $R$=(Post compound latency−Post vehicle latency)/
((Baseline latency−Post vehicle latency)×100%

TABLE 8

| Cpd No. | Salt Form | Dose | Route | Vehicle | Treatment Time, hours relative to Cg | Percent Reversal, relative to vehicle |
|---|---|---|---|---|---|---|
| 306 | $CO_2^-Na^+$ | 30 | p.o. | HPbCD | −2 | 64 |
|  |  |  |  |  | 1 | 100 |
| 496 | $CO_2^-Na^+$ | 30 | p.o. | HPbCD | −2 | 74 |
|  |  |  |  |  | 1 | 106 |

Example 5

In Vivo Model for of Chronic Inflammatory Pain:
Complete Freund's Adjuvant (CFA)-induced
Hyperalgesia Intraplantar injection of complete Freund's adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether test compounds of the formula (I) reverse established hypersensitivity, a 100 μL intraplantar injection of CFA (suspended in a 1:1 emulsion of saline and heat-killed *Mycobacterium tuberculosis* in mineral oil) can be injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and antihyperalgesic effect of numerous effective clinical agents, including acetaminophen, NSAIDS such as aspirin and ibuprofen, and opioids, such as morphine.

Example 5a

CFA-induced Paw Radiant Heat Hypersensitivity

Each rat is placed in a test chamber on a warm glass surface and allowed to acclimate for approximately 10 minutes. A radiant thermal stimulus (beam of light) is then focused through the glass onto the plantar surface of each hind paw in turn. The thermal stimulus is automatically shut off by a photoelectric relay when the paw is moved or when the cut-off time is reached (20 seconds for radiant heat at ~5 Amps). An initial (baseline) response latency to the thermal stimulus is recorded for each animal prior to the injection of CFA. Twenty-four hours following intraplantar CFA injection, the response latency of the animal to the thermal stimulus is then re-evaluated and compared to the animal's baseline response time. Only rats that exhibit at least a 25% reduction in response latency (i.e. hyperalgesia) are included in further analysis. Immediately following the post-CFA latency assessment, test compound or vehicle (usually Solutol, hydroxypropyl methylcellulose, hydroxypropyl beta-cyclodextrin or PEG-400) is administered i.p. or p.o. to rats. Post-compound treatment withdrawal latencies are assessed at fixed time intervals, typically 30, 60 and 120 minutes. The percent reversal (% R) of hypersenstivitiy is calculated according to the following formula:

% Reversal=(Treatment Response-CFA Response)/
(Baseline Response-CFA Response)×100.

TABLE 9

| Cpd No. | Salt Form | High Dose | Route | Vehicle | Treatment Time, min | Percent Reversal | ED50 |
|---|---|---|---|---|---|---|---|
| 306 | $CO_2^-Na^+$ | 10 | p.o. | HPbCD | 100 | 91 |  |
| 306 | $CO_2^-Na^+$ | 3 | p.o. | HPbCD | 100 | 31 | 4 |
|  |  | 5.6 |  |  |  | 76 |  |
|  |  | 10 |  |  |  | 93 |  |
|  |  | 30 |  |  |  | 59 |  |
| 361 | $CO_2^-Na^+$ | 10 | p.o. | HPbCD | 100 | 28 |  |
| 496 | $CO_2^-Na^+$ | 10 | p.o. | HPbCD | 60 | 79 |  |
| 496 | $CO_2^-Na^+$ | 1 | p.o. | HPbCD | 60 | 9 |  |
|  |  | 3 |  |  |  | −10 |  |
|  |  | 5.6 |  |  |  | 10 |  |
|  |  | 10 |  |  |  | 24 |  |
|  |  | 30 |  |  |  | 30 |  |
| 496 | $CO_2^-Na^+$ | 10 | p.o. | HPbCD | 60 | 52 |  |

Example 5b

CFA-induced Paw Cold Hypersensitivity

Prior to intraplantar CFA injection, mice or rats are placed individually in elevated observation chambers having wire mesh floors. Through the mesh floor a series of three applications of acetone (0.04-0.10 mL/application) is sprayed onto the bottom of the paw using a multidose syringe device. A positive response takes the form of an abrupt withdrawal and licking of the paw. The cumulative duration of licking is recorded for each of the three trials which are then averaged to give the individual's response. Twenty-four hours following CFA injection acetone licking durations are markedly elevated implying a hypersensitivity to cooling. Test compounds of the formula (I) can be assessed for its ability to return acetone-evoked paw licking durations to pre-CFA levels (typically near zero) following systemic administration. Percent inhibition is calculated as follows % Inhibition=[1−(treatment licking duration/vehicle licking duration)]×10.

Example 6

Chemically-induced Abdominal Irritant Models of Visceral Pain

A chemical irritant (such as acetic acid, kaolin, bradykinin, phenyl-p-(benzo) quinine, bromo-acetylcholine, or zymosan) is injected in mice intraperitoneally, causing a contraction of the abdominal musculature, which is characterized by an elongation of the body extending through to the hind limbs. The number of such responses is quantitated and is reduced by pretreatment of analgesic agents, thus forming the basis for a screening test (Collier H O et al. Br J Pharmacol Chemother 1968, 32(2): 295-310). This type of abdominal irritant test has been used to predict the analgesic effect of numerous clinically effective agents, the potency of which in the abdominal irritant test parallels the magnitude of the dose needed in the relief of clinical pain. Such agents include acetaminophen, NSAIDS such as aspirin and ibuprofen, opioids, such as morphine and codeine, and other centrally acting analgesics, such as tramadol.

One modification of the chemically-induced abdmonial irritant model of visceral pain is to pretreat animals with agents known to induce inflammatory responses following intraperitoneal injection (such as LPS, zymosan, or thioglycolate). A small intraperitoneal dose of such an inflammogen, administered hours or days before the acute chemical irritant challenge, has been shown to increase the number of abdominal contractions observed (Ribeiro R A, et al. Eur J Pharmacol 2000, 387(1): 111-8). While some analgesic agents are effective at mitigating acute viscerochemical nociception, others, particularly those dependent upon receptor induction are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide analgesic action in human clinical use.

The ability of compounds of the formula (I) to mitigate chemical irritant—induced abdominal contractions following a pre-conditioning inflammatory stimulus can be studied as follows. Thioglycolate (3%, w/v, 2-3 mL i.p.) is injected into male CD1 mice (20-40 g, Charles River Labs), at a maximum dosage volume of 80 mL/kg, to induce peritoneal inflammation. Following a twenty-four hour pre-inflammation period these mice are dosed orally with compounds of the formula (I) (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, mice are placed individually in glass bell jars (approximately 15 cm in diameter) for counting of abdominal contractions over the next 15 minutes. The total number of abdominal contractions is summed for each treatment group and employed in the following formula to calculate Percent Inhibition (% I):

% I=[1−(test compound contractions/vehicle contractions)]×100.

Example 7

In Vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) are performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors are evoked by the testing procedures and that normal use of the paw (e.g., walking) is relatively uncompromised, apart from occasional "guarding" of the paw. Subsequent to the surgery, the subjects' behaviors, such as grooming, feeding, and weight gain, are normal, except for hypersensitivity (as defined above) of the affected paw.

In addition to induction by nerve damage resulting from accidental trauma or surgical procedures, neuropathic pain can also be induced by diabetes (Fox, A et al., Pain 81:307-316, 1999) or by treatment with chemotherapeutic agents, such as paclitaxel or vincristine (Yaksh, T L et al., Pain 93:69-76, 2001).

Agents that attenuate neuropathic pain in the clinic also are effective in rodent neuropathic pain models. These agents include the recently approved Cymbalta (Duloxetine, lyengar, S., et al., JPET 2004 311:576-584), morphine (Suzuki, R et al., Pain 1999 80:215-228) and gabapentin (Hunter, J C et al., Eur J Pharmacol 1997 324:153-160). The dual TRPV1/TRPM8 receptor antagonist BCTC reduced mechanical hyperalgesia and tactile allodynia in the chronic constriction injury rodent neuropathic pain model (Pomonis, J D et al., JPET 2003 306:387-393; Behrendt, H et al., Brit J Pharm 2004 141:737). Cold allodynia is a particularly debilitating symptom of neuropathic pain conditions (Jorum E et al. Pain 2003 101: 229-235). The antiallodynic effect of compounds of the formula (I) in this rodent model is predictive of clinical effect for these novel agents.

Example 7a

Chronic Constriction Injury (CCI)-induced Model of Neuropathic Pain

Acetone-induced Hypersensitivity

Male Sprague Dawley rats (225-450 g; n=5-8/treatment) were used to evaluate the ability of selected compounds of the formula (I) to reverse CCI-induced cold hypersensitivity. Four loose ligatures of 4-0 chromic gut were surgically placed around the left sciatic nerve under inhalation anesthesia as described by Bennett et al (Bennett G J, Xie Y K. Pain 1988, 33(1): 87-107). Fourteen to 35 days following CCI surgery, subjects were placed in elevated observation chambers containing wire mesh floors and five applications of acetone (0.05 mL/application separated by approximately 5 minutes)

were spritzed onto the plantar surface of the paw using a multidose syringe. An abrupt withdrawal or lifting of the paw was considered a positive response. The number of positive responses was recorded for each rat over the five trials. Following baseline withdrawal determinations, compounds of formula (I) are administered in an appropriate vehicle, such as hydroxypropyl-β-cyclodextrin (HP β CD), methylcellulose, Methocel, 10% Solutol, or $H_2O$, or the like, by the appropriate route, i.p. or p.o. The number of withdrawals were redetermined 1 to 3 h after compound administration. Results are presented as a percent inhibition of shakes, which was calculated for each subject as [1−(test compound withdrawals/pretest withdrawals)]×100 and then averaged by treatment. Results are shown in Table 10.

TABLE 10

| Cpd No. | Salt Form | Dose, mg/kg | Route of Administration | Vehicle | Pretreatment Time, hr | Percent Inhibition | ED50, mg/kg |
|---|---|---|---|---|---|---|---|
| 7 | $CO_2H$ | 30 | p.o. | 10% Solutol | 1 | 47 | |
|  |  | 30 | i.p. | 10% Solutol | 2 | 66 | |
| 177 | $CO_2H$ | 3 | p.o. | 10% Solutol | 1 | 23 | |
|  |  | 10 |  |  |  | 49 | |
|  |  | 30 |  |  |  | 46 | |
|  |  | 100 |  |  |  | 70 | |
|  |  | 30 | i.p. | 10% Solutol | 3 | 60 | |
| 292 | $CO_2^-Na^+$ | 30 | p.o. | Water | 2 | 60 | |
| 292 | $CO_2^-Na^+$ | 3 | p.o. | Water | 3 | 7 | 70 |
|  |  | 10 |  |  |  | 16 | |
|  |  | 30 |  |  |  | 21 | |
|  |  | 100 |  |  |  | 67 | |
| 272 | $CO_2^-Na^+$ | 30 | p.o. | HPbCD | 1 | 31 | |
| 273 | $CO_2^-Na^+$ | 30 | p.o. | HPbCD | 0.5 | 49 | |
| 271 | $CO_2^-Na^+$ | 30 | p.o. | HPbCD | 1 | 77 | |
| 271 | $CO_2^-Na^+$ | 10 | p.o. | HPbCD | 1 | 24 | |
|  |  | 30 |  |  |  | 44 | |
|  |  | 100 |  |  |  | 56 | |
| 306 | $CO_2^-Na^+$ | 30 | p.o. | HPbCD | 6 | 69 | |
| 306 | $CO_2^-Na^+$ | 3 | p.o. | HPbCD, Water | 4 | 20 | 15 |
|  |  | 10 |  |  |  | 38 | |
|  |  | 17.8 |  |  |  | 57 | |
|  |  | 30 |  |  |  | 68 | |
|  |  | 56 |  |  |  | 77 | |
|  |  | 100 |  |  |  | 77 | |
| 361 | $CO_2^-Na^+$ | 30 | p.o. | Water | 4 | 74 | |
| 361 | $CO_2^-Na^+$ | 3 | p.o. | Water | 2 | 9 | 13 |
|  |  | 10 |  |  |  | 17 | |
|  |  | 30 |  |  |  | 91 | |
| 395 | $CO_2^-Na^+$ | 30 | p.o. | Water | 2 | 23 | |
| 395 | $CO_2^-Na^+$ | 30 | p.o. | Water | 2 | 38 | |
| 396 | $CO_2^-Na^+$ | 30 | p.o. | Water | 4 | 50 | |
| 400 | $CO_2^-Na^+$ | 30 | p.o. | Water | 1 | 40 | |
| 400 | $CO_2^-Na^+$ | 30 | p.o. | Water | 3 | 25 | |
| 487 | $CO_2^-Na^+$ | 30 | p.o. | HPbCD | 3 | 66 | |
| 487 | $CO_2^-Na^+$ | 10 | p.o. | HPbCD | 3 | 43 | |
| 488 | $CO_2^-Na^+$ | 30 | p.o. | HPbCD | 2 | 43 | |
| 489 | $CO_2^-Na^+$ | 30 | p.o. | Water | 3 | 86 | |
| 489 | $CO_2^-Na^+$ | 10 | p.o. | Water | 4 | 13 | 23 |
|  |  | 17.8 |  |  |  | 60 | |
|  |  | 30 |  |  |  | 57 | |
|  |  | 56 |  |  |  | 70 | |
| 490 | $CO_2^-Na^+$ | 30 | p.o. | HPbCD | 1 | 23 | |
| 496 | $CO_2^-Na^+$ | 30 | p.o. | Water | 2 | 74 | |
| 496 | $CO_2^-Na^+$ | 10 | p.o. | Water | 4 | 76 | |
|  |  | 17.8 |  |  |  | 64 | |
|  |  | 30 |  |  |  | 72 | |
|  |  | 56 |  |  |  | 68 | |
| 496 | $CO_2^-Na^+$ | 0.3 | p.o. | HPbCD | 4 | 28 | 3.5 |
|  |  | 1 |  |  |  | 32 | |
|  |  | 3 |  |  |  | 23 | |
|  |  | 5.6 |  |  |  | 72 | |
|  |  | 10 |  |  |  | 71 | |
| 497 | $CO_2^-Na^+$ | 30 | p.o. | Water | 4 | 60 | |
| 505 | $CO_2^-Na^+$ | 30 | p.o. | HPbCD | 1 | 11 | |
| 524 | $CO_2^-Na^+$ | 30 | p.o. | HPbCD | 3 | 46 | |

Example 7b

Chronic Constriction Injury (CCI)-induced Model of Neuropathic Pain—Cold Plate-induced Hypersensitivity In male SD rats (175-325 g), four loose ligatures of 4-0 chromic gut are surgically placed around the left sciatic nerve under inhalation anesthesia as described by Bennet et al (Bennett G J, Xie Y K. *Pain* 1988, 33(1): 87-107). Seven to 21 days following sciatic chronic constriction injury (CCI) surgery, the subjects can be placed onto a commercial cold plate device cooled by peltier elements such that the surface temperature is held at 1° C. Each subject can undergo a 6 minute conditioning period followed by a 3 minute assessment period during which the total duration of hind paw lifting is recorded. This procedure is repeated at several intervals prior to and following systemic drug administration. Compounds of the formula (I) can be assessed for their ability to return duration of paw lifting back to pre-lesion levels. The duration of paw lifting during the 3 minute test period following administration of test compound is taken as a percentage of the duration of paw lifting during the 3 minute test period prior to test compound treatment.

Example 7c

Chronic Constriction Injury (CCI)-induced Model of Neuropathic Pain—Mechanical Allodynia (Von Frey Test)

In male SD rats (175-325 g), four loose ligatures of 4-0 chromic gut are surgically placed around the left sciatic nerve under inhalation anesthesia as described by Bennet et al (Bennett G J, Xie Y K. *Pain* 1988, 33(1): 87-107). Seven to 21 days following sciatic chronic constriction injury (CCI) surgery, the subjects can be placed onto an elevated rack of plexigas chambers having wire mesh or another type of perforated flooring. The measurement of mechanical allodynia can be performed using the von Frey hairs (Semmes-Weinstein Monofilaments, Stoelting Co., IL) wherein the rats can be habituated to the wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. This procedure is repeated at several intervals prior to and following systemic drug administration. Compounds of the formula (I) can be assessed for their ability to return the threshold force which elicits paw lifting back to pre-lesion levels.

Example 8

Inflammatory Agent-induced Models of Pyresis/Antipyresis

Compounds of the formula (I) can be tested in animal models of pyresis, according to previously documented and validated methods, such as those described by Kozak et al (Kozak W, Fraifeld V. *Front Biosci* 2004, 9: 3339-55). Fever is a frequent accompaniment of inflammatory disease. Animal models make use of the pyretic properties of yeast and other inflammatory agents, injecting a yeast suspension or other agent subcutaneously (Tomazetti J et al. *J Neurosci Methods* 2005, 147(1): 29-35); Van Miert A S, Van Duin C T. *Eur J Pharmacol* 1977, 44(3): 197-204). For example, Male Wistar rats (75-100 g) can be housed in groups of four to a cage at controlled temperature (23±1° C.) with a 12 h light: 12 h dark cycle (lights on at 07:00 h) and with standard lab chow and tap water ad libitum. All measured temperatures can be taken between 08:00 and 19:00 h. Each animal can be used in only one study. Rectal temperature (TR) can be measured by inserting a lubricated thermistor probe (external diameter: 3 mm) 2.8 cm into the rectum of the animal. The probe can be linked to a digital device, which displayed the temperature at the tip of the probe with a 0.1° C. precision and logs the values over time. Immediately after measuring the initial basal rectal temperature, the animals can be injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes can be recorded every hour up to 12 h, and expressed as the difference from the basal value. Since it has been previously reported that handling and temperature measuring-related stress alter rectal temperature, these animals can be habituated to the injection and measuring procedure for 2 days before experiments are carried out. In these sessions, the animals can be subjected to the same temperature measuring procedure described above, and can be injected intraperitoneally (i.p.) with 0.9% NaCl (10 ml/kg).

To assess the effect of potential antipyretic compounds on basal rectal temperature study animals can have their TR measured for 4 h, and after the fourth TR measurement they can be subcutaneously (s.c.) injected with vehicle (such as 10% Solutol in sterile water 5 ml/kg) or compounds of the formula (I) prepared in vehicle. TR can then be recorded every hour up to 8 h after the compound injections. To assess the effect of compounds of the formula (I) on baker yeast-induced hyperthermia, study animals can have their basal TR measured and then be injected with a pyrogenic dose of baker yeast (for example, 0.135 g/kg). TR changes can be recorded every hour up to 4 h, when potential antipyretics agents such as those compounds of the formula (I) are administered. Rectal temperature can then be monitored over the following 8 h. Basal rectal temperature and changes in rectal temperature can be expressed as means±S.E.M. of the differences from TR at 07:00 h. Data can be analyzed by two-way analysis of variance (ANOVA), with time of measures treated as within subject factor, depending on the experimental design. Post hoc analysis can be carried out by the F-test for simple effect and the Student-Newman-Keuls test, when appropriate. A value of $P<0.05$ would be considered statistically significant.

The modification of the subsequent pyretic response by therapeutic agents can also be monitored by rectal telemetry or other measurements of body temperature. Several clinically relevant agents such as acetaminophen, aspirin and ibuprofen, reduce fever in these models. The antipyretic effect of TRPM8 antagonists, such as compounds of the formula (I), in these tests would also be predictive of their clinical effect.

Example 9

CFA-induced Model of Rheumatoid Arthritis

Compounds of the formula (I) can be tested in animal models of rheumatoid arthritis, according to previously documented and validated methods, such as those described by Nagakura et al (Nagakura Y, et al. *J Pharmacol Exp Ther* 2003, 306(2): 490-7). For example, arthritis can be induced by the CFA inoculation in the rats (Male Lewis rats 150-225 g; Charles River). Briefly, 100 mg of *Mycobacterium butyricum* (Difco, Detroit, Mich.) can be thoroughly mixed with 20 mL of paraffin oil. Then mixture can be autoclaved for 20 min at 120° C. Each rat can be injected in the right footpad (hind paw) with the mixture in a 0.1-mL volume under inhalation anesthesia. The rats serving as controls can be injected with 0.1 mL of saline. Pain and other disease development parameters can be measured in the CFA- or saline-treated rats just before inoculation and up to 28 days post-inoculation. The measurement for pain parameters can be conducted for both mechanical and thermal (hot or cold) endpoints. The measurement of mechanical allodynia can be performed using the von Frey hairs (Semmes-Weinstein Monofilaments, Stoelting Co., IL) wherein the rats can be habituated to wire mesh bottom cages before the start of the experiment. Static allodynia can be tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response can be elicited. The lowest amount of force required to elicit a response can be recorded as the withdrawal threshold in log g. Thermal hyperalgesia can be assessed using the radiant heat test wherein a mobile radiant heat source can be located under a glass surface upon which the rat is placed. The beam of light can be focused on the hind paw, and the paw withdrawal latencies are defined as the time taken by the rat to remove its hind paw from the heat source. The measurement of joint hyperalgesia can be performed by a modification of the previously reported method (Rupniak N M J et al. *Pain* 1997, 71: 89-97). The torso of each rat can be held from the back with the left palm, and the bending and extension (one after the other and five times in each direction) of the ankle within its limits of range of motion can be performed with the right fingers. The total number of vocalizations emitted after the manipulation (the bending and extension, five times in each direction) can be recorded for each paw (the maximum score is 10 for each paw).

The scoring of mobility can be performed by modifying the evaluation scale reported by Butler et al. (Butler S H et al *Pain* 1992, 48: 73-81): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score 1, crawls only using the fore paws; and score 0, does not move. Paw volumes can be measured by volume displacement of electrolyte solution in a commercially available plethysmometer device. The hind paw can be immersed to the junction of the hairy skin, and the volumes can be read on a digital display. The scoring of joint stiffness can be performed as follows: the body of rats can be held from the back with the left palm, and the bending and extension (once in each direction) of the ankle within its limits of range of motion can be performed with the right fingers. It can be confirmed beforehand that there is no restriction of ankle joint movement in the bending and extension manipulations in naive rats, and the scoring can be performed according to the evaluation scale reported by Butler (Butler S H et al *Pain* 1992, 48: 73-81): score 2, there are restrictions of full range of movement of the ankle in both bending and extension; score 1, there is a restriction of full range of movement of the ankle in bending or extension; and score 0, no restriction. The measurements for paw volume and joint stiffness can be conducted for both hind paws.

Compounds of the formula (I) can be assessed for antihyperalgesic efficacy as follows: thirty-two rats (8 rats per dose and four doses per compound) that are be treated with the CFA and another eight rats as naive controls can be used for each drug evaluation. The analgesic effects can be evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia can be measured for the 32 rats that are to be used for compound evaluation. The rats are allocated to four groups (eight rats per group) such that the differences in the averages of those parameters among the groups became small. All the analgesic effect evaluations and behavioral observations can be carried out by the observer who is blind to the drug treatment.

Data can be expressed as the mean+/–S.E.M. The time-course curves for mechanical allodynia, thermal hyperalgesia, joint hyperalgesia, body weight, and paw volume can be subjected to two-way repeated measures analysis of variance with post hoc t test. In experiments for evaluation of compounds of formula (I), the difference in scores between the vehicle-treated and naive control groups can be analyzed by Student's t test to confirm significant changes in the pain parameters in the ipsilateral paw. The analgesic effects can be analyzed by Dunnett's t test, and in each case the drug-treated groups can be compared with the vehicle-treated group. In each statistical analysis, the comparison can be conducted for paws on the corresponding side. $P<0.05$ is considered statistically significant. In this model, the centrally acting analgesics morphine and tramadol fully relieved pain, whereas the NSAIDs, indomethacin and diclofenac are partially effective, evidencing the model's clinical predictability. The analgesic effect of compounds of the formula (I) in this test would predict their clinical usefulness in treating arthritis.

Example 10

In vivo Model for Arthritis: Inflammogen-induced Hyperalgesia of the Knee Joint

Compounds of the formula (I) can be tested in animal models of osteoarthritis, according to previously documented and validated methods, such as those described by Sluka et al (Sluka K A, Westlund K N. *Pain* 1993, 55(3): 367-77). For example, male Sprague-Dawley rats (Harlan, Indianapolis, Ind.) weighing 225 to 350 g can be briefly anesthetized with vaporized halothane and then injected with a mixture of 3% carrageenan and 3% kaolin (100 µL in 0.9% sterile saline) into the joint cavity of one knee. After the injection, the animals can be returned to their cages until the time of testing. For behavioral testing animals can be placed in individual clear plastic cages on top of an elevated wire mesh surface that restricted movement. The animals should be allowed to acclimate for approximately 1 hour before testing. Von Frey filaments, as described above, can then be used to test for enhanced responses to mechanical stimuli. The filaments can be successively applied through the wire mesh perpendicularly to the plantar surface in between the pads of the third and fourth phalanges. The response threshold to mechanical stimuli can be determined before inflammation of the knee joint; 4 hours after inflammation to confirm the development of hyperalgesia; immediately after the administration of test compound such as those of Formula (I) i.e. 5 hours after inflammation; and at 8, 12, and 24 hours after inflammation.

The Kruskal-Wallis test, a nonparametric test, can be used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups can be executed by using the Mann-Whitney signed rank test. The data can be presented as median with 25th and 75th percentiles. Significance is $P \leq 0.05$.

Additionally, the gait of the animal or other pain-related behavior can be scored as the dependent measure of the painful effect of the arthritis on the animal's activity (Hallas B, Lehman S, Bosak A, et al. *J Am Osteopath Assoc* 1997, 97(4): 207-14). The effect of test drug on the animal's normal behavior can be quantified from zero, meaning no response, to three for incapacitating impairment. Effective analgesic treatment includes the clinically used indomethacin (Motta A F, et al. *Life Sci* 2003, 73(15): 1995-2004). Thus the benefit of compounds of the formula (I) in this model would predict their clinical relevance.

Example 11

Sarcoma Cell-induced Models of Bone Cancer Pain

Compounds of the formula (I) can be tested in animal models of bone cancer pain, according to previously documented and validated methods, such as those described in the scientific literature (El Mouedden M, Meert T F. *Pharmacol Biochem Behav* 2005, 82(1): 109-19; Ghilardi J R, et al. *J Neurosci* 2005, 25(12): 3126-31). In preparation for cell inoculation and tumor induction, osteolytic murine sarcoma cells (NCTC 2472, American Type Culture Collection (ATCC), Rockville, Md., USA) can be cultured in NCTC 135 medium (Invitrogen) containing 10% horse serum (Gibco) and passaged 2 times weekly according to ATCC guidelines. For their administration, cells can be detached by scraping and then centrifuged at 1000×g. The pellet can be suspended in fresh NCTC 135 medium ($2.5 \times 10^6$ cells/20 µL) and then used for intramedullary femur inoculation. Male C3H/HeN-Crl mice (25-30 g, Charles River Labs) can be used in such experiments. After induction of general anesthesia with xylazine (10 mg/kg i.p.) and ketamine (100 mg/kg i.p.) the left hind paw can be shaved and disinfected with povidone-iodine followed by 70% ethanol. A superficial incision of 1 cm can then be made over the knee overlaying the patella. The patellar ligament can then be cut, exposing the condyles of the distal femur. A 23-gauge needle can be inserted at the level of the intercondylar notch and the intramedullary canal of the femur to create a cavity for injection of the cells. Twenty microliters of media (sham animals) or media containing tumor cells (approximately $2.5 \times 10^6$ cells) can then be injected into the bone cavity using a syringe. To prevent leakage of cells outside the bone, the injection site can be sealed with dental acrylic and the wound closed with skin stitches.

Pain behaviors can be evaluated in separate groups (n=6) of sham and bone tumor mice with confirmed hyperalgesia as assessed by spontaneous lifting behavior. Animals can be behaviorally tested during a 3-week period prior to and after tumor inoculation. Body weight of the mice can be recorded throughout the experimental period to help monitor general health status. To measure the spontaneous lifting, the animals can be habituated in a transparent acrylic cylinder of 20 cm diameter put on an horizontal surface and thereafter observed during 4 min for spontaneous lifting behavior of the left hind paw. After spontaneous lifting behavior assessment, animals can be immediately placed on a mouse rotarod (e.g. ENV-575M, Med Associates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia may be made by exposing the ipsilateral hind paw of the mouse to 5 repeated applications of acetone (20 µL) and quantifying the lift/licking frequency and/or duration. Post-mortem evaluation of bone destruction can be assessed by ACT processing followed by scanning using a system such as the Skyscan 1076 microtomograph system for small animal imaging (Skyscan 1076\, Skyscan, Aartselaar, Belgium). Measured histomorphometry parameters of bone destruction can be subsequently correlated with behavioral endpoints.

The antihyperalgesic, antiallodynic and disease modifying effects of compounds of the formula (I) can be tested in this murine model of bone cancer pain in separate groups (n=6 per dose group). Animals with confirmed hyperalgesia, as assessed by spontaneous or acetone-evoked lifting, can be behaviorally tested, for example, on days 15 and 22 after distal femur tumor inoculation before and 1 h after systemic administration of vehicle (e.g. 20% HPbCD in sterile water) or compounds of the formula (I). The statistical analysis can be performed by one-way ANOVA to compare behavioral measurements and bone parameters among the experimental groups. To compare behavioral measurements and bone parameters between sham and tumor-bearing animals, a Mann-Whitney U test can be used. Results are considered statistically significant at P<0.05 (two-tailed). Data are expressed as mean+/−S.E.M.

Bone cancer causes intense pain in humans, mimicked in animal models of bone cancer pain in rodents such as that described above. Analgesic treatments that are effective in this model include COX-2 inhibitors (Sabino M A, Ghilardi J R, Jongen J L, et al. *Cancer Res* 2002, 62(24): 7343-9) and high doses of morphine (Luger N M et al. *Pain* 2002, 99(3): 397-406), agents used clinically for pain relief in patients experiencing bone cancer pain. Because this model so closely mimics the human disease state, the finding that cold allodynia is a prominent symptom (Lee, Seong et al. *Yonsei Med J* 2005, 46(2): 252-9) strongly supports the concept that TRPM8 antagonists of the present invention will provide relief of pain associated with human bone cancer.

Example 12

Respiratory Irritant-induced Models of Cough

Compounds of the formula (I) can be tested in animal models of antitussive activity, according to previously documented and validated methods, such as those described by: Tanaka, M. and Maruyama, K. *J Pharmacol. Sci* 2005, 99(1), 77-82; Trevisani, M. et al., *Throax* 2004, 59(9), 769-72; and Hall, E. et al., *J Med. Microbiol* 1999, 48: 95-98. Testing is conducted in transparent ventilated chambers with a constant airflow of 400 mL/min. The tussive agent (citric acid 0.25 M or capsaicin 30 mM) can be nebulised via a miniultrasonic nebuliser with an output of 0.4 mL/min. The appearance of cough can be detected by means of a tie clip microphone and confirmed by the characteristic posture of the animal. The cough sounds can be recorded and digitally stored. A blinded observer subsequently counts the number of elicited cough efforts. In some cases, animals can be sensitized by pre-exposure to certain agents such as ovalbumin. A test compound can be administered to at the peak of irritant-induced cough to evaluate the antitussive effects of the compound. In addition, prophylactic or multiple dosing regimes can be utilized to evaluate the test compound for modulation of the onset and duration of irritant-induced cough. Variations of these tests predict the antitussive effects of effective clinical agents, including NMDA antagonists such as dextrorphan and dextromethorphan, opioids such as codeine, beta 2 agonists such as salbutamol and antimuscarinics such as ipratropium (Bolser, D. C. et al., *Eur J Pharmacol* 1995, 277(2-3), 159-64; Braga, P. C. *Drugs Exper Clin Res* 1994, 20, 199-203). The antitussive action of menthol in both guinea pig and humans Eccles R. *Curr Allergy Asthma Rep* 2003, 3(3): 210-4; Laude E A, et al. *Pulm Pharmacol* 1994, 7(3): 179-84; Morice A H, et al. *Thorax* 1994, 49(10): 1024-6) is predictive of the clinical utility of compounds of the formula (I) as antitussive agents.

Example 13

Chemical Irritant-induced Models of Itch, Contact Dermatitis, Eczema and Other Manifestations of Dermal Allergy, Hypersensitivity and/or Inflammation Compounds of the formula (I) can be tested in animal models of contact dermatitis or itch, according to previously documented and validated methods, such as those described in the scientific literature (Saint-Mezard P et al. *Eur J Dermatol* 2004, 14(5): 284-95; Thomsen J. S., et al. *J Exp Dermatol* 2002, 11(4): 370-5; Weisshaar E, et al. Arch Dermatol Res 1998, 290(6): 306-11; Wille J J, et al. *Skin Pharmacol Appl Skin Physiol* 1999, 12(1-2): 18-27). Mice (or species such as guinea pig or rat) can be sensitized with 25 mL of 0.5% dinitrofluorobenzene solution (DNFB diluted 4:1 in acetone:olive oil immediately before application or other haptens, such as 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB a nonirritant dose) can be applied onto both sides of the right ear and the same amount of solvent alone onto the left ear. Ear thickness can be monitored daily using a caliper. Compounds of the formula (I) can be administered at the peak of inflammation to evaluate the anti-allergy activity of compounds. In addition, prophylactic or multiple dosing regimes can be utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (Weisshaar E, Gollnick H. Skin Therapy Lett 2000, 5(5): 1-2,5). Additionally, the contact sensitizing property of commercially important drugs and the ability of ion channel modulators to prevent and treat skin sensitization in these models (Kydonieus A, et al., *Proceedings of the International Symposium on Controlled Release of Bioactive Materials* 24th:23-24, 1997) demonstrate the therapeutic utility of compounds of the formula (I) in dermal sensitization.

Example 14

Chemical Irritant-induced Models of Rhinitis and Other Manifestations of Nasal Hypersensitivity and/or Inflammation Compounds of the formula (I) can be tested in animal models of rhinitis, according to previously documented and validated methods, such as those described in the scientific literature (Hirayama Y, et al. *Eur J Pharmacol* 2003, 467(1-3): 197-203; Magyar T, et al *Vaccine* 2002, 20(13-14): 1797-802; Tiniakov R L, et al. *J Appl Physiol* 2003, 94(5): 1821-8). Testing can be conducted in mouse, guinea pig, dog or human in response to intranasal challenge with one or more irritants such as cold air, capsaicin, bradykinin, histamine, pollens, dextran sulfate, 2,4-tolylene diisocyanate, *Bordetella bronchiseptica, Pasteurella multodica* or acetic acid. In some cases, animals can be sensitized by pre-exposure to certain agents including, but not limited to, ragweed or ovalbumin. Prior to or following irritant administration, the test subject can receive, respectively, the prophylactic or therapeutic administration one or more times of compounds of the formula (I), or vehicle control, by the enteral or parenteral route. Significant differences indicative of nasal rhinitis or sensitization for the test compound-treated subjects compared with vehicle-treated subjects can be taken as evidence of antirhinitis activity. Independent variables include dose, frequency and route of administration, time interval between prophylactic or therapeutic test compound administration and irritant challenge as well as sex and non-sex genotype of the test subject. The intimate role of neurogenic inflammation in these hypersensitivity states demonstrates that compounds of the formula (I) desensitize or block the sensitization underlying these disease states.

Example 15

Conflict-induced Models of Anxiety, Panic Disorder and Other Non-adaptive Stressful or Phobic Responses Compounds of the formula (I) can be tested in animal models of anxiety, panic disorders and other non-adaptive responses, according to previously documented and validated methods, such as those described by Cryan and Holmes (Cryan J F, Holmes A. *Nat Rev Drug Discov* 2005, 4(9): 775-90) or Braw et.al. (Y. Braw et al. *Behav Brain Res* 2006, 167: 261-269). Specifically, for studies in rats, the following apparati may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings can be analyzed using the 'Observer' system (Noldus Information Technology). A subject rat can be removed from its home cage, weighed and placed gently in the center of the open-field arena. The rat can be allowed to explore the open-field freely while its behavior is videotaped for 5 min. Afterwards, it can be transferred to the plus-maze and placed at the center, facing a closed arm. The rat's behavior can again be videotaped for 5 min, after which it can be returned to its home cage. The apparatus can cleaned using a 70% ethanol solution between rats.

Open-field and plus-maze measures can be grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity can be analyzed by one-way ANOVA's on each of the measures, for each the between-subject comparisons. Plus-maze analyses can be conducted in a similar fashion.

Testing may also be conducted in mouse or rat in this fashion in order to measure avoidance of other aversive environmental stimuli such as Geller or Vogel anticonflict tests, the light/dark test and the hole-board test (see Cryan J F, Holmes A. *Nat Rev Drug Discov* 2005, 4(9): 775-90). Prior to environmental exposure, the test subject can receive the prophylactic administration one or more times of compounds of the formula (I), or vehicle control (e.g. 10% Solutol in sterile water), by the enteral or parenteral route. The cumulative time or number of times spent engaged in the aversive behavior can be measured. Significant differences in one or more of these measures for the test compound-treated subjects compared with vehicle-treated subjects can be taken as evidence of anxiolytic activity. Because these models are pharmacologically validated by the effectiveness of clinically useful anxiolytics (Cryan J F, Holmes A. *Nat Rev Drug Discov* 2005, 4(9): 775-90), they will be useful for the detection of anxiolytic compounds of the formula (I).

Example 16

Bladder Pressure- and Hypertrophy-induced Models of Urinary Incontinence

Compounds of the formula (I) can be tested in animal models of urinary incontinence according to previously documented and validated methods, such as those described by in the scientific literature (Kaiser S, Plath T, (Metagen Pharmaceuticals GmbH, Germany DE Patent 10215321; McMurray G, et al. *Br J Pharmacol* 2006, 147 Suppl 2: S62-79). TRPM8 is expressed in human prostate, testicle, seminiferous tubules, scrotal skin and inflamed bladder (Stein R J, et al. *J Urol* 2004, 172(3): 1175-8; Stein R J, et al. *J Urol* 2004, 172(3): 1175-8; Mukerji et al. *BMC Urology* 2006, 6:6). Excitation of TRPM8 receptors through cooling or application of menthol causes contraction in the bladder and a decrease in micturition threshold volume (Tsukimi Y, Mizuyachi K, et al. *Urology* 2005, 65(2): 406-10). To assess compounds of the formula (I) for potential urinary incontinence activity, Sprague-Dawley rats are surgically implanted with bladder catheters allowing for the delivery of fluid (typically saline) and the monitoring of pressure (using a pressure transducer). Cystometry recordings can be monitored with a polygraph to evaluate voiding interval, threshold pressure, bladder capacity, bladder compliance, and the number of spontaneous bladder contractions. For example, the bladder catheter can be connected to a Harvard infusion pump, and bladders perfused overnight with saline at 2 mL/h. The next morning the bladder catheter can be attached (using a "T" connector) to a Statham pressure transducer (Model P23 Db) and to a Harvard infusion pump. A plastic beaker attached to a force displacement transducer (Grass FTO3) can be placed under the rat's cage to collect and record urine volume. The cystometric evaluation of bladder function can be started by infusing saline (20 mL/h) and after the first micturition the infusion is maintained for 20 min. Two hours after the first cystometry period, the rats can be dosed orally with compounds of the formula (I) and a second cystometry is performed between 30 min and 4 h after administration of test compound. The appropriate vehicle (e.g. 10% Solutol in sterile water) can be similarly administered to groups of rats that served as controls and the cystometry can be performed at the same respective time points.

Compounds of the formula (I) can also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (Woods M. et al., *J Urology* 2001, 166:1142-47). Cystometry recordings can then be evaluated as described above. Such preclinical procedures are sensitive to compounds having clinical utility for the treatment of urinary incontinence (Soulard C, et al. *J Pharmacol Exp Ther* 1992, 260(3): 1152-8), and the activity of compounds of the formula (I) in this model would be predictive of clinical utility.

Example 17

In vivo Model for Cold-enhanced Central Pain States

Injury to the brain or spinal cord, such as that caused by trauma, interrupted blood flow or neurodegenerative diseases, often precipitates a central pain condition. Examples of such injuries characterized, in part by, a hypersensitivity to cold stimuli include multiple sclerosis (Morin C, et al. *Clin J Pain* 2002, 18(3): 191-5; Svendsen K B, et al. *Pain* 2005, 114(3): 473-81), stroke or cerebral ischemia (Greenspan J D, et al. *Pain*. 2004, 109(3): 357-66) and spinal cord injury (Defrin R, Ohry A, Blumen N, Urca G. *Pain* 2001, 89(2-3): 253-63; Defrin R, et al. *Brain* 2002, 125(Pt 3): 501-10; Finnerup N B, et al. *Anesthesiology* 2005, 102(5): 1023-30). Each of these conditions may be readily modeled in animals for assessment of the ability of compounds of the formula (I) to mollify the hypersensitive state. For example, a spinal cord injury (SCI) can be performed in adult Sprague-Dawley rats having a body weight of 150-200 g at time of surgery (Erichsen et al. *Pain* 2005, 116: 347-358). The rats can be anaesthetized with chloral hydrate (300 mg/kg, i.p., Sigma, USA) and a catheter can be inserted into the jugular vein. A midline skin incision can then be made along the back to expose the T11-L2 vertebrae. The animals can be positioned beneath a tunable argon ion laser (Innova model 70, Coherent Laser Products Division, CA, USA) operating at a wavelength of 514 nm with an average power of 0.17 W. The laser light can be focused into a thin beam covering the single T13 vertebra, which can be irradiated for 10 min. Immediately before the irradiation, erythrosin B (Aldrich, 32.5 mg/kg dissolved in 0.9% saline) can be injected intravenously via the jugular catheter. Due to rapid metabolism of erythrosin B, the injection can be repeated after 5 min in order to maintain adequate blood concentrations. During irradiation, the body core temperature can be maintained at 37-38° C. by a heating pad. After irradiation the wound can be closed in layers and the skin sutured together.

SCI rats can be routinely tested for the presence of pain-like behaviors from 3-4 weeks after surgery. The fur of the animals can be shaved at least a day prior to examination of the cutaneous pain threshold to avoid sensitization of the skin receptors. During testing, the rats can be gently held in a standing position by the experimenter and the flank area and hindlimbs can be examined for hypersensitivity to sensory stimulation. On the day of drug testing, SCI rats can be administered drug according to the experimental schedule and the time course of pain-like behaviors can be measured. To test for the presence of cold allodynia, ethyl chloride or acetone can be sprayed onto the skin of the animals, often that which has been previously determined to be sensitive to mechanical stimulation by von Frey filament testing. The subsequent response to cold stimulation can be observed and classified according to the following scale: 0, no visible response; 1, localized response (skin twitch) without vocalization; 2, transient vocalization; 3, sustained vocalization. Kruskal Wallis ANOVA on ranks can be used to analyze the overall effects of non-parametric data obtained in response to cold stimulation following pretreatment with either compounds of the formula (I) or vehicle.

Example 18

In vivo Model for Post-anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (Bhatnagar S, et al. *Anaesth Intensive Care* 2001, 29(2): 149-54; Tsai Y C, Chu K S. *Anesth Analg* 2001, 93(5): 1288-92). Compounds of the formula (I) may be assessed for their ability to mitigate post-ansethetic induced-shaking by using animal models such as that described by Nikki et al (Nikki P, Tammisto T. *Acta Anaesthesiol Scand* 1968, 12(3): 125-34) and Grahn (Grahn, D A, et al. *J Applied Physiology* 1996, 81: 2547-2554). For example, Wistar rats (males, weighing 250-450 g) may be surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia can be monitored throughout the experiment using copper-constantin thermocouples. The EEG and EMG signals can be recorded on polygraph paper (5 mm/s, Grass model 7E polygraph) and, during recovery from anesthesia, the EEG is computer scored in 10 second epochs as either synchronized: high amplitude (0.100 μV), low frequency (1-4 Hz dominated) activity characteristic of slow-wave sleep (SWS-like) or desynchronized: low amplitude (75 μV), high frequency (5-15 Hz dominated), characteristic of waking and rapid-eye-movement sleep (W-like). The EMG activity can be quantified as the averaged summed voltage/time interval by processing the raw EMG signal through an integrator (Grass model 7P3, 0.5 s time constant). On the day of an experiment, the animal can be placed in a small acrylic box (15×15×15 cm) and exposed to a halothane vapor-air mixture (4% halothane). Immediately after the induction of anesthesia, the animal can be removed from the enclosure and subsequently anesthetized through a nose cone. Following cessation of anesthesia, two stages of recovery can be judged: emergence from anesthesia and restoration of behavioral activity (behavioral recovery). Emergence from anesthesia may be defined as an increase in tonic EMG activity and a change in the EEG from a SWS-like pattern to a W-like pattern. Behaviorally, recovery has occurred when the animal rises from a prone position and initiated coordinated movements. The time intervals from termination of anesthesia to emergence and behavioral recovery can be measured in all animals. Time interval data can be subjected to a repeated measure analysis of variance, and the Scheffe's method can be employed for testing differences between pairs of means.

Example 19

Cold-evoked Cardiovascular Pressor Responses

Compounds of the formula (I) can be tested in animals and humans for their ability to mitigate cardiovascular pressor responses evoked by cold exposure. Seasonal environmental cooling is directly associated with elevated blood pressure and an increased incidence of coronary events in human populations worldwide (Barnett, A G et al. *J Epidemiol Community Heath* 2005, 59 551-557). Cold-evoked pulmonary hypertension and cold aggravation of chronic obstructive pulmonary disease are clinical indications succeptible to heightened cardiopulmonary sensitivity to cold (Marno P et al. *Eur Respiratory Review* 2006, 15 (101): 185.; Acikel M et al *Int J of Cardiol* (2004) 97: 187-192). The clinical cold pressor test assesses changes in blood pressure (BP) and cold pain perception during a 2-3 minute immersion of one hand into ice water. This test may be utilized to characterize analgesic compounds (Koltzenberg M et al. *Pain* 2006, 126(1-3): 165-74) and to assess cold hypersensitivity (Desmeules J A et al. *Arthritis Rheum* 2003, 48(5): 1420-9). Compounds of the formula (I) can be studied in an anesthetized rat cold pressor paradigm to determine whether TRPM8 antagonism would interfere with the blood pressure pressor response to cold stimulation of the forepaws. Male Sprague-Dawley rats (300-450 g) anesthetized with sodium pentobarbital are instrumented with a jugular catheter and an indwelling carotid artery cannula connected to a pressure transducer. Vehicle (e.g. 20% HPbCD in sterile water) or test compound is infused (1 mL/kg) over one minute through the intravenous catheter. Ten minutes later both forelimbs are packed in crushed ice for 5 minutes. Alternatively, the test compound and vehicle treatments may be administered orally at an appropriated time prior to the surgical cannulations and cold challenge. Percent changes in mean arterial pressure in response to this cold stimulus are calculated for vehicle and test compound pretreatments. Percent inhibition attributed to treatment with test compound is then determined using the following formula: % Inhibition=[1-(cold evoked % change in BP post-test compound/cold evoked % change in BP post-vehicle)]×100. Results are shown in Table 11

TABLE 11

| Cpd No. | Salt Form | Dose | Route | Vehicle | Treatment Time, hours relative to Cold Challenge | Percent Inhibition, relative to vehicle |
|---|---|---|---|---|---|---|
| 306 | $CO_2^- Na^+$ | 1 | p.o. | HPbCD | 1.5 | 16 |
|  |  | 3 |  |  |  | 41 |
|  |  | 10 |  |  |  | 62 |
|  |  | 30 |  |  |  | 75 |

Example 20

Cold-induced Vasoconstriction: Ramifications for Tissue Perfusion

Damage may occur to a bodily tissue when blood flow is compromised or interrupted. Reasons for vascular compromise include peripheral vascular disease (Lamah M et al, European journal of vascular and endovascular surgery (1999), 18(1), 48-51), prior traumatic or frostbite injury, Raynaud's syndrome (Lutolf, O et al Microvascular research (1993), 46(3), 374-82), diabetic neuropathy (Forst T et al, Clinical science (London, England: 1979) (1998), 94(3), 255-61.), surgical intervention and autonomic dysregulation (Gherghel D et al, Investigative opthalmology & visual science (2004), 45(10), 3546-54). In the case of marginal resting perfusion, vasoconstriction as enchanced by cool temperature may aggravate symptoms and potentiate tissue injury (Cankar K et al, The Journal of hand surgery (2000), 25(3), 552-8; LutolfO et al Microvascular research (1993), 46(3), 374-82.). Several of these conditions may be readily modeled in animals to assess of the ability of TRPM8 antagonists such as compounds of the formula (I) to preserve tissue perfusion in the face of local cooling. For example, laser Doppler assessment of skin blood flow may be studied in the paws of anesthetized rats (Hord A H et al, Anesthesia and analgesia (1999), 88(1), 103-8), wherein the paw is subject to a series of decreasing temperatures steps as applied by physical contact with a Peltier cooling element under computer control. The laser Doppler measures skin perfusion in the face of cooling-induced vasoconstriction thereby generating a temperature x perfusion relationship. Systemic administration of a TRPM8 antagonist is anticipated to shift this curve toward preserving perfusion at reduced temperatures relative to vehicle pretreatment. This activity is envisioned to be therapeutic in protecting tissue from hypo-perfusion and ischemia thereby minimizing the associated symptoms (e.g. pain) and potential tissue damage.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of the formula (I)

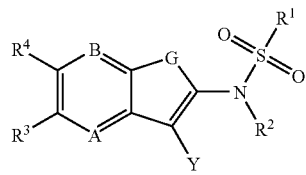

(I)

wherein
A is $CR^5$;
B is $CR^6$;
G is S;
Y is
  (i) H;
  (ii) isopropenyl;
  (iii) $C_{1-6}$ alkylcarbonyl optionally substituted with 1 to 3 fluoro substituents;
  (iv) $C_{3-6}$ cycloalkylcarbonyl;
  (v) phenylcarbonyl optionally substituted with one to three substituents independently selected from $C_{1-4}$ alkyl, fluoro, or chloro;
  (vi) phenylcarbonyl substituted with trifluoromethyl and optionally one additional substituent selected from trifluoromethyl, chloro, fluoro, or $C_{1-4}$ alkyl;
  (vii) heteroaryl optionally substituted with one to two substituents independently selected from chloro, fluoro, bromo, trifluoromethyl, $C_{1-4}$ alkoxy, hydroxy, $C_{1-4}$ alkyl, $C_{1-3}$ alkoxycarbonyl, $C_{1-3}$ alkylthio, cyano, amino, $C_{1-3}$ alkylamino, or di($C_{1-3}$)alkylamino;
  (viii) benzo-fused heteroaryl optionally substituted with one to two substituents independently selected from chloro, fluoro, bromo, trifluoromethyl, $C_{1-4}$ alkyl, $C_{1-4}$ alkoxy, hydroxy, $C_{1-4}$ alkoxycarbonyl, $C_{1-3}$ alkylthio, cyano, amino, $C_{1-3}$ alkylamino, or di($C_{1-3}$)alkylamino;
  (ix) bromo;
  (x) chloro;
  (xi) fluoro;
  (xii) iodo;
  (xiii) cyano;
  (xiv) formyl;
  (xv) $C_{1-6}$ alkyl optionally substituted with 1 to 3 substituents independently selected from hydroxy, fluoro, or chloro;
  (xvi) $C(OH)(C_{1-3}$ alkyl$)_2$;
  (xvii) $C_{3-6}$ cycloalkyl;
  (xviii) $C_{1-2}$ alkyl substituted with 1 substituent independently selected from $C_{1-4}$ alkoxycarbonyl, cyano, $C_{1-3}$ alkylthio, $C_{1-4}$ alkoxy, or $NR^7R^8$ wherein $R^7$ is hydrogen, $C_{1-4}$ alkyl, $C_{1-3}$ alkylcarbonyl, or $C_{1-3}$ alkylsulfonyl and $R^8$ is hydrogen or $C_{1-4}$ alkyl; or $R^7$ and $R^8$ are taken together with the nitrogen atom to which they are attached to form a 5 or 6 membered ring optionally containing one additional heteroatom selected from nitrogen, oxygen, or sulfur;
  (xix) $C_{1-4}$ alkoxycarbonyl;
  (xx) $C_{1-3}$ alkoxy;
  (xxi) hydroxy;
  (xxii) $C_{6-10}$ aryl optionally substituted with one to three substituents independently selected from chloro, fluoro, bromo, $C_{1-4}$ alkoxy, hydroxy, $C_{1-3}$ alkoxycarbonyl, $C_{1-3}$ alkylthio, cyano, amino, $C_{1-2}$ alkylamino, di($C_{1-2}$)alkylamino, or $C_{1-6}$ alkyl optionally substituted with one to three halogen substituents; with the proviso that not more than two of the substituents are selected from the group consisting of $C_{1-3}$ alkoxycarbonyl, $C_{1-3}$ alkylthio, cyano, amino, $C_{1-2}$ alkylamino, di($C_{1-2}$)alkylamino, and $C_{1-6}$ alkyl substituted with one to three halogen substituents;
  (xxiii) $NR^9R^{10}$ wherein $R^9$ is hydrogen, $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; and wherein said 5 or 6 membered ring is optionally substituted with a $C_{1-4}$ alkyl substituent; with the proviso that when G is S and $R^{10}$ is hydrogen, $R^9$ is other than hydrogen and $C_{1-4}$ alkyl;
  (xxiv) aminocarbonyl;
  (xxv) methylaminocarbonyl;
  (xxvi) dimethylaminocarbonyl; or
  (xxvii) arylhydroxy($C_{1-3}$)alkyl;
$R^1$ is
  (i) $CF_3$;
  (ii) $C_{1-6}$ alkyl optionally substituted with 1 substituent selected from $C_{1-3}$ alkylsulfonyl, $C_{1-4}$ alkoxycarbonyl, formyl, hydroxy, carboxy, trifluoromethyl, $C_{1-4}$ alkoxy, $C_{1-3}$ alkylthio, bromo, cyano, $R^{11}$, or $R^{12}$;
  (iii) aryl($C_{1-2}$ alkyl) wherein the ring of the aryl group is optionally substituted with 1 to 3 substituents independently selected from $C_{1-4}$ alkyl, fluoro, chloro, trifluoromethyl, hydroxy, $C_{1-4}$ alkoxy, $C_{1-4}$ alkoxycarbonyl, or carboxy; with the proviso that not more than two of the substituents are selected from the group consisting of trifluoromethyl, $C_{1-4}$ alkoxycarbonyl, and carboxy;

(iv) $C_{3-8}$ cycloalkyl; or cyclohexyl substituted at the 4-position with one substituent selected from the group consisting of cyano, $C_{1-4}$ alkoxycarbonyl, carboxy, aminocarbonyl, $C_{1-3}$ alkylaminocarbonyl, di($C_{1-3}$ alkyl)aminocarbonyl, amino-methyl, methylamino-methyl, dimethylamino-methyl, $R^{11}$, and $R^{12}$;

(v) benzo-fused $C_{5-6}$cycloalkyl attached at the benzo portion of the ring system, and wherein the $C_{5-6}$cycloalkyl portion of benzo-fused $C_{5-6}$cycloalkyl is optionally substituted with amino, ($C_{1-3}$ alkyl)amino, or di($C_{1-3}$ alkyl)amino;

(vi) phenyl substituted with 3- or 4-imidazolyl, wherein the point of attachment of the imidazolyl is through a nitrogen heteroatom; and wherein the imidazolyl is optionally independently substituted with one to two substituents selected from the group consisting of $C_{1-3}$ alkyl, 2-cyano, chloro, bromo, amino-$C_{1-2}$ alkyl, ($C_{1-2}$ alkyl)amino-$C_{1-2}$ alkyl, and di($C_{1-2}$ alkyl)amino-$C_{1-2}$ alkyl; wherein di($C_{1-3}$ alkyl) is optionally taken together with the nitrogen atom to which it is attached to form a 5 or 6 membered ring optionally containing one additional heteroatom selected from nitrogen, oxygen, or sulfur; and wherein the ring formed by di($C_{1-3}$ alkyl)amino is optionally substituted with $C_{1-3}$alkyl; with the proviso that not more than one of the substituents is amino-$C_{1-2}$ alkyl, ($C_{1-2}$ alkyl)amino-$C_{1-2}$ alkyl, or di($C_{1-2}$ alkyl)amino-$C_{1-2}$ alkyl;

(vii) phenyl optionally substituted with one to three substituents independently selected from $C_{1-4}$ alkyl optionally substituted with one to three chloro or fluoro substituents or one hydroxy substituent, chloro, fluoro, bromo, $C_{1-4}$ alkoxy, trifluoromethoxy, 3- or 4-phenyloxy, 3- or 4-heteroaryloxy wherein the heteroaryl ring is a 6 membered ring containing carbon ring members and 1 or 2 nitrogen heteroatom ring members, $C_{1-3}$ alkylsulfonyl, $C_{1-4}$ alkoxycarbonyl, $C_{1-3}$ alkylthio, hydroxy, carboxy, cyano, nitro, 3- or 4-heteroaryl wherein said heteroaryl is other than imidazolyl, $C_{1-3}$ alkylcarbonyl, aminocarbonyl, $C_{1-3}$ alkylaminocarbonyl, di($C_{1-3}$)alkylaminocarbonyl, $C_{1-3}$ alkylsulfonylaminocarbonyl, di($C_{1-3}$)alkylaminosulfonyl, P(O)(OC$_{1-3}$ alkyl)$_2$, P(O)(OH)$_2$, SO$_3$H, C(O)NHOH, C(=N)NH$_2$, C(=NOH)NH$_2$, C(=N(methylcarbonyloxy))NH$_2$, or SO$_2$NH$_2$; with the proviso that not more than two of the substituents are selected from the group consisting of trifluoromethoxy, 3- or 4-substituted phenyloxy, 3- or 4-heteroaryloxy, $C_{1-3}$ alkylsulfonyl, $C_{1-4}$ alkoxycarbonyl, $C_{1-3}$ alkylthio, carboxy, cyano, 3- or 4-heteroaryl, $C_{1-3}$ alkylcarbonyl, aminocarbonyl, $C_{1-3}$ alkylaminocarbonyl, di($C_{1-3}$) alkylaminocarbonyl, $C_{1-3}$ alkylsulfonylaminocarbonyl, di($C_{1-3}$) alkylaminosulfonyl, and P(O)(OC$_{1-3}$ alkyl)$_2$ and not more than one of the substituents is selected from the group consisting of —P(O)(OH)$_2$, —SO$_3$H, carboxy, C(O)NHOH, C(=N)NH$_2$, C(=NOH)NH$_2$, C(=N(C$_{1-3}$alkylcarbonyloxy))NH$_2$, and —SO$_2$NH$_2$; wherein the phenyloxy is optionally substituted with one to two substituents independently selected from the group consisting of methyl and fluoro; and wherein the heteroaryl substituent is optionally independently substituted with one to two substituents selected from the group consisting of $C_{1-3}$ alkyl, trifluoromethyl, trifluoromethoxy, cyano, amino, methylamino, dimethylamino, chloro, bromo, carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl)amino-$C_{1-2}$ alkyl; with the proviso that not more than one of the substituents is selected from the group consisting of carboxy, $C_{1-2}$ alkoxycarbonyl, $C_{1-2}$ alkoxycarbonylmethyl, carboxymethyl, amino-$C_{1-2}$ alkyl, ($C_{1-2}$ alkyl)amino-$C_{1-2}$ alkyl, and di($C_{1-2}$ alkyl) amino-$C_{1-2}$ alkyl;

(viii) naphthyl optionally substituted with one substituent selected from the group consisting of hydroxy, chloro, fluoro, bromo, $C_{1-4}$ alkoxycarbonyl, and carboxy;

(ix) $C_{6-10}$ aryl substituted with phenyl optionally substituted with one to two substituents selected from chloro, fluoro, $C_{1-4}$ alkoxy, $C_{1-4}$ alkoxycarbonyl, carboxy, hydroxy, or $C_{1-3}$ alkyl;

(x) phenyl substituted with $R^{11}$ or $R^{12}$ at the 3 or 4 position; and optionally one additional substituent selected from fluoro, chloro, or $C_{1-3}$ alkyl;

(xi) a ring that is phenyl, wherein said ring is substituted with NR$^{15}$R$^{16}$; wherein R$^{15}$ is hydrogen, $C_{1-4}$ alkyl, $C_{1-4}$ alkylcarbonyl, trifluoromethylcarbonyl, trifluoromethylsulfonyl, $C_{3-6}$ cycloalkylsulfonyl, or $C_{1-3}$ alkylsulfonyl; and R$^{16}$ is hydrogen or $C_{1-4}$ alkyl; or R$^{15}$ and R$^{16}$ are taken together with the nitrogen atom to which they are attached to form a 5 or 6 membered ring optionally containing one additional heteroatom selected from nitrogen, oxygen, or sulfur optionally substituted with one or two oxo substituents; and wherein the ring formed by NR$^5$R$^{16}$ is optionally substituted with $C_{1-3}$alkyl, $C_{1-2}$ alkoxycarbonyl, or carboxy; and wherein said phenyl is optionally substituted with one to two additional substituents independently selected from the group consisting of $C_{1-4}$ alkyl, $C_{1-4}$ alkoxy, hydroxy, fluoro, chloro, and bromo;

(xii) phenyl substituted with C(O)NR$^{17}$R$^{18}$ wherein R$^{17}$ is hydrogen, $C_{1-4}$ alkyl, $C_{1-4}$ alkylcarbonyl, pyrrolidin-3-yl, or $C_{1-3}$ alkylsulfonyl; and R$^{18}$ is hydrogen or $C_{1-4}$ alkyl; or R$^{17}$ and R$^{18}$ are taken together with the nitrogen atom to which they are attached to form a 5 or 6 membered ring optionally containing one additional heteroatom selected from nitrogen, oxygen, or sulfur; and wherein said ring is optionally substituted with $C_{1-3}$alkyl;

(xiii) phenyl substituted with 4 or 5 fluoro substituents;

(xiv) phenyl substituted at the 4-position with —Q—C(R$^x$R$^y$)—(CH$_2$)$_{0-1}$CO$_2$H wherein Q is a bond or O; and wherein R$^x$ and R$^y$ are independently hydrogen or methyl; or R$^x$ and R$^y$ are taken together with the carbon atom to which they are both attached to form a cyclopropyl ring;

(xv) amino;

(xvi) $C_{1-6}$ alkylamino; or (xvii) di($C_{1-6}$ alkyl)amino;

$R^2$ is (i) $C_{3-6}$ cycloalkyl;

(ii) $C_{1-2}$ alkyl substituted with adamantyl or norbornanyl;

(iii) $C_{1-6}$ alkyl substituted with two $C_{6-10}$ aryl groups wherein one of said aryl groups is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$) alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl; and the other of said aryl groups is optionally substituted with 1 substituent selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl;

(iv) $C_{1-6}$ alkyl substituted with one $C_{6-10}$ aryl group and optionally one additional substituent selected from hydroxy or oxo, wherein said $C_{6-10}$ aryl group is optionally substituted with 1 to 3 substituents independently selected from chloro, fluoro, bromo, $C_{1-4}$ alkyl, $C_{1-4}$ alkoxy optionally substituted with 1 to 3 fluoro substituents, hydroxy, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$)alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, or $C_{1-3}$ alkylcarbonyl; with the proviso that not more than two of the substituents are selected from the group consisting of $C_{1-4}$ alkoxy substituted with 1 to 3 fluoro substituents, $C_{1-4}$ alkoxycarbonyl, $C_{1-3}$ alkylthio, trifluoromethylthio, cyano, trifluoromethyl, aminocarbonyl, $C_{1-3}$ alkylaminocarbonyl, di($C_{1-3}$) alkylaminocarbonyl, $C_{1-3}$ alkylsulfonyl optionally substituted with 1 to 3 fluoro substituents, nitro, amino, $C_{1-3}$ alkylamino, di($C_{1-3}$)alkylamino, and $C_{1-3}$ alkylcarbonyl;

(v) $C_{1-6}$ alkyl substituted with phenyl, wherein phenyl is substituted with 4 or 5 fluoro substituents; or phenyl is substituted with methoxy and 3 to 4 fluoro substituents; or (vi) $C_{2-6}$ alkyl optionally substituted with 1 to 2 substituents independently selected from cyano, trifluoromethyl, $C_{1-6}$ alkylcarbonyl, $C_{1-6}$ alkylthio, $C_{1-6}$ alkylsulfonyl, amino, $C_{1-3}$ alkylamino, di($C_{1-3}$) alkylamino, $C_{2-6}$ alkenyl, $C_{2-6}$ alkynyl, fluoro, $C_{1-6}$ alkoxy, $C_{1-6}$ alkoxycarbonyl, $C_{1-4}$ alkoxycarbonylamino, P(O)(O$C_{1-3}$)$_2$, $C_{3-6}$ cycloalkyloxy, $C_{3-4}$ cycloalkyl, or $C_{5-8}$ cycloalkyl optionally substituted with one to three substituents independently selected from the group consisting of halogen, oxo and $C_{1-4}$ alkyl optionally substituted with one to three substituents independently selected from halogen or hydroxy; with the proviso that not more than one of the substituents on the $C_{1-4}$ alkyl of the $C_{1-4}$ alkyl substituted $C_{5-8}$ cycloalkyl is hydroxy, and not more than two of the substituents on the $C_{5-8}$ cycloalkyl are oxo;

$R^3$ is
(i) hydrogen,
(ii) $C_{1-6}$ alkyl,
(iii) trifluoromethyl,
(iv) $C_{1-4}$ alkoxy,
(v) bromo,
(vi) chloro,
(vii) fluoro, or
(viii) hydroxy;

$R^4$ is
(i) hydrogen,
(ii) fluoro,
(iii) chloro, or
(iv) methyl;

$R^5$ is hydrogen;
$R^6$ is hydrogen,
$R^{11}$ is selected from

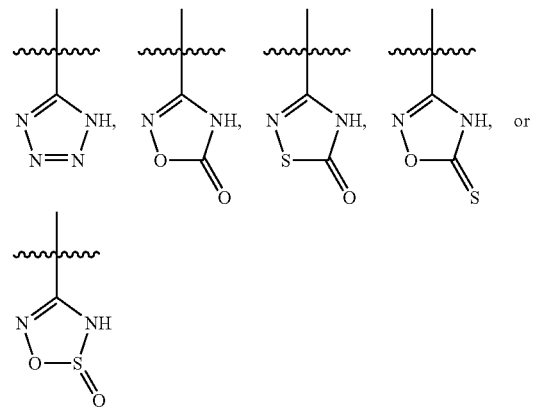

$R^{12}$ is selected from

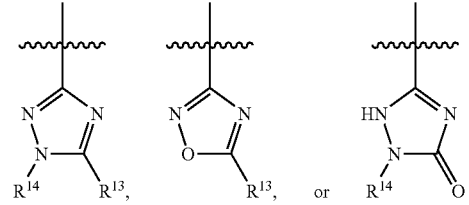

wherein $R^{13}$ is H, —$C_{1-4}$ alkyl, —$CH_2CO_2CH_3$, —$CH_2NH$ ($C_{1-3}$alkyl), —$CH_2 N(C_{1-3}$alkyl)$_2$, or —$CH_2CO_2H$; and $R^{14}$ is —$C_{6-10}$ aryl, —$C_{1-6}$ alkyl, —$C_{1-3}$ alkyl-OH, or —$C_{1-3}$ alkylCO$_2$H;

with the proviso that when $R^1$ is $C_{6-10}$ aryl, wherein $C_{6-10}$ aryl is phenyl, substituted with carboxy at the 2 position, Y is not hydrogen;

with the proviso that when $R^2$ is $C_{1-6}$ alkyl substituted with at least one P(O)(OCH$_3$)$_2$ substituent, $R^1$ is optionally substituted $C_{6-10}$ aryl;

with the proviso that when $R^2$ is $C_{1-6}$ alkyl substituted with at least one $C_{1-6}$ alkoxycarbonyl substituent, $R^1$ is optionally substituted $C_{6-10}$ aryl;

with the proviso that when Y is unsubstituted phenyl, and $R^1$ is ethyl, $R^2$ is not 4-fluoro-3-trifluoromethyphenylmethyl;

with the proviso that Formula (I) is other than
a compound wherein G is S, Y is H, $R^1$ is 4-cyanophenyl, $R^2$ is 4,4,4-trifluorobutyl, $R^3$, $R^4$, $R^5$, and $R^6$ are hydrogen, A is CR$^5$, and B is CR$^6$;

a compound wherein G is S, Y is 1-hydroxyethyl, R$^1$ is 2,2,2-trifluoroethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound wherein G is S, Y is methyl, R$^1$ is 4-piperazin-1-ylcarbonylphenyl, R$^2$ is 2-(cyclopropyl)ethyl, R$^3$, R$^4$, R$^5$, and R$^6$ are hydrogen, A is CR$^5$, and B is CR$^6$;

a compound wherein G is S, Y is methylcarbonylamino, R$^1$ is 4-carboxyphenyl, R$^2$ is n-butyl, R$^3$, R$^4$, R$^5$, and R$^6$ are hydrogen, A is CR$^5$, and B is CR$^6$;

a compound wherein G is S, Y is H, R$^1$ is 3-aminocarbonylphenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound wherein G is S, Y is bromo, R$^1$ is 4-(1-hydroxy-1-methyl-ethyl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound wherein G is S, Y is methylaminocarbonyl, R$^1$ is 4-carboxyphenyl, R$^2$ is n-butyl, R$^3$, R$^4$, R$^5$, and R$^6$ are hydrogen, A is CR$^5$, and B is CR$^6$;

a compound wherein G is S, Y is H, R$^1$ is 4-(5-thioxo-4,5-dihydro-[1,2,4]oxadiazol-3-yl)phenyl, R$^2$ is n-butyl, R$^3$, R$^4$, R$^5$, and R$^6$ are hydrogen, A is CR$^5$, and B is CR$^6$;

a compound wherein G is S, Y is 4-methyl-piperazin-1-ylcarbonyl, R$^1$ is phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound wherein G is S, Y is bromo, R$^1$ is 4-(1-hydroxyethyl)phenyl, R$^2$ is 4-fluoro-3-trifluoromethylphenylmethyl, R$^3$, R$^4$, R$^5$, and R$^6$, are hydrogen, A is CR$^5$, and B is CR$^6$;

a compound wherein G is S, Y is dimethylaminomethyl, R$^1$ is 4-carboxyphenyl, R$^2$ is n-butyl, R$^3$, R$^4$, R$^5$, and R$^6$ are hydrogen, A is CR$^5$, and B is CR$^6$;

a compound wherein G is S, Y is H, R$^1$ is 3-cyanophenyl, R$^2$ is 5,5,5-trifluoropentyl, R$^3$, R$^4$, R$^5$, and R$^6$ are hydrogen, A is CR$^5$, and B is CR$^6$;

a compound wherein G is S, Y is methylcarbonyl, R$^1$ is 4-carboxyphenyl, R$^2$ is 3-fluoropropyl, R$^3$, R$^4$, R$^5$, and R$^6$ are hydrogen, A is CR$^5$, and B is CR$^6$;

a compound wherein G is S, Y is H, R$^1$ is 4-carboxyphenyl, R$^2$ is 2-fluoroethyl, R$^3$, R$^4$, R$^5$, and R$^6$ are hydrogen, A is CR$^5$, and B is CR$^6$;

a compound wherein G is S, Y is H, R$^1$ is 4-carboxyphenyl, R$^2$ is 3-fluoropropyl, R$^3$, R$^4$, R$^5$, and R$^6$ are hydrogen, A is CR$^5$, and B is CR$^6$; and a compound wherein G is S, Y is methyl, R$^1$ is 4-carboxyphenyl, R$^2$ is 2-fluoroethyl, R$^3$, R$^4$, R$^5$, and R$^6$ are hydrogen, A is CR$^5$, and B is CR$^6$;

a compound wherein G is S, Y is H, R$^1$ is 3-(1H-tetrazol-5-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

or an enantiomer, diastereomer, or pharmaceutically acceptable salts thereof.

2. A compound of claim 1 of the formula II:

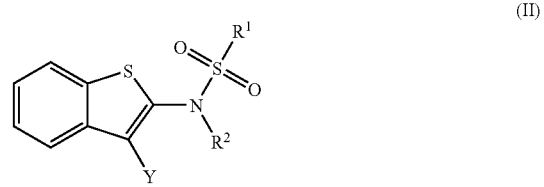

(II)

or an enantiomer, diastereomer, or pharmaceutically acceptable salts thereof.

3. A compound of any one of claim 1 or 2 wherein when R$^1$ is C$_{6-10}$ aryl, wherein C$_{6-10}$ aryl is phenyl, substituted with carboxy at the 2 position, and Y is chloro.

4. A compound of claim 1 wherein Y is hydrogen, isopropenyl, formyl, methyl, isopropyl, trifluoromethyl, methoxy, chloro, acetyl, hydroxymethyl, 1-hydroxyethyl, 1-methoxyethyl, 1-hydroxy-1-methyl-ethyl, methylamino-methyl, dimethylamino-methyl, n-propylamino-methyl, pyrrolidin-1-yl-methyl, 4-methyl-piperazin-1-yl, piperazin-1-yl; cyclopropyl, cyclobutyl, cyclopentyl, aminocarbonyl, methylaminocarbonyl, dimethylaminocarbonyl, methylcarbonyl, methanesulfonylamino, bromo, pyrimidin-5-yl, thien-3-yl, 2-fluorophenyl, or 4-fluorophenyl.

5. A compound of claim 1 wherein Y is hydrogen, methyl, isopropyl, isopropenyl, trifluoromethyl, methoxy, chloro, acetyl, hydroxymethyl, 1-hydroxyethyl, 1-methoxyethyl, 1-hydroxy-1-methyl-ethyl, methylamino-methyl, dimethylamino-methyl, cyclopropyl, cyclobutyl, cyclopentyl, aminocarbonyl, methylaminocarbonyl, dimethylaminocarbonyl, methylcarbonyl, or bromo.

6. A compound as in claim 1 wherein R$^1$ is phenyl substituted with 3- or 4-imidazolyl, wherein the point of attachment of the imidazolyl is through a nitrogen heteroatom; and wherein the imidazolyl is optionally independently substituted with one to two substituents selected from the group consisting of C$_{1-3}$ alkyl, amino-C$_{1-2}$ alkyl, (C$_{1-2}$ alkyl)amino-C$_{1-2}$ alkyl, and di(C$_{1-2}$ alkyl)amino-C$_{1-2}$ alkyl; wherein di(C$_{1-3}$ alkyl) is optionally taken together with the nitrogen atom to which it is attached to form a pyrrolidinyl or piperadinyl ring; with the proviso that not more than one of the substituents is amino-C$_{1-2}$ alkyl, (C$_{1-2}$ alkyl)amino-C$_{1-2}$ alkyl, or di(C$_{1-2}$ alkyl)amino-C$_{1-2}$ alkyl.

7. A compound of as in claim 1 wherein R$^1$ is phenyl optionally substituted with one to three substituents independently selected from hydroxyl, fluoro, chloro, bromo, cyano, nitro, 3- or 4-heteroaryl, 3- or 4-phenyloxy, 3- or 4-heteroaryloxy, C$_{1-3}$ alkylsulfonylaminocarbonyl, di(C$_{1-3}$)alkylaminosulfonyl, C(=NOH)NH$_2$, C(O)NHOH, C(C=N(C$_{1-3}$ alkylcarbonyloxy))NH$_2$, aminocarbonyl, C$_{1-4}$ alkyl subsitituted with one to three chloro or fluoro substitituents or one hydroxyl substituent, C$_{1-3}$alkylcarbonyl, C$_{1-3}$ alkoxycarbonyl, C$_{1-3}$ alkoxy, or carboxy; wherein the phenyloxy is optionally substituted with one to two substituents independently selected from the group consisting of methyl and fluoro.

8. A compound as in claim 1 wherein R$^1$ is phenyl optionally substituted with one to three substituents independently selected from C$_{1-4}$ alkyl, ydroxyl, fluoro, bromo, cyano, nitro, thiadazolyl, pyrazol-1-yl, 2-methyl-pyrimidin-4-yl, oxazol-5-yl, 1H-tetrazol-5-yl, 2H-tetrazol-5-yl, 1H-tetrazol-5-yl, 3- or 4-phenyloxy, 3- or 4-pyridinyloxy, methanesulfonylaminocarbonyl, di(methyl)aminosulfonyl, C(=NOH)NH$_2$, C(O)NHOH, C(C=N(methylcarbonyloxy))NH$_2$, trifluoromethyl, methoxycarbonyl, aminocarbonyl, methoxy, or carboxy; wherein the $C_{1-4}$ alkyl is optionally substituted with one hydroxyl substituent and the phenyloxy is optionally substituted with a fluoro substituent.

9. The compound of claim 8 wherein the $R^1$ is phenyl, 3-cyanophenyl, 4-cyanophenyl, 2,5-dibromophenyl, 4-bromophenyl, 4-(1-hydroxy-1-methyl-ethyl)phenyl, phenyl, 4-hydroxy-3-fluorophenyl, 4-(5-oxo-4,5-dihydro-[1,2,4]thiadiazol-3-yl)phenyl, 4-(5-oxo-4,5-dihydro-[1,2,4]oxadiazol-3-yl)phenyl, 4-(2-oxo-3H-[1,2,3,5]oxathiadiazol-4-yl)phenyl, 4-(5-oxo-4,5-dihydro-1H-[1,2,4]triazol-3-yl)phenyl, 4-(1-methyl-5-oxo-4,5-dihydro-1H-[1,2,4]triazol-3-yl)-phenyl, 3-(5-methyl-[1,3,4]oxadiazol-2-yl)phenyl, 3-fluoro-4-(phenylmethoxy)phenyl, 3-fluoro-4-(4-fluorophenylmethoxy)phenyl, 4-pyridin-3-yloxyphenyl, 4-pyridin-4-yloxyphenyl, 4-methoxycarbonylphenyl, 4-methylcarbonylphenyl, 3-dimethylaminosulfonylphenyl, 4-(methanesulfonylaminocarbonyl)phenyl, 4-fluorophenyl, 3,4-difluorophenyl, 4-carboxyphenyl, 3-carboxyphenyl, 4-(2-dimethylaminomethyl-imidazol-1-yl)phenyl, 4-(N-hydroxy-acetamidinyl)phenyl, 4-hydroxyaminocarbonylphenyl, 4-(N-(methylcarbonyloxy)acetamidinyl)phenyl, 4-(pyrazol-1-yl)phenyl, 3-(2-methyl-pyrimidin-4-yl)phenyl, 4-(oxazol-5-yl)phenyl, 3-(1H-tetrazol-5-yl)phenyl, 3-(2H-tetrazol-5-yl)phenyl, 4-(1H-tetrazol-5-yl)phenyl, or 3-methoxyphenyl.

10. A compound of claim 1 wherein $R^1$ is phenyl substituted with $R^{11}$ or $R^{12}$ at the 3 or 4 position; and optionally one additional substituent selected from fluoro, chloro, or $C_{1-3}$ alkyl.

11. A compound of claim 1 wherein $R^1$ is phenyl wherein said phenyl is substituted with $NR^{15}R^{16}$; wherein $R^{15}$ is hydrogen, $C_{1-4}$ alkyl, methylcarbonyl, trifluoromethylcarbonyl, cyclopropylsulfonyl, or $C_{1-3}$ alkylsulfonyl; and $R^{16}$ is hydrogen or $C_{1-4}$ alkyl; or $R^{15}$ and $R^{16}$ are taken together with the nitrogen atom to which they are attached to form morpholin-4-yl, piperazin-1-yl, piperadin-1-yl, thiomorpholin-4-yl, or pyrrolidin-1-yl; and wherein the ring formed by $NR^{15}R^{16}$ is optionally substituted with $C_{1-3}$alkyl; and wherein said phenyl is optionally substituted with one to two additional substituents independently selected from the group consisting of methoxy, hydroxy, chloro, and bromo.

12. A compound of claim 1 wherein $R^1$ is phenyl substituted with $C(O)NR^{17}R^{18}$ wherein $R^{17}$ is hydrogen, $C_{1-4}$ alkyl, or $C_{1-3}$ alkylsulfonyl; and $R^{18}$ is hydrogen; or $R^{17}$ and $R^{18}$ are taken together with the nitrogen atom to which they are attached to form 4-methyl-piperazin-1-yl.

13. A compound of claim 1 wherein $R^2$ is $C_{1-2}$ alkyl substituted with phenyl, wherein phenyl is substituted with 4 or 5 fluoro substituents; or phenyl is substituted with methoxy and 3 to 4 fluoro substituents.

14. A compound of claim 1 wherein $R^2$ is $C_{1-6}$ alkyl substituted with- phenyl optionally substituted with one to three substituents independently selected from $C_{1-4}$ alkyl, trifluoromethyl, $C_{1-4}$ alkoxy optionally substituted with 1 to 3 fluoro substituents, $C_{1-3}$ alkylthio, trifluoromethylthio, $C_{1-3}$ alkoxycarbonyl, aminocarbonyl, $C_{1-3}$ alkylaminocarbonyl, di($C_{1-3}$) alkylaminocarbonyl, $C_{1-3}$ alkylsulfonyl optionally substituted with 1 to 3 fluoro substituents, chloro, fluoro, bromo, or nitro with the proviso that not more than two of the substituents are selected from the group consisting of trifluoromethyl, $C_{1-4}$ alkoxy substituted with 1 to 3 fluoro substituents, $C_{1-3}$ alkylthio, trifluoromethylthio, $C_{1-3}$ alkoxycarbonyl, aminocarbonyl, $C_{1-3}$ alkylaminocarbonyl, di($C_{1-3}$) alkylaminocarbonyl; $C_{1-3}$ alkylsulfonyl optionally substituted with 1 to 3 fluoro substituents, and nitro.

15. A compound of claim 14 wherein the $R^2$ is $C_{1-6}$ alkyl substituted with phenyl optionally substituted with one to two substituents independently selected from methoxy, fluoro, nitro, trifluoromethoxy, trifluoromethyl, methylthio, trifluoromethylthio, methoxycarbonyl, methylsulfonyl, trifluoromethylsulfonyl, methyl, chloro, or bromo.

16. A compound of claim 15 wherein the $R^2$ is 3-methoxyphenylmethyl, 4-methoxyphenylmethyl, 2-fluorophenylmethyl, 3-fluorophenylmethyl, 4-fluorophenylmethyl, 3,4,5-trifluorophenylmethyl, 3,4-difluorophenylmethyl, 2-nitrophenylmethyl, 2-trifluoromethoxyphenylmethyl, 3-trifluoromethoxyphenylmethyl, 4-trifluoromethoxyphenylmethyl, 4-difluoromethoxyphenylmethyl, 4-chloro-2-fluoro-5-methoxyphenylmethyl, phenylmethyl, 4-fluoro-3-trifluoromethylphenylmethyl, 4-fluoro-2-trifluoromethylphenylmethyl, 2-methylphenylmethyl, 3-methylphenylmethyl, 2,5-dichlorophenylmethyl, 3-chloro-4-fluorophenylmethyl, 4-chloro-3-fluorophenylmethyl, 2-(phenyl)ethyl, 4-chlorophenylmethyl, 2-methoxyphenylmethyl, 5-bromo-2-methoxyphenylmethyl, 3-methoxyphenylmethyl, 4-fluoro-3-methoxyphenylmethyl, 2-bromo-5-methoxyphenylmethyl, 4-methoxy-3-bromophenylmethyl, 3-nitrophenylmethyl, 3-methoxycarbonylphenylmethyl, 4-methoxycarbonylphenylmethyl, 4-trifluoromethylthiophenylmethyl, 4-trifluoromethylsulfonylphenylmethyl, or 3-hydroxyphenylmethyl.

17. A compound of claim 1 wherein the $R^2$ is $C_{1-6}$ alkyl substituted with one substituent selected from benzo[1,3]dioxol-5-ylmethyl, or 2,2-difluoro-benzo[1,3]dioxol-5-ylmethyl.

18. A compound of claim 17 wherein the $R^2$ is benzo[1,3]dioxol-5-ylmethyl, or 2,2-difluoro-benzo[1,3]dioxol-5-ylmethyl.

19. A compound of claim 1 wherein $R^{11}$ is selected from

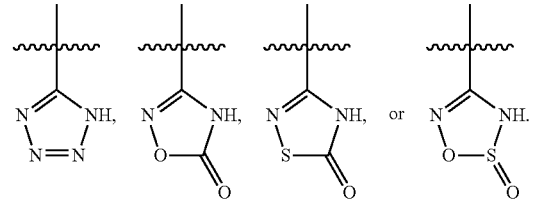

20. A compound of claim 1 wherein $R^{12}$ is selected from

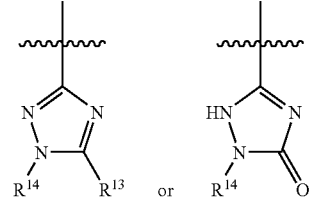

wherein $R^{13}$ is H, —$C_{1-4}$ alkyl, —$CH_2NH(C_{1-3}$alkyl), —$CH_2NH(C_{1-3}$alkyl)$_2$, or —$CH_2CO_2H$; and $R^{14}$ is —$C_{1-2}$ alkyl, —$C_{1-3}$ alkyl-OH, or —$C_{1-3}$alkylCO$_2$H.

21. A compound of claim 1 that is
a compound of formula (I) wherein G is S, Y is Br, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;
a compound of formula (I) wherein G is S, Y is hydroxymethyl, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$; or a compound of formula (I) wherein G is S, Y is methyl, $R^1$ is 4-(5-oxo-4,5-dihydro-[1,2,4]thiadiazol-3-yl)phenyl, $R^2$ is 4-trifluoromethoxyphenylmethyl, $R^3$, $R^4$, $R^5$, and $R^6$ are hydrogen, A is $CR^5$, and B is $CR^6$; or a pharmaceutically acceptable salt thereof.

22. A pharmaceutical composition comprising a compound of claim 1 and at least one of a pharmaceutically acceptable carrier, pharmaceutically acceptable excipient, and a pharmaceutically acceptable diluent.

23. The pharmaceutical composition of claim 22, wherein the composition is a solid oral dosage form.

24. The pharmaceutical composition of claim 22, wherein the composition is a syrup, an elixor, or a suspension.

25. A compound of claim 1 wherein $R^1$ is $C_{1-4}$ alkyl optionally substituted with 1 substituent selected from the group consisting of $C_{1-3}$ alkylsulfonyl, $C_{1-3}$ alkoxycarbonyl, hydroxy, carboxy, formyl, trifluoromethyl, bromo, and a 5 to 6 membered heteroaryl optionally substituted with $C_{1-4}$ alkyl, aminomethyl, methylamino-methyl, or dimethylamino-methyl.

26. A compound of claim 1 wherein $R^1$ is unsubstituted cyclopropyl or cyclohexyl substituted at the 4-position with one substituent selected from the group consisting of $C_{1-4}$ alkoxycarbonyl, carboxy, aminocarbonyl, $C_{1-3}$ alkylaminocarbonyl, di($C_{1-3}$ alkyl)aminocarbonyl, aminomethyl, methylamino-methyl, dimethylamino-methyl, $R^{11}$, and $R^{12}$.

27. A compound of claim 1 wherein $R^1$ is methyl, ethyl, propyl, butyl, phenylmethyl, carboxymethyl, methoxycarbonylmethyl, 2-(methoxycarbonyl)ethyl, 2,2,2-trifluoroethyl, 2-bromoethyl, 2-hydroxyethyl, 2-formylethyl, 2-carboxyethyl, 3-bromopropyl, 3-hydroxypropyl, 3-(methoxycarbonyl)propyl, 3-(imidazol-1-yl)propyl, 4-(imidazol-1-yl)butyl, 3-hydroxy-3-methyl-butyl, 4-bromobutyl, 4-hydroxybutyl, 4-(4-methyl-piperazin-1-yl)butyl, 4-hydroxy-4-methylpentyl, or methanesulfonylmethyl.

28. A compound of claim 1 wherein $R^1$ is amino, methylamino, or dimethylamino.

29. A compound of claim 1 wherein $R^1$ is $CF_3$.

30. A compound of claim 1 wherein $R^2$ is cyclohexyl.

31. A compound of claim 1 wherein $R^2$ is $C_{1-6}$ alkyl substituted with one substituent selected from cyclopropyl, cyclobutyl, cyclopentyl, or cyclohexyl.

32. A compound of claims 1 wherein $R^2$ is cyclopropylmethyl, cyclobutylmethyl, cyclopentylmethyl, 2-(cyclopropyl)ethyl, or cyclohexylmethyl.

33. A compound as in claim 1 wherein Y is hydrogen; isopropenyl; pyrimidinyl; thienyl; bromo; chloro; fluoro; iodo; cyano; formyl; aminocarbonyl; methylaminocarbonyl; dimethylaminocarbonyl; $C_{1-6}$ alkylcarbonyl; $C_{3-6}$ cycloalkyl; $C_{1-3}$ alkoxy; $C_{1-2}$ alkyl optionally substituted with 1 substituent selected from $C_{1-4}$ alkoxy or $NR^7R^8$ wherein $R^7$ is hydrogen, $C_{1-4}$ alkyl, $C_{1-3}$ alkylcarbonyl, or $C_{1-3}$ alkylsulfonyl and $R^8$ is hydrogen or $C_{1-4}$ alkyl or $R^7$ and $R^8$ are taken together with the nitrogen atom to which they are attached to form a 5 or 6 membered ring optionally containing one additional heteroatom selected from nitrogen, oxygen, or sulfur; $C_{1-2}$ alkyl optionally substituted with 1 to 3 groups independently selected from hydroxy, fluoro, or chloro; $NR^9R^{10}$ wherein $R^9$ is $C_{1-4}$ alkyl, $C_{1-3}$ alkylcarbonyl, or $C_{1-3}$ alkylsulfonyl and $R^{10}$ is hydrogen or $C_{1-4}$ alkyl, or $R^9$ and $R^{10}$ are taken together with the nitrogen atom to which they are attached to form a 5 or 6 membered ring optionally containing one additional heteroatom selected from nitrogen, oxygen, or sulfur; and wherein said 5 or 6 membered ring is optionally substituted with a $C_{1-4}$ alkyl substituent; with the proviso that when G is S and $R^{10}$ is hydrogen, $R^9$ is other than hydrogen and $C_{1-4}$ alkyl; or $C_{6-10}$ aryl optionally substituted with 1 to three groups independently selected from chloro, fluoro, or bromo.

34. A compound of claim 1 that is a compound of formula (I) wherein G is S, Y is Br, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is adamant-1-ylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-carboxyphenyl, $R_2$ is adamant-1-ylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Cl, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-fluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-trifluoromethoxyphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is 4-hydroxyphenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is ethyl, $R_2$ is 3,4-difluorophenyl methyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-fluoro-3-methoxyphenylmethyl, $R_3$, $R_4$, $R_5$, and $R_6$ are hydrogen, A is $CR_5$, and B is $CR_6$;

a compound of formula (I) wherein G is S, Y is formyl, $R_1$ is 4-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3-methyl phenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-methoxy-3-bromophenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 4-fluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is 3-fluorophenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is methyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3-methoxyphenyl methyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is phenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is ethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is methyl, $R_1$ is phenyl, $R_2$ is 3,4-difluoro phenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-hydroxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 3,4-difluorophenyl methyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 3-hydroxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is acetyl, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is acetyl, $R_1$ is methyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is methyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-carboxyphenyl, $R_2$ is n-butyl, $R_3$, $R_4$, $R_5$, and $R_6$ are hydrogen, A is $CR_5$, and B is $CR_6$;

a compound of formula (I) wherein G is S, Y is Br, $R_1$ is 3-methoxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is phenyl, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is methyl, $R_1$ is 3-phenoxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is dimethylamino, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is 2-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is 3-hydroxyphenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is ethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is 3-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is 3-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is 2-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is 3-fluorophenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is formyl, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is n-hexyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3-trifluoromethoxy phenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3-phenylpropyl, $R_3$, $R_4$, $R_5$, and $R_6$ are hydrogen, A is $CR_5$, and B is $CR_6$;

a compound of formula (I) wherein G is S, Y is methyl, $R_1$ is phenyl, $R_2$ is 2-phenylethyl, $R_3$, $R_4$, $R_5$, and $R_6$ are hydrogen, A is $CR_5$, and B is $CR_6$;

a compound of formula (I) wherein G is S, Y is methyl, $R_1$ is 2-fluorophenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is Br, $R_1$ is dimethylamino, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 4-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-methoxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is cyano, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3-nitrophenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 4-chlorophenylmethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 4-trifluoromethoxyphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is phenyl, $R_2$ is 2-(methoxycarbonyl)-2-methylethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-trifluoromethoxyphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 4-trifluoromethoxyphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-fluorophenylmethyl, $R_3$, $R_4$, $R_5$, and $R_6$ are hydrogen, A is $CR_5$, and B is $CR_6$;

a compound of formula (I) wherein G is S, Y is formyl, $R_1$ is ethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-carboxyphenyl, $R_2$ is 3,3,3-trifluoropropyl, $R_3$, $R_4$, $R_5$, and $R_6$ are hydrogen, A is $CR_5$, and B is $CR_6$;

a compound of formula (I) wherein G is S, Y is formyl, $R_1$ is methyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2(S)-methoxycarbonyl-2-methylethyl, $R_3$, $R_4$, $R_5$, and $R_6$ are hydrogen, A is $CR_5$, and B is $CR_6$;

a compound of formula (I) wherein G is S, Y is Br, $R_1$ is ethyl, $R_2$ is n-butyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 3,3,3-trifluoropropyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 5-(ethoxycarbonyl) pentyl, $R_3$, $R_4$, $R_5$, and $R_6$ are hydrogen, A is $CR_5$, and B is $CR_6$;

a compound of formula (I) wherein G is S, Y is methyl, $R_1$ is 4-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is formyl, $R_1$ is phenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 4-chlorophenyl methyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is methyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is hydroxymethyl, $R_1$ is methyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2(S)-methoxycarbonyl-2-methylethyl $R_3$, $R_4$, $R_5$, and $R_6$ are hydrogen, A is $CR_5$, and B is $CR_6$;

a compound of formula (I) wherein G is S, Y is Br, $R_1$ is 3-methoxycarbonyl phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is acetyl, $R_1$ is ethyl, $R_2$ is 3,4difluorophenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 2-(tert-butoxy)ethyl $R_3$, $R_4$, $R_5$, and $R_6$ are hydrogen, A is $CR_5$, and B is $CR_6$;

a compound of formula (I) wherein G is S, Y is Cl, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$; or a compound of formula (I) wherein G is S, Y is methyl, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 3-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is trifluoromethyl, $R^1$ is phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(pyrazol-1-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(5-methyl-[1,3,4]oxadiazol-2-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(oxazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxyethyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-chloro-4-methylcarbonylamino-phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-(1-hydroxy-1-methyl-ethyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methylcarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 3,4-difluoro-phenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1-hydroxy-1-methyl-ethyl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1-hydroxy-1-methyl-ethyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is pentyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is hexyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 3-t-butoxypropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 2-t-butoxyethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 3-t-butoxypropyl, $R^3$, $R^4$, $R^5$, and $R^6$ are hydrogen, A is $CR^5$, and B is $CR^6$;

a compound of formula (I) wherein G is S, Y is methoxy, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-fluoro-3-trifluoromethylphenylmethyl, $R^4$ is fluoro, $R^3$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is cyclobutylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is cyclopentylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-cyclohexyloxy-ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 3-methoxy-3-methyl-butyl, $R^3$, $R^4$, $R^5$, and $R^6$ are hydrogen, A is $CR^5$, and B is $CR^6$;

a compound of formula (I) wherein G is S, Y is methylaminocarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is aminocarbonyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(N-hydroxy-acetamidinyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, R$^1$ is 4-carboxyphenyl, R$^2$ is n-butyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 2-(cyclopropyl)ethyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 3,3,3-trifluoropropyl, R$^3$, R$^4$, R$^5$, and R$^6$ are hydrogen, A is CR$^5$, and B is CR$^6$;

a compound of formula (I) wherein G is S, Y is H, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is phenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-fluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3,4-difluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3-chloro-4-fluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-difluoromethoxyphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is pentafluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethylsulfonylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethoxyphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3-fluoro-4-trifluoromethylphenylmethyl, R$^3$, R$^4$, R$^5$, and R$^6$ are hydrogen, A is CR$^5$, and B is CR$^6$;

a compound of formula (I) wherein G is S, Y is H, R$^1$ is 4-aminophenyl, R$^2$ is 3,3,3-trifluoropropyl, R$^3$, R$^4$, R$^5$, and R$^6$ are hydrogen, A is CR$^5$, and B is CR$^6$;

a compound of formula (I) wherein G is S, Y is cyclopentyl, R$^1$ is 4-carboxyphenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 2-carboxyethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is bromo, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 4-(5-oxo-4,5-dihydro-[1,2,4]oxadiazol-3-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3,4,5-trifluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2-fluoro-5-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2,5-dichlorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-chloro-3-fluorophenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 2,2-difluoro-benzo[1,3]dioxol-5-ylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 3,4-dimethoxyphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-carboxyphenyl, R$^2$ is 4-trifluoromethylthiophenylmethyl, R$^3$, R$^4$, R$^5$, and R$^6$ are hydrogen, A is CR$^5$, and B is CR$^6$;

a compound of formula (I) wherein G is S, Y is 1S*-hydroxy-ethyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is 1R*-hydroxy-ethyl, R$^1$ is ethyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 4,4,4-trifluorobutyl, R$^3$, R$^4$, R$^5$, and R$^6$ are hydrogen, A is CR$^5$, and B is CR$^6$;

a compound of formula (I) wherein G is S, Y is chloro, R$^1$ is 4-carboxyphenyl, R$^2$ is 5,5,5-trifluoropentyl R$^3$, R$^4$, R$^5$, and R$^6$ are hydrogen, A is CR$^5$, and B is CR$^6$;

a compound of formula (I) wherein G is S, Y is methyl, R$^1$ is 4-(1H-tetrazol-5-yl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is H, R$^1$ is 4-(2-oxo-3H-[1,2,3,5]oxathiadiazol-4-yl)-phenyl, R$^2$ is n-butyl, R$^3$, R$^4$, R$^5$, and R$^6$ are hydrogen, A is CR$^5$ and B is CR$^6$;

a compound of formula (I) wherein G is S, Y is methyl, R$^1$ is 4-(5-oxo-4,5-dihydro-[1,2,4]oxadiazol-3-yl)phenyl, R$^2$ is n-butyl, R$^3$, R$^4$, R$^5$, and R$^6$ are hydrogen, A is CR$^5$, and B is CR$^6$;

a compound of formula (I) wherein G is S, Y is methyl, R$^1$ is 4-(1H-tetrazol-5-yl)phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(2-oxo-3H-[1,2,3,5]oxathiadiazol-4-yl)-phenyl, R$^2$ is 4-fluoro-3-trifluoromethylphenylmethyl, R$^3$, R$^4$, R$^5$, and R$^6$ are hydrogen, A is CR$^5$, and B is CR$^6$;

a compound of formula (I) wherein G is S, Y is methyl, R$^1$ is 4-(5-oxo-4,5-dihydro-[1,2,4]oxadiazol-3-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is isopropyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(morpholin-4-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-aminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-amino-3-bromophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-2-fluorophenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2-(methoxycarbonyl)ethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(2-oxo-3H-[1,2,3,5]oxathiadiazol-4-yl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(methanesulfonylaminocarbonyl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(2-oxo-3H-[1,2,3,5]oxathiadiazol-4-yl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(1H-tetrazol-5-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-amino-3-bromophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-aminophenyl, $R^2$ is 4-fluoro-3-trifluoromethylphenylmethyl $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 3-bromo-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-aminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-aminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 3-bromo-4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-carboxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxypropyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is hydroxymethyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxy-2-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(5-oxo-4,5-dihydro-[1,2,4]thiadiazol-3-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2-formylethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-hydroxy-3-methyl-butyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is phenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-bromophenyl, $R^2$ is 3-chloro-4-fluorophenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 4-fluorophenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(morpholin-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is cyclobutyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-(methoxycarbonyl)propyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-hydroxybutyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-carboxypropyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 5-chloro-2-methoxy-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is cyclopropyl, $R^2$ is 3-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-bromobutyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-cyanophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-3-fluorophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxy-3-fluorophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 2-fluoro-3-methoxyphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-carboxyphenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]thiadiazol-3-yl)phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(1H-tetrazol-5-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2-hydroxyethyl, $R^2$ is 4-fluoro-3-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 2-bromoethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-dimethylaminophenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(morpholin-4-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(5-oxo-4,5-dihydro-[1,2,4]oxadiazol-3-yl)phenyl, $R^2$ is 4-trifluoromethoxyphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is ethyl, $R^2$ is 2,4,5-trifluoro-3-methoxyphenylmethyl, $R^3$, $R^4$, $R^5$, and $R^6$ are hydrogen, A is $CR^5$, and B is $CR^6$; or a pharmaceutically acceptable salt thereof.

35. A compound of claim 1 that is a compound of formula (I) wherein G is S, Y is Cl, $R_1$ is 3-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is n-butyl, $R_3$, $R_4$, $R_5$, and $R_6$ are hydrogen, A is $CR_5$, and B is $CR_6$;

a compound of formula (I) wherein G is S, Y is H, $R_1$ is 3-fluorophenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-(methylsulfanyl)ethyl, $R_3$, $R_4$, $R_5$, and $R_6$ are hydrogen, A is $CR_5$, and B is $CR_6$;

a compound of formula (I) wherein G is S, Y is H, $R_1$ is methyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 2-(tert-butoxycarbonylamino)ethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is n-butyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 5-bromo-2-methoxyphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-methylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is methanesulfonylmethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is H, $R_1$ is ethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is H, $R_1$ is 2-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-bromo-5-methoxyphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-nitrophenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-fluorophenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is ethyl, $R_2$ is 3,3,3-trifluoropropyl, $R_3$, $R_4$, $R_5$, and $R_6$ are hydrogen, A is $CR_5$, and B is $CR_6$;

a compound of formula (I) wherein G is S, Y is Br, $R_1$ is 4-carboxyphenyl, $R_2$ is 2,2-difluoroethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 3-methylphenylmethyl, $R_3$, $R_4$, $R_5$, and $R_6$ are hydrogen, A is $CR_5$, and B is $CR_6$;

a compound of formula (I) wherein G is S, Y is H, $R_1$ is n-propyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 3-nitrophenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 3-methoxyphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-phenylethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 4-chlorophenylmethyl, $R_3$, $R_4$, $R_5$, and $R_6$ are hydrogen, A is $CR_5$, and B is $CR_6$;

a compound of formula (I) wherein G is S, Y is Cl, $R_1$ is 4-methoxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-(methanesulfonyl)ethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 2,2-difluoroethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is ethyl, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-(dimethylamino)ethyl, $R_3$, $R_4$, $R_5$, and $R_6$ are hydrogen, A is $CR_5$, and B is $CR_6$;

a compound of formula (I) wherein G is S, Y is H, $R_1$ is n-butyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-trifluoromethoxyphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 3-trifluoromethoxyphenylmethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 2-methoxyphenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2-(dimethylphospho)ethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is cyclohexyl, $R_3$, $R_4$, $R_5$, and $R_6$ are hydrogen, A is $CR_5$, and B is $CR_6$;

a compound of formula (I) wherein G is S, Y is chloro, $R^1$ is methylamino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is dimethylamino, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is dimethylamino-methyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylamino-methyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is methyl, $R^2$ is 2-t-butoxyethyl, $R^3$, $R^4$, $R^5$, and $R^6$ are hydrogen, A is $CR^5$, and B is $CR^6$;

a compound of formula (I) wherein G is S, Y is methyl, $R^1$ is 4-pyridin-3-yloxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 3-methoxycarbonylphenyl, $R^2$ is 4-fluoro-3-trifluoromethylphenylmethyl, $R^4$ is fluoro, $R^3$, $R^5$, and $R^6$ are hydrogen, A is $CR^5$, and B is $CR^6$;

a compound of formula (I) wherein G is S, Y is methyl, $R^1$ is 6-methylthiopyridin-3-yl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is propyl, $R^3$, $R^4$, $R^5$, and $R^6$ are hydrogen, A is $CR^5$, and B is $CR^6$;

a compound of formula (I) wherein G is S, Y is methylamino-methyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is dimethylamino-methyl, $R^1$ is phenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-dimethylaminophenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-morpholin-4-yl-phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(1H-tetrazol-5-yl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-carboxyphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is aminocarbonyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, $R^1$ is 4-(N-hydroxy-acetamidinyl)phenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is 4-methanesulfonylphenylmethyl, $R^3$, $R^4$, $R^5$, and $R^6$ are hydrogen, A is $CR^5$, and B is $CR^6$;

a compound of formula (I) wherein G is $S(O_2)$, Y is dimethylamino, $R^1$ is 4-carboxyphenyl, $R^2$ is n-butyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 3-cyanophenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is n-butyl, $R^4$ is trifluoromethyl, $R^3$, $R^5$, and $R^6$ are hydrogen, A is $CR_5$, and B is $CR_6$;

a compound of formula (I) wherein G is S, Y is bromo, $R^1$ is 4-dimethylaminophenyl, $R^2$ is n-butyl, $R^3$, $R^4$, $R^5$, and $R^6$ are hydrogen, A is $CR^5$, and B is $CR^6$;

a compound of formula (I) wherein G is S, Y is isopropyl, $R^1$ is 4-methoxycarbonylphenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(2-oxo-3H-[1,2,3,5]oxathiadiazol-4-yl)-phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 2-carboxyethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 4-(5-oxo-4,5-dihydro-[1,2,4]oxadiazol-3-yl)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]oxadiazol-3-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-carboxy-2-fluorophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-methanesulfonylaminophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is 1-hydroxy-1-methyl-ethyl, $R^1$ is 4-bromophenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is methyl, $R^1$ is 2,2,2-trifluoroethyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is cyclopropyl, $R^1$ is 4-methoxycarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-(methanesulfonylamino)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is bromo, $R^1$ is 4-(methanesulfonylamino)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is chloro, $R^1$ is 3,5-dichloro-4-(methanesulfonylamino)phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]thiadiazol-3-yl)-phenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is H, $R^1$ is 4-(5-oxo-4,5-dihydro-[1,2,4]thiadiazol-3-yl)-phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is H, $R^1$ is 4-methylaminophenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 2,2,2-trifluoroethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 4-methanesulfonylamino-2-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is chloro, $R^1$ is 2-hydroxy-4-(methanesulfonylamino)phenyl, $R^2$ is 4-fluoro-3-trifluoromethylphenylmethyl, $R^3$, $R^4$, $R^5$, and $R^6$ are hydrogen, A is $CR^5$, and B is $CR^6$; or a pharmaceutically acceptable salt thereof.

36. A compound of claim 1 that is a compound of formula (I) wherein G is S, Y is H, $R_1$ is phenyl, $R_2$ is 2-methylsulfanylethyl, $R_3$, $R_4$, $R_5$, and $R_6$ are hydrogen, A is $CR_5$, and B is $CR_6$;

a compound of formula (I) wherein G is S, Y is H, $R_1$ is phenyl, $R_2$ is 4-methoxyphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 2-(dimethylamino)ethyl, $R_3$, $R_4$, $R_5$, and $R_6$ are hydrogen, A is $CR_5$, and B is $CR_6$;

a compound of formula (I) wherein G is S, Y is H, $R_1$ is methyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is ethyl, $R_2$ is 2,2-difluoroethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 2-(methanesulfonyl)ethyl, $R_3$, $R_4$, $R_5$, and $R_6$ are hydrogen, A is $CR_5$, and B is $CR_6$;

a compound of formula (I) wherein G is S, Y is Cl, $R_1$ is phenyl, $R_2$ is 2-aminoethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 2-(methylsulfanyl)ethyl, $R_3$, $R_4$, $R_5$, and $R_6$ are hydrogen, A is $CR_5$, and B is $CR_6$;

a compound of formula (I) wherein G is S, Y is Br, $R_1$ is dimethylamino, $R_2$ is 2,2-difluoroethyl, $R_3$, $R_4$, $R_5$, and $R_6$ are hydrogen, A is $CR_5$, and B is $CR_6$;

a compound of formula (I) wherein G is S, Y is Br, $R_1$ is amino, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is 1-hydroxyethyl, $R_1$ is ethyl, $R_2$ is cyclopropylmethyl, $R_3$, $R_4$, $R_5$, and $R_6$ are hydrogen, A is $CR_5$, and B is $CR_6$;

a compound of formula (I) wherein G is S, Y is acetyl, $R_1$ is ethyl, $R_2$ is 2-(tert-butoxy)ethyl, $R_3$, $R_4$, $R_5$, and $R_6$ are hydrogen, A is $CR_5$, and B is $CR_6$;

a compound of formula (I) wherein G is S, Y is Cl, $R_1$ is amino, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Cl, $R_1$ is 4-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is 3-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is 4-methoxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is 2-fluorophenyl, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is amino, $R_2$ is 4-fluoro-3-trifluoromethylphenyl, $R_3$, $R_4$, $R_5$, and $R_6$ are hydrogen, A is $CR_5$, and B is $CR_6$;

a compound of formula (I) wherein G is S, Y is Cl, $R_1$ is 2-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is methyl, $R_1$ is ethyl, $R_2$ is 2-methoxyethyl, $R_3$, $R_4$, $R_5$, and $R_6$ are hydrogen, A is $CR_5$, and B is $CR_6$;

a compound of formula (I) wherein G is S, Y is Br, $R_1$ is 2-carboxyphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is H, $R_1$ is 4-methoxycarbonylphenyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is 4-fluorophenyl, $R_1$ is ethyl, $R_2$ is 4-fluoro-3-trifluoromethylphenylmethyl, $R_3$, $R_4$, $R_5$, and $R_6$ are hydrogen, A is $CR_5$, and B is $CR_6$;

a compound of formula (I) wherein G is S, Y is Br, $R_1$ is 4-trifluoromethylphenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is H, $R_1$ is 4-trifluoromethylphenyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is Br, $R_1$ is phenyl, $R_2$ is 2,3-dihydroxypropyl, $R_3$, $R_4$, $R_5$, and $R_6$ are hydrogen, A is $CR_5$, and B is $CR_6$;

a compound of formula (I) wherein G is S, Y is methyl, $R_1$ is phenylmethyl, $R_2$ is 3,4-difluorophenylmethyl, $R_3$, $R_4$, $R_5$, and $R_6$ are hydrogen, A is $CR_5$, and B is $CR_6$;

a compound of formula (I) wherein G is S, Y is bromo, $R^1$ is amino, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is n-propylamino-methyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is n-propylamino-methyl, $R^1$ is ethyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methylcarbonylphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is 3-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is H, $R^1$ is methyl, $R^2$ is n-butyl, $R^3$, $R^4$, $R^5$, and $R^6$ are hydrogen, A is $CR^5$, and B is $CR^6$;

a compound of formula (I) wherein G is S, Y is methylcarbonyl, $R^1$ is 4-carboxyphenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-carboxyphenyl, $R^2$ is ethyl, $R^3$, $R^4$, $R^5$, and $R^6$ are hydrogen, A is $CR^5$, and B is $CR^6$;

a compound of formula (I) wherein G is S, Y is H, $R^1$ is 4-cyanophenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-methoxycarbonylphenyl, $R^2$ is 4,4,4-trifluorobutyl, $R^4$ is fluoro, $R^3$, $R^5$, and $R^6$ are hydrogen, A is $CR^5$, and B is $CR^6$;

a compound of formula (I) wherein G is S, Y is H, $R^1$ is 4-aminocarbonylphenyl, $R^2$ is 4,4,4-trifluorobutyl, $R^3$, $R^4$, $R^5$, and $R^6$ are hydrogen, A is $CR^5$, and B is $CR^6$;

a compound of formula (I) wherein G is S, Y is formyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is dimethylamino-methyl, $R^1$ is 4-methoxycarbonylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is bromo, $R^1$ is 4-carboxyphenyl, $R^2$ is 2-dimethylamino-ethyl, $R^3$, $R^4$, $R^5$, and $R^6$ are hydrogen, A is $CR^5$, and B is $CR^6$;

a compound of formula (I) wherein G is S, Y is H, $R^1$ is 4-pyrrolidin-1-ylphenyl, $R^2$ is n-butyl, $R^3$, $R^4$, $R^5$, and $R^6$ are hydrogen, A is $CR^5$, and B is $CR^6$;

a compound of formula (I) wherein G is S, Y is H, R¹ is 4-(1-methyl-piperazin-4-yl)phenyl, R² is n-butyl, R³, R⁴, R⁵, and R⁶ are hydrogen, A is CR⁵, and B is CR⁶;

a compound of formula (I) wherein G is S, Y is H, R¹ is 4-carboxyphenyl, R² is 3,3,3-trifluoropropyl, R³, R⁴, R⁵, and R⁶ are hydrogen, A is CR⁵, and B is CR⁶;

a compound of formula (I) wherein G is S, Y is H, R¹ is 3-dimethylaminosulfonylphenyl, R² is 3,3,3-trifluoropropyl, R³, R⁴, R⁵, and R⁶ are hydrogen, A is CR⁵, and B is CR⁶;

a compound of formula (I) wherein G is S, Y is H, R¹ is 3-dimethylaminosulfonylphenyl, R² is 4-fluoro-3-trifluoromethylphenylmethyl, R³, R⁴, R⁵, and R⁶ are hydrogen, A is CR⁵, and B is CR⁶;

a compound of formula (I) wherein G is S, Y is methylaminocarbonyl, R¹ is 4-methoxycarbonylphenyl, R² is n-butyl, R³, R⁴, R⁵, and R⁶ are hydrogen, A is CR⁵, and B is CR⁶;

a compound of formula (I) wherein G is S, Y is aminocarbonyl, R¹ is 4-carboxyphenyl, R² is n-butyl, R³, R⁴, R⁵, and R⁶ are hydrogen, A is CR⁵, and B is CR⁶;

a compound of formula (I) wherein G is S, Y is dimethylaminocarbonyl, R¹ is 4-carboxyphenyl, R² is n-butyl, R³, R⁴, R⁵, and R⁶ are hydrogen, A is CR⁵, and B is CR⁶;

a compound of formula (I) wherein G is S, Y is H, R¹ is 4-(2-oxo-3H-[1,2,3,5]oxathiadiazol-4-yl)phenyl R² is n-butyl, R³, R⁴, R⁵, and R⁶ are hydrogen, A is CR⁵ and B is CR⁶;

a compound of formula (I) wherein G is S, Y is H, R¹ is 4-bromophenyl, R² is 3,3,3-trifluoropropyl, R³, R⁴, R⁵, and R⁶ are hydrogen, A is CR⁵, and B is CR⁶;

a compound of formula (I) wherein G is S, Y is bromo, R¹ is 4-(5-thioxo-4,5-dihydro-[1,2,4]oxadiazol-3-yl)phenyl, R² is n-butyl, R³, R⁴, R⁵, and R⁶ are hydrogen, A is CR⁵, and B is CR⁶;

a compound of formula (I) wherein G is S, Y is H, R¹ is 4-nitrophenyl, R² is 3,3,3-trifluoropropyl, R³, R⁴, R⁵, and R⁶ are hydrogen, A is CR⁵, and B is CR⁶;

a compound of formula (I) wherein G is S, Y is methylcarbonylamino, R¹ is 4-methoxycarbonylphenyl, R² is n-butyl, R³, R⁴, R⁵, and R⁶ are hydrogen, A is CR⁵, and B is CR⁶;

a compound of formula (I) wherein G is S, Y is cyclopentyl, R¹ is 4-methoxycarbonylphenyl, R² is 4-fluoro-3-trifluoromethylphenylmethyl, R³, R⁴, R⁵, and R⁶ are hydrogen, A is CR⁵, and B is CR⁶;

a compound of formula (I) wherein G is S, Y is methanesulfonylamino, R¹ is phenyl, R² is 4-fluoro-3-trifluoromethylphenylmethyl, R³, R⁴, R⁵, and R⁶ are hydrogen, A is CR⁵, and B is CR⁶;

a compound of formula (I) wherein G is S, Y is chloro, R¹ is 4-(5-oxo-4,5-dihydro-[1,2,4]oxadiazol-3-yl)-phenyl, R² is 4,4,4-trifluoro-butyl, R³, R⁴, R⁵, and R⁶ are hydrogen, A is CR⁵, and B is CR⁶;

a compound of formula (I) wherein G is S, Y is chloro, R¹ is 4-methoxycarbonylphenyl, R² is 4,4,4-trifluorobutyl, R³, R⁴, R⁵, and R⁶ are hydrogen, A is CR⁵, and B is CR⁶;

a compound of formula (I) wherein G is S, Y is H, R¹ is methylamino, R² is n-butyl, R³, R⁴, R⁵, and R⁶ are hydrogen, A is CR⁵, and B is CR⁶;

a compound of formula (I) wherein G is S, Y is chloro, R¹ is methylamino, R² is n-butyl, R³, R⁴, R⁵, and R⁶ are hydrogen, A is CR⁵, and B is CR⁶;

a compound of formula (I) wherein G is S, Y is bromo, R¹ is methylamino, R² is n-butyl, R³, R⁴, R⁵, and R⁶ are hydrogen, A is CR⁵, and B is CR⁶;

a compound of formula (I) wherein G is S, Y is isopropyl, R¹ is 4-carboxyphenyl, R² is 2-(cyclopropyl)ethyl, R³, R⁴, R⁵, and R⁶ are hydrogen, A is CR⁵, and B is CR⁶;

a compound of formula (I) wherein G is S, Y is isopropyl, R¹ is 4-methoxycarbonylphenyl, R² is 2-(cyclopropyl)ethyl, R³, R⁴, R⁵, and R⁶ are hydrogen, A is CR⁵, and B is CR⁶;

a compound of formula (I) wherein G is S, Y is H, R¹ is 4-(1H-tetrazol-5-yl)phenyl, R² is 3,3,3-trifluoropropyl, R³, R⁴, R⁵, and R⁶ are hydrogen, A is CR⁵, and B is CR⁶;

a compound of formula (I) wherein G is S, Y is H, R¹ is 3-cyanophenyl, R² is 3,3,3-trifluoropropyl, R³, R⁴, R⁵, and R⁶ are hydrogen, A is CR⁵, and B is CR⁶;

a compound of formula (I) wherein G is S, Y is H, R¹ is 3-cyanophenyl, R² is 4,4,4-trifluorobutyl, R³, R⁴, R⁵, and R⁶ are hydrogen, A is CR⁵, and B is CR⁶;

a compound of formula (I) wherein G is S, Y is H, R¹ is 3-cyanophenyl, R² is 2-(cyclopropyl)ethyl, R³, R⁴, R⁵, and R⁶ are hydrogen, A is CR⁵, and B is CR⁶;

a compound of formula (I) wherein G is S, Y is H, R¹ is 4-(2-oxo-2,3-dihydro-2 4-[1,2,3,5]oxathiadiazol-4-yl)phenyl, R² is 3,3,3-trifluoropropyl, R³, R⁴, R⁵, and R⁶ are hydrogen, A is CR⁵, and B is CR⁶;

a compound of formula (I) wherein G is S, Y is H, R¹ is 4-(5-oxo-4,5-dihydro-[1,2,4]oxadiazol-3-yl)phenyl, R² is 3,3,3-trifluoropropyl, R³, R⁴, R⁵, and R⁶ are hydrogen, A is CR⁵, and B is CR⁶;

a compound of formula (I) wherein G is S, Y is methyl, R¹ is 2-carboxyethyl, R² is 3,3,3-trifluoropropyl, R³, R⁴, R⁵, and R⁶ are hydrogen, A is CR⁵, and B is CR⁶;

a compound of formula (I) wherein G is S, Y is methyl, R¹ is 2-carboxyethyl, R² is 4,4,4-trifluorobutyl, R³, R⁴, R⁵, and R⁶ are hydrogen, A is CR⁵, and B is CR⁶;

a compound of formula (I) wherein G is S, Y is H, R¹ is 4-(2-oxo-2,3-dihydro-2 4-[1,2,3,5]oxathiadiazol-4-yl)-phenyl, R² is 2-(cyclopropyl)ethyl, R³, R⁴, R⁵, and R⁶ are hydrogen, A is CR⁵, and B is CR⁶;

a compound of formula (I) wherein G is S, Y is H, R¹ is 4-bromophenyl, R² is 2-(cyclopropyl)ethyl, R³, R⁴, R⁵, and R⁶ are hydrogen, A is CR⁵, and B is CR⁶;

a compound of formula (I) wherein G is S, Y is H, R¹ is 4-bromophenyl, R² is 5,5,5-trifluoropentyl, R³, R⁴, R⁵, and R⁶ are hydrogen, A is CR⁵, and B is CR⁶;

a compound of formula (I) wherein G is S, Y is methyl, R¹ is trifluoromethyl, R² is 5,5,5-trifluoropentyl, R³, R⁴, R⁵, and R⁶ are hydrogen, A is CR⁵, and B is CR⁶;

a compound of formula (I) wherein G is S, Y is H, R¹ is trifluoromethyl, R² is 4-fluoro-3-trifluoromethylphenylmethyl, R³, R⁴, R⁵, and R⁶ are hydrogen, A is CR⁵, and B is CR⁶;

a compound of formula (I) wherein G is S, Y is methyl, R¹ is trifluoromethyl, R² is 4-fluoro-3-trifluoromethylphenylmethyl, R³, R⁴, R⁵, and R⁶ are hydrogen, A is CR⁵, and B is CR⁶;

a compound of formula (I) wherein G is S, Y is methyl, R¹ is trifluoromethyl, R² is 2-(cyclopropyl)ethyl, R³, R⁴, R⁵, and R⁶ are hydrogen, A is CR⁵, and B is CR⁶;

a compound of formula (I) wherein G is S, Y is H, R¹ is 4-methanesulfonylaminophenyl, R² is 5,5,5-trifluoropentyl, R³, R⁴, R⁵, and R⁶ are hydrogen, A is CR⁵, and B is CR⁶;

a compound of formula (I) wherein G is S, Y is chloro, R¹ is 4-trifluoromethylcarbonylaminophenyl, R² is 2-(cyclopropyl)ethyl, R³, R⁴, R⁵, and R⁶ are hydrogen, A is CR⁵, and B is CR⁶;

a compound of formula (I) wherein G is S, Y is H, $R^1$ is 3-methanesulfonylaminophenyl, $R^2$ is 3,3,3-trifluoropropyl, $R^3$, $R^4$, $R^5$, and $R^6$ are hydrogen, A is $CR^5$, and B is $CR^6$;

a compound of formula (I) wherein G is S, Y is methyl, $R^1$ is 4-(thiomorpholin-4-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(piperazin-1-yl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is H, $R^1$ is 4-methanesulfonylamino-2-methoxyphenyl, $R^2$ is 4-fluoro-3-trifluoromethylphenylmethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(thiomorpholin-4-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(piperidin-1-yl)phenyl, $R^2$ is 2-(cyclopropyl)ethyl $R^3$, $R^4$, $R^5$, and $R^6$ are hydrogen, A is $CR^5$, and B is $CR^6$;

a compound of formula (I) wherein G is S, Y is methyl, $R^1$ is 4-(piperidin-1-yl)phenyl, $R^2$ is 5,5,5-trifluoropentyl, $R^3$, $R^4$, $R^5$, and $R^6$ are hydrogen, A is $CR^5$, and B is $CR^6$;

a compound of formula (I) wherein G is S, Y is methyl, $R^1$ is 4-(4-methyl-piperazin-1-ylcarbonyl)phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(pyrrolidin-3S-ylaminocarbonyl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is 4-(pyrrolidin-3R-ylaminocarbonyl)-phenyl, $R^2$ is 2-(cyclopropyl)ethyl, $R^3$, $R^4$, $R^5$, and $R^6$ are hydrogen, A is $CR^5$, and B is $CR^6$;

a compound of formula (I) wherein G is S, Y is methyl, $R^1$ is carboxymethyl, $R^2$ is 4-fluoro-3-trifluoromethylphenylmethyl, $R^3$, $R^4$, $R^5$, and $R^6$ are hydrogen, A is $CR^5$, and B is $CR^6$; or a pharmaceutically acceptable salt thereof.

37. A compound selected from the group consisting of

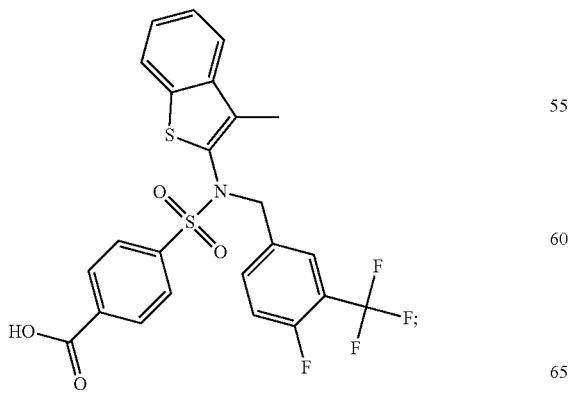

-continued

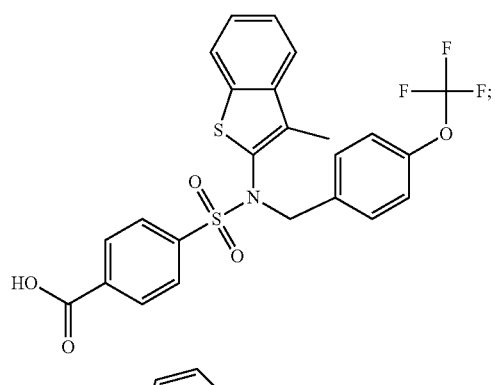

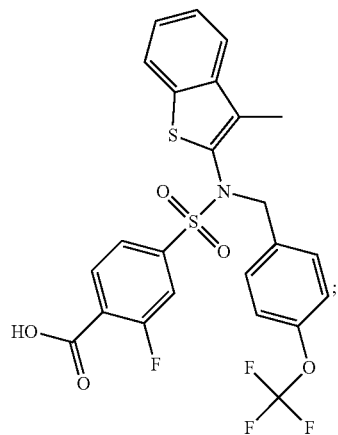

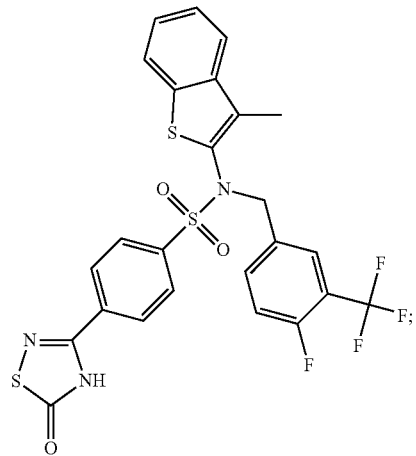

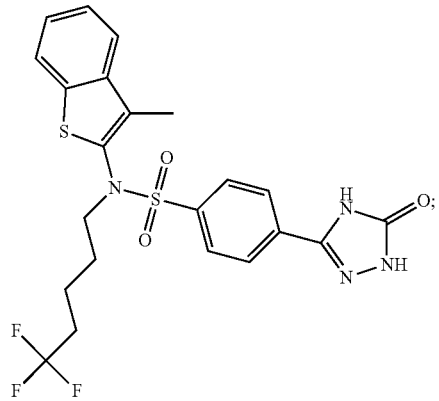

467
-continued
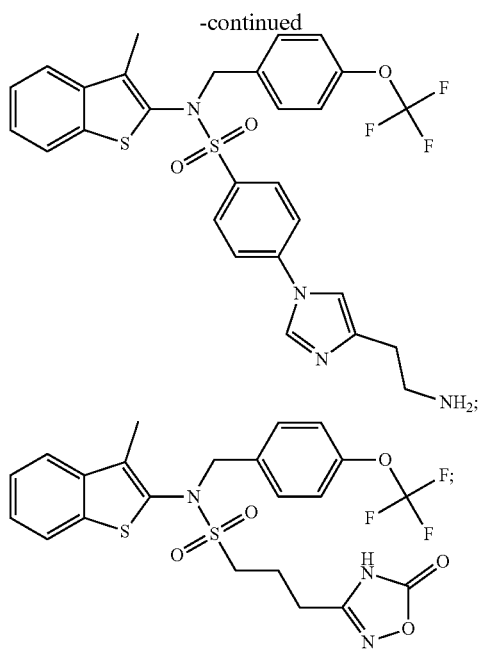
468
-continued
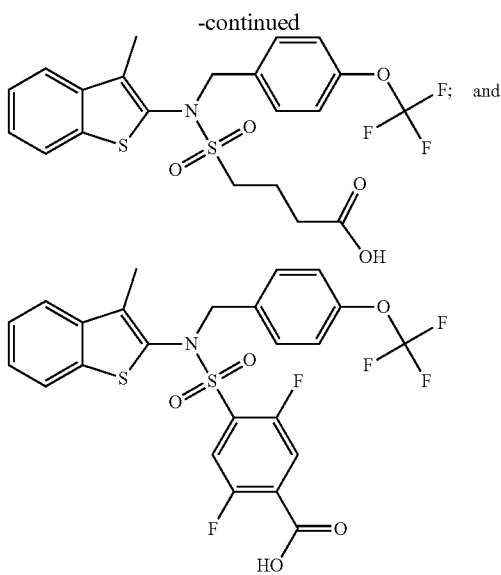
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 8,153,682 B2 | Page 1 of 1 |
| APPLICATION NO. | : 12/175740 | |
| DATED | : April 10, 2012 | |
| INVENTOR(S) | : Branum et al. | |

It is certified that error appears in the above-identified patent and that said Letters Patent is hereby corrected as shown below:

IN THE CLAIMS

Column 438
Line 14, delete
"salts" and insert --salt--

Column 450
Line 22, delete
"a compound of formula (I) wherein G is S, Y is methyl, $R^1$ is 4-carboxyphenyl, $R^2$ is 2,2-difluoro-benzo[1,3]di-oxol-5-ylmethyl, $R^3$, $R^4$, $R^5$, and $R^6$ are hydrogen, A is $CR^5$, and B is $CR^6$;"
and insert
--a compound of formula (I) wherein G is S, Y is methyl, $R^1$ is 4-carboxyphenyl, $R^2$ is 4-fluoro-2-trifluoromethylphenylmethyl, $R^3$, $R^4$, $R^5$, and $R^6$ are hydrogen, A is $CR^5$, and B is $CR^6$;--

Column 455
Line 57, delete
"a compound of formula (I) wherein G is S, Y is methyl, $R^1$ is 2-hydroxyethyl, $R^2$ is 4-fluoro-3-(cyclopropyl)ethyl, $R^3$, $R^4$, $R^5$, and $R^6$ are hydrogen, A is $CR^5$, and B is $CR^6$;"
and insert
--a compound of formula (I) wherein G is S, Y is methyl, $R^1$ is 2-hydroxyethyl, $R^2$ is 4-fluoro-3-trifluoromethylphenylmethyl, $R^3$, $R^4$, $R^5$, and $R^6$ are hydrogen, A is $CR^5$, and B is $CR^6$;--

Column 459
Lines 11-13, delete
"a compound of formula (I) wherein G is $S(O_2)$, Y is dimethylamino, $R^1$ is 4-carboxyphenyl, $R^2$ is n-butyl, $R^3$, $R^4$, $R^5$, and $R^6$ are hydrogen, A is $CR^5$, and B is $CR^6$;"

Signed and Sealed this
Twenty-sixth Day of January, 2016

Michelle K. Lee
*Director of the United States Patent and Trademark Office*